US008557971B2

(12) United States Patent
Pedersen et al.

(10) Patent No.: US 8,557,971 B2

(45) Date of Patent: Oct. 15, 2013

(54) CHIMERIC VIRAL ENVELOPES

(75) Inventors: Finn Skou Pedersen, Aarhus V (DK); Shervin Bahrami, Aarhus C (DK); Mogens Ryttergaard Duch, Risskov (DK); Lars Østergaard, Lystrup (DK); Martin Tolstrup, Aarhus N (DK)

(73) Assignee: Aarhus Universitet (DK)

( * ) Notice: Subject to any disclaimer, the term of this patent is extended or adjusted under 35 U.S.C. 154(b) by 0 days.

(21) Appl. No.: 12/225,268

(22) PCT Filed: Mar. 16, 2007

(86) PCT No.: PCT/DK2007/000131

§ 371 (c)(1), (2), (4) Date: Nov. 6, 2008

(87) PCT Pub. No.: WO2007/107156

PCT Pub. Date: Sep. 27, 2007

(65) Prior Publication Data

US 2009/0324553 A1 Dec. 31, 2009

Related U.S. Application Data

(60) Provisional application No. 60/783,041, filed on Mar. 17, 2006, provisional application No. 60/783,046, filed on Mar. 17, 2006, provisional application No. 60/847,946, filed on Sep. 29, 2006.

(51) Int. Cl.

*C07H 21/04* (2006.01)

*A01N 63/00* (2006.01)

(52) U.S. Cl.

USPC ....................................... 536/23.72; 424/93.6

(58) Field of Classification Search

USPC ....................................... 536/23.72; 424/93.6

See application file for complete search history.

(56) References Cited

U.S. PATENT DOCUMENTS

| | | | |
|---|---|---|---|
| 4,405,712 | A | 9/1983 | Vande Woude et al. |
| 4,650,764 | A | 3/1987 | Temin et al. |
| 5,985,655 | A | 11/1999 | Anderson et al. |

FOREIGN PATENT DOCUMENTS

| | | |
|---|---|---|
| WO | WO 91/10728 | 7/1991 |
| WO | WO 99/36561 | 7/1999 |
| WO | WO 03/076596 | 9/2003 |
| WO | WO 03/097674 | 11/2003 |

OTHER PUBLICATIONS

Adachi et al. (Jun. 1984), Characterization of the env Gene and Long Terminal Repeat of Molecularly Cloned Friend Mink Cell Focus-Inducing Virus DNA, Journal of Virology vol. 50, No. 3, p. 813-821.

Adair et al. (May 1983), Identification and Visualization of the Sexual Agglutinin from the Mating-Type Plus Flagellar Membrane of Chlamydomonas, Cell vol. 33, p. 183-193.

Argos Patrick (1990), An Investigation of Oligopeptides Linking Domains in Protein Tertiary Structures and Possible Candidates for General Gene Fusion, J. Mol. Biol. 211, p. 943-958.

Bachrach et al. (2002), Efficient Gene Transfer into Spleen Cells of Newborn Mice by a Replication-Competent Retroviral Vector, Virology 293, p. 328-334.

Bahrami et al. (2003), Mutational library analysis of selected amino acids in the receptor binding domain of envelope of Akv murine leukemia virus by conditionally replication competent bicistronic vectors, Gene 315, p. 51-61.

Bahrami et al. (Sep. 2004), Change of Tropism of SL3-2 Murine Leukemia Virus, Using Random Mutational Libraries, Journal of Virology vol. 78, No. 17, p. 9343-9351.

Baldwin J. M. (1994), Structure and function of receptors coupled to G proteins, Cell Biology 6, p. 180-190.

Battini et al. (Feb. 1995), Receptor-Binding Domain of Murine Leukemia Virus Envelope Glycoproteins, Journal of Virology vol. 69, No. 2, p. 713-719.

Battini et al. (Feb. 1999), A human cell surface receptor for xenotropic and polytropic murine leukemia viruses: Possible role in G protein coupled signal transduction, Proc. Natl. Acad. Sci. USA vol. 96, p. 1385-1390.

Battini et al. (Mar. 1992), Receptor Choice Determinants in the Envelope Glycoproteins of Amphotropic, Xenotropic, and Polytropic Murine Leukemia Viruses, Journal of Virology vol. 66, No. 3, p. 1468-1475.

Beck et al. (1982), Nucleotide sequence and exact localization of the neomycin phosphotransferase gene from transposon Tn5, Gene 19, p. 327-336.

Bender et al. (May 1987), Evidence that the Packaging Signal of Moloney Murine Leukemia Virus Extends into the gag Region, Journal of Virology vol. 6, No. 5, p. 1639-1646.

Bestwick et al. (Sep. 1984), Molecular Cloning of Biologically Active Rauscher Spleen Focus-Forming Virus and the Sequences of Its env Gene and Long Terminal Repeat, Journal of Virology vol. 51, No. 3, p. 695-705.

Bosselman et al. (Oct. 1982), Analysis of the env Gene of a Molecularly Cloned and Biologically Active Moloney Mink Cell Focus-Forming Proviral DNA, Journal of Virology, vol. 44, No. 1, p. 19-31.

Chadwick et al. (1999), Modification of Retroviral Tropism by Display of IGF-I, J. Mol. Biol. 285, p. 485-494.

(Continued)

*Primary Examiner* — Marcia S Noble

(74) *Attorney, Agent, or Firm* — McLane, Graf, Raulerson & Middleton, PA

(57) ABSTRACT

The invention relates to chimeric polytropic viral envelope polypeptides and uses thereof, as well as to polynucleotides encoding said chimeric polypeptides and constructs comprising said polypeptides and/or polynucleotides. The invention also relates to chimeric retroviral envelope polypeptides, polynucleotides and vectors encoding said chimeric retroviral envelope polypeptides, virus particles and cells harboring said chimeric envelope polypeptides. Said chimeric polypeptide comprise an envelope polypeptide, or fragment thereof, and a polypeptide sequence of a receptor binding region, ligand or polypeptide sequence of a ligand binding region, and optionally a linker sequence. The invention include methods of targeting receptors, methods of treatment and methods for delivery of agents using said chimeric retroviral envelope polypeptides. The invention is applicable for directed targeting and controlled fusion of virus particles with other cellular membranes.

16 Claims, 34 Drawing Sheets

(56) References Cited

OTHER PUBLICATIONS

Chattopadhyay et al. (1989), Biologic and Molecular Genetic Characteristics of a Unique MCF Virus That Is Highly Leukemogenic in Ecotropic Virus-Negative Mice, Virology 168: p. 90-100.
Chattopadhyay et al. (Jan. 7, 1982), Celluar origin and role of mink cell focus-forming viruses in murine thymic lymphomas, Nature vol. 295, p. 25-31.
Chun et al. (1999), A Growing Family of Receptor Genes for Lysophosphatidic Acid (LPA) and other Lysophospholipids (LPs), Cell Biochemistry and Biophysics vol. 30, p. 213-242.
Cosset et al. (1996), Targeting retrovirus entry, Gene Therapy 3, p. 946-956.
Cosset et al. (Dec. 1995), High-Titer Packaging Cells Producing Recombinant Retroviruses Resistant to Human Serum, Journal of Virology vol. 69, No. 12, p. 7430-7436.
Cosset et al. (Oct. 1995), Retroviral Retargeting by Envelopes Expressing an N-Terminal Binding Domain, Journal of Virology, vol. 69, No. 10, p. 6314-6322.
Coughlin S. R. (1994), Expanding horizons for receptors coupled to G proteins: diversity and disease, Cell Biology 6, p. 191-197.
Crystal R. G. (Oct. 20, 1995), Transfer of Genes to Humans: Early Lessons and Obstacles to Success, Science vol. 270, No. 5235, p. 404-410.
Dai et al. (1990), Multiple Sequence Elements in the U3 Region of the Leukemogenic Murine Retrovirus SL3-2 Contribute to Cell-Dependent Gene Expression, Virology 175, p. 581-585.
Eckert et al. (2001), Mechanisms of Viral Membrane Fusion and Its Inhibition, Annu. Rev. Biochem 70, p. 777-810.
Erlwein et al. (2002), Chimeric ecotropic MVL envelope proteins that carry EGF receptor specific ligands and the *Pseudomonas* exotoxin A translocation domain to target gene transfer, Virology 302, p. 333-341.
Etzerodt et al. (1984), The Nucleotide Sequence of the Akv Murine Leukemia Virus Genome, Virology 134, p. 196-207.
Fan et al. (2003), Structural and Functional Study of the Apelin-13 Peptide, an Endogenous Ligand of the HIV-1 Coreceptor, APJ, Biochemistry 42 (34), p. 10163-10168.
Fielding et al. (Apr. 10, 2000), A Hyperfusogenic Gibbon Ape Leukemia Envelope Glyprotein: Targeting of a Cytotoxic Gene by Ligand Display, Human Gene Therapy 11, p. 817-826.
Friedmann T. (Jun. 16, 1989), Progress Toward Human Gene Therapy, Science vol. 244, No. 4910, p. 1275-1281.
Gollan et al. (Apr. 2002), Redirecting Retroviral Tropism by Insertion of Short, Nondisruptive Peptide Ligands into Envelope, Journal of Virology vol. 76, No. 7, p. 3558-3563.
Gollan et al. (Apr. 2002), Selective Targeting and Inducible Destruction of Human Cancer Cells by Retroviruses with Envelope Proteins Bearing Short Peptide Ligands, Journal of Virology vol. 76, No. 7, p. 3564-3569.
Graham et al. (1973), A New Technique for the Assay of Infectivity of Human Adenovirus 5 DNA, Virology 52, p. 456-467.
Graham et al. (1973), Transformation of Rat Cells by DNA of Human Adenovirus 5, Virology 54, p. 536-539.
Grohmann et al. (1995), Multiple Point Mutations in an Endogenous Retroviral Gene Confer High Immunogenicity on a Drug-Treated Murine Tumor, Journal of Immunology 154, p. 4630-4641.
Habert-Ortoli et al. (Oct. 1994), Molecular cloning of a functional human galanin receptor, Proc. Natl. Acad. Sci. USA vol. 91, p. 9780-9783.
Hartley et al. (Feb. 1977), A new class of murine leukemia virus associated with development spontaneous lymphomas, Proc. Natl. Acad. Sci. USA vol. 74, No. 2, p. 789-792.
Hatziioannou et al. (1998), Incorporation of Fowl Plague Virus Hemagglutinin into Murine Leukemia Virus Particles and Analysis of the Infectivity of the Pseudotyped Retroviruses, Journal of Virology, vol. 72, No. 6, p. 5313-5317.
Heard et al. (Aug. 1991), An Amino-Terminal Fragment of the Friend Murine Leukemia Virus Envelope Glycoprotein Binds the Ecotropic Receptor, Journal of Virology vol. 65, No. 8, p. 4026-4032.
Herr W. (Feb. 1984), Nucleotide Sequence of AKV Murine Leukemia Virus, Journal of Virology vol. 49, No. 2, p. 471-478.
Hoatlin et al. (May 1998), Origin and Rapid Evolution of a Novel Murine Erythroleleukemia Virus of the Spleen Focus-Forming Virus Family, Journal of Virology vol. 72, No. 5, p. 3602-3609.
Jang et al. (1990), Cap-independent translation of encephalomyocarditis virus RNA: structural elements of the internal ribosomal entry site and involvement of a celluar 57-kD RNA-binding protein, Genes Dev. a, p. 1560-1572.
Jespersen et al. (Jul. 1997), Efficient Non-PCR-Mediated Overlap Extension of PCR Fragments by Exonuclease “End Polishing”, BioTechniques 23, vol. 23, No. 1, p. 48, 50, 52.
Kask et al. (1997), Galanin Receptors: Involvement in Feeding , Pain, Depression and Alzheimer’s Disease, Life Sciences vol. 60, No. 18, p. 1523-1533.
Kavanaugh et al. (Jul. 1994), Cell-surface receptors for gibbon ape leukemia virus and amphotropic murine retrovirus are inducible sodium-dependent phosphate symporters, Proc. Natl. Acad. Sci. USA vol. 91, p. 7071-7075.
Kawamata et al. (2001), Molecular properties of apelin: tissue distribution and receptor binding, Biochimica et Biophysica Acta 1538, p. 162-171.
Kelly et al. (Jan. 1983), Nucleotide Sequence of the 3' End of MCF 247 Murine Leukemia Virus, Journal of Virology vol. 45, No. 1, p. 291-298.
Khan A.S. (Jun. 1984), Nucleotide Sequence Analysis Establishes the Role of Endogenous Murine Leukemia Virus DNA Segments in Formation of Recombiant Mink Cell Focus-Forming Murine Leukemia Viruses, Journal of Virology vol. 50, No. 3, p. 864-871.
Koch et al. (Mar. 1984), Molecular Analysis of the Envelope Gene and Long Terminal Repeat of Friend Mink Cell Focus-Inducing Virus: Implications for the Functions of These Sequences, Journal of Virology vol. 49, No. 3, p. 828-840.
Koo et al. (1992), A Spleen Necrosis Virus-Based Retroviral Vector Which Expresses Two Genes from a Dicistronic mRNA, Virology 186, p. 669-675.
Levy et al. (Dec. 1985), Normal Expression of Polymorphic Endogenous Retroviral RNA Containing Segments Identical to Mink Cell Focus-Forming Virus, Journal of Virology vol. 56, No. 3, p. 691-700.
Lund et al. (1999), The nucleotide sequence of the high-leukemogenic murine retrovirus SL3-3 reveals a patch of mink cell focus forming-like sequences upstream of the ecotropic envelope gene, Arch Virol 144, p. 2207-2212.
Mann et al. (May 1983), Construction of a Retrovirus Packaging Mutant and its Use to Produce Helper-Free Defective Retrovirus, Cell vol. 33, issue 1, p. 153-159.
Marin et al. (May 1996), Targeted Infection of Human Cells via Major Histocompability Complex Class I Molecules by Moloney Murine Leukemia Virus-Derived Viruses Displaying Single-Chain Antibody Fragment-Envelope Fusion Proteins, Journal of Virology, p. 2957-2962.
Mark et al. (Feb. 1984), Envelope Gene Sequence of Two In Vitro-Generated Mink Cell Focus-Forming Murine Leukemia Viruses Which Contain the Entire gp70 Sequence of the Endogenous Nonecotropic Parent, Journal of Virology vol. 49, No. 2, p. 530-539.
Massey et al. (Nov. 1990), Origin of Pathogenic Determinants of Recombinant Murine Leukemia Viruses: Analysis of Bxv-1-Related Xenotropic Viruses from CWD Mice, Journal of Virology vol. 64, No. 11, p. 5491-5499.
Masuda et al. (May 1992), Molecular Characterization of a Neuropathogenic and Nonerythroleleukemogenic Variant of Friend Murine Leukemia Virus PVC-211, Journal of Virology vol. 66, No. 5, p. 2798-2806.
McKnight et al. (Mar. 1998), The EGF-TM7 family: unusual structures at the leukocyte surface, Journal of Leukocyte Biology vol. 63, p. 271-280.
Miller A. D. (1990), Retrovirus Packaging Cells, Human Gene Therapy 1, p. 5-14.
Miller et al. (Oct. 1989), Improved Retroviral Vectors for Gene Transfer and Expression, Biotechniques 7(9), p. 980-990.
Morgan et al. (1992), Retroviral vectors containing putative internal ribosome entry sites: development of a polycistronic gene transfer

(56) References Cited

OTHER PUBLICATIONS system and applications to human gene therapy, Nucleic Acids Research vol. 20, No. 6, p. 1293-1299.
Morgan et al. (Aug. 1993), Analysis of the Functional and Host Range-Determining Regions of the Murine Ecotropic and Amphotropic Retrovirus Envelope Proteins, Journal of Virology vol. 67, No. 8, p. 4712-4721.
Morita et al. (2000), Plat-E: an efficient and stable system for transient packaging of retroviruses, Gene Therapy 7, p. 1063-1066.
Morling et al. (1997), Masking of Retroviral Envelope Functions by Oligomerizing Polypeptide Adaptors, Virology 234, p. 51-61.
Mulligan R. C. (May 14, 1993), The Basic Science of Gene Therapy, Science vol. 260, No. 5110, p. 926-932.
O'Neill et al. (Jan. 1985), Envelope and Long Terminal Repeat Sequences of a Cloned Infectious NZB Xenotropic Murine Leukemia Virus, Journal of Virology vol. 53, No. 1, p. 100-106.
Ott et al. (Feb. 1990), Sequence Analysis of Amphotropic and 10A1 Murine Leukemia Viruses: Close Relationship to Mink Cell Focus-Inducing Viruses, Journal of Virology vol. 64, No. 2, p. 757-766.
Pear et al. (Sep. 1993), Production of high-titer helper-free retroviruses by transient transfection, Proc. Natl. Acad. Sci. USA vol. 90, p. 8392-8396.
Pedersen et al. (Jul. 9, 1981), Novel leukaemogenic retroviruses isolated from cell line derived from spontaneous AKR tumour, Nature vol. 292, p. 167-170.
Puffer et al. (2000), Expression and Coreceptor Function of APJ for Primate Immunodeficiency Viruses, Virology 276, p. 435-444.
Purcell et al. (Feb. 1996), An Array of Murine Leukemia Virus-Related Elements Is Transmitted and Expressed in an Primate Recipient of Retroviral Gene Transfer, Journal of Virology vol. 70, No. 2, p. 887-897.
Quartara et al. (1997), The tachykinin NK, receptor. Part I: ligands and mechanisms of cellular activation, Neuropeptides 31 (6), p. 537-563.
Raisch et al. (2003), Molecular cloning, complete sequence, and biological characterization of a xenotropic murine leukemia virus constitutively released from the human B-lymphoblastoid cell line DG-75, Virology 308, p. 83-91.
Raming et al. (1998), Identification of a Novel G-Protein Coupled Receptor Expressed in Distinct Brain Regions and a Defined Olfactory Zone, Receptor and Channels vol. 6, p. 141-151.
Rein A. (1982), Interference Grouping of Murine Viruses: A Distinct Receptor for the MCF-Recombinant Viruses in Mouse Cells, Virology 120, p. 251-257.
Rein et al. (1984), Different Recombinant Murine Leukemia Viruses Use Different Cell Surface Receptors, Virology 136, p. 144-152.
Shinnick et al. (Oct. 15, 1981), Nucleotide sequence of Moloney murine leukaemia virus, Nature vol. 293, p. 543-548.
Sommerfelt et al. (1990), Receptor Interference Groups of 20 Retroviruses Plating on Human Cells, Virology 176, p. 58-69.
Sommerfelt et al. (Dec. 1990), Localization of the Receptor Gene for Type D Simian Retroviruses on Human Chromosome 19, Journal of Virology vol. 64, No. 12, p. 6214-6220.
Strosberg A. D. (1991), Structure/function relationship of proteins belonging to the family of receptors coupled to GTP-binding proteins, Eur. J. Biochem. 196, p. 1-10.
Thomas et al. (1996), Chemoreceptors expressed in taste, olfactory and male reproductive tissues, Gene 178, p. 1-5.
Towers et al. (Oct. 24, 2000), A conserved mechanism of retroviruses restriction in mammals, PNAS vol. 97, No. 22, p. 12295-12299.
Valsesia-Wittmann et al. (Marts 1996), Improvement of Retroviral Retargeting by Using Amino Acid Spacers between an Additional Binding Domain and the N Terminus of Moloney Murine Leukemia Virus SU, Journal of Virology, vol. 70, No. 3, p. 2059-2064.
Van Beveren et al. (1985), RNA tumour viruses, CSHL Press, New York, p. 790-805.
Vogt et al. (1986), Specific Sequences of the env Gene Determine the Host Range of Two XC-Negative Viruses of the Rauscher Virus Complex, Virology 154, p. 420-424.
Wang et al. (Oct. 1996), Modulation of Ecotropic Murine Retroviruses by N-Linked Glycosylation of the Cell Surface Receptor/Amino Acid Transporter, Journal of Virology vol. 70, No. 10, p. 6884-6891.
Watson S. et al. (1994), The G-Protein Linked Receptor Facts Book, Academic Press, San Diego Calif., p. 7-9, 19-22, 32-35, 130-131, 214-216, 221-222.
Zavorotinskaya et al. (Jan. 2004), A Point Mutation in the Binding Subunit of a Retroviral Envelope Protein Arrests Virus Entry at Hemifusion, Journal of Virology vol. 78, No. 1, p. 473-481.
Aagaard et al. (2002), Fv1-like restriction of N-tropic replication-competent murine leukaemia viruses in mCAT-1-expressing human cells, Journal of General Virology 83, p. 439-442.
Huang et al., "Structure of a V3-Containing HIV-1 gp 120 Core," *Science* 301, 2005, 1025-1028.
Miller et al., "Two Base Changes Restore Infectivity to a Noninfectious Molecular Clone of Moloney Murine Leukemia Virus (pMLV-1)," Journal of Virology, vol. 49, No. 1, Jan. 1984, pp. 214-222.
Ter-Grigorov et al., "A new transmissible AIDS-like disease in mice induced by alloimmune stimuli," Nature Medicine, vol. 3, No. 1, Jan. 1997, pp. 37-41.
Valsesia-Wittmann et al., "Modifications in the Binding Domain of Avian Retrovirus Envelope Protein to Redirect the Host Range of Retroviral Vectors," Journal of Virology, vol. 68, No. 7, Jul. 1994, pp. 4609-4619.
Vanin et al., "Characterization of Replication-Competent Retroviruses from Nonhuman Primates with Virus-Induced T-Cell Lymphomas and Observations Regarding the Mechanism of Oncogenesis," Journal of Virology, vol. 68, No. 7, Jul. 1994, pp. 4241-4250.
Wang et al., "Cell-surface receptor for ecotropic murine retroviruses is a basic amino-acid transporter," Nature, vol. 352, Aug. 1991, pp. 729-731.
Wang et al., "Plasma Membrane Receptors for Ecotropic Murine Retroviruses Require a Limiting Accessory Factor," Journal of Virology, vol. 65, No. 12, Dec. 1991, pp. 6468-6477.
Zaborotinskaya et al., "A Point Mutation in the Binding Subunit of a Retroviral Envelope protein Arrests Virus Entry at Hemifusion," Journal of Virology, vol. 78, No. 1, Jan. 2004, pp. 473-481.

```
                                              277                293
                   SL3-2   (199) ASKA|GLSLYRS|R|...
                  MCF-247  (199) GPKV|GLSL|RS|G|...
                  MCF CI-3 (199) GPKV|GLSL|RS|G|...
                 Ampho-MCF (199) GPKV|GLSL|DS|G|...
                    ERV-1  (199) GPKV|GLSL|RS|G|...
  Endogenous from 129 GIX+ mice (199) GPKV|GLSL|RS|G|...
              Friend MCF #2 (199) GPKV|GLSL|RS|G|...
                Friend MCF (199) GPKV|GLSL|RS|G|...
                Friend SFV (199) GPKV|GLSL|RS|G|...
                Invitro MCF (199) GPKV|GLSL|RS|G|...
                  MCF 1223 (199) GPKV|GLSL|RF|G|...
                 MLV DBA/2 (199) GPKV|GLSL|RS|G|...
            MCF (Broscius) (199) GPKV|GLSL|QS|G|...
                    Mo-MCF (199) GPKV|GLSL|RS|G|...
               Ns-6(186) MCF (199) GPKV|GLSL|RS|G|...
                Rauscher sfv (199) GPKV|GLSL|RS|G|...
                     R-XC- (199) GPKV|GLSL|RS|G|...
          MCF (Tar-Grigorov) (199) GPKV|GLSL|RS|G|...
                       AKV (252) TGHY|GLSL|VS|G|...
                    Friend (237) IGHY|GLSL|VS|G|...
                   Moloney (234) TGHY|GLSL|VS|G|...
                     SL3-3 (252) TGHY|GLSL|VS|G|...
                Friend fass (237) IGHY|GLSL|VS|G|...
                      10A1 (209) GPKS|GLSL|RT|G|...
                     4070A (209) GPKS|GLSL|RT|G|...
              Xeno CWM-S-5X (202) APKV|GLSL|RS|G|...
                  DG-75 Xeno (302) APKV|GLSL|RS|G|...
                 Xeno NZB-9-1 (202) APKV|GLSL|RS|G|...
           Xeno Bxv-1-related (203) APKV|GLSL|RS|G|...
                 Xeno R-MCF-1 (202) GPKV|GLSL|RS|G|...
                  Consensus (277) GPKVWGLSLYRSGDP
```

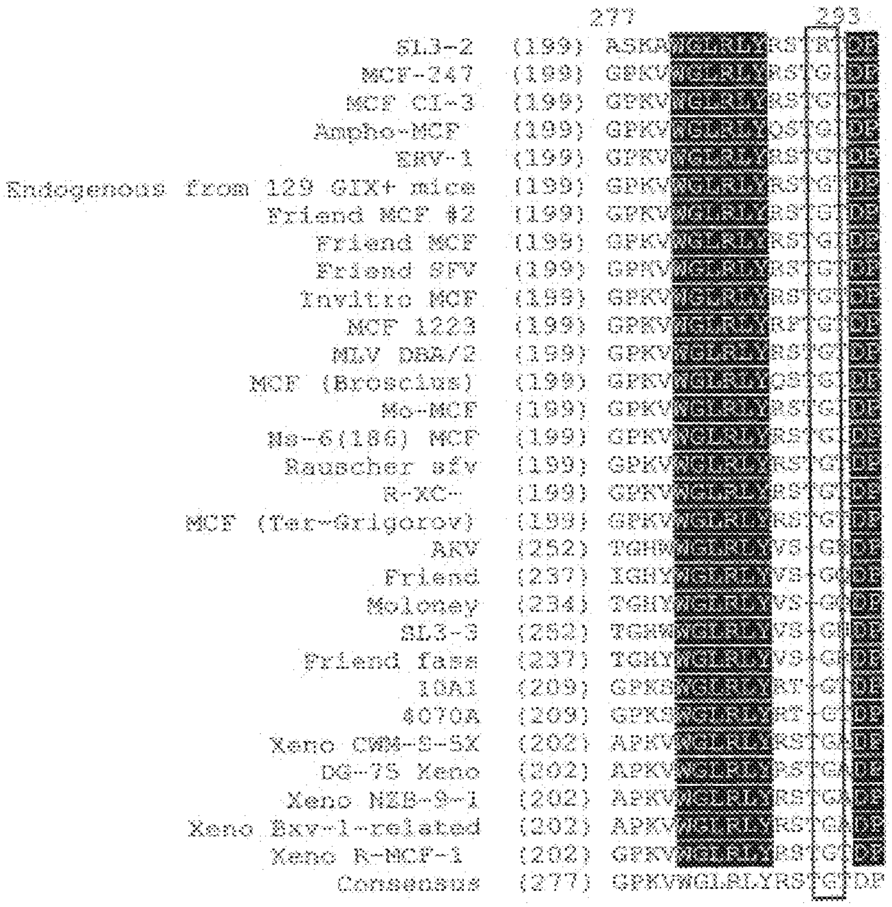

```
                        1                                                50
       SL3-2     (1)    MEGPAFSKPLKDKINPWGPLIVLGILMRARVSVQH--DSPHQVFNVTWRV
 Xeno NZB-9-1    (1)    MEGSAFSKPLKDKINPWGPLIVMGILVRAGASVQR--DSPHQIFNVTWRV
     Moloney     (1)    MARSTLSKPLKNKVNPRGPLIPLILLMLRGVSTASPGSSPHQVYNITWEV
       4070A     (1)    MARSTLSKPPQDKINPWKPLIVMGVLLGVGMA------ESPHQVFNVTWRV
     MCF-247     (1)    MEGPAFSKPLKDKINPWGPLIVLGILIRAGVSVRH--DSPHQVFNVTWRV
      FeLV B     (1)    MEGPTHPKPSKDKTFSWDLMILVGVLLRLDVGMAN--PSPHQIYNVTWTI
   Consensus     (1)    MEGSTFSKPLKDKINPWGPLIVLGILLRAGVSV    DSPHQVFNVTWRV
                        51                                              100
       SL3-2    (49)    TNLMTGQTANATSLLGTMTDAFPKLYFDLCDLIGDDWD------ETGLGC
 Xeno NZB-9-1   (49)    TNLMTGQTANATSLLGTMTDTFPKLYFDLCDLVGDYWDD--PEPDIGDGC
     Moloney    (51)    TNGDR-ETVWATSGNHPLWTWWPDLTPDLCMLAHHGPSY--WGLEYQSPF
       4070A    (46)    TNLMTGRTANATSLLGTVQDAFPKLYFDLCDLVGEEWDPSDQEPYVGYGC
     MCF-247    (49)    TNLMTGQTANATSLLGTMTDAFPKLYFDLCDLIGDDWD------ETGLGC
      FeLV B    (49)    TNLVTGTKANATSMLGTLTDAFPTMYFDLCDIIGNTWNPSDQEPFPGYGC
   Consensus    (51)    TNLMTGQTANATSLLGTMTDAFPKLYFDLCDLIGDDWD     EPE G GC
                        101                                             150
       SL3-2    (93)    RTPGG--------------------------------------RKRARIF
 Xeno NZB-9-1   (97)    RTPGG--------------------------------------RKRTRLY
     Moloney    (98)    SSPPGPPCCSGGSSPGCSRDCEEPLTSLTPRCNTAWNRLKLDQTTHKSNE
       4070A    (96)    KYPAG--------------------------------------RQRTRTF
     MCF-247    (93)    RTPGG--------------------------------------RKRARTF
      FeLV B    (99)    DQPMR--------------------------------------RWQQRNT
   Consensus   (101)    RTPGG                                      RKR R F
                        151                                             200
       SL3-2   (105)    DFYVCPG---HTVLAGCGGPREGYCGKWGCETTGQAYWKPSSSWDLISLK
 Xeno NZB-9-1  (109)    DFYVCPG---HTVPIGCGGPGEGYCGKWGCETTGQAYWKPSSSWDLISLK
     Moloney   (148)    GFYVCPGPHRPRESKSCGGPDSFYCAYWGCETTGRAYWKPSSSWDFITVN
       4070A   (108)    DFYVCPG---HTVKSGCGGPGEGYCGKWGCETTGQAYWKPTSSWDLISLK
     MCF-247   (105)    DFYVCPG---HTVPTGCGGPREGYCGKWGCETTGQAYWKPSSSWDLISLK
      FeLV B   (111)    PFYVCPG---HANRKQCGGPQDGFCAVWGCETTGETYWRPTSSWDYITVK
   Consensus   (151)    DFYVCPG   HTV  GCGGP EGYCGKWGCETTGQAYWKPSSSWDLISLK
                        201                                             250
       SL3-2   (152)    RGNTPKGQG-------PCYDSSVVSSSAQGATPGGRCNPLVLEFTDAGKR
 Xeno NZB-9-1  (156)    RGNTPKDQG-------PCYDSSVSSG-VQGATPGGRCNPLVLEFTDAGRK
     Moloney   (198)    N-NLT------------------SDQAVQVCKDNKWCNPLVIRFTDAGRR
       4070A   (155)    RGNTPWDTGCSKVACGPCYDLSKVSNSFQGATRGGRCNPLVLEFTDAGKK
     MCF-247   (152)    RGNTPQNQG-------PCYDSSAVSSDIKGATPGGRCNPLVLEFTDAGKK
      FeLV B   (158)    KGVTQGIYQCSGGGWCGPCYDKAVHSSTTGASEGGRCNPLILQFTQKGRQ
   Consensus   (201)    RGNTP  QG       PCYDSS VSSSIQGATPGGRCNPLVLEFTDAGKK
                        251                                             300
       SL3-2   (195)    -ASWDASKAWGLRLYRSTRTDPVTRFSLTRQVLNIGPRVPIGPNPVIIDQ
 Xeno NZB-9-1  (198)    -ASWDAPKVWGLRLYRSTGADPVTRFSLTRQVLNVGPRVPIGPNPVITDQ
     Moloney   (229)    VTSWTTGHYWGLRLY-VSGQDPGLTFGIRLRYQNLGPRVPIGPNPVLADQ
       4070A   (205)    -ANWDGPKSWGLRLY-RTGTDPITMFSLTRQVLNVGPRVPIGPNPVLPDQ
     MCF-247   (195)    -ASWDGPKVWGLRLYRSTGIDPVTRFSLTRQVLNIGPRVPIGPNPVITDQ
      FeLV B   (208)    -TSWDGPKSWGLRLY-RSGYDPIALFSVSRQVMTITLPQAMGPNLVLPDQ
   Consensus   (251)     ASWDGPKSWGLRLYRSTG DPVTRFSLTRQVLNIGPRVPIGPNPVI DQ
```

Fig. 5B

```
                     301
                                                350
       SL3-2  (244) LPPSRPVQIMLPRPPQPPP-------------PGAASSVPETAPPSQQPG

Xeno NZB-9-1  (247) LPPSQPVQIMLPRPPHPPP--------------SGTVSMVPGAPPPSQQPG
     Moloney  (278) QPLSKPKPVKSPSVTKPP--------------------SGTPLSPTQLPPAG
       4070A  (253) RLPSSPSEIVPAPQPPSPLNTSYPPSTT-----STPSTSPTSPSVPQPPPG
     MCF-247  (244) LPPSRPVQIMLPRPPQPPP--------------PGAASSVPETAPPSQQPG
      FeLV B  (256) KPPSRQSQIESRVTPHHSQGNGGTPGITLVNASIAPLSTPVTPASPKRIG
   Consensus  (301) LPPSRPVQIMLPRPP PPP              SGAASSVP TPPPSQQPG
                    351                                             400
       SL3-2  (281) TGDRLLNLVNGAYQALNLSSPDKTQECWLCLVAGPPYYEGVAVLGTYSNH
Xeno NZB-9-1  (284) TGDRLLNLVEGAYQALNLTSPDKTQECWLCLVSGPPYYEGVAVLGTYSNH
     Moloney  (310) TENRLLNLVDGAYQALNLTSPDKTQECWLCLVAGPPYYEGVAVLGTYSNH
       4070A  (299) TGDRLLALVKGAYQALNLTNPDKTQECWLCLVSGPPYYEGVAVVGTYTNH
     MCF-247  (281) TGDRLLNLVKGAYQALNLTSPDKTQECWLCLVSGPPYYEGVAVLGTYSNH
      FeLV B  (306) TGNRLINLVQGTYLALNVTNPNKTKDCWLCLVSRPPYYEGIAVLGNYSNQ
   Consensus  (351) TGDRLLNLV GAYQALNLTSPDKTQECWLCLVSGPPYYEGVAVLGTYSNH
                    401                                             450
       SL3-2  (331) TSAPANCSVASQHKLTLSEVTGQGLCVGAVPKTHQALCNTTQKTSNGSYY
Xeno NZB-9-1  (334) TSAPANCSVASQHKLTLSEVTGQGLCVGAVPKTHQALCNTTQKTSDGSYY
     Moloney  (360) TSAPANCSVASQHKLTLSEVTGQGLCIGAVPKTHQALCNTTQTSSRGSYY
       4070A  (349) STAPANCTATSQHKLTLSEVTGQGLCMGAVPKTHQALCNTTQSAGSGSYY
     MCF-247  (331) TSAPANCSVASQHKLTLSEVTGQGLCIGAVPKTHQALCNTTQKTSDGSYY
      FeLV B  (356) TNPPPSCLSDPQHKLTISEVSGQGSCIGTVPKTHQALCKKTQKGHKGTHY
   Consensus  (401) TSAPANCSVASQHKLTLSEVTGQGLCIGAVPKTHQALCNTTQKTS GSYY
                    451                                             500
       SL3-2  (381) LAAPAGTIWACNTGLTPCLSTTVLDLTTDYCVLVELWPKVTYHSPGYVYG
Xeno NZB-9-1  (384) LAAPAGTIWACNTGLTPCLSTTVLNLTTDYCVLVELWPKVTYHSPDYVYG
     Moloney  (410) LVAPTGTMWACSTGLTPCISTTILNLTTDYCVLVELWPRVTYHSPSYVYG
       4070A  (399) LAAPAGTMWACSTGLTPCLSTTVLNLTTDYCVLVELWPRVIYHSPDYMYG
     MCF-247  (381) LAAPIGTIWACSTGLTPCISTTILDLTTDYCVLVELWPRVTYHSPSYVYH
      FeLV B  (406) LAAPSGTYWACNTGLTPCISMAVLNWTSDFCVLIELWPRVTYHQPEYVYT
   Consensus  (451) LAAPAGTIWACSTGLTPCISTTVLNLTTDYCVLVELWPRVTYHSPDYVYG
                    501                                             550
       SL3-2  (431) QFEEKTKYKREPVSLTLALLLGGLTMGGIAAGVGTGTTALVATQQFQQLQ
Xeno NZB-9-1  (434) QFEKKTKYKREPVSLTLALLLGGLTMGGIAAGVGTGTTALVATKQFEQLQ
     Moloney  (460) LFEKSNRHKREPVSLTLALLLGGLTMGGIAAGIGTGTTALMATQQFQQLQ
       4070A  (449) QLEQKTKYKREPVSLTLALLLGGLTMGGIAAGIGTGTTALIKTQQFEQLH
     MCF-247  (431) QFEKRAKYKREPVSLTLALLLGGLTMGGIAAGVGTGTTALVATQQFQQFQ
      FeLV B  (456) HFDKTVRLRREPISLTVALMLGGLTVGGIAAGVGTGTKALLETAQFGQLQ
   Consensus  (501) QFEKKTKYKREPVSLTLALLLGGLTMGGIAAGVGTGTTALVATQQFQQLQ
                    551                                             600
       SL3-2  (481) AAMQDDLKEVKKSITNLEKSLTSLSEVVLQNRRGLDLLFLKEGGLCAALK
Xeno NZB-9-1  (484) AAIHTDLGALEKSVSALEKSLTSLSEVVLQNRRGLDLLFLKEGGLCAALK
     Moloney  (510) AAVQDDLREVEKSISNLEKSLTSLSEVVLQNRRGLDLLFLKEGGLCAALK
       4070A  (499) AAIQTDLNEVEKSITNLEKSLTSLSEVVLQNRRGLDLLFLKEGGLCAALK
     MCF-247  (481) AAMQDDLKEVEKSITNLEKSLTSLSEVVLQNRRGLDLLFLKEGGLCAALK
      FeLV B  (506) MAMHTDIQALEESISALEKSLTSLSEVVLQNRRGLDILFLQEGGLCAALK
   Consensus  (551) AAMQTDLKEVEKSISNLEKSLTSLSEVVLQNRRGLDLLFLKEGGLCAALK
```

Fig. 5C

```
                         601
                                   650
        SL3-2   (531)  EECCFYADHTGLVRDSMAKLRERLSQRQKLFESQQGWFEGLFNKSPWFTT
  Xeno NZB-9-1  (534)  EECCFYADHTGVVRDSMAKLRERLNQRQKLFESGQGWFEGLFNRSPWFTT
      Moloney   (560)  EECCFYADHTGLVRDSMAKLRERLNQRQKLFESTQGWFEGLFNRSPWFTT
        4070A   (549)  EECCFYADHTGLVRDSMAKLRERLNQRQKLFETGQGWFEGLFNRSPWFTT
      MCF-247   (531)  EECCFYADHTGLVRDSMAKLRERLSQRQKLFESQQGWFEGLFNKSPWFTT
       FeLV B   (556)  EECCFYADHTGLVRDNMAKLRERLKQRQQLFDSQQGWFEGWFNKSPWFTT
    Consensus   (601)  EECCFYADHTGLVRDSMAKLRERLNQRQKLFESQQGWFEGLFNKSPWFTT
                       651                                              700
        SL3-2   (581)  LISTIMGPLIILLLILLFGPCILNHLVQFIKDVSVVQALVLTQQYHQLK
  Xeno NZB-9-1  (584)  LISTIMGPLIVLLLILLLGPCILNRLVQFVKDRISVVQALTLTQQYHQLK
      Moloney   (610)  LISTIMGPLIVLMLILLFGPCILNRLVQFVKDRISVVQALVLTQQYHQLK
        4070A   (599)  LISTIMGPLIVLLLILLFGPCILNRLVQFVKDRISVVQALVLTQQYHQLK
      MCF-247   (581)  LISTIMGPLIILLLILLFGPCILNRLVQFVKDRISVVQALVLTQQYHQLK
       FeLV B   (606)  LISSIMGPLLIILLILLFGPCILNRLVQFVKDRISVVQALILTQQYQQLK
    Consensus   (651)  LISTIMGPLIILLLILLFGPCILNRLVQFVKDRISVVQALVLTQQYHQLK
                       701       711
        SL3-2   (631)  TIED--CESRE
  Xeno NZB-9-1  (634)  SIEPEEVESRE
      Moloney   (660)  PIEYEP------
        4070A   (649)  PIEYEP------
      MCF-247   (631)  SIDPEEVESRE
       FeLV B   (656)  QYDPDQP----
    Consensus   (701)  SIEPE  ESRE
```

```
                                                          SL3-2 Library                    Section 2
                        (85)
                                 86            100       110       120         130       140       150       160       170
             SL3-2      (65)     TMTCAPPKLYPCLCDLIGDDWD------ETGLTGRTPGG----------------------------------------RKRARI
           MCF-247      (65)     TMTCAPPKLYPCLCDLIGDDWD------ETGLTGRTPGG----------------------------------------RKRART
           MCFCL-3      (65)     TMTCAPPKLYPCLCDLVGDDWD------ETGLTGRTPGG----------------------------------------RKRART
             ERV-1      (65)     TMTCAPPKLYPCLCDLIGDDWD------ETGLTGRTPGG----------------------------------------RKRART
        Friend MCF      (65)     TMTCAPPKLYPCLCDLIGDDWD------ETGLTGRTPGG----------------------------------------RKRART
        Friend SFV      (65)     TMTCAPPKLYPCLCDLIGDDWD------ETGLTGRTPGG----------------------------------------RKRARI
       Invitro MCF      (65)     TMTCAPPKLYPCLCDLVGDDWD------ETGLTGRTPGG----------------------------------------RKRART
          MCF 1223      (65)     TMTCAPPKLYPCLCDLIGDDWD------ETGLTGRTPGG----------------------------------------RKRART
         MLV DBA/2      (65)     TMTCAPPKLYPCLCDLIGDDWD------ETGLTGRTPGG----------------------------------------RKRART
            Mo-MCF      (65)     TMTCAPPKLYPCLCDLIGDDWD------ETGLTGRTPGG----------------------------------------RKRART
      Ns6(186) MCF      (65)     TMTCAPPKLYPCLCDLIGDDWD------ETGLTGRTPGG----------------------------------------RKRART
      Rauscher sfv      (65)     TMTCAPPKLYPCLCDLIGDDWD------ETGLTGRTPGG----------------------------------------RKRART
Endogenous from 129 GIX+ mice (65) TMTCAPPKLYPCLCDLIGDDWD------ETGLTGRTPGG----------------------------------------RKRART
        Ampho-MCF       (65)     TMTCAPPKLYPCLCDLIGDDWD------ETGLTGRTPGG----------------------------------------RKRART
MCF (Tor-Grigorov)      (65)     TMTCAPPKLYPCLCDLIGDDWD------ETGLTGRTPGG----------------------------------------RKRART
    MCF (Brosolus)      (65)     TMTCAPPKLYPCLCDLIGDDWD------ETGLTGRTPGG----------------------------------------RKRART
     Friend MCF #2      (65)     TMTCAPPKLYPCLCDLIGDDWD------ETGLTGRTPGG----------------------------------------RKRART
             R-XC-      (65)     TMTCAPPKLYPCLCDLIGDDWD------ETGLTGRTPGG----------------------------------------RKRART
     Xeno R-MCF-1       (65)     TMTCAPPKLYPCLCDLVGDYWDD--PEPDIGDTGRTPGG----------------------------------------RRRTRL
       DG-75 Xeno       (65)     TMTCTPPKLYPCLCDLVGDYWDD--PEPDIGDTGRTPGG----------------------------------------RRRTRL
     Xeno NZB-9-1       (65)     TMTCTPPKLYPCLCDLVGDYWDD--PEPDIGDTGRTPGG----------------------------------------RRRTRL
     Xeno CWM-S-5X       (65)     TMTCTPPKLYPCLCDLVGDHWDD--PEPDIGDTGRSPGG----------------------------------------RKRSRL
Xeno Brv-1-related      (65)     TMTCTPPKLYPCLCDLVGDHWDD--PEPDIGDTGRSPGG----------------------------------------RKRSRL
            4070A       (62)     TVQCAPPKLYPCLCDLVGEEWDPSDQEPYVGYTGKYPAG----------------------------------------RQRTRT
             10A1       (62)     TVQCAPPKLYPCLCDLVGEEWDPSDQEPYVGYTGKYPGG----------------------------------------RKRTRT
              AKV       (82)     PLWTWWPDLTPCLCMLALHCPSY--WGLEYRAPPSPPGGPPCCSGSSGSSAGCSRDCDEPLTSLTPRCNTAWNRLRLSKVTHAHN
            SL3-3       (82)     PLWTWWPDLTPCLCMLALHCPSY--WGLEYRAPYSSPGGPPCCSGSSDSTPGCSRDCEEPLTSYTPRCNTAWNRLRLSKVTHAHN
           Friend       (67)     PLWTWWPDLTPCLCMLALSGPPH--WGLEYRAPGRCPGGPPCCSGSSGSSAGCARDCDEPLTSLTPRCNTAWNRLRLDQVTHKSS
          Maloney       (65)     PLWTWWPDLTPCLCMLAHHGPSY--WGLEYQSPPSSPGGPPCCSG--GSSPGCSRDCDEPLTSLTPRCNTAWNRLRLDQTTHKSN
      Friend fass       (67)     PLWTWWPVLTPCLCMLALSGPPH--WGLEYQAPYSSPGGPPCCSGSSGSSAGCSRDCDEPLTSLTPRCNTAWNRLRLDQVTHKSS
        Consensus       (85)     TMTCAPPKLYPCLCDLIGDDWD      ETGLGCRTPGG                                        RKRART
```

Fig. 5E

D17 CD4 CXCR4

Panel 1

D17 CD4 CXCR4
NeoSL3-2Mo RT L1

Panel 2

D17 CD4 CXCR4
NeoSL3-2Mo GI L1

Panel 3

HIV-1 Syncytia

D17 CD4 CXCR4
NeoSL3-2Mo GI L3

Panel 4

D17 CD4 CXCR4
NeoSL3-2Mo GI L2

Panel 5

D17 CD4 CXCR4
Control pLXSN

Panel 6

HIV-1 Syncytia

Fusion mediated by HIV envleope with Jurkat cells expressing SL3-2 envelope

Fusion mediated by HIV envleope with Jurkat cells expressing SL3-2-V3 chimeric envelope

CHIMERIC VIRAL ENVELOPES

This application is a §371 national phase filing of PCT/DK2007/000131 filed Mar. 16, 2007; and claims priority to
U.S. Appln. No. 60/783,041 filed Mar. 17, 2006,
U.S. Appln. No. 60/783,046 filed Mar. 17, 2006, and
U.S. Appln. No. 60/847,946 filed Sep. 29, 2006.

All patent and non-patent references cited in the application, or in the present application, are also hereby incorporated by reference in their entirety.

FIELD OF INVENTION

The present invention relates to chimeric polytropic viral envelope polypeptides and uses thereof, as well as to polynucleotides encoding said chimeric polypeptides and constructs comprising said polypeptides and/or polynucleotides.

The present invention also relates to chimeric retroviral envelope polypeptides, polynucleotides and vectors encoding said chimeric retroviral envelope polypeptides, virus particles and cells harbouring said chimeric envelope polypeptides. The present invention further relates to methods of targeting receptors, methods of treatment and methods for delivery of agents using said chimeric retroviral envelope polypeptides.

BACKGROUND OF INVENTION

Retroviruses

Retroviruses are RNA viruses. When a host cell is infected with a retrovirus, the genomic RNA is reverse transcribed into a DNA intermediate which is integrated very efficiently into the chromosomal DNA of infected cells. The integrated DNA intermediate is referred to as a provirus. The family Retroviridae are enveloped single-stranded RNA viruses that typically infect mammals, such as, for example, bovines, monkeys, sheep, and humans, as well as avian species.

Retro Viral Envelope Proteins

Retroviruses carry their genomes as two copies of a single RNA molecule and the simplest retroviruses contain the gag, pro, pol and env genes.

The first step in the replication cycle of a retrovirus is its entry into a host cell (see FIG. 1). The envelope protein (env) is responsible for binding of the retrovirus to a specific cell surface receptor. A retroviral receptor is a membrane integral protein in the plasma membrane of the host cell and as such has a function unrelated to virus infection.

However, retroviral envelopes that use non-protein receptors are known, e.g., the vesicular stomatitis virus.

Retroviruses can be thought of as a protein-package comprising RNA wrapped in a lipid membrane that contains glycoproteins. The lipid bi-layer is derived from the cell membrane after budding and is thought to be associated with a viral gene product, a peripheral membrane protein called Matrix (MA). Traversing through the lipid bi-layer is another viral gene product, the envelope protein, which consists of two subunits: the transmembrane (TM) and the surface unit (SU). The function of the envelope protein is binding of the virus to its target cell and mediating fusion of the viral and cellular membranes.

The retroviral envelope protein can be seen as a nanodevice that mediates receptor-dependent fusion of biological membranes. When the envelope protein is attached to the lipid-bilayer membrane surrounding the virus, the net result of fusion with a cellular membrane is entry of the nucleoprotein core of the virus into the cytoplasm. Such fusion is triggered by the envelope protein's recognition of a receptor on the plasma membrane or an endosomal membrane. Natural receptors for retroviral infection are integral membrane proteins with multiple membrane-spanning domains. For the gammaretroviruses such as murine leukemia viruses, several natural receptors are known to have transporter functions for e.g. amino acids. When expressed on the plasma membrane of a cell, the viral envelope protein may also mediate cell to cell fusion. The dynamics of the fusion process is generated by the viral envelope protein which is produced in an activated state and has "one shot" to trigger membrane fusion.

The ability of redirecting the retroviral fusion machinery to a desired receptor would have wide biotechnological and potentially also nanotechnological applications. However, the regulatory mechanisms that interconnect receptor binding with fusion are poorly understood, which has made intelligent engineering of the envelope protein difficult. Many attempts at redirecting the receptor-specificity have found that incorporation of a ligand into the envelope protein may cause receptor-dependent binding without activation of the fusion machinery.

SL3-2 Murine Leukaemia Virus Envelope Polypeptide

In an amino acid sequence alignment between SL3-2 and MCF-247, a region has been found to display differences in the 15 amino acids long stretch upstream of the proline rich region. This region has been named VR3 by the present inventors. Further, a sequence alignment of MLVs from different sub-families show conserved amino acids at positions 203-208 WGLRLY and at positions 214-215 DP based on SL3-2 sequence, thus defining a 13 amino acid stretch (see FIGS. 4-5).

In the present context, the term "VR3 region" comprises all of the amino acids found between the residue found at two positions after the conserved tryptophan 197 and the residue before the conserved aspartic acid 214 (according to the sequence shown in SEQ ID NO:2) including these two positions.

Tropism of Murine Leukaemia Virus (MLV)

The MLVs are a group of gammaretroviruses that has been divided into families based on their host range and interference properties. The families are the ecotropic, amphotropic, xenotropic and polytropic subfamilies. Ecotropic viruses are defined by their usage of the mCAT-1 receptor (Wang et al. 1991). Ecotropic viruses are able to infect only murine cells. Examples of ecotrpic viruses are Moloney MLV and AKV. Amphotropic viruses infect murine, human and other species through the Pit-2 receptor (Kavanaugh et al. 1994). One example of an amphotopic virus is the 4070A virus. Xenotropic and polytropic viruses utilize the same (Xpr1) receptor. However, the xenotropic and polytropic viruses differ in their species tropism. Xenotropic viruses such as NZB-9-1 infect human and other species but not murine species, whereas polytropic viruses infect murine, human and other species as exemplified by the mink cell focus-forming viruses (MCF) for example the MCF 247 virus. However, the polytropic SL3-2 virus has a host range as the mouse ecotropic viruses in that it infects and replicates in mouse cells, but are impaired in its ability to infect and replicate in mink cells or human cells. The SL3-2 envelope protein virus utilizes the polytropic (Xpr1) receptor.

Retroviral Vectors in Therapy

Retroviral vector particles are useful agents for introducing polynucleotides into cells, such as eukaryotic cells. The term "introducing" as used herein encompasses a variety of methods of transferring polynucleotides into a cell, such methods including transformation, transduction, transfection, and transinfection.

Retroviruses typically have three common open reading frames, gag, pol, and env, which encode the structural proteins, encode enzymes including reverse transcriptase, and encode envelope proteins, respectively. Typically, retroviral vector particles are produced by packaging cell lines that provide the necessary gag, pol, and env gene products in trans. (Miller, et al., Human Gene Therapy, Vol. 1, pgs. 5-14 (1990)). This approach results in the production of retroviral vector particles which transduce mammalian cells, but are incapable of further replication after they have integrated into the genome of the cell.

Thus, retroviral vector particles have been used for introducing polynucleotides into cells for gene therapy purposes. In one approach, cells are obtained from a patient, and retroviral vector particles are used to introduce a desired polynucleotide into the cells, and such modified cells are returned to the patient with the engineered cells for a therapeutic purpose. In another approach, retroviral vector particles may be administered to the patient in viva, whereby the retroviral vector particles transduce cells of the patient in vivo. Chimeric retroviruses have also been suggested in order to induce immune reactions against viruses, however no positive data have been reported showing this effect in humans.

Viral Interference

Among viruses such as the murine γ-retroviruses a phenomenon termed receptor interference has been used to classify viruses based on their tropism (Sommerfelt et al. 1990). Upon infection the virus synthesize de novo envelope proteins for the production of new viral particles. Some of these envelope proteins will engage the receptor via an unknown mechanism and shield the receptor (FIG. 2). This shielding prevents the recurrence of an infective event by an exogenous virus. In cell culture the interference is very effective in that complete block of infection can be observed.

HIV-1 is somewhat different with regard to receptor usage. For HIV-1 entry to occur a two-step binding mechanism is required. First the HIV-1 envelope protein binds the CD4 receptor (primary receptor) (Eckert et al 2001). This event initiates a conformational change that exposes a region termed V3 (Variable loop 3) which is responsible for a second interaction with a co-receptor (either CCR-5 or CXCR-4) (Huang et al 2005). This co-receptor interaction is absolutely required for infection to occur. In cell culture the same degree of receptor interference is not observed by HIV-1 infection, which may be due to the dual receptor requirement.

The retroviral phenomenon of superinfection resistance (SIR) defines an interference mechanism that is established after primary infection, preventing the infected cell from being superinfected by a similar type of virus.

In most cases, virus-encoded proteins are responsible for the phenomenon of SIR. A simple form of SIR is receptor occupancy by viral Env proteins, preventing the binding of a second virus, but many additional mechanisms have been described. SIR is furthermore not restricted to retroviruses.

Uses of Chimeric Retroviral Envelopes

Ecotropic and amphotropic MLVs have been widely used as research tools. Ecotropic viruses are usually chosen because of safety concerns, while the amphotropic viruses have the ability to infect human cells. Different packaging cell lines that express the ecotropic or amphotropic envelopes have been designed to fulfil these different requirements.

Several functional chimeric envelopes have already been described but none of these can mediate transduction at efficiencies comparable to the efficiencies obtained with wild type envelope proteins. The described functional chimeric MLV-envelopes can be divided into two groups. The first group has the heterologous ligand inserted in the N-terminal of the SU-protein and can mediate transduction without co-expression of wild type envelope, whereas the other group has the ligand inserted internally in SU and is dependent of co-expressed wild type envelope. Peptide linkers and a single chain antibody specific for the human major histocompatibility complex class I(MHC-I) molecule have e.g. been inserted at four internal positions in Akv-env.

The first attempts to direct virus particles towards receptors not normally recognised by retroviruses were done by antibody-bridging and by usage of chemical modifications. By cross-linking monoclonal antibodies against SU and the transferring receptor with a sheep anti-mouse kappaiight chain antibody binding of the virus to human HEp2 cells, and subsequent internalisation was shown. However, internalisation of the virus by this infection route was not followed by establishment of the proviral state.

Others used a similar approach to target the attachment of ecotropic viruses by streptavidin bridging biotinylated antibodies against SU and against specific membrane markers expressed on human cells. By this method human cells expressing MHC class I, MHC class II, epidermal growth factor and insulin were successfully infected, whereas this method did not prove feasible for promoting infection of cells expressing transferrin, high density lipoprotein and galactose receptors.

Also, chemically coupled galactose residues to ecotropic Env, making the virus particles capable of infecting human hepatoma cells through the asialoglycoprotein receptor, have been tried.

Infection of human cells by an ecotropic virus displaying chimeric-envelope proteins on the surface of the virion is also known to a person skilled in the art. This can be achieved by e.g. substituting a part of MoMLV SU with a sequence encoding the erythropoietin hormone (EPO), insertion of a sequence encoding human heregulin for infection of human breast cancer cells overexpressing the human epidermal growth factor receptor, substitution of an internal fragment of SU with a single-chain variable fragment (ScFv) derived from a monoclonal antibody recognising the human low density lipoprotein receptor which gave a chimeric envelope capable of infecting human cells.

In these reports with chimeric envelopes, targeted infection was only obtained when wild type env was co-expressed with the chimeric construct from the packaging cell line.

This indicates that functional domains are contained within the ecotropic envelope, which is necessary for mediating infection beyond the point of receptor binding.

The obtained targeting efficiencies with chimeric envelopes reported until now are considerably lower than the efficiencies obtained with wild type envelopes. The reasons for these low transduction efficiencies of target cells are probably diverse, including the choice of insertion site, stability of the chimeric envelope protein, the tertiary protein structure and the choice of target cells. Furthermore, the choice of ligand is probably also very important for obtaining infection, as several chimeric envelopes have failed to promote infection. One more positive example relates to insertion of a short nondisruptive peptide (RDG) known to bind to several integrins displayed on the surface of cells (Golan T J and Green-M R, 2002).

The above-described examples all utilised the ecotropic envelope. One advantage of using this envelope is that it is restricted in infecting human cells as the surface protein part of the envelope does not recognise a human receptor. The concept is that if the envelope can be engineered to bind to a human receptor by inserting a heterologous sequence in the envelope mediating this binding, the otherwise intact fusogenic properties of the envelope would mediate the fusion.

Retroviruses

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The family Retroviridae are enveloped single-stranded RNA viruses that typically infect mammals, such as, for example, bovines, monkeys, sheep, and humans, as well as avian and murine species. Retroviruses are unique among RNA viruses in that their multiplication involves the synthesis of a DNA copy of the RNA which is then integrated into the genome of the infected cell.

The Retroviridae family comprises a number of retroviruses such as the lentiviruses exemplified by HIV-1, HIV-2 and SIV, and the gammaretroviruses such as the leukaemia viruses for example murine leukaemia viruses (MLVs), and feline leukaemia viruses.

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Integration is thought to occur essentially at random within the target cell genome. However, by modifying the long-terminal repeats it is possible to control the integration of a retroviral genome.

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is important in the control of virus latency and the temporal sequence in which viral genes are expressed.

Murine Leukaemia viruses are a family of simple retroviruses isolated from laboratory mice. Retroviruses carry their genomes as two copies of a single RNA molecule and the simplest retroviruses contain the gag, pro, pol and env genes. These genes are found in the same order in all known retroviruses, reflecting the phylogenetic relationship of retroviruses.

Retroviral integration can activate genes in the vicinity of the integration site. In this way, retroviruses have been used to identify oncogenes since activation of these genes result in tumour growth. In much the same way the integration of a provirus can disrupt the expression of genes, hence inactivation of a tumour suppressor gene may contribute to tumour formation. A high number of integrations are desirable in such studies since not all integrations result in tumour generation and multiple hits are required. Very few integration events are expected to be near oncogene or tumour suppressor genes. Tumour formation might also involve multiple gene regulations.

Retroviral infections usually result in a single integration event since the envelope protein blocks receptors on an infected cell. This is the basis of the superinfection resistance (also called interference) phenomenon in which a virus-infected cell shows resistance to superinfection by viruses, which utilise the same receptor for entry. Thus, use of viruses with different receptor usage increases the number of integration events. Entry by different receptors may even provide access to retroviral disease induction in different mouse tissues.

The integration mechanism of retroviruses can be used to introduce any DNA sequence into a host genome, if the appropriate cis elements of the retroviral genome are maintained in the transducing vector and the DNA sequence can be encompassed in the vector (less than 9000 bp). Therefore retroviral vectors are attractive tools for gene therapy. Most simple retroviral receptors are found on many different cell types of the same species. That is why vector systems utilising wild type envelopes from simple retroviruses cannot be used to introduce genes in a selective manner into specific cells/tissues.

The retroviral envelope protein is a nano-device that mediates receptor-dependent fusion of biological membranes. When the envelope protein is attached to the lipid-bilayer membrane surrounding the virus, the net result of fusion with a cellular membrane is entry of the nucleoprotein core of the virus into the cytoplasm. Such fusion is triggered by the envelope protein's recognition of a receptor on the plasma membrane or an endosomal membrane. Natural receptors for retroviral infection are integral membrane proteins with multiple membrane-spanning domains. For the gammaretroviruses such as murine leukemia viruses, several natural receptors are known to have transporter functions for e.g. amino acids. When expressed on the plasma membrane of a cell, the viral envelope protein may also mediate cell to cell fusion. The dynamics of the fusion process is generated by the viral envelope protein which is produced in an activated state and has "one shot" to trigger membrane fusion.

The ability of redirecting the retroviral fusion machinery to a desired receptor would have wide biotechnological and potentially also nanotechnological applications. However, the regulatory mechanisms that interconnect receptor binding with fusion are poorly understood, which has made intelligent engineering of the envelope protein difficult. Many attempts at redirecting the receptor-specificity have found that incorporation of a ligand into the envelope protein may cause receptor-dependent binding without activation of the fusion machinery.

Several functional chimeric envelopes have already been described but none of these can mediate transduction at efficiencies comparable to the efficiencies obtained with wild type envelope proteins. The described functional chimeric MLV-envelopes can be divided into two groups. The first group has the heterologous ligand inserted in the N-terminal of the SU-protein and can mediate transduction without co-expression of wild type envelope, whereas the other group has the ligand inserted internally in SU and is dependent of co-expressed wild type envelope. Peptide linkers and a single chain antibody specific for the human major histocompatibility complex class I(MHC-I) molecule have e.g. been inserted at four internal positions in Akv-env.

The first attempts to direct virus particles towards receptors not normally recognised by retroviruses were done by antibody-bridging and by usage of chemical modifications. By cross-linking monoclonal antibodies against SU and the transferring receptor with a sheep anti-mouse kappa light chain antibody binding of the virus to human HEp2 cells, and subsequent internalisation was shown. However, internalisation of the virus by this infection route was not followed by establishment of the proviral state.

Others used a similar approach to target the attachment of ecotropic viruses by streptavidin bridging biotinylated antibodies against SU and against specific membrane markers expressed on human cells. By this method human cells expressing MHC class I, MHC class II, epidermal growth factor and insulin were successfully infected, whereas this method did not prove feasible for promoting infection of cells expressing transferrin, high density lipoprotein and galactose receptors.

Also, chemically coupled galactose residues to ecotropic Env, making the virus particles capable of infecting human hepatoma cells through the asialoglycoprotein receptor, have been tried.

Infection of human cells by an ecotropic virus displaying chimeric-envelope proteins on the surface of the virion is also known to a person skilled in the art. This can be achieved by e.g. substituting a part of MoMLV SU with a sequence encoding theerythropoietin hormone (EPO), insertion of a sequence encoding human heregulin for infection of human breast cancer cells overexpressing the human epidermal growth factor receptor, substitution of an internal fragment of SU with a single-chain variable fragment (ScFv) derived from a monoclonal antibody recognising the human low density lipoprotein receptor which gave a chimeric envelope capable of infecting human cells.

In these reports with chimeric envelopes, targeted infection was only obtained when wild type env was co-expressed with the chimeric construct (from thet1) 2 packaging cell line). This indicates that functional domains are contained within the ecotropic envelope, which is necessary for mediating infection beyond the point of receptor binding.

The obtained targeting efficiencies with chimeric envelopes reported until now are considerably lower than the efficiencies obtained with wild type envelopes. The reasons for these low transduction efficiencies of target cells are probably diverse, including the choice of insertion site, stability of the chimeric envelope protein, the tertiary protein structure and the choice of target cells. Furthermore, the choice of ligand is probably also very important for obtaining infection, as several chimeric envelopes have failed to promote infection. One more positive example relates to insertion of a short nondisruptive peptide (RDG) known to bind to several integrins displayed on the surface of cells (Golan T J and Green-M R, 2002).

The above-described examples all utilised the ecotropic envelope. One advantage of using this envelope is that it is restricted in infecting human cells as the surface protein part of the envelope does not recognise a human receptor. The concept is that if the envelope can be engineered to bind to a human receptor by inserting a heterologous sequence in the envelope mediating this binding, the otherwise intact fusogenic properties of the envelope would mediate the fusion.

The present invention provides improved chimeric envelope proteins with novel ligands and ligand insertion sites within the envelope polypeptide that are advantageous over prior art chimeric envelopes, for example in relation to improving therapeutic efficacy of gene therapies.

SUMMARY OF INVENTION

The present invention provides an isolated chimeric viral envelope polypeptide comprising:

(i) a first polypeptide sequence consisting of the polypeptide sequence of a gamma retrovirus envelope polypeptide, or a homologue or fragment thereof;

wherein into said first polypeptide sequence has been inserted or attached at one end:

(ii) a second polypeptide sequence comprising a receptor-binding domain of a second, different viral envelope polypeptide, or a fragment or homologue thereof, wherein said second polypeptide sequence further optionally comprises one or more flexible linker sequence(s).

Said first polypeptide sequence preferably has a sequence that is at least 70% identical to the amino acid sequence shown in SEQ ID NO:2, or is a fragment of a sequence that is at least 70% identical to the amino acid sequence shown in SEQ ID NO:2, and can for example be a polytropic murine leukaemia virus. In one preferred embodiment, the inserted receptor-binding domain is the V-3 loop domain of HIV-1 or a fragment or homologue thereof.

The present invention further relates to isolated polynucleotides encoding the chimeric viral envelope polypeptide, as well as vectors and replication-competent retroviruses comprising the chimeric viral envelope polypeptides. Stable cell lines are also provided, which may be used a packaging cell lines producing the replication-competent retroviruses.

Pharmaceutical compositions comprising the polypeptides and/or retroviruses of the present invention are also provided, which can be used in various therapeutic methods, including gene therapy and methods for prevention of viral infection.

Without being bound by theory, it is believed that the chimeric polypeptides trigger a type of artificial “superinfection resistance” in an individual thus treated. Thus, in the case of HIV treatment, one can for example use an engineered SL3-2 envelope that contains the V3 region of HIV to block the HIV co-receptors CCR-5 and/or CXCR-4 and thereby prevent or reduce HIV infection. The inventors have furthermore found that the envelope proteins can interfere with cell-cell fusion caused by the HIV-envelope.

The present invention in one aspect provides a chimeric viral envelope polypeptide comprising (i) an envelope polypeptide, or fragment thereof, (ii) a polypeptide sequence of a receptor binding region, ligand or polypeptide sequence of a ligand binding region, and optionally a linker sequence, wherein the receptor binding domain of said envelope polypeptide has a sequence that is at least 36% identical to the amino acid sequence shown in SEQ ID NO: 60, or is a fragment of a sequence that is at least 36% identical to the amino acid sequence shown in SEQ ID NO: 60.

Aspects of the present invention also relate to a polynucleotide encoding the chimeric viral envelope polypeptide, a retroviral vector comprising the polynucleotide or fragment thereof, a virus particle expressing the chimeric viral envelope polypeptide.

Further aspects pertain to a virus particle comprising:
(i) the polynucleotide as described above,
(ii) an agent for delivery to the target cell, optionally selected from the group consisting of a therapeutic agent, a gene or gene product, a diagnostic label, a label for bioimaging, or a toxic agents, which agent is operatively associated with a retroviral packaging sequence.

Also aspects relating to a cell transfected with
a. the polynucleotide as described above or
b. the retroviral vector as described above,
a stable cell line comprising cells as described above, and an animal model comprising such cells, a packaging cell line comprising the retroviral vector are disclosed in the present invention.

Aspects of the present invention relates to a method for targeting an agent to a G-protein coupled receptor, comprising the steps of:
(i) providing the chimeric envelope polypeptide
(ii) causing said chimeric envelope polypeptide to contact a target cell wherein said target cell comprises a receptor for the ligand of said chimeric envelope polypeptide,
a method for specifically tethering a chimeric retroviral envelope polypeptide to a specific cell type, comprising the steps of:
(i) providing an virus particle expressing a chimeric retroviral envelope polypeptide, said envelope polypeptide comprising a ligand capable of binding said specific cell-type,
(ii) allowing said chimeric envelope polypeptide to specifically contact a cell of said specific cell type,
(iii) allowing the outer membrane of the virus to undergo a hemifusion process with the outer membrane of said cell, and
a method for labelling one or more object of interest on a cell, comprising:
(i) providing the labelled vector, polypeptide or recombinant retrovirus,
(ii) allowing said labelled vector, polypeptide or recombinant retrovirus to contact said object of interest on said cell.

Further aspects of the present invention relates to a method for quantifying the amount or number of an object of interest in a biological specimen, such as a cell, said method comprising the steps of:
(i) providing the labelled vector, chimeric envelope polypeptide or virus particle,
(ii) allowing said labelled vector, chimeric envelope polypeptide or virus particle to contact said object of interest on said cell, and a method for screening for and analysis of drugs that target the envelope-receptor interaction, comprising the virus particle.

The present invention further discloses methods relating to therapy such as a therapeutic method for treatment of an individual in need thereof, said method comprising administering the chimeric viral envelope polypeptide, the vector, or virus particle.

For example the invention relates to a therapeutic method for treatment of an individual in need thereof, said method comprising administering a si-RNA, a method for delivering an agent to a mammalian target cell in an individual in need thereof, comprising the steps of:
(i) providing the chimeric envelope polypeptide or virus particle
(ii) causing said chimeric envelope polypeptide or virus particle to contact a target cell population of said individual's cells, wherein said target cell comprises a receptor for the ligand of said chimeric envelope polypeptide
(iii) allowing the virus particle to bind said receptor.

Furthermore the present invention relates to aspects of an antibody capable of specifically binding a molecule, or a medicament comprising the chimeric envelope polypeptide, vector, or viral particle.

Panel G is a replication competent retroviral vector expressing an envelope gene from a mono-cistronic mRNA by directing translation of the envelope gene by an internal ribosome entry site (IRES).

Panel H same as Panel G except that an insert (ScFv—but can be any suitable insert as described herein) has been inserted into the envelope gene for redirection of tropism.

In the present context ScFv can be any heterologous peptide sequence that mediates redirection of envelope tropism, such as the V3 peptide.

FIG. 4 shows an alignment of amino acid sequences of selected MLVs in the VR3 region. Residues corresponding to arginine 212 are shown in the rectangular box. The sequences shown in FIG. 4 are as follows: SL3-2 (SEQ ID NO:115), MCF-247 (SEQ ID NO: 116), MCF CI-3 (SEQ ID NO:117), Ampho-MCF (SEQ ID NO:118), ERV-1 (SEQ ID NO:119), Endogenous from 129 GIX+ mice (SEQ ID NO:120), Friend MCF #2 (SEQ ID NO:121), Friend MCF (SEQ ID NO:122), Friend SFV (SEQ ID NO:123), Invitro MCF (SEQ ID NO:124), MCF 1223 (SEQ ID NO:125), MLV DBA/2 (SEQ ID NO:126), MCF (Broscius) (SEQ ID NO:127), Mo-MCF (SEQ ID NO:128), Ns-6(186) MCF (SEQ ID NO:129), Rauscher sfv (SEQ ID NO:130), R-XC- (SEQ ID NO:131), MCF (Ter-Grigorov) (SEQ ID NO:132), AKV (SEQ ID NO:133), Friend (SEQ ID NO:134), Moloney (SEQ ID NO:135), SL3-3 (SEQ ID NO:136), Friend fass (SEQ ID NO:137), 10A1 (SEQ ID NO:138), 4070A (SEQ ID NO:139), Xeno CWM-S-5X (SEQ ID NO:140), DG-75 Xeno (SEQ ID NO:141), Xeno NZB-9-1 (SEQ ID NO:142), Xeno Bxv-1-related (SEQ ID NO:143), Xeno R-MCF-1 (SEQ ID NO: (144), Consensus (SEQ ID NO:145).

FIGS. 5A-5G show sequence alignments showing homology between various viral envelope polypeptides. See Example 5 for description of sequences.

Figure 6:
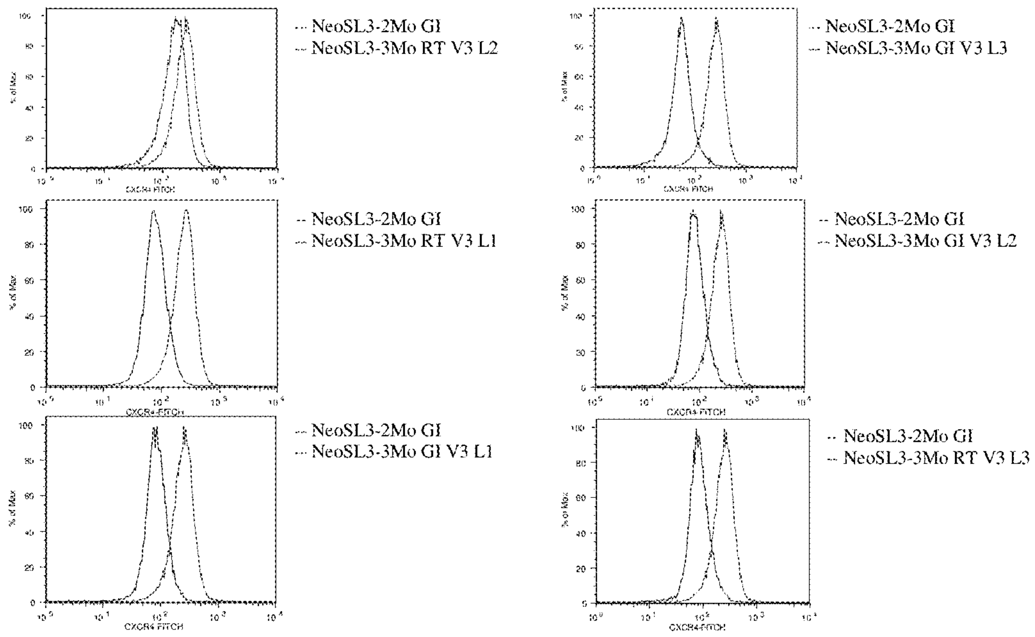

FIG. 6 shows flow cytometric analysis of cell surface expression of CXCR4 cells transduced with a vector expressing SL3-2 envelope with an inserted V3 loop.

Figure 7:
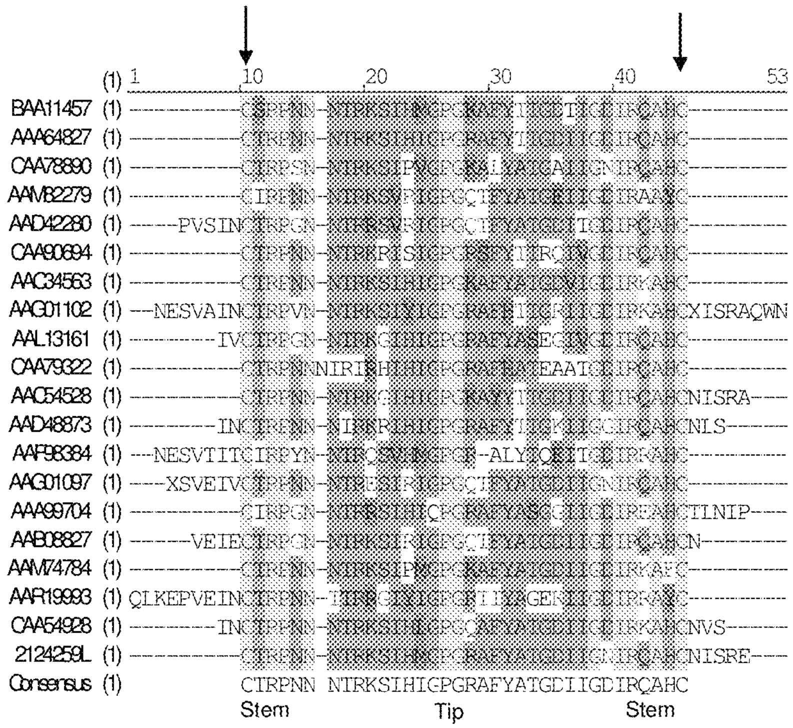

FIG. 7 shows a sequence alignment of V3 loop from different HIV-1 subtypes. The arrows indicate important highly conserved Cysteine residues. Genebank accession numbers are indicated.

Figure 8:
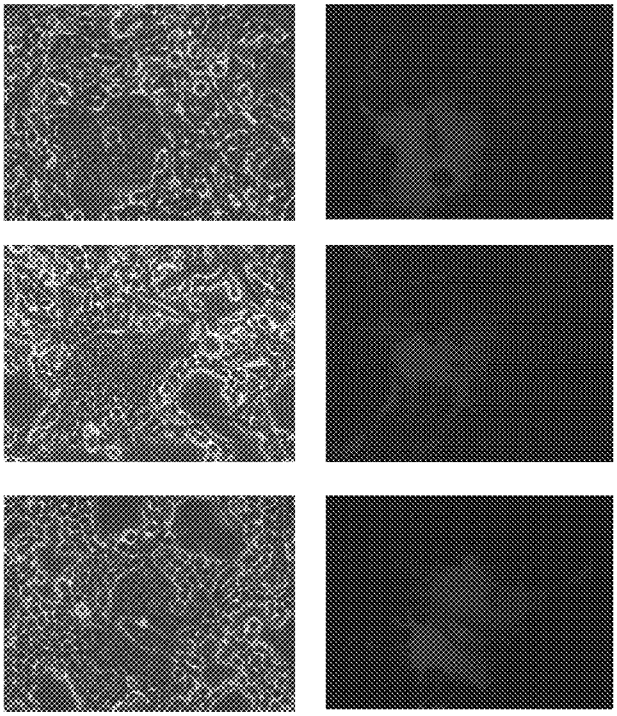
Figure 9:
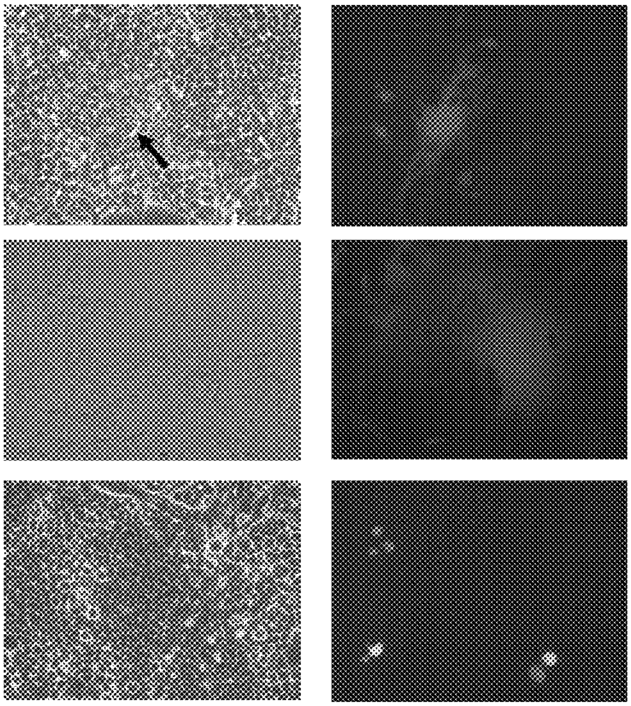

FIGS. 8-9 show syncytia formation of 293T cells expressing the HIV-1 envelope protein (indicated by fluorescent signal in the right hand panel) and D17 CD4 CXCR4 cells. The first panel ("panel 1") indicates D17 CD4 CXCR4 cells (without SL3-2 envelope), the following four panels ("panel 2"-"panel 5") are D17 CD4 CXCR4 cells transduced by different variants of the SL3-2 envelope with V3 inserted. Final panel ("panel 6) is a transfection control of the vector pLXSN (expressing egfp) without the HIV-1 envelope.

Figure 10:
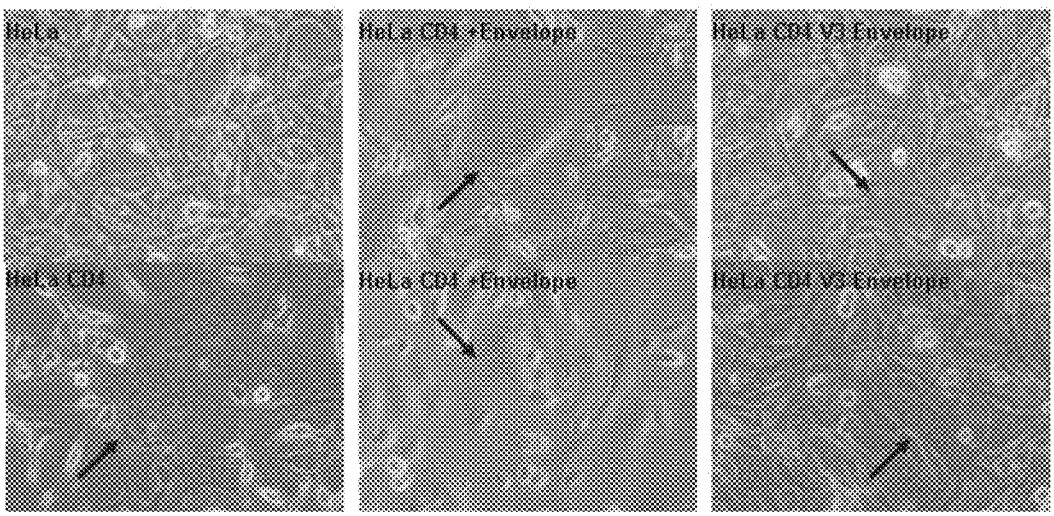

FIG. 10 shows further results of Syncitia assays. The arrows indicate multi-nuclei cell syncytia. NIH cells stably expressing the HIV-1 envelope protein were co-cultured with different HeLa target cells (HeLa expresses CXCR-4 endogenously). Top left HeLa cells lacking the CD4 receptor. Bottom left HeLa cells with CD4. Middle, HeLa CD4 cells transfected with Moloney MLV envelope. Right, HeLa CD4 cells transfected with two variants of chimeric Moloney/V3 envelopes. We note a reduction in syncytia formation in the presence of V3 envelope, in particular in the upper right panel.

Figure 11:
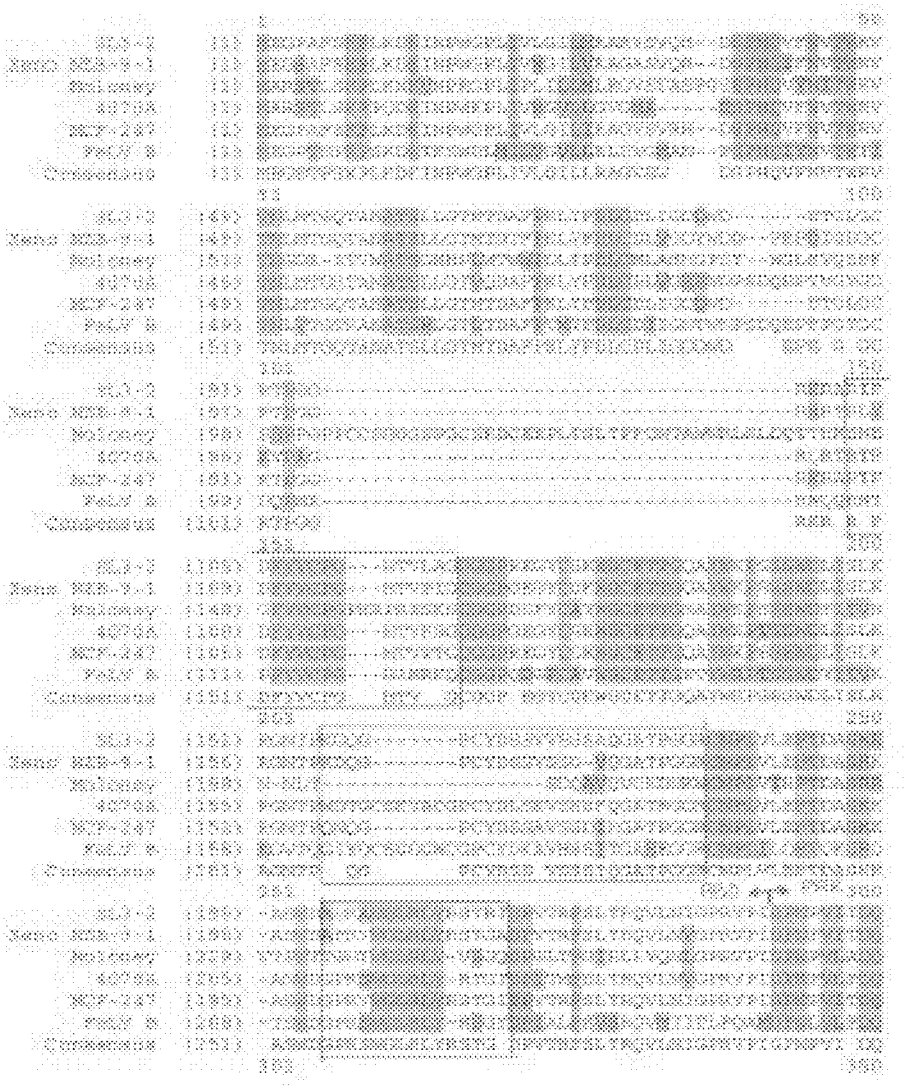

FIG. 11 shows an alignment of part of the envelope amino acid sequence of a number of gammaretroviruses. The border of the receptor binding domain (RBD) and the praline rich repeat (PRR) is shown. The position of the variable region A and B (VRA and VRB is indicated as is the variable region 3 (VR3).

Figure 12:
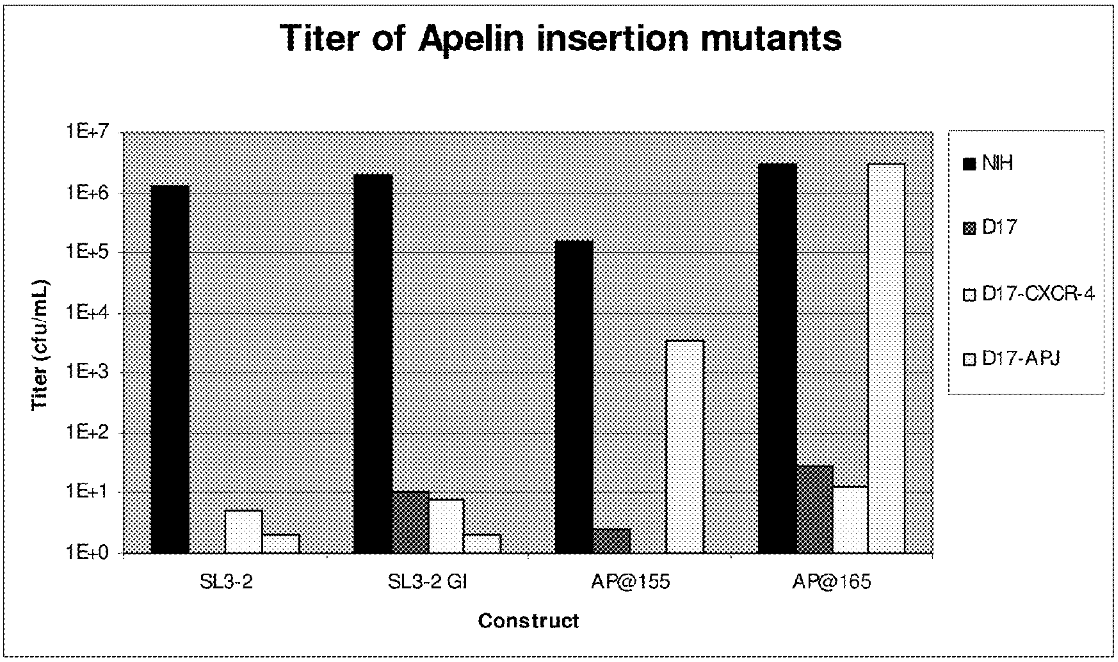

FIG. 12 shows the titers of the constructs in which apelin has been inserted. The GPCR APJ mediates specific entry into D17 dog cells of an SL3-2 envelope virus engineered to harbor its cognate ligand at a critical position (see FIG. 4). The insertion site in AP@155 is suboptimal relative to AP@165. NIH cells are mouse cells that can be infected by the wt SL3-2 as well as the three mutants. SL3-2GI is a mutant that infects human cells, but not dog cells.

Figure 13:
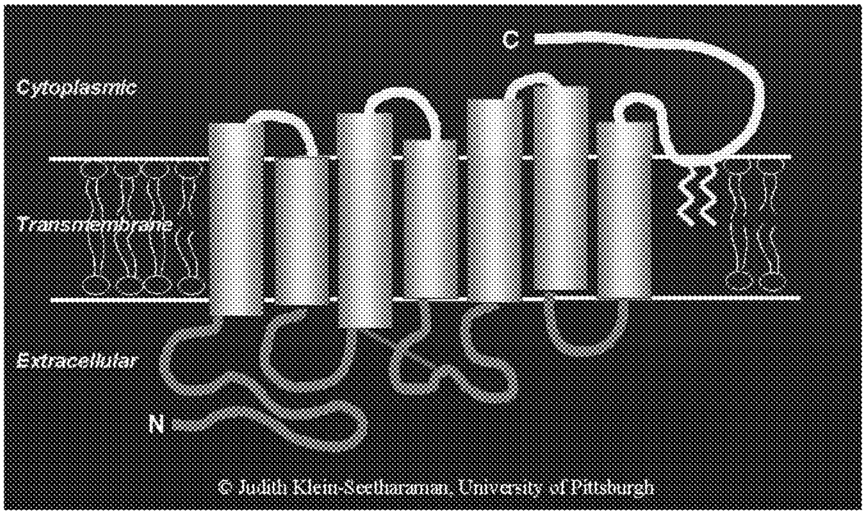

FIG. 13 shows a G-protein coupled receptor with the typical 7-transmembrane helix-organization.

Figure 14:
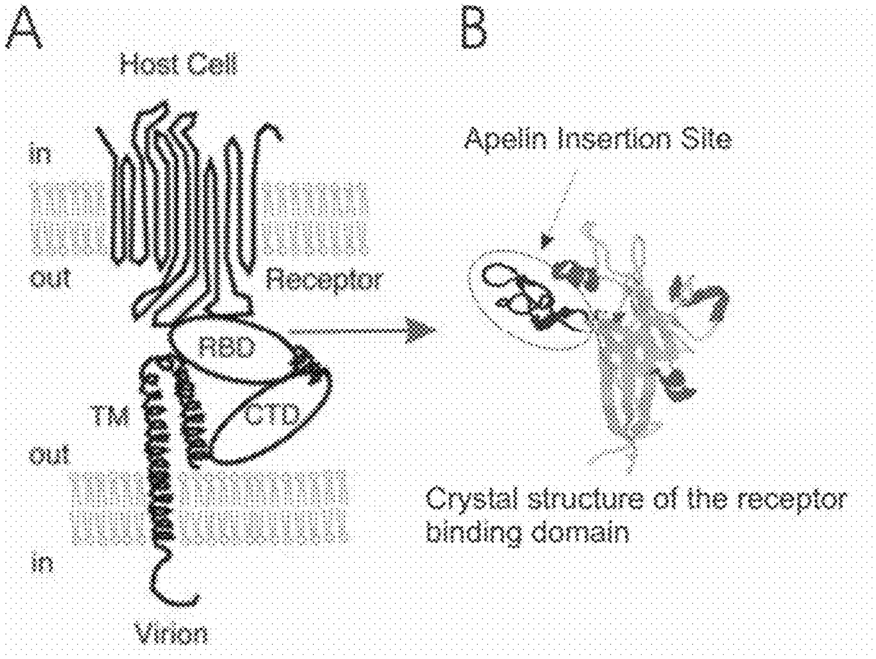

FIG. 14 discloses A) the functional domains of a retroviral envelope protein. RBD, receptor-binding domain; CTD. C-terminal domain; TM, transmembrane protein, harboring a folded-back helix that is extended into the receptor membrane upon activation, B) the crystal structure of the receptor binding domain and the apelin insertion site.

Figure 15:
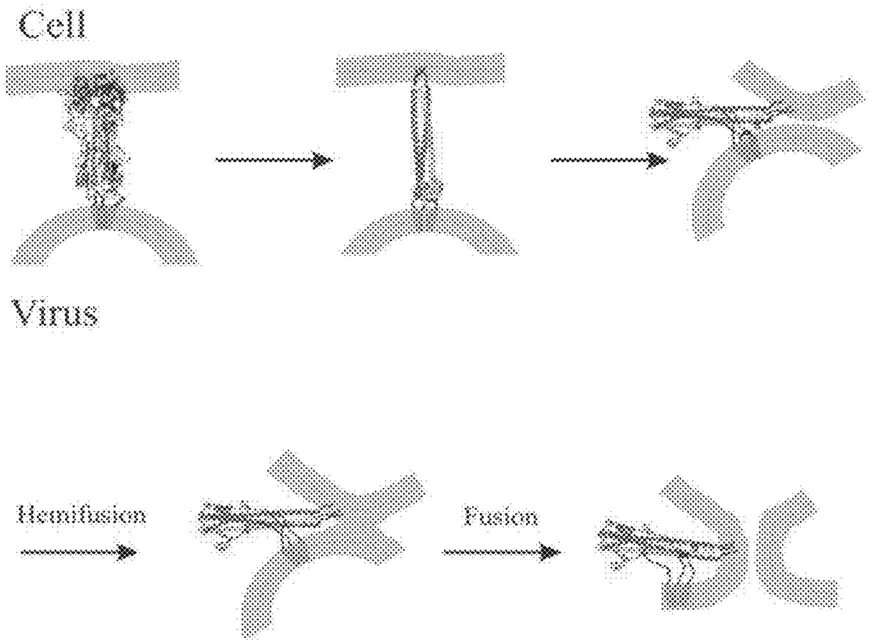

FIG. 15 shows a schematic illustration of the steps in the membrane fusion process directed by a retroviral envelope protein; note the intermediate hemifusion stage that allows the mixing of lipids in the outer, but not the inner leaflets of the two membranes.

Figure 16:
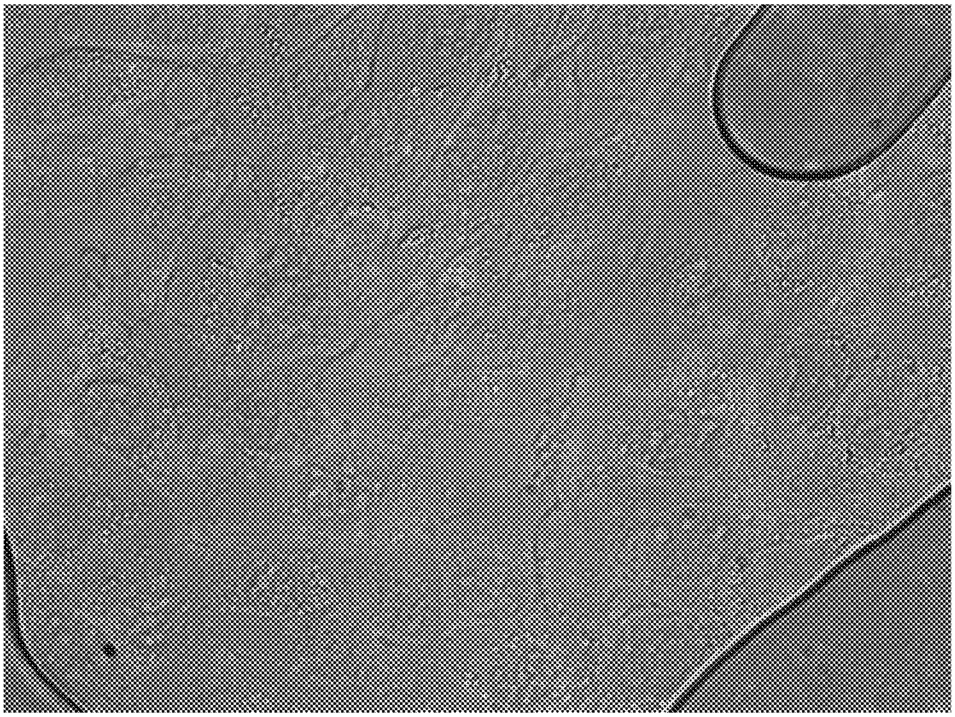
Figure 17:
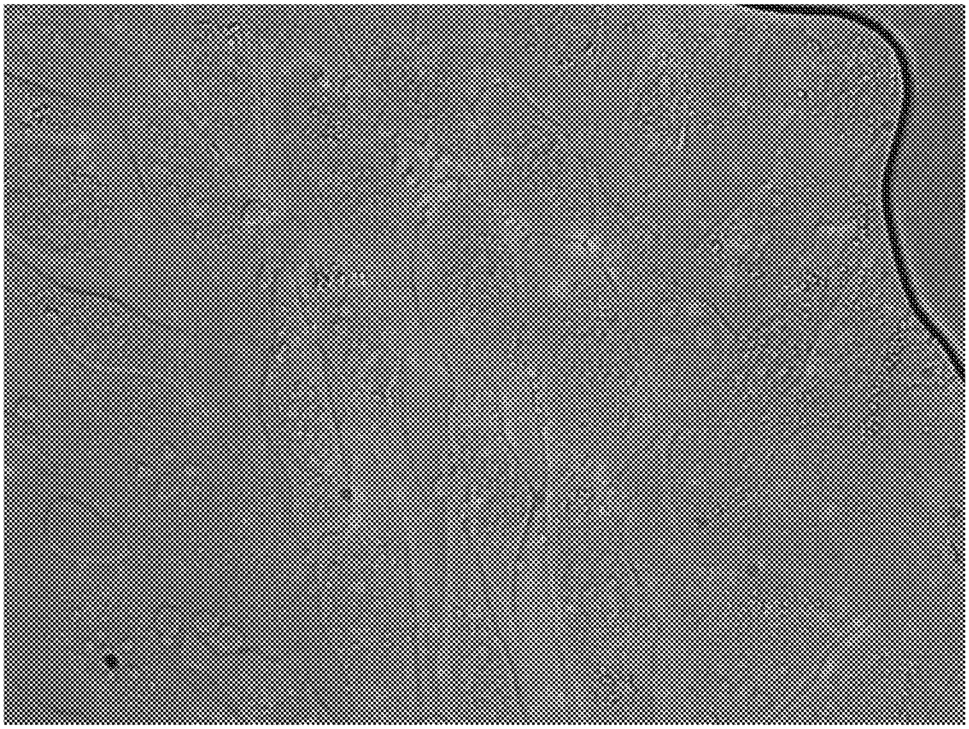
Figure 18:
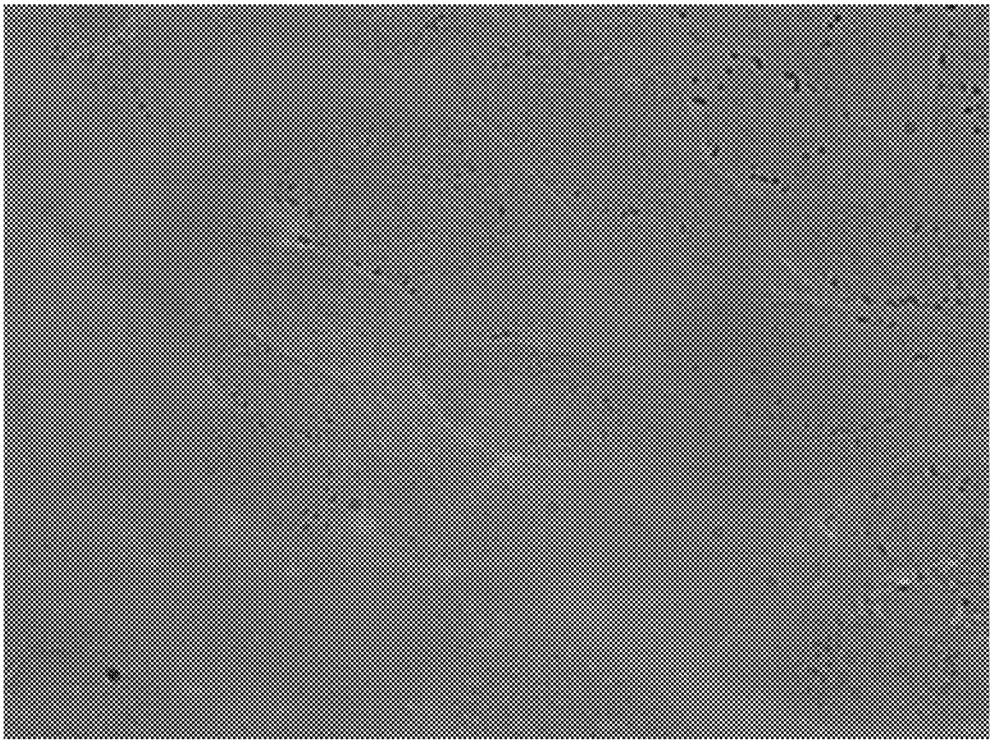

FIGS. 16-18. NIH3T3 cells were incubated with SL3-2 containing a hexa histidine motif in position 165 (or control virus) on ice for 1 h. Liposomes containing the FRET pair: NBD-PE and Rh-PE were subsequently incubated with the virus/cell mix on ice for another hour followed by incubation in 37° C. for 1 h. Fusion is expected to result in increase and dispersal of the green fluorescence. FIG. 16 and FIG. 17 show hexahistidine tagged virus incubated with NTA containing liposomes. FIG. 18 show control virus incubated with liposomes without NTA. All figures show overlays of green, red fluorescences with whitefield.

Figure 19:
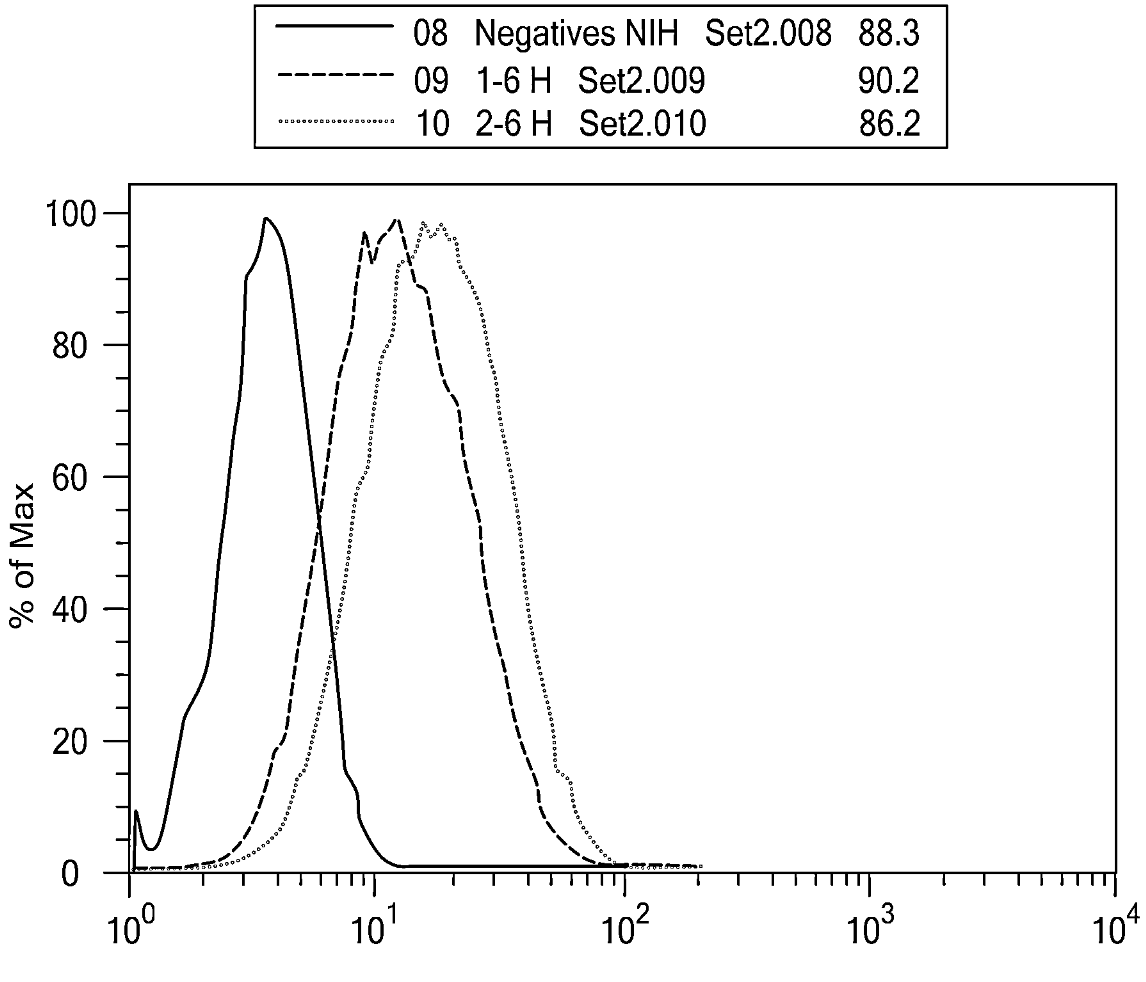

FIG. 19 shows that NTA holding liposomes have higher binding affinity for hexa histidine containing viral envelope (dotted line) than liposomes without NTA (dashed line).

Figure 20:
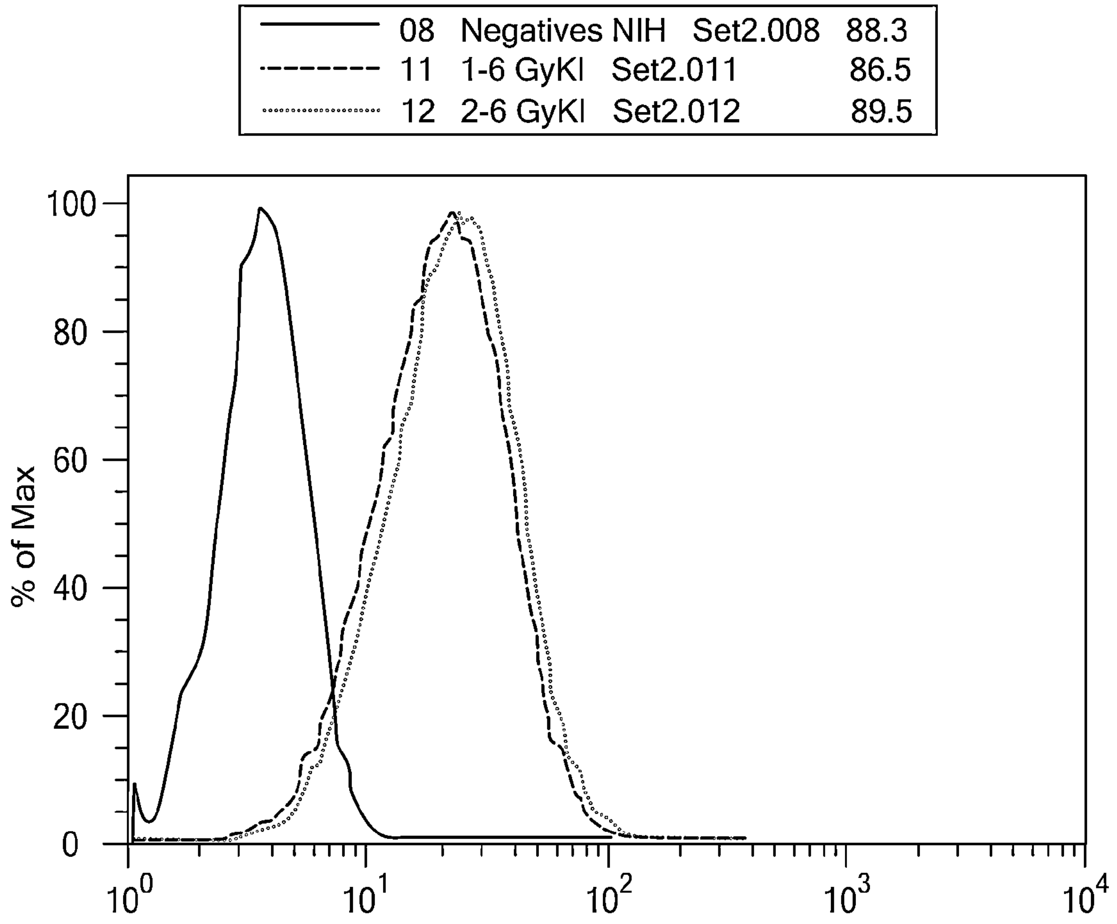

FIG. 20 shows that binding of NTA containing liposomes (dotted line) is not higher than liposomes without NTA (dashed line) to control virus (solid line).

Figure 21:
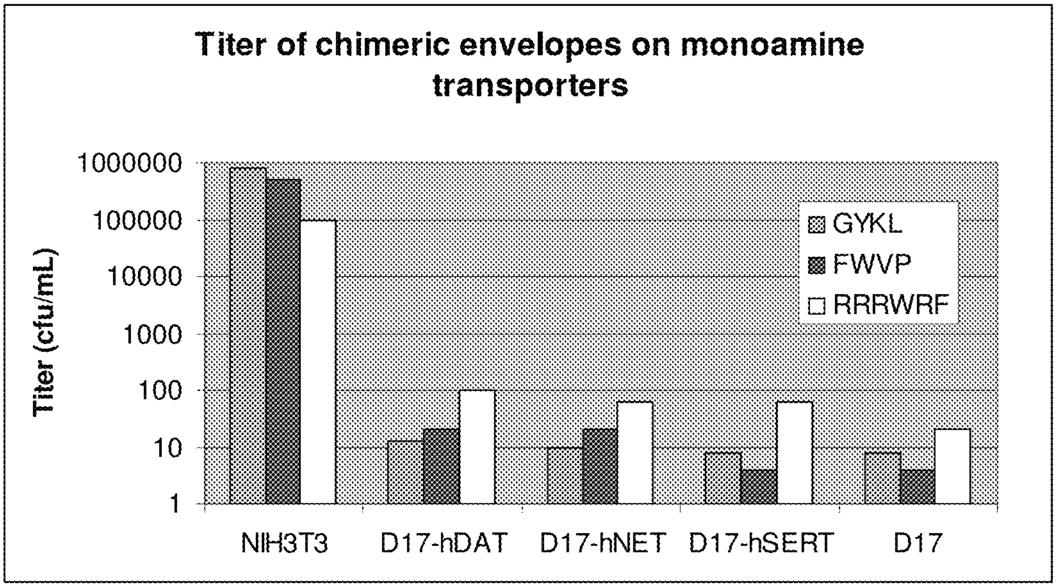

FIG. 21: titer of the chimeric envelopes on mono-amine transporters.

Figure 22:
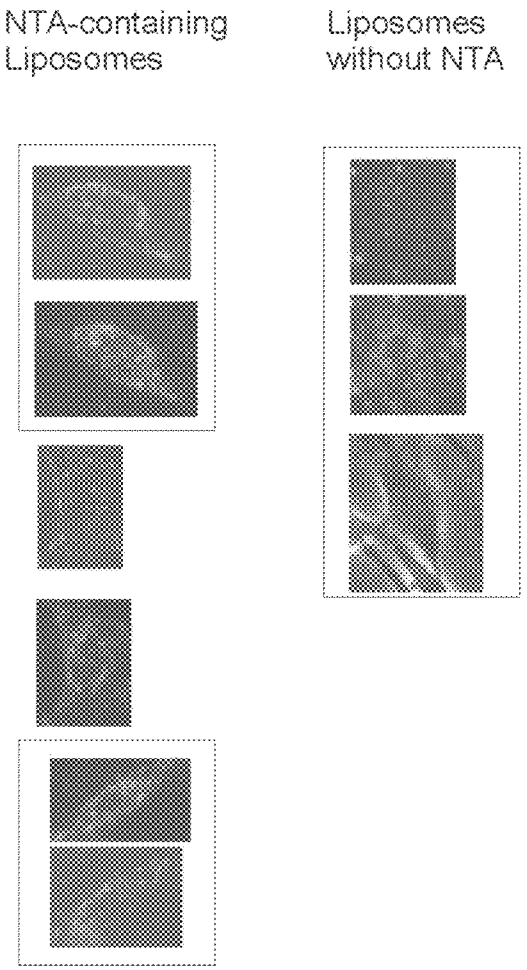

FIG. 22: Liposome fusion to mouse fibroblasts in the presence of hexa histidine-tagged virus. Note the confinement of green fluorescence in the plasma membrane of cells incubated with NTA-containing liposomes.

Figure 23:
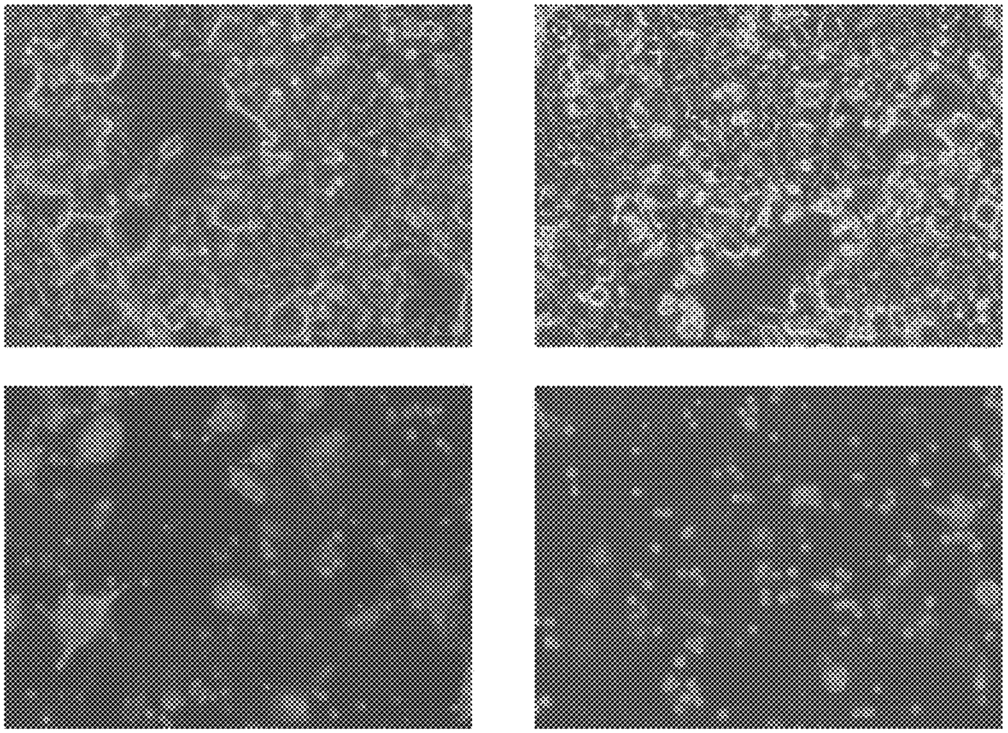

FIG. 23: Syncytia formation by HIV-envelope expressed in 293T cells and Jurkat cells (labeled with the red fluorescence dye R18). Notice the reduced size and frequency of syncytia in Jurkat cells expressing the SL3-2-V3 chimeric envelope (right panel).

Figure 24:
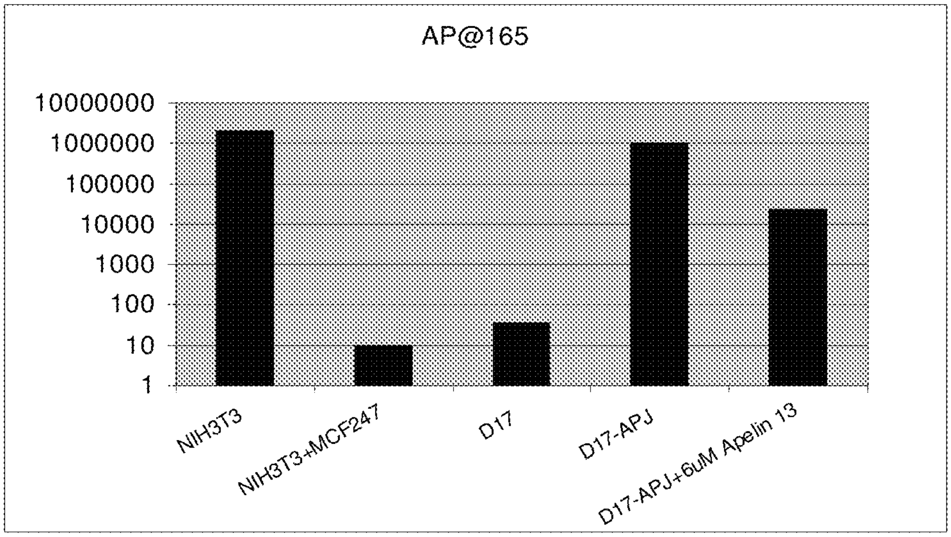

FIG. 24. The SL3-2 chimeric envelopes can use two different receptors. The figure shows the titer of SL3-2AP@165 envelope on different cells. NIH3T3: Murine cells, NIH3T3+MCF247: murine cells infected with MCF247, thus having a blocked polytropic receptor, D17: Dog cells, D17-APJ: Dog cells expressing APJ, D17-APJ-6 uM Apelin 13: Dog cells expressing APJ incubated with 6 uM apelin-13 peptide for 1 h. The data show that infection can occur through both the polytropic Xpr1 and the heterologous APJ receptors.

Figure 25:
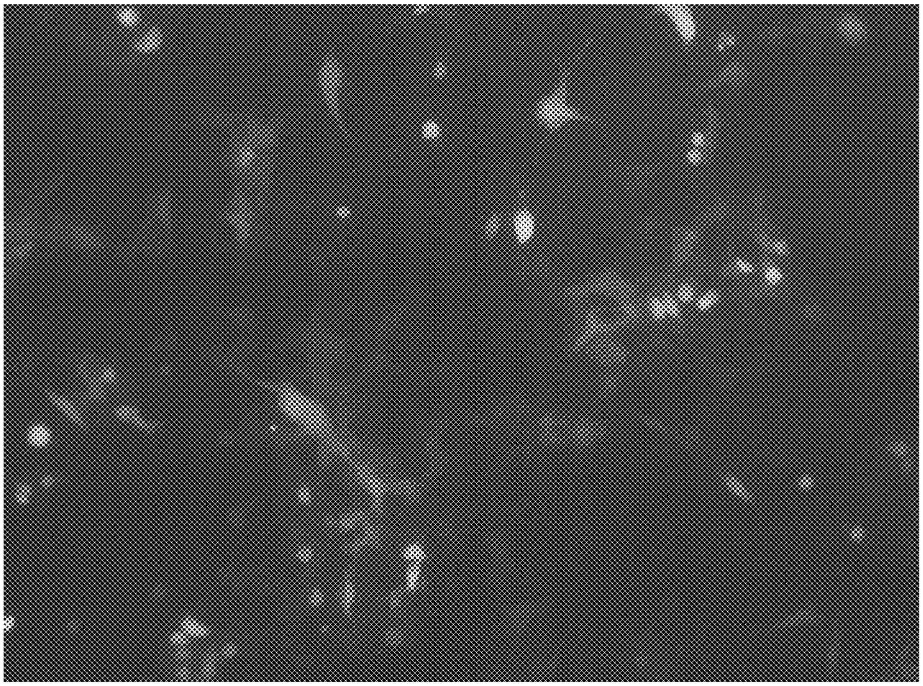
Figure 26:
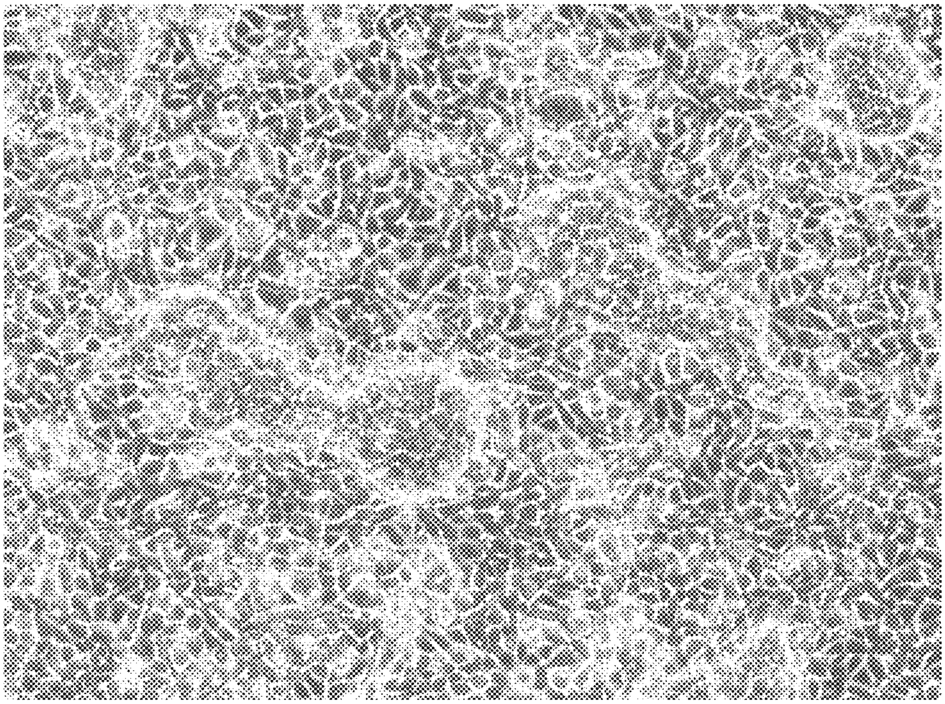
Figure 27:
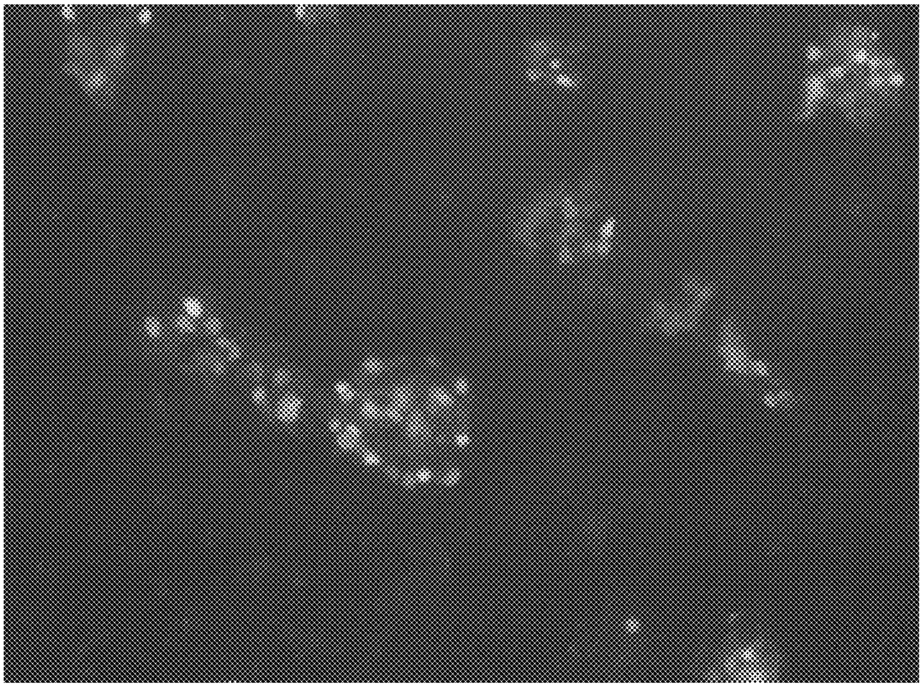
Figure 28:
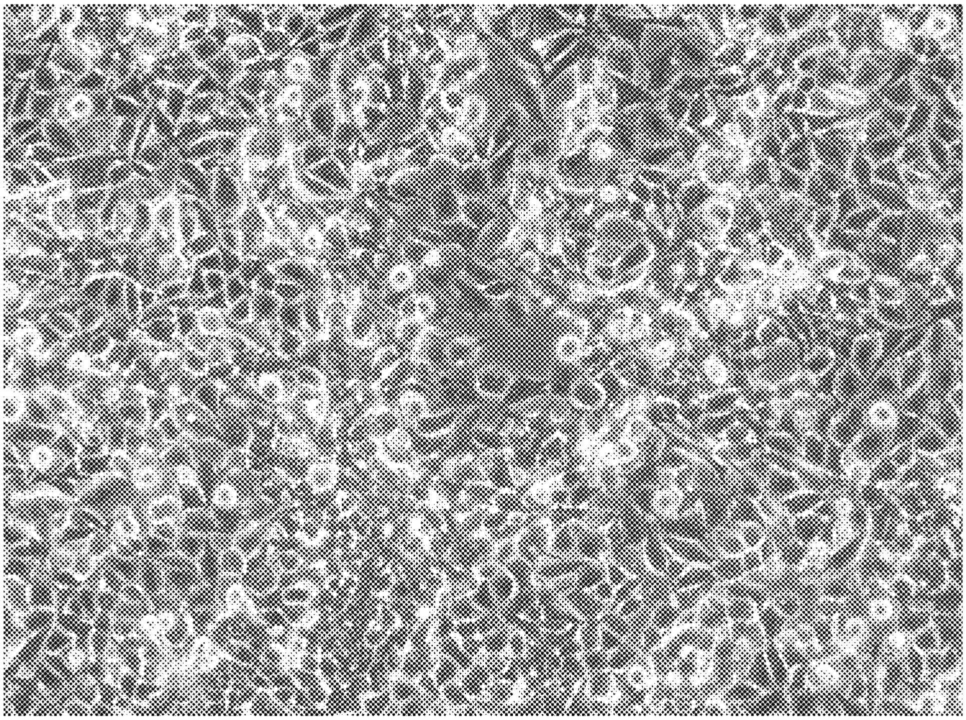

FIGS. 25-28 shows that the chimeric SL3-2AP@165 envelope can induce syncytia in XC cells using APJ but not Xpr-1. XC or APJ expressing XC cells were co-cultured with 293T cells transfected with R-peptide less SL3-2AP@165 envelope expression vector for 24 h. Syncyita is best visible in the green fluorescent as large star-shaped cells. No syncytia are visible without APJ expression in XC cells. FIG. 25: Fluorescence picture of XC-APJ cells and fluorescent SL3-2AP@165 expressing 293T cells. FIG. 26: XC cells and fluorescent SL3-2AP@165 expressing 293T cells. FIG. 27: fluorescence picture of XC cells and fluorescent SL3-2AP@165 expressing 293T cells. FIG. 28: XC-APJ cells and fluorescent SL3-2AP@165 expressing 293T cells.

DETAILED DESCRIPTION OF THE INVENTION

Definitions

The term "polypeptide" as used herein means a polymer of amino acids and does not refer to any particular length of polymer. Such term also includes post-translationally modified polypeptides or proteins (e.g., glycosylated, acetylated, phosphorylated, etc.).

"Polynucleotide" or "nucleic acid sequence" refers to a polymeric form of nucleotides at least 2 bases in length. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA or RNA which is incorporated into a viral vector. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can also refer to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAS or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

The polypeptides, vectors, retroviruses, antibodies, and polynucleotides according to the present invention are preferably isolated and/or purified, and can for example be produced using recombinant methods known to one skilled in the art.

Sequence Homology:

The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences will be.

Methods of alignment of sequences for comparison are well known in the art. Various programs and alignment algorithms are described and present a detailed consideration of sequence alignment methods and homology calculations, such as VECTOR NTI.

The NCBI Basic Local Alignment Search Tool (BLAST) is available from several sources, including the National Center for Biotechnology Information (NBCI, Bethesda, Md.) and on the Internet, for use in connection with the sequence analysis programsblastp,biastn,blastx,tblastn and tblastx. It can be accessed at www.ncbi.nlm.nih.gov/BLAST/. A description of how to determine sequence identity using this program is available at www.ncbi.nim.nih.gov/BLAST/blast~help.html.

The term "Homologue" as described herein refers to a molecule characterised by possession of at least 40% sequence identity (such as at least at least 45% sequence identity, for example at least 50% sequence identity, such as at least at least 55% sequence identity, such as at least at least 50% sequence identity, for example at least 55% sequence identity, such as at least at least 60% sequence identity, for example at least 65% sequence identity, for example at least 70% sequence identity, such as at least at least 75% sequence identity, for example at least 80% sequence identity, such as at least at least 85% sequence identity, for example at least 87% sequence identity, such as at least at least 90% sequence identity, for example at least 91% sequence identity, such as at least at least 92% sequence identity, for example at least 93% sequence identity, such as at least at least 94% sequence identity, for example at least 95% sequence identity, such as at least at least 96% sequence identity, for example at least 97% sequence identity, such as at least at least 98% sequence identity, for example at least 98.5% sequence identity, such as at least at least 99% sequence identity, for example at least 99.5% sequence identity) counted over the full length alignment with the disclosed polypeptide or polynucleotide sequence using e.g. the NCBI Basic Blast 2.0, gappedblast with databases such as the nr or swissprot database. Alternatively, one may manually align the sequences and count the number of identical amino acids or nucleotides. This number divided by the total number of amino acids or nucleotide in your sequence multiplied by 100 results in the percent identity.

Chimeric Viral Envelope Polypeptide

In a first aspect of the present invention is provided a chimeric viral envelope polypeptide comprising:

(i) a first polypeptide sequence consisting of the polypeptide sequence of a gamma retrovirus envelope polypeptide, or a homologue or fragment thereof;

wherein into said first polypeptide sequence has been inserted or attached at one end:

(ii) a second polypeptide sequence comprising a receptor-binding domain of a second, different viral envelope polypeptide, or a fragment or homologue thereof, wherein said second polypeptide sequence further optionally comprises one or more flexible linker sequence(s).

Said chimeric viral envelope polypeptide is preferably isolated and/or purified.

First Polypeptide Sequence

The first polypeptide sequence of the chimeric viral envelope polypeptide according to the present invention comprises or consists of the polypeptide sequence of a gamma retrovirus envelope polypeptide, or a homologue or fragment thereof.

Said first polypeptide can for example be a gamma retrovirus envelope polypeptide, wherein said gamma retrovirus is selected from the group consisting of ecotropic viruses, polytropic viruses, amphotropic viruses and xenotropic viruses. Thus, said gamma retrovirus can be selected from the group consisting of a polytropic, amphotropic, or xenotropic gamma retroviruses. In another embodiment, said gamma retrovirus is selected from the group consisting of a polytropic or amphotropic gamma retroviruses. In another embodiment, said gamma retrovirus is polytropic, such as selected from the group consisting of: SL3-2, MCF-247, MCF CI-3, ERV-1, Friend MCF, Friend SFV, Invitro MCF, MCF 1223, MLV DBA/2, Mo-MCF, Ns-6(186)MCF, Rauscher sfv, "Endogenous from 129 Glx+ mice", Ampho-MCF, MCF (Ter-Grigorov), MCF (Brosclus), Friend MCF#2, R-XC, Gibbon ape leukemia virus (GaLV), Feline leukemia virus (FeLV) subtypes A, B, and C, Koala Retrovirus (KoRV) and Xeno R-MC1-1. These viral types are described in more detail in Example 5.

In another embodiment, said gamma retrovirus is amphotropic, such as selected from the group consisting of: 10A1 and AKV. These viral types are described in more detail in Example 5.

In another embodiment, said gamma retrovirus is xenotropic, such as selected from the group consisting of: DG-75 Xeno, Xeno NZ8-9-1, Xeno CWM-S-5X, Xeno Bxv-1-related, and 40701.

These viral types are described in more detail in Example 5.

In another embodiment, said gamma retrovirus is ecotropic, such as selected from the group consisting of: SL3-3, Friend, Maloney, Friend fass and Consensus virus. These viral types are described in more detail in Example 5.

In another embodiment, said gamma retrovirus is mouse leukaemia virus (MLV), such as a polytropic MLV or SL3-2. Thus, in one embodiment of the present invention is provided a chimeric viral envelope polypeptide wherein the first polypeptide sequence comprises or consists of the polypeptide sequence of the SL3-2 murine leukaemia virus envelope polypeptide, or fragment or homologue thereof.

In one embodiment, the first polypeptide is an envelope protein from the Murine Leukaemia Virus (MLV) strain SL3-2, which is capable of infecting murine cells through usage of the polytropic receptor encoded by the Rmcl locus, but lacks the ability of infecting human cells expressing the corresponding xenotropic receptor encoded by the RMC1 locus.

It is preferred that the first polypeptide sequence has a sequence that is at least 80% identical to the amino acid sequence shown in SEQ ID NO:2 (the SL3-3 envelope polypeptide), or is a fragment of a sequence that is at least 80% identical to the amino acid sequence shown in SEQ ID NO:2. Thus, the first polypeptide sequence can have a sequence that is at least 85% identical to the amino acid sequence shown in SEQ ID NO:2, or is a fragment of a sequence that is at least 85% identical to the amino acid sequence shown in SEQ ID NO:2. For example, said first polypeptide sequence can have a sequence that is at least 90% identical to the amino acid sequence shown in SEQ ID NO:2, or is a fragment of a sequence that is at least 90% identical to the amino acid sequence shown in SEQ ID NO:2. For example, said first polypeptide sequence can have a sequence that is at least 95% identical to the amino acid sequence shown in SEQ ID NO:2, or is a fragment of a sequence that is at least 95% identical to the amino acid sequence shown in SEQ ID NO:2. For example, said first polypeptide sequence can have a sequence that is at least 95% identical to the amino acid sequence shown in SEQ ID NO:2, or is a fragment of a sequence that is at least 95% identical to the amino acid sequence shown in SEQ ID NO:2. For example, said first polypeptide sequence has a sequence that is at least 98% identical to the amino acid sequence shown in SEQ ID NO:2, or is a fragment of a sequence that is at least 98% identical to the amino acid sequence shown in SEQ ID NO:2. For example, said first polypeptide sequence is the envelope polypeptide of a polytropic murine leukaemia virus. For example, said first polypeptide sequence can comprise or consist of SEQ ID NO: 2, or a fragment thereof.

It has also been found that changing specific amino acids within the VR3 region of this MLV SL3-2 envelope polypeptide, or a polytropic homologue thereof, enables alteration of the host tropism of said envelope polypeptide. The present inventors have pin-pointed exactly which amino acid that is essential for this host tropism shift. Thus, in the case that the first polypeptide is homologous to SEQ ID NO:2, one embodiment is that said first polypeptide includes at least one substitution in the VR3 region, or a region homologous thereto. In the present context, the term "VR3 region" comprises all of the amino acids found between the residue found at two positions after the conserved tryptophan 197 and the residue before the conserved aspartic acid 214 (according to the sequence shown in SEQ ID NO: 2) including these two positions. In one embodiment of the present invention, said first polypeptide includes at least one substitution in the region homologous to the VR3 region, such as 1, 2, 3, 4, 5 or 6 substitutions in the VR3 region. Examples of substitutions which are likely to provide the same effect are alanine, asparagine, aspartic acid, cysteine, glutamic acid, phenylalanine, glycine, histidine, isoleucine, lysine, leucine, methionine, proline, glutamin, serine, threonine, valine, tryptophan or tyrosine.

In one preferred embodiment, the substitution changes the arginine to glycine. In another preferred embodiment the substitution results in a methionine. For example, said substitution can be at position 212 in SEQ ID NO: 2, or a region homologous thereto. It is preferred that said at least one substitution alters the host tropism of a virus or an infectious particle comprising said polypeptide, in a manner described in more detail in WO 03/097674 (Pipeline Biotech A/S).

Examples of suitable first polypeptide sequences (with the insert site marked for insertion of the second polypeptide sequence) have SEQ ID NO: 33-41, 49, 51, 53, 55, 57 or 59, or are homologues and/or fragments thereof. These are e.g. encoded by polynucleotides with SEQ ID NO: 48, 50, 52, 54, 56 or 58, or suitable homologues and/or fragments thereof.

Second Polypeptide Sequence

Into the first polypeptide sequence of the chimeric viral envelope polypeptide according to the present invention is inserted or attached at one end: a second polypeptide sequence comprising a receptor-binding domain of a second, different viral envelope polypeptide, or a fragment or homologue thereof. Said second polypeptide sequence is preferably inserted within a site homologous to amino acids 80-106 in SEQ ID NO:2, such as within a site homologous to amino acids 80-106 in SEQ ID NO:2, such as within a site homologous to amino acids 80-100 in SEQ ID NO:2, or such as within a site homologous to amino acids 80-90 in SEQ ID NO:2, or such as within a site homologous to amino acids 90-106 in SEQ ID NO:2, or such as within a site homologous to amino acids 90-95 in SEQ ID NO:2, or such as within a site homologous to amino acids 80-82 in SEQ ID NO:2, or such as within a site homologous to amino acids 80-84 in SEQ ID NO:2.

In another preferred embodiment of the present invention, said second polypeptide sequence is inserted within a site homologous to within amino acids 152-181 in SEQ ID NO:2, such as within a site homologous to amino acids 152-164 in SEQ ID NO:2, or such as within a site homologous to amino acids 152-160 in SEQ ID NO:2, or such as within a site homologous to amino acids 160-170 in SEQ ID NO:2, or such as within a site homologous to amino acids 165-175 in SEQ ID NO:2, or such as within a site homologous to amino acids 175-181 in SEQ ID NO:2, or such as within a site homologous to amino acids 160-165 in SEQ ID NO:2, or such as within a site homologous to amino acids 152-158 in SEQ ID NO:2.

In another preferred embodiment of the present invention, said second polypeptide sequence is inserted into a site homologous to a.a. 192-213 in SEQ ID NO:2, such as within a site homologous to amino acids 192-202 in SEQ ID NO:2, or such as within a site homologous to amino acids 198-203 in SEQ ID NO:2, or such as within a site homologous to amino acids 205-213 in SEQ ID NO:2, or such as within a site homologous to amino acids 200-213 in SEQ ID NO:2.

In another preferred embodiment of the present invention, said second polypeptide sequence is inserted into a site homologous to a.a. 229-281 in SEQ ID NO:2, such as within a site homologous to amino acids 229-259 in SEQ ID NO:2, or such as within a site homologous to amino acids 239-269 in SEQ ID NO:2, or such as within a site homologous to amino acids 249-281 in SEQ ID NO:2, or such as within a site homologous to amino acids 259-281 in SEQ ID NO:2, or such as within a site homologous to amino acids 271-281 in SEQ ID NO:2, or such as within a site homologous to amino acids 235-245 in SEQ ID NO:2, or such as within a site homologous to amino acids 245-255 in SEQ ID NO:2.

The inserted sequence can be inserted between two contiguous amino acids of the insert site, or can replace one or more amino acids at said insert site, such as replacing one, two, three or more amino acids at the insert site, such as replacing 1-10 amino acids at the insert site.

The second polypeptide sequence comprises a receptor-binding domain of a second, different viral envelope polypeptide.

Said receptor-binding domain of said second, different viral envelope polypeptide is in one embodiment a co-receptor-binding domain, or a fragment or homologue thereof.

In one preferred embodiment of the present invention, said receptor binding region is a receptor binding region of a human virus, such as e.g. Vesicular stomatitis virus (VSV) (Protein G), cytomegalovirus envelope (CMV), HIV, or influenza virus hemagglutinin (HA).

For example, said receptor-binding domain of said second, different viral envelope polypeptide can be a fragment or homologue of the influenza hemagglutinin or the V3 domain of HIV.

Thus, in one embodiment of the present invention, the second, different viral envelope polypeptide is the V3-loop domain of HIV or a fragment or homologue thereof. Said HIV may for example be a CXCR-4 tropic HIV and/or, a strain of HIV-1 or a strain of HIV-2.

Thus, in one preferred embodiment of the present invention the receptor-binding domain of the second, different viral envelope polypeptide has a sequence selected from the group consisting of: any of SEQ ID NO: 9-32, or a fragment or homologue thereof. For example, said sequence can be selected from the group consisting of a fragment or homologue of any of SEQ ID NO: 9-16. In another embodiment, said sequence can be selected from the group consisting of a fragment or homologue of any of SEQ ID NO: 9-12. In another embodiment, said sequence can be selected from the group consisting of a fragment or homologue of any of SEQ ID NO: 16-24. In another embodiment, said sequence can be selected from the group consisting of a fragment or homologue of any of SEQ ID NO: 16-20. In another embodiment, said sequence can be selected from the group consisting of a fragment or homologue of any of SEQ ID NO: 21-25. In another embodiment, said sequence can be selected from the group consisting of a fragment or homologue of any of SEQ ID NO: 25-32. In another embodiment, said sequence can be selected from the group consisting of a fragment or homologue of SEQ ID NO: 32.

In another embodiment of the present invention, the receptor binding region is a hepatitis B virus surface protein binding region, preferably binding to a liver cell.

In another embodiment of the present invention, the receptor binding region is the receptor binding region of gp46 of HTLV-I virus, preferably binding to a T cell.

Optionally, a portion of the first retroviral envelope protein is deleted and the second polypeptide is inserted into said deleted portion. Preferably, the only portion of the retroviral envelope protein that is deleted is (i) a portion or all of the receptor binding region, (ii) a portion of the receptor binding region and a portion or all of the hinge region, or (iii) all of the receptor binding region and a portion or all of the hinge region. Thus, in one embodiment of the present invention, a portion of the receptor binding region of the first polypeptide sequence is deleted, for example all of the receptor binding region of the retroviral envelope protein is deleted, for example all of the receptor binding region and a portion of the hinge region of the first polypeptide are deleted.

Flexible Linker Sequence

The second polypeptide sequence of the chimeric viral envelope polypeptide further optionally comprises one or more flexible linker sequence(s) of one or more amino acid residues as known by one skilled in the art—for example 2-30 amino acid residues, such as 2-20 amino acid residues, such as 2-10 amino acid residues. The linker sequences are preferably placed at the N-terminal and/or C-terminal of the insert region, preferably whereby such linkers increase rotational flexibility and/or minimize steric hindrance of the modified envelope polypeptide. Thus, in one embodiment of the present invention, a linker sequence is positioned at each end of the second polypeptide sequence, that is to say at either end of the second polypeptide sequence. Any suitable linker sequence known to one skilled in the art can be used: examples of suitable linker sequences include, but are not restricted to, linkers described by Argos et al., 1990 (Argos, 1990). One preferred linker sequence has the polypeptide sequence SGGSG. Other preferred linkers can for example be QGIYQC or CG or QGIYQC or CG, or homologues thereof with one, two or more amino acid substitutions.

Preferred Sequences of the Chimeric Viral Envelope Polypeptide According to the Present Invention In one embodiment of the present invention, the chimeric viral envelope polypeptide has a sequence comprising or consisting of any of SEQ ID NO: 6-8 or 45-47, or a fragment or homologue thereof. Thus, the chimeric viral envelope polypeptide can comprise or consist of SEQ ID NO: 6, or a homologue thereof. In another embodiment, said chimeric viral envelope polypeptide can comprise or consist of SEQ ID NO: 7, or a homologue thereof. In another embodiment, said chimeric viral envelope polypeptide can comprise or consist of SEQ ID NO: 8, or a homologue thereof. In another embodiment, said chimeric viral envelope polypeptide can comprise or consist of SEQ ID NO: 45, or a homologue thereof. In another embodiment, said chimeric viral envelope polypeptide can comprise or consist of SEQ ID NO: 46, or a homologue thereof. In another embodiment, said chimeric viral envelope polypeptide can comprise or consist of SEQ ID NO: 47, or a homologue thereof.

Polynucleotide

The present invention further discloses isolated nucleic acid sequences capable of encoding the envelope polypeptide sequences of the present invention.

As known to a person skilled in the art, a codon of an amino acid can be generated by various nucleic acid sequences, thus the present invention relates to all isolated nucleic acid sequences capable of encoding an envelope polypeptide having an amino acid sequence as described in the present application. Thus, the present invention relates to an isolated polynucleotide comprising or consisting of a polynucleotide encoding the chimeric viral envelope polypeptide according to the present invention.

Thus, in one embodiment, said polynucleotide has a sequence comprising or consisting of SEQ ID NO: 3, or a homologue thereof. In another embodiment, said polynucleotide has a sequence comprising or consisting of SEQ ID NO: 4, or a homologue thereof. In another embodiment, said polynucleotide has a sequence comprising or consisting of SEQ ID NO: 5, or a homologue thereof. In another embodiment, said polynucleotide has a sequence comprising or consisting of SEQ ID NO: 42, or a homologue thereof. In another embodiment, said polynucleotide has a sequence comprising or consisting of SEQ ID NO: 43, or a homologue thereof. In another embodiment, said polynucleotide has a sequence comprising or consisting of SEQ ID NO: 44, or a homologue thereof.

The polynucleotides may be constructed by genetic engineering techniques known to those skilled in the art. For example, a first expression plasmid may be constructed which includes a polynucleotide encoding the unmodified envelope. The plasmid then is engineered such that a polynucleotide encoding the second polypeptide is inserted between two codons encoding consecutively numbered amino acid residues of the first envelope polypeptide, or is engineered such that a polynucleotide encoding a portion of the unmodified envelope is removed, whereby such portion may be replaced with a polynucleotide encoding the second polypeptide. The polynucleotide encoding the second polypeptide may be contained in a second expression plasmid or may exist as a naked polynucleotide sequence. The polynucleotide encoding the second polypeptide or the plasmid containing such polynucleotide is cut at appropriate restriction enzyme sites and cloned into the first expression plasmid which also has been cut at appropriate restriction enzyme sites. The resulting expression plasmid thus includes a polynucleotide encoding the chimeric envelope polypeptide. Such polynucleotide then may be cloned out of the expression plasmid, and into a vector, such as a retroviral plasmid vector. The resulting vector, which includes the polynucleotide encoding the modified envelope protein, and which also may include a polynucleotide encoding a heterologous protein or peptide, is transfected into an appropriate packaging cell line to form a producer cell line for generating the modified envelope protein, such as for generating the retroviral vector particles of the present invention. Alternatively, a naked polynucleotide sequence encoding the modified envelope protein can be transfected into a "pre-packaging" cell line including nucleic acid sequences encoding the gag and pol proteins, thereby forming a packaging cell line, or is transfected into a packaging cell line including nucleic acid sequences encoding the gag, pol, and wild-type (i.e., unmodified) env proteins, thereby forming a packaging cell line including nucleic acid sequences encoding wild-type env protein and the modified envelope protein. Such packaging cells then may be transfected with a retroviral plasmid vector, which may include a nucleic acid sequence encoding a heterologous protein or peptide, thereby forming a producer cell line for generating retroviral vector particles including the modified envelope protein. Such a polynucleotide thus may be contained in the above-mentioned retroviral vector particle, or in a producer cell for generating the above-mentioned retroviral vector particle.

The polynucleotide according to the present invention can be comprised in a suitable vector known to one skilled in the art. Thus, one aspect of the present invention relates to a vector comprising a polynucleotide encoding the chimeric viral envelope polypeptide according to the present invention. A vector in the present context preferably comprises all vectors capable of directing expression of any given envelope by directing expression of vector DNA into RNA, poly-adenylation of said RNA, splicing of said RNA, if necessary, export out of the nucleus of said RNA, and finally translation of said RNA outside of the nucleus. The vector can for example be a plasmid, or a recombinant virus particle.

Thus, the vector can also in one embodiment comprise the chimeric viral envelope polypeptide encoded by said polynucleotide, preferably as part of the viral envelope. The virus particle is preferably replication competent. For example, the virus can comprise a heterologous translation cassette, such as a heterologous translation cassette comprising or consisting of an IRES-gene element.

Figure 3:
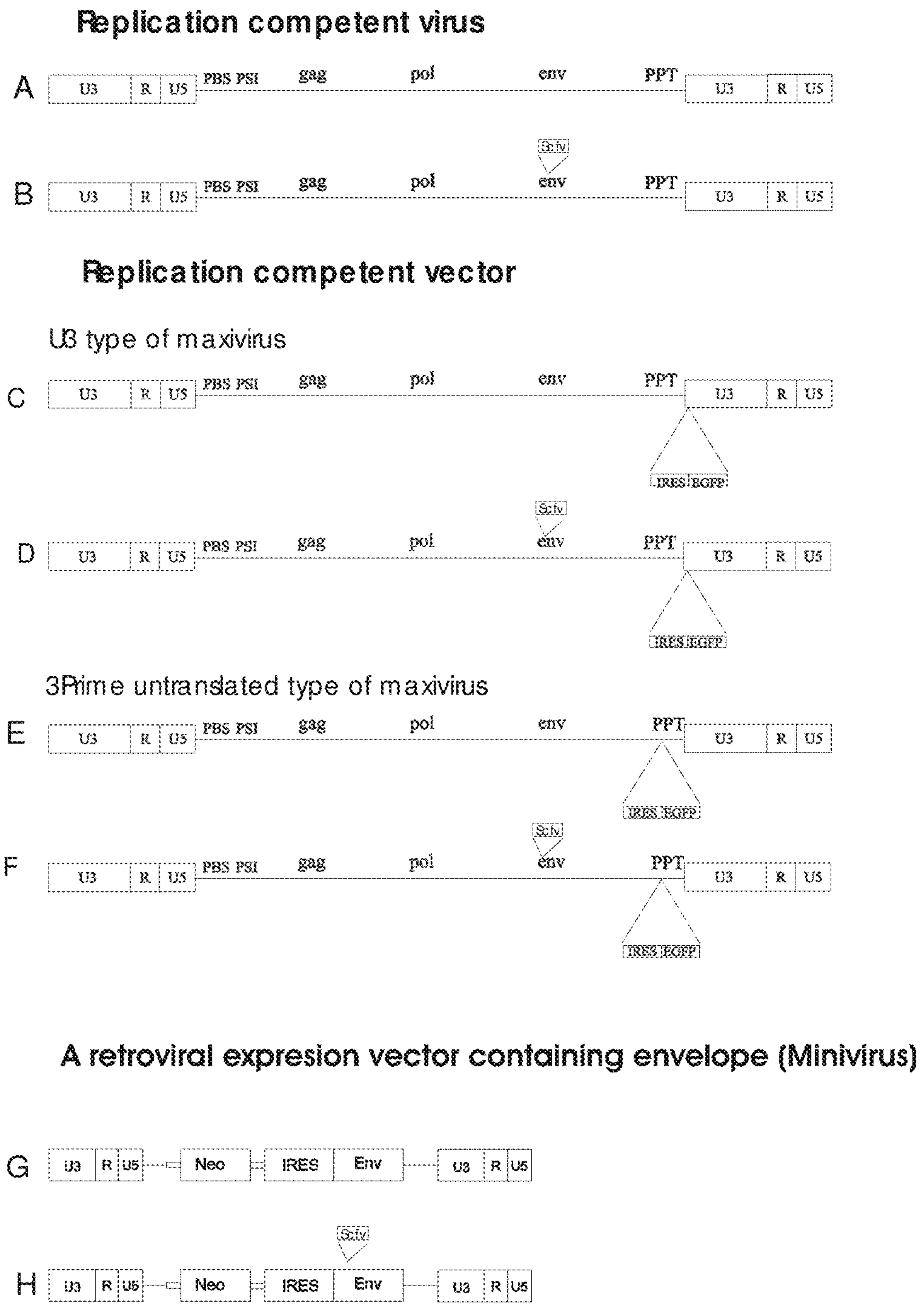
FIG. 3:
Depicted in panel A is a wild type replication competent virus.
In panel B said replication competent virus has an insert ("ScFv") in the envelope for redirection of tropism, which can be any suitable insert sequence, such as those described herein
Panel C and E are replication competent vectors where a heterologous translational cassette has been inserted into either the U3 region panel C or in the 3 un-translated region downstream of the envelope gene Panel E.
Panel D and F are the same as panel C and E except the insert ("ScFv"—although in this case, can be any suitable sequence, as described herein) has been inserted in the envelope for redirection of tropism.
Figure 5D:
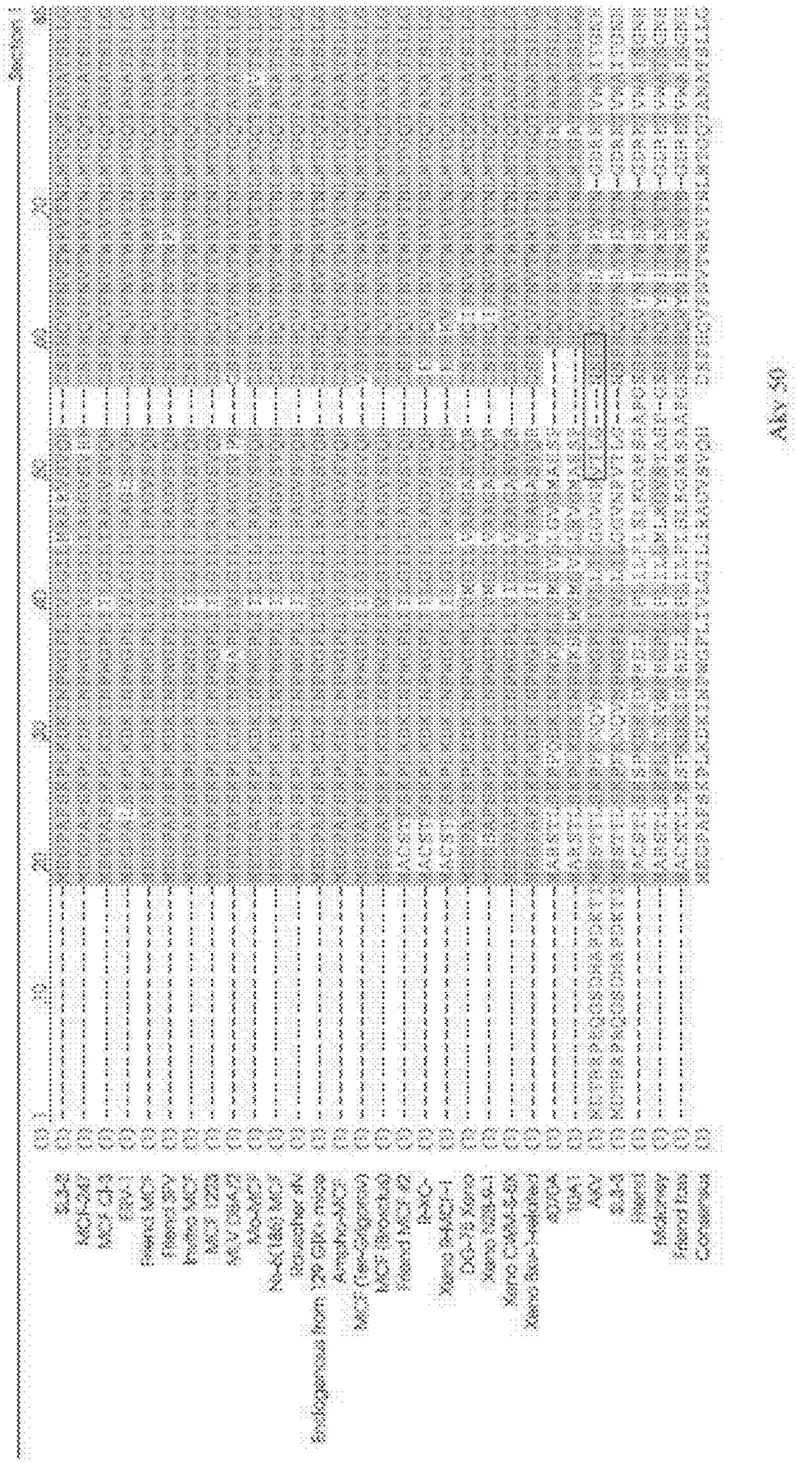
Figure 5F:
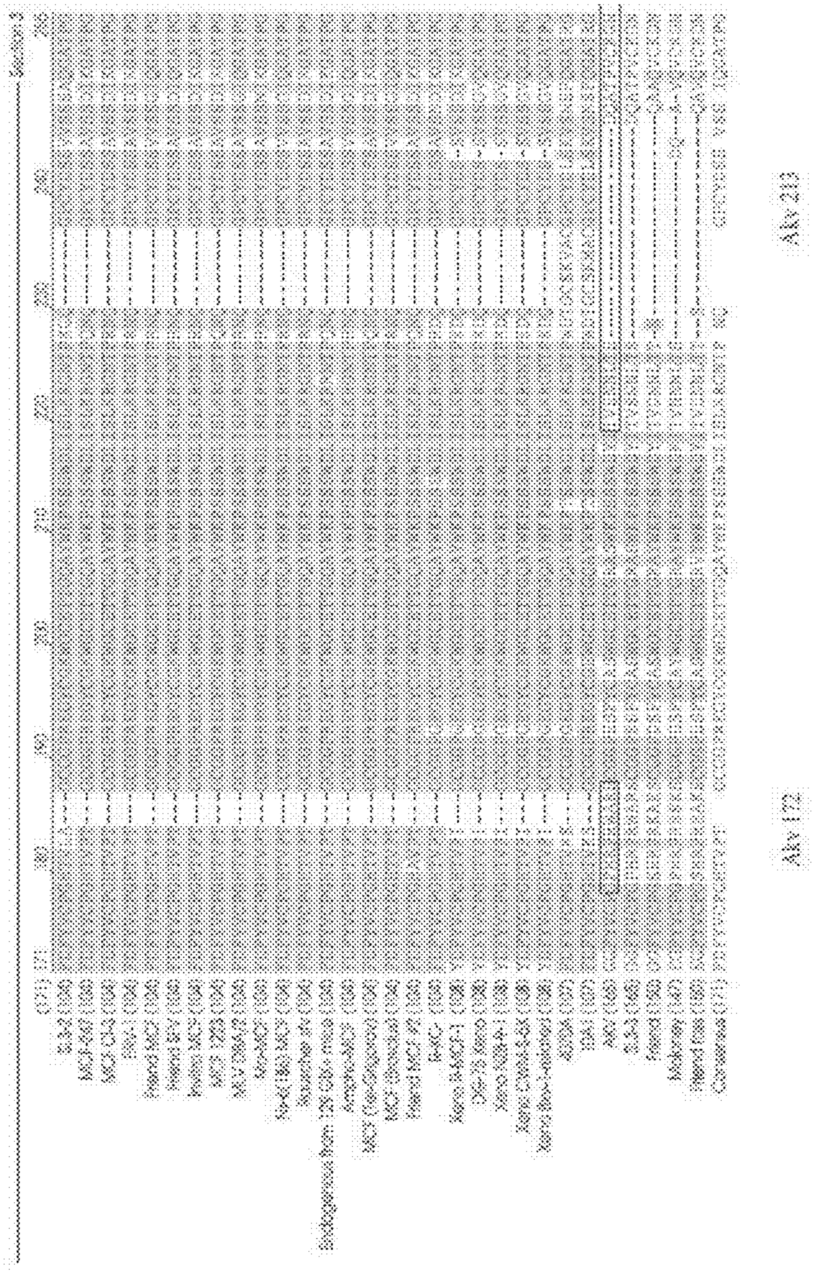
Figure 5G:
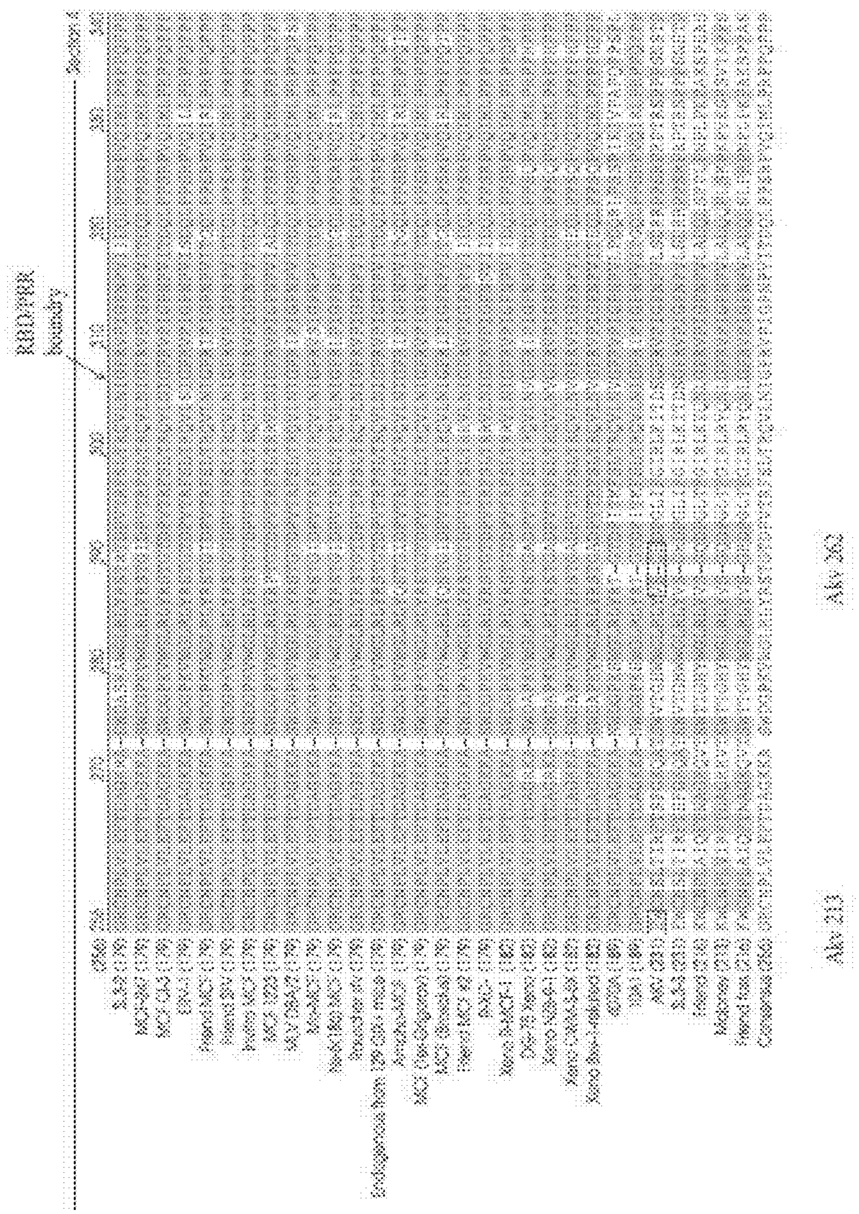

A replication competent retrovirus can further comprise all genes necessary for replication of a retrovirus, and for RNA being exported out of the cell and packaged in proteins expressed by said proteins. Said RNA further comprises all RNA and DNA elements necessary for said RNA to be reverse transcribed into double stranded DNA and integrated into the host genome, as exemplified in FIG. 3 panel A. In panel B this replication competent retrovirus further comprises a heterologous peptide inserted into the envelope gene for redirection of host cell tropism. Only the ScFv is depicted in FIG. 3, but other insertions could be similarly useful.

The exemplified replication competent retroviral vector further comprises a replication competent virus where a heterologous gene is being expressed from a position in the U3 region of the virus, panel C and D, or from a position in the 3 prime untranslated region downstream of the envelope and upstream of the downstream LTR, panel E and F. Said replication competent vectors can further be redirected in host cell tropism by insertion of an ScFv or any heterologous peptide in the envelopes, panel D and F. Only the ScFv is depicted in FIG. 3. Based upon this example, the text of the present application and common knowledge of a person of ordinary skill in the art will be able to make other useful embodiments.

The virus particle is preferably a retroviral vector being capable of transcribed into RNA and capable of being packaged into a retroviral particle, reverse transcribed into double stranded DNA and inserted into the host genome by the retroviral enzymatic machinery. For translation of said envelope an internal ribosome entry site (IRES) has been inserted upstream of the envelope in the exemplified retroviral expression vector, panel G and H. The host cell tropism of said retrovirus can further be redirected by inserting an ScVf or any heterologous peptide in the envelope, panel H. Only the ScFv is depicted in FIG. 3, but other inserts could be similar useful.

A particular embodiment of the present invention relates to any of the replication competent vectors described in the present application and further comprising a heterologous translation cassette.

Thus, a presently preferred particular embodiment relates to a replication competent vector comprising a heterologous translation cassette, wherein said heterologous translation cassette comprises an IRES-gene element.

Another embodiment of the present invention relates to a vector according to the present invention further comprising at least one heterologous gene to be expressed.

In another embodiment, the present application relates to a vector according to the present invention further comprising at least one heterologous gene to be expressed, wherein said expression is directed by a IRES-element.

Embodiments Relating to Gene Therapy

The recombinant virus particle can further comprise an agent for delivery to the target cell, optionally selected from the group consisting of a therapeutic agent or a gene or gene product, which agent is optionally operatively associated with a retroviral packaging sequence. Thus, the virus particle can in one embodiment comprise at least one heterologous gene to be expressed in the host after a gene therapy procedure. Said heterelogous gene to be expressed can for example comprise the polynucleotide encoding the chimeric envelope polypeptide according to the present invention.

The agent is preferably a therapeutic agent, such as a polynucleotide sequence, or a polynucleotide sequence encoding a therapeutic agent.

The polynucleotide encoding the therapeutic agent is under the control of a suitable promoter. Suitable promoters which may be employed include, but are not limited to, the retroviral LTR; the SV40 promoter; the cytomegalovirus (CMV) promoter; the Rous Sarcoma Virus (RSV) promoter; the histone promoter; the polIII promoter, the .beta.-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex Virus thymidine kinase promoter; retroviral LTRS; human growth hormone promoters, and the MxIFN inducible promoter. The promoter also may be the native promoter which controls the polynucleotide encoding the therapeutic agent. It is to be understood, however, that the scope of the present invention is not to be limited to specific foreign genes or promoters.

The polynucleotides encoding the modified envelope polypeptide and the therapeutic agent may be placed into an appropriate vector by genetic engineering techniques known to those skilled in the art. When the modified vector is a retroviral vector particle, the polynucleotides encoding the modified envelope polypeptide and the therapeutic agent can e.g. be placed into an appropriate retroviral plasmid vector.

In one embodiment, the retroviral plasmid vector may be derived from Moloney Murine Leukemia Virus and is of the LN series of vectors, such as those hereinabove mentioned, and described further in Bender, et al., J. Virol., Vol. 61, pgs. 1639-1649 (1987) and Miller, et al., Biotechniques, Vol. 7, pgs 980-990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. patent application Ser. No. 08/340,805, filed Nov. 17, 1994, and in PCT Application No. WO91/10728, published Jul. 25, 1991, and incorporated herein by reference in their entireties.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes at least one desired polynucleotide encoding a therapeutic agent which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980-990 (1989), or any other promoter (e.g., cellular promoters such as eukaryotic cellular promoters including, but not limited to, the histone, pol III, and .beta.-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

Cell Lines and Animal Models

In another embodiment, there is provided a packaging cell which includes a nucleic acid sequence encoding a modified chimeric envelope in accordance with the invention, and which may further include nucleic acid sequences encoding the gag and pol proteins. A producer cell for generating viral particles which includes a modified envelope in accordance with the invention can for example be produced by introducing into such packaging cell either a retroviral vector particle or a retroviral plasmid vector, in each case including a polynucleotide encoding a therapeutic agent. The producer cell line thus generates infectious retroviral particles including the modified chimeric envelope and the polynucleotide encoding the therapeutic agent.

Thus, in another aspect of the present invention is provided a cell transfected with the vector according to the present invention. In one preferred embodiment, said cell is comprised in a stable cell line comprising such cells. The present invention further relates to "packaging cell lines" for producing the vectors of the present invention.

MLV based packaging cells are widespread tools for research. Packaging cells based on ecotropic viruses have the advantage of being harmless to humans and are used in biosafety level 1 laboratories.

One embodiment of the present invention relates to a packaging cell construct comprising the vector comprising a nucleic acid coding for a polypeptide envelope as described in the present application, and optionally a non-viral or viral promoter and poly-adenylation signals.

Another embodiment of the present invention relates to use of any of the vectors according to the present invention for the generation of a packaging cell.

The packaging cell line can for example be engineered to produce the viral Gag, Pol and Env proteins from constructs that lack the packaging signal (to prevent them from being taken up by budding virions). Thus, when a vector is inserted into a packaging cell line, it will be packaged into budding virions and can be transferred into target cells. Representative examples of packaging cell lines include, but are not limited to, the PE501 and PA317 cell lines disclosed in Miller, et al., Biotechniques, Vol. 7 pgs. 980-990 (1989).

In one embodiment, the packaging cell line is a "prepackaging" cell line which includes polynucleotides encoding the gag and pol retroviral proteins, but not the envelope, or env, protein. Examples of such "pre-packaging" cell lines include, but are not limited to, GP8 cells, GPL cells, and GPNZ cells as described in Morgan, et al., J. Virol., Vol. 67, No. 8, pgs. 4712-4721 (August 1993). Such cell lines, upon transduction with the retroviral plasmid vector, generates infectious retroviral particles including the modified, or chimeric, envelope and a polynucleotide encoding the therapeutic agent.

In another embodiment, a retroviral plasmid vector which includes a polynucleotide encoding a modified polynucleotide encoding a modified envelope polypeptide in accordance with the invention and a polynucleotide encoding a therapeutic agent is used to transduce a packaging cell line including nucleic acid sequences encoding the gag, pol, and wild-type (i.e., unmodified) env retroviral proteins. Examples of such packaging cell lines include, but are not limited to, the PE501, PA317 (ATCC No. CRL 9078), .psi.-2, .psi.-AM, PA12, T19-14X, VT-19-17-H2, .psi.CRE, .psi.CRIP, GP+E-86, GP+envAm12, and DAN cell lines as described in Miller, Human Gene Therapy, Vol. 1, pgs. 5-14 (1990), which is incorporated herein by reference in its entirety. The vector may transduce the packaging cells through any means known in the art. Such means include, but are not limited to, electroporation, and use of liposomes, such as hereinabove described, and $CaPO_4$ precipitation. Such producer cells generate infectious retroviral vector particles which include the modified envelope, the wild-type retroviral envelope, a polynucleotide encoding the modified, or chimeric, envelope, and a polynucleotide encoding a therapeutic agent.

In another preferred embodiment, said cell is comprised in an animal model using methods known to one skilled in the art. Said model is preferably a mouse, Antibodies The present invention further relates to an antibody capable of specifically binding one of the molecules provided in the present invention, such as a chimeric envelope polypeptide according to the present invention, and/or a retroviral particle expressing said chimeric envelope polypeptide.

The term “antibody” refers to intact immunoglobulin molecules as well as to fragments thereof, such as Fab, F(ab')2, and Fv fragments, which are capable of binding an epitopic determinant. Antibodies can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

Therapeutic Methods Using any of the Aspects of the Present Invention

Any of the polynucleotide, vectors and/or envelope polypeptides provided herein can be used in therapeutic methods and/or prophylaxis of disease, such as viral disease. These polynucleotides, vectors and/or envelope polypeptides are herein below described as “constructs”, by which it is meant that any of the polynucleotides, vectors and/or envelope polypeptides can advantageously be used. Preferably, said construct is a retroviral particle as described herein.

Thus, the present invention relates in one embodiment to a therapeutic method for treatment of an individual in need thereof, said method comprising administering a construct according to the present invention to an individual in need thereof.

The present invention further relates to a method for prevention or reduction of a viral infection in an individual in need thereof, comprising the steps of:

(i) providing constructs (preferably virus particles) according to the present invention as disclosed herein;

(ii) causing said constructs to contact a target population of said individual’s cells, wherein cells within said target population comprise a receptor capable of being specifically bound by said construct, (iii) allowing the construct to bind said receptor.

It is preferred that said binding of a construct to said receptor blocks binding of other viral molecules to the cell bound by said construct.

In one embodiment, the bound construct (preferably a recombinant virus particle) is taken up into the cell which it has specifically bound.

The binding can also lead to prevention and/or reduction of syncitial formation between another, pathogenic virus and the cell bound by the construct of the present invention.

Another effect of the binding can be reduction in the expression level of the bound viral receptor (such as a viral co-receptor, such as the CXCR4 co-receptor) on the surface of the cell bound by said construct.

In one embodiment of the above method, an agent is delivered to said cell by said construct (preferably a virus particle). Said agent can for example be an anti-viral drug or a polynucleotide.

Where said agent is a polynucleotide, said method is advantageous to use for gene therapy. The polynucleotide introduced into the cell by said gene therapy method can for example be the polynucleotide according to the present invention encoding the chimeric envelope polypeptides described herein, however said polynucleotide can in equally be another anti-viral polynucleotide, such as encoding a polypeptide with anti-viral activity. The term “introducing” as used herein encompasses a variety of methods of transferring polynucleotides into a cell, such methods including transformation, transduction, transfection, and transinfection.

Thus, retroviral vector particles of the present invention can be used for introducing polynucleotides into cells for gene therapy purposes. In one approach, cells are obtained from a patient, and retroviral vector particles are used to introduce a desired polynucleotide into the cells, and such modified cells are returned to the patient with the engineered cells for a therapeutic purpose. In another approach, retroviral vector particles may be administered to the patient in viva, whereby the retroviral vector particles transduce cells of the patient in vivo.

Methods for in vivo and ex vivo gene therapy are well known in the art, such as for example described in e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, each of which are incorporated herein by reference in their entirety). An increasing number of these methods are currently being applied in human clinical trials (Morgan, R., 1993, BioPharm, 6(1):32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

It may be preferable to remove the majority of a target cell population prior to therapy, for example surgically.

In fact, any of the therapies described herein can be in vivo or ex vivo, that is to say that said contacting occurs outside the individual, and then the target population is returned to the individual’s body.

The present invention further provides a therapeutic method for specifically tethering a chimeric retroviral envelope polypeptide to a specific cell type and preventing or reducing retroviral infection, comprising the steps of:

(i) providing an enveloped virus expressing a chimeric retroviral envelope polypeptide as disclosed herein, (ii) allowing said chimeric envelope polypeptide to specifically contact a cell of said specific cell type, (iii) allowing the outer membrane of the virus to undergo a hemifusion process with the outer membrane of said cell.

Said specific cell type can for example be T cells, a cell expressing CXCR5 or CXCR4, or macrophage cells.

In another embodiment of the present invention is provided a method for treatment or prevention of a viral disease, comprising administering a construct as disclosed herein to an individual in need thereof. Said construct is preferably the viral envelope polypeptide as disclosed herein, or the recombinant virus particle as disclosed herein. Said viral disease is preferably selected from HIV (for example, HIV-1 or HIV-1)

Target Cell Populations for any of the Therapeutic Methods of the Present Invention In one preferred embodiment of the therapeutic method of the present invention, the target cell population comprises or consists of T cells. In another preferred embodiment of the therapeutic method of the present invention, said target population comprises or consists of cells expressing CXCR5 or CXCR4. In another preferred embodiment of the therapeutic method of the present invention, said target population comprises or consists of macrophage cells.

Further example of cells which may be targeted for binding, infection or transduction with the chimeric envelope polypeptides or vector particles of the present invention include, but are not limited to, T cell, endothelial cells, tumor cells, chondrocytes, fibroblasts and fibroelastic cells of connective tissues; osteocytes and osteoblasts in bone; endothelial and smooth muscle cells of the vasculature; epithelial and subepithelial cells of the gastrointestinal and respiratory tracts; vascular cells, connective tissue cells, and hepatocytes of a fibrotic liver, the reparative mononuclear and granulocytic infiltrates of inflamed tissues, liver cells, T-cells, lymphocytes, endothelial cells, T4 helper cells, or macrophages.

In another embodiment, the receptor binding region is a hepatitis B virus surface protein binding region, and the target cell is e.g. a liver cell.

Pharmaceutical Formulations, Administration and Dosages

In another aspect of the present invention is further disclosed a pharmaceutical formulation comprising any of the constructs described herein, such as a chimeric envelope polypeptide or viral particle as disclosed herein.

The constructs of the present invention may be directly administered to a desired target cell ex vivo, and such cells may then be administered to a patient as part of a gene therapy procedure.

Although the chimeric polypeptides and/or vector particles may be administered directly to a target cell, they may also be engineered such that they are resistant to inactivation by human serum, and thus may be administered to a patient by (e.g. intravenous) injection, and travel directly to a desired target cell or tissue without being inactivated by human serum.

The vector particles, may be concentrated from dilute vector stocks in vitro by contacting a dilute vector stock with an extracellular matrix component to which the modified viral surface protein will bind. Such binding enables one to obtain a concentrated stock of the vector particles.

In addition, the modified viral surface proteins of the present invention may be employed to form proteoliposomes; i.e., the modified viral surface protein forms a portion of the liposome wall. Such proteoliposomes may be employed for gene transfer or for drug delivery to cells located at a site of an exposed extracellular matrix component.

Any of the constructs disclosed herein may be administered to a host in an amount effective to produce a therapeutic effect in the host. The host may be a mammalian host, which may be a human or non-human primate host. The exact dosage which may be administered is dependent upon a variety of factors, including the age, sex, and weight of the patient, the cells which are to be transduced, the therapeutic agent which is to be administered, and the severity of the disorder to be treated.

The constructs, such as viral particles, may be administered systemically, such as, for example, by intravenous, intracolonic, intratracheal, intraperitoneal, intranasal, intravascular, intrathecal, intraarterial, intracranial, intramarrow, intrapleural, intradermal, subcutaneous, intramuscular, intraocular, intraosseous and/or intrasynovial administration. The constructs also may be administered topically.

Rational Drug Design

Another aspect of the present invention relates to use of the polypeptides disclosed herein for rational drug design.

To facilitate understanding of the invention, a number of terms are defined below.

The term "polynucleotide" or "nucleic acid sequence" refers to a polymeric form of nucleotides at least 2 bases in length. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA or RNA which is incorporated into a viral vector. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein can also refer to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

The term "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

A "detectable label" refers to a reporter molecule or enzyme that is capable of generating a measurable signal and is covalently or noncovalently joined to a polynucleotide or polypeptide.

A "fragment" is a unique portion of the polynucleotide encoding the chimeric retroviral envelope polypeptide of the present invention which is identical in sequence to but shorter in length than the parent sequence. Similarly the term 'fragment' refers to the chimeric retroviral envelope polypeptide of the present invention A fragment may comprise up to the entire length of the defined sequence, minus one nucleotide or amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

The term "Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

The term "insertion" refer to changes in an amino acid or nucleotide sequence resulting in the addition of one or more amino acid residues or nucleotides, respectively.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

The term "operably linked" refers to the situation in which a first nucleic acid sequence, amino acid sequence or ligand is placed in a functional relationship with a second nucleic acid sequence, amino acid sequence or ligand. For instance, a promoter is operably linked to a coding sequence if the promoter affects the transcription or expression of the coding sequence. Operably linked DNA sequences or protein or ligands may be in close proximity or contiguous and, where necessary to join two protein coding regions, in the same reading frame.

Homologies

Methods of alignment of sequences for comparison are well-known in the art. Various programs and alignment algorithms are described and present a detailed consideration of sequence alignment methods and homology calculations, such as VECTOR NTI. The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences will be.

The NCBI Basic Local Alignment Search Tool (BLAST) is available from several sources, including the National Center for Biotechnology Information (NBCI, Bethesda, Md.) and on the Internet, for use in connection with the sequence analysis programs blastp, blastn, blastx, tblastn and tblastx. It can be accessed at www.ncbi.nlm.nih.gov/BLAST/. A description of how to determine sequence identity using this program is available at www.ncbi.nlm.nih.gov/BLAST/blast_help.html.

Homologs of the disclosed polypeptides are typically characterised by possession of at least 94% sequence identity counted over the full length alignment with the disclosed amino acid sequence using the NCBI Basic Blast 2.0, gapped blastp with databases such as the nr or swissprot database.

Alternatively, one may manually align the sequences and count the number of identical amino acids. This number divided by the total number of amino acids in your sequence multiplied by 100 results in the percent identity.

Chimeric Retroviral Envelope Polypeptide

In a first aspect of the present invention is provided a chimeric viral envelope polypeptide comprising (i) an envelope polypeptide, or fragment thereof, (ii) a polypeptide sequence of a receptor binding region, ligand or polypeptide sequence of a ligand binding region, and optionally a linker sequence, wherein the receptor binding domain of said envelope polypeptide has a sequence that is at least 36% identical to the amino acid sequence shown in SEQ ID NO: 60, or is a fragment of a sequence that is at least 36% identical to the amino acid sequence shown in SEQ ID NO: 60.

However, in other embodiments of the present invention the said receptor binding domain has a sequence that is for example at least 40%, such as at least 45%, for example at least 50%, such as at least 55%, for example at least 60%, such as at least 65%, for example at least 67%, such as at least 70%, for example at least 72%, such as at least 75%, for example at least 77%, such as at least 80%, for example at least 81%, such as at least 82%, for example at least 83%, such as at least 84%, for example at least 85%, such as at least 86%, for example at least 87%, such as at least 88%, for example at least 89%, such as at least 90%, for example at least 91%, such as at least 92%, for example at least 93%, such as at least 94%, for example at least 95%, such as at least 96%, for example at least 97%, such as at least 98%, for example at least 99% identical to the amino acid sequence shown in SEQ ID NO: 60.

In another embodiment of the present invention said receptor binding domain of said envelope polypeptide is a fragment of a sequence that is for example at least at least 40%, such as at least 45%, for example at least 50%, such as at least 55%, for example at least 60%, such as at least 65%, for example at least 67%, such as at least 70%, for example at least 72%, such as at least 75%, for example at least 77%, such as at least 80%, for example at least 81%, such as at least 82%, for example at least 83%, such as at least 84%, for example at least 85%, such as at least 86%, for example at least 87%, such as at least 88%, for example at least 89%, such as at least 90%, for example at least 91%, such as at least 92%, for example at least 93%, such as at least 94%, for example at least 95%, such as at least 96%, for example at least 97%, such as at least 98%, for example at least 99% identical to the amino acid sequence shown in SEQ ID NO: 60.

The envelope polypeptide of the chimeric retroviral envelope according to claim 66 may derive from gamma retroviruses. In one embodiment the gammaretroviruses are murine leukaemia viruses, such as SL3-2 (SEQ ID NO: 60), for example FeLV-B, such as MCF 247, for example MCF CI-3, such as ERV-1, for example Friend MCF, such as .Friend SFV, for example Invitro MCF, such as MCF 1223, for example MLV DBA/2, such as Mo-MCF, for example Ns-6(186) MCF, such as Rauscher sfv, for example Endogenous from 129 GIX+ mice, such as Ampho-MCF, for example MCF (Ter-Grigorov), such as MCF (Broscius), for example Friend MCF #2, such as R-XC-, for example Xeno R-MCF-1, such as DG-75 Xeno, for example Xeno NZB-9-1, such as Xeno CWM-S-5-X, for example Xeno Bxv-1 related, such as 4070A, for example 10A1, such as Akv, for example SL3-3, such as Friend. It is appreciated that each of these viruses may be used individually in the present invention.

Amino acid sequences and polynucleotides that represent particular embodiments of the present invention are listed in the sequence listing herein.

A chimeric viral envelope polypeptide comprising (i) an envelope polypeptide, or fragment thereof, (ii) a polypeptide sequence of a receptor binding region, ligand or a polypeptide sequence of a ligand binding region, and optionally a linker sequence according to the present invention has an altered host range mediated by a non-viral receptor of the target cell. The polypeptide sequence of a receptor binding region, ligand or polypeptide sequence of a ligand binding region of the chimeric envelope polypeptide enables the viral particle to enter a cell expressing the protein on its cell surface, for example a receptor or transporter, ion channel, symporter, antisporter which is recognised by the receptor binding region, ligand or polypeptide sequence of a ligand binding region.

Envelope Polypeptide

Retroviruses can be thought of as a protein-package comprising RNA wrapped in a lipid membrane that contains glycoproteins. The lipid bi-layer is derived from the cell membrane after budding and is thought to be associated with a viral gene product, a peripheral membrane protein called Matrix (MA). Traversing through the lipid bi-layer is another viral gene product, the envelope protein, which upon cleavage in the endoplasmatic reticulum by cellular proteases consists of two subunits: the n-terminal transmembrane (TM) subunit and the C-terminal surface subunit (SU). The function of the envelope protein is binding of the virus to its target cell and mediating fusion of the viral and cellular membranes. The SU is responsible for receptor recognition and binding. The TM is engaged in fusion of the viral and cellular membranes.

A number of regions of the envelope polypeptide have been identified in gammaretroviruses. In the present invention the receptor binding domain (RBD) of the envelope polypeptide is defined as the region delineated by the first amino acid of SEQ ID NO: 60 and the amino acid preceding the proline rich region (PPR) corresponding to the amino acid number 214 of SEQ ID NO: 60, see FIG. 11). Within the RBD are found two variable regions A and B, see FIG. 11. It is appreciated that the position of RBD varies in the various retroviruses. The exact position of the regions varies from species of the gammaretroviruses as can be seen from FIG. 11.

Embodiments for insertion of the polypeptide sequence of a receptor binding domain, ligand, or polypeptide sequence of a ligand binding region.

The polypeptide sequence of a receptor binding domain, ligand, or polypeptide sequence of a ligand binding region is inserted into an insert site within the envelope polypeptide. In one embodiment the polypeptide sequence of a receptor binding domain, ligand, or polypeptide sequence of a ligand binding region is inserted into the receptor binding domain of said envelope polypeptide or fragment thereof. As described above the receptor binding domain in the present invention is defined as the first amino acid of SEQ ID NO: 60 and the amino acid preceding the proline rich region (PPR) corresponding to the amino acid number 214 of SEQ ID NO: 60. Thus, in one embodiment the insert site is in the region of SEQ ID NO: 60 delineated by amino acid number 1 and amino acid number 214. In another embodiment the insert site is in the region of SEQ ID NO: 60 delineated by amino acid number 1 and amino acid number 101. In another embodiment the insert site is in the region of SEQ ID NO: 60 delineated by amino acid number 102 and amino acid number 117, corresponding to the variable region A (VRA). In yet another embodiment the insert site is in the region of SEQ ID NO: 60 delineated by amino acid number 118 and amino acid number 156. In yet another embodiment the insert site is in the region of SEQ ID NO: 60 delineated by amino acid number 157 and amino acid number 173, corresponding to the variable region B (VRB). In a further preferred embodiment the insert site is in the region of SEQ ID NO: 60 delineated by amino acid number 174 and amino acid number 214.

In one embodiment the insert site is in the region of SEQ ID NO: 60 delineated by amino acid number 155 and amino acid number 165. In a preferred embodiment of the present invention the insert site is at position 155 of SEQ ID NO: 60. Another preferred embodiment of the present invention the insert site is at position 155 of SEQ ID NO: 60. Yet another preferred embodiment of the present invention the insert site is at position 165 of SEQ ID NO: 60.

Tropism of Murine Leukaemia Virus (MLV)

The MLVs are a group of gammaretroviruses that has been divided into families based on their host range and interference properties. The families are the ecotropic, amphotropic, xenotropic and polytropic subfamilies. Ecotropic viruses are defined by their usage of the mCAT-1 receptor (Wang et al. 1991). Ecotropic viruses are able to infect only murine cells. Examples of ecotopic viruses are Moloney MLV and AKV. Amphotropic viruses infect murine, human and other species through the Pit-2 receptor (Kavanaugh et al. 1994). One example of an amphotopic virus is the 4070A virus. Xenotropic and polytropic viruses utilize the same (Xpr1) receptor. However, the xenotropic and polytropic viruses differ in their species tropism. Xenotropic viruses such as NZB-9-1 infect human and other species but not murine species, whereas polytropic viruses infect murine, human and other species as exemplified by the mink cell focus-forming viruses (MCF) for example the MCF 247 virus. However, the polytropic SL3-2 virus has a host range as the mouse ecotropic viruses in that it infects and replicates in mouse cells, but are impaired in its ability to infect and replicate in mink cells or human cells. The SL3-2 envelope protein virus utilizes the polytropic (Xpr1) receptor.

One embodiment of the present invention relates to a chimeric retroviral envelope polypeptide comprising an envelope polypeptide, or fragment thereof, and a polypeptide sequence of a receptor binding region, ligand or polypeptide sequence of a ligand binding region, wherein the envelope polypeptide is from a gamma retrovirus, for example the murine leukaemia viruses as listed herein but also the Feline-B virus is one example of a virus. In one embodiment according to the present invention the envelope polypeptide is from MLV. Another embodiment is a chimeric retroviral envelope polypeptide, wherein the envelope polypeptide is from for example ecotropic viruses, such as xenotropic viruses, for example amphotropic viruses, or such as polytropic viruses. In one particular embodiment of the present invention the envelope polypeptide is from the SL3-2 virus.

In one embodiment of the present invention the envelope polypeptide is derived from all viruses except ecotropic viruses One aspect of the invention relates to a chimeric viral envelope polypeptide comprising (i) an envelope polypeptide, or fragment thereof, (ii) a polypeptide sequence of a receptor binding region, ligand or polypeptide sequence of a ligand binding region, and optionally a linker sequence, wherein the envelope polypeptide, or fragment thereof is defined according to the tropism of virus from where the originates. Thus, one embodiment of the present invention pertains to a chimeric viral envelope polypeptide comprising (i) an envelope polypeptide, or fragment thereof, (ii) a polypeptide sequence of a receptor binding region, ligand or polypeptide sequence of a ligand binding region, and optionally a linker sequence, wherein the envelope polypeptide, or fragment or homologue thereof is selected from the group consisting of envelope polypeptides from polytropic viruses. Examples of polytropic viruses are SL3-2, MCF-247, MCF CI-3, ERV-1, Friend MCF, Friend SFV, Invitro MCF, MCF1223, MLV DBA/2, Mo-MCF, Ns-6(186) MCF, Rauscher sfv, endogenous from 129 GIX+ mice, ampho-MCF, MCF (Ter-Grigorov), MCF (Broscius), Friend MCF#2 or R-XC. In one embodiment of the present invention the envelope polypeptide, or fragment or homologue thereof is selected from the group consisting of envelope polypeptides from SL3-2, MCF-247, MCF CI-3, ERV-1, Friend MCF, Friend SFV, Invitro MCF, MCF1223. In another embodiment of the present invention the envelope polypeptide, or fragment or homologue thereof is selected from the group consisting of envelope polypeptides from SL3-2, MLV DBA/2, Mo-MCF, Ns-6(186) MCF, Rauscher sfv, endogenous from 129 GIX+ mice, ampho-MCF, MCF (Ter-Grigorov), MCF (Broscius), Friend MCF#2 or R-XC. In yet another embodiment of the present invention the envelope polypeptide, or fragment or homologue thereof is selected from the group consisting of envelope polypeptides from SL3-2, Friend MCF, Friend SFV, Invitro MCF, MCF1223, MLV DBA/2, Mo-MCF, Ns-6(186) MCF, Rauscher sfv, endogenous from 129 GIX+ mice, ampho-MCF, MCF (Ter-Grigorov). In a further embodiment of the present invention the envelope polypeptide, or fragment or homologue thereof is selected from the group consisting of envelope polypeptides from SL3-2, MCF-247, MCF CI-3, ERV-1. It is understood that the envelope polypeptide, or fragment or homologue thereof are individual embodiments of the present invention. In a particular embodiment of the present invention the envelope polypeptide, or fragment or homologue thereof is SL3-2.

It has also been found that changing specific amino acids within the VR3 region of this MLV SL3-2 envelope polypeptide, or a polytropic homologue thereof, enables alteration the host tropism of said envelope polypeptide. The present inventors have pin-pointed exactly which amino acid that is essential for this host tropism shift.

In the case that the first polypeptide is homologous to SEQ ID NO: 60, one embodiment is that said first polypeptide includes at least one substitution in the VR3 region, or a region homologous thereto. In the present context, the term "VR3 region" comprises all of the amino acids found between the residue found at two positions after the conserved tryptophan 197 and the residue before the conserved aspartic acid 214 (according to the sequence shown in SEQ ID NO: 60) including these two positions. In one embodiment of the present invention, said first polypeptide includes at least one substitution in the region homologous to the VR3 region, such as 1, 2, 3, 4, 5 or 6 substitutions in the VR3 region. Examples of substitutions which are likely to provide the same effect are alanine, asparagine, aspartic acid, cysteine, glutamic acid, phenylalanine, glycine, histidine, isoleucine, lysine, leucine, methionine, proline, glutamin, serine, threonine, valine, tryptophan or tyrosine.

In one preferred embodiment the substitution changes the arginine to glycine. In another preferred embodiment the substitution results in a methionine. For example, said substitution can be at position 212 in SEQ ID NO: 60, or a region homologous thereto. It is preferred that said at least one substitution alters the host tropism of a virus or an infectious particle comprising said polypeptide, in a manner described in more detail in WO 03/097674 (Pipeline Biotech A/S).

Polypeptide sequence of a receptor binding region, ligand or polypeptide sequence of a ligand binding regions As used herein, the term "ligand" is used broadly herein to refer to a molecule that can bind to a protein, for example a receptor, a transporter, ion channel, or symporter, expressed on the surface of a target cell or, conversely, to a receptor that can bind a molecule expressed on the surface of a target cell.

As used herein in the following, the term 'polypeptide sequence of a receptor binding region' is used broadly to refer to a polypeptide or fragment thereof that can bind to a receptor, transporter, ion channel, or symporter expressed on the surface of a target cell or, conversely, to a receptor, transporter, ion channel, or symporter that can bind a polypeptide sequence of a receptor binding region expressed on the surface of a target cell.

The term ligand and 'polypeptide sequence of a receptor binding region thus can be any molecule binding to a protein, for example a receptor, transporter, ion channels, or symporter expressed on the surface of a target cell. One embodiment of the present invention relates to the chimeric viral envelope polypeptide according to claim 66, wherein said receptor binding region, ligand or polypeptide sequence of a ligand binding region is selected from the group consisting of receptor binding region, ligand or polypeptide sequence of a ligand binding region or a fragment or homologue thereof for receptors or co-receptors. The said receptor binding region, ligand or polypeptide sequence of a ligand binding region or a fragment or homologue is for receptors, however, in another embodiment the said receptor binding region, ligand or polypeptide sequence of a ligand binding region or a fragment or homologue bind to co-receptors.

For clarity the term ligand for is identical to the term ligand binds to a receptor or coreceptor.

According to the present invention said receptor binding region, ligand or polypeptide sequence of a ligand binding region or a fragment or homologue thereof of the chimeric viral envelope polypeptide bind to any protein expressed on the surface of a target cell.

In one embodiment the chimeric viral envelope binds to a G-protein-coupled receptor. However, the chimeric viral envelope may also bind to transporter molecules, for example monoamine transporters.

In one embodiment of the present invention the said receptor binding region, ligand or polypeptide sequence of a ligand binding region or a fragment or homologue thereof is selected from the group consisting of apelin, substance P, neurokinin A, neurokinin B, neurotensin receptor 1 and neurotensin receptor 2, or a fragment or homologue thereof. In another embodiment of the present invention the said receptor binding region, ligand or polypeptide sequence of a ligand binding region or a fragment or homologue thereof is selected from the group consisting of, substance P, neurokinin A, neurokinin B, neurotensin receptor 1 and neurotensin receptor 2 or a fragment or homologue thereof. Another embodiment of the present invention comprises the said receptor binding region, ligand or polypeptide sequence of a ligand binding region or a fragment or homologue thereof selected from the group consisting of apelin, neurokinin A and neurokinin B or a fragment or homologue thereof. In yet another embodiment of the present invention the said receptor binding region, ligand or polypeptide sequence of a ligand binding region or a fragment or homologue thereof is selected from the group consisting of neurokinin A and neurokinin B or a fragment or homologue thereof. In yet another embodiment of the present invention the said receptor binding region, ligand or polypeptide sequence of a ligand binding region or a fragment or homologue thereof is selected from the group consisting of neurotensin receptor 1 and neurotensin receptor 2 or a fragment or homologue thereof.

A further embodiment of the present invention the said receptor binding region, ligand or polypeptide sequence of a ligand binding region or a fragment or homologue thereof is the each of these ligands individually for example apelin, such as substance P, for example neurokinin A, or such as neurokinin B, for example neurotensin receptor 1, such as neurotensin receptor 2 or a fragment or homologue thereof.

Further embodiments are found as list of G-protein-coupled receptors bound by the receptor binding region or said ligand or a fragment or homologue thereof elsewhere herein.

In one embodiment of the present invention the polypeptide sequence of a receptor binding region which binds to a coreceptor is a viral envelope polypeptide, or a fragment or homologue thereof.

Said polypeptide sequence of a receptor binding region may in one embodiment be a co-receptor-binding domain, or a fragment or homologue thereof.

In one preferred embodiment of the present invention, said receptor binding region is a receptor binding region of a human virus, such as e.g. Vesicular stomatitis virus (VSV) (Protein G), cytomegalovirus envelope (CMV), HIV, or influenza virus hemagglutinin (HA).

For example, said polypeptide sequence of said receptor binding region can be a fragment or homologue binding to the coreceptor CCR-5 or CXCR-4. However, said polypeptide sequence of said receptor binding region can be a fragment or homologue binding to each of the co-receptors as individual co-receptors CCR-5, or CXCR-4.

Thus, in one embodiment of the present invention, the second, different viral envelope polypeptide is the V3-loop domain of HIV or a fragment or homologue thereof. Said HIV may for example be a strain of HIV-1 or a strain of HIV-2.

In another embodiment of the present invention, the receptor binding region is a hepatitis B virus surface protein binding region, preferably binding to a liver cell.

In another embodiment of the present invention, the receptor binding region is the receptor binding region of gp46 of HTLV-I virus, preferably binding to a T cell.

Another embodiment of the present invention is the use of non-peptide ligands for G-protein-coupled receptors (GPCR) or other receptors. One example is the use of nitrilotriacetic acid (NTA) as an adaptor molecule to associate a non-peptide ligand with the SL3-2 envelope. NTA is a chelating agent and binds strongly to a $Ni^{2+}$ ion leaving two coordination sites for interaction with the nitrogen atoms on two neighbouring His residues in proteins.

Non-peptide ligands of a GPCR can be fused to the tail of one or more NTA molecules, such as 1 NTA molecule and/or 2 NTA molecules and/or 3 NTA molecules and/or 4 NTA molecules and/or 5 NTA molecules and/or 6 NTA molecules and/or, while engineering several histidine residues in the binding site of the envelope polypeptide, or fragment thereof. The ligand-NTA molecule will then be able to bind to the envelope upon addition of $Ni^{2+}$ ions. The whole complex is able to target the virus towards the desired protein expressed on the surface of a target cell, for example a GPCR or a transporter.

The present invention is not limited to NTA or its derivatives such as commercially available [(1S)—N-(5-amino-1-carboxypentyl)iminodiacetic acid; NTA-$NH_2$]), but any adaptor molecule may be used. Other adaptor molecules are for example but not restricted to DNA, or small peptides.

In one embodiment of the present invention, said receptor binding region is a combination of multiple receptor binding peptides. In another embodiment, said receptor binding region comprises 1 receptor binding peptide, and/or 2 receptor binding peptides, and/or 3 receptor binding peptides, and/or 4 receptor binding peptides, and/or 5 receptor binding peptides, and/or 6 receptor binding peptides. The multiple receptor binding peptides may either be identical peptides or a combination of different peptides.

One preferred embodiment of the present invention is the SL3-2 envelope polypeptide in which ligands are inserted for the Tachykinin NK1 receptor for which many non-peptide ligands are known. Several ligands described in (Quartara and Maggi, 1997) contain amid-bonds. The $NH_2$ group of these bonds is replaced with that of NTA-$NH_2$ In yet another embodiment of the present invention relates to an indirect targeting of a protein expressed on the surface of a cell, by inserting a tetracystein tag into the viral envelope. The tetracysteine tag is inserted into the SL3-2 envelope protein at amino acid position 165 as described in example 6. The tetracystein tag comprises the motif CCXXCC, where C is cystein and X is any amino acid. In one preferred embodiment the motif comprises CCPGCC, where P is proline and G is glycin. The tetracystein tag may also comprise amino acids linking the CCXXCC motif to the viral envelope sequence in order to achieve optimal effect of subsequent binding to a ligand for the tag.

In one embodiment the ligand for tetracystein tag may be a biarsenical reagent. In one embodiment upon binding to the tetracystein tag the biarsenical reagent converts into a fluorescent state. However, in another embodiment the biarsenical reagent is not fluorescent upon binding to the tetracysteine tag. Nonlimiting examples of biarsenical reagents are ReAsH Reagent™ (Invitrogen), ReAsH-$EDT_2$™ (Invitrogen), or FlAsH-$EDT_2$™ (Invitrogen). The biarsenical reagent may be linked to a ligand for a desired protein expressed on the surface of a cell.

The ligand which may be fitted with a biarsenical reagent may thus be any ligand. In one embodiment the ligand is selected from the group consisting of ligands for monoamine transporters. In one embodiment the ligand is RTI-55 (3 beta-(4-iodophenyl)tropan-2 beta-carboxylic acid methyl ester). However, the present invention is not limited to any ligand.

The protein expressed on the surface of a target cell may be any protein for example the receptors as listed elsewhere herein. However, the listed examples are not meant to be limiting present invention. In one embodiment the receptor is a monoamine transporter. The receptor may be selected from the group consisting of SERT (Serotonin transporter), DAT (Dopamine transporter) and NET (norepinephrine transporter). In one embodiment the receptor is selected from the group consisting of hSERT (human Serotonin transporter), hDAT (human Dopamine transporter), and hNET (human norepinephrine transporter). In another embodiment the receptor is hSERT (human Serotonin transproter), hDAT (human Dopamine transporter), or hNET (human norepinephrine transporter).

The protein expressed on the surface of a target cell may be an ion channel protein, or a symporter.

Example 6 describes embodiments involving non-peptide ligands.

Proteins on the surface of a target cell, to which ligands of the present invention bind The receptors to which the ligands of the present invention bind are any surface protein of any type in which the insertion of peptides or non-peptide molecules into the viral envelope protein may act directly as a ligand for a specific receptor. However, the inserted peptide, or non-peptide molecules may bind to a label present on a ligand for a specific receptor, thus targeting the specific receptor in an indirect fashion.

In one embodiment the present invention relates to g-protein-coupled receptors. (GPCRs) are a protein family of transmembrane receptors. The GPCRs are the largest protein family known, involved in all types of stimulus response pathways. GPCRs are integral membrane proteins characterized by the presence of seven hydrophobic transmembrane domains which together form a bundle of antiparallel alpha (.alpha.) helices. GPCRs range in size from under 400 to over 1000 amino acids (Strosberg, A. D. (1991) Eur. J. Biochem. 196:1-10; Coughlin, S. R. (1994) Curr. Opin. Cell Biol. 6:191-197). The amino-terminus of a GPCR is extracellular, is of variable length, and is often glycosylated. The carboxy-terminus is cytoplasmic and generally phosphorylated. Extracellular loops alternate with intracellular loops and link the transmembrane domains. Cysteine disulfide bridges linking the second and third extracellular loops may interact with agonists and antagonists. The most conserved domains of GPCRs are the transmembrane domains and the first two cytoplasmic loops. The transmembrane domains account, in part, for structural and functional features of the receptor. In most cases, the bundle of a helices forms a ligand-binding pocket. The extracellular N-terminal segment, or one or more of the three extracellular loops, may also participate in ligand binding. Ligand binding activates the receptor by inducing a conformational change in intracellular portions of the receptor. In turn, the large, third intracellular loop of the activated receptor interacts with a heterotrimeric guanine nucleotide binding (G) protein complex which mediates further intracellular signaling activities, including the activation of second messengers such as cyclic AMP (cAMP), phospholipase C, and inositol triphosphate, and the interaction of the activated GPCR with ion channel proteins. (See, e.g., Watson, S, and S. Arkinstall (1994) The G-protein Linked Receptor Facts Book, Academic Press, San Diego Calif., pp. 2-6; Bolander, F. F. (1994) Molecular Endocrinology, Academic Press, San Diego Calif., pp. 162-176; Baldwin, J. M. (1994) Curr. Opin. Cell Biol. 6:180-190.) GPCRs can be divided into three major subfamilies: the rhodopsin-like, secretin-like, and metabotropic glutamate receptor subfamilies. Members of these GPCR subfamilies share similar functions and the characteristic seven transmembrane structure, but have divergent amino acid sequences. The largest family consists of the rhodopsin-like GPCRs, which transmit diverse extracellular signals including hormones, neurotransmitters, and light. Rhodopsin is a photosensitive GPCR found in animal retinas. In vertebrates, rhodopsin molecules are embedded in membranous stacks found in photoreceptor (rod) cells. Each rhodopsin molecule responds to a photon of light by triggering a decrease in cGMP levels which leads to the closure of plasma membrane sodium channels. In this manner, a visual signal is converted to a neural impulse. Other rhodopsin-like GPCRs are directly involved in responding to neurotransmitters. These GPCRs include the receptors for adrenaline (adrenergic receptors), acetylcholine (muscarinic receptors), adenosine, galanin, and glutamate (N-methyl-D-aspartate/NMDA receptors). (Reviewed in Watson, S, and S. Arkinstall (1994) The G-Protein Linked Receptor Facts Book, Academic Press, San Diego Calif., pp. 7-9, 19-22, 32-35, 130-131, 214-216, 221-222; Habert-Ortoli, E. et al. (1994) Proc. Natl. Acad. Sci. USA 91:9780-9783.)

The galanin receptors mediate the activity of the neuroendocrine peptide galanin, which inhibits secretion of insulin, acetylcholine, serotonin and noradrenaline, and stimulates prolactin and growth hormone release. Galanin receptors are involved in feeding disorders, pain, depression, and Alzheimer's disease (Kask, K. et al. (1997) Life Sci. 60:1523-1533). Other nervous system rhodopsin-like GPCRs include a growing family of receptors for lysophosphatidic acid and other lysophospholipids, which appear to have roles in development and neuropathology (Chun, J. et al. (1999) Cell Biochem. Biophys. 30:213-242).

The largest subfamily of GPCRs, the olfactory receptors, are also members of the rhodopsin-like GPCR family. These receptors function by transducing odorant signals. Numerous distinct olfactory receptors are required to distinguish different odors. Each olfactory sensory neuron expresses only one type of olfactory receptor, and distinct spatial zones of neurons expressing distinct receptors are found in nasal passages. For example, the RA1c receptor which was isolated from a rat brain library, has been shown to be limited in expression to very distinct regions of the brain and a defined zone of the olfactory epithelium (Raming, K et al. (1998) Receptors Channels 6:141-151). However, the expression of olfactory-like receptors is not confined to olfactory tissues. For example, three rat genes encoding olfactory-like receptors having typical GPCR characteristics showed expression patterns not only in taste and olfactory tissue, but also in male reproductive tissue (Thomas; M. B. et al. (1996) Gene 178: 1-5).

Members of the secretin-like GPCR subfamily have as their ligands peptide hormones such as secretin, calcitonin, glucagon, growth hormone-releasing hormone, parathyroid hormone, and vasoactive intestinal peptide. For example, the secretin receptor responds to secretin, a peptide hormone that stimulates the secretion of enzymes and ions in the pancreas and small intestine (Watson, supra, pp. 278-283). Secretin receptors are about 450 amino acids in length and are found in the plasma membrane of gastrointestinal cells. Binding of secretin to its receptor stimulates the production of cAMP.

Examples of secretin-like GPCRs implicated in inflammation and the immune response include the EGF module-containing, mucin-like hormone receptor (Emr1) and CD97 receptor 7 proteins. These GPCRs are members of the recently characterized EGF-TM7 receptors subfamily. These seven transmembrane hormone receptors exist as heterodimers in vivo and contain between three and seven potential calcium-binding EGF-like motifs. CD97 is predominantly expressed in leukocytes and is markedly upregulated on activated B and T cells (McKnight, A. J. and S. Gordon (1998) J. Leukoc. Biol. 63:271-280).

The third GPCR subfamily is the metabotropic glutamate receptor family. Glutamate is the major excitatory neurotransmitter in the central nervous system. The metabotropic glutamate receptors modulate the activity of intracellular effectors, and are involved in long-term potentiation (Watson, supra, p. 130). The Ca.sup.2+-sensing receptor, which senses changes in the extracellular concentration of calcium ions, has a large extracellular domain including clusters of acidic amino acids which may be involved in calcium binding. The metabotropic glutamate receptor family also includes pheromone receptors, the GABA.sub.B receptors, and the taste receptors.

Other subfamilies of GPCRs include two groups of chemoreceptor genes found in the nematodes *Caenorhabditis elegans* and *Caenorhabditis briggsae*, which are distantly related to the mammalian olfactory receptor genes. The yeast pheromone receptors STE2 and STE3, involved in the response to mating factors on the cell membrane, have their own seven-transmembrane signature, as do the cAMP receptors from the slime mold Dictyostelium discoideum, which are thought to regulate the aggregation of individual cells and control the expression of numerous developmentally-regulated genes.

In another embodiment of the present invention relates to transporters, for example monoamine transporters. Monoamine transporters are a protein family of integral membrane transporters that are involved in transporting for example neurotransmitters in or out of a cell, for example removing neurotransmitters from the extracellular fluid. The present invention relates to group of monoamine transporters consisting of the serotonin transporter (SERT), the dopamine transporter (DAT) and the norepinephrine transporter (NET). In one embodiment the invention relates to the monoamine transporters of human origin, and thus the receptors may be selected from the group consisting of hSERT, hDAT and hNET. In another embodiment the receptor is hSERT, hDAT, or hNET.

In one embodiment of the present invention the chimeric viral envelope polypeptide, said receptor binding region, ligand or polypeptide sequence of a ligand binding region is selected from the group consisting of g-protein-coupled receptors.

Thus, the receptor binding region, ligand or polypeptide sequence of a ligand binding region or a fragment or homologue thereof may be selected from the group of ligands consisting of apelin, substance P, neurokinin A, neurokinin B. In one embodiment the ligand is apelin. In another embodiment the ligand is neurokinin A. In a third embodiment the ligand is neurokinin B. In yet another embodiment the ligand is substance P.

However, the receptor binding region, ligand or polypeptide sequence of a ligand binding region or a fragment or homologue thereof binding GPRCs may be selected from the group of GPRCs consisting of Rhodopsin receptor, alfa$_{2A}$ adrenergic receptor, beta$_1$ adrenergic receptor, beta$_2$ adrenergic receptor, dopamine $D_1$ receptor, dopamine $D_2$ receptor, dopamine $D_3$ receptor, dopamine $D_4$ receptor, dopamine $D_5$ receptor, serotonin $5HT_{1B}$ receptor, serotonin $5HT_{1D}$ receptor, serotonin $5HT_{2A}$ receptor, serotonin $5HT_{2C}$ receptor, serotonin $5HT_6$ receptor, histamine $H_1$ receptor, histamine $H_2$ receptor, histamine $H_3$ receptor, cysteinyl leukotriene receptor, $CysLT_1$ receptor, $CysLT_2$ receptor, angiotensin II type 1 receptor, endothelin A receptor, endothelin B receptor, luteinizing hormone receptor, follicle stimulating hormone (FSH) receptor, melanocortin MC1R receptor, melanocortin MC4R receptor, adenocorticotropic hormone receptor (ACTHR), gonadotropin releasing hormone (GnH) receptor, parathyroid hormone receptor (PTHR1), thyrotropin receptor (TSHR), vasopressin V2 receptor (AV2), mu-opioid receptor (MOR), delta-opioid receptor (DOR), orexin 2 receptor, chemokine CCR2 receptor, chemokine CCR3 receptor, chemokine CCR5 receptor, chemokine receptor CX3CR1 receptor, thromboxane A2 receptor, and Ca-sensing receptor.

In another embodiment the receptor binding region, ligand or polypeptide sequence of a ligand binding region or a fragment or homologue thereof binding GPRCs may be selected from the group of GPRCs consisting of Rhodopsin receptor, alfa$_{2A}$ adrenergic receptor, beta$_1$ adrenergic receptor, beta$_2$ adrenergic receptor, dopamine $D_1$ receptor, dopamine $D_2$ receptor, dopamine $D_3$ receptor, dopamine $D_4$ receptor, dopamine $D_5$ receptor, serotonin $5HT_{1B}$ receptor, serotonin $5HT_{1D}$ receptor, serotonin $5HT_{2A}$ receptor, serotonin $5HT_{2C}$ receptor, serotonin $5HT_6$ receptor, histamine $H_1$ receptor, histamine $H_2$ receptor, histamine $H_3$ receptor.

In yet another embodiment the receptor binding region, ligand or polypeptide sequence of a ligand binding region or a fragment or homologue thereof binding GPRCs may be selected from the group of GPRCs consisting of cysteinyl leukotriene receptor, $CysLT_1$ receptor, $CysLT_2$ receptor, angiotensin II type 1 receptor, endothelin A receptor, endothelin B receptor, luteinizing hormone receptor, follicle stimulating hormone (FSH) receptor, melanocortin MC1R receptor, melanocortin MC4R receptor, adenocorticotropic hormone receptor (ACTHR), gonadotropin releasing hormone (GnH) receptor, parathyroid hormone receptor (PTHR1), thyrotropin receptor (TSHR), vasopressin V2 receptor (AV2), mu-opioid receptor (MOR), delta-opioid receptor (DOR), orexin 2 receptor, chemokine CCR2 receptor, chemokine CCR3 receptor, chemokine CCR5 receptor, chemokine receptor CX3CR1 receptor, thromboxane A2 receptor, and Ca-sensing receptor.

In a further another embodiment the receptor binding region, ligand or polypeptide sequence of a ligand binding region or a fragment or homologue thereof binding GPRCs may be selected from the group of GPRCs consisting of dopamine $D_1$ receptor, dopamine $D_2$ receptor, dopamine $D_3$ receptor, dopamine $D_4$ receptor, dopamine $D_5$ receptor, serotonin $5HT_{1B}$ receptor, serotonin $5HT_{1D}$ receptor, serotonin $5HT_{2A}$ receptor, serotonin $5HT_{2C}$ receptor, serotonin $5HT_6$ receptor, histamine $H_1$ receptor, histamine $H_2$ receptor, histamine $H_3$ receptor, cysteinyl leukotriene receptor, $CysLT_1$ receptor, $CysLT_2$ receptor, angiotensin II type 1 receptor, endothelin A receptor, endothelin B receptor, luteinizing hormone receptor, follicle stimulating hormone (FSH) receptor, melanocortin MC1R receptor, melanocortin MC4R receptor.

In yet a further embodiment the receptor binding region, ligand or polypeptide sequence of a ligand binding region or a fragment or homologue thereof binding GPRCs may be selected from the group of GPRCs consisting of melanocortin MC1R receptor, melanocortin MC4R receptor, adenocorticotropic hormone receptor (ACTHR), gonadotropin releasing hormone (GnH) receptor, parathyroid hormone receptor (PTHR1), thyrotropin receptor (TSHR), vasopressin V2 receptor (AV2), mu-opioid receptor (MOR), delta-opioid receptor (DOR), orexin 2 receptor, chemokine CCR2 receptor, chemokine CCR3 receptor, chemokine CCR5 receptor, chemokine receptor CX3CR1 receptor, thromboxane A2 receptor, and Ca-sensing receptor.

In yet another embodiment the protein expressed on the surface of a target cell which is bound by the chimeric envelope according to the present invention is a ion channel. Ion channels are pore-forming proteins that help to establish and control the small voltage gradient, existing across the plasma membrane of all living by allowing the flow of ions down their electrochemical gradient. They are present in the membranes that surround all biological cells. Non limiting examples of ion channels are voltage-gated sodium channels, voltage-gated calcium channels, potassium channels, calcium-activated potassium channels, inward-rectifier potassium channels, two-pore-domain potassium channels, chloride channels, transient receptor potential channels, cyclic nucleotide-gated channels, hyperpolarization-activated, cyclic nucleotide-gated channels, light-gated channels, ligand-gated channels (LGICs) (Examples of LGICs include the cation-permeable “nicotinic” Acetylcholine receptor, ionotropic glutamate-gated receptors and ATP-gated P2X receptors, and the anion-permeable γ-aminobutyric acid-gated $GABA_A$ receptor).

Non-limiting examples of voltage-gated sodium channels are $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ Voltage-dependent calcium channels (VDCC) are a group of voltage-gated ion channels found in excitable cells, for example neurons, glial cells, muscle cells, etc. with a permeability to the ion $Ca^{2+}$, which plays a role in the membrane potential. VDCCs are involved in the release of neurotransmitters and hormones, muscular contraction, excitability of neurons and gene expression. Non-limiting examples of voltage-gated calcium channels are α 1 subunit pores of the L, N and T type, β subunit proteins, α2δ subunits, or γ subunits.

Potassium channels form potassium-selective pores that span cell membranes and are found in most cells, controlling cell function. In excitable cells such as neurons, they shape action potentials and set the resting membrane potential. Non-limiting examples of potassium channels are voltage-gated potassium channels, calcium-activated potassium channels (BK channels, also called MaxiK or slo1 channels), inward-rectifier potassium channels, and two-pore-domain potassium channels.

In yet a further embodiment the protein expressed on the surface of a target cell which is bound by the chimeric envelope according to the present invention is a symporter. A symporter, also known as a cotransporter, is an integral membrane protein that is involved in secondary active transport. It works by binding to two molecules at a time and using the gradient of one solute's concentration to force the other molecule against its gradient. Non limiting examples of symporters are the sodium-iodide symporter, H+-Pi symporter, sodium-chloride symporter.

Linker Sequence

The polypeptide sequence of a receptor binding region, ligand or polypeptide sequence of a ligand binding region may optionally comprise one or more flexible linkers. By linker sequence is meant flexible linker sequence(s) s) of one or more amino acid residues as known by one skilled in the art—for example 2-30 amino acid residues, such as 2-20 amino acid residues, such as 2-10 amino acid residues. The linker sequences are preferably placed at the N-terminal and/or C-terminal of the polypeptide sequence of a receptor binding region, ligand or polypeptide sequence of a ligand binding region. It is understood that the linker sequence(s) link the envelope polypeptide and the polypeptide sequence of a receptor binding region, ligand or polypeptide sequence of a ligand binding region. The linker(s) is/are preferably positioned whereby such linkers increase rotational flexibility and/or minimize steric hindrance of the modified envelope polypeptide. Thus, in one embodiment of the present invention, a linker sequence is positioned at each end of the second polypeptide sequence that is to say at either end of the second polypeptide sequence. Any suitable linker sequence known to one skilled in the art can be used: examples of suitable linker sequences include, but are not restricted to, linkers described by Argos et al., 1990 (Argos, 1990). One preferred linker sequence has the polypeptide sequence SGGSG.

Agents

The chimeric viral envelope polypeptide or virus particle may further comprise an agent for delivery to a target cell. Such an agent may be selected from the group consisting of therapeutic agents, a gene or gene product, a diagnostic label, a label for bioimaging, enzymes for activating prodrugs, a si-RNA or a toxic agent.

It is understood that also a virus particle comprising the chimeric envelope polypeptide is also an embodiment of the present invention.

In one embodiment of the present invention the agent may be comprised in the chimeric viral envelope. Other embodiments are that the agent is packaged into the virus particle during the budding of the virus particle from the host cell. Packaging of said agent may be obtained by operatively associating said agent with a packaging sequence directing the packaging of the agent into a virus particle.

Hemifusion

Hemifusion is the process where only the outer leaflets of the two-lipid-bilayer membranes of a virus particle and a target cell for the virus particle are fused. Hemifusion can be thought of as an intermediate in the normal fusion process. A technology to lock enveloped particles at the hemifused stage by the mutation of a critical histidine residue has been described (Zavorotinskaya T, et al. 2004). Hemifusion may also provide innovative means for the delivery of cargo to the plasma membrane. Hemifused particles are expected to be in a locked state on the membrane as a result of the limited diffusion of integral membrane proteins that span both bilayers. It is conceivable that the hemif used stage will only be reached following a very accurate interaction with the receptor at physiological temperature, which suggests that this way of labelling live cells could be very specific as well as stable.

One embodiment of the present invention therefore comprises the chimeric envelope polypeptide, polynucleotids, vectors, and virus particles in which the amino acid sequence or nucleotide sequence has been altered to yield chimeric envelope polypeptides or virus particles capable of hemifusion.

A person skilled in the art will know to alter the critical histidine residue of the envelope polypeptide. For example envelope mutants are arrested at at hemifusion by a single amino acid mutation (his8) as shown in (Zavorotinskaya T, et al. 2004).

Methods Using any of the Aspects of the Present Invention

Any of the polynucleotide, vectors and/or envelope polypeptides provided herein can be used in the methods as described below. These polynucleotides, vectors and/or envelope polypeptides are herein below described as "constructs", by which it is meant that any of the polynucleotides, vectors and/or envelope polypeptides can advantageously be used. Preferably, said construct is a retroviral particle as described herein.

One could envisage the virus particles or chimeric envelope polypeptides or homologues or fragments thereof to be used as devices mediating receptor-dependent fusion or hemifusion of biological membranes.

In the field of bioimaging the present invention presents novel means for the detection and imaging of specific cell surface proteins on cells by receptor-dependent attachment of labelled viral particles or labelled chimeric envelope polypeptides. The attachment may subsequently be followed by membrane hemifusion as described elsewhere herein.

For example membrane association of drugs may be studied using the methods described herein. The methods may also be used for studies of drug target validation.

Also prodrug activating agents such as for examples enzymes or other activating agents may be studied in the methods of the present invention or employed in therapeutic methods.

Thus, one aspect of the present invention pertains to a method for targeting an agent to a G-protein coupled receptor, comprising the steps of: providing the chimeric envelope polypeptide; causing said chimeric envelope polypeptide to contact a target cell wherein said target cell comprises a receptor for the ligand of said chimeric envelope polypeptide.

Furthermore, another aspect is a method for specifically tethering a chimeric retroviral envelope polypeptide to a specific cell type, comprising the steps of: providing an virus particle expressing a chimeric retroviral envelope polypeptide, said envelope polypeptide comprising a ligand capable of binding said specific cell-type; allowing said chimeric envelope polypeptide to specifically contact a cell of said specific cell type; allowing the outer membrane of the virus to undergo a hemifusion process with the outer membrane of said cell.

However, yet another aspect relates to a method for labelling one or more object of interest on a cell, comprising: providing the labelled vector, polypeptide or recombinant retrovirus; allowing said labelled vector, polypeptide or recombinant retrovirus to contact said object of interest on said cell. One embodiment of this aspect further comprises the step of evaluating the presence of said object(s) of interest on said cell, preferably by taking an image of at least part of the cell. A person skilled in the art will be familiar with the type of imaging possible and the labels used for such imaging.

Thus, a further aspect relates to a method for quantifying the amount or number of an object of interest in a biological specimen, such as a cell, said method comprising the steps of: providing the labelled vector, chimeric envelope polypeptide or virus particle allowing said labelled vector, chimeric envelope polypeptide or virus particle to contact said object of interest on said cell.

Yet a further aspect relates to a method for screening for and analysis of drugs that target the envelope-receptor interaction, comprising the virus particle.

An example wherein the process of hemifusion in relation to the embodiments and aspects of the present invention is employed is shown in example 4. It is appreciated that the methods employing hemifusion is not limited to the particular example.

Another aspect of the present invention relates to targeting and penetration of virus receptor bearing cells by nanoparticles coated with said chimeric envelope proteins as disclosed herein.

In another aspect of the present invention, application of virus with liposome allow for delivery of a range of compounds directly to the cytoplasm, thus bypassing the hostile endosomal pathway. In one embodiment, said compounds include DNA and/or RNA, including mRNA, siRNA, miRNA, and tRNA. In another embodiment, said compounds include chemically modified nucleic acids, nucleic acids analogues such as peptide nucleic acids (PNA) and linked nucleic acids (LNA). In yet another embodiment, said compounds include drugs and/or nano-particles and/or fluorescence markers. In a further embodiment, said compounds include lipophile compounds or compounds joined to a lipophilic group to the plasma membrane for purposes of imaging (e.g. fluourescence markers), induction of apoptosis, antigens to activate the immune system.

Another aspect of the present invention pertains to selectively killing cells by receptor-dependent induction of syncytia. In one embodiment, the formation of syncytia is induced by the chimeric viral envelope peptide disclosed herein. In one embodiment, the induction of syncytia is directed towards tumor cells. In another embodiment, the induction of syncytia is directed towards membranes of parasites, including malaria. In another embodiment, the induction of syncytia is directed towards bacterial cells, including *E. coli* and/or *salmonella.*

Embodiments Relating to Gene Therapy

The recombinant virus particle can further comprise an agent for delivery to the target cell, optionally selected from the group consisting of a therapeutic agent or a gene or gene product, which agent is optionally operatively associated with a retroviral packaging sequence. Thus, the virus particle can in one embodiment comprise at least one heterologous gene to be expressed in the host after a gene therapy procedure. Said heterelogous gene to be expressed can for example comprise the polynucleotide encoding the chimeric envelope polypeptide according to the present invention. The agent is preferably a therapeutic agent, such as a polynucleotide sequence.

The polynucleotide encoding the therapeutic agent is under the control of a suitable promoter. Suitable promoters which may be employed include, but are not limited to, the retroviral LTR; the SV40 promoter; the cytomegalovirus (CMV) promoter; the Rous Sarcoma Virus (RSV) promoter; the histone promoter; the polIII promoter, the .beta.-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex Virus thymidine kinase promoter; retroviral LTRS; human growth hormone promoters, and the MxIFN inducible promoter. The promoter also may be the native promoter which controls the polynucleotide encoding the therapeutic agent. It is to be understood, however, that the scope of the present invention is not to be limited to specific foreign genes or promoters.

The polynucleotides encoding the modified envelope polypeptide and the therapeutic agent may be placed into an appropriate vector by genetic engineering techniques known to those skilled in the art. When the modified vector is a retroviral vector particle, the polynucleotides encoding the modified envelope polypeptide and the therapeutic agent can e.g. be placed into an appropriate retroviral plasmid vector.

In one embodiment, the retroviral plasmid vector may be derived from Moloney Murine Leukemia Virus and is of the LN series of vectors, such as those hereinabove mentioned, and described further in Bender, et al., J. Virol., Vol. 61, pgs. 1639-1649 (1987) and Miller, et al., Biotechniques, Vol. 7, pgs 980-990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. patent application Ser. No. 08/340,805, filed Nov. 17, 1994, and in PCT Application No. WO91/10728, published Jul. 25, 1991, and incorporated herein by reference in their entireties.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes at least one desired polynucleotide encoding a therapeutic agent which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980-990 (1989), or any other promoter (e.g., cellular promoters such as eukaryotic cellular promoters including, but not limited to, the histone, pol III, and .beta.-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

Cell Lines and Animal Models

In another embodiment, there is provided a packaging cell which includes a nucleic acid sequence encoding a modified chimeric envelope in accordance with the invention, and which may further include nucleic acid sequences encoding the gag and pol proteins. A producer cell for generating viral particles which includes a modified envelope in accordance with the invention is produced by introducing into such packaging cell either a retroviral vector particle or a retroviral plasmid vector, in each case including a polynucleotide encoding a therapeutic agent. The producer cell line thus generates infectious retroviral particles including the modified chimeric envelope and the polynucleotide encoding the therapeutic agent.

Thus, in another aspect of the present invention is provided a cell transfected with the vector according to the present invention. In one preferred embodiment, said cell is comprised in a stable cell line comprising such cells. The present invention further relates to "packaging cell lines" for producing the vectors of the present invention.

MLV based packaging cells are widespread tools for research. Packaging cells based on ecotropic viruses have the advantage of being harmless to humans and are used in biosafety level 1 laboratories.

One embodiment of the present invention relates to a packaging cell construct comprising the vector comprising a nucleic acid coding for a polypeptide envelope as described in the present application, and optionally a non-viral or viral promoter and poly-adenylation signals.

Another embodiment of the present invention relates to use of any of the vectors according to the present invention for the generation of a packaging cell.

The packaging cell line can for example be engineered to produce the viral Gag, Pol and Env proteins from constructs that lack the packaging signal (to prevent them from being taken up by budding virions). Thus, when a vector is inserted into a packaging cell line, it will be packaged into budding virions and can be transferred into target cells. Representative examples of packaging cell lines include, but are not limited to, the PE501 and PA317 cell lines disclosed in Miller, et al., Biotechniques, Vol. 7 pgs. 980-990 (1989).

In one embodiment, the packaging cell line is a "pre-packaging" cell line which includes polynucleotides encoding the gag and pol retroviral proteins, but not the envelope, or env, protein. Examples of such "pre-packaging" cell lines include, but are not limited to, GP8 cells, GPL cells, and GPNZ cells as described in Morgan, et al., J. Virol., Vol. 67, No. 8, pgs. 4712-4721 (August 1993). Such cell lines, upon transduction with the retroviral plasmid vector, generates infectious retroviral particles including the modified, or chimeric, envelope and a polynucleotide encoding the therapeutic agent.

In another embodiment, a retroviral plasmid vector which includes a polynucleotide encoding a modified polynucleotide encoding a modified envelope polypeptide in accordance with the invention and a polynucleotide encoding a therapeutic agent is used to transduce a packaging cell line including nucleic acid sequences encoding the gag, pol, and wild-type (i.e., unmodified) env retroviral proteins. Examples of such packaging cell lines include, but are not limited to, the PE501, PA317 (ATCC No. CRL 9078), .psi.-2, .psi.-AM, PA12, T19-14X, VT-19-17-H2, .psi.CRE, .psi.CRIP, GP+E-86, GP+envAm12, and DAN cell lines as described in Miller, Human Gene Therapy, Vol. 1, pgs. 5-14 (1990), which is incorporated herein by reference in its entirety. The vector may transduce the packaging cells through any means known in the art. Such means include, but are not limited to, electroporation, and use of liposomes, such as hereinabove described, and CaPO.sub.4 precipitation. Such producer cells generate infectious retroviral vector particles which include the modified envelope, the wild-type retroviral envelope, a polynucleotide encoding the modified, or chimeric, envelope, and a polynucleotide encoding a therapeutic agent.

In another preferred embodiment, said cell is comprised in an animal model using methods known to one skilled in the art. Said model is preferably a mouse, Antibodies The present invention further relates to an antibody capable of specifically binding one of the molecules provided in the present invention, such as a chimeric envelope polypeptide according to the present invention, and/or a retroviral particle expressing said chimeric envelope polypeptide.

It is understood that the term “antibody” refers to intact immunoglobulin molecules as well as to fragments thereof, such as Fab, F(ab').sub.2, and Fv fragments, which are capable of binding an epitopic determinant. Antibodies that bind GCREC polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

Therapeutic Methods Using any of the Aspects of the Present Invention

Any of the polynucleotide, vectors and/or envelope polypeptides provided herein can be used in therapeutic methods and/or prophylaxis of disease, such as viral disease. These polynucleotides, vectors and/or envelope polypeptides are herein below described as “constructs”, by which it is meant that any of the polynucleotides, vectors and/or envelope polypeptides can advantageously be used. Preferably, said construct is a retroviral particle as described herein.

Thus, the present invention relates in one embodiment to a therapeutic method for treatment of an individual in need thereof, said method comprising administering the chimeric viral envelope polypeptide. Similarly embodiments for a therapeutic method for treatment of an individual in need thereof, said method comprising administering the vector or a virus particle.

Therefore, the present invention relates to a method for delivering an agent to a mammalian target cell in an individual in need thereof, comprising the steps of: (i) providing the chimeric envelope polypeptide or virus particle, (ii) causing said chimeric envelope polypeptide or virus particle to contact a target cell population of said individual’s cells, wherein said target cell comprises a receptor for the ligand of said chimeric envelope polypeptide, (iii) allowing the virus particle to bind said receptor.

The binding of said chimeric viral envelope polypeptide or virus particle displaying said chimeric viral envelope polypeptide to the cognate receptor may result in blockage of the binding of other ligands for the cognate receptor which may in some diseases be of relevance in terms of treatment.

Likewise one embodiment of the present invention relates to the binding of said chimeric viral envelope polypeptide or virus particle displaying said chimeric viral envelope polypeptide to the cognate receptor may block binding of other viral molecules to the cell bound by said construct. Without being bound by theory this may be achieved by the mechanism of viral interference or superinfection.

The binding can also lead to prevention and/or reduction of syncitial formation between another, pathogenic virus and the cell bound by the construct of the present invention.

Another effect of the binding can be reduction in the expression level of the bound viral receptor (such as a viral co-receptor, such as the CXCR4 co-receptor) on the surface of the cell bound by said construct.

In one embodiment, the bound construct (preferably a virus particle) is taken up into the cell which it has specifically bound.

An agent for delivery into the target cell may further be comprised in the chimeric viral envelope polypeptide, or virus particle. Such an agent may be an si-RNA molecule directed against a gene expression product of interest in the treatment of an individual.

Similarly, the agent may be a polynucleotide which will have a therapeutic effect when delivered to a target cell. The polynucleotide may be a heterologous gene. The polynucleotide affects the signalling pathway of the target cell. However, a person skilled in the art will appreciate that a number of therapeutic genes may be delivered to the target cell in the treatment of a number of diseases.

In one embodiment of the above method, an agent is delivered to said cell by said construct (preferably a virus particle). Said agent can for example be an anti-viral drug or a polynucleotide.

Where said agent is a polynucleotide, said method is advantageous to use for gene therapy. The polynucleotide introduced into the cell by said gene therapy method can for example be the polynucleotide according to the present invention encoding the chimeric envelope polypeptides described herein, however said polynucleotide can in equally be another anti-viral polynucleotide, such as encoding a polypeptide with anti-viral activity. The term “introducing” as used herein encompasses a variety of methods of transferring polynucleotides into a cell, such methods including transformation, transduction, transfection, and transinfection.

Thus, retroviral vector particles of the present invention can be used for introducing polynucleotides into cells for gene therapy purposes. In one approach, cells are obtained from a patient, and retroviral vector particles are used to introduce a desired polynucleotide into the cells, and such modified cells are returned to the patient with the engineered cells for a therapeutic purpose. In another approach, retroviral vector particles may be administered to the patient in viva, whereby the retroviral vector particles transduce cells of the patient in vivo.

Methods for in vivo and ex vivo gene therapy are well known in the art, such as for example described in e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, each of which are incorporated herein by reference in their entirety). An increasing number of these methods are currently being applied in human clinical trials (Morgan, R., 1993, BioPharm, 6(1):32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

It may be preferable to remove the majority of a target cell population prior to therapy, for example surgically.

In fact, any of the therapies described herein can be in vivo or ex vivo, that is to say that said contacting occurs outside the individual, and then the target population is returned to the individual's body.

Said specific cell type can for example be T cells, a cell expressing CXCR5 or CXCR4, or macrophage cells.

In another embodiment of the present invention is provided a method for treatment or prevention of a viral disease, comprising administering a construct as disclosed herein to an individual in need thereof. Said construct is preferably the viral envelope polypeptide as disclosed herein, or the recombinant virus particle as disclosed herein. Said viral disease is preferably selected from HIV (for example, HIV-1 or HIV-1)

Target cell populations for any of the therapeutic methods of the present invention In one embodiment of the present invention the target cell population are cells that express receptors or transporters on their surface, for example G-protein-coupled receptors on the cell surface and/or monoamine transporters.

In one embodiment, said cell is a Keratinizing epithelial cell, such as selected from the group consisting of:

Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell).

In another embodiment, said cell is a wet stratified barrier epithelial cell, such as selected from the group consisting of:

Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina Urinary epithelium cell (lining urinary bladder and urinary ducts)

In another embodiment, said cell is a Exocrine secretory epithelial cell, such as selected from the group consisting of:

Salivary gland mucous cell (polysaccharide-rich secretion, Salivary gland serous cell (glycoprotein enzyme-rich secretion), Von Ebner's gland cell in tongue (washes taste buds), Mammary gland cell (milk secretion), Lacrimal gland cell (tear secretion) Ceruminous gland cell in ear (wax secretion), Eccrine sweat gland dark cell (glycoprotein secretion), Eccrine sweat gland clear cell (small molecule secretion) Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus)

Seminal vesicle cell (secretes seminal fluid components, including fructose for swimming sperm), Prostate gland cell (secretes seminal fluid components), bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion) Clara cell of lung.

In another embodiment, said cell is a Hormone secreting cell, such as selected from the group consisting of:

Anterior pituitary cells
Somatotropes
Lactotropes
Thyrotropes
Gonadotropes
Corticotropes
Intermediate pituitary cell, secreting melanocyte-stimulating hormone
Magnocellular neurosecretory cells
secreting oxytocin
secreting vasopressin
Gut and respiratory tract cells secreting serotonin
secreting endorphin
secreting somatostatin
secreting gastrin
secreting secretin
secreting cholecystokinin
secreting insulin
secreting glucagon
secreting bombesin
Thyroid gland cells
thyroid epithelial cell
parafollicular cell
Parathyroid gland cells
Parathyroid chief cell
oxyphil cell
Adrenal gland cells
chromaffin cells
secreting steroid hormones (m ineralcorticoids and gluco corticoids)
Leydig cell of testes secreting testosterone
Theca interna cell of ovarian follicle secreting estrogen
Corpus luteum cell of ruptured ovarian follicle secreting progesterone
Kidney juxtaglomerular apparatus cell (renin secretion)
Macula densa cell of kidney
Peripolar cell of kidney
Mesangial cell of kidney In another embodiment, said cell is a cell of the Gut, Exocrine Glands and Urogenital Tract, such as selected from the group consisting of:

Intestinal brush border cell (with microvilli)
Exocrine gland striated duct cell
Gall bladder epithelial cell
Kidney proximal tubule brush border cell
Kidney distal tubule cell
Ductulus efferens nonciliated cell
Epididymal principal cell
Epididymal basal cell In another embodiment, said cell is a Metabolism and storage cell, such as selected from the group consisting of:

Hepatocyte (liver cell)
White fat cell
Brown fat cell
Liver lipocyte

In another embodiment, said cell is a cell of the Lung, Gut, Exocrine Glands or Urogenital Tract, such as selected from the group consisting of:

Type I pneumocyte (lining air space of lung)
Pancreatic duct cell (centroacinar cell)
Nonstriated duct cell (of sweat gland, salivary gland, mammary gland, etc.)
Kidney glomerulus parietal cell
Kidney glomerulus podocyte
Loop of Henle thin segment cell (in kidney)
Kidney collecting duct cell
Duct cell (of seminal vesicle, prostate gland, etc.)

In another embodiment, said cell is an epithelial cell lining a closed internal body cavity, such as selected from the group consisting of:

Blood vessel and lymphatic vascular endothelial fenestrated cell
Blood vessel and lymphatic vascular endothelial continuous cell
Blood vessel and lymphatic vascular endothelial splenic cell
Synovial cell (lining joint cavities, hyaluronic acid secretion)
Serosal cell (lining peritoneal, pleural, and pericardial cavities)
Squamous cell (lining perilymphatic space of ear)
Squamous cell (lining endolymphatic space of ear)
Columnar cell of endolymphatic sac with microvilli (lining endolymphatic space of ear)
Columnar cell of endolymphatic sac without microvilli (lining endolymphatic space of ear)
Dark cell (lining endolymphatic space of ear)
Vestibular membrane cell (lining endolymphatic space of ear)
Stria vascularis basal cell (lining endolymphatic space of ear)
Stria vascularis marginal cell (lining endolymphatic space of ear)
Cell of Claudius (lining endolymphatic space of ear)
Cell of Boettcher (lining endolymphatic space of ear)
Choroid plexus cell (cerebrospinal fluid secretion)
Pia-arachnoid squamous cell
Pigmented ciliary epithelium cell of eye
Nonpigmented ciliary epithelium cell of eye
Corneal endothelial cell In another embodiment, said cell is a Ciliated cell with propulsive function, such as selected from the group consisting of:

Respiratory tract ciliated cell
Oviduct ciliated cell (in female)
Uterine endometrial ciliated cell (in female)
Rete testis cilated cell (in male)
Ductulus efferens ciliated cell (in male)
Ciliated ependymal cell of central nervous system (lining brain cavities)

In another embodiment, said cell is an Extracellular matrix secretion cell, such as selected from the group consisting of:

Ameloblast epithelial cell (tooth enamel secretion)
Planum semilunatum epithelial cell of vestibular apparatus of ear (proteoglycan secretion)
Organ of Corti interdental epithelial cell (secreting tectorial membrane covering hair cells)
Loose connective tissue fibroblasts
Corneal fibroblasts
Tendon fibroblasts
Bone marrow reticular tissue fibroblasts
Other nonepithelial fibroblasts
Pericyte
Nucleus pulposus cell of intervertebral disc
Cementoblast/cementocyte (tooth root bonelike cementum secretion)
Odontoblast/odontocyte (tooth dentin secretion)
Hyaline cartilage chondrocyte
Fibrocartilage chondrocyte
Elastic cartilage chondrocyte
Osteoblast/osteocyte
Osteoprogenitor cell (stem cell of osteoblasts)
Hyalocyte of vitreous body of eye
Stellate cell of perilymphatic space of ear In another embodiment, said cell is a Contractile cell, such as selected from the group consisting of:

Red skeletal muscle cell (slow)
White skeletal muscle cell (fast)
Intermediate skeletal muscle cell
nuclear bag cell of Muscle spindle
nuclear chain cell of Muscle spindle
Satellite cell (stem cell)
Ordinary heart muscle cell
Nodal heart muscle cell
Purkinje fiber cell
Smooth muscle cell (various types)
Myoepithelial cell of iris
Myoepithelial cell of exocrine glands
Red Blood Cell In another embodiment, said cell is a Blood or immune system cell, such as selected from the group consisting of:

Erythrocyte (red blood cell)
Megakaryocyte (platelet precursor)
Monocyte
Connective tissue macrophage (various types)
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Mast cell
Helper T cell
Suppressor T cell
Cytotoxic T cell
B cells
Natural killer cell
Reticulocyte
Stem cells and committed progenitors for the blood and immune system (various types)

In another embodiment, said cell is a Sensory transducer cell, such as selected from the group consisting of:

Auditory inner hair cell of organ of Corti
Auditory outer hair cell of organ of Corti
Basal cell of olfactory epithelium (stem cell for olfactory neurons)
Cold-sensitive primary sensory neurons
Heat-sensitive primary sensory neurons
Merkel cell of epidermis (touch sensor)
Olfactory receptor neuron
Pain-sensitive primary sensory neurons (various types)
Photoreceptor rod cell of eye
Photoreceptor blue-sensitive cone cell of eye
Photoreceptor green-sensitive cone cell of eye
Photoreceptor red-sensitive cone cell of eye
Proprioceptive primary sensory neurons (various types)
Touch-sensitive primary sensory neurons (various types)
Type I carotid body cell (blood pH sensor)
Type II carotid body cell (blood pH sensor)
Type I hair cell of vestibular apparatus of ear (acceleration and gravity)

Type II hair cell of vestibular apparatus of ear (acceleration and gravity)
Type I taste bud cell In another embodiment, said cell is an Autonomic neuron cell, such as selected from the group consisting of:
Cholinergic neural cell (various types)
Adrenergic neural cell (various types)
Peptidergic neural cell (various types)

In another embodiment, said cell is a sense organ or peripheral neuron supporting cell, such as selected from the group consisting of:
Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Type I taste bud supporting cell
Olfactory epithelium supporting cell
Schwann cell
Satellite cell (encapsulating peripheral nerve cell bodies)
Enteric glial cell In another embodiment, said cell is a Central nervous system neuron or glial cell, such as selected from the group consisting of:
Astrocyte (various types)
Neuron cells (large variety of types, still poorly classified)
Oligodendrocyte
Spindle neuron In another embodiment, said cell is a lens cell, such as selected from the group consisting of:
Anterior lens epithelial cell
Crystallin-containing lens fiber cell
is in body when heart is breathing hard In another embodiment, said cell is a pigment cell, such as selected from the group consisting of:
Melanocyte
Retinal pigmented epithelial cell In another embodiment, said cell is a Germ cell, such as selected from the group consisting of:
Oogonium/Oocyte
Spermatid
Spermatocyte
Spermatogonium cell (stem cell for spermatocyte)
Spermatozoon In another embodiment, said cell is a nurse cell, such as selected from the group consisting of:
Ovarian follicle cell
Sertoli cell (in testis)
Thymus epithelial cell In another embodiment of the therapeutic method of the present invention, the target cell population comprises or consists of T cells. In another preferred embodiment of the therapeutic method of the present invention, said target population comprises or consists of cells expressing CXCR5 or CXCR4. In another embodiment of the therapeutic method of the present invention, said target population comprises or consists of macrophage cells.

Further example of cells which may be targeted for binding, infection or transduction with the chimeric envelope polypeptides or vector particles of the present invention include, but are not limited to, T cell, endothelial cells, tumor cells, chondrocytes, fibroblasts and fibroelastic cells of connective tissues; osteocytes and osteoblasts in bone; endothelial and smooth muscle cells of the vasculature; epithelial and subepithelial cells of the gastrointestinal and respiratory tracts; vascular cells, connective tissue cells, and hepatocytes of a fibrotic liver, the reparative mononuclear and granulocytic infiltrates of inflamed tissues, liver cells, T-cells, lymphocytes, endothelial cells, T4 helper cells, or macrophages.

In another embodiment, the receptor binding region is a hepatitis B virus surface protein binding region, and the target cell is e.g. a liver cell.

Medicament, pharmaceutical formulations, administration and dosages

In another aspect of the present invention is further disclosed a medicament or pharmaceutical formulation comprising any of the constructs described herein, such as a chimeric envelope polypeptide or viral particle as disclosed herein.

The constructs of the present invention may be directly administered to a desired target cell ex vivo, and such cells may then be administered to a patient as part of a gene therapy procedure.

Although the chimeric polypeptides and/or vector particles may be administered directly to a target cell, they may also be engineered such that they are resistant to inactivation by human serum, and thus may be administered to a patient by (e.g. intravenous) injection, and travel directly to a desired target cell or tissue without being inactivated by human serum.

The vector particles may be concentrated from dilute vector stocks in vitro by contacting a dilute vector stock with an extracellular matrix component to which the modified viral surface protein will bind. Such binding enables one to obtain a concentrated stock of the vector particles.

In addition, the modified viral surface proteins of the present invention may be employed to form proteoliposomes; i.e., the modified viral surface protein forms a portion of the liposome wall. Such proteoliposomes may be employed for gene transfer or for drug delivery to cells located at a site of an exposed extracellular matrix component.

Any of the constructs disclosed herein may be administered to a host in an amount effective to produce a therapeutic effect in the host. The host may be a mammalian host, which may be a human or non-human primate host. The exact dosage which may be administered is dependent upon a variety of factors, including the age, sex, and weight of the patient, the cells which are to be transduced, the therapeutic agent which is to be administered, and the severity of the disorder to be treated.

The vector particles may be administered systemically, such as, for example, by intravenous, intracolonic, intratracheal, intraperitoneal, intranasal, intravascular, intrathecal, intraarterial, intracranial, intramarrow, intrapleural, intradermal, subcutaneous, intramuscular, intraocular, intraosseous and/or intrasynovial administration. The vector particles also may be administered topically.

EXAMPLES

Example 1

Sequence identity: The percent sequence identity between the protein sequences of gammaretroviruses when compared with the SL3-2 envelope protein sequence of gammaretroviruses was calculated using the VECTOR NTI computer program:

| Name | Tropism | Percent sequence identity in envelope protein | Percent sequence identity in RBD of envelope protein |
|---|---|---|---|
| FeLV-B | Pit-1 receptor but from cats | 60.2 | 52.3 |
| MoMLV | Ecotropic | 63.5 | 35.4 |
| MCF247 | Polytropic | 92.7 | 92.0 |
| NZB-9-1 | Xenotropic | 76.4 | 71.0 |
| 4070A | Amphotropic | 87.6 | 84.7 |

Wherein RBD is the receptor binding domain. The RBD domain can be defined as the domain corresponding to the polypeptide domain that by itself is able to bind to the receptor. In the present invention the RBD of the envelope polypeptide is preferably defined as the region delineated by the first amino acid of the envelope polypeptide and the amino acid preceding the proline rich region (PPR).

The amino acid sequence of SL3-2 is identical to that of SEQ ID NO. 2.

The amino acid sequence of MCF247, NZB-9-1, MoMLV and 4070A can be obtained from the NCBI databank at the link www.ncbi.nlm.nih.gov/entrez/query.fcgi?CMD=search&DB=nucleotide or from the original scientific journals: MCF247 (Kelly et al. 1983; Khan 1984), MoMLV (Shinnick et al. 1981; Miller and Verma 1984), 4070A (Ott et al. 1990), NZB-9-1 (O'Neill et al. 1985).

Example 2

Flow Cytometry to Detect CXCR4CSE

Method: Flow cytometric analysis was carried out of Cell Surface Expression (CSE) of CXCR4 of cells transduced with vectors comprising the chimeric envelope polypeptide of the present invention. D17 CD4 CXCR4 cells were transduced with a vector expressing SL3-2 envelope with V3 loop inserted at positions indicated.

The transductions were done by co transfecting Moloney gagpol 2 ug, VSV-G expressing vector 2 ug and a mini-virus expressing the SL3-2 (V3 construct 6 ug) in 293T cells using calcium phosphate transfection protocol (see detailed protocol in Bahrami et al., "Mutational library analysis of selected amino acids in the receptor binding domain of envelope of Akv murine leukemia virus by conditionally replication competent bicistronic vectors", Gene. 2003 Oct. 2; 315:51-61). The virus containing supernatant was subsequently used to transduce the D17 CXCR4CD4 cells.

Six chimeric variants have been tested (sequences used shown in SEQ ID NO: 3-8 and 42-47). In all panels the control D17 CD4 CXCR4 cells with SL3-3 envelope only (without the V3 insert) was tested against the same envelope comprising a V3 loop variant.

Protocol for flow cytometry:

Harvest cells (by nice trypzination) and spin down gently (1200 rpm, 5 min)

Keep cells on ice in all subsequent steps.

Wash once in wash buffer (2% Serum, 98% PBS—cold) ⇒ 2% Wash

Resuspend in small amount of wash buffer: 0, 1-1 ml (>$10^7$ cells/ml)

Count the total number of cells

Dilute the suspension appropriate (wash buffer) and transfer $5*10^5$-$10^6$ cells in 100 μl volume to Flow tubes Add 5 μl primary IgG (AbCam, UK) diluted in 100 μl PBS with 10% FBS Vortex and incubate 45 min at 4° C. in dark (i.e., Fridge)

Wash cells twice in 1 ml wash buffer (1200 rpm, 5 min)

Pour of buffer

Add 5 μl secondary Ab (goat anti Mouse IgG—PE/FITCH conjugated) diluted in 100 μl PBS with 10% FBS and vortex briefly Incubate 45 min at 4° C. in dark (ie. Fridge)

Wash cells twice in 1 ml wash buffer (1200 rpm, 5 min)

After final spin, resuspend cells in 500 μl 1% formaldehyde in PBS, pH 7.4

Store samples in the fridge until Flow analysis

Remember to include uninfected control cells, and make the staining of these cells with and without primary Ig. That is minimum number of samples are 4 (test, pos.control, 2 neg. control)

Conclusions: Results are shown in FIG. 6. The results show that the V3 constructs are able to significantly inhibit binding of the anti CXCR-4 antibody to the CXCR4 receptor significantly. The effect is a result of the V3 domain insertion in the SL3-2 backbone as the wild-type SL3-2 control does not affect the expression levels of CXCR-4.

Example 3a

Syncytia Assay

Protocol:

293T cells are cultured in DMEM media with 10% Foetal Bovine Serum and 1% penicillin/streptomycin.

D17 CD4 CXCR4 cells are cultured in α-MEM media with 10% Foetal Bovine Serum and 1% penicillin/streptomycin.

Day 1: 293T cells are seeded at $1*10^4$ cells/$cm^2$ in 6-well plate (Nunc, Roskilde)

Day 2: Fresh media is added to 293T three hours prior to transfection. 293T cells are transfected with an HIV-1 Envelope expressing constructs (see sequence information below) via $CaPO_4$-precipitation method.

Day 3: Media is replenished on 293T cells and D17 CD4 CXCR4 cells are co-cultured in the 6-well plate at a density of $2*10^4$ cells/$cm^2$.

Day 4: Syncytia formation is determined visually and pictures are taken of the plaques formed. Nuclei are counted.

Results: The capability of performing cell-cell fusion mediated by the interaction of the HIV-1 envelope protein and the CD4/CXCR4 receptors utilising 293T and D17 cells is seen. The egfp expression localises to the syncytia formation. Control transfection (egfp expression plasmid without HIV-1) yields no syncytia.

This is shown in FIGS. 8-9.

Conclusions: The comparison of control D17 CD4 CXCR4 cells to the D17 CD4 CXCR4 cells transduced with SL3-3 envelope with V3 loop inserted reveal a trend toward smaller syncytia (as determined by number of nuclei pr syncytia). That is fewer cells have the ability to undergo membrane fusion as mediated by envelope receptor interaction.

Sequence information of vector sequence used:

EgfpHIVMo (derived from a mouse Virus (MLV) containing elements from the virus for gene transcription, together with an egfp marker gene—an IRES element that is needed for bicistronic RNA translation—and the HIV-1 envelope:

(SEQ ID NO: 184)

```
tcgcgcgtttcggtgatgacggtgaaaacctctgacacatgcagctcccg

gagacggtcacagcttgtctgtaagcggatgccgggagcagacaagcccg
```

-continued tcagggcgcgtcagcgggtgttggcgggtgtcggggctggcttaactatg
'agagcagattgtactgagagtgcaccatatgcggtgtgaaata
ccgcacagatgcgtaaggagaaaataccgcatcaggcgccattcgccatt
caggctgcgcaactgttgggaagggcgatcggtgcgggcctcttcgctat
tacgccagctggcgaaagggggatgtgctgcaaggcgattaagttgggta
acgccagggttttcccagtcacgacgttgtaaaacgacggccagtgaatt
ctaccttacgtttccccgaccagagctgatgttctcagaaaaacaagaac
aaggaagtacagagaggctggaaagtaccgggactagggccaaacaggat
atctgtggtcaagcactagggccccggcccagggccaagaacagatggtc
cccagaaacagagaggctggaaagtaccgggactagggccaaacaggata
tctgtggtcaagcactagggccccggcccagggccaagaacagatggtcc
ccagaaatagctaaaacaacaacagtttcaagagacccagaaactgtctc
aaggttccccagatgaccggggatcaaccccaagcctcatttaaactaac
caatcagctcgcttctcgcttctgtacccgcgcttattgctgcccagctc
tataaaaagggtaagaaccccacactcggcgcgccagtcctccgatagac
tgagtcgcccgggtacccgtgtatccaataaagccttttgctgttgcatc
cgaatcgtggtctcgctgatccttgggagggtctcctcagagtgattgac
tgcccagcctgggggtctttcatttgggggctcgtccgggatttggagac
ccccgcccagggaccaccgacccaccgtcgggaggtaagctggccagcga
tcgttttgtctccgtctctgtctttgtgcgtgtgtgtgtgtgtgccggca
tctacttttttgcgcctgcgtctgattctgtactagttagctaactagatc
tgtatctggcggctccgtggaagaactgacgagttcgtattcccgaccgc
agccctgggagacgtctcagaggcatcgggggggggatccagagctcgag
atggtgagcaagggcgaggagctgttcaccggggtggtgcccatcctggt
cgagctggacggcgacgtaaacggccacaagttcagcgtgtccggcgagg
gcgagggcgatgccacctacggcaagctgaccctgaagttcatctgcacc
accggcaagctgcccgtgccctggcccaccctcgtgaccaccctgaccta
cggcgtgcagtgcttcagccgctaccccgaccacatgaagcagcacgact
tcttcaagtccgccatgcccgaaggctacgtccaggagcgcaccatcttc
ttcaaggacgacggcaactacaagacccgcgccgaggtgaagttcgaggg
cgacaccctggtgaaccgcatcgagctgaagggcatcgacttcaaggagg
acggcaacatcctggggcacaagctggagtacaactacaacagccacaac
gtctatatcatggccgacaagcagaagaacggcatcaaggtgaacttcaa
gatccgccacaacatcgaggacggcagcgtgcagctcgccgaccactacc
agcagaacacccccatcggcgacggccccgtgctgctgcccgacaaccac
tacctgagcacccagtccgccctgagcaaagaccccaacgagaagcgcga
tcacatggtcctgctggagttcgtgaccgccgccgggatcactctcggca
tggacgagctgtacaagtaaagcggccgtacgcgttgatcagttaacgaa
ttcgaagggtcccaggcctcggagatctgggcccatgcggccgcccccta
acgttactggccgaagccgcttggaataaggccggtgtgcgtttgtctat -continued atgttattttccaccatattgccgtcttttggcaatgtgagggcccggaa
acctggccctgtcttcttgacgagcattcctaggggtctttcccctctcg
ccaaaggaatgcaaggtctgttgaatgtcgtgaaggaagcagttcctctg
gaagcttcttgaagacaaacaacgtctgtagcgaccctttgcaggcagcg
gaacccccccacctggcgacaggtgcctctgcggccaaaagccacgtgtat
aagatacacctgcaaaggcggcacaaccccagtgccacgttgtgagttgg
atagttgtggaaagagtcaaatggctctcctcaagcgtattcaacaaggg
gctgaaggatgcccagaaggtaccccattgtatgggatctgatctggggc
ctcggtgcacatgctttacatgtgtttagtcgaggttaaaaaacgtctag
gccccccgaaccacggggacgtggttttcctttgaaaaacacgataatac
catgagagcagaagacagtggcaatgagagtgaaggagaaatatcagcac
ttgtggagatgggggtggagatggggcaccatgctccttgggatgttgat
gatctgtagtgctacagaaaaattgtgggtcacagtctattatggggtac
ctgtgtggaaggaagcaaccaccactctattttgtgcatcagatgctaaa
gcatatgatacagaggtacataatgtttgggccacacatgcctgtgtacc
cacagaccccaacccacaagaagtagtattggtaaatgtgacagaaaatt
ttaacatgtggaaaaatgacatggtagaacagatgcatgaggatataatc
agtttatgggatcaaagcctaaagccatgtgtaaaattaaccccactctg
tgttagtttaaagtgcactgatttgaagaatgatactaataccaatagta
gtagcgggagaatgataatggagaaaggagagataaaaaactgctctttc
aatatcagcacaagcataagaggtaaggtgcagaaagaatatgcattttt
ttataaacttgatataataccaatagataatgatactaccagctataagt
tgacaagttgtaacacctcagtcattacacaggcctgtccaaaggtatcc
tttgagccaattcccatacattattgtgccccggctggttttgcgattct
aaaatgtaataataagacgttcaatggaacaggaccatgtacaaatgtca
gcacagtacaatgtacacatggaattaggccagtagtatcaactcaactg
ctgttaaatggcagtctagcagaagaagaggtagtaattagatctgtcaa
tttcacggacaatgctaaaaccataatagtacagctgaacacatctgtag
aaattaattgtacaagacccaacaacaatacaagaaaaagaatccgtatc
cagagaggaccagggagagcatttgttacaataggaaaaataggaaatat
gagacaagcacattgtaacattagtagagcaaaatggaataacactttaa
aacagatagctagcaaattaagagaacaatttggaaataataaaacaata
atctttaagcaatcctcaggaggggacccagaaattgtaacgcacagttt
taattgtggaggggaatttttctactgtaattcaacacaactgtttaata
gtacttggtttaatagtacttggagtactgaagggtcaaataacactgaa
ggaagtgacacaatcaccctcccatgcagaataaaacaaattataaacat
gtggcagaaagtaggaaaagcaatgtatgcccctcccatcagtggacaaa
ttagatgttcatcaaatattacagggctgctattaacaagagatggtggt
aatagcaacaatgagtccgagatcttcagacctggaggaggagatatgag
ggacaattggagaagtgaattatataaatataaagtagtaaaaattgaac -continued cattaggagtagcacccaccaaggcaaagagaagagtggtgcagagagaa aaaagagcagtgggaataggagctttgttccttgggttcttgggagcagc aggaagcactatgggcgcagcctcaatgacgctgacggtacaggccagac aattattgtctggtatagtgcagcagcagaacaatttgctgagggctatt gaggcgcaacagcatctgttgcaactcacagtctggggcatcaagcagct ccaggcaagaatcctggctgtggaaagatacctaaaggatcaacagctcc tggggatttggggttgctctggaaaactcatttgcaccactgctgtgcct tggaatgctagttggagtaataaatctctggaacagatttggaatcacac gacctggatggagtgggacagagaaattaacaattacacaagcttaatac actccttaattgaagaatcgcaaaaccagcaagaaaagaatgaacaagaa ttattggaattagataaatgggcaagtttgtggaattggtttaacataac aaattggctgtggtatataaaattattcataatgatagtaggaggcttgg taggtttaagaatagtttttgctgtactttctatagtgaatagagttagg cagggatattaaccattatcgttcttaagacaatagaagattgtaaatca cgtgaataaaagattttattcagtttacagaaagagggggaatgaaaga ccccttcataaggcttagccagctaactgcagtaacgccattttgcaagg catgggaaaataccagagctgatgttctcagaaaaacaagaacaaggaag tacagagaggctggaaagtaccgggactagggccaaacaggatatctgtg gtcaagcactagggccccggcccagggccaagaacagatggtccccagaa acagagaggctggaaagtaccgggactagggccaaacaggatatctgtgg tcaagcactagggccccggcccagggccaagaacagatggtccccagaaa tagctaaaacaacaacagtttcaagagacccagaaactgtctcaaggttc cccagatgaccggggatcaaccccaagcctcatttaaactaaccaatcag ctcgcttctcgcttctgtacccgcgcttattgctgcccagctctataaaa agggtaagaaccccacactcggcgcgccagtcctccgatagactgagtcg cccgggtacccgtgtatccaataaagccttttgctgttgcatccgaatcg tggtctcgctgatccttgggagggtctcctcctctgtcggtcgacctgca ggcatgcaagcttggcgtaatcatggtcatagctgtttcctgtgtgaaat tgttatccgctcacaattccacacaacatacgagccggaagcataaagtg taaagcctggggtgcctaatgagtgagctaactcacattaattgcgttgc gctcactgcccgctttccagtcgggaaacctgtcgtgccagctgcattaa tgaatcggccaacgcgcggggagaggcggtttgcgtattgggcgctcttc cgcttcctcgctcactgactcgctgcgctcggtcgttcggctgcggcgag cggtatcagctcactcaaaggcggtaatacggttatccacagaatcaggg gataacgcaggaaagaacatgtgagcaaaaggccagcaaaaggccaggaa ccgtaaaaaggccgcgttgctggcgtttttccataggctccgcccccctg acgagcatcacaaaaatcgacgctcaagtcagaggtggcgaaacccgaca ggactataaagataccaggcgtttccccctggaagctccctcgtgcgctc tcctgttccgaccctgccgcttaccggatacctgtccgcctttctccctt cgggaagcgtggcgctttctcaatgctcacgctgtaggtatctcagttcg -continued gtgtaggtcgttcgctccaagctgggctgtgtgcacgaaccccccgttca gcccgaccgctgcgccttatccggtaactatcgtcttgagtccaacccgg taagacacgacttatcgccactggcagcagccactggtaacaggattagc agagcgaggtatgtaggcggtgctacagagttcttgaagtggtggcctaa ctacggctacactagaaggacagtatttggtatctgcgctctgctgaagc cagttaccttcggaaaaagagttggtagctcttgatccggcaaacaaacc accgctggtagcggtggtttttttgtttgcaagcagcagattacgcgcag aaaaaaaggatctcaagaagatcctttgatcttttctacggggtctgacg ctcagtggaacgaaaactcacgttaagggattttggtcatgagattatca aaaaggatcttcacctagatccttttaaattaaaaatgaagttttaaatc aatctaaagtatatatgagtaaacttggtctgacagttaccaatgcttaa tcagtgaggcacctatctcagcgatctgtctatttcgttcatccatagtt gcctgactccccgtcgtgtagataactacgatacgggagggcttaccatc tggccccagtgctgcaatgataccgcgagacccacgctcaccggctccag atttatcagcaataaaccagccagccggaagggccgagcgcagaagtggt cctgcaactttatccgcctccatccagtctattaattgttgccgggaagc tagagtaagtagttcgccagttaatagtttgcgcaacgttgttgccattg ctacaggcatcgtggtgtcacgctcgtcgtttggtatggcttcattcagc tccggttcccaacgatcaaggcgagttacatgatcccccatgttgtgcaa aaaagcggttagctccttcggtcctccgatcgttgtcagaagtaagttgg ccgcagtgttatcactcatggttatggcagcactgcataattctcttact gtcatgccatccgtaagatgcttttctgtgactggtgagtactcaaccaa gtcattctgagaatagtgtatgcggcgaccgagttgctcttgcccggcgt caatacgggataataccgcgccacatagcagaactttaaaagtgctcatc attggaaaacgttcttcggggcgaaaactctcaaggatcttaccgctgtt gagatccagttcgatgtaacccactcgtgcacccaactgatcttcagcat cttttactttcaccagcgtttctgggtgagcaaaaacaggaaggcaaaat gccgcaaaaaagggaataagggcgacacggaaatgttgaatactcatact cttcctttttcaatattattgaagcatttatcagggttattgtctcatga gcggatacatatttgaatgtatttagaaaaataaacaaataggggttccg cgcacatttccccgaaaagtgccacctgacgtctaagaaaccattattat catgacattaacctataaaaataggcgtatcacgaggccctttcgtc

Example 3b

FIG. 10 shows further results of Syncitia assays. The arrows indicate multi-nuclei cell syncytia. NIH cells stably expressing the HIV-1 envelope protein were co-cultured with different HeLa target cells (HeLa expresses CXCR-4 endogenously). Top left HeLa cells lacking the CD4 receptor. Bottom left HeLa cells with CD4. Middle, HeLa CD4 cells transfected with Moloney MLV envelope. Right, HeLa CD4 cells transfected with two variants of chimeric Moloney/V3 envelopes. We note a reduction in syncytia formation in the presence of V3 envelope, in particular in the upper right panel.

Example 4

Generating the Envelope Protein of SL3-2

The envelope protein of SL3-2 was taken from genomic DNA of NIH 3T3 cells infected with SL3-2 virus. PCR was used to amplify the envelope. The upstream primer was chosen to match a conserved sequence upstream of the splice acceptor site among different MLV strains. The downstream primer was designed according to the known sequence of SL3-2 LTR (Dai et al., 1990). The amplified PCR fragment was subsequently cloned into the mini-virus to replace the original Akv envelope. The new construct was designated NeoSL3-2mo. Three clones were chosen for sequencing.

One of the clones contained a frameshift mutation and was not infectious. This SL3-2 envelope shows a 92% homology on nucleotide level with the envelope protein of MCF-247 polytropic MLV. The latter has a wide host range and is able to infect cells from many species (Rein 1982), (Hartley et al., 1977), (Chattopadhyay et al., 1982), whereas the original reports claimed that SL3-2 has the same host range as the ecotropic viruses (Pedersen et al., 1981), (Rein et al., 1984). Cloning of SL3-2 envelope The envelope of SL3-2 was amplified by the following PCR from the genomic DNA of infected NIH 3T3 cells.

PCR Conditions:

10, uL 10× buffer, 0.8 mM dNTP (0.2 mM of each nucleotide), 0.25 pM of each primer and 2.625 units of enzyme (Expand High Fidelity PCR System (Roche)).

```
Using primers:
                                        (SEQ ID NO: 185)
204820: CTCTCCAAGCTCACTTACAGGCCCTC

                                        (SEQ ID NO: 186)
205585: TGCGGCCGCGTCGACTGGCTAAGCCTTATGAA
95 C: 2 min., 45 x (95 C: 1 min, 60 C: 30 sec.,
73 C: 4 min.), 73 C: 5 min.
```

Example 5

Sequence Alignment of Various Envelope Polypeptides, Showing Homology

Sequence alignments were undertaken for a variety of homologous viral envelope polypeptides, see FIGS. 5A-5G.

The sequences for the alignment shown in FIGS. 5A-5C are as follows:

SL3-2 (SEQ ID NO:146)
Xeno NZB-9-1 (SEQ ID NO:147)
Moloney (SEQ ID NO:148)
4070A (SEQ ID NO:149)
MCF-247 (SEQ ID NO:150)
FeLV B (SEQ ID NO:151)
Consensus (SEQ ID NO:152)

For FIGS. 5D-5G, all of the sequences except that of SL3-2 were downloaded from NCBI databank at the following World Wide Web address: www.ncbi.nlm.nih.gov/entrez/query.fcgi?CMD=search&DB=nucleotide Information on the aligned sequences is as follows:

1. SL3-2: (SEQ ID NO:153)
2. MCF 247: (SEQ ID NO:154)

DEFINITION Mink cell focus-forming 247 MuLV env gene, 3' end and LTR. Kelly, M., Holland, C. A., Lung, M. L., Chattopadhyay, S. K., Lowy, D. R. and Hopkins, N. H.
TITLE Nucleotide sequence of the 3' end of MCF 247 murine leukemia virus JOURNAL J. Virol. 45, 291-298 (1983)
DEFINITION Mink cell-focus forming 247 murine leukemia provirus pol gene, 3' end and env gene, 5' end.
AUTHORS Khan, A. S.
TITLE Nucleotide sequence analysis establishes the role of endogenous murine leukemia virus DNA segments in formation of recombinant mink cell focus-forming murine leukemia viruses
JOURNAL J. Virol. 50, 864-871 (1984)

3. MCF CI-3: (SEQ ID NO:155)

DEFINITION MCF-MuLV proviral DNA (isolated from in vitro-transformed mink lung epithelial C3H/MCA 5 cells), clone pCI-3.
AUTHORS Mark, G. E. and Rapp, U. R.
TITLE Envelope gene sequence of two in vitro-generated mink cell focus-forming murine leukemia viruses which contain the entire gp70 sequence of the endogenous non-ecotropic parent
JOURNAL J. Virol. 49, 530-539 (1984)

4. ERV-1: (SEQ ID NO:156)

DEFINITION Murine leukemia virus erv1 envelope protein gene, complete cds.
AUTHORS Liu, S., Li, H., Barker, C. and Cloyd, M. TITLE Envelope sequences of ecotropic recombinant virus
JOURNAL Unpublished 5. Friend MCF: (SEQ ID NO:157)

AUTHORS Adachi, A., Sakai, K., Kitamura, N., Nakanishi, S., Niwa, O., Matsuyama, M. and Ishimoto, A.
TITLE Characterization of the env gene and long terminal repeat of molecularly cloned Friend mink cell focus-inducing virus DNA
JOURNAL J. Virol. 50 (3), 813-821 (1984)

6. Friend SFV: (SEQ ID NO:158)

AUTHORS Hoatlin, M. E., Gomez-Lucia, E., Lilly, F., Beckstead, J. H. and Kabat, D. TITLE Direct Submission
JOURNAL Submitted (15 Oct. 1997) Biochemistry and Molecular Biology, Oregon Health Sciences University, 3181 SW Sam Jackson Park Way, Portland, Oreg. 97201, USA 7. Invitro MCF: (SEQ ID NO:159)

AUTHORS Mark, G. E. and Rapp, U. R.
TITLE Envelope gene sequence of two in vitro-generated mink cell focus-forming murine leukemia viruses which contain the entire gp70 sequence of the endogenous non-ecotropic parent
JOURNAL J. Virol. 49 (2), 530-539 (1984)

8. MCF 1223: (SEQ ID NO:160)

TITLE Direct Submission
JOURNAL Submitted (17 Aug. 1994) Elisabeth J. A. Sijts, Immunohematology and Blood Bank, University Hospital Leiden, Leiden, Zuid-Holland, 2300 RC, Netherland-sCOMMENT MCF1233 is a type I env recombinant MuLV, composed of an ecotropic backbone with acquired polytropic sequences in the 3' pol-5' env region. The U3 LTR contains multiple mutations, distinguishing this sequence from ecotropic U3 sequences. Boundaries of repeat regions and protein-encoding regions, annotated in the feature table, are based on alignment with the sequence of the ecotropic Akv MuLV (Herr, W., J. Virol. 49, 471-478 (1984)).

9. MLV DBA/2: (SEQ ID NO:161)

AUTHORS Grohmann, U., Puccetti, P., Belladonna, M. L., Fallarino, F., Bianchi, R., Binaglia, L., Sagakuchi, K., Mage, M. G., Appella, E. and Fioretti, M.C. TITLE Multiple point mutations in an endogenous retroviral gene confer high immunogenicity on a drug-treated murine tumor
JOURNAL J. Immunol. 154 (9), 4630-4641 (1995)

10. Mo-MCF: (SEQ ID NO:162)
AUTHORS Bosselman, R. A., van Straaten, F., van Beveren, C. P., Verma, I. M. and Vogt, M.
TITLE Analysis of the env gene of a molecularly cloned and biologically active moloney mink cell focus-forming proviral DNA
JOURNAL J. Virol. 44, 19-31 (1982)
11. Ns-6(186) MCF: (SEQ ID NO:163)
AUTHORS Chattopadhyay, S. K., Baroudy, B. M., Holmes, K. L., Fredrickson, T. N., Lander, M. R., Morse, H.C. III. and Hartley, J. W.
TITLE Biologic and molecular genetic characteristics of a unique MCF virus that is highly leukemogenic in ecotropic virus-negative mice
JOURNAL Virology 168 (1), 90-100 (1989)
12. Rauscher sfv: (SEQ ID NO:164)
AUTHORS Bestwick, R. K., Boswell, B. A. and Kabat, D.
TITLE Molecular cloning of biologically active Rauscher spleen focus-forming virus and the sequences of its env gene and long terminal repeat
JOURNAL J. Virol. 51 (3), 695-705 (1984)
13. Endogenous from 129 GIX+ mice: (SEQ ID NO:165)
AUTHORS Levy, D. E., Lerner, R. A. and Wilson, M.C.
TITLE Normal expression of polymorphic endogenous retroviral RNA containing segments identical to mink cell focus-forming virus
JOURNAL J. Virol. 56 (3), 691-700 (1985)
14. Ampho-MCF: (SEQ ID NO:166)
DEFINITION: Murine leukemia virus Mo Ampho MCF recombinant gPr80 envelope polyprotein (env) gene, complete cds.
AUTHORS Vanin, E. F., Kaloss, M., Broscius, C. and Nienhuis, A. W.
TITLE Characterization of replication-competent retroviruses from nonhuman primates with virus-induced T-cell lymphomas and observations regarding the mechanism of oncogenesis
JOURNAL J. Virol. 68 (7), 4241-4250 (1994)
15. MCF (Ter-Grigorov): (SEQ ID NO:167)
AUTHORS Ter-Grigorov, V. S., Krifuks, O., Liubashevsky, E., Nyska, A., Trainin, Z. and Toder, V.
TITLE A new transmissible AIDS-like disease in mice induced by alloimmune stimuli
JOURNAL Nat. Med. 3 (1), 37-41 (1997)
16. MCF (Broscius): (SEQ ID NO:168)
AUTHORS Purcell, D. F. J., Broscius, C. M., Vanin, E. F., Buckler, C. E., Nienhuis, A. W. and Martin, M. A.
TITLE Direct Submission
JOURNAL Submitted (23 Sep. 1995) Damian F. J. Purcell, AIDS Cellular Biology Unit, Macfarlane Burnet Centre for Medical Research, Yarra Bend Road, PO Box 254, Fairfield, Victoria 3078, Australia
17. Friend MCF #2: (SEQ ID NO:169)
AUTHORS Koch, W., Zimmermann, W. A., Oliff, A. and Friedrich, R. W.
TITLE Molecular analysis of the envelope gene and long terminal repeat of Friend mink cell focus-inducing virus: implications for the functions of these sequences JOURNAL J. Virol. 49, 828-840 (1984)
18. R-XC-: (SEQ ID NO:170)
AUTHORS Vogt, M., Haggblom, C., Swift, S, and Haas, M.
TITLE Specific sequences of the env gene determine the host range of two XC-negative viruses of the Rauscher virus complex
JOURNAL Virology 154 (2), 420-424 (1986)
19. Xeno R-MCF-1: (SEQ ID NO:171)
AUTHORS Vogt, M., Haggblom, C., Swift, S, and Haas, M.
TITLE Specific sequences of the env gene determine the host range of two XC-negative viruses of the Rauscher virus complex
JOURNAL Virology 154 (2), 420-424 (1986)
20. DG-75 Xeno: (SEQ ID NO:172)
DEFINITION DG-75 Murine leukemia virus, complete genome.
AUTHORS Raisch, K. P., Pizzato, M., Sun, H.-Y., Takeuchi, Y., Cashdollar, L. W. and Grossberg, S. E.
TITLE Molecular cloning, complete sequence, and biological characterization of a xenotropic murine leukemia virus constitutively released from the human B-lymphoblastoid cell line, DG-75
JOURNAL Unpublished
21. Xeno NZB-9-1: (SEQ ID NO:173)
DEFINITION Murine leukemia virus NZB-9-1 xenotropic proviral DNA, pol and env genes, and 5' leader sequences.
AUTHORS O'Neill, R. R., Buckler, C. E., Theodore, T. S., Martin, M. A. and Repaske, R.
TITLE Envelope and long terminal repeat sequences of a cloned infectious NZB xenotropic murine leukemia virus
JOURNAL J. Virol. 53, 100-106 (1985)
22. Xeno CWM-S-5-X: (SEQ ID NO:174)
AUTHORS Massey, A. C., Coppola, M. A. and Thomas, C.Y.
TITLE Origin of pathogenic determinants of recombinant murine leukemia viruses: analysis of Bxv-1-related xenotropic viruses from CWD mice
JOURNAL J. Virol. 64 (11), 5491-5499 (1990)
23. Xeno Bxv-1 related: (SEQ ID NO:175)
AUTHORS Massey, A. C., Coppola, M. A. and Thomas, C.Y.
TITLE Origin of pathogenic determinants of recombinant murine leukemia viruses: analysis of Bxv-1-related xenotropic viruses from CWD mice
JOURNAL J. Virol. 64 (11), 5491-5499 (1990)
24. 4070A: (SEQ ID NO:176)
DEFENITION 4070A Amphotropic Murine leukemia virus envelope gene, complete cds.
AUTHORS Ott, D. E., Friedrich, R. and Rein, A.
TITLE Sequence analysis of amphotropic and 10A1 murine leukemia viruses: Close relationship to mink cell focus-inducing viruses
JOURNAL J. Virol. 64, 757-766 (1990)
25. 10A1: (SEQ ID NO:177)
AUTHORS Vaillancourt, P. and Grafsky, A. J.
TITLE Direct Submission
JOURNAL Submitted (9 Jan. 2001) Technical Services, Stratagene, 11011 N. Torrey Pines Rd, La Jolla, Calif. 92037, USA
26. Akv: (SEQ ID NO:178)
DEFINITION AKV murine leukemia virus, complete proviral genome.
AUTHORS Etzerodt M., Mikkelsen T., Pedersen F S., Kjeldgaard N O., and Jorgensen P.
TITLE The nucleotide sequence of the Akv murine leukemia virus genome.
JOURNAL Virology. 1984 Apr. 15; 134(1):196-207.
27. SL3-3: (SEQ ID NO:179)
DEFINITION Murine leukemia virus SL3-3, complete genome.
AUTHORS Lund, A. H. and Pedersen, F. S.
TITLE The nucleotide sequence of the high-leukemogenic murine retrovirus SL3-3 reveals a patch of mink cell focus forming-like sequences upstream of the ecotropic envelope gene. Brief report JOURNAL Arch. Virol. 144 (11), 2207-2212 (1999)

28. Friend: (SEQ ID NO:180)
DEFINITION Friend murine leukemia virus, complete genome.
AUTHORS Masuda, M., Remington, M. P., Hoffman, P. M. and Ruscetti, S. K.
TITLE Molecular characterization of a neuropathogenic and nonerythroleukemigenic variant of Friend murine leukemia virus PVC211
JOURNAL J. Virol. 66, 2798-2806 (1992)
29. Moloney: (SEQ ID NO:181)
AUTHORS Shinnick, T. M., Lerner, R. A. and Sutcliffe, J. G.
TITLE Nucleotide sequence of Moloney murine leukaemia virus
JOURNAL Nature 293 (5833), 543-548 (1981)
AUTHORS Miller, A. D. and Verma, I. M.
TITLE Two base changes restore infectivity to a noninfectious molecular clone of Moloney murine leukemia virus (pMLV-1)
JOURNAL J. Virol. 49 (1), 214-222 (1984)
30. Friend fass (SEQ ID NO:182)
31. Consensus (SEQ ID NO:183)

Examples 6-11

Constructs

The underlined sequence is inserted in between the designated amino acids in SL3-2 envelope. Apelin sequence is double underlined and the linker sequence is underlined with a broken line. Please see below for the insertion sites.

The given primers are used to make an overlap extension fragment (Jespersen et al., 1997) that was ligated into the NcoI og BstEII sites of the SL3-2 expression vector (Bahrami et al., 2004).

SL3-2 Apelin @155

(SEQ ID NO: 187)

GNT *QGIYQC* SGGSG QRPRLSHKGPMPF SGGSG *CG* PCYD

Primer →

(SEQ ID NO: 188)

*TCC GGT GGC AGT GGA* Cag cgg ccc cgc ctc tcc cat aag gga ccc atg cct ttc *AGC GGT GGA TCT GGC TGT*

*GGG* CCC TGT TAT GAT TCC TCG GTG GTC

Primer ←

(SEQ ID NO: 189)

GGG CCG CTG TCC ACT GCC ACC GGA GCA CTG GTA GAT

TCC TTG AGT GTT TCC TCG CTT AAG GGA

SL3-2 Apelin @165

Between amino acid no 144 (D) and 157 (G) in the FeLV-B amino acid sequence is inserted:

(SEQ ID NO: 190)

PCYDS SGGSG QRPRLSHKGPMPF SGGSG SSSAQGA

Primer forward (SEQ ID NO: 191)

*TCC GGT GGC AGT GGA* Cag cgg ccc cgc ctc tcc cat aag gga ccc atg cct ttc *AGC GGT GGA TCT GGC* TCC

AGT AGC GCC CAG GGT GCC ACA

Primer reverse:

(SEQ ID NO: 192)

GGG CCG CTG TCC ACT GCC ACC GGA GGA ATC ATA ACA

GGG GCC CTG GCC

Transfection and Transduction

Transfections were done by calcium phosphate precipitation method, described by Graham and van der Eb (Graham and van der Eb, 1973) leaving the calcium precipitate on the cells for 24 hours. 293T cells were transfected using 8 μg of envelope expression plasmid, 2 μg gagpol expression plasmid (Morita et al., 2000) and 1 μg of an EGFP expressing plasmid. EGFP was included as a visual aid to determine the success of transfections. Medium on the transfected cells was renewed every day until it was used for transduction, usually between 48 and 72 hours after transfection, depending on the number of green fluorescing cells.

The day before transduction, medium was changed from fetal calf serum to newborn calf serum containing medium. Semi-packaging cells (Bahrami et al., 2003) were seeded at concentration of $10^4$ cells/cm$^2$ 24 hours before transduction.

Supernatant from transfected cells was filtered (0.22μ). The supernatant with 6 μg/mL polybrene was added to the target cells. 24 hours later, the infected cells were selected using medium described before containing 600 μg/mL G418 for 10 days.

Example 6

Sequence Identity Between Gamma Retroviruses

The percent sequence identity between the protein sequences of gammaretroviruses when compared with the SL3-2 envelope protein sequence of gammaretroviruses was calculated using the VECTOR NTI computer program:

| Name | Tropism | Percent sequence identity in envelope protein | Percent sequence identity in RBD of envelope protein |
|---|---|---|---|
| FeLV-B | Pit-1 receptor but from cats | 60.2 | 52.3 |
| MoMLV | Ecotropic | 63.5 | 35.4 |
| MCF247 | Polytropic | 92.7 | 92.0 |
| NZB-9-1 | Xenotropic | 76.4 | 71.0 |
| 4070A | Amphotropic | 87.6 | 84.7 |

Where RBD is the receptor binding domain. corresponding to the receptor binding domain (RCB) of the envelope polypeptide is defined as the region delineated by the first amino acid of SEQ ID NO: 60 and the amino acid preceding the proline rich region (PPR) corresponding to the amino acid number 114 of SEQ ID NO: 60.

The amino acid sequence of SL3-2 is identical to that of SEQ ID NO: 60. The amino acid sequence of MCF247, NZB-9-1, MoMLV and 4070A can be obtained from the NCBI databank at the link www.ncbi.nlm.nih.gov/entrez/query.fcgi?CMD=search&DB=nucleotide or from the original scientific journals: MCF247 (Kelly et al. 1983; Khan 1984), MoMLV (Shinnick et al. 1981; Miller and Verma 1984), 4070A (Ott et al. 1990), NZB-9-1 (O'Neill et al. 1985).

Information on the definition and references regarding gammaretroviruses is found below.

1. SL3-2:

Sequence presented in this Ph.D. thesis.

2. MCF 247:

DEFINITION Mink cell focus-forming 247 MuLV env gene, 3' end and LTR. Kelly, M., Holland, C. A., Lung, M. L., Chattopadhyay, S. K., Lowy, D. R. and Hopkins, N. H.

TITLE Nucleotide sequence of the 3' end of MCF 247 murine leukemia virus JOURNAL J. Virol. 45, 291-298 (1983)

DEFINITION Mink cell-focus forming 247 murine leukemia provirus pol gene, 3' end and env gene, 5' end.

AUTHORS Khan, A. S.

TITLE Nucleotide sequence analysis establishes the role of endogenous murine leukemia virus DNA segments in formation of recombinant mink cell focus-forming murine leukemia viruses JOURNAL J. Virol. 50, 864-871 (1984)

6. MCF CI-3:

DEFINITION MCF-MuLV proviral DNA (isolated from in vitro-transformed mink lung epithelial C3H/MCA 5 cells), clone pCI-3.

AUTHORS Mark, G. E. and Rapp, U. R.

TITLE Envelope gene sequence of two in vitro-generated mink cell focus-forming murine leukemia viruses which contain the entire gp70 sequence of the endogenous non-ecotropic parent JOURNAL J. Virol. 49, 530-539 (1984)

7. ERV-1:

DEFINITION Murine leukemia virus erv1 envelope protein gene, complete cds.

AUTHORS Liu, S., Li, H., Barker, C. and Cloyd, M. TITLE Envelope sequences of ecotropic recombinant virus JOURNAL Unpublished 8. Friend MCF:

AUTHORS Adachi, A., Sakai, K., Kitamura, N., Nakanishi, S., Niwa, O., Matsuyama, M. and Ishimoto, A.

TITLE Characterization of the env gene and long terminal repeat of molecularly cloned Friend mink cell focus-inducing virus DNA JOURNAL J. Virol. 50 (3), 813-821 (1984)

6. Friend SFV:

AUTHORS Hoatlin, M. E., Gomez-Lucia, E., Lilly, F., Beckstead, J. H. and Kabat, D. TITLE Direct Submission JOURNAL Submitted (15 Oct. 1997) Biochemistry and Molecular Biology, Oregon Health Sciences University, 3181 SW Sam Jackson Park Way, Portland, Oreg. 97201, USA 7. Invitro MCF:

AUTHORS Mark, G. E. and Rapp, U. R.

TITLE Envelope gene sequence of two in vitro-generated mink cell focus-forming murine leukemia viruses which contain the entire gp70 sequence of the endogenous non-ecotropic parent JOURNAL J. Virol. 49 (2), 530-539 (1984)

8. MCF 1223:

TITLE Direct Submission

JOURNAL Submitted (17 Aug. 1994) Elisabeth J. A. Sijts, Immunohematology and Blood Bank, University Hospital Leiden, Leiden, Zuid-Holland, 2300 RC, Netherlands COMMENT MCF1233 is a type I env recombinant MuLV, composed of an ecotropic backbone with acquired polytropic sequences in the 3' pol-5' env region. The U3 LTR contains multiple mutations, distinguishing this sequence from ecotropic U3 sequences. Boundaries of repeat regions and protein-encoding regions, annotated in the feature table, are based on alignment with the sequence of the ecotropic Akv MuLV (Herr, W., J. Virol. 49, 471-478 (1984)).

11. MLV DBA/2:

AUTHORS Grohmann, U., Puccetti, P., Belladonna, M. L., Fallarino, F., Bianchi, R., Binaglia, L., Sagakuchi, K., Mage, M. G., Appella, E. and Fioretti, M.C. TITLE Multiple point mutations in an endogenous retroviral gene confer high immunogenicity on a drug-treated murine tumor JOURNAL J. Immunol. 154 (9), 4630-4641 (1995)

12. Mo-MCF:

AUTHORS Bosselman, R. A., van Straaten, F., van Beveren, C. P., Verma, I. M. and Vogt, M.

TITLE Analysis of the env gene of a molecularly cloned and biologically active moloney mink cell focus-forming proviral DNA JOURNAL J. Virol. 44, 19-31 (1982)

11. Ns-6(186) MCF:

AUTHORS Chattopadhyay, S. K., Baroudy, B. M., Holmes, K. L., Fredrickson, T. N., Lander, M. R., Morse, H.C. III. and Hartley, J. W.

TITLE Biologic and molecular genetic characteristics of a unique MCF virus that is highly leukemogenic in ecotropic virus-negative mice JOURNAL Virology 168 (1), 90-100 (1989)

12. Rauscher sfv:

AUTHORS Bestwick, R. K., Boswell, B. A. and Kabat, D.

TITLE Molecular cloning of biologically active Rauscher spleen focus-forming virus and the sequences of its env gene and long terminal repeat JOURNAL J. Virol. 51 (3), 695-705 (1984)

13. Endogenous from 129 GIX+ mice:

AUTHORS Levy, D. E., Lerner, R. A. and Wilson, M.C.

TITLE Normal expression of polymorphic endogenous retroviral RNA containing segments identical to mink cell focus-forming virus JOURNAL J. Virol. 56 (3), 691-700 (1985)

30. Ampho-MCF:

DEFENTION: Murine leukemia virus Mo Ampho MCF recombinant gPr80 envelope polyprotein (env) gene, complete cds.

AUTHORS Vanin, E. F., Kaloss, M., Broscius, C. and Nienhuis, A. W.

TITLE Characterization of replication-competent retroviruses from nonhuman primates with virus-induced T-cell lymphomas and observations regarding the mechanism of oncogenesis JOURNAL J. Virol. 68 (7), 4241-4250 (1994)

31. MCF (Ter-Grigorov):

AUTHORS Ter-Grigorov, V. S., Krifuks, O., Liubashevsky, E., Nyska, A., Trainin, Z. and Toder, V.

TITLE A new transmissible AIDS-like disease in mice induced by alloimmune stimuli JOURNAL Nat. Med. 3 (1), 37-41 (1997)

32. MCF (Broscius):

AUTHORS Purcell, D. F. J., Broscius, C. M., Vanin, E. F., Buckler, C. E., Nienhuis, A. W. and Martin, M. A.

TITLE Direct Submission

JOURNAL Submitted (23 Sep. 1995) Damian F. J. Purcell, AIDS Cellular Biology Unit, Macfarlane Burnet Centre for Medical Research, Yarra Bend Road, PO Box 254, Fairfield, Victoria 3078, Australia 33. Friend MCF #2:

AUTHORS Koch, W., Zimmermann, W. A., Oliff, A. and Friedrich, R. W.

TITLE Molecular analysis of the envelope gene and long terminal repeat of Friend mink cell focus-inducing virus: implications for the functions of these sequences JOURNAL J. Virol. 49, 828-840 (1984)

34. R-XC-:
AUTHORS Vogt, M., Haggblom, C., Swift, S, and Haas, M.
TITLE Specific sequences of the env gene determine the host range of two XC-negative viruses of the Rauscher virus complex
JOURNAL Virology 154 (2), 420-424 (1986)
35. Xeno R-MCF-1:
AUTHORS Vogt, M., Haggblom, C., Swift, S, and Haas, M.
TITLE Specific sequences of the env gene determine the host range of two XC-negative viruses of the Rauscher virus complex
JOURNAL Virology 154 (2), 420-424 (1986)
36. DG-75 Xeno:
DEFINITION DG-75 Murine leukemia virus, complete genome.
AUTHORS Raisch, K. P., Pizzato, M., Sun, H.-Y., Takeuchi, Y., Cashdollar, L. W. and Grossberg, S. E.
TITLE Molecular cloning, complete sequence, and biological characterization of a xenotropic murine leukemia virus constitutively released from the human B-lymphoblastoid cell line, DG-75
JOURNAL Unpublished
37. Xeno NZB-9-1:
DEFINITION Murine leukemia virus NZB-9-1 xenotropic proviral DNA, pol and env genes, and 5' leader sequences.
AUTHORS O'Neill, R. R., Buckler, C. E., Theodore, T. S., Martin, M. A. and Repaske, R. TITLE Envelope and long terminal repeat sequences of a cloned infectious NZB xenotropic murine leukemia virus
JOURNAL J. Virol. 53, 100-106 (1985)
38. Xeno CWM-S-5-X:
AUTHORS Massey, A. C., Coppola, M. A. and Thomas, C. Y.
TITLE Origin of pathogenic determinants of recombinant murine leukemia viruses: analysis of Bxv-1-related xenotropic viruses from CWD mice
JOURNAL J. Virol. 64 (11), 5491-5499 (1990)
39. Xeno Bxv-1 related:
AUTHORS Massey, A. C., Coppola, M. A. and Thomas, C. Y.
TITLE Origin of pathogenic determinants of recombinant murine leukemia viruses: analysis of Bxv-1-related xenotropic viruses from CWD mice
JOURNAL J. Virol. 64 (11), 5491-5499 (1990)
40. 4070A:
DEFENITION 4070A Amphotropic Murine leukemia virus envelope gene, complete cds.
AUTHORS Ott, D. E., Friedrich, R. and Rein, A.
TITLE Sequence analysis of amphotropic and 10A1 murine leukemia viruses: Close relationship to mink cell focus-inducing viruses
JOURNAL J. Virol. 64, 757-766 (1990)
41. 10A1:
AUTHORS Vaillancourt, P. and Grafsky, A. J.
TITLE Direct Submission
JOURNAL Submitted (9 Jan. 2001) Technical Services, Stratagene, 11011 N. Torrey Pines Rd, La Jolla, Calif. 92037, USA
42. Akv:
DEFINITION AKV murine leukemia virus, complete proviral genome.
AUTHORS Etzerodt M., Mikkelsen T., Pedersen F S., Kjeldgaard N O., and Jorgensen P.
TITLE The nucleotide sequence of the Akv murine leukemia virus genome.
JOURNAL Virology. 1984 Apr. 15; 134(1):196-207.
43. SL3-3:
DEFINITION Murine leukemia virus SL3-3, complete genome.
AUTHORS Lund, A. H. and Pedersen, F. S.
TITLE The nucleotide sequence of the high-leukemogenic murine retrovirus SL3-3 reveals a patch of mink cell focus forming-like sequences upstream of the ecotropic envelope gene. Brief report JOURNAL Arch. Virol. 144 (11), 2207-2212 (1999)
44. Friend:
DEFINITION Friend murine leukemia virus, complete genome.
AUTHORS Masuda, M., Remington, M. P., Hoffman, P. M. and Ruscetti, S. K.
TITLE Molecular characterization of a neuropathogenic and nonerythroleukemigenic variant of Friend murine leukemia virus PVC211
JOURNAL J. Virol. 66, 2798-2806 (1992)

Example 7

Targeting the APJ Receptor

The ability of redirecting the retroviral fusion machinery to a desired receptor would have wide biotechnological and potentially also nanotechnological applications. However, the regulatory mechanisms that interconnect receptor binding with fusion are poorly understood, which has made intelligent engineering of the envelope protein difficult. Many attempts at redirecting the receptor-specificity have found that incorporation of a ligand into the envelope protein may cause receptor-dependent binding without activation of the fusion machinery. Using the envelope protein of the SL3-2 murine leukemia virus isolate (Pedersen et al., 1981) as a backbone and insertion of the 13 amino acid peptide ligand apelin by structure based design, we achieved efficient membrane fusion in a manner dependent upon APJ, the receptor for apelin (Fan et al., 2003; Kawamata et al., 2001) (FIG. 12). APJ belongs to the large family of G-protein-coupled receptors (GPCRs) involved in cell signaling with more than 1000 members in man (Puffer et al., 2000). All GPCRs are characterized by having 7 transmembrane helices (7-TM). Some of the receptors respond to peptide ligands such as apelin. All peptide-binding GPCRs have the organization shown in FIG. 13, where the ligand is known to bind to the N-terminal part, located extracellularly.

The results of titer experiments are shown below

Titer Experiment 1

| Construct | NIH 3T3 | NIH 3T3 MCF 247 | D17 | D17 CXCR-4 | D17 APJ |
|---|---|---|---|---|---|
| 155RT | $5 \times 10^5$ | 0 | 0 | ND | $1.75 \times 10^3$ |
| 155GI | $7.5 \times 10^5$ | $0.25 \times 10^1$ | 2.5 | ND | $4 \times 10^2$ |
| 165RT | $3 \times 10^6$ | $0.75 \times 10^1$ | $2.75 \times 10^1$ | $1.25 \times 10^1$ | $2.5 \times 10^6$ |
| 165GI | $4 \times 10^6$ | 0 | $1.25 \times 10^1$ | ND | $1.25 \times 10^6$ |

The results of titer experiment 2 is shown in FIG. 12.

The chimeric envelope peptides (exemplified by AP@155 RT and GI, and AP@165 RT and GI, respectively) mediate specific entry into D17 dog cells of an SL3-2 envelope virus engineered to harbor its cognate ligand at a critical position (see FIG. 14). The insertion site in AP@155 is suboptimal relative to AP@165. NIH cells are mouse cells that can be infected by the wt SL3-2 as well as the three mutants. SL3-2GI is a mutant that infects human cells, but not dog cells.

Example 8

Targeting the Tachykinin NK1 Receptor

The tachykinin NK1 receptor is well-characterized, and pharmacologically important. This receptor has several natural small-peptide ligands such as substance P (11 amino acids), neurokinin A and neurokinin B (both 10 amino acids) (Quartara and Maggi, 1997). An expression vector for the human tachykinin NK1 receptor is available and the peptide motifs for its ligands will be engineered into the SL3-2 envelope as done for Apelin. The redirection of receptor specificity will be tested on D17 dog cells with or without the Tachykinin NK1 receptor and possibly other cell lines from various species if needed to reduce the background of receptor-independent infection. The system most optimal for receptor-dependent infection will be used to test the ability of soluble tachykinin NK1 ligands (peptides and synthetic non-peptide ligands) to inhibit infection in a competitive manner, parallel to what we have found for the apelin/APJ model (data not shown).

Example 9

Targeting Receptor-Dependent Cell Labelling by Hemifusion

In the field of bioimaging, this work may suggest novel means for the detection and imaging of specific cell surface proteins on live cells by the receptor-dependent attachment of labelled viral particles to cell surfaces by membrane hemifusion, where only the outer leaflets of the two lipid-bilayer membranes are fused. This is an intermediate in the normal fusion process (see FIG. 15). Hemifusion may also provide innovative means for the delivery of cargo to the plasma membrane. Hemifused particles are expected to be in a locked state on the membrane as a result of the limited diffusion of integral membrane proteins that span both bi-layers. It is conceivable that the hemif used stage will only be reached following a very accurate interaction with the receptor at physiological temperature, which suggests that this way of labelling live cells could be very specific as well as stable. A technology to lock enveloped particles at the hemif used stage by the mutation of a critical histidine residue has been described (Zavorotinskaya T, et al. 2004). We will use fluorochrome-labelled virus particles with or without this mutation to study the attachment of virus particles to cells in vitro with respect to the sensitivity of detection, the specificity of labeling, and the stability of the complex. The receptor-ligand panel to be used in the experiments include SL3-2 wild-type/Xpr1 receptor; Akv/mCAT receptor; SL3-2 apelin/APJ, and SL3-2 substanceP/Tachykinin NK1). Quantitative and qualitative read-out of cell labeling will be done by flow cytometry and fluorescence microscopy, respectively.

Example 10

Targeting HIV Coreceptors and Obtaining Viral Interference

Figure 1A:
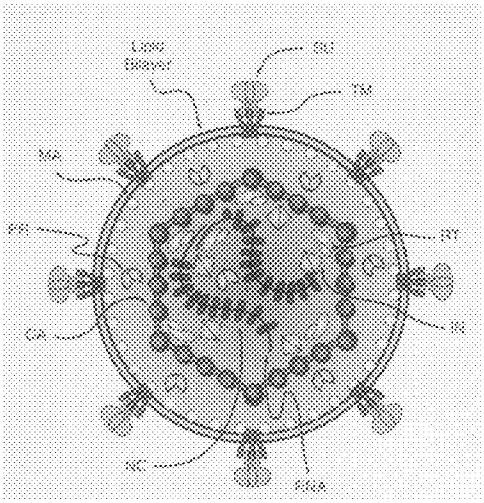
FIG. 1A: Schematic depiction of a retrovirus, showing viral envelope polypeptide
Figure 1B:
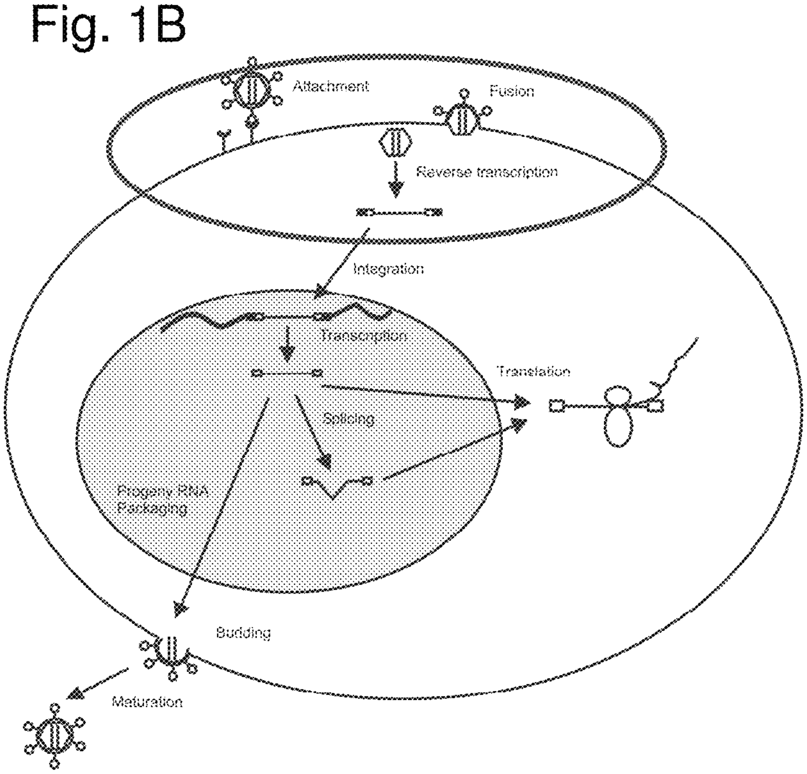
FIG. 1B: Schematic depiction of retroviral life cycle
Figure 2:
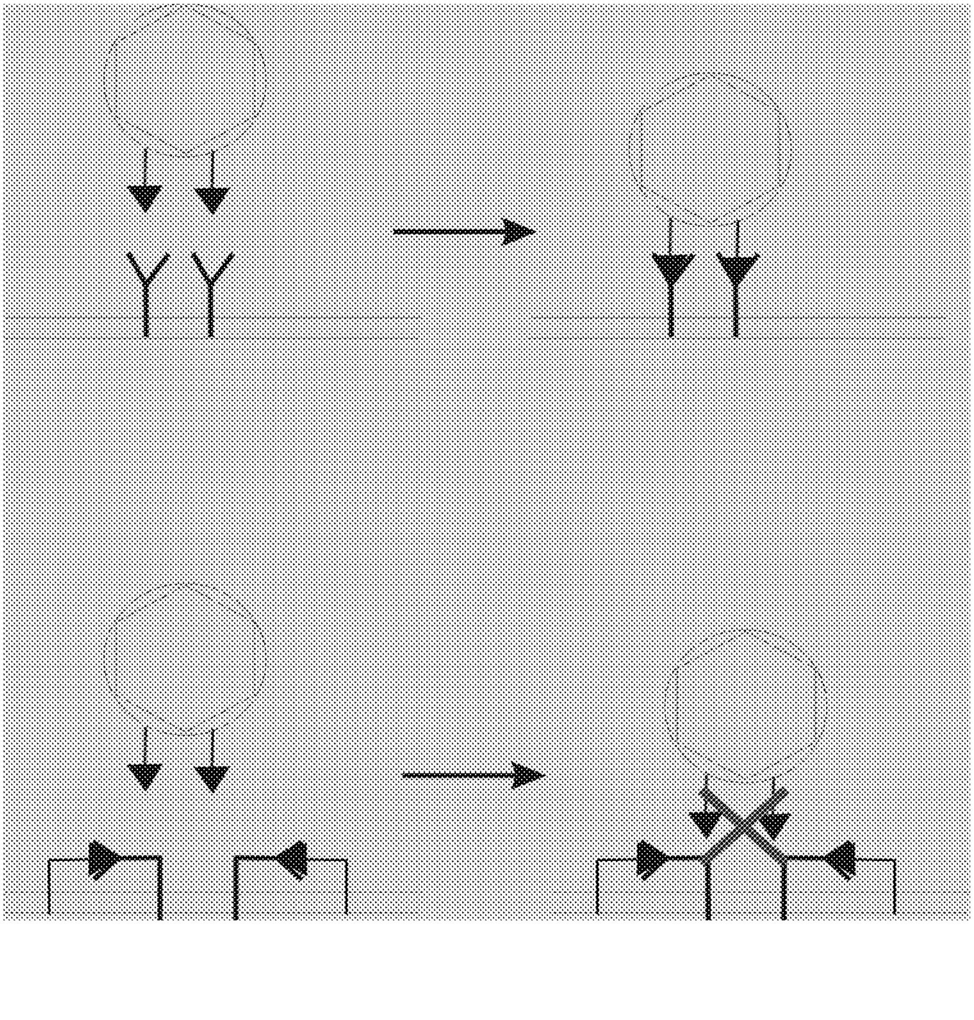
FIG. 2 shows a schematic depiction of retroviral interference. Top: Normal infection mechanism via receptor binding. Bottom: Receptor shielding by endogenous expressed envelope.

Among the murine γ-retroviruses a phenomenon termed receptor interference has been used to classify viruses based on their tropism (Sommerfelt et al. 1990). Upon infection the virus synthesize de novo envelope proteins for the production of new viral particles. Some of these envelope proteins will engage the receptor via an unknown mechanism and shield the receptor (see FIG. 2). This shielding prevents the recurrence of an infective event by an exogenous virus. In cell culture the interference is very effective in that complete block of infection can be observed.

HIV-1 is somewhat different with regard to receptor usage. For HIV-1 entry to occur a two-step binding mechanism is required. First the HIV-1 envelope protein binds the CD4 receptor (primary receptor) (Eckert et al 2001). This event initiates a conformational change that exposes a region termed V3 (Variable loop 3) which is responsible for a second interaction with a co-receptor (either CCR-5 or CXCR-4) (Huang et al 2005). This co-receptor interaction is absolutely required for infection to occur. In cell culture the same degree of receptor interference is not observed by HIV-1 infection, which may be due to the dual receptor requirement.

We wish to take advantage of the ability of the γ-retroviral envelopes to confer superinfection resistance to block entry of HIV into CD4+ cells, a further development of the above mentioned targeting principle. The idea is to use an engineered SL3-2 envelope that contains the V3 region of HIV in place of the Apelin peptide (see FIG. 14) to block the HIV co-receptors CCR-5 and CXCR-4 and thereby preventing HIV infection. We have preliminary data suggesting that expression of the V3 region in the gamma-retroviral envelope can interfere with cell-cell fusion caused by the HIV-envelope (see FIG. 10).

Example 11

Construction of a Chimeric SL3-2 Envelope Comprising a Tetra Cystein Motif at Amino Acid Position 165.

Insertion of a cloning linker at position 165 of SL3-2 envelope (neo SL3-2 link@165 mo):

The sequence TCA GGT GGC TCC GGA GGG TCT GGC TCG (SEQ ID NO:193) was inserted at position 165 in the SL3-2 env gene between sequences: CCC TGT TAT GAT TCC . . . . . . . . . . . . . . . AGT AGC (SEQ ID NO:194).

The linker sequence has three unique restriction sites:

```
                                        (SEQ ID NO: 195)
CCC TGT TAT GAT TCC TCA GGT GGC TCC GGA GGG TCT

GGC TCG AGT AGC

BspEI site:    T^CCGG^A
XhoI site:     C^TCGA^G
Bsu36I site:   CC^TNA^GG
```

Insertion of any ligand sequence into the XhoI and Bsu36I site results in minimal alteration of the native SL3-2 sequence flanking the insert.

Insertion of any ligand sequence into the BSpEI site result in regeneration of the SGGSG linker on each side of the insert.

Cloning Procedure:

Two PCR fragments were made using primers:

```
Fragment 1:
                                        (SEQ ID NO: 196)
TCA GGT GGC TCC GGA GGG TCT GGC TCG AGT AGC GCC

CAG GGT GCC ACA CCG
And
                                        (SEQ ID NO: 197)
CGG GTC GGG AGG GGG GTA ACT

Fragment 2:
                                        (SEQ ID NO: 198)
GCC AGA CCC TCC GGA GCC ACC TGA GGA ATC ATA ACA

GGG GCC CTG GCC
And
                                        (SEQ ID NO: 199)
TGA AAA ACA CGA TAA TAC CAT
```

And the plasmid NeoSL3-2mo as the template.

The fragments were coupled together in an overlap extension reaction. The resulting fragment was digested with BstEII and NcoI and ligeted into the BstEII, NcoI fragment of the plasmid NeoSL3-2mo.

The resulting envelope gene has the following sequence:

(SEQ ID NO: 200)

ATGgAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGAcCA

CTGGACAGGCATACTGGAAGCCATCATCATCATGGGACCTAATTTCCCTT

AAGCGAGGAAACACTCCTAAAGGCCAGGGCCCCTGTTATGATTCC

*TCA GGT GGC TCC GGA GGG TCT GGC TCG*

AGTAGCGcCCAGGGTGCCACACCGGGGGGTCGATGCAACCCCCTAGTCCT

AGAATTCACTGACGCGGGTaaaagggccagctgggACGCCTCCAAAGCAT

GGGGACTAAGACTGTACCGATCCACAAGGACCGACCCGGTGACCCGGTTC

TCTTTGACCCGCCAGGTCCTCAATATAGGGCCCCGCGTCCCCATTGGGCC

TAATCCCGTGATCATTGACCAGTTACCCCCCTCCCGACCCGTGCAGATCA

TGCTCCCCAGGCCTCCTCAGCCTCCTCCACCAGGCGCAGCCTCTACAGTC

CCTGAGACTGCCCCACCTTCCCAACAACCTGGGACGGGAGACAGGCTGCT

AAACCTGGTAAATGGAGCCTACCAAGCTCTCAACCTCACCAGTCCTGACA

AAACCCAA

GAGTGCTGGTTGTGTCTGGTAGCGGGACCCCCCTACTACGAAGGGGTTGC

CGTCCTAGGTACTTATTCCAACCATACCTCTGCCCCAGCTAACTGCTCCG

TGGCCTCCCAACACAAGCTGACCCTGTCCGAAGTGACCGGACAGGGACTC

TGCGTAGGAGCAGTTCCCAAAACCCATCAGGCCCTGTGTAATACCACCCA

GAAGACGAGCAAGGGGTCCTACTATCTGGCTGCTCCCGCCGGGACCATTT

GGGCTTGCAACACCGGGCTCACTCCCTGCCTATCTACCACTGTGCTCGAC

CTCACCACCGATTACTGTGTCCTGGTTGAGCTCTGGCCAAAAGTGACCTA

CCACTCCCCTGGTTATGTTTATGGCCAGTTTGAAGAAAAAACCAAATATA

AAAGAGAACCCGTCTCACTAACTCTGGCCCTACTATTAGGAGGACTCACT

ATGGGCGGAATTGCCGCCGGAGTGGGAACAGGGACTACCGCCCTAGTGGC

CACTCAGCAGTTCCAACAACTCCAGGCTGCCATGCAGGATGACCTTAAAG

AAGTTGAAAAGTCCATCACTAATCTAGAAAGATCTTTGACCTCCTTGTCC

GAAGTAGTGTTACAGAATCGTAGAGGCCTAGATCTACTATTCCTAAAAGA

GGGAGGTTTGTGTGCTGCCTTAAAAGAAGAATGCTGTTTCTATGCCGACC

ACACAGGATTGGTACGGGATAGCATGGCCAAACTTAGAGAAAGATTGAGT

CAGAGACAAAAACTCTTTGAATCCCAACAAGGGTGGTTTGAAGGGCTGTT

-continued

TAACAAGTCCCCTTGGTTCACCACCCTGATATCCACCATCATGGGTCCCC

TGATAATCCTCTTGTTAATTTTACTCTTTGGGCCTTGTATTCTCAATCAC

CTGGTCCAGTTTATCAAACACAGGGTTTCGGTAGTGCAGGCCCTGGTCCT

GACTCAACAATATCATCAACTTAAGACAATAGAAGATTGTgAATCACGTG

AATAA

Construction of the envelope genes containing the tetracystein motifs.

Two constructs were made, one (neo SL3-2 tetC6@165mo) contained the SGGSG CCPGCC SGGSG (SEQ ID NO:201) and the other (neo SL3-2 tetC12@165mo) contained the sequence SGGSG HRWCCPGCCKTF SGGSG (SEQ ID NO:202) sequence at position 165 of SL3-2.

neoSL3-2 tetC6@165mo was made by annealing the following primers together and cloning them into the XhoI and Bsu36I site of the neo SL3-2 link@165 mo plasmid:

(SEQ ID NO: 203)

TCA GGT GGC TCC GGT TGT TGT CCA GGC TGC TGC AGT

GGG GGC AGC GGC

And (SEQ ID NO: 204)

TCG AGC CGC TGC CCC CAC TGC AGC AGC CTG GAC AAC

AAC CGG AGC CAC C neoSL3-2 tetC12@165mo was made by annealing the following primers together and cloning them into the XhoI and Bsu36I site of the neo SL3-2 link@165 mo plasmid:

(SEQ ID NO: 205)

TCA GGT GGC TCC GGT CAT AGA TGG TGT TGT CCA GGC

TGC TGC AAG ACG TTC AGT GGG GGC AGC GGC

And (SEQ ID NO: 206)

TCG AGC CGC TGC CCC CAC TGA ACG TCT TGC AGC AGC

CTG GAC AAC ACC ATC TAT GAC CGG AGC CAC C

The constructs have been tested on NIH3T3 murine cells. NeoSL3-2 tetC6@165mo infects these cells with wt efficiency, whereas neoSL3-2 tetC12@165mo has a titer of approximately two orders of magnitude lower.

The envelope genes have the following sequences:

neoSL3-2 tetC6@165mo:

(SEQ ID NO: 207)

ATGgAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGAcCA

-continued

CTGGACAGGCATACTGGAAGCCATCATCATCATGGGACCTAATTTCCCTT

AAGCGAGGAAACACTCCTAAAGGCCAGGGCCCCTGTTATGATTCCTCAGG

TGGCTCCGGTTGTTGTCCAGGCTGCTGCAGTGGGGGCAGCGGCTCGAGTA

GCGcCCAGGGTGCCACACCGGGGGGTCGATGCAACCCCCTAGTCCTAGAA

TTCACTGACGCGGGTaaaagggccagctgggACGCCTCCAAAGCATGGGG

ACTAAGACTGTACCGATCCACAAGGACCGACCCGGTGACCCGGTTCTCTT

TGACCCGCCAGGTCCTCAATATAGGGCCCCGCGTCCCCATTGGGCCTAAT

CCCGTGATCATTGACCAGTTACCCCCCTCCCGACCCGTGCAGATCATGCT

CCCCAGGCCTCCTCAGCCTCCTCCACCAGGCGCAGCCTCTACAGTCCCTG

AGACTGCCCCACCTTCCCAACAACCTGGGACGGGAGACAGGCTGCTAAAC

CTGGTAAATGGAGCCTACCAAGCTCTCAACCTCACCAGTCCTGACAAAAC

CCAAGAGTGCTGGTTGTGTCTGGTAGCGGGACCCCCCTACTACGAAGGGG

TTGCCGTCCTAGGTACTTATTCCAACCATACCTCTGCCCCAGCTAACTGC

TCCGTGGCCTCCCAACACAAGCTGACCCTGTCCGAAGTGACCGGACAGGG

ACTCTGCGTAGGAGCAGTTCCCAAAACCCATCAGGCCCTGTGTAATACCA

CCCAGAAGACGAGCAACGGGTCCTACTATCTGGCTGCTCCCGCCGGGACC

ATTTGGGCTTGCAACACCGGGCTCACTCCCTGCCTATCTACCACTGTGCT

CGACCTCACCACCGATTACTGTGTCCTGGTTGAGCTCTGGCCAAAAGTGA

CCTACCACTCCCCTGGTTATGTTTATGGCCAGTTTGAAGAAAAAACCAAA

TATAAAAGAGAACCCGTCTCACTAACTCTGGCCCTACTATTAGGAGGACT

CACTATGGGCGGAATTGCCGCCGGAGTGGGAACAGGGACTACCGCCCTAG

TGGCCACTCAGCAGTTCCAACAACTCCAGGCTGCCATGCAGGATGACCTT

AAAGAAGTTGAAAACTCCATCACTAATCTAGAAAGATCTTTGACCTCCTT

GTCCGAAGTAGTGTTACAGAATCGTAGAGGCCTAGATCTACTATTCCTAA

AAGAGGGAGGTTTGTGTGCTGCCTTAAAAGAAGAATGCTGTTTCTATGCC

GACCACACAGGATTGGTACGGGATAGCATGGCCAAACTTAGAGAAAGATT

GAGTCAGAGACAAAAACTCTTTGAATCCCAACAAGGGTGGTTTGAAGGGC

TGTTTAACAAGTCCCCTTGGTTCACCACCCTGATATCCACCATCATGGGT

CCCCTGATAATCCTCTTGTTAATTTTACTCTTTGGGCCTTGTATTCTCAA

TCACCTGGTCCAGTTTATCAAAGACAGGGTTTCGGTAGTGCAGGCCCTGG

TCCTGACTCAACAATATCATCAACTTAAGACAATAGAAGATTGTgAATCA

CGTGAATAA neoSL3-2 tetC12@165mo:

(SEQ ID NO: 208)

ATGgAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

-continued

GTGTGGAGGGCCGAGAGAGGGCTACTGTGGCAAATGGGGATGTGAGAcCA

CTGGACAGGCATACTGGAAGCCATCATCATCATGGGACCTAATTTCCCTT

AAGCGAGGAAACACTCCTAAAGGCCAGGGCCCCTGTTATGATTCCTCAGG

TGGCTCCGGTCATAGATGGTGTTGTCCAGGCTGCTGCAAGACGTTCAGTG

GGGGCAGCGGCTCGAGTAGCGcCCAGGGTGCCACACCGGGGGGTCGATGC

AACCCCCTAGTCCTAGAATTCACTGACGCGGGTaaaagggccagctgggA

CGCCTCCAAAGCATGGGGACTAAGACTGTACCGATCCACAAGGACCGACC

CGGTGACCCGGTTCTCTTTGACCCGCCAGGTCCTCAATATAGGGCCCCGC

GTCCCCATTGGGCCTAATCCCGTGATCATTGACCAGTTACCCCCCTCCCG

ACCCGTGCAGATCATGCTCCCCAGGCCTCCTCAGCCTCCTCCACCAGGCG

CAGCCTCTACAGTCCCTGAGACTGCCCCACCTTCCCAACAACCTGGGACG

GGAGACAGGCTGCTAAACCTGGTAAATGGAGCCTACCAAGCTCTCAACCT

CACCAGTCCTGACAAAACCCAAGAGTGCTGGTTGTGTCTGGTAGCGGGAC

CCCCCTACTACGAAGGGGTTGCCGTCCTAGGTACTTATTCCAACCATACC

TCTGCCCCAGCTAACTGCTCCGTGGCCTCCCAACACAAGCTGACCCTGTC

CGAAGTGACCGGACAGGGACTCTGCGTAGGAGCAGTTCCCAAAACCCATC

AGGCCCTGTGTAATACCACCCAGAAGACGAGCAACGGGTCCTACTATCTG

GCTGCTCCCGCCGGGACCATTTGGGCTTGCAACACCGGGCTCACTCCCTG

CCTATCTACCACTGTGCTCGACCTCACCACCGATTACTGTGTCCTGGTTG

AGCTCTGGCCAAAAGTGACCTACCACTCCCCTGGTTATGTTTATGGCCAG

TTTGAAGAAAAAACCAAATATAAAAGAGAACCCGTCTCACTAACTCTGGC

CCTACTATTAGGAGGACTCACTATGGGCGGAATTGCCGCCGGAGTGGGAA

CAGGGACTACCGCCCTAGTGGCCACTCAGCAGTTCCAACAACTCCAGGCT

GCCATGCAGGATGACCTTAAAGAAGTTGAAAAGTCCATCACTAATCTAGA

AAGATCTTTGACCTCCTTGTCCGAAGTAGTGTTACAGAATCGTAGAGGCC

TAGATCTACTATTCCTAAAAGAGGGAGGTTTGTGTGCTGCCTTAAAAGAA

GAATGCTGTTTCTATGCCGACCACACAGGATTGGTACGGGATAGCATGGC

CAAACTTAGAGAAAGATTGAGTCAGAGACAAAAACTCTTTGAATCCCAAC

AAGGGTGGTTTGAAGGGCTGTTTAACAAGTCCCCTTGGTTCACCACCCTG

ATATCCACCATCATGGGTCCCCTGATAATCCTCTTGTTAATTTTACTCTT

TGGGCCTTGTATTCTCAATCACCTGGTCCAGTTTATCAAAGACAGGGTTT

CGGTAGTGCAGGCCCTGGTCCTGACTCAACAATATCATCAACTTAAGACA

ATAGAAGATTGTgAATCACGTGAATAA

Sequence Listing (Homologues and/or fragments of the below sequences are also within the scope of the present invention)

SEQ ID NO: 1: polynucleotide sequence coding for SL3-2 viral envelope polypeptide:

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

-continued

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCCTAAAGGCCAGGGCCCCTGTTATGATTCCTCGGT

GGTCTCCAGTAGCGCCCAGGGTGCCACACCGGGGGGTCGATGCAACCCCC

TAGTCCTAGAATTCACTGACGCGGGTAAAAGGGCCAGCTGGGACGCCTCC

AAAGCATGGGGACTAAGACTGTACCGATCCACAAGGACCGACCCGGTGAC

CCGGTTCTCTTTGACCCGCCAGGTCCTCAATATAGGGCCCCGCGTCCCCA

TTGGGCCTAATCCCGTGATCATTGACCAGTTACCCCCCTCCCGACCCGTG

CAGGTCATGCTCCCCAGGCCTCCTCAGCCTCCTCCACCAGGCGCAGCCTC

TACAGTCCCTGAGACTGCCCCACCTTCCCAACAACCTGGGACGGGAGACA

GGCTGCTAAACCTGGTAAATGGAGCCTACCAAGCTCTCAACCTCACCAGT

CCTGACAAAACCCAAGAGTGCTGGTTGTGTCTGGTAGCGGGACCCCCCTA

CTACGAAGGGGTTGCCGTCCTAGGTACTTATTCCAACCATACCTCTGCCC

CAGCTAACTGCTCCGTGGCCTCCCAACACAAGCTGACCCTGTCCGAAGTG

ACCGGACAGGGACTCTGCGTAGGAGCAGTTCCCAAAACCCATCAGGCCCT

GTGTAATACCACCCAGAAGACGAGCAACGGGTCCTACTATCTGGCTGCTC

CCGCCGGGACCATTTGGGCTTGCAACACCGGGCTCACTCCCTGCCTATCT

ACCACTGTGCTCGACCTCACCACCGATTACTGTGTCCTGGTTGAGCTCTG

GCCAAAAGTGACCTACCACTCCCCTGGTTATGTTTATGGCCAGTTTGAAG

AAAAAACCAAATATAAAAGAGAACCCGTCTCACTAACTCTGGCCCTACTA

TTAGGAGGACTCACTATGGGCGGAATTGCCGCCGGAGTGGGAACAGGGAC

TACCGCCCTAGTGGCCACTCAGCAGTTCCAACAACTCCAGGCTGCCATGC

AGGATGACCTTAAAGAAGTTGAAAAGTCCATCACTAATCTAGAAAGATCT

TTGACCTCCTTGTCCGAAGTAGTGTTACAGAATCGTAGAGGCCTAGATCT

ACTATTCCTAAAAGAGGGAGGTTTGTGTGCTGCCTTAAAAGAAGAATGCT

GTTTCTATGCCGACCACACAGGATTGGTACGGGATAGCATGGCCAAACTT

AGAGAAAGATTGAGTCAGAGACAAAAACTCTTTGAATCCCAACAAGGGTG

GTTTGAAGGGCTGTTTAACAAGTCCCCTTGGTTCACCACCCTGATATCCA

CCATCATGGGTCCCCTGATAATCCTCTTGTTAATTTTACTCTTTGGGCCT

TGTATTCTCAATCACCTGGTCCAGTTTATCAAAGACAGGGTTTCGGTAGT

GCAGGCCCTGGTCCTGACTCAACAATATCATCAACTTAAGACAATAGAAG

ATTGTGAATCACGTGAATAA

SEQ ID NO: 2: SL3-2 Envelope polypeptide sequence:

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

-continued

ARIFDFYVCPGHTVLAGCGGPREGYCGKWGCETTGQAYWKPSSSWDLISL

KRGNTPKGQGPCYDSSVVSSSAQGATPGGRCNPLVLEFTDAGKRASWDAS

KAWGLRLYRSTRTDPVTRFSLTRQVLNIGPRVPIGPNPVIIDQLPPSRPV

QIMLPRPPQPPPPGAASTVPETAPPSQQPGTGDRLLNLVNGAYQALNLTS

PDKTQECWLCLVAGPPYYEGVAVLGTYSNHTSAPANCSVASQHKLTLSEV

TGQGLCVGAVPKTHQALCNTTQKTSNGSYYLAAPAGTIWACNTGLTPCLS

TTVLDLTTDYCVLVELWPKVTYHSPGYVYGQFEEKTKYKREPVSLTLALL

LGGLTMGGIAAGVGTGTTALVATQQFQQLQAAMQDDLKEVKKSITNLERS

LTSLSEVVLQNRRGLDLLFLKEGGLCAALKEECCFYADHTGLVRDSMAKL

RERLSQRQKLFESQQGWFEGLFNKSPWFTTLISTIMGPLIILLLILLFGP

CILNHLVQFIKDRVSVVQALVLTQQYHQLKTIEDCESRE

SEQ ID NO: 3: SL3-2/V3 loop chimeric envelope polynucleotide, "L2 RT" (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGGACAATGA

CCGATGCCTTTCCTAAACTGTACTTTGACTTGTGCAGATTTAATAGGGGA

CGACTGGGATGAGACTGGACTCGGGTGTCGCACTCCCGGGGGAAGAAAAA

GGGCAAGAATATTTGACTTCTATGTTTGCCCCGGTCACACTGTGCTAGCA

GGGTGTGGAGGGCCGAGAGAGGGCTACTGTGGCAAATGGGGATGTGAGAC

CACTGGACAGGCATACTGGAAGCCATCATCATCATGGGACCTAATTTCCC

TTAAGCGAGGAAACACTCAAGGAATCTACCAGTGTACAAGACCCAACAAC

AATACAAGAAAAAGAATCCGTATCCAGAGAGGACCAGGGAGAGCATTTGT

TACAATAGGAAAAATAGGAAATATGAGACAAGCACATTGTGGGCCCTGTT

ATGATTCCTCGGTGGTCTCCAGTAGCGCCCAGGGTGCCACACCGGGGGGT

CGATGCAACCCCCTAGTCCTAGAATTCACTGACGCGGGTAAAAGGGCCAG

CTGGGACGCCTCCAAAGCATGGGGACTAAGACTGTACCGATCCACAAGGA

CCGACCCGGTGACCCGGTTCTCTTTGACCCGCCAGGTCCTCAATATAGGG

CCCCGCGTCCCCATTGGGCCTAATCCCGTGATCATTGACCAGTTACCCCC

CTCCCGACCCGTGCAGGTCATGCTCCCCAGGCCTCCTCAGCCTCCTCCAC

CAGGCGCAGCCTCTACAGTCCCTGAGACTGCCCCACCTTCCCAACAACCT

GGGACGGGAGACAGGCTGCTAAACCTGGTAAATGGAGCCTACCAAGCTCT

CAACCTCACCAGTCCTGACAAAACCCAAGAGTGCTGGTTGTGTCTGGTAG

CGGGACCCCCCTACTACGAAGGGGTTGCCGTCCTAGGTACTTATTCCAAC

CATACCTCTGCCCCAGCTAACTGCTCCGTGGCCTCCCAACACAAGCTGAC

CCTGTCCGAAGTGACCGGACAGGGACTCTGCGTAGGAGCAGTTCCCAAAA

CCCATCAGGCCCTGTGTAATACCACCCAGAAGACGAGCAACGGGTCCTAC

TATCTGGCTGCTCCCGCCGGGACCATTTGGGCTTGCAACACCGGGCTCAC

TCCCTGCCTATCTACCACTGTGCTCGACCTCACCACCGATTACTGTGTCC

-continued

TGGTTGAGCTCTGGCCAAAAGTGACCTACCACTCCCCTGGTTATGTTTAT
GGCCAGTTTGAAGAAAAAACCAAATATAAAAGAGAACCCGTCTCACTAAC
TCTGGCCCTACTATTAGGAGGACTCACTATGGGCGGAATTGCCGCCGGAG
TGGGAACAGGGACTACCGCCCCTAGTGGCCACTCAGCAGTTCCAACAACTC
CAGGCTGCCATGCAGGATGACCTTAAAGAAGTTGAAAAGTCCATCACTAA
TCTAGAAAGATCTTTGACCTCCTTGTCCGAAGTAGTGTTACAGAATCGTA
GAGGCCTAGATCTACTATTCCTAAAAGAGGGAGGTTTGTGTGCTGCCTTA
AAAGAAGAATGCTGTTTCTATGCCGACCACACAGGATTGGTACGGGATAG
CATGGCCAAACTTAGAGAAAGATTGAGTCAGAGACAAAAACTCTTTGAAT
CCCAACAAGGGTGGTTTGAAGGGCTGTTTAACAAGTCCCCTTGGTTCACC
ACCCTGATATCCACCATCATGGGTCCCCTGATAATCCTCTTGTTAATTTT
ACTCTTTGGGCCTTGTATTCTCAATCACCTGGTCCAGTTTATCAAAGACA
GGGTTTCGGTAGTGCAGGCCCTGGTCCTGACTCAACAATATCATCAACTT
AAGACAATAGAAGATTGTGAATCACGTGAATAA

SEQ ID NO: 4: SL3-2/V3 loop chimeric envelope polynucleotide, “L3 RT”, (shaded section represents the inserted section):

ATGGAAGGTCAGCGTTCTCAAAACCCCTTAAAGATAAGATTAACCCGTGG
GGCCCCCTAATAGTCCTGGGAATCTTAATGAGGGCAAGAGTATCAGTACA
ACATGACAGCCCTCATCAGGTCTTCAATGTTACTTGGAGAGTTACCAACT
TAATGACAGGACAAACAGCTAATGCTACCTCCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGTAATTTCCCTTAAGCGAGG
AAACACTCCTAAAGGCCAGGGCCCCTGTACAAGACCCAACAACAATACAA
GAAAAAGAATCCGTATCCAGAGAGGACCAGGGAGAGCATTTGTTACAATA
GGAAAAATAGGAAATATGAGACAAGCACATTGTAACCCCCTAGTCCTAGA
ATTCACTGACGCGGGTAAAGGGCCAGCTGGGACGCCTCCAAAGCATGGG
GACTAAGACTGTACCGATCCACAAGGACCGACCCGGTGACCCGGTTCTCT
TTGACCCGCCAGGTCCTCAATATAGGGCCCCGCGTCCCCATTGGGCCTAA
TCCCGTGATCATTGACCAGTTACCCCCCTCCCGACCCGTGCAGGTCATGC
TCCCCAGGCCTCCTCAGCCTCCTCCACCAGGCGCAGCCTCTACAGTCCCT

-continued

GAGACTGCCCCACCTTCCCAACAACCTGGGACGGGAGACAGGCTGCTAAA
CCTGGTAAATGGAGCCTACCAAGCTCTCAACCTCACCAGTCCTGACAAAA
CCCAAGAGTGCTGGTTGTGTCTGGTAGCGGGACCCCCCTACTACGAAGGG
GTTGCCGTCCTAGGTACTTATTCCAACCATACCTCTGCCCCAGCTAACTG
CTCCGTGGCCTCCCAACACAAGCTGACCCTGTCCGAAGTGACCGGACAGG
GACTCTGCGTAGGAGCAGTTCCCAAAACCCATCAGGCCCTGTGTAATACC
ACCCAGAAGACGAGCAACGGGTCCTACTACTGGCTGCTCCCGCCGGGACC
ATTTGGGCTTGCAACACCGGGCTCACTCCCTGCCTATCTACCACTGTGCT
CGACCTCACCACCGATTACTGTGTCCTGGTTGAGCTCTGGCCAAAAGTGA
CCTACCACTCCCCTGGTTATGTTTATGGCCAGTTTGAAGAAAAAACCAAA
TATAAAAGAGAACCCGTCTCACTAACTCTGGCCCTACTATTAGGAGGACT
CACTATGGGCGGAATTGCCGCCGGAGTGGGAACAGGGACTACCGCCCCTAG
TGGCCACTCAGCAGTTCCAACAACTCCAGGCTGCCATGCAGGATGACCTT
AAAGAAGTTGAAAAGTCCATCACTAATCTAGAAAGATCTTTGACCTCCTT
GTCCGAAGTAGTGTTACAGAATCGTAGAGGCCTAGATCTACTATTCCTAA
AAGAGGGAGGTTTGTGTGCTGCCTTAAAAGAAGAATGCTGTTTCTATGCC
GACCACACAGGATTGGTACGGGATAGCATGGCCAAACTTAGAGAAAGATT
GAGTCAGAGACAAAAACTCTTTGAATCCCAACAAGGGTGGTTTGAAGGG
CTGTTTAACAAGTCCCCTTGGTTCACCACCCTGATATCCACCATCATGGG
TCCCCTGATAATCCTCTTGTTAATTTTACTCTTTGGGCCTTGTATTCTCA
ATCACCTGGTCCAGTTTATCAAAGACAGGGTTTCGGTAGTGCAGGCCCTG
GTCCTGACTCAACAATATCATCAACTTAAGACAATAGAAGATTGTGAATC
ACGTGAATAA

SEQ ID NO: 5: SL3-2/V3 loop chimeric envelope polynucleotide, “L1 RT”, (shaded section represents the inserted section):

ATGGAAGGTCCAGCGTTCTCAAAACCCCTTAAAGATAAGATTAACCCGTGG
GGCCCCCTAATAGTCCTGGGAATCTTAATGAGGGCAAGAGTATCAGTACAA
CATGACAGCCCTCATCAGGTCTTCAATGTTACTTGGAGAGTTACCAACTTA
ATGACAGGACAAACAGCTAATGCTACCTCCCTCCTGGGGACAATGACCGAT
GCCTTTCCTAAACTGTACTTTGACTTGTGTACAAGACCCAACAACAATACA
AGAAAAAGAATCCGTATCCAGAGAGGACCAGGGAGAGCATTTGTTACAATA
GGAAAAATAGGAAATATGAGACAAGCACATTGTCGCACTCCCGGGGGAAGA
AAAAGGGCAAGAATATTTGACTTCTATGTTTGCCCCGGTCACACTGTGCTA
GCAGGGTGTGGAGGGCCGAGAGAGGGCTACTGTGGCAAATGGGGATGTGAG
ACCACTGGACAGGCATACTGGAAGCCATCATCATCATGGGACCTAATTTCC
CTTAAGCGAGGAAACACTCCTAAAGGCCAGGGCCCCTGTTATGATTCCTCG
GTGGTCTCCAGTAGCGCCCAGGGTGCCACACCGGGGGGTCGATGCAACCCC
CTAGTCCTAGAATTCACTGACGCGGGTAAAAGGGCCAGCTGGGACGCCTCC
AAAGCATGGGGACTAAGACTGTACCGATCCACAAGGACCGACCCGGTGACC
CGGTTCTCTTTGACCCGCCAGGTCCTCAATATAGGGCCCCGCGTCCCCATT
GGGCCTAATCCCGTGATCATTGACCAGTTACCCCCCTCCCGACCCGTGCAG
GTCATGCTCCCCAGGCCTCCTCAGCCTCCTCCACCAGGCGCAGCCTCTACA
GTCCCTGAGACTGCCCCACCTTCCCAACAACCTGGGACGGGAGACAGGCTG
CTAAACCTGGTAAATGGAGCCTACCAAGCTCTCAACCTCACCAGTCCTGAC
AAAACCCAAGAGTGCTGGTTGTGTCTGGTAGCGGGACCCCCCTACTACGAA
GGGGTTGCCGTCCTAGGTACTTATTCCAACCATACCTCTGCCCCAGCTAAC
TGCTCCGTGGCCTCCCAACACAAGCTGACCCTGTCCGAAGTGACCGGACAG
GGACTCTGCGTAGGAGCAGTTCCCAAAACCCATCAGGCCCTGTGTAATACC
ACCCAGAAGACGAGCAACGGGTCCTACTATCTGGCTGCTCCCGCCGGGACC
ATTTGGGCTTGCAACACCGGGCTCACTCCCTGCCTATCTACCACTGTGCTC
GACCTCACCACCGATTACTGTGTCCTGGTTGAGCTCTGGCCAAAAGTGACC
TACCACTCCCCTGGTTATGTTTATGGCCAGTTTGAAGAAAAAACCAAATAT
AAAAGAGAACCCGTCTCACTAACTCTGGCCCTACTATTAGGAGGACTCACT
ATGGGCGGAATTGCCGCCGGAGTGGGAACAGGGACTACCGCCCCTAGTGGC
CACTCAGCAGTTCCAACAACTCCAGGCTGCCATGCAGGATGACCTTAAAGA
AGTTGAAAAGTCCATCACTAATCTAGAAAGATCTTTGACCTCCTTGTCCGA

-continued

```
AGTAGTGTTACAGAATCGTAGAGGCCTAGATCTACTATTCCTAAAAGAGGG
AGGTTTGTGTGCTGCCTTAAAAGAAGAATGCTGTTTCTATGCCGACCACAC
AGGATTGGTACGGGATAGCATGGCCAAACTTAGAGAAAGATTGAGTCAGAG
ACAAAAACTCTTTGAATCCCAACAAGGGTGGTTTGAAGGGCTGTTTAACAA
GTCCCCTTGGTTCACCACCCTGATATCCACCATCATGGGTCCCCTGATAAT
CCTCTTGTTAATTTTACTCTTTGGGCCTTGTATTCTCAATCACCTGGTCCA
GTTTATCAAAGACAGGGTTTCGGTAGTGCAGGCCCTGGTCCTGACTCAACA
ATATCATCAACTTAAGACAATAGAAGATTGTGAATCACGTGAATAA
```

SEQ ID NO: 6: SL3-2/V3 loop chimeric envelope polypeptide, “L2 RT”, (shaded section represents the inserted section):

```
MEGPAFSKPLKDKINPWGPLIVLGILMRARVSVQHDSPHQVFNVTWRVTN
LMTGQTANATSLLLGTMTDAFPKLYFDLCDLIGDDWDETGLGCRTPGGRK
RARIFDFYVCPGHTVLAGCGGPREGYCGKWGCETTGQAYWKPSSSWDLIS
LKRGNTQGIYQCTRPNNNTRKRIRIQRGPGRAFVTIGKIGNMRQAHCGPC
YDSSVVSSSAQGATPGGRCNPLVLEFTDAGKRASWDASKAWGLRLYRSTR
TDPVTRFSLTRQVLNIGPRVPIGPNPVIIDQLPPSRPVQVMLPRPPQPPP
PGAASTVPETAPPSQQPGTGDRLLNLVNGAYQALNLTSPDKTQECWLCLV
AGPPYYEGVAVLGTYSNHTSAPANCSVASQHKLTLSEVTGQGLCVGAVPK
THQALCNTTQKTSNGSYYLAAPAGTIWACNTGLTPCLSTTVLDLTTDYCV
LVELWPKVTYHSPGYVYGQFEEKTKYKREPVSLTLALLLGGLTMGGIAAG
VGTGTTALVATQQFQQLQAAMQDDLKEVEKSITNLERSLTSLSEVVLQNR
RGLDLLFLKEGGLCAALKEECCFYADHTGLVRDSMAKLREFLSQRQKLFE
SQQGWFEGLFNKSPWFTTLISTIMGPLIILLLILLFGPCILNHLVQFIKD
RVSVVQALVLTQQYHQLKTIEDCESRE*
```

SEQ ID NO: 7: SL3-2/V3 loop chimeric envelope polypeptide, “L3 RT”, (shaded section represents the inserted section),”:

```
MEGPAFSKPLKDKINPWGPLIVLGILMRARVSVQHDSPHQVFNVTWRVTNL
MTGQTANATSLLGTMTDAFPKLYFDLCDLIGDDWDETGLGCRTPGGRKRAR
IFDFYVCPGHTVLAGCGGPREGYCGKWGCETTGQAYWKPSSSWDLISKLKR
GNTPKGQGPCTRPNNNTRKRIRIQRGPGRAFVTIGKIGNMRQAHCNPLVLE
FTDAGKRASWDASKAWGLRLYRSTRTDPVTRFSLTRQVLNIGPRVPIGPNP
VIIDQLPPSRPVQVMLPRPPQPPPPGAASTVPETAPPSQQPGTGDRLLNLV
NGAYQALNLTSPDFTQECWLCLVAGPPYYEGVAVLGTYSNHTSAPANCSVA
SQHKLTLSEVTGQGLCVGAVPKTHQALCNTTQKTSNGSYYLAAPAGTIWAC
NTGLTPCLSTTVLDLTTDYCVLVELWPKVTYHSPGYVYGQFEEKTKYKREP
VSLTLALLLGGLTMGGIAAGVGTGTTALVATQQFQQLQAAMQDDLKEVEKS
ITNLERSLTSLSEVVLQNRRGLDLLFLKEGGLCAALKEECCFYADHTGLVR
DSMAKLRERLSQRQKLFESQQGWFEGLFNKSPWFTTLISTIMGPLIILLLI
LLFGPCILNHLVQFIKDRVSVVQALVLTQQYHQLKTIEDCESRE
```

SEQ ID NO: 8: SL3-2/V3 loop chimeric envelope polypeptide, “L1 RT”, (shaded section represents the inserted section):

```
MEGPAFSKPLKDKINPWGPLIVLGILMRARVSVQHDSPHQVFNVTWRVTN
LMTGQTANATSLLGTMTDAFPKLYFDLCTRPNNNTRKRIRIQRGPGRAFV
TIGKIGNMRQAHCRTPGGRKRARIFDFYVCPGHTVLAGCGGPREGYCGKW
GCETTGQAYWKPSSSWDLISLKRGNTPKGQGPCYDSSVVSSSAQGATPGG
RCNPLVLEFTDAGKRASWDASKAWAGLRLYRSTRTDPVTRFSLTRQVLNI
GPRVPIGPNPVIIDQLPPSRPVQVMLPRPPQPPPPGAASTVPETAPPSQQ
PGTGDRLLNLVNGAYQALNLTSPDKTQECWLCLVAGPPYYEGVAVLGTYS
NHTSAPANCSVASQHKLTLSEVTGQGLCVGAVPKTHQALCNTTQKTSNGS
YYLAAPAGTIWACNTGLTPCLSTTVLDLTTDYCVLVELWPKVTYHSPGYV
YGQFEEKTKYKREPVSLTLALLLGGLTMGGIAAGVGTGTTALVATQQFQQ
LQAAMQDDLKEVEKSITNLERSLTSLSEVVLQNRRGLDLLFLKEGGLCAA
LKEECCFYADHTGLVRDSMAKLRERLSQRQKLFESQQGWFEGLFNKSPWF
TTLISTIMGPLIILLLILLFGPCILNHLVQFIKDRVSVVQALVLTQQYHQ
LKTIEDCESRE
```

SEQ ID NO: 9

```
CTRPNNNTRKRIRIQRGPGRAFVTIGKIGNMRQAHC
```

SEQ ID NO: 10

```
CTRPNNNIRIRHIQRGPGRAFVTIGKIGNMRQAHC
```

SEQ ID NO: 11

```
CTRPNNNTRKRIRIQRGPGRAFVTIGKIGNMRQAHC
```

V3 sequences of different HIV isolates:

```
              ↓                                      ↓
          (1)1        10        20        30        40           53
BAA11457  (1)---------CSRPNN-NTRKSIHMGPGKAFYTTGDTIGDIRQAHC-------- SEQ ID NO: 12
AAA64827  (1)---------CTRPNN-NTRKSIHIGPGRAFYTTGDIIGDIRQAHC-------- SEQ ID NO: 13
CAA78890  (1)---------CTRPSN-NTRKSIPVGPGKALYATGAIIGNIRQAHC-------- SEQ ID NO: 14
AAM82279  (1)---------CIRPNN-NTRKSVRIGPGQTFYATGEIIGDIRAAYC-------- SEQ ID NO: 15
AAD42280  (1)----PVSINCTRPGN-NTRRSVRIGPGQTFYATGDITGDIRQAHC-------- SEQ ID NO: 16
CAA90694  (1)---------CTRPNN-NTRKRISIGPGRSFYTTRQIVGDIRQAHC-------- SEQ ID NO: 17
AAC34563  (1)---------CTRPNN-NTRKSIHIGPGKAFYATGDVIGDIRKAHC-------- SEQ ID NO: 18
AAG01102  (1)--NESVAINCTRPVN-NTRKSIYIGPGRAFHTTGRIIGDIRKAHCXISRAQWN SEQ ID NO: 19
AAL13161  (1)-------IVCTRPGN-NTRKGIHIGPGRAFYASEGIVGDIRQAHC-------- SEQ ID NO: 20
CAA79322  (1)---------CTRPNNNIRIRHIHIGPGRAFHATEAATGDIRQAHC-------- SEQ ID NO: 21
AAC54528  (1)---------CTRPNN-NTRKGIHIGPGKAYYTTGDIIGDIRQAHCNISRA--- SEQ ID NO: 22
AAD48873  (1)-------INCTRPNN-NIRKRIHIGPGRAFYTTGKIIGGIRQAHCNLS----- SEQ ID NO: 23
AAP98384  (1)--NESVTITCIRPYN-NIRQSVEMGPGR-ALYTQEITGDIRRAHC-------- SEQ ID NO: 24
AAG01097  (1)---XSVEIVCTRPNN-NTRESIRIGPGQTFYATGDIIGNIRQAHC-------- SEQ ID NO: 25
AAA99704  (1)---------CIRPGN-NTRRSIHIQPGRAFYASGGIIGDIREAHCTLNIP--- SEQ ID NO: 26
AAB08827  (1)-----VEIECTRPGN-NTRKSIPIGPGQTFYATGDIIGDIRQAHCN------- SEQ ID NO: 27
AAM74784  (1)---------CTRPNN-NTRKSIPMGPGKAFYATGDIIGDIRKAFC-------- SEQ ID NO: 28
AAR19993  (1)QLKEPVEINCTRPNN-TTRRGIYIGPGRTIYAGEKIIGDIRRAYC-------- SEQ ID NO: 29
CAA54928  (1)-------INCTRPNN-NTRKSIHLGPGQAFYATGDIIGDIRKAHCNVS----- SEQ ID NO: 30
2124259L  (1)---------CTRPNN-NTRKSIHMGPGRAFYATGDIIGNIRQAHCNISRE--- SEQ ID NO: 31
Consensus (1)         CTRPNN NTRKSIHIGPGRAFYATGDIIGDIRQAHC         SEQ ID NO: 32
                      Stem            Tip             Stem
```

Preferred first polypeptide sequences, with insert sites:

SEQ ID NO: 33

("X" indicates preferred insert site for the second polypeptide and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQXGPCYDSSVVSSSAQGATPGGRCNPLVLEFTDAGKRASWD
ASKAWGLRLYRSTRTDPVTRFSLTRQVLNIGPRVPIGPNPVIIDQLPPSR
PVQVMLPRPPQPPPPGAASTVPETAPPSQQPGTGDRLLNLVNGAYQALNL
TSPDKTQECWLCLVAGPPYYEGVAVLGTYSNHTSAPANCSVASQHKLTLS
EVTGQGLCVGAVPKTHQALCNTTQKTSNGSYYLAAPAGTIWACNTGLTPC
LSTTVLDLTTDYCVLVELWPKVTYHSPGYVYGQFEEKTKYKREPVSLTLA
LLLGGLTMGGIAAGVGTGTTALVATQQFQQLQAAMQDDLKEVEKSITNLE
RSLTSLSEVVLQNRRGLDLLFLKEGGLCAALKEECCFYADHTGLVRDSMA
KLRERLSQRQKLFESQQGWFEGLFNKSPWFTTLISTIMGPLIILLLILLF
GPCILNHLVQFIKDRVSVVQALVLTQQYHQLKTIEDCESRE*

SEQ ID NO: 34

("X" indicates preferred insert site for the second polypeptide and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTPKGQGPXNPLVLEFTDAGKRASWDASKAWGLRLYRSTRTDPVTRF

-continued

SLTRQVLNIGPRVPIGPNPVIIDQLPPSRPVQVMLPRPPQPPPPGAASTV
PETAPPSQQPGTGDRLLNLVNGAYQALNLTSPDKTQECWLCLVAGPPYYE
GVAVLGTYSNHTSAPANCSVASQHKLTLSEVTGQGLCVGAVPKTHQALCN
TTQKTSNGSYYLAAPAGTIWACNTGLTPCLSTTVLDLTTDYCVLVELWPK
VTYHSPGYVYGQFEEKTKYKREPVSLTLALLLGGLTMGGIAAGVGTGTTA
LVATQQFQQLQAAMQDDLKEVEKSITNLERSLTSLSEVVLQNRRGLDLLF
LKEGGLCAALKEECCFYADHTGLVRDSMAKLRERLSQRQKLFESQQGWFE
GLFNKSPWFTTLISTIMGPLIILLLILLFGPCILNHLVQFIKDRVSVVQA
LVLTQQYHQLKTIEDCESRE

SEQ ID NO: 35

("X" indicates preferred insert site for the second polypeptide and optional linker sequence(s))

MEGPAFSKPLKDKINPWGPLIVLGILMRARVSVQHDSPHQVFNVTWRVTN
LMTGQTANATSLLGTMTDAFPKLYFDLXRTPGGRKRARIFDFYVCPGHTV
LAGCGGPREGYCGKWGCETTGQAYWKPSSSWDLISLKRGNTPKGQGPCYD
SSVVSSSAQGATPGGRCNPLVLEFTDAGKRASWDASKAWGLRLYRSTGID
PVTRFSLTRQVLNIGPRVPIGPNPVIIDQLPPSRPVQVMLPRPPQPPPPG
AASTVPETAPPSQQPGTGDRLLNLVNGAYQALNLTSPDKTQECWLCLVAG
PPYYEGVAVLGTYSNHTSAPANCSVASQHKLTLSEVTGQGLCVGAVPKTH
QALCNTTQKTSNGSYYLAAPAGTIWACNTGLTPCLSTTVLDLTTDYCVLV
ELWPKVTYHSPGYVYGQFEEKTKYKREPVSLTLALLLGGLTMGGIAAGVG
TGTTALVATQQFQQLQAAMQDDLKEVEKSITNLERSLTSLSEVVLQNRRG
LDLLFLKEGGLCAALKEECCFYADHTGLVRDSMAKLRERLSQRQKLFESQ
QGWFEGLFNKSPWFTTLISTIMGPLIILLLILLFGPCILNHLVQFIKDRV
SVVQALVLTQQYHQLKTIEDCESRE

SEQ ID NO: 36

("X" indicates preferred insert site for the second polypeptide and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQXGPCYDSSVVSSSAQGATPGGRCNPLVLEFTDAGKRASWD
ASKAWGLRLYRSTGIDPVTRFSLTRQVLNIGPRVPIGPNPVIIDQLPPSR
PVQVMLPRPPQPPPPGAASTVPETAPPSQQPGTGDRLLNLVNGAYQALNL
TSPDKTQECWLCLVAGPPYYEGVAVLGTYSNHTSAPANCSVASQHKLTLS
EVTGQGLCVGAVPKTHQALCNTTQKTSNGSYYLAAPAGTIWACNTGLTPC
LSTTVLDLTTDYCVLVELWPKVTYHSPGYVYGQFEEKTKYKREPVSLTLA
LLLGGLTMGGIAAGVGTGTTALVATQQFQQLQAAMQDDLKEVEKSITNLE
RSLTSLSEVVLQNRRGLDLLFLKEGGLCAALKEECCFYADHTGLVRDSMA
KLRERLSQRQKLFESQQGWFEGLFNKSPWFTTLISTIMGPLIILLLILLF
GPCILNHLVQFIKDRVSVVQALVLTQQYHQLKTIEDCESRE

SEQ ID NO: 37

("X" indicates preferred insert site for the second polypeptide and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTPKGQGPXNPLVLEFTDAGKRASWDASKAWGLRLYRSTGIDPVTRF
SLTRQVLNIGPRVPIGPNPVIIDQLPPSRPVQVMLPRPPQPPPPGAASTV
PETAPPSQQPGTGDRLLNLVNGAYQALNLTSPDKTQECWLCLVAGPPYYE
GVAVLGTYSNHTSAPANCSVASQHKLTLSEVTGQGLCVGAVPKTHQALCN
TTQKTSNGSYYLAAPAGTIWACNTGLTPCLSTTVLDLTTDYCVLVELWPK
VTYHSPGYVYGQFEEKTKYKREPVSLTLALLLGGLTMGGIAAGVGTGTTA
LVATQQFQQLQAAMQDDLKEVEKSITNLERSLTSLSEVVLQNRRGLDLLF
LKEGGLCAALKEECCFYADHTGLVRDSMAKLRERLSQRQKLFESQQGWFE
GLFNKSPWFTTLISTIMGPLIILLLILLFGPCILNHLVQFIKDRVSVVQA
LVLTQQYHQLKTIEDCESRE

SEQ ID NO: 38

("X" indicates preferred insert site for the second polypeptide and optional linker sequence(s))

MEGPAFSKPLKDKINPWGPLIVLGILMRARVSVQHDSPHQVFNVTWRVTN
LMTGQTANATSLLGTMTDAFPKLYFDLXRTPGGRKRARIFDFYVCPGHTV
LAGCGGPREGYCGKWGCETTGQAYWKPSSSWDLISLKRGNTPKGQGPCYD
SSVVSSSAQGATPGGRCNPLVLEFTDAGKRASWDASKAWGLRLYRSTRTD
PVTRFSLTRQVLNIGPRVPIGPNPVIIDQLPPSRPVQVMLPRPPQPPPPG
AASTVPETAPPSQQPGTGDRLLNLVNGAYQALNLTSPDKTQECWLCLVAG

-continued

PPYYEGVAVLGTYSNHTSAPANCSVASQHKLTLSEVTGQGLCVGAVPKTH
QALCNTTQKTSNGSYYLAAPAGTIWACNTGLTPCLSTTVLDLTTDYCVLV
ELWPKVTYHSPGYVYGQFEEKTKYKREPVSLTLALLLGGLTMGGIAAGVG
TGTTALVATQQFQQLQAAMQDDLKEVEKSITNLERSLTSLSEVVLQNRRG
LDLLFLKEGGLCAALKEECCFYADHTGLVRDSMAKLRERLSQRQKLFESQ
QGWFEGLFNKSPWFTTLISTIMGPLIILLLILLFGPCILNHLVQFIKDRV
SVVQALVLTQQYHQLKTIEDCESRE

SEQ ID NO: 39:—Envelope sequence derived from SL3-2 envelope protein (suitable insert site is represented by the symbol "X"):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGXLVLEFTDAGKRASWDASKAWGLRLYRSTRTDPVTRFSLTRQVLNIG
PRVPIGPNPVIIDQLPPSRPVQIMLPRPPQPPPPGAASTVPETAPPSQQP
GTGDRLLNLVNGAYQALNLTSPDKTQECWLCLVAGPPYYEGVAVLGTYSN
HTSAPANCSVASQHKLTLSEVTGQGLCVGAVPKTHQALCNTTQKTSNGSY
YLAAPAGTIWACNTGLTPCLSTTVLDLTTDYCVLVELWPKVTYHSPGYVY
GQFEEKTKYKREPVSLTLALLLGGLTMGGIAAGVGTGTTALVATQQFQQL
QAAMQDDLKEVKKSITNLERSLTSLSEVVLQNRRGLDLLFLKEGGLCAAL
KEECCFYADHTGLVRDSMAKLRERLSQRQKLFESQQGWFEGLFNKSPWFT
TLISTIMGPLIILLLILLFGPCILNHLVQFIKDRVSVVQALVLTQQYHQL
KTIEDCESRE

SEQ ID NO: 40:—Envelope sequence derived from MCF 247 (suitable insert site is represented by the symbol "X"):

MEGPAFSKPLKDKINPWGPLIVLGILIRAGVSVRHDSPHQVFNVTWRVTN
LMTGQTANATSLLGTMTDAFPKLYFDLCDLIGDDWDETGLGCRTPGGRKR
ARTFDFYVCPGHTVPTGCGGPREGYCGKWGCETTGQAYWKPSSSWDLISL
KRGXLVLEFTDAGKKASWDGPKVWGLRLYRSTGIDPVTRFSLTRQVLNIG
PRVPIGPNPVITDQLPPSRPVQIMLPRPPQPPPPGAASTVPETAPPSQQP
GTGDRLLNLVKGAYQALNLTSPDKTQECWLCLVSGPPYYEGVAVLGTYSN
HTSAPANCSVASQHKLTLSEVTGQGLCIGAVPKTHQALCNTTQKTSDGSY
YLAAPTGTTWACSTGLTPCISTTILDLTTDYCVLVELWPRVTYHSPSYVY
HQFERRAKYKREPVSLTLALLLGGLTMGGIAAGVGTGTTALVATQQFQQF
QAAMQDDLKEVEKSITNLEKSLTSLSEVVLQNRRGLDLLFLKEGGLCAAL
KEECCFYADHTGLVRDSMAKLRERLSQRQKLFESQQGWFEGLFNKSPWFT
TLISTIMGPLIILLLILLFGPCILNRLVQFVKDRISVVQALVLTQQYHQL
KSIDPEEVESRE

SEQ ID NO: 41:—Envelope sequence derived from Feline B (suitable insert site is represented by the symbol "X"):

```
MEGPTHPKPSKDKTFSWDLMILVGVLLRLDVGMANPSPHQIYNVTWTITN

LVTGTKANATSMLGTLTDAFPTMYFDLCDIIGNTWNPSDQEPFPGYGCDQ

PMRRWQQRNTPFYVCPGHANRKQCGGPQDGFCAVWGCETTGETYWRPTSS

WDYITVKKGXLILQFTQKGRQTSWDGPKSWGLRLYRSGYDPIALFSVSRQ

VMTITLPQAMGPNLVLPDQKPPSRQSQIESRVTPHHSQGNGGTPGITLVN

ASIAPLSTPVTPASPKRIGTGNRLINLVQGTYLALNVTNPNKTKDCWLCL

VSRPPYYEGIAVLGNYSNQTNPPPSCLSDPQHKLTISEVSGQGSCIGTVP

KTHQALCKKTQKGHKGTHYLAAPSGTYWACNTGLTPCISMAVLNWTSDFC

VLIELWPRVTYHQPEYVYTHFDKTVRLRREPISLTVALMLGGLTVGGIAA

GVGTGTKALLETAQFGQLQMAMHTDIQALEESISALEKSLTSLSEVVLQN

RRGLDILFLQEGGLCAALKEECCFYADHTGLVRDNMAKLRERLKQRQQLF

DSQQGWFEGWFNKSPWFTTLISSIMGPLLILLLILLFGPCILNRLVQFVK

DRISVVQALILTQQYQQIKQYDPDQP
```

SEQ ID NO: 42: SL3-2/V3 loop chimeric envelope polypeptide, "L2 GI", (shaded section represents the inserted section):

```
ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCAAGGAATCTACCAGTGTACAAGACCCAACAACAA
TACAAGAAAAAGAATCCGTATCCAGAGAGGACCAGGGAGAGCATTTGTTA
CAATAGGAAAAATAGGAAATATGAGACAAGCACATTGTGGCCCTGTTAT
GATTCCTCGGTGGTCTCCAGTAGCGCCCAGGGTGCCACACCGGGGGGTCG
ATGCAACCCCCTAGTCCTAGAATTCACTGACGCGGGTAAAAGGGCCAGCT
GGGACGCCTCCAAAGCATGGGGACTAAGACTGTACCGATCCACAGGGATC
GACCCGGTGACCCGGTTCTCTTTGACCCGCCAGGTCCTCAATATAGGGCC
CCGCGTCCCCATTGGGCCTAATCCCGTGATCATTGACCAGTTACCCCCCT
CCCGACCCGTGCAGGTCATGCTCCCCAGGCCTCCTCAGCCTCCTCCACCA
GGCGCAGCCTCTACAGTCCCTGAGACTGCCCCACCTTCCCAACAACCTGG
GACGGGAGACAGGCTGCTAAACCTGGTAAATGGAGCCTACCAAGCTCTCA
ACCTCACCAGTCCTGACAAAACCCAAGAGTGCTGGTTGTGTCTGGTAGCG
GGACCCCCCTACTACGAAGGGGTTGCCGTCCTAGGTACTTATTCCAACCA
TACCTCTGCCCCAGCTAACTGCTCCGTGGCCTCCCAACACAAGCTGACCC
TGTCCGAAGTGACCGGACAGGGACTCTGCGTAGGAGCAGTTCCCAAAACC
CATCAGGCCCTGTGTAATACCACCCAGAAGACGAGCAACGGGTCCTACTA
TCTGGCTGCTCCCGCCGGGACCATTTGGGCTTGCAACACCGGGCTCACTC
CCTGCCTATCTACCACTGTGCTCGACCTCACCACCGATTACTGTGTCCTG
GTTGAGCTCTGGCCAAAAGTGACCTACCACTCCCCTGGTTATGTTTATGG
CCAGTTTGAAGAAAAAACCAAATATAAAAGAGAACCCGTCTCACTAACTC
TGGCCCTACTATTAGGAGGACTCACTATGGGCGGAATTGCCGCCGGAGTG
GGAACAGGGACTACCGCCCTAGTGGCCACTCAGCAGTTCCAACAACTCCA
GGCTGCCATGCAGGATGACCTTAAAGAAGTTGAAAAGTCCATCACTAATC
TAGAAAGATCTTTGACCTCCTTGTCCGAAGTAGTGTTACAGAATCGTAGA
GGCCTAGATCTACTATTCCTAAAAGAGGGAGGTTTGTGTGCTGCCTTAAA
AGAAGAATGCTGTTTCTATGCCGACCACACAGGATTGGTACGGGATAGCA
TGGCCAAACTTAGAGAAAGATTGAGTCAGAGACAAAAACTCTTTGAATCC
CAACAAGGGTGGTTTGAAGGGCTGTTTAACAAGTCCCCTTGGTTCACCAC
CCTGATATCCACCATCATGGGTCCCCTGATAATCCTCTTGTTAATTTTAC
TCTTTGGGCCTTGTATTCTCAATCACCTGGTCCAGTTTATCAAAGACAGG
GTTTCGGTAGTGCAGGCCCTGGTCCTGACTCAACAATATCATCAACTTAA
GACAATAGAAGATTGTGAATCACGTGAATAA
```

SEQ ID NO: 43: SL3-2/V3 loop chimeric envelope polypeptide, "L3 GI", (shaded section represents the inserted section):

```
ATGGAAGGTCCAGCGTTCTCAAAACCCCTTAAAGATAAGATTAACCCGTGG
GGCCCCCTAATAGTCCTGGGAATCTTAATGAGGGCAAGAGTATCAGTACAA
CATGACAGCCCTCATCAGGTCTTCAATGTTACTTGGAGAGTTACCAACTTA
ATGACAGGACAAACAGCTAATGCTACCTCCCTCCTGGGGACAATGACCGAT
GCCTTTCCTAAACTGTACTTTGACTTGTGCGATTTAATAGGGGACGACTGG
GATGAGACTGGACTCGGGTGTCGCACTCCCGGGGGAAGAAAAAGGGCAAGA
ATATTTGACTTCTATGTTTGCCCCGGTCACACTGTGCTAGCAGGGTGTGGA
GGGCCGAGAGAGGGCTACTGTGGCAAATGGGGATGTGAGACCACTGGACAG
GCATACTGGAAGCCATCATCATCATGGGACCTAATTTCCCTTAAGCGAGGA
AACACTCCTAAAGGCCAGGGCCCCTGTACAAGACCCAACAACAATACAAGA
AAAAGAATCCGTATCCAGAGAGGACCAGGGAGAGCATTTGTTACAATAGGA
AAAATAGGAAATATGAGACAAGCACATTGTAACCCCCTAGTCCTAGAATTC
ACTGACGCGGGTAAAAGGGCCAGCTGGGACGCCTCCAAAGCATGGGGACTA
AGACTGTACCGATCCACAGGGATCGACCCGGTGACCCGGTTCTCTTTGACC
CGCCAGGTCCTCAATATAGGGCCCCGCGTCCCCATTGGGCCTAATCCCGTG
ATCATTGACCAGTTACCCCCCTCCCGACCCGTGCAGGTCATGCTCCCCAGG
CCTCCTCAGCCTCCTCCACCAGGCGCAGCCTCTACAGTCCCTGAGACTGCC
CCACCTTCCCAACAACCTGGGACGGGAGACAGGCTGCTAAACCTGGTAAAT
GGAGCCTACCAAGCTCTCAACCTCACCAGTCCTGACAAAACCCAAGAGTGC
TGGTTGTGTCTGGTAGCGGGACCCCCCTACTACGAAGGGGTTGCCGTCCTA
GGTACTTATTCCAACCATACCTCTGCCCCAGCTAACTGCTCCGTGGCCTCC
CAACACAAGCTGACCCTGTCCGAAGTGACCGGACAGGGACTCTGCGTAGGA
GCAGTTCCCAAAACCCATCAGGCCCTGTGTAATACCACCCAGAAGACGAGC
AACGGGTCCTACTATCTGGCTGCTCCCGCCGGGACCATTTGGGCTTGCAAC
ACCGGGCTCACTCCCTGCCTATCTACCACTGTGCTCGACCTCACCACCGAT
TACTGTGTCCTGGTTGAGCTCTGGCCAAAAGTGACCTACCACTCCCCTGGT
TATGTTTATGGCCAGTTTGAAGAAAAAACCAAATATAAAAGAGAACCCGTC
TCACTAACTCTGGCCCTACTATTAGGAGGACTCACTATGGGCGGAATTGCC
GCCGGAGTGGGAACAGGGACTACCGCCCTAGTGGCCACTCAGCAGTTCCAA
CAACTCCAGGCTGCCATGCAGGATGACCTTAAAGAAGTTGAAAAGTCCATC
ACTAATCTAGAAAGATCTTTGACCTCCTTGTCCGAAGTAGTGTTACAGAAT
CGTAGAGGCCTAGATCTACTATTCCTAAAAGAGGGAGGTTTGTGTGCTGCC
TTAAAAGAAGAATGCTGTTTCTATGCCGACCACACAGGATTGGTACGGGAT
AGCATGGCCAAACTTAGAGAAAGATTGAGTCAGAGACAAAAACTCTTTGAA
TCCCAACAAGGGTGGTTTGAAGGGCTGTTTAACAAGTCCCCTTGGTTCACC
ACCCTGATATCCACCATCATGGGTCCCCTGATAATCCTCTTGTTAATTTTA
CTCTTTGGGCCTTGTATTCTCAATCACCTGGTCCAGTTTATCAAAGACAGG
GTTTCGGTAGTGCAGGCCCTGGTCCTGACTCAACAATATCATCAACTTAAG
ACAATAGAAGATTGTGAATCACGTGAATAA
```

SEQ ID NO: 44: SL3-2/V3 loop chimeric envelope polypeptide, "L1 GI", (shaded section represents the inserted section):

```
ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGTACAAGACCCAACAACA

ATACAAGAAAAAGAATCCGTATCCAGAGAGGACCAGGGAGAGCATTTGTT

ACAATAGGAAAAATAGGAAATATGAGACAAGCACATTGTCGCACTCCCGG

GGGAAGAAAAAGGGCAAGAATATTTGACTTCTATGTTTGCCCCGGTCACA

CTGTGTGCTAGCAGGGTGTGGAGGGCCGAGAGAGGGCTACTGTGGCAAAT

GGGGATGTGAGACCACTGGACAGGCATACTGGAAGCCATCATCATCATGG

GACCTAATTTCCCTTAAGCGAGGAAACACTCCTAAAGGCCAGGGCCCCTG

TTATGATTCCTCGGTGGTCTCCAGTAGCGCCCAGGGTGCCACACCGGGGG

GTCGATGCAACCCCCTAGTCCTAGAATTCACTGACGCGGGTAAAAGGGCC

AGCTGGGACGCCTCCAAAGCATGGGGACTAAGACTGTACCGATCCACAGG

GATCGACCCGGTGACCCGGTTCTCTTTGACCCGCCAGGTCCTCAATATAG

GGCCCCGCGTCCCCATTGGCCTAATCCCGTGATCATTGACCAGTTACCCC
```

-continued

CCTCCCGACCCGTGCAGGTCATGCTCCCCAGGCCTCCTCAGCCTCCTCCA
CCAGGCGCAGCCTCTACAGTCCCTGAGACTGCCCCACCTTCCCAACAACC
TGGGACGGGAGACAGGCTGCTAAACCTGGTAAATGGAGCCTACCAAGCTC
TCAACCTCACCAGTCCTGACAAAAACCCAAGAGTGCTGGTTGTGTCTGGT
AGCGGGACCCCCCTACTACGAAGGGGTTGCCGTCCTAGGTACTTATTCCA
ACCATACCTCTGCCCCAGCTAACTGCTCCGTGGCCTCCCAACACAAGCTG
ACCCTGTCCGAAGTGACCGGACAGGGACTCTGCGTAGGAGCAGTTCCCAA
AACCCATCAGGCCCTGTGTAATACCACCCAGAAGACGAGCAACGGGTCCT
ACTATCTGGCTGCTCCCGCCGGGACCATTTGGGCTTGCAACACCGGGCTC
ACTCCCTGCCTATCTACCACTGTGCTCGACCTCACCACCGATTACTGTGT
CCTGGTTGAGCTCTGGCCAAAAGTGACCTACCACTCCCCTGGTTATGTTT
ATGGCCAGTTTGAAGAAAAAACCAAATATAAAAGAGAACCCGTCTCACTA
ACTCTGGCCCTACTATTAGGAGGACTCACTATGGGCGGAATTGCCGCCGG
AGTGGGAACAGGGACTACCGCCCTAGTGGCCACTCAGCAGTTCCAACAAC
TCCAGGCTGCCATGCAGGATGACCTTAAAGAAGTTGAAAAGTCCATCACT
AATCTAGAAAGATCTTTGACCTCCTTGTCCGAAGTAGTGTTACAGAATCG
TAGAGGCCTAGATCTACTATTCCTAAAAGAGGGAGGTTTGTGTGCTGCCT
TAAAAGAAGAATGCTGTTTCTATGCCGACCACACAGGATTGGTACGGGAT
AGCATGGCCAAACTTAGAGAAAGATTGAGTCAGAGACAAAAACTCTTTGA
ATCCCAACAAGGGTGGTTTGAAGGGCTGTTTAACAAGTCCCCTTGGTTCA
CCACCCTGATATCCACCATCATGGGTCCCCTGATAATCCTCTTGTTAATT
TTACTCTTTGGGCCTTGTATTCTCAATCACCTGGTCCAGTTTATCAAAGA
CAGGGTTTCGGTAGTGCAGGCCCTGGTCCTGACTCAACAATATCATCAAC
TTAAGACAATAGAAGATTGTGAATCACGTGAATAA

SEQ ID NO: 45: SL3-2/V3 loop chimeric envelope polypeptide, "L2-GI", (shaded section represents the inserted section):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQCTRPNNNTRKRIRIQRGPGRAFVTIGKIGNMRQAHCGPCY
DSSVVSSSAWGATPGGRCNPLVLEFTDAGKRASWDASKAWGLRLYRSTGI
DPVTRFSLTRQVLNIGPRVPIGPNPVIIDQLPPSRPVQVMLPRPPQPPPP
GAASTVPETAPPSQQPGTGDRLLNLVNGAYQALNLTSPDKTQECWLCLVA
GPPYYEGVAVLGTYSNHTSAPANCSVASQHKLTLSEVTGQGLCVGAVPKT
HQALCNTTQKTSNGSYYLAAPAGTIWACNTGLTPCLSTTVLDLTTDYCVL
VELWPKVTHYHSPGYVYGQFEEKTKYKREPVSLTLALLLGGLTMGGIAAG
VGTGTTALVATQQFQQLQAAMQDDLKEVEKSITNLERSLTSLSEVVLQNR
RGLDLLFLKEGGLCAALKEECCFYADHTGLVRDSMAKLRERLSQRQKLFE
SQQGWFEGLFNKSPWFTTLISTIMGPLIILLLILLPGPCILNHLVQFIKD
RVSVVQALVLTQQYHQLKTIEDCESRE

SEQ ID NO: 46: SL3-2/V3 loop chimeric envelope polypeptide, "L3-GI", (shaded section represents the inserted section):

MEGPAFSKPLKDKINPWGPIVLGILMRARVSVQHDSPHQVFNVTWRVTNL
MTGQTANATSLLGTMTDAFPKLYFDLCDLIGDDWDETGLGCRTPGGRKRA
RIFFYVCPGHTVLAGCGGPREGYCGKWGCETTGQAYWKPSSSWDLISLKR
GNTPKGQGPCTRPNNNTRKRIIQRGPGRAFVTIGKIGNMRQAHCNPLVLEF
TDAGKRASWDASKAWGLRLYRSTGIDPVTRFSLTRQVLNIGPRVPIGPNP
VIIDQLPPSRPVQVMLPRPPQPPPPGAASTVPETAPPSQQPGTGDRLLNL
VNGAYQALNLTSPDKTQECWLCLVAGPPYYEGVAVLGTYSNHTSAPANCS
VASQHKLTLSEVTGQGLCVGAVPKTHQALCTTQKTSNGSYYLAAPAGTIW
ACNTGLPCLSTTVLDLTTDYCVLVELWPKVTYHSPGYVYGQFEEKTKYKR
EPVSLTLALLLGGLTMGGIAAGVGTGTTALVATQQFQQLQAAMQDDLKEV
EKSITNLERSLTSLSEVVLQNRRGLDLLFLKEGGLCAALKEECCFYADHT
GLVRDSMAKLRERLSQRQKLFESQQGWFEGLFNKSPWFTTLISTIMGPLI
ILLLILLFGPCILNHLVQFIKDRVSVVQALVLTQQYHQLKTIEDCESRE

SEQ ID NO: 47: SL3-2/V3 loop chimeric envelope polypeptide, "L1-RT", (shaded section represents the inserted section):

MEGPAFSKPLKDKINPWGPLIVLGILMRARVSVQHDSPHQVFNVTWRVTN
LMTGQTANATSLLGTMTDAFPKLYFDLCTRPNNNTRKRIRIQRGPGRAFV
TIGKIGNMRQAHCRTPGGRKRARIFDFYVCPGHTVLAGCGGPREGYCGKW
GCETTGQAYWKPSSSWDLISLKRGNTPKGQGPCYDSSVVSSSAQGATPGG
RCNPLVLEFTDAGKRASWDASKAWGLRLYRSTRTDPVTRFSLTRQVLNIG
PRVPIGPNPVIIDQLPPSRPVQVMLPRPPQPPPPGAASTVPETAPPSQQP
GTGDRLLNLVNGAYQALNLTSPDKTQECWLCLVAGPPYYEGVALGTYSNH
TSAPANCSVASQHKLTLSEVTGQGLCVGAVPKTHQALCNTTQKTSNGSYY
LAAPAGTIWACNTGLTPCLSTTVLDLTTDYCVLVELWPKVTYHSPGYVYG
QFEEKTKYKREPVSLTLALLLGGLTMGGIAAGVGTGTTALVATQQFQQLQ
AAMQDDLKEVEKSITNLERSLTSLSEVVLQNRRGLDLLFLKEGGLCAALK
EECFFYAGHTGLVRDSMAKLRERLSQRQKLFESQQGWFEGLFNKSPWFTT
LISTIMGPLIILLLILLFGPCILNHLVQFIKDRVSVVQALVLTQQYHQLK
TIEDCESRE

SEQ ID NO: 48:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATXGGACTCGGGTGTCGCACTCCCGGGGGAAGAAAAAGGGCAAG

-continued

AATATTTGACTTCTATGTTTGCCCCGGTCACACTGTGCTAGCAGGGTGTG
GAGGGCCGAGAGAGGGCTACTGTGGCAAATGGGGATGTGAGACCACTGGA
CAGGCATACTGGAAGCCATCATCATCATGGACCTAATTTCCCTTAAGCG
AGGAAACACTCCTAAAGGCCAGGGCCCCTGTTATGATTCCTCGGTGGTCT
CCAGTAGCGCCCAGGGTGCCACACCGGGGGGTCGATGCAACCCCCTAGTC
CTAGAATTCACTGACGCGGGTAAAAGGGCCAGCTGGGACGCCTCCAAAGC
ATGGGGACTAAGACTGTACCGATCCACAAGGACCGACCCGGTGACCCGGT
TCTCTTTGACCCGCCAGGTCCTCAATATAGGGCCCCGCGTCCCCATTGGG
CCTAATCCCGTGATCATTGACCAGTTACCCCCCTCCCGACCCGTGCAGGT
CATGCTCCCCAGGCCTCCTCAGCCTCCTCCACCAGGCGCAGCCTCTACAG
TCCCTGAGACTGCCCCACCTTCCCAACAACCTGGGACGGGAGACAGGCTG
CTAAACCTGGTAAATGGAGCCTACCAAGCTCTCAACCTCACCAGTCCTGA
CAAAACCCAAGAGTGCTGGTTGTGTCTGGTAGCGGGACCCCCCTACTACG
AAGGGGTTGCCGTCCTAGGTACTTATTCCAACCATACCTCTGCCCCAGCT
AACTGCTCCGTGGCCTCCCAACACAAGCTGACCCTGTCCGAAGTGACCGG
ACAGGGACTCTGCGTAGGAGCAGTTCCCAAAACCCATCAGGCCCTGTGTA
ATACCACCCAGAAGACGAGCAACGGGTCCTACTATCTGGCTGCTCCCGCC
GGGACCATTTGGGCTTGCAACACCGGGCTCACTCCCTGCCTATCTACCAC
TGTGCTCGACCTCACCACCGATTACTGTGTCCTGGTTGAGCTCTGGCCAA
AAGTGACCTACCACTCCCCTGGTTATGTTTATGGCCAGTTTGAAGAAAAA
ACCAAATATAAAAGAGAACCCGTCTCACTAACTCTGGCCCTACTATTAGG
AGGACTCACTATGGGCGGAATTGCCGCCGGAGTGGGAACAGGGACTACCG
CCCTAGTGGCCACTCAGCAGTTCCAACAACTCCAGGCTGCCATGCAGGAT
GACCTTAAAGAAGTTGAAAAGTCCATCACTAATCTAGAAAGATCTTTGAC
CTCCTTGTCCGAAGTAGTGTTACAGAATCGTAGAGGCCTAGATCTACTAT
TCCTAAAAGAGGGAGGTTTGTGTGCTGCCTTAAAAGAAGAATGCTGTTTC
TATGCCGACCACACAGGATTGGTACGGGATAGCATGGCCAAACTTAGAGA
AAGATTGAGTCAGAGACAAAAACTCTTTGAATCCCAACAAGGGTGGTTTG
AAGGGCTGTTTAACAAGTCCCCTTGGTTCACCACCCTGATATCCACCATC
ATGGGTCCCCTGATAATCCTCTTGTTAATTTTACTCTTTGGGCCTTGTAT
TCTCAATCACCTGGTCCAGTTTATCAAAGACAGGGTTTCGGTAGTGCAGG
CCCTGGTCCTGACTCAACAATATCATCAACTTAAGACAATAGAAGATTGT
GAATCACGTGAATAA

SEQ ID NO: 49:—(suitable insert site is represented by the symbol "X"):

MEGPAFSKPLKDKINPWGPLIVLGILMRARVSVQHDSPHQVFNVTWRVTN
LMTGQTANATSLLGTMTDAFPKLYFDLCDLIGDDWD XGLGCRTPGGRKR
ARIFDFYVCPGHTVLAGCGGPREGYCGKWGCETTGQAYWKPSSSWDLISLK
RGNTPKGQGPCYDSSVVSSSAQGATPGGRCNPLVLEFTDAGKRASWDASK
AWGLRLYRSTRTDPVTRFSLTRQVLNIGPRVPIGPNPVIIDQLPPSRPVQ
VMLPRPPQPPPPGAASTVPETAPPSQQPGTGDRLLNLVNGAYQALNLTSP
DKTQECWLCLVAGPPYYEGVAVLGTYSNHTSAPANCSVASQHKLTLSEVT
GQGLCVGAVPKTHQALCNTTQKTSNGSYYLAAPAGTIWACNTGLTPCLST
TVLDLTTDYCVLVELWPKVTYHSPGYVYGQFEEKTKYKREPVSLTLALLL
GGLTMGGIAAGVGTGTTALVATQQFQQLQAAMQDDLKEVEKSITNLERSL
TSLSEVVLQNRRGLDLLFLKEGGLCAALKEECCFYADHTGLVRDSMAKLR
ERLSQRQKLFESQQGWFEGLFNKSPWFTTLISTIMGPLIILLLILLFGPC
ILNHLVQFIKDRVSVVQALVLTQQYHQLKTIEDCESRE

SEQ ID NO: 50:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGAT XGGACTCGGGTGTCGCACTCCCGGGGGAAGAAAAAGGGCAA
GAATATTTGACTTCTATGTTTGCCCCGGTCACACTGTGCTAGCAGGGTGTG
GAGGGCCGAGAGAGGGCTACTGTGGCAAATGGGGATGTGAGACCACTGGA
CAGGCATACTGGAAGCCATCATCATCATGGACCTAATTTCCCTTAAGCG
AGGAAACACTCCTAAAGGCCAGGGCCCCTGTTATGATTCCTCGGTGGTCT
CCAGTAGCGCCCAGGGTGCCACACCGGGGGGTCGATGCAACCCCCTAGTC
CTAGAATTCACTGACGCGGGTAAAAGGGCCAGCTGGGACGCCTCCAAAGC
ATGGGGACTAAGACTGTACCGATCCACAGGGATCGACCCGGTGACCCGGT
TCTCTTTGACCCGCCAGGTCCTCAATATAGGGCCCCGCGTCCCCATTGGG
CCTAATCCCGTGATCATTGACCAGTTACCCCCCTCCCGACCCGTGCAGGT
CATGCTCCCCAGGCCTCCTCAGCCTCCTCCACCAGGCGCAGCCTCTACAG
TCCCTGAGACTGCCCCACCTTCCCAACAACCTGGGACGGGAGACAGGCTG
CTAAACCTGGTAAATGGAGCCTACCAAGCTCTCAACCTCACCAGTCCTGA
CAAAACCCAAGAGTGCTGGTTGTGTCTGGTAGCGGGACCCCCCTACTACG
AAGGGGTTGCCGTCCTAGGTACTTATTCCAACCATACCTCTGCCCCAGCT
AACTGCTCCGTGGCCTCCCAACACAAGCTGACCCTGTCCGAAGTGACCGG
ACAGGGACTCTGCGTAGGAGCAGTTCCCAAAACCCATCAGGCCCTGTGTA
ATACCACCCAGAAGACGAGCAACGGGTCCTACTATCTGGCTGCTCCCGCC
GGGACCATTTGGGCTTGCAACACCGGGCTCACTCCCTGCCTATCTACCAC
TGTGCTCGACCTCACCACCGATTACTGTGTCCTGGTTGAGCTCTGGCCAA
AAGTGACCTACCACTCCCCTGGTTATGTTTATGGCCAGTTTGAAGAAAAA
ACCAAATATAAAAGAGAACCCGTCTCACTAACTCTGGCCCTACTATTAGG
AGGACTCACTATGGGCGGAATTGCCGCCGGAGTGGGAACAGGGACTACCG
CCCTAGTGGCCACTCAGCAGTTCCAACAACTCCAGGCTGCCATGCAGGAT
GACCTTAAAGAAGTTGAAAAGTCCATCACTAATCTAGAAAGATCTTTGAC

-continued

CTCCTTGTCCGAAGTAGTGTTACAGAATCGTAGAGGCCTAGATCTACTAT

TCCTAAAAGAGGGAGGTTTGTGTGCTGCCTTAAAAGAAGAATGCTGTTTC

TATGCCGACCACACAGGATTGGTACGGGATAGCATGGCCAAACTTAGAGA

AAGATTGAGTCAGAGACAAAAACTCTTTGAATCCCAACAAGGGTGGTTTG

AAGGGCTGTTTAACAAGTCCCCTTGGTTCACCACCCTGATATCCACCATC

ATGGGTCCCCTGATAATCCTCTTGTTAATTTTACTCTTTGGGCCTTGTAT

TCTCAATCACCTGGTCCAGTTTATCAAAGACAGGGTTTCGGTAGTGCAGG

CCCTGGTCCTGACTCAACAATATCATCAACTTAAGACAATAGAAGATTGT

GAATCACGTGAATAA

SEQ ID NO: 51:—(suitable insert site is represented by the symbol "X"):

MEGPAFSKPLKDKINPWGPLIVLGILMRARVSVQHDSPHQVFNVTWRVTN

LMTGQTANATSLLGTMTDAFPKLYFDLCDLIGDDWD XGLGCRTPGGRKR

ARIFDFYVCPGHTVLAGCGGPREGYCGKWGCETTGQAYWKPSSSWDLISLK

RGNTPKGQGPCYDSSVVSSSAQGATPGGRCNPLVLEFTDAGKRASWDASK

AWGLRLYRSTGIDPVTRFSLTRQVLNIGPRVPIGPNPVIIDQLPPSRPVQ

VMLPRPPQPPPPGAASTVPETAPPSQQPGTGDRLLNLVNGAYQALNLTSP

DKTQECWLCLVAGPPYYEGVAVLGTYSNHTSAPANCSVASQHKLTLSEVT

GQGLCVGAVPKTHQALCNTTQKTSNGSYYLAAPAGTIWACNTGLTPCLST

TVLDLTTDYCVLVELWPKVTYHSPGYVYGQFEEKTKYKREPVSLTLALLL

GGLTMGGIAAGVGTGTTALVATQQFQQLQAAMQDDLKEVEKSITNLERSL

TSLSEVVLQNRRGLDLLFLKEGGLCAALKEECCFYADHTGLVRDSMAKLR

ERLSQRQKLFESQQGWFEGLFNKSPWFTTLISTIMGPLIILLLILLFGPC

ILNHLVQFIKDRVSVVQALVLTQQYHQLKTIEDCESRE

SEQ ID NO: 52:—(suitable insert site is represented by the symbol "X"):

ATGGAAGGTCCAGCGTTCTCAAAACCCCTTAAAGATAAGATTAACCCGTG

GGGCCCCCTAATAGTCCTGGGAATCTTAATGAGGGGCAAGAGTATCAGTA

CAACATGACAGCCCTCATCAGGTCTTCAATGTTACTTGGAGAGTTACCAA

CTTAATGACAGGACAAACAGCTAATGCTACCTCCCTCCTGGGGACAATGA

CCGATGCCTTTCCTAAACTGTACTTTGACTTGTGCGATTTAATAGGGGAC

GACTGGGATGAGACTGGACTCGGGTGTCGCACTCCCGGGGGAAGAAAAAG

GGCAAGAATATTTGACTTCTATGTTTGCCCCGGTCACACTGTGCTAGCAG

GGTGTGGAGGGCCGAGAGAGGGCTACTGTGGCAAATGGGGATGTGAGACC

ACTGGACAGGCATACTGGAAGCCATCATCATCATGGGACCTAATTTCCCT

TAAGCGAGGAAACACTCAAGGAATCTACCAGTGCXTGTGGGCCCTGTTAT

GATTCCTCGGTGGTCTCCAGTAGCGCCCAGGGTGCCACACCGGGGGGTCG

ATGCAACCCCCTAGTCCTAGAATTCACTGACGCGGGTAAAAGGGCCAGCT

GGGACGCCTCCAAAGCATGGGGACTAAGACTGTACCGATCCACAAGGACC

GACCCGGTGACCCGGTTCTCTTTGACCCGCCAGGTCCTCAATATAGGGCC

CCGCGTCCCCATTGGGCCTAATCCCGTGATCATTGACCAGTTACCCCCCT

CCCGACCCGTGCAGGTCATGCTCCCCAGGCCTCCTCAGCCTCCTCCACCA

GGCGCAGCCTCTACAGTCCCTGAGACTGCCCCACCTTCCCAACAACCTGG

GACGGGAGACAGGCTGCTAAACCTGGTAAATGGAGCCTACCAAGCTCTCA

ACCTCACCAGTCCTGACAAAACCCAAGAGTGCTGGTTGTGTCTGGTAGCG

GGACCCCCCTACTACGAAGGGGTTGCCGTCCTAGGTACTTATTCCAACCA

TACCTCTGCCCCAGCTAACTGCTCCGTGGCCTCCCAACACAAGCTGACCC

TGTCCGAAGTGACCGGACAGGGACTCTGCGTAGGAGCAGTTCCCAAAACC

CATCAGGCCCTGTGTAATACCACCCAGAAGACGAGCAACGGGTCCTACTA

TCTGGCTGCTCCCGCCGGGACCATTTGGGCTTGCAACACCGGGCTCACTC

CCTGCCTATCTACCACTGTGCTCGACCTCACCACCGATTACTGTGTCCTG

GTTGAGCTCTGGCCAAAAGTGACCTACCACTCCCCTGGTTATGTTTATGG

CCAGTTTGAAGAAAAAACCAAATATAAAAGAGAACCCGTCTCACTAACTC

TGGCCCTACTATTAGGAGGACTCACTATGGGCGGAATTGCCGCCGGAGTG

GGAACAGGGACTACCGCCCTAGTGGCCACTCAGCAGTTCCAACAACTCCA

GGCTGCCATGCAGGATGACCTTAAAGAAGTTGAAAAGTCCATCACTAATC

TAGAAAGATCTTTGACCTCCTTGTCCGAAGTAGTGTTACAGAATCGTAGA

GGCCTAGATCTACTATTCCTAAAAGAGGGAGGTTTGTGTGCTGCCTTAAA

AGAAGAATGCTGTTTCTATGCCGACCACACAGGATTGGTACGGGATAGCA

TGGCCAAACTTAGAGAAAGATTGAGTCAGAGACAAAAACTCTTTGAATCC

CAACAAGGGTGGTTTGAAGGGCTGTTTAACAAGTCCCCTTGGTTCACCAC

CCTGATATCCACCATCATGGGTCCCCTGATAATCCTCTTGTTAATTTTAC

TCTTTGGGCCTTGTATTCTCAATCACCTGGTCCAGTTTATCAAAGACAGG

GTTTCGGTAGTGCAGGCCCTGGTCCTGACTCAACAATATCATCAACTTAA

GACAATAGAAGATTGTGAATCACGTGAATAA

SEQ ID NO: 53:—(suitable insert site is represented by the symbol "X"):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQCXCGPCYDSSVVSSSAQGATPGGRCNPLVLEFTDAGKRAS
WDASKAWGLRLYRSTRTDPVTRFSLTRQVLNIGPRVPIGPNPVIIDQLPP
SRPVQVMLPRPPQPPPPGAASTVPETAPPSQQPGTGDRLLNLVNGAYQAL
NLTSPDKTQECWLCLVAGPPYYEGVAVLGTYSNHTSAPANCSVASQHKLT
LSEVTGQGLCVGAVPKTHQALCNTTQKTSNGSYYLAAPAGTIWACNTGLT
PCLSTTVLDLTTDYCVLVELWPKVTYHSPGYVYGQFEEKTKYKREPSLTL
ALLLGGLTMGGIAAGVGTGTTALVATQQFQQLQAAMQDDLKEVEKSITNL
ERSLTSLSEVVLQNRRGLDLLFLKEGGLCAALKEECCFYADHTGLVRDSM
AKLRERLSQRQKLFESQQGWFEGLFNKSPWFTTLISTIMGPLIILLLILL
FGPCILNHLVQFIKDRVSVVQALVLTQQYHQLKTIEDCESRE

SEQ ID NO: 54:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCAAGGAATCTACCAGTGCXTGTGGGCCCTGTTATG
ATTCCTCGGTGGTCTCCAGTAGCGCCCAGGGTGCCACACCGGGGGGTCGA
TGCAACCCCCTAGTCCTAGAATTCACTGACGCGGGTAAAAGGGCCAGCTG
GGACGCCTCCAAAGCATGGGGACTAAGACTGTACCGATCCACAGGGATCG
ACCCGGTGACCCGGTTCTCTTTGACCCGCCAGGTCCTCAATATAGGGCCC
CGCGTCCCCATTGGGCCTAATCCCGTGATCATTGACCAGTTACCCCCCTC
CCGACCCGTGCAGGTCATGCTCCCCAGGCCTCCTCAGCCTCCTCCACCAG
GCGCAGCCTCTACAGTCCCTGAGACTGCCCCACCTTCCCAACAACCTGGG
ACGGGAGACAGGCTGCTAAACCTGGTAAATGGAGCCTACCAAGCTCTCAA
CCTCACCAGTCCTGACAAAACCCAAGAGTGCTGGTTGTGTCTGGTAGCGG
GACCCCCCTACTACGAAGGGGTTGCCGTCCTAGGTACTTATTCCAACCAT
ACCTCTGCCCCAGCTAACTGCTCCGTGGCCTCCCAACACAAGCTGACCCT
GTCCGAAGTGACCGGACAGGGACTCTGCGTAGGAGCAGTTCCCAAAACCC
ATCAGGCCCTGTGTAATACCACCCAGAAGACGAGCAACGGGTCCTACTAT
CTGGCTGCTCCCGCCGGGACCATTTGGGCTTGCAACACCGGGCTCACTCC
CTGCCTATCTACCACTGTGCTCGACCTCACCACCGATTACTGTGTCCTGG
TTGAGCTCTGGCCAAAAGTGACCTACCACTCCCCTGGTTATGTTTATGGC
CAGTTTGAAGAAAAAACCAAATATAAAAGAGAACCCGTCTCACTAACTCT
GGCCCTACTATTAGGAGGACTCACTATGGGCGGAATTGCCGCCGGAGTGG
GAACAGGGACTACCGCCCTAGTGGCCACTCAGCAGTTCCAACAACTCCAG
GCTGCCATGCAGGATGACCTTAAAGAAGTTGAAAAGTCCATCACTAATCT
AGAAAGATCTTTGACCTCCTTGTCCGAAGTAGTGTTACAGAATCGTAGAG
GCCTAGATCTACTATTCCTAAAAGAGGGAGGTTTGTGTGCTGCCTTAAAA
GAAGAATGCTGTTTCTATGCCGACCACACAGGATTGGTACGGGATAGCAT
GGCCAAACTTAGAGAAAGATTGAGTCAGAGACAAAAACTCTTTGAATCCC
AACAAGGGTGGTTTGAAGGGCTGTTTAACAAGTCCCCTTGGTTCACCACC
CTGATATCCACCATCATGGGTCCCCTGATAATCCTCTTGTTAATTTTACT
CTTTGGGCCTTGTATTCTCAATCACCTGGTCCAGTTTATCAAAGACAGGG
TTTCGGTAGTGCAGGCCCTGGTCCTGACTCAACAATATCATCAACTTAAG
ACAATAGAAGATTGTGAATCACGTGAATAA

SEQ ID NO: 55:—(suitable insert site is represented by the symbol "X"):

MEGPAFSKPLKDKINPWGPLIVLGILMRARVSVQHDSPHQVFNVTWRVTN
LMTGQTANATLSLLGTMTDAFPKLYFDLCDLIGDDWDETGLGCRTPGGRK
RARIFDFYVPGHTVLAGCGGPREGYCGKWGCETTGQAYWKPSSSWDLISL
KRGNTQGIYQCXCGPCYDSSVVSSSAQGATPGGRCNPLVLEFTDAGKRAS
WDASKAWGLRLYRSTGIDPVTRFSLTRQVLNIGPRVPIGPNPVIIDQLPP
SRPVQVMLPRPPQPPPPGAASTVPETAPPSQQPGTGDRLLNLVNGAYQAL
NLTSPDKTQECWLCLVAGPPYYEGVAVLGTYSNHTSAPANCSVASQHKLT
LSEVTGQGLCVGAVPKTHQALCNTTQKTSNGSYYLAAPAGTIWACNTGLT
PCLSTTVLDLTTDYCVLVELWPKVTYHSPGYVYGQFEEKTKYKREPVSLT
ALLLGGLTMGGIAAGVGTGTTALVATQQFQQLQAAMQDDLKEVEKSITNL
ERSLTSLSEVVLQNRRGLDLLFLKEGGLCAALKEECCFYADHTGLVRDSM
AKLRERLSQRQKLFESQQGWFEGLFNKSPWFTTLISTIMGPLIILLLILL
FGPCILNHLVQFIKDRVSVQALVLTQQYHQLKTIEDCESRE

SEQ ID NO: 56:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCCTAAAGGCCAGGGCCCCTGTTATGATTCC XTCC
AGTAGCGCCCAGGGTGCCACACCGGGGGGTCGATGCAACCCCCTAGTCCTA
GAATTCACTGACGCGGGTAAAAGGGCCAGCTGGGACGCCTCCAAAGCATG
GGGACTAAGACTGTACCGATCCACAAGGACCGACCCGGTGACCCGGTTCT
CTTTGACCCGCCAGGTCCTCAATATAGGGCCCCGCGTCCCCATTGGGCCT
AATCCCGTGATCATTGACCAGTTACCCCCCTCCCGACCCGTGCAGGTCAT
GCTCCCCAGGCCTCCTCAGCCTCCTCCACCAGGCGCAGCCTCTACAGTCC
CTGAGACTGCCCCACCTTCCCAACAACCTGGGACGGGAGACAGGCTGCTA
AACCTGGTAAATGGAGCCTACCAAGCTCTCAACCTCACCAGTCCTGACAA
AACCCAAGAGTGCTGGTTGTGTCTGGTAGCGGGACCCCCCTACTACGAAG
GGGTTGCCGTCCTAGGTACTTATTCCAACCATACCTCTGCCCCAGCTAAC
TGCTCCGTGGCCTCCCAACACAAGCTGACCCTGTCCGAAGTGACCGGACA
GGGACTCTGCGTAGGAGCAGTTCCCAAAACCCATCAGGCCCTGTGTAATA
CCACCCAGAAGACGAGCAACGGGTCCTACTATCTGGCTGCTCCCGCCGGG

-continued

ACCATTTGGGCTTGCAACACCGGGCTCACTCCCTGCCTATCTACCACTGT

GCTCGACCTCACCACCGATTACTGTGTCCTGGTTGAGCTCTGGCCAAAAG

TGACCTACCACTCCCCTGGTTATGTTTATGGCCAGTTTGAAGAAAAAACC

AAATATAAAAGAGAACCCGTCTCACTAACTCTGGCCCTACTATTAGGAGG

ACTCACTATGGGCGGAATTGCCGCCGGAGTGGGAACAGGGACTACCGCCC

TAGTGGCCACTCAGCAGTTCCAACAACTCCAGGCTGCCATGCAGGATGAC

CTTAAAGAAGTTGAAAAGTCCATCACTAATCTAGAAAGATCTTTGACCTC

CTTGTCCGAAGTAGTGTTACAGAATCGTAGAGGCCTAGATCTACTATTCC

TAAAAGAGGGAGGTTTGTGTGCTGCCTTAAAAGAAGAATGCTGTTTCTAT

GCCGACCACACAGGATTGGTACGGGATAGCATGGCCAAACTTAGAGAAAG

ATTGAGTCAGAGACAAAAACTCTTTGAATCCCAACAAGGGTGGTTTGAAG

GGCTGTTTAACAAGTCCCCTTGGTTCACCACCCTGATATCCACCATCATG

GGTCCCCTGATAATCCTCTTGTTAATTTTACTCTTTGGGCCTTGTATTCT

CAATCACCTGGTCCAGTTTATCAAAGACAGGGTTTCGGTAGTGCAGGCCC

TGGTCCTGACTCAACAATATCATCAACTTAAGACAATAGAAGATTGTGAA

TCACGTGAATAA

SEQ ID NO: 57:—(suitable insert site is represented by the symbol “X”):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDS XSSSAQGATPGGRCNPLVLEFTDAGKRASWDASK

AWGLRLYRSTRTDPVTRFSLTRQVLNIGPRVPIGPNPVIIDQLPPSRPVQV

MLPRPPQPPPPGAASTVPETAPPSQQPGTGDRLLNLVNGAYQALNLTSPD

KTQECWLCLVAGPPYYEGVAVLGTYSNHTSAPANCSVASQHKLTLSEVTG

QGLCVGAVPKTHQALCNTTQKTSNGSYYLAAPAGTIWACNTGLTPCLSTT

VLDLTTDYCVLVELWPKVTYHSPGYVYGQFEEKTKYKREPVSLTLALLLG

GLTMGGIAAGVGTGTTALVATQQFQQLQAAMQDDLKEVEKSITNLERSLT

SLSEVVLQNRRGLDLLFLKEGGLCAALKEECCFYADHTGLVRDSMAKLRE

RLSQRQKLFESQQGWFEGLFNKSPWFTTLISTIMGPLIILLLILLFGPCI

LNHLVQFIKDRVSVVQALVLTQQYHQLKTIEDCESRE

SEQ ID NO: 58:—(suitable insert site is represented by the symbol “X”):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

-continued

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCCTAAAGGCCAGGGCCCCTGTTATGATTCC XTCC

AGTAGCGCCCAGGGTGCCACACCGGGGGGTCGATGCAACCCCCTAGTCCTA

GAATTCACTGACGCGGGTAAAAGGGCCAGCTGGGACGCCTCCAAAGCATG

GGGACTAAGACTGTACCGATCCACAGGGATCGACCCGGTGACCCGGTTCT

CTTTGACCCGCCAGGTCCTCAATATAGGGCCCCGCGTCCCCATTGGGCCT

AATCCCGTGATCATTGACCAGTTACCCCCCTCCCGACCCGTGCAGGTCAT

GCTCCCCAGGCCTCCTCAGCCTCCTCCACCAGGCGCAGCCTCTACAGTCC

CTGAGACTGCCCCACCTTCCCAACAACCTGGGACGGGAGACAGGCTGCTA

AACCTGGTAAATGGAGCCTACCAAGCTCTCAACCTCACCAGTCCTGACAA

AACCCAAGAGTGCTGGTTGTGTCTGGTAGCGGGACCCCCCTACTACGAAG

GGGTTGCCGTCCTAGGTACTTATTCCAACCATACCTCTGCCCCAGCTAAC

TGCTCCGTGGCCTCCCAACACAAGCTGACCCTGTCCGAAGTGACCGGACA

GGGACTCTGCGTAGGAGCAGTTCCCAAAACCCATCAGGCCCTGTGTAATA

CCACCCAGAAGACGAGCAACGGGTCCTACTATCTGGCTGCTCCCGCCGGG

ACCATTTGGGCTTGCAACACCGGGCTCACTCCCTGCCTATCTACCACTGT

GCTCGACCTCACCACCGATTACTGTGTCCTGGTTGAGCTCTGGCCAAAAG

TGACCTACCACTCCCCTGGTTATGTTTATGGCCAGTTTGAAGAAAAAACC

AAATATAAAAGAGAACCCGTCTCACTAACTCTGGCCCTACTATTAGGAGG

ACTCACTATGGGCGGAATTGCCGCCGGAGTGGGAACAGGGACTACCGCCC

TAGTGGCCACTCAGCAGTTCCAACAACTCCAGGCTGCCATGCAGGATGAC

CTTAAAGAAGTTGAAAAGTCCATCACTAATCTAGAAAGATCTTTGACCTC

CTTGTCCGAAGTAGTGTTACAGAATCGTAGAGGCCTAGATCTACTATTCC

TAAAAGAGGGAGGTTTGTGTGCTGCCTTAAAAGAAGAATGCTGTTTCTAT

GCCGACCACACAGGATTGGTACGGGATAGCATGGCCAAACTTAGAGAAAG

ATTGAGTCAGAGACAAAAACTCTTTGAATCCCAACAAGGGTGGTTTGAAG

GGCTGTTTAACAAGTCCCCTTGGTTCACCACCCTGATATCCACCATCATG

GGTCCCCTGATAATCCTCTTGTTAATTTTACTCTTTGGGCCTTGTATTCT

CAATCACCTGGTCCAGTTTATCAAAGACAGGGTTTCGGTAGTGCAGGCCC

TGGTCCTGACTCAACAATATCATCAACTTAAGACAATAGAAGATTGTGAA

TCACGTGAATAA

SEQ ID NO: 59:—(suitable insert site is represented by the symbol “X”):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDS XSSSAQGATPGGRCNPLVLEFTDAGKRASWDASK

AWGLRLYRSTGIDPVTRFSLTRQVLNIGPRVPIGPNPVIIDQLPPSRPVQV

MLPRPPQPPPPGAASTVPETAPPSQQPGTGDRLLNLVNGAYQALNLTSPD

-continued

KTQECWLCLVAGPPYYEGVAVLGTYSNHTSAPANCSVASQHKLTLSEVTG

QGLCVGAVPKTHQALCNTTQKTSNGSYYLAAPAGTIWACNTGLTPCLSTT

VLDLTTDYCVLVELWPKVTYHSPGYVYGQFEEKTKYKREPVSLTLALLLG

GLTMGGIAAGVGTGTTALVATQQFQQLQAAMQDDLKEVEKSITNLERSLT

SLSEVVLQNRRGLDLLFLKEGGLCAALKEECCFYADHTGLVRDSMAKLRE

RLSQRQKLFESQQGWFEGLFNKSPWFTTLISTIMGPLIILLLILLFGPCI

LNHLVQFIKDRVSVVQALVLTQQYHQLKTIEDCESRE

Homologues and/or fragments of the below sequences are also within the scope of the present invention SEQ ID NO: 60: SL3-2 Envelope polypeptide sequence:

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDSSVVSSSAQGATPGGRCNPLVLEFTDAGKRASWDAS

KAWGLRLYRSTRTDPVTRFSLTRQVLNIGPRVPIGPNPVIIDQLPPSRPV

QIMLPRPPQPPPPGAASTVPETAPPSQQPGTGDRLLNLVNGAYQALNLTS

PDKTQECWLCLVAGPPYYEGVAVLGTYSNHTSAPANCSVASQHKLTLSEV

TGQGLCVGAVPKTHQALCNTTQKTSNGSYYLAAPAGTIWACNTGLTPCLS

TTVLDLTTDYCVLVELWPKVTYHSPGYVYGQFEEKTKYKREPVSLTLALL

LGGLTMGGIAAGVGTGTTALVATQQFQQLQAAMQDDLKEVKKSITNLERS

LTSLSEVVLQNRRGLDLLFLKEGGLCAALKEECCFYADHTGLVRDSMAKL

RERLSQRQKLFESQQGWFEGLFNKSPWFTTLISTIMGPLIILLLILLFGP

CILNHLVQFIKDRVSVVQALVLTQQYHQLKTIEDCESRE

SEQ ID NO: 61:SL3-2/apelin chimeric envelope polypeptide 'AP165 RT' (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDSSGGSGQRPRLSHKGPMPFSGGSGSSSAQGATPGGR

CNPLVLEFTDAGKRASWDASKAWGLRLYRSTRTDPVTRFSLTRQVLNIGP

RVPIGPNPVIIDQLPPSRPVQVMLPRPPQPPPPGAASTVPETAPPSQQPG

TGDRLLNLVNGAYQALNLTSPDKTQECWLCLVAGPPYYEGVAVLGTYSNH

TSAPANCSVASQHKLTLSEVTGQGLCVGAVPKTHQALCNTTQKTSNGSYY

LAAPAGTIWACNTGLTPCLSTTVLDLTTDYCVLVELWPKVTYHSPGYVYG

QFEEKTKYKREPVSLTLALLLGGLTMGGIAAGVGTGTTALVATQQFQQLQ

AAMQDDLKEVEKSITNLERSLTSLSEVVLQNRRGLDLLFLKEGGLCAALK

EECCFYADHTGLVRDSMAKLRERLSQRQKLFESQQGWFEGLFNKSPWFTT

LISTIMGPLIILLLILLFGPCILNHLVQFIKDRVSVVQALVLTQQYHQLK

TIEDCESRE

SEQ ID NO: 62 SL3-2/V3 loop chimeric envelope polypeptide, "L2 RT", (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTQGIYQCTRPNNNTRKRIRIQRGPGRAFVTIGKIGNMRQAHCGPCY

DSSVVSSSAQGATPGGRCNPLVLEFTDAGKRASWDASKAWGLRLYRSTRT

DPVTRFSLTRQVLNIGPRVPIGPNPVIIDQLPPSRPVQVMLPRPPQPPPP

GAASTVPETAPPSQQPGTGDRLLNLVNGAYQALNLTSPDKTQECWLCLVA

GPPYYEGVAVLGTYSNHTSAPANCSVASQHKLTLSEVTGQGLCVGAVPKT

HQALCNTTQKTSNGSYYLAAPAGTIWACNTGLTPCLSTTVLDLTTDYCVL

VELWPKVTYHSPGYVYGQFEEKTKYKREPVSLTLALLLGGLTMGGIAAGV

GTGTTALVATQQFQQLQAAMQDDLKEVEKSITNLERSLTSLSEVVLQNRR

GLDLLFLKEGGLCAALKEECCFYADHTGLVRDSMAKLRERLSQRQKLFES

QQGWFEGLFNKSPWFTTLISTIMGPLIILLLILLFGPCILNHLVQFIKDR

VSVVQALVLTQQYHQLKTIEDCESRE*

SEQ ID NO: 63: SL3-2/V3 loop chimeric envelope polypeptide, "L3 RT", (shaded section represents the inserted section),":

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCTRPNNNTRKRIRIQRGPGRAFVTIGKIGNMRQAHCNPL

VLEFTDAGKRASWDASKAWGLRLYRSTRTDPVTRFSLTRQVLNIGPRVPI

GPNPVIIDQLPPSRPVQVMLPRPPQPPPPGAASTVPETAPPSQQPGTGDR

LLNLVNGAYQALNLTSPDKTQECWLCLVAGPPYYEGVAVLGTYSNHTSAP

ANCSVASQHKLTLSEVTGQGLCVGAVPKTHQALCNTTQKTSNGSYYLAAP

AGTIWACNTGLTPCLSTTVLDLTTDYCVLVELWPKVTYHSPGYVYGQFEE

KTKYKREPVSLTLALLLGGLTMGGIAAGVGTGTTALVATQQFQQLQAAMQ

DDLKEVEKSITNLERSLTSLSEVVLQNRRGLDLLFLKEGGLCAALKEECC

FYADHTGLVRDSMAKLRERLSQRQKLFESQQGWFEGLFNKSPWFTTLIST

IMGPLIILLLILLFGPCILNHLVQFIKDRVSVVQALVLTQQYHQLKTIED

CESRE

SEQ ID NO: 64: SL3-2/V3 loop chimeric envelope polypeptide, "L1 RT", (shaded section represents the inserted section):

MEGPAFSKPLKDKINPWGPLIVLGILMRARVSVQHDSPHQVFNVTWRVTN

LMTGQTANATSLLGTMTDAFPKLYFDLCTRPNNNTRKRIRIQRGPGRAFV

TIGKIGNMRQAHCRTPGGRKRARIFDFYVCPGHTVLAGCGGPREGYCGKW

GCETTGQAYWKPSSSWDLISLKRGNTPKGQGPCYDSSVVSSSAQGATPGG

-continued

RCNPLVLEFTDAGKRASWDASKAWGLRLYRSTRTDPVTRFSLTRQVLNIG

PRVPIGPNPVIIDQLPPSRPVQVMLPRPPQPPPPGAASTVPETAPPSQQP

GTGDRLLNLVNGAYQALNLTSPDKTQECWLCLVAGPPYYEGVAVLGTYSN

HTSAPANCSVASQHKLTLSEVTGQGLCVGAVPKTHQALCNTTQKTSNGSY

YLAAPAGTIWACNTGLTPCLSTTVLDLTTDYCVLVELWPKVTYHSPGYVY

GQFEEKTKYKREPVSLTLALLLGGLTMGGIAAGVGTGTTALVATQQFQQL

QAAMQDDLKEVEKSITNLERSLTSLSEVVLQNRRGLDLLFLKEGGLCAAL

KEECCFYADHTGLVRDSMAKLRERLSQRQKLFESQQGWFEGLFNKSPWFT

TLISTIMGPLIILLLILLFGPCILNHLVQFIKDRVSVVQALVLTQQYHQL

KTIEDCESRE

SEQ ID NO: 65: polynucleotide sequence coding for SL3-2 viral envelope polypeptide:

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCCTAAAGGCCAGGGCCCCTGTTATGATTCCTCGGT

GGTCTCCAGTAGCGCCCAGGGTGCCACACCGGGGGGTCGATGCAACCCCC

TAGTCCTAGAATTCACTGACGCGGGTAAAAGGGCCAGCTGGGACGCCTCC

AAAGCATGGGGACTAAGACTGTACCGATCCACAAGGACCGACCCGGTGAC

CCGGTTCTCTTTGACCCGCCAGGTCCTCAATATAGGGCCCCGCGTCCCCA

TTGGGCCTAATCCCGTGATCATTGACCAGTTACCCCCCTCCCGACCCGTG

CAGGTCATGCTCCCCAGGCCTCCTCAGCCTCCTCCACCAGGCGCAGCCTC

TACAGTCCCTGAGACTGCCCCACCTTCCCAACAACCTGGGACGGGAGACA

GGCTGCTAAACCTGGTAAATGGAGCCTACCAAGCTCTCAACCTCACCAGT

CCTGACAAAACCCAAGAGTGCTGGTTGTGTCTGGTAGCGGGACCCCCCTA

CTACGAAGGGGTTGCCGTCCTAGGTACTTATTCCAACCATACCTCTGCCC

CAGCTAACTGCTCCGTGGCCTCCCAACACAAGCTGACCCTGTCCGAAGTG

ACCGGACAGGGACTCTGCGTAGGAGCAGTTCCCAAAACCCATCAGGCCCT

GTGTAATACCACCCAGAAGACGAGCAACGGGTCCTACTATCTGGCTGCTC

CCGCCGGGACCATTTGGGCTTGCAACACCGGGCTCACTCCCTGCCTATCT

ACCACTGTGCTCGACCTCACCACCGATTACTGTGTCCTGGTTGAGCTCTG

GCCAAAAGTGACCTACCACTCCCCTGGTTATGTTTATGGCCAGTTTGAAG

AAAAAACCAAATATAAAAGAGAACCCGTCTCACTAACTCTGGCCCTACTA

TTAGGAGGACTCACTATGGGCGGAATTGCCGCCGGAGTGGGAACAGGGAC

-continued

TACCGCCCTAGTGGCCACTCAGCAGTTCCAACAACTCCAGGCTGCCATGC

AGGATGACCTTAAAGAAGTTGAAAAGTCCATCACTAATCTAGAAAGATCT

TTGACCTCCTTGTCCGAAGTAGTGTTACAGAATCGTAGAGGCCTAGATCT

ACTATTCCTAAAAGAGGGAGGTTTGTGTGCTGCCTTAAAAGAAGAATGCT

GTTTCTATGCCGACCACACAGGATTGGTACGGGATAGCATGGCCAAACTT

AGAGAAAGATTGAGTCAGAGACAAAAACTCTTTGAATCCCAACAAGGGTG

GTTTGAAGGGCTGTTTAACAAGTCCCCTTGGTTCACCACCCTGATATCCA

CCATCATGGGTCCCCTGATAATCCTCTTGTTAATTTTACTCTTTGGGCCT

TGTATTCTCAATCACCTGGTCCAGTTTATCAAAGACAGGGTTTCGGTAGT

GCAGGCCCTGGTCCTGACTCAACAATATCATCAACTTAAGACAATAGAAG

ATTGTGAATCACGTGAATAA

SEQ ID NO: 66: SL3-2/V3 loop chimeric envelope polynucleotide, “L2 RT” (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCAAGGAATCTACCAGTGTACAAGACCCAACAACAA

TACAAGAAAAAGAATCCGTATCCAGAGAGGACCAGGGAGAGCATTTGTTA

CAATAGGAAAAATAGGAAATATGAGACAAGCACATTGTGGGCCCTGTTAT

GATTCCTCGGTGGTCTCCAGTAGCGCCCAGGGTGCCACACCGGGGGGTCG

ATGCAACCCCCTAGTCCTAGAATTCACTGACGCGGGTAAAAGGGCCAGCT

GGGACGCCTCCAAAGCATGGGGACTAAGACTGTACCGATCCACAAGGACC

GACCCGGTGACCCGGTTCTCTTTGACCCGCCAGGTCCTCAATATAGGGCC

CCGCGTCCCCATTGGGCCTAATCCCGTGATCATTGACCAGTTACCCCCCT

CCCGACCCGTGCAGGTCATGCTCCCCAGGCCTCCTCAGCCTCCTCCACCA

GGCGCAGCCTCTACAGTCCCTGAGACTGCCCCACCTTCCCAACAACCTGG

GACGGGAGACAGGCTGCTAAACCTGGTAAATGGAGCCTACCAAGCTCTCA

ACCTCACCAGTCCTGACAAAACCCAAGAGTGCTGGTTGTGTCTGGTAGCG

GGACCCCCCTACTACGAAGGGGTTGCCGTCCTAGGTACTTATTCCAACCA

TACCTCTGCCCCAGCTAACTGCTCCGTGGCCTCCCAACACAAGCTGACCC

TGTCCGAAGTGACCGGACAGGGACTCTGCGTAGGAGCAGTTCCCAAAACC

CATCAGGCCCTGTGTAATACCACCCAGAAGACGAGCAACGGGTCCTACTA

TCTGGCTGCTCCCGCCGGGACCATTTGGGCTTGCAACACCGGGCTCACTC

CCTGCCTATCTACCACTGTGCTCGACCTCACCACCGATTACTGTGTCCTG

-continued

GTTGAGCTCTGGCCAAAAGTGACCTACCACTCCCCTGGTTATGTTTATGG

CCAGTTTGAAGAAAAAACCAAATATAAAAGAGAACCCGTCTCACTAACTC

TGGCCCTACTATTAGGAGGACTCACTATGGGCGGAATTGCCGCCGGAGTG

GGAACAGGGACTACCGCCCTAGTGGCCACTCAGCAGTTCCAACAACTCCA

GGCTGCCATGCAGGATGACCTTAAAGAAGTTGAAAAGTCCATCACTAATC

TAGAAAGATCTTTGACCTCCTTGTCCGAAGTAGTGTTACAGAATCGTAGA

GGCCTAGATCTACTATTCCTAAAAGAGGGAGGTTTGTGTGCTGCCTTAAA

AGAAGAATGCTGTTTCTATGCCGACCACACAGGATTGGTACGGGATAGCA

TGGCCAAACTTAGAGAAAGATTGAGTCAGAGACAAAAACTCTTTGAATCC

CAACAAGGGTGGTTTGAAGGGCTGTTTAACAAGTCCCCTTGGTTCACCAC

CCTGATATCCACCATCATGGGTCCCCTGATAATCCTCTTGTTAATTTTAC

TCTTTGGGCCTTGTATTCTCAATCACCTGGTCCAGTTTATCAAAGACAGG

GTTTCGGTAGTGCAGGCCCTGGTCCTGACTCAACAATATCATCAACTTAA

GACAATAGAAGATTGTGAATCACGTGAATAA

SEQ ID NO: 67: SL3-2/V3 loop chimeric envelope polynucleotide, “L3 RT”, (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGACCTAATTTCCCTT

AAGCGAGGAAACACTCCTAAAGGCCAGGGCCCCTGTACAAGACCCAACAA

CAATACAAGAAAAAGAATCCGTATCCAGAGAGGACCAGGGAGAGCATTTG

TTACAATAGGAAAAATAGGAAATATGAGACAAGCACATTGTAACCCCCTA

GTCCTAGAATTCACTGACGCGGGTAAAAGGGCCAGCTGGGACGCCTCCAA

AGCATGGGGACTAAGAQTGTACCGATCCACAAGGACCGACCCGGTGACCC

GGTTCTCTTTGACCCGCCAGGTCCTCAATATAGGGCCCCGCGTCCCCATT

GGGCCTAATCCCGTGATCATTGACCAGTTACCCCCCTCCCGACCCGTGCA

GGTCATGCTCCCCAGGCCTCCTCAGCCTCCTCCACCAGGCGCAGCCTCTA

CAGTCCCTGAGACTGCCCCACCTTCCCAACAACCTGGGACGGGAGACAGG

CTGCTAAACCTGGTAAATGGAGCCTACCAAGCTCTCAACCTCACCAGTCC

TGACAAAACCCAAGAGTGCTGGTTGTGTCTGGTAGCGGGACCCCCCTACT

ACGAAGGGGTTGCCGTCCTAGGTACTTATTCCAACCATACCTCTGCCCCA

GCTAACTGCTCCGTGGCCTCCCAACACAAGCTGACCCTGTCCGAAGTGAC

CGGACAGGGACTCTGCGTAGGAGCAGTTCCCAAAACCCATCAGGCCCTGT

-continued

GTAATACCACCCAGAAGACGAGCAACGGGTCCTACTATCTGGCTGCTCCC

GCCGGGACCATTTGGGCTTGCAACACCGGGCTCACTCCCTGCCTATCTAC

CACTGTGCTCGACCTCACCACCGATTACTGTGTCCTGGTTGAGCTCTGGC

CAAAAGTGACCTACCACTCCCCTGGTTATGTTTATGGCCAGTTTGAAGAA

AAAACCAAATATAAAAGAGAACCCGTCTCACTAACTCTGGCCCTACTATT

AGGAGGACTCACTATGGGCGGAATTGCCGCCGGAGTGGGAACAGGGACTA

CCGCCCTAGTGGCCACTCAGCAGTTCCAACAACTCCAGGCTGCCATGCAG

GATGACCTTAAAGAAGTTGAAAAGTCCATCACTAATCTAGAAAGATCTTT

GACCTCCTTGTCCGAAGTAGTGTTACAGAATCGTAGAGGCCTAGATCTAC

TATTCCTAAAAGAGGGAGGTTTGTGTGCTGCCTTAAAAGAAGAATGCTGT

TTCTATGCCGACCACACAGGATTGGTACGGGATAGCATGGCCAAACTTAG

AGAAAGATTGAGTCAGAGACAAAAACTCTTTGAATCCCAACAAGGGTGGT

TTGAAGGGCTGTTTAACAAGTCCCCTTGGTTCACCACCCTGATATCCACC

ATCATGGGTCCCCTGATAATCCTCTTGTTAATTTTACTCTTTGGGCCTTG

TATTCTCAATCACCTGGTCCAGTTTATCAAAGACAGGGTTTCGGTAGTGC

AGGCCCTGGTCCTGACTCAACAATATCATCAACTTAAGACAATAGAAGAT

TGTGAATCACGTGAATAA

SEQ ID NO: 68: SL3-2/V3 loop chimeric envelope polynucleotide, “L1 RT”, (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGTACAAGACCCAACAACA

ATACAAGAAAAAGAATCCGTATCCAGAGAGGACCAGGGAGAGCATTTGTT

ACAATAGGAAAAATAGGAAATATGAGACAAGCACATTGTCGCACTCCCGG

GGGAAGAAAAAGGGCAAGAATATTTGACTTCTATGTTTGCCCCGGTCACA

CTGTGCTAGCAGGGTGTGGAGGGCCGAGAGAGGGCTACTGTGGCAAATGG

GGATGTGAGACCACTGGACAGGCATACTGGAAGCCATCATCATCATGGGA

CCTAATTTCCCTTAAGCGAGGAAACACTCCTAAAGGCCAGGGCCCCTGTT

ATGATTCCTCGGTGGTCTCCAGTAGCGCCCAGGGTGCCACACCGGGGGGT

CGATGCAACCCCCTAGTCCTAGAATTCACTGACGCGGGTAAAAGGGCCAG

CTGGGACGCCTCCAAAGCATGGGGACTAAGACTGTACCGATCCACAAGGA

CCGACCCGGTGACCCGGTTCTCTTTGACCCGCCAGGTCCTCAATATAGGG

CCCCGCGTCCCCATTGGGCCTAATCCCGTGATCATTGACCAGTTACCCCC

CTCCCGACCCGTGCAGGTCATGCTCCCCAGGCCTCCTCAGCCTCCTCCAC

CAGGCGCAGCCTCTACAGTCCCTGAGACTGCCCCACCTTCCCAACAACCT

GGGACGGGAGACAGGCTGCTAAACCTGGTAAATGGAGCCTACCAAGCTCT

CAACCTCACCAGTCCTGACAAAACCCAAGAGTGCTGGTTGTGTCTGGTAG

CGGGACCCCCCTACTACGAAGGGGTTGCCGTCCTAGGTACTTATTCCAAC

-continued

CATACCTCTGCCCCAGCTAACTGCTCCGTGGCCTCCCAACACAAGCTGAC

CCTGTCCGAAGTGACCGGACAGGGACTCTGCGTAGGAGCAGTTCCCAAAA

CCCATCAGGCCCTGTGTAATACCACCCAGAAGACGAGCAACGGGTCCTAC

SEQ ID NO: 71

CTRPNNNNTRKRIRIQRGPGRAFVTIGKIGNMRQAHC

V3 sequences of different HIV isolates:

```
                      ↓                                    ↓
              (1)1        10       20        30        40          53
BAA11457  (1)---------CSRPNN-NTRKSIHMGPGKAFYTTGDTIGDIRQAHC--------  SEQ ID NO: 12
AAA64827  (1)---------CTRPNN-NTRKSIHIGPGRAFYTTGDIIGDIRQAHC--------  SEQ ID NO: 13
CAA78890  (1)---------CTRPSN-NTRKSIPVGPGKALYATGAIIGNIRQAHC--------  SEQ ID NO: 14
AAM82279  (1)---------CIRPNN-NTRKSVRIGPGQTFYATGEIIGDIRAAYC--------  SEQ ID NO: 15
AAD42280  (1)----PVSINCTRPGN-NTRRSVRIGPGQTFYATGDITGDIRQAHC--------  SEQ ID NO: 16
CAA90694  (1)---------CTRPNN-NTRKRISIGPGRSFYTTRQIVGDIRQAHC--------  SEQ ID NO: 17
AAC34563  (1)---------CTRPNN-NTRKSIHIGPGKAFYATGDVIGDIRKAHC--------  SEQ ID NO: 18
AAG01102  (1)--NESVAINCTRPVN-NTRKSIYIGPGRAFHTTGRIIGDIRKAHCXISRAQWN  SEQ ID NO: 19
AAL13161  (1)-------IVCTRPGN-NTRKGIHIGPGRAFYASEGIVGDIRQAHC--------  SEQ ID NO: 20
CAA79322  (1)---------CTRPNNNIRIRHIHIGPGRAFHATEAATGDIRQAHC--------  SEQ ID NO: 21
AAC54528  (1)---------CTRPNN-NTRKGIHIGPGKAYYTTGDIIGDIRQAHCNISRA---  SEQ ID NO: 22
AAD48873  (1)-------INCTRPNN-NIRKRIHIGPGRAFYTTGKIIGGIRQAHCNLS-----  SEQ ID NO: 23
AAP98384  (1)--NESVTITCIRPYN-NIRQSVEMGPGR-ALYTQEITGDIRRAHC--------  SEQ ID NO: 24
AAG01097  (1)---XSVEIVCTRPNN-NTRESIRIGPGQTFYATGDIIGNIRQAHC--------  SEQ ID NO: 25
AAA99704  (1)---------CIRPGN-NTRRSIHIQPGRAFYASGGIIGDIREAHCTLNIP---  SEQ ID NO: 26
AAB08827  (1)-----VEIECTRPGN-NTRKSIPIGPGQTFYATGDIIGDIRQAHCN-------  SEQ ID NO: 27
AAM74784  (1)---------CTRPNN-NTRKSIPMGPGKAFYATGDIIGDIRKAFC--------  SEQ ID NO: 28
AAR19993  (1)QLKEPVEINCTRPNN-TTRRGIYIGPGRTIYAGEKIIGDIRRAYC--------  SEQ ID NO: 29
CAA54928  (1)-------INCTRPNN-NTRKSIHLGPGQAFYATGDIIGDIRKAHCNVS-----  SEQ ID NO: 30
2124259L  (1)---------CTRPNN-NTRKSIHMGPGRAFYATGDIIGNIRQAHCNISRE---  SEQ ID NO: 31
Consensus (1)         CTRPNN NTRKSIHIGPGRAFYATGDIIGDIRQAHC          SEQ ID NO: 32
                      Stem            Tip           Stem
```

-continued

TATCTGGCTGCTCCCGCCGGGACCATTTGGGCTTGCAACACCGGGCTCAC

TCCCTGCCTATCTACCACTGTGCTCGACCTCACCACCGATTACTGTGTCC

TGGTTGAGCTCTGGCCAAAAGTGACCTACCACTCCCCTGGTTATGTTTAT

GGCCAGTTTGAAGAAAAAACCAAATATAAAAGAGAACCCGTCTCACTAAC

TCTGGCCCTACTATTAGGAGGACTCACTATGGGCGGAATTGCCGCCGGAG

TGGGAACAGGGACTACCGCCCTAGTGGCCACTCAGCAGTTCCAACAACTC

CAGGCTGCCATGCAGGATGACCTTAAAGAAGTTGAAAAGTCCATCACTAA

TCTAGAAAGATCTTTGACCTCCTTGTCCGAAGTAGTGTTACAGAATCGTA

GAGGCCTAGATCTACTATTCCTAAAAGAGGGAGGTTTGTGTGCTGCCTTA

AAAGAAGAATGCTGTTTCTATGCCGACCACACAGGATTGGTACGGGATAG

CATGGCCAAACTTAGAGAAAGATTGAGTCAGAGACAAAAACTCTTTGAAT

CCCAACAAGGGTGGTTTGAAGGGCTGTTTAACAAGTCCCCTTGGTTCACC

ACCCTGATATCCACCATCATGGGTCCCCTGATAATCCTCTTGTTAATTTT

ACTCTTTGGGCCTTGTATTCTCAATCACCTGGTCCAGTTTATCAAAGACA

GGGTTTCGGTAGTGCAGGCCCTGGTCCTGACTCAACAATATCATCAACTT

AAGACAATAGAAGATTGTGAATCACGTGAATAA

SEQ ID NO: 69

CTRPNNNTRKRIRIQRGPGRAFVTIGKIGNMRQAHC

SEQ ID NO: 70

CTRPNNNIRIRHRIQRGPGRAFVTIGKIGNMRQAHC

Preferred first polypeptide sequences, with insert sites:

SEQ ID NO: 72

("X" indicates preferred insert site for the polypeptide sequence of receptor binding region, ligand or polypeptide sequence of a ligand binding region and optional linker sequence(s))

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTQGIYQXGPCYDSSVVSSSAQGATPGGRCNPLVLEFTDAGKRASWD

ASKAWGLRLYRSTRTDPVTRFSLTRQVLNIGPRVPIGPNPVIIDQLPPSR

PVQVMLPRPPQPPPPGAASTVPETAPPSQQPGTGDRLLNLVNGAYQALNL

TSPDKTQECWLCLVAGPPYYEGVAVLGTYSNHTSAPANCSVASQHKLTLS

EVTGQGLCVGAVPKTHQALCNTTQKTSNGSYYLAAPAGTIWACNTGLTPC

LSTTVLDLTTDYCVLVELWPKVTYHSPGYVYGQFEEKTKYKREPVSLTLA

LLLGGLTMGGIAAGVGTGTTALVATQQFQQLQAAMQDDLKEVEKSITNLE

RSLTSLSEVVLQNRRGLDLLFLKEGGLCAALKEECCFYADHTGLVRDSMA

KLRERLSQRQKLFESQQGWFEGLFNKSPWFTTLISTIMGPLIILLLILLF

GPCILNHLVQFIKDRVSVVQALVLTQQYHQLKTIEDCESRE*

SEQ ID NO: 73

("X" indicates preferred insert site for the polypeptide sequence of receptor binding region, ligand or polypeptide sequence of a ligand binding region and optional linker sequence(s))

and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTPKGQGPXNPLVLEFTDAGKRASWDASKAWGLRLYRSTRTDPVTRF
SLTRQVLNIGPRVPIGPNPVIIDQLPPSRPVQVMLPRPPQPPPPGAASTV
PETAPPSQQPGTGDRLLNLVNGAYQALNLTSPDKTQECWLCLVAGPPYYE
GVAVLGTYSNHTSAPANCSVASQHKLTLSEVTGQGLCVGAVPKTHQALCN
TTQKTSNGSYYLAAPAGTIWACNTGLTPCLSTTVLDLTTDYCVLVELWPK
VTYHSPGYVYGQFEEKTKYKREPVSLTLALLLGGLTMGGIAAGVGTGTTA
LVATQQFQQLQAAMQDDLKEVEKSITNLERSLTSLSEVVLQNRRGLDLLF
LKEGGLCAALKEECCFYADHTGLVRDSMAKLRERLSQRQKLFESQQGWFE
GLFNKSPWFTTLISTIMGPLIILLLILLFGPCILNHLVQFIKDRVSVVQA
LVLTQQYHQLKTIEDCESRE

SEQ ID NO: 74

("X" indicates preferred insert site for the polypeptide sequence of receptor binding region, ligand or polypeptide sequence of a ligand binding region and optional linker sequence(s)) and optional linker sequence(s))

MEGPAFSKPLKDKINPWGPLIVLGILMRARVSVQHDSPHQVFNVTWRVTN
LMTGQTANATSLLGTMTDAFPKLYFDLXRTPGGRKRARIFDFYVCPGHTV
LAGCGGPREGYCGKWGCETTGQAYWKPSSSWDLISLKRGNTPKGQGPCYD
SSVVSSSAQGATPGGRCNPLVLEFTDAGKRASWDASKAWGLRLYRSTGID
PVTRFSLTRQVLNIGPRVPIGPNPVIIDQLPPSRPVQVMLPRPPQPPPPG
AASTVPETAPPSQQPGTGDRLLNLVNGAYQALNLTSPDKTQECWLCLVAG
PPYYEGVAVLGTYSNHTSAPANCSVASQHKLTLSEVTGQGLCVGAVPKTH
QALCNTTQKTSNGSYYLAAPAGTIWACNTGLTPCLSTTVLDLTTDYCVLV
ELWPKVTYHSPGYVYGQFEEKTKYKREPVSLTLALLLGGLTMGGIAAGVG
TGTTALVATQQFQQLQAAMQDDLKEVEKSITNLERSLTSLSEVVLQNRRG
LDLLFLKEGGLCAALKEECCFYADHTGLVRDSMAKLRERLSQRQKLFESQ
QGWFEGLFNKSPWFTTLISTIMGPLIILLLILLFGPCILNHLVQFIKDRV
SVVQALVLTQQYHQLKTIEDCESRE

SEQ ID NO: 75

("X" indicates preferred insert site for the polypeptide sequence of receptor binding region, ligand or polypeptide sequence of a ligand binding region and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQXGPCYDSSVVSSSAQGATPGGRCNPLVLEFTDAGKRASWD
ASKAWGLRLYRSTGIDPVTRFSLTRQVLNIGPRVPIGPNPVIIDQLPPSR
PVQVMLPRPPQPPPPGAASTVPETAPPSQQPGTGDRLLNLVNGAYQALNL

-continued

TSPDKTQECWLCLVAGPPYYEGVAVLGTYSNHTSAPANCSVASQHKLTLS
EVTGQGLCVGAVPKTHQALCNTTQKTSNGSYYLAAPAGTIWACNTGLTPC
LSTTVLDLTTDYCVLVELWPKVTYHSPGYVYGQFEEKTKYKREPVSLTLA
LLLGGLTMGGIAAGVGTGTTALVATQQFQQLQAAMQDDLKEVEKSITNLE
RSLTSLSEVVLQNRRGLDLLFLKEGGLCAALKEECCFYADHTGLVRDSMA
KLRERLSQRQKLFESQQGWFEGLFNKSPWFTTLISTIMGPLIILLLILLF
GPCILNHLVQFIKDRVSVVQALVLTQQYHQLKTIEDCESRE

SEQ ID NO: 76

("X" indicates preferred insert site for the polypeptide sequence of receptor binding region, ligand or polypeptide sequence of a ligand binding region and optional linker sequence(s))

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTPKGQGPXNPLVLEFTDAGKRASWDASKAWGLRLYRSTGIDPVTRF
SLTRQVLNIGPRVPIGPNPVIIDQLPPSRPVQVMLPRPPQPPPPGAASTV
PETAPPSQQPGTGDRLLNLVNGAYQALNLTSPDKTQECWLCLVAGPPYYE
GVAVLGTYSNHTSAPANCSVASQHKLTLSEVTGQGLCVGAVPKTHQALCN
TTQKTSNGSYYLAAPAGTIWACNTGLTPCLSTTVLDLTTDYCVLVELWPK
VTYHSPGYVYGQFEEKTKYKREPVSLTLALLLGGLTMGGIAAGVGTGTTA
LVATQQFQQLQAAMQDDLKEVEKSITNLERSLTSLSEVVLQNRRGLDLLF
LKEGGLCAALKEECCFYADHTGLVRDSMAKLRERLSQRQKLFESQQGWFE
GLFNKSPWFTTLISTIMGPLIILLLILLFGPCILNHLVQFIKDRVSVVQA
LVLTQQYHQLKTIEDCESRE

SEQ ID NO: 77

("X" indicates preferred insert site for the polypeptide sequence of receptor binding region, ligand or polypeptide sequence of a ligand binding region and optional linker sequence(s))

MEGPAFSKPLKDKINPWGPLIVLGILMRARVSVQHDSPHQVFNVTWRVTN
LMTGQTANATSLLGTMTDAFPKLYFDLXRTPGGRKRARIFDFYVCPGHTV
LAGCGGPREGYCGKWGCETTGQAYWKPSSSWDLISLKRGNTPKGQGPCYD
SSVVSSSAQGATPGGRCNPLVLEFTDAGKRASWDASKAWGLRLYRSTRTD
PVTRFSLTRQVLNIGPRVPIGPNPVIIDQLPPSRPVQVMLPRPPQPPPPG
AASTVPETAPPSQQPGTGDRLLNLVNGAYQALNLTSPDKTQECWLCLVAG
PPYYEGVAVLGTYSNHTSAPANCSVASQHKLTLSEVTGQGLCVGAVPKTH
QALCNTTQKTSNGSYYLAAPAGTIWACNTGLTPCLSTTVLDLTTDYCVLV
ELWPKVTYHSPGYVYGQFEEKTKYKREPVSLTLALLLGGLTMGGIAAGVG
TGTTALVATQQFQQLQAAMQDDLKEVEKSITNLERSLTSLSEVVLQNRRG
LDLLFLKEGGLCAALKEECCFYADHTGLVRDSMAKLRERLSQRQKLFESQ

-continued

QGWFEGLFNKSPWFTTLISTIMGPLIILLLILLFGPCILNHLVQFIKDRV

SVVQALVLTQQYHQLKTIEDCESRE

SEQ ID NO: 78:—Envelope sequence derived from SL3-2 envelope protein (suitable insert site is represented by the symbol "X"):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGXLVLEFTDAGKRASWDASKAWGLRLYRSTRTDPVTRFSLTRQVLNIG

PRVPIGPNPVIIDQLPPSRPVQIMLPRPPQPPPPGAASTVPETAPPSQQP

GTGDRLLNLVNGAYQALNLTSPDKTQECWLCLVAGPPYYEGVAVLGTYSN

HTSAPANCSVASQHKLTLSEVTGQGLCVGAVPKTHQALCNTTQKTSNGSY

YLAAPAGTIWACNTGLTPCLSTTVLDLTTDYCVLVELWPKVTYHSPGYVY

GQFEEKTKYKREPVSLTLALLLGGLTMGGIAAGVGTGTTALVATQQFQQL

QAAMQDDLKEVKKSITNLERSLTSLSEVVLQNRRGLDLLFLKEGGLCAAL

KEECCFYADHTGLVRDSMAKLRERLSQRQKLFESQQGWFEGLFNKSPWFT

TLISTIMGPLIILLLILLFGPCILNHLVQFIKDRVSVVQALVLTQQYHQL

KTIEDCESRE

SEQ ID NO: 79:—Envelope sequence derived from MCF 247 (suitable insert site is represented by the symbol "X"):

MEGPAFSKPLKDKINPWGPLIVLGILIRAGVSVRHDSPHQVFNVTWRVTN

LMTGQTANATSLLGTMTDAFPKLYFDLCDLIGDDWDETGLGCRTPGGRKR

ARTFDFYVCPGHTVPTGCGGPREGYCGKWGCETTGQAYWKPSSSWDLISL

KRGXLVLEFTDAGKKASWDGPKVWGLRLYRSTGIDPVTRFSLTRQVLNIG

PRVPIGPNPVITDQLPPSRPVQIMLPRPPQPPPPGAASTVPETAPPSQQP

GTGDRLLNLVKGAYQALNLTSPDKTQECWLCLVSGPPYYEGVAVLGTYSN

HTSAPANCSVASQHKLTLSEVTGQGLCIGAVPKTHQALCNTTQKTSDGSY

YLAAPTGTTWACSTGLTPCISTTILDLTTDYCVLVELWPRVTYHSPSYVY

HQFERRAKYKREPVSLTLALLLGGLTMGGIAAGVGTGTTALVATQQFQQF

QAAMQDDLKEVEKSITNLEKSLTSLSEVVLQNRRGLDLLFLKEGGLCAAL

KEECCFYADHTGLVRDSMAKLRERLSQRQKLFESQQGWFEGLFNKSPWFT

TLISTIMGPLIILLLILLFGPCILNRLVQFVKDRISVVQALVLTQQYHQL

KSIDPEEVESRE

SEQ ID NO: 80:—Envelope sequence derived from Feline B (suitable insert site is represented by the symbol "X"):

MEGPTHPKPSKDKTFSWDLMILVGVLLRLDVGMANPSPHQIYNVTWTITN

LVTGTKANATSMLGTLTDAFPTMYFDLCDIIGNTWNPSDQEPFPGYGCDQ

PMRRWQQRNTPFYVCPGHANRKQCGGPQDGFCAVWGCETTGETYWRPTSS

WDYITVKKGXLILQFTQKGRQTSWDGPKSWGLRLYRSGYDPIALFSVSRQ

VMTITLPQAMGPNLVLPDQKPPSRQSQIESRVTPHHSQGNGGTPGITLVN

ASIAPLSTPVTPASPKRIGTGNRLINLVQGTYLALNVTNPNKTKDCWLCL

VSRPPYYEGIAVLGNYSNQTNPPPSCLSDPQHKLTISEVSGQGSCIGTVP

KTHQALCKKTQKGHKGTHYLAAPSGTYWACNTGLTPCISMAVLNWTSDFC

VLIELWPRVTYHQPEYVYTHFDKTVRLRREPISLTVALMLGGLTVGGIAA

GVGTGTKALLETAQFGQLQMAMHTDIQALEESISALEKSLTSLSEVVLQN

RRGLDILFLQEGGLCAALKEECCFYADHTGLVRDNMAKLRERLKQRQQLF

DSQQGWFEGWFNKSPWFTTLISSIMGPLLILLLILLFGPCILNRLVQFVK

DRISVVQALILTQQYQQIKQYDPDQP

SEQ ID NO: 81: SL3-2/V3 loop chimeric envelope polypeptide, "L2 GI", (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCAAGGAATCTACCAGTGTACAAGACCCAACAACAA

TACAAGAAAAAGAATCCGTATCCAGAGAGGACCAGGGAGAGCATTTGTTA

CAATAGGAAAAATAGGAAATATGAGACAAGCACATTGTGGGCCCTGTTAT

GATTCCTCGGTGGTCTCCAGTAGCGCCCAGGGTGCCACACCGGGGGGTCG

ATGCAACCCCCTAGTCCTAGAATTCACTGACGCGGGTAAAAGGGCCAGCT

GGGACGCCTCCAAAGCATGGGGACTAAGACTGTACCGATCCACAGGGATC

GACCCGGTGACCCGGTTCTCTTTGACCCGCCAGGTCCTCAATATAGGGCC

CCGCGTCCCCATTGGGCCTAATCCCGTGATCATTGACCAGTTACCCCCCT

CCCGACCCGTGCAGGTCATGCTCCCCAGGCCTCCTCAGCCTCCTCCACCA

GGCGCAGCCTCTACAGTCCCTGAGACTGCCCCACCTTCCCAACAACCTGG

GACGGGAGACAGGCTGCTAAACCTGGTAAATGGAGCCTACCAAGCTCTCA

ACCTCACCAGTCCTGACAAAACCCAAGAGTGCTGGTTGTGTCTGGTAGCG

GGACCCCCCTACTACGAAGGGGTTGCCGTCCTAGGTACTTATTCCAACCA

TACCTCTGCCCCAGCTAACTGCTCCGTGGCCTCCCAACACAAGCTGACCC

TGTCCGAAGTGACCGGACAGGGACTCTGCGTAGGAGCAGTTCCCAAAACC

CATCAGGCCCTGTGTAATACCACCCAGAAGACGAGCAACGGGTCCTACTA

TCTGGCTGCTCCCGCCGGGACCATTTGGGCTTGCAACACCGGGCTCACTC

CCTGCCTATCTACCACTGTGCTCGACCTCACCACCGATTACTGTGTCCTG

GTTGAGCTCTGGCCAAAAGTGACCTACCACTCCCCTGGTTATGTTTATGG

CCAGTTTGAAGAAAAAACCAAATATAAAAGAGAACCCGTCTCACTAACTC

-continued

TGGCCCTACTATTAGGAGGACTCACTATGGGCGGAATTGCCGCCGGAGTG
GGAACAGGGACTACCGCCCTAGTGGCCACTCAGCAGTTCCAACAACTCCA
GGCTGCCATGCAGGATGACCTTAAAGAAGTTGAAAAGTCCATCACTAATC
TAGAAAGATCTTTGACCTCCTTGTCCGAAGTAGTGTTACAGAATCGTAGA
GGCCTAGATCTACTATTCCTAAAAGAGGGAGGTTTGTGTGCTGCCTTAAA
AGAAGAATGCTGTTTCTATGCCGACCACACAGGATTGGTACGGGATAGCA
TGGCCAAACTTAGAGAAAGATTGAGTCAGAGACAAAAACTCTTTGAATCC
CAACAAGGGTGGTTTGAAGGGCTGTTTAACAAGTCCCCTTGGTTCACCAC
CCTGATATCCACCATCATGGGTCCCCTGATAATCCTCTTGTTAATTTTAC
TCTTTGGGCCTTGTATTCTCAATCACCTGGTCCAGTTTATCAAAGACAGG
GTTTCGGTAGTGCAGGCCCTGGTCCTGACTCAACAATATCATCAACTTAA
GACAATAGAAGATTGTGAATCACGTGAATAA

SEQ ID NO: 82: SL3-2/V3 loop chimeric envelope polypeptide, "L3 GI", (shaded section represents the inserted section):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCCTAAAGGCCAGGGCCCCTGTACAAGACCCAACAA
CAATACAAGAAAAAGAATCCGTATCCAGAGAGGACCAGGGAGAGCATTTG
TTACAATAGGAAAAATAGGAAATATGAGACAAGCACATTGTAACCCCCTA
GTCCTAGAATTCACTGACGCGGGTAAAAGGGCCAGCTGGGACGCCTCCAA
AGCATGGGGACTAAGACTGTACCGATCCACAGGGATCGACCCGGTGACCC
GGTTCTCTTTGACCCGCCAGGTCCTCAATATAGGGCCCCGCGTCCCCATT
GGGCCTAATCCCGTGATCATTGACCAGTTACCCCCCTCCCGACCCGTGCA
GGTCATGCTCCCCAGGCCTCCTCAGCCTCCTCCACCAGGCGCAGCCTCTA
CAGTCCCTGAGACTGCCCCACCTTCCCAACAACCTGGGACGGGAGACAGG
CTGCTAAACCTGGTAAATGGAGCCTACCAAGCTCTCAACCTCACCAGTCC
TGACAAAACCCAAGAGTGCTGGTTGTGTCTGGTAGCGGGACCCCCCTACT
ACGAAGGGGTTGCCGTCCTAGGTACTTATTCCAACCATACCTCTGCCCCA
GCTAACTGCTCCGTGGCCTCCCAACACAAGCTGACCCTGTCCGAAGTGAC
CGGACAGGGACTCTGCGTAGGAGCAGTTCCCAAAACCCATCAGGCCCTGT
GTAATACCACCCAGAAGACGAGCAACGGGTCCTACTATCTGGCTGCTCCC
GCCGGGACCATTTGGGCTTGCAACACCGGGCTCACTCCCTGCCTATCTAC

-continued

CACTGTGCTCGACCTCACCACCGATTACTGTGTCCTGGTTGAGCTCTGGC
CAAAAGTGACCTACCACTCCCCTGGTTATGTTTATGGCCAGTTTGAAGAA
AAAACCAAATATAAAAGAGAACCCGTCTCACTAACTCTGGCCCTACTATT
AGGAGGACTCACTATGGGCGGAATTGCCGCCGGAGTGGGAACAGGGACTA
CCGCCCTAGTGGCCACTCAGCAGTTCCAACAACTCCAGGCTGCCATGCAG
GATGACCTTAAAGAAGTTGAAAAGTCCATCACTAATCTAGAAAGATCTTT
GACCTCCTTGTCCGAAGTAGTGTTACAGAATCGTAGAGGCCTAGATCTAC
TATTCCTAAAAGAGGGAGGTTTGTGTGCTGCCTTAAAAGAAGAATGCTGT
TTCTATGCCGACCACACAGGATTGGTACGGGATAGCATGGCCAAACTTAG
AGAAAGATTGAGTCAGAGACAAAAACTCTTTGAATCCCAACAAGGGTGGT
TTGAAGGGCTGTTTAACAAGTCCCCTTGGTTCACCACCCTGATATCCACC
ATCATGGGTCCCCTGATAATCCTCTTGTTAATTTTACTCTTTGGGCCTTG
TATTCTCAATCACCTGGTCCAGTTTATCAAAGACAGGGTTTCGGTAGTGC
AGGCCCTGGTCCTGACTCAACAATATCATCAACTTAAGACAATAGAAGAT
TGTGAATCACGTGAATAA

SEQ ID NO: 83: SL3-2/V3 loop chimeric envelope polypeptide, "L1 GI", (shaded section represents the inserted section):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGTACAAGACCCAACAACA
ATACAAGAAAAAGAATCCGTATCCAGAGAGGACCAGGGAGAGCATTTGTT
ACAATAGGAAAAATAGGAAATATGAGACAAGCACATTGTCGCACTCCCGG
GGGAAGAAAAAGGGCAAGAATATTTGACTTCTATGTTTGCCCCGGTCACA
CTGTGCTAGCAGGGTGTGGAGGGCCGAGAGAGGGCTACTGTGGCAAATGG
GGATGTGAGACCACTGGACAGGCATACTGGAAGCCATCATCATCATGGGA
CCTAATTTCCCTTAAGCGAGGAAACACTCCTAAAGGCCAGGGCCCCTGTT
ATGATTCCTCGGTGGTCTCCAGTAGCGCCCAGGGTGCCACACCGGGGGGT
CGATGCAACCCCCTAGTCCTAGAATTCACTGACGCGGGTAAAAGGGCCAG
CTGGGACGCCTCCAAAGCATGGGGACTAAGACTGTACCGATCCACAGGGA
TCGACCCGGTGACCCGGTTCTCTTTGACCCGCCAGGTCCTCAATATAGGG
CCCCGCGTCCCCATTGGGCCTAATCCCGTGATCATTGACCAGTTACCCCC
CTCCCGACCCGTGCAGGTCATGCTCCCCAGGCCTCCTCAGCCTCCTCCAC
CAGGCGCAGCCTCTACAGTCCCTGAGACTGCCCCACCTTCCCAACAACCT
GGGACGGGAGACAGGCTGCTAAACCTGGTAAATGGAGCCTACCAAGCTCT
CAACCTCACCAGTCCTGACAAAACCCAAGAGTGCTGGTTGTGTCTGGTAG
CGGGACCCCCCTACTACGAAGGGGTTGCCGTCCTAGGTACTTATTCCAAC
CATACCTCTGCCCCAGCTAACTGCTCCGTGGCCTCCCAACACAAGCTGAC
CCTGTCCGAAGTGACCGGACAGGGACTCTGCGTAGGAGCAGTTCCCAAAA

-continued

CCCATCAGGCCCTGTGTAATACCACCCAGAAGACGAGCAACGGGTCCTAC
TATCTGGCTGCTCCCGCCGGGACCATTTGGGCTTGCAACACCGGGCTCAC
TCCCTGCCTATCTACCACTGTGCTCGACCTCACCACCGATTACTGTGTCC
TGGTTGAGCTCTGGCCAAAAGTGACCTACCACTCCCCTGGTTATGTTTAT
GGCCAGTTTGAAGAAAAAACCAAATATAAAAGAGAACCCGTCTCACTAAC
TCTGGCCCTACTATTAGGAGGACTCACTATGGGCGGAATTGCCGCCGGAG
TGGGAACAGGGACTACCGCCCTAGTGGCCACTCAGCAGTTCCAACAACTC
CAGGCTGCCATGCAGGATGACCTTAAAGAAGTTGAAAAGTCCATCACTAA
TCTAGAAAGATCTTTGACCTCCTTGTCCGAAGTAGTGTTACAGAATCGTA
GAGGCCTAGATCTACTATTCCTAAAAGAGGGAGGTTTGTGTGCTGCCTTA
AAAGAAGAATGCTGTTTCTATGCCGACCACACAGGATTGGTACGGGATAG
CATGGCCAAACTTAGAGAAAGATTGAGTCAGAGACAAAAACTCTTTGAAT
CCCAACAAGGGTGGTTTGAAGGGCTGTTTAACAAGTCCCCTTGGTTCACC
ACCCTGATATCCACCATCATGGGTCCCCTGATAATCCTCTTGTTAATTTT
ACTCTTTGGGCCTTGTATTCTCAATCACCTGGTCCAGTTTATCAAAGACA
GGGTTTCGGTAGTGCAGGCCCTGGTCCTGACTCAACAATATCATCAACTT
AAGACAATAGAAGATTGTGAATCACGTGAATAA

SEQ ID NO: 84: SL3-2/V3 loop chimeric envelope polypeptide, “L2-GI”, (shaded section represents the inserted section):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQCTRPNNNTRKRIRIQRGPGRAFVTIGKIGNMRQAHCGPCY
DSSVVSSSAQGATPGGRCNPLVLEFTDAGKRASWDASKAWGLRLYRSTGI
DPVTRFSLTRQVLNIGPRVPIGPNPVIIDQLPPSRPVQVMLPRPPQPPPP
GAASTVPETAPPSQQPGTGDRLLNLVNGAYQALNLTSPDKTQECWLCLVA
GPPYYEGVAVLGTYSNHTSAPANCSVASQHKLTLSEVTGQGLCVGAVPKT
HQALCNTTQKTSNGSYYLAAPAGTIWACNTGLTPCLSTTVLDLTTDYCVL
VELWPKVTYHSPGYVYGQFEEKTKYKREPVSLTLALLLGGLTMGGIAAGV
GTGTTALVATQQFQQLQAAMQDDLKEVEKSITNLERSLTSLSEVVLQNRR
GLDLLFLKEGGLCAALKEECCFYADHTGLVRDSMAKLRERLSQRQKLFES
QQGWFEGLFNKSPWFTTLISTIMGPLIILLLILLFGPCILNHLVQFIKDR
VSVVQALVLTQQYHQLKTIEDCESRE

SEQ ID NO: 85: SL3-2/V3 loop chimeric envelope polypeptide, “L3-GI”, (shaded section represents the inserted section):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL

-continued

KRGNTPKGQGPCTRPNNNTRKRIRIQRGPGRAFVTIGKIGNMRQAHCNPL
VLEFTDAGKRASWDASKAWGLRLYRSTGIDPVTRFSLTRQVLNIGPRVPI
GPNPVIIDQLPPSRPVQVMLPRPPQPPPPGAASTVPETAPPSQQPGTGDR
LLNLVNGAYQALNLTSPDKTQECWLCLVAGPPYYEGVAVLGTYSNHTSAP
ANCSVASQHKLTLSEVTGQGLCVGAVPKTHQALCNTTQKTSNGSYYLAAP
AGTIWACNTGLTPCLSTTVLDLTTDYCVLVELWPKVTYHSPGYVYGQFEE
KTKYKREPVSLTLALLLGGLTMGGIAAGVGTGTTALVATQQFQQLQAAMQ
DDLKEVEKSITNLERSLTSLSEVVLQNRRGLDLLFLKEGGLCAALKEECC
FYADHTGLVRDSMAKLRERLSQRQKLFESQQGWFEGLFNKSPWFTTLIST
IMGPLIILLLILLFGPCILNHLVQFIKDRVSVVQALVLTQQYHQLKTIED
CESRE

SEQ ID NO: 86: SL3-2/V3 loop chimeric envelope polypeptide, “L1-RT”, (shaded section represents the inserted section):

MEGPAFSKPLKDKINPWGPLIVLGILMRARVSVQHDSPHQVFNVTWRVTN
LMTGQTANATSLLGTMTDAFPKLYFDLCTRPNNNTRKRIRIQRGPGRAFV
TIGKIGNMRQAHCRTPGGRKRARIFDFYVCPGHTVLAGCGGPREGYCGKW
GCETTGQAYWKPSSSWDLISLKRGNTPKGQGPCYDSSVVSSSAQGATPGG
RCNPLVLEFTDAGKRASWDASKAWGLRLYRSTRTDPVTRFSLTRQVLNIG
PRVPIGPNPVIIDQLPPSRPVQVMLPRPPQPPPPGAASTVPETAPPSQQP
GTGDRLLNLVNGAYQALNLTSPDKTQECWLCLVAGPPYYEGVAVLGTYSN
HTSAPANCSVASQHKLTLSEVTGQGLCVGAVPKTHQALCNTTQKTSNGSY
YLAAPAGTIWACNTGLTPCLSTTVLDLTTDYCVLVELWPKVTYHSPGYVY
GQFEEKTKYKREPVSLTLALLLGGLTMGGIAAGVGTGTTALVATQQFQQL
QAAMQDDLKEVEKSITNLERSLTSLSEVVLQNRRGLDLLFLKEGGLCAAL
KEECCFYADHTGLVRDSMAKLRERLSQRQKLFESQQGWFEGLFNKSPWFT
TLISTIMGPLIILLLILLFGPCILNHLVQFIKDRVSVVQALVLTQQYHQL
KTIEDCESRE

SEQ ID NO: 87:—(suitable insert site is represented by the symbol “X”):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATXGGACTCGGGTGTCGCACTCCCGGGGGAAGAAAAAGGGCAAG
AATATTTGACTTCTATGTTTGCCCCGGTCACACTGTGCTAGCAGGGTGTG
GAGGGCCGAGAGAGGGCTACTGTGGCAAATGGGGATGTGAGACCACTGGA
CAGGCATACTGGAAGCCATCATCATCATGGGACCTAATTTCCCTTAAGCG
AGGAAACACTCCTAAAGGCCAGGGCCCCTGTTATGATTCCTCGGTGGTCT

-continued

CCAGTAGCGCCCAGGGTGCCACACCGGGGGGTCGATGCAACCCCCTAGTC
CTAGAATTCACTGACGCGGGTAAAAGGGCCAGCTGGGACGCCTCCAAAGC
ATGGGGACTAAGACTGTACCGATCCACAAGGACCGACCCGGTGACCCGGT
TCTCTTTGACCCGCCAGGTCCTCAATATAGGGCCCCGCGTCCCCATTGGG
CCTAATCCCGTGATCATTGACCAGTTACCCCCCTCCCGACCCGTGCAGGT
CATGCTCCCCAGGCCTCCTCAGCCTCCTCCACCAGGCGCAGCCTCTACAG
TCCCTGAGACTGCCCCACCTTCCCAACAACCTGGGACGGGAGACAGGCTG
CTAAACCTGGTAAATGGAGCCTACCAAGCTCTCAACCTCACCAGTCCTGA
CAAAACCCAAGAGTGCTGGTTGTGTCTGGTAGCGGGACCCCCCTACTACG
AAGGGGTTGCCGTCCTAGGTACTTATTCCAACCATACCTCTGCCCCAGCT
AACTGCTCCGTGGCCTCCCAACACAAGCTGACCCTGTCCGAAGTGACCGG
ACAGGGACTCTGCGTAGGAGCAGTTCCCAAAACCCATCAGGCCCTGTGTA
ATACCACCCAGAAGACGAGCAACGGGTCCTACTATCTGGCTGCTCCCGCC
GGGACCATTTGGGCTTGCAACACCGGGCTCACTCCCTGCCTATCTACCAC
TGTGCTCGACCTCACCACCGATTACTGTGTCCTGGTTGAGCTCTGGCCAA
AAGTGACCTACCACTCCCCTGGTTATGTTTATGGCCAGTTTGAAGAAAAA
ACCAAATATAAAAGAGAACCCGTCTCACTAACTCTGGCCCTACTATTAGG
AGGACTCACTATGGGCGGAATTGCCGCCGGAGTGGGAACAGGGACTACCG
CCCTAGTGGCCACTCAGCAGTTCCAACAACTCCAGGCTGCCATGCAGGAT
GACCTTAAAGAAGTTGAAAAGTCCATCACTAATCTAGAAAGATCTTTGAC
CTCCTTGTCCGAAGTAGTGTTACAGAATCGTAGAGGCCTAGATCTACTAT
TCCTAAAAGAGGGAGGTTTGTGTGCTGCCTTAAAAGAAGAATGCTGTTTC
TATGCCGACCACACAGGATTGGTACGGGATAGCATGGCCAAACTTAGAGA
AAGATTGAGTCAGAGACAAAAACTCTTTGAATCCCAACAAGGGTGGTTTG
AAGGGCTGTTTAACAAGTCCCCTTGGTTCACCACCCTGATATCCACCATC
ATGGGTCCCCTGATAATCCTCTTGTTAATTTTACTCTTTGGGCCTTGTAT
TCTCAATCACCTGGTCCAGTTTATCAAAGACAGGGTTTCGGTAGTGCAGG
CCCTGGTCCTGACTCAACAATATCATCAACTTAAGACAATAGAAGATTGT
GAATCACGTGAATAA

SEQ ID NO: 88:—(suitable insert site is represented by the symbol “X”):

MEGPAFSKPLKDKINPWGPLIVLGILMRARVSVQHDSPHQVFNVTWRVTN
LMTGQTANATSLLGTMTDAFPKLYFDLCDLIGDDWDXGLGCRTPGGRKRA
RIFDFYVCPGHTVLAGCGGPREGYCGKWGCETTGQAYWKPSSSWDLISLK
RGNTPKGQGPCYDSSVVSSSAQGATPGGRCNPLVLEFTDAGKRASWDASK
AWGLRLYRSTRTDPVTRFSLTRQVLNIGPRVPIGPNPVIIDQLPPSRPVQ
VMLPRPPQPPPPGAASTVPETAPPSQQPGTGDRLLNLVNGAYQALNLTSP
DKTQECWLCLVAGPPYYEGVAVLGTYSNHTSAPANCSVASQHKLTLSEVT
GQGLCVGAVPKTHQALCNTTQKTSNGSYYLAAPAGTIWACNTGLTPCLST
TVLDLTTDYCVLVELWPKVTYHSPGYVYGQFEEKTKYKREPVSLTLALLL

-continued

GGLTMGGIAAGVGTGTTALVATQQFQQLQAAMQDDLKEVEKSITNLERSL
TSLSEVVLQNRRGLDLLFLKEGGLCAALKEECCFYADHTGLVRDSMAKLR
ERLSQRQKLFESQQGWFEGLFNKSPWFTTLISTIMGPLIILLLILLFGPC
ILNHLVQFIKDRVSVVQALVLTQQYHQLKTIEDCESRE

SEQ ID NO: 89:—(suitable insert site is represented by the symbol “X”):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATXGGACTCGGGTGTCGCACTCCCGGGGGAAGAAAAAGGGCAAG
AATATTTGACTTCTATGTTTGCCCCGGTCACACTGTGCTAGCAGGGTGTG
GAGGGCCGAGAGAGGGCTACTGTGGCAAATGGGGATGTGAGACCACTGGA
CAGGCATACTGGAAGCCATCATCATCATGGGACCTAATTTCCCTTAAGCG
AGGAAACACTCCTAAAGGCCAGGGCCCCTGTTATGATTCCTCGGTGGTCT
CCAGTAGCGCCCAGGGTGCCACACCGGGGGGTCGATGCAACCCCCTAGTC
CTAGAATTCACTGACGCGGGTAAAAGGGCCAGCTGGGACGCCTCCAAAGC
ATGGGGACTAAGACTGTACCGATCCACAGGGATCGACCCGGTGACCCGGT
TCTCTTTGACCCGCCAGGTCCTCAATATAGGGCCCCGCGTCCCCATTGGG
CCTAATCCCGTGATCATTGACCAGTTACCCCCCTCCCGACCCGTGCAGGT
CATGCTCCCCAGGCCTCCTCAGCCTCCTCCACCAGGCGCAGCCTCTACAG
TCCCTGAGACTGCCCCACCTTCCCAACAACCTGGGACGGGAGACAGGCTG
CTAAACCTGGTAAATGGAGCCTACCAAGCTCTCAACCTCACCAGTCCTGA
CAAAACCCAAGAGTGCTGGTTGTGTCTGGTAGCGGGACCCCCCTACTACG
AAGGGGTTGCCGTCCTAGGTACTTATTCCAACCATACCTCTGCCCCAGCT
AACTGCTCCGTGGCCTCCCAACACAAGCTGACCCTGTCCGAAGTGACCGG
ACAGGGACTCTGCGTAGGAGCAGTTCCCAAAACCCATCAGGCCCTGTGTA
ATACCACCCAGAAGACGAGCAACGGGTCCTACTATCTGGCTGCTCCCGCC
GGGACCATTTGGGCTTGCAACACCGGGCTCACTCCCTGCCTATCTACCAC
TGTGCTCGACCTCACCACCGATTACTGTGTCCTGGTTGAGCTCTGGCCAA
AAGTGACCTACCACTCCCCTGGTTATGTTTATGGCCAGTTTGAAGAAAAA
ACCAAATATAAAAGAGAACCCGTCTCACTAACTCTGGCCCTACTATTAGG
AGGACTCACTATGGGCGGAATTGCCGCCGGAGTGGGAACAGGGACTACCG
CCCTAGTGGCCACTCAGCAGTTCCAACAACTCCAGGCTGCCATGCAGGAT
GACCTTAAAGAAGTTGAAAAGTCCATCACTAATCTAGAAAGATCTTTGAC
CTCCTTGTCCGAAGTAGTGTTACAGAATCGTAGAGGCCTAGATCTACTAT
TCCTAAAAGAGGGAGGTTTGTGTGCTGCCTTAAAAGAAGAATGCTGTTTC
TATGCCGACCACACAGGATTGGTACGGGATAGCATGGCCAAACTTAGAGA
AAGATTGAGTCAGAGACAAAAACTCTTTGAATCCCAACAAGGGTGGTTTG

-continued

AAGGGCTGTTTAACAAGTCCCCTTGGTTCACCACCCTGATATCCACCATC
ATGGGTCCCCTGATAATCCTCTTGTTAATTTTACTCTTTGGGCCTTGTAT
TCTCAATCACCTGGTCCAGTTTATCAAAGACAGGGTTTCGGTAGTGCAGG
CCCTGGTCCTGACTCAACAATATCATCAACTTAAGACAATAGAAGATTGT
GAATCACGTGAATAA

SEQ ID NO: 90:—(suitable insert site is represented by the symbol "X"):

MEGPAFSKPLKDKINPWGPLIVLGILMRARVSVQHDSPHQVFNVTWRVTN
LMTGQTANATSLLGTMTDAFPKLYFDLCDLIGDDWDXGLGCRTPGGRKRA
RIFDFYVCPGHTVLAGCGGPREGYCGKWGCETTGQAYWKPSSSWDLISLK
RGNTPKGQGPCYDSSVVSSSAQGATPGGRCNPLVLEFTDAGKRASWDASK
AWGLRLYRSTGIDPVTRFSLTRQVLNIGPRVPIGPNPVIIDQLPPSRPVQ
VMLPRPPQPPPPGAASTVPETAPPSQQPGTGDRLLNLVNGAYQALNLTSP
DKTQECWLCLVAGPPYYEGVAVLGTYSNHTSAPANCSVASQHKLTLSEVT
GQGLCVGAVPKTHQALCNTTQKTSNGSYYLAAPAGTIWACNTGLTPCLST
TVLDLTTDYCVLVELWPKVTYHSPGYVYGQFEEKTKYKREPVSLTLALLL
GGLTMGGIAAGVGTGTTALVATQQFQQLQAAMQDDLKEVEKSITNLERSL
TSLSEVVLQNRRGLDLLFLKEGGLCAALKEECCFYADHTGLVRDSMAKLR
ERLSQRQKLFESQQGWFEGLFNKSPWFTTLISTIMGPLIILLLILLFGPC
ILNHLVQFIKDRVSVVQALVLTQQYHQLKTIEDCESRE

SEQ ID NO: 91:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCAAGGAATCTACCAGTGCXTGTGGGCCCTGTTATG
ATTCCTCGGTGGTCTCCAGTAGCGCCCAGGGTGCCACACCGGGGGGTCGA
TGCAACCCCCTAGTCCTAGAATTCACTGACGCGGGTAAAAGGGCCAGCTG
GGACGCCTCCAAAGCATGGGGACTAAGACTGTACCGATCCACAAGGACCG
ACCCGGTGACCCGGTTCTCTTTGACCCGCCAGGTCCTCAATATAGGGCCC
CGCGTCCCCATTGGGCCTAATCCCGTGATCATTGACCAGTTACCCCCCTC
CCGACCCGTGCAGGTCATGCTCCCCAGGCCTCCTCAGCCTCCTCCACCAG
GCGCAGCCTCTACAGTCCCTGAGACTGCCCCACCTTCCCAACAACCTGGG
ACGGGAGACAGGCTGCTAAACCTGGTAAATGGAGCCTACCAAGCTCTCAA

-continued

CCTCACCAGTCCTGACAAAACCCAAGAGTGCTGGTTGTGTCTGGTAGCGG
GACCCCCCTACTACGAAGGGGTTGCCGTCCTAGGTACTTATTCCAACCAT
ACCTCTGCCCCAGCTAACTGCTCCGTGGCCTCCCAACACAAGCTGACCCT
GTCCGAAGTGACCGGACAGGGACTCTGCGTAGGAGCAGTTCCCAAAACCC
ATCAGGCCCTGTGTAATACCACCCAGAAGACGAGCAACGGGTCCTACTAT
CTGGCTGCTCCCGCCGGGACCATTTGGGCTTGCAACACCGGGCTCACTCC
CTGCCTATCTACCACTGTGCTCGACCTCACCACCGATTACTGTGTCCTGG
TTGAGCTCTGGCCAAAAGTGACCTACCACTCCCCTGGTTATGTTTATGGC
CAGTTTGAAGAAAAAACCAAATATAAAAGAGAACCCGTCTCACTAACTCT
GGCCCTACTATTAGGAGGACTCACTATGGGCGGAATTGCCGCCGGAGTGG
GAACAGGGACTACCGCCCTAGTGGCCACTCAGCAGTTCCAACAACTCCAG
GCTGCCATGCAGGATGACCTTAAAGAAGTTGAAAAGTCCATCACTAATCT
AGAAAGATCTTTGACCTCCTTGTCCGAAGTAGTGTTACAGAATCGTAGAG
GCCTAGATCTACTATTCCTAAAAGAGGGAGGTTTGTGTGCTGCCTTAAAA
GAAGAATGCTGTTTCTATGCCGACCACACAGGATTGGTACGGGATAGCAT
GGCCAAACTTAGAGAAAGATTGAGTCAGAGACAAAAACTCTTTGAATCCC
AACAAGGGTGGTTTGAAGGGCTGTTTAACAAGTCCCCTTGGTTCACCACC
CTGATATCCACCATCATGGGTCCCCTGATAATCCTCTTGTTAATTTTACT
CTTTGGGCCTTGTATTCTCAATCACCTGGTCCAGTTTATCAAAGACAGGG
TTTCGGTAGTGCAGGCCCTGGTCCTGACTCAACAATATCATCAACTTAAG
ACAATAGAAGATTGTGAATCACGTGAATAA

SEQ ID NO: 92:—(suitable insert site is represented by the symbol "X"):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQCXCGPCYDSSVVSSSAQGATPGGRCNPLVLEFTDAGKRAS
WDASKAWGLRLYRSTRTDPVTRFSLTRQVLNIGPRVPIGPNPVIIDQLPP
SRPVQVMLPRPPQPPPPGAASTVPETAPPSQQPGTGDRLLNLVNGAYQAL
NLTSPDKTQECWLCLVAGPPYYEGVAVLGTYSNHTSAPANCSVASQHKLT
LSEVTGQGLCVGAVPKTHQALCNTTQKTSNGSYYLAAPAGTIWACNTGLT
PCLSTTVLDLTTDYCVLVELWPKVTYHSPGYVYGQFEEKTKYKREPVSLT
LALLLGGLTMGGIAAGVGTGTTALVATQQFQQLQAAMQDDLKEVEKSITN
LERSLTSLSEVVLQNRRGLDLLFLKEGGLCAALKEECCFYADHTGLVRDS
MAKLRERLSQRQKLFESQQGWFEGLFNKSPWFTTLISTIMGPLIILLLIL
LFGPCILNHLVQFIKDRVSVVQALVLTQQYHQLKTIEDCESRE

SEQ ID NO: 93:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC

-continued

AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCAAGGAATCTACCAGTGCXTGTGGGCCCTGTTATG
ATTCCTCGGTGGTCTCCAGTAGCGCCCAGGGTGCCACACCGGGGGGTCGA
TGCAACCCCCTAGTCCTAGAATTCACTGACGCGGGTAAAAGGGCCAGCTG
GGACGCCTCCAAAGCATGGGGACTAAGACTGTACCGATCCACAGGGATCG
ACCCGGTGACCCGGTTCTCTTTGACCCGCCAGGTCCTCAATATAGGGCCC
CGCGTCCCCATTGGGCCTAATCCCGTGATCATTGACCAGTTACCCCCCTC
CCGACCCGTGCAGGTCATGCTCCCCAGGCCTCCTCAGCCTCCTCCACCAG
GCGCAGCCTCTACAGTCCCTGAGACTGCCCCACCTTCCCAACAACCTGGG
ACGGGAGACAGGCTGCTAAACCTGGTAAATGGAGCCTACCAAGCTCTCAA
CCTCACCAGTCCTGACAAAACCCAAGAGTGCTGGTTGTGTCTGGTAGCGG
GACCCCCCTACTACGAAGGGGTTGCCGTCCTAGGTACTTATTCCAACCAT
ACCTCTGCCCCAGCTAACTGCTCCGTGGCCTCCCAACACAAGCTGACCCT
GTCCGAAGTGACCGGACAGGGACTCTGCGTAGGAGCAGTTCCCAAAACCC
ATCAGGCCCTGTGTAATACCACCCAGAAGACGAGCAACGGGTCCTACTAT
CTGGCTGCTCCCGCCGGGACCATTTGGGCTTGCAACACCGGGCTCACTCC
CTGCCTATCTACCACTGTGCTCGACCTCACCACCGATTACTGTGTCCTGG
TTGAGCTCTGGCCAAAAGTGACCTACCACTCCCCTGGTTATGTTTATGGC
CAGTTTGAAGAAAAAACCAAATATAAAAGAGAACCCGTCTCACTAACTCT
GGCCCTACTATTAGGAGGACTCACTATGGGCGGAATTGCCGCCGGAGTGG
GAACAGGGACTACCGCCCTAGTGGCCACTCAGCAGTTCCAACAACTCCAG
GCTGCCATGCAGGATGACCTTAAAGAAGTTGAAAAGTCCATCACTAATCT
AGAAAGATCTTTGACCTCCTTGTCCGAAGTAGTGTTACAGAATCGTAGAG
GCCTAGATCTACTATTCCTAAAAGAGGGAGGTTTGTGTGCTGCCTTAAAA
GAAGAATGCTGTTTCTATGCCGACCACACAGGATTGGTACGGGATAGCAT
GGCCAAACTTAGAGAAAGATTGAGTCAGAGACAAAAACTCTTTGAATCCC
AACAAGGGTGGTTTGAAGGGCTGTTTAACAAGTCCCCTTGGTTCACCACC
CTGATATCCACCATCATGGGTCCCCTGATAATCCTCTTGTTAATTTTACT
CTTTGGGCCTTGTATTCTCAATCACCTGGTCCAGTTTATCAAAGACAGGG
TTTCGGTAGTGCAGGCCCTGGTCCTGACTCAACAATATCATCAACTTAAG
ACAATAGAAGATTGTGAATCACGTGAATAA

SEQ ID NO: 94:—(suitable insert site is represented by the symbol "X"):

MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTQGIYQCXCGPCYDSSVVSSSAQGATPGGRCNPLVLEFTDAGKRAS
WDASKAWGLRLYRSTGIDPVTRFSLTRQVLNIGPRVPIGPNPVIIDQLPP
SRPVQVMLPRPPQPPPPGAASTVPETAPPSQQPGTGDRLLNLVNGAYQAL
NLTSPDKTQECWLCLVAGPPYYEGVAVLGTYSNHTSAPANCSVASQHKLT
LSEVTGQGLCVGAVPKTHQALCNTTQKTSNGSYYLAAPAGTIWACNTGLT
PCLSTTVLDLTTDYCVLVELWPKVTYHSPGYVYGQFEEKTKYKREPVSLT
LALLLGGLTMGGIAAGVGTGTTALVATQQFQQLQAAMQDDLKEVEKSITN
LERSLTSLSEVVLQNRRGLDLLFLKEGGLCAALKEECCFYADHTGLVRDS
MAKLRERLSQRQKLFESQQGWFEGLFNKSPWFTTLISTIMGPLIILLLIL
LFGPCILNHLVQFIKDRVSVVQALVLTQQYHQLKTIEDCESRE

SEQ ID NO: 95:—(suitable insert site is represented by the symbol "X"):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCCTAAAGGCCAGGGCCCCTGTTATGATTCCXTCCA
GTAGCGCCCAGGGTGCCACACCGGGGGGTCGATGCAACCCCCTAGTCCTA
GAATTCACTGACGCGGGTAAAAGGGCCAGCTGGGACGCCTCCAAAGCATG
GGGACTAAGACTGTACCGATCCACAAGGACCGACCCGGTGACCCGGTTCT
CTTTGACCCGCCAGGTCCTCAATATAGGGCCCCGCGTCCCCATTGGGCCT
AATCCCGTGATCATTGACCAGTTACCCCCCTCCCGACCCGTGCAGGTCAT
GCTCCCCAGGCCTCCTCAGCCTCCTCCACCAGGCGCAGCCTCTACAGTCC
CTGAGACTGCCCCACCTTCCCAACAACCTGGGACGGGAGACAGGCTGCTA
AACCTGGTAAATGGAGCCTACCAAGCTCTCAACCTCACCAGTCCTGACAA
AACCCAAGAGTGCTGGTTGTGTCTGGTAGCGGGACCCCCCTACTACGAAG
GGGTTGCCGTCCTAGGTACTTATTCCAACCATACCTCTGCCCCAGCTAAC
TGCTCCGTGGCCTCCCAACACAAGCTGACCCTGTCCGAAGTGACCGGACA
GGGACTCTGCGTAGGAGCAGTTCCCAAAACCCATCAGGCCCTGTGTAATA
CCACCCAGAAGACGAGCAACGGGTCCTACTATCTGGCTGCTCCCGCCGGG

-continued

ACCATTTGGGCTTGCAACACCGGGCTCACTCCCTGCCTATCTACCACTGT

GCTCGACCTCACCACCGATTACTGTGTCCTGGTTGAGCTCTGGCCAAAAG

TGACCTACCACTCCCCTGGTTATGTTTATGGCCAGTTTGAAGAAAAAACC

AAATATAAAAGAGAACCCGTCTCACTAACTCTGGCCCTACTATTAGGAGG

ACTCACTATGGGCGGAATTGCCGCCGGAGTGGGAACAGGGACTACCGCCC

TAGTGGCCACTCAGCAGTTCCAACAACTCCAGGCTGCCATGCAGGATGAC

CTTAAAGAAGTTGAAAAGTCCATCACTAATCTAGAAAGATCTTTGACCTC

CTTGTCCGAAGTAGTGTTACAGAATCGTAGAGGCCTAGATCTACTATTCC

TAAAAGAGGGAGGTTTGTGTGCTGCCTTAAAAGAAGAATGCTGTTTCTAT

GCCGACCACACAGGATTGGTACGGGATAGCATGGCCAAACTTAGAGAAAG

ATTGAGTCAGAGACAAAAACTCTTTGAATCCCAACAAGGGTGGTTTGAAG

GGCTGTTTAACAAGTCCCCTTGGTTCACCACCCTGATATCCACCATCATG

GGTCCCCTGATAATCCTCTTGTTAATTTTACTCTTTGGGCCTTGTATTCT

CAATCACCTGGTCCAGTTTATCAAAGACAGGGTTTCGGTAGTGCAGGCCC

TGGTCCTGACTCAACAATATCATCAACTTAAGACAATAGAAGATTGTGAA

TCACGTGAATAA

SEQ ID NO: 96:—(suitable insert site is represented by the symbol "X"):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDSXSSSAQGATPGGRCNPLVLEFTDAGKRASWDASKA

WGLRLYRSTRTDPVTRFSLTRQVLNIGPRVPIGPNPVIIDQLPPSRPVQV

MLPRPPQPPPPGAASTVPETAPPSQQPGTGDRLLNLVNGAYQALNLTSPD

KTQECWLCLVAGPPYYEGVAVLGTYSNHTSAPANCSVASQHKLTLSEVTG

QGLCVGAVPKTHQALCNTTQKTSNGSYYLAAPAGTIWACNTGLTPCLSTT

VLDLTTDYCVLVELWPKVTYHSPGYVYGQFEEKTKYKREPVSLTLALLLG

GLTMGGIAAGVGTGTTALVATQQFQQLQAAMQDDLKEVEKSITNLERSLT

SLSEVVLQNRRGLDLLFLKEGGLCAALKEECCFYADHTGLVRDSMAKLRE

RLSQRQKLFESQQGWFEGLFNKSPWFTTLISTIMGPLIILLLILLFGPCI

LNHLVQFIKDRVSVVQALVLTQQYHQLKTIEDCESRE

SEQ ID NO: 97:—(suitable insert site is represented by the symbol "X"):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

-continued

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCCTAAAGGCCAGGGCCCCTGTTATGATTCCXTCCA

GTAGCGCCCAGGGTGCCACACCGGGGGGTCGATGCAACCCCCTAGTCCTA

GAATTCACTGACGCGGGTAAAAGGGCCAGCTGGGACGCCTCCAAAGCATG

GGGACTAAGACTGTACCGATCCACAGGGATCGACCCGGTGACCCGGTTCT

CTTTGACCCGCCAGGTCCTCAATATAGGGCCCCGCGTCCCCATTGGGCCT

AATCCCGTGATCATTGACCAGTTACCCCCCTCCCGACCCGTGCAGGTCAT

GCTCCCCAGGCCTCCTCAGCCTCCTCCACCAGGCGCAGCCTCTACAGTCC

CTGAGACTGCCCCACCTTCCCAACAACCTGGGACGGGAGACAGGCTGCTA

AACCTGGTAAATGGAGCCTACCAAGCTCTCAACCTCACCAGTCCTGACAA

AACCCAAGAGTGCTGGTTGTGTCTGGTAGCGGGACCCCCCTACTACGAAG

GGGTTGCCGTCCTAGGTACTTATTCCAACCATACCTCTGCCCCAGCTAAC

TGCTCCGTGGCCTCCCAACACAAGCTGACCCTGTCCGAAGTGACCGGACA

GGGACTCTGCGTAGGAGCAGTTCCCAAAACCCATCAGGCCCTGTGTAATA

CCACCCAGAAGACGAGCAACGGGTCCTACTATCTGGCTGCTCCCGCCGGG

ACCATTTGGGCTTGCAACACCGGGCTCACTCCCTGCCTATCTACCACTGT

GCTCGACCTCACCACCGATTACTGTGTCCTGGTTGAGCTCTGGCCAAAAG

TGACCTACCACTCCCCTGGTTATGTTTATGGCCAGTTTGAAGAAAAAACC

AAATATAAAAGAGAACCCGTCTCACTAACTCTGGCCCTACTATTAGGAGG

ACTCACTATGGGCGGAATTGCCGCCGGAGTGGGAACAGGGACTACCGCCC

TAGTGGCCACTCAGCAGTTCCAACAACTCCAGGCTGCCATGCAGGATGAC

CTTAAAGAAGTTGAAAAGTCCATCACTAATCTAGAAAGATCTTTGACCTC

CTTGTCCGAAGTAGTGTTACAGAATCGTAGAGGCCTAGATCTACTATTCC

TAAAAGAGGGAGGTTTGTGTGCTGCCTTAAAAGAAGAATGCTGTTTCTAT

GCCGACCACACAGGATTGGTACGGGATAGCATGGCCAAACTTAGAGAAAG

ATTGAGTCAGAGACAAAAACTCTTTGAATCCCAACAAGGGTGGTTTGAAG

GGCTGTTTAACAAGTCCCCTTGGTTCACCACCCTGATATCCACCATCATG

GGTCCCCTGATAATCCTCTTGTTAATTTTACTCTTTGGGCCTTGTATTCT

CAATCACCTGGTCCAGTTTATCAAAGACAGGGTTTCGGTAGTGCAGGCCC

TGGTCCTGACTCAACAATATCATCAACTTAAGACAATAGAAGATTGTGAA

TCACGTGAATAA

SEQ ID NO: 98:—(suitable insert site is represented by the symbol "X"):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDSXSSSAQGATPGGRCNPLVLEFTDAGKRASWDASKA

WGLRLYRSTGIDPVTRFSLTRQVLNIGPRVPIGPNPVIIDQLPPSRPVQV

MLPRPPQPPPPGAASTVPETAPPSQQPGTGDRLLNLVNGAYQALNLTSPD

-continued

KTQECWLCLVAGPPYYEGVAVLGTYSNHTSAPANCSVASQHKLTLSEVTG

QGLCVGAVPKTHQALCNTTQKTSNGSYYLAAPAGTIWACNTGLTPCLSTT

VLDLTTDYCVLVELWPKVTYHSPGYVYGQFEEKTKYKREPVSLTLALLLG

GLTMGGIAAGVGTGTTALVATQQFQQLQAAMQDDLKEVEKSITNLERSLT

SLSEVVLQNRRGLDLLFLKEGGLCAALKEECCFYADHTGLVRDSMAKLRE

RLSQRQKLFESQQGWFEGLFNKSPWFTTLISTIMGPLIILLLILLFGPCI

LNHLVQFIKDRVSVVQALVLTQQYHQLKTIEDCESRE

SEQ ID NO: 99: SL3-2/apelin chimeric envelope polynucleotide, “Apelin@86 RT”, (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATTCCGGTGGCAGTGGACAGCGGCCCCGCCTCTCCCATAAGGGA

CCCATGCCTTTCAGCGGTGGATCTGGCGGACTCGGGTGTCGCACTCCCGG

GGGAAGAAAAAGGGCAAGAATATTTGACTTCTATGTTTGCCCCGGTCACA

CTGTGCTAGCAGGGTGTGGAGGGCCGAGAGAGGGCTACTGTGGCAAATGG

GGATGTGAGACCACTGGACAGGCATACTGGAAGCCATCATCATCATGGGA

CCTAATTTCCCTTAAGCGAGGAAACACTCCTAAAGGCCAGGGCCCCTGTT

ATGATTCCTCGGTGGTCTCCAGTAGCGCCCAGGGTGCCACACCGGGGGGT

CGATGCAACCCCCTAGTCCTAGAATTCACTGACGCGGGTAAAAGGGCCAG

CTGGGACGCCTCCAAAGCATGGGGACTAAGACTGTACCGATCCACAAGGA

CCGACCCGGTGACCCGGTTCTCTTTGACCCGCCAGGTCCTCAATATAGGG

CCCCGCGTCCCCATTGGGCCTAATCCCGTGATCATTGACCAGTTACCCCC

CTCCCGACCCGTGCAGGTCATGCTCCCCAGGCCTCCTCAGCCTCCTCCAC

CAGGCGCAGCCTCTACAGTCCCTGAGACTGCCCCACCTTCCCAACAACCT

GGGACGGGAGACAGGCTGCTAAACCTGGTAAATGGAGCCTACCAAGCTCT

CAACCTCACCAGTCCTGACAAAACCCAAGAGTGCTGGTTGTGTCTGGTAG

CGGGACCCCCCTACTACGAAGGGGTTGCCGTCCTAGGTACTTATTCCAAC

CATACCTCTGCCCCAGCTAACTGCTCCGTGGCCTCCCAACACAAGCTGAC

CCTGTCCGAAGTGACCGGACAGGGACTCTGCGTAGGAGCAGTTCCCAAAA

CCCATCAGGCCCTGTGTAATACCACCCAGAAGACGAGCAACGGGTCCTAC

TATCTGGCTGCTCCCGCCGGGACCATTTGGGCTTGCAACACCGGGCTCAC

TCCCTGCCTATCTACCACTGTGCTCGACCTCACCACCGATTACTGTGTCC

TGGTTGAGCTCTGGCCAAAAGTGACCTACCACTCCCCTGGTTATGTTTAT

GGCCAGTTTGAAGAAAAAACCAAATATAAAAGAGAACCCGTCTCACTAAC

TCTGGCCCTACTATTAGGAGGACTCACTATGGGCGGAATTGCCGCCGGAG

TGGGAACAGGGACTACCGCCCTAGTGGCCACTCAGCAGTTCCAACAACTC

-continued

CAGGCTGCCATGCAGGATGACCTTAAAGAAGTTGAAAAGTCCATCACTAA

TCTAGAAAGATCTTTGACCTCCTTGTCCGAAGTAGTGTTACAGAATCGTA

GAGGCCTAGATCTACTATTCCTAAAAGAGGGAGGTTTGTGTGCTGCCTTA

AAAGAAGAATGCTGTTTCTATGCCGACCACACAGGATTGGTACGGGATAG

CATGGCCAAACTTAGAGAAAGATTGAGTCAGAGACAAAAACTCTTTGAAT

CCCAACAAGGGTGGTTTGAAGGGCTGTTTAACAAGTCCCCTTGGTTCACC

ACCCTGATATCCACCATCATGGGTCCCCTGATAATCCTCTTGTTAATTTT

ACTCTTTGGGCCTTGTATTCTCAATCACCTGGTCCAGTTTATCAAAGACA

GGGTTTCGGTAGTGCAGGCCCTGGTCCTGACTCAACAATATCATCAACTT

AAGACAATAGAAGATTGTGAATCACGTGAATAA

SEQ ID NO: 100: SL3-2/apelin chimeric envelope polypeptide, “Apelin@86 RT”, (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDSGGSGQRPRLSHKG

PMPFSGGSGGLGCRTPGGRKRARIFDFYVCPGHTVLAGCGGPREGYCGKW

GCETTGQAYWKPSSSWDLISLKRGNTPKGQGPCYDSSVVSSSAQGATPGG

RCNPLVLEFTDAGKRASWDASKAWGLRLYRSTRTDPVTRFSLTRQVLNIG

PRVPIGPNPVIIDQLPPSRPVQVMLPRPPQPPPPGAASTVPETAPPSQQP

GTGDRLLNLVNGAYQALNLTSPDKTQECWLCLVAGPPYYEGVAVLGTYSN

HTSAPANCSVASQHKLTLSEVTGQGLCVGAVPKTHQALCNTTQKTSNGSY

YLAAPAGTIWACNTGLTPCLSTTVLDLTTDYCVLVELWPKVTYHSPGYVY

GQFEEKTKYKREPVSLTLALLLGGLTMGGIAAGVGTGTTALVATQQFQQL

QAAMQDDLKEVEKSITNLERSLTSLSEVVLQNRRGLDLLFLKEGGLCAAL

KEECCFYADHTGLVRDSMAKLRERLSQRQKLFESQQGWFEGLFNKSPWFT

TLISTIMGPLIILLLILLFGPCILNHLVQFIKDRVSVVQALVLTQQYHQL

KTIEDCESRE

SEQ ID NO: 101: SL3-2/apelin chimeric envelope polynucleotide, “Apelin@86 GI”, (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATTCCGGTGGCAGTGGACAGCGGCCCCGCCTCTCCCATAAGGGA

CCCATGCCTTTCAGCGGTGGATCTGGCGGACTCGGGTGTCGCACTCCCGG

GGGAAGAAAAAGGGCAAGAATATTTGACTTCTATGTTTGCCCCGGTCACA

CTGTGCTAGCAGGGTGTGGAGGGCCGAGAGAGGGCTACTGTGGCAAATGG

GGATGTGAGACCACTGGACAGGCATACTGGAAGCCATCATCATCATGGGA

CCTAATTTCCCTTAAGCGAGGAAACACTCCTAAAGGCCAGGGCCCCTGTT

-continued

ATGATTCCTCGGTGGTCTCCAGTAGCGCCCAGGGTGCCACACCGGGGGGT
CGATGCAACCCCCTAGTCCTAGAATTCACTGACGCGGGTAAAAGGGCCAG
CTGGGACGCCTCCAAAGCATGGGGACTAAGACTGTACCGATCCACAGGGA
TCGACCCGGTGACCCGGTTCTCTTTGACCCGCCAGGTCCTCAATATAGGG
CCCCGCGTCCCCATTGGGCCTAATCCCGTGATCATTGACCAGTTACCCCC
CTCCCGACCCGTGCAGGTCATGCTCCCCAGGCCTCCTCAGCCTCCTCCAC
CAGGCGCAGCCTCTACAGTCCCTGAGACTGCCCCACCTTCCCAACAACCT
GGGACGGGAGACAGGCTGCTAAACCTGGTAAATGGAGCCTACCAAGCTCT
CAACCTCACCAGTCCTGACAAAACCCAAGAGTGCTGGTTGTGTCTGGTAG
CGGGACCCCCCTACTACGAAGGGGTTGCCGTCCTAGGTACTTATTCCAAC
CATACCTCTGCCCCAGCTAACTGCTCCGTGGCCTCCCAACACAAGCTGAC
CCTGTCCGAAGTGACCGGACAGGGACTCTGCGTAGGAGCAGTTCCCAAAA
CCCATCAGGCCCTGTGTAATACCACCCAGAAGACGAGCAACGGGTCCTAC
TATCTGGCTGCTCCCGCCGGGACCATTTGGGCTTGCAACACCGGGCTCAC
TCCCTGCCTATCTACCACTGTGCTCGACCTCACCACCGATTACTGTGTCC
TGGTTGAGCTCTGGCCAAAAGTGACCTACCACTCCCCTGGTTATGTTTAT
GGCCAGTTTGAAGAAAAAACCAAATATAAAAGAGAACCCGTCTCACTAAC
TCTGGCCCTACTATTAGGAGGACTCACTATGGGCGGAATTGCCGCCGGAG
TGGGAACAGGGACTACCGCCCTAGTGGCCACTCAGCAGTTCCAACAACTC
CAGGCTGCCATGCAGGATGACCTTAAAGAAGTTGAAAAGTCCATCACTAA
TCTAGAAAGATCTTTGACCTCCTTGTCCGAAGTAGTGTTACAGAATCGTA
GAGGCCTAGATCTACTATTCCTAAAAGAGGGAGGTTTGTGTGCTGCCTTA
AAAGAAGAATGCTGTTTCTATGCCGACCACACAGGATTGGTACGGGATAG
CATGGCCAAACTTAGAGAAAGATTGAGTCAGAGACAAAAACTCTTTGAAT
CCCAACAAGGGTGGTTTGAAGGGCTGTTTAACAAGTCCCCTTGGTTCACC
ACCCTGATATCCACCATCATGGGTCCCCTGATAATCCTCTTGTTAATTTT
ACTCTTTGGGCCTTGTATTCTCAATCACCTGGTCCAGTTTATCAAAGACA
GGGTTTCGGTAGTGCAGGCCCTGGTCCTGACTCAACAATATCATCAACTT
AAGACAATAGAAGATTGTGAATCACGTGAATAA

SEQ ID NO: 102: SL3-2/apelin chimeric envelope polypeptide, "Apelin@86 GI", (shaded section represents the inserted section):

MEGPAFSKPLKDKINPWGPLIVLGILMRARVSVQHDSPHQVFNVTWRVTN
LMTGQTANATSLLGTMTDAFPKLYFDLCDLIGDDWDSGGSGQRPRLSHKG
PMPFSGGSGGLGCRTPGGRKRARIFDFYVCPGHTVLAGCGGPREGYCGKW
GCETTGQAYWKPSSSWDLISLKRGNTPKGQGPCYDSSVVSSSAQGATPGG
RCNPLVLEFTDAGKRASWDASKAWGLRLYRSTGIDPVTRFSLTRQVLNIG
PRVPIGPNPVIIDQLPPSRPVQVMLPRPPQPPPPGAASTVPETAPPSQQP
GTGDRLLNLVNGAYQALNLTSPDKTQECWLCLVAGPPYYEGVAVLGTYSN
HTSAPANCSVASQHKLTLSEVTGQGLCVGAVPKTHQALCNTTQKTSNGSY

-continued

YLAAPAGTIWACNTGLTPCLSTTVLDLTTDYCVLVELWPKVTYHSPGYVY
GQFEEKTKYKREPVSLTLALLLGGLTMGGIAAGVGTGTTALVATQQFQQL
QAAMQDDLKEVEKSITNLERSLTSLSEVVLQNRRGLDLLFLKEGGLCAAL
KEECCFYADHTGLVRDSMAKLRERLSQRQKLFESQQGWFEGLFNKSPWFT
TLISTIMGPLIILLLILLFGPCILNHLVQFIKDRVSVVQALVLTQQYHQL
KTIEDCESRE

SEQ ID NO: 103: SL3-2/apelin chimeric envelope polynucleotide, "Apelin@155 RT", (shaded section represents the inserted section):

ATGGAAGGTCCAGCGTTCTCAAAACCCCTTAAAGATAAGATTAACCCGTG
GGGCCCCCTAATAGTCCTGGGAATCTTAATGAGGGCAAGAGTATCAGTAC
AACATGACAGCCCTCATCAGGTCTTCAATGTTACTTGGAGAGTTACCAAC
TTAATGACAGGACAAACAGCTAATGCTACCTCCCTCCTGGGGACAATGAC
CGATGCCTTTCCTAAACTGTACTTTGACTTGTGCGATTTAATAGGGGACG
ACTGGGATGAGACTGGACTCGGGTGTCGCACTCCCGGGGGAAGAAAAAGG
GCAAGAATATTTGACTTCTATGTTTGCCCCGGTCACACTGTGCTAGCAGG
GTGTGGAGGGCCGAGAGAGGGCTACTGTGGCAAATGGGGATGTGAGACCA
CTGGACAGGCATACTGGAAGCCATCATCATCATGGGACCTAATTTCCCTT
AAGCGAGGAAACACTCAAGGAATCTACCAGTGCTCCGGTGGCAGTGGACA
GCGGCCCCGCCTCTCCCATAAGGGACCCATGCCTTTCAGCGGTGGATCTG
GCTGTGGGCCCTGTTATGATTCCTCGGTGGTCTCCAGTAGCGCCCAGGGT
GCCACACCGGGGGGTCGATGCAACCCCCTAGTCCTAGAATTCACTGACGC
GGGTAAAAGGGCCAGCTGGGACGCCTCCAAAGCATGGGGACTAAGACTGT
ACCGATCCACAAGGACCGACCCGGTGACCCGGTTCTCTTTGACCCGCCAG
GTCCTCAATATAGGGCCCCGCGTCCCCATTGGGCCTAATCCCGTGATCAT
TGACCAGTTACCCCCCTCCCGACCCGTGCAGGTCATGCTCCCCAGGCCTC
CTCAGCCTCCTCCACCAGGCGCAGCCTCTACAGTCCCTGAGACTGCCCCA
CCTTCCCAACAACCTGGGACGGGAGACAGGCTGCTAAACCTGGTAAATGG
AGCCTACCAAGCTCTCAACCTCACCAGTCCTGACAAAACCCAAGAGTGCT
GGTTGTGTCTGGTAGCGGGACCCCCCTACTACGAAGGGGTTGCCGTCCTA
GGTACTTATTCCAACCATACCTCTGCCCCAGCTAACTGCTCCGTGGCCTC
CCAACACAAGCTGACCCTGTCCGAAGTGACCGGACAGGGACTCTGCGTAG
GAGCAGTTCCCAAAACCCATCAGGCCCTGTGTAATACCACCCAGAAGACG
AGCAACGGGTCCTACTATCTGGCTGCTCCCGCCGGGACCATTTGGGCTTG
CAACACCGGGCTCACTCCCTGCCTATCTACCACTGTGCTCGACCTCACCA
CCGATTACTGTGTCCTGGTTGAGCTCTGGCCAAAAGTGACCTACCACTCC
CCTGGTTATGTTTATGGCCAGTTTGAAGAAAAAACCAAATATAAAAGAGA
ACCCGTCTCACTAACTCTGGCCCTACTATTAGGAGGACTCACTATGGGCG
GAATTGCCGCCGGAGTGGGAACAGGGACTACCGCCCTAGTGGCCACTCAG
CAGTTCCAACAACTCCAGGCTGCCATGCAGGATGACCTTAAAGAAGTTGA
AAAGTCCATCACTAATCTAGAAAGATCTTTGACCTCCTTGTCCGAAGTAG

-continued

TGTTACAGAATCGTAGAGGCCTAGATCTACTATTCCTAAAAGAGGGAGGT

TTGTGTGCTGCCTTAAAAGAAGAATGCTGTTTCTATGCCGACCACACAGG

ATTGGTACGGGATAGCATGGCCAAACTTAGAGAAAGATTGAGTCAGAGAC

AAAAACTCTTTGAATCCCAACAAGGGTGGTTTGAAGGGCTGTTTAACAAG

TCCCCTTGGTTCACCACCCTGATATCCACCATCATGGGTCCCCTGATAAT

CCTCTTGTTAATTTTACTCTTTGGGCCTTGTATTCTCAATCACCTGGTCC

AGTTTATCAAAGACAGGGTTTCGGTAGTGCAGGCCCTGGTCCTGACTCAA

CAATATCATCAACTTAAGACAATAGAAGATTGTGAATCACGTGAATAA

SEQ ID NO: 104: SL3-2/apelin chimeric envelope peptide, “Apelin@155 RT”, (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTQGIYQCSGGSGQRPRLSHKGPMPFSGGSGCGPCYDSSVVSSSAQG

ATPGGRCNPLVLEFTDAGKRASWDASKAWGLRLYRSTRTDPVTRFSLTRQ

VLNIGPRVPIGPNPVIIDQLPPSRPVQVMLPRPPQPPPPGAASTVPETAP

PSQQPGTGDRLLNLVNGAYQALNLTSPDKTQECWLCLVAGPPYYEGVAVL

GTYSNHTSAPANCSVASQHKLTLSEVTGQGLCVGAVPKTHQALCNTTQKT

SNGSYYLAAPAGTIWACNTGLTPCLSTTVLDLTTDYCVLVELWPKVTYHS

PGYVYGQFEEKTKYKREPVSLTLALLLGGLTMGGIAAGVGTGTTALVATQ

QFQQLQAAMQDDLKEVEKSITNLERSLTSLSEVVLQNRRGLDLLFLKEGG

LCAALKEECCFYADHTGLVRDSMAKLRERLSQRQKLFESQQGWFEGLFNK

SPWFTTLISTIMGPLIILLLILLFGPCILNHLVQFIKDRVSVVQALVLTQ

QYHQLKTIEDCESRE

SEQ ID NO: 105: SL3-2/apelin chimeric envelope polynucleotide, “Apelin@155 GI”, (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCAAGGAATCTACCAGTGCTCCGGTGGCAGTGGACA

GCGGCCCCGCCTCTCCCATAAGGGACCCATGCCTTTCAGCGGTGGATCTG

GCTGTGGGCCCTGTTATGATTCCTCGGTGGTCTCCAGTAGCGCCCAGGGT

-continued

GCCACACCGGGGGGTCGATGCAACCCCCTAGTCCTAGAATTCACTGACGC

GGGTAAAAGGGCCAGCTGGGACGCCTCCAAAGCATGGGGACTAAGACTGT

ACCGATCCACAGGGATCGACCCGGTGACCCGGTTCTCTTTGACCCGCCAG

GTCCTCAATATAGGGCCCCGCGTCCCCATTGGGCCTAATCCCGTGATCAT

TGACCAGTTACCCCCCTCCCGACCCGTGCAGGTCATGCTCCCCAGGCCTC

CTCAGCCTCCTCCACCAGGCGCAGCCTCTACAGTCCCTGAGACTGCCCCA

CCTTCCCAACAACCTGGGACGGGAGACAGGCTGCTAAACCTGGTAAATGG

AGCCTACCAAGCTCTCAACCTCACCAGTCCTGACAAAACCCAAGAGTGCT

GGTTGTGTCTGGTAGCGGGACCCCCCTACTACGAAGGGGTTGCCGTCCTA

GGTACTTATTCCAACCATACCTCTGCCCCAGCTAACTGCTCCGTGGCCTC

CCAACACAAGCTGACCCTGTCCGAAGTGACCGGACAGGGACTCTGCGTAG

GAGCAGTTCCCAAAACCCATCAGGCCCTGTGTAATACCACCCAGAAGACG

AGCAACGGGTCCTACTATCTGGCTGCTCCCGCCGGGACCATTTGGGCTTG

CAACACCGGGCTCACTCCCTGCCTATCTACCACTGTGCTCGACCTCACCA

CCGATTACTGTGTCCTGGTTGAGCTCTGGCCAAAAGTGACCTACCACTCC

CCTGGTTATGTTTATGGCCAGTTTGAAGAAAAAACCAAATATAAAAGAGA

ACCCGTCTCACTAACTCTGGCCCTACTATTAGGAGGACTCACTATGGGCG

GAATTGCCGCCGGAGTGGGAACAGGGACTACCGCCCTAGTGGCCACTCAG

CAGTTCCAACAACTCCAGGCTGCCATGCAGGATGACCTTAAAGAAGTTGA

AAAGTCCATCACTAATCTAGAAAGATCTTTGACCTCCTTGTCCGAAGTAG

TGTTACAGAATCGTAGAGGCCTAGATCTACTATTCCTAAAAGAGGGAGGT

TTGTGTGCTGCCTTAAAAGAAGAATGCTGTTTCTATGCCGACCACACAGG

ATTGGTACGGGATAGCATGGCCAAACTTAGAGAAAGATTGAGTCAGAGAC

AAAAACTCTTTGAATCCCAACAAGGGTGGTTTGAAGGGCTGTTTAACAAG

TCCCCTTGGTTCACCACCCTGATATCCACCATCATGGGTCCCCTGATAAT

CCTCTTGTTAATTTTACTCTTTGGGCCTTGTATTCTCAATCACCTGGTCC

AGTTTATCAAAGACAGGGTTTCGGTAGTGCAGGCCCTGGTCCTGACTCAA

CAATATCATCAACTTAAGACAATAGAAGATTGTGAATCACGTGAATAA

SEQ ID NO: 106: SL3-2/apelin chimeric envelope peptide, “Apelin@155 GI”, (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTQGIYQCSGGSGQRPRLSHKGPMPFSGGSGCGPCYDSSVVSSSAQG

ATPGGRCNPLVLEFTDAGKRASWDASKAWGLRLYRSTGIDPVTRFSLTRQ

VLNIGPRVPIGPNPVIIDQLPPSRPVQVMLPRPPQPPPPGAASTVPETAP

PSQQPGTGDRLLNLVNGAYQALNLTSPDKTQECWLCLVAGPPYYEGVAVL

GTYSNHTSAPANCSVASQHKLTLSEVTGQGLCVGAVPKTHQALCNTTQKT

SNGSYYLAAPAGTIWACNTGLTPCLSTTVLDLTTDYCVLVELWPKVTYHS

PGYVYGQFEEKTKYKREPVSLTLALLLGGLTMGGIAAGVGTGTTALVATQ

-continued

QFQQLQAAMQDDLKEVEKSITNLERSLTSLSEVVLQNRRGLDLLFLKEGG

LCAALKEECCFYADHTGLVRDSMAKLRERLSQRQKLFESQQGWFEGLFNK

SPWFTTLISTIMGPLIILLLILLFGPCILNHLVQFIKDRVSVVQALVLTQ

QYHQLKTIEDCESRE

SEQ ID NO: 107: SL3-2/apelin chimeric envelope polynucleotide, "AP@165 RT", (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCCTAAAGGCCAGGGCCCCTGTTATGATTCCTCCGG

TGGCAGTGGACAGCGGCCCCGCCTCTCCCATAAGGGACCCATGCCTTTCA

GCGGTGGATCTGGCTCCAGTAGCGCCCAGGGTGCCACACCGGGGGGTCGA

TGCAACCCCCTAGTCCTAGAATTCACTGACGCGGGTAAAAGGGCCAGCTG

GGACGCCTCCAAAGCATGGGGACTAAGACTGTACCGATCCACAAGGACCG

ACCCGGTGACCCGGTTCTCTTTGACCCGCCAGGTCCTCAATATAGGGCCC

CGCGTCCCCATTGGGCCTAATCCCGTGATCATTGACCAGTTACCCCCCTC

CCGACCCGTGCAGGTCATGCTCCCCAGGCCTCCTCAGCCTCCTCCACCAG

GCGCAGCCTCTACAGTCCCTGAGACTGCCCCACCTTCCCAACAACCTGGG

ACGGGAGACAGGCTGCTAAACCTGGTAAATGGAGCCTACCAAGCTCTCAA

CCTCACCAGTCCTGACAAAACCCAAGAGTGCTGGTTGTGTCTGGTAGCGG

GACCCCCCTACTACGAAGGGGTTGCCGTCCTAGGTACTTATTCCAACCAT

ACCTCTGCCCCAGCTAACTGCTCCGTGGCCTCCCAACACAAGCTGACCCT

GTCCGAAGTGACCGGACAGGGACTCTGCGTAGGAGCAGTTCCCAAAACCC

ATCAGGCCCTGTGTAATACCACCCAGAAGACGAGCAACGGGTCCTACTAT

CTGGCTGCTCCCGCCGGGACCATTTGGGCTTGCAACACCGGGCTCACTCC

CTGCCTATCTACCACTGTGCTCGACCTCACCACCGATTACTGTGTCCTGG

TTGAGCTCTGGCCAAAAGTGACCTACCACTCCCCTGGTTATGTTTATGGC

CAGTTTGAAGAAAAAACCAAATATAAAAGAGAACCCGTCTCACTAACTCT

GGCCCTACTATTAGGAGGACTCACTATGGGCGGAATTGCCGCCGGAGTGG

GAACAGGGACTACCGCCCTAGTGGCCACTCAGCAGTTCCAACAACTCCAG

GCTGCCATGCAGGATGACCTTAAAGAAGTTGAAAAGTCCATCACTAATCT

AGAAAGATCTTTGACCTCCTTGTCCGAAGTAGTGTTACAGAATCGTAGAG

GCCTAGATCTACTATTCCTAAAAGAGGGAGGTTTGTGTGCTGCCTTAAAA

-continued

GAAGAATGCTGTTTCTATGCCGACCACACAGGATTGGTACGGGATAGCAT

GGCCAAACTTAGAGAAAGATTGAGTCAGAGACAAAAACTCTTTGAATCCC

AACAAGGGTGGTTTGAAGGGCTGTTTAACAAGTCCCCTTGGTTCACCACC

CTGATATCCACCATCATGGGTCCCCTGATAATCCTCTTGTTAATTTTACT

CTTTGGGCCTTGTATTCTCAATCACCTGGTCCAGTTTATCAAAGACAGGG

TTTCGGTAGTGCAGGCCCTGGTCCTGACTCAACAATATCATCAACTTAAG

ACAATAGAAGATTGTGAATCACGTGAATAA

SEQ ID NO: 108: SL3-2/apelin chimeric envelope polynucleotide, “AP@165 GI”, (shaded section represents the inserted section):

ATGGAAGGTCCAGCGTTCTCAAAACCCCTTAAAGATAAGATTAACCCGTG

GGGCCCCCTAATAGTCCTGGGAATCTTAATGAGGGCAAGAGTATCAGTAC

AACATGACAGCCCTCATCAGGTCTTCAATGTTACTTGGAGAGTTACCAAC

TTAATGACAGGACAAACAGCTAATGCTACCTCCCTCCTGGGGACAATGAC

CGATGCCTTTCCTAAACTGTACTTTGACTTGTGCGATTTAATAGGGGACG

ACTGGGATGAGACTGGACTCGGGTGTCGCACTCCCGGGGGAAGAAAAAGG

GCAAGAATATTTGACTTCTATGTTTGCCCCGGTCACACTGTGCTAGCAGG

GTGTGGAGGGCCGAGAGAGGGCTACTGTGGCAAATGGGGATGTGAGACCA

CTGGACAGGCATACTGGAAGCCATCATCATCATGGGACCTAATTTCCCTT

AAGCGAGGAAACACTCCTAAAGGCCAGGGCCCCTGTTATGATTCCTCCGG

TGGCAGTGGACAGCGGCCCCGCCTCTCCCATAAGGGACCCATGCCTTTCA

GCGGTGGATCTGGCTCCAGTAGCGCCCAGGGTGCCACACCGGGGGGTCGA

TGCAACCCCCTAGTCCTAGAATTCACTGACGCGGGTAAAAGGGCCAGCTG

GGACGCCTCCAAAGCATGGGGACTAAGACTGTACCGATCCACAGGGATCG

ACCCGGTGACCCGGTTCTCTTTGACCCGCCAGGTCCTCAATATAGGGCCC

CGCGTCCCCATTGGGCCTAATCCCGTGATCATTGACCAGTTACCCCCCTC

CCGACCCGTGCAGGTCATGCTCCCCAGGCCTCCTCAGCCTCCTCCACCAG

GCGCAGCCTCTACAGTCCCTGAGACTGCCCCACCTTCCCAACAACCTGGG

ACGGGAGACAGGCTGCTAAACCTGGTAAATGGAGCCTACCAAGCTCTCAA

CCTCACCAGTCCTGACAAAACCCAAGAGTGCTGGTTGTGTCTGGTAGCGG

GACCCCCCTACTACGAAGGGGTTGCCGTCCTAGGTACTTATTCCAACCAT

ACCTCTGCCCCAGCTAACTGCTCCGTGGCCTCCCAACACAAGCTGACCCT

GTCCGAAGTGACCGGACAGGGACTCTGCGTAGGAGCAGTTCCCAAAACCC

ATCAGGCCCTGTGTAATACCACCCAGAAGACGAGCAACGGGTCCTACTAT

CTGGCTGCTCCCGCCGGGACCATTTGGGCTTGCAACACCGGGCTCACTCC

CTGCCTATCTACCACTGTGCTCGACCTCACCACCGATTACTGTGTCCTGG

TTGAGCTCTGGCCAAAAGTGACCTACCACTCCCCTGGTTATGTTTATGGC

CAGTTTGAAGAAAAAACCAAATATAAAAGAGAACCCGTCTCACTAACTCT

GGCCCTACTATTAGGAGGACTCACTATGGGCGGAATTGCCGCCGGAGTGG

GAACAGGGACTACCGCCCTAGTGGCCACTCAGCAGTTCCAACAACTCCAG

GCTGCCATGCAGGATGACCTTAAAGAAGTTGAAAAGTCCATCACTAATCT

AGAAAGATCTTTGACCTCCTTGTCCGAAGTAGTGTTACAGAATCGTAGAG

GCCTAGATCTACTATTCCTAAAAGAGGGAGGTTTGTGTGCTGCCTTAAAA

GAAGAATGCTGTTTCTATGCCGACCACACAGGATTGGTACGGGATAGCAT

GGCCAAACTTAGAGAAAGATTGAGTCAGAGACAAAAACTCTTTGAATCCC

AACAAGGGTGGTTTGAAGGGCTGTTTAACAAGTCCCCTTGGTTCACCACC

CTGATATCCACCATCATGGGTCCCCTGATAATCCTCTTGTTAATTTTACT

CTTTGGGCCTTGTATTCTCAATCACCTGGTCCAGTTTATCAAAGACAGGG

TTTCGGTAGTGCAGGCCCTGGTCCTGACTCAACAATATCATCAACTTAAG

ACAATAGAAGATTGTGAATCACGTGAATAA

SEQ ID NO: 109: SL3-2/apelin chimeric envelope polypeptide, "AP@165 RT", (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDSSGGSGQRPRLSHKGPMPFSGGSGSSSAQGATPGGR

CNPLVLEFTDAGKRASWDASKAWGLRLYRSTGIDPVTRFSLTRQVLNIGP

RVPIGPNPVIIDQLPPSRPVQVMLPRPPQPPPPGAASTVPETAPPSQQPG

TGDRLLNLVNGAYQALNLTSPDKTQECWLCLVAGPPYYEGVAVLGTYSNH

TSAPANCSVASQHKLTLSEVTGQGLCVGAVPKTHQALCNTTQKTSNGSYY

LAAPAGTIWACNTGLTPCLSTTVLDLTTDYCVLVELWPKVTYHSPGYVYG

QFEEKTKYKREPVSLTLALLLGGLTMGGIAAGVGTGTTALVATQQFQQLQ

AAMQDDLKEVEKSITNLERSLTSLSEVVLQNRRGLDLLFLKEGGLCAALK

EECCFYADHTGLVRDSMAKLRERLSQRQKLFESQQGWFEGLFNKSPWFTT

LISTIMGPLIILLLILLFGPCILNHLVQFIKDRVSVVQALVLTQQYHQLK

TIEDCESRE

SEQ ID NO: 110: SL3-2/substance P chimeric envelope polypeptide, (shaded section represents the inserted section):

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDSSGGSGRPKPEEFFGLMSGGSGSSSAQGATPGGRCN

PLVLEFTDAGKRASWDASKAWGLRLYRSTGIDPVTRFSLTRQVLNIGPRV

PIGPNPVIIDQLPPSRPVQVMLPRPPQPPPPGAASTVPETAPPSQQPGTG

DRLLNLVNGAYQALNLTSPDKTQECWLCLVAGPPYYEGVAVLGTYSNHTS

APANCSVASQHKLTLSEVTGQGLCVGAVPKTHQALCNTTQKTSNGSYYLA

APAGTIWACNTGLTPCLSTTVLDLTTDYCVLVELWPKVTYHSPGYVYGQF

EEKTKYKREPVSLTLALLLGGLTMGGIAAGVGTGTTALVATQQFQQLQAA

MQDDLKEVEKSITNLERSLTSLSEVVLQNRRGLDLLFLKEGGLCAALKEE

CCFYADHTGLVRDSMAKLRERLSQRQKLFESQQGWFEGLFNKSPWFTTLI

STIMGPLIILLLILLFGPCILNHLVQFIKDRVSVVQALVLTQQYHQLKTI

EDCESRE

SEQ ID NO: 111: substance P

RPKPEEFFGLM

SEQ ID NO: 112: Protein sequence of the chimeric envelopes

GKYL:

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDS <u>SGGSG GKYL SGGSG</u> SSSAQGATPGGRCNPLV

LEFTDAGKRASWDASKAWGLRLYRSTRTDPVTRFSLTRQVLNIGPRVPIG

PNPVIIDQLPPSRPVQIMLPRPPQPPPPGAASTVPETAPPSQQPGTGDRL

LNLVNGAYQALNLTSPDKTQECWLCLVAGPPYYEGVAVLGTYSNHTSAPA

NCSVASQHKLTLSEVTGQGLCVGAVPKTHQALCNTTQKTSNGSYYLAAPA

GTIWACNTGLTPCLSTTVLDLTTDYCVLVELWPKVTYHSPGYVYGQFEEK

TKYKREPVSLTLALLLGGLTMGGIAAGVGTGTTALVATQQFQQLQAAMQD

DLKEVKKSITNLERSLTSLSEVVLQNRRGLDLLFLKEGGLCAALKEECCF

YADHTGLVRDSMAKLRERLSQRQKLFESQQGWFEGLFNKSPWFTTLISTI

MGPLIILLLILLFGPCILNHLVQFIKDRVSVVQALVLTQQYHQLKTIEDC

ESRE

SEQ ID NO: 113: Protein sequence of the chimeric envelopes

FWVP:

MEGPAFSKPLKDKINPWGPLIVLGILMRARVSVQHDSPHQVFNVTWRVTN

LMTGQTANATSLLGTMTDAFPKLYFDLCDLIGDDWDETGLGCRTPGGRKR

ARIFDFYVCPGHTVLAGCGGPREGYCGKWGCETTGQAYWKPSSSWDLISL

KRGNTPKGQGPCYDS <u>SGGSG FWVP SGGSG</u> SSSAQGATPGGRCNPLV

LEFTDAGKRASWDASKAWGLRLYRSTRTDPVTRFSLTRQVLNIGPRVPIG

PNPVIIDQLPPSRPVQIMLPRPPQPPPPGAASTVPETAPPSQQPGTGDRL

LNLVNGAYQALNLTSPDKTQECWLCLVAGPPYYEGVAVLGTYSNHTSAPA

NCSVASQHKLTLSEVTGQGLCVGAVPKTHQALCNTTQKTSNGSYYLAAPA

GTIWACNTGLTPCLSTTVLDLTTDYCVLVELWPKVTYHSPGYVYGQFEEK

TKYKREPVSLTLALLLGGLTMGGIAAGVGTGTTALVATQQFQQLQAAMQD

DLKEVKKSITNLERSLTSLSEVVLQNRRGLDLLFLKEGGLCAALKEECCF

YADHTGLVRDSMAKLRERLSQRQKLFESQQGWFEGLFNKSPWFTTLISTI

MGPLIILLLILLFGPCILNHLVQFIKDRVSVVQALVLTQQYHQLKTIEDC

ESRE

SEQ ID NO: 112: Protein sequence of the chimeric envelopes RRRWRF:

```
MEGPAFSKPLKDKINPWGPLIVLGILMRARVSVQHDSPHQVFNVTWRVTN
LMTGQTANATSLLGTMTDAFPKLYFDLCDLIGDDWDETGLGCRTPGGRKR
ARIFDFYVCPGHTVLAGCGGPREGYCGKWGCETTGQAYWKPSSSWDLISL
KRGNTPKGQGPCYDS SGGSG RRRWRF SGGSG SSSAQGATPGGRCNP
LVLEFTDAGKRASWDASKAWGLRLYRSTRTDPVTRFSLTRQVLNIGPRVP
IGPNPVIIDQLPPSRPVQIMLPRPPQPPPPGAASTVPETAPPSQQPGTGD
RLLNLVNGAYQALNLTSPDKTQECWLCLVAGPPYYEGVAVLGTYSNHTSA
PANCSVASQHKLTLSEVTGQGLCVGAVPKTHQALCNTTQKTSNGSYYLAA
PAGTIWACNTGLTPCLSTTVLDLTTDYCVLVELWPKVTYHSPGYVYGQFE
EKTKYKREPVSLTLALLLGGLTMGGIAAGVGTGTTALVATQQFQQLQAAM
QDDLKEVKKSITNLERSLTSLSEVVLQNRRGLDLLFLKEGGLCAALKEEC
CFYADHTGLVRDSMAKLRERLSQRQKLFESQQGWFEGLFNKSPWFTTLIS
TIMGPLIILLLILLFGPCILNHLVQFIKDRVSVVQALVLTQQYHQLKTIE
DCESRE
```

REFERENCES

Aagaard L, Mikkelsen J G, Warming S, Duch M, Pedersen F S., 2002, J. Gen. Virol., 83: 439-42

Battini J. L., HeardJ. M., and DanosO., 1992, J. Virol. 66, 1468-1475;

BattiniJ-L., DanosO., and Heard J. M., 1995, J. Virol. 69, 713-719. Bachrach, E., M;

Pelegrin, M. Piechaczyk, F. S. Pedersen, and M. Duch. 2002. Virology 293, 328-334;

Beck E., Ludwig G., Auerswald E. A., Reiss B., and Schaller H., 1982, Gene 19, 327-336;

Chattopadhyay S. K., Cloyd M. W., Linemeyer D. L., Lander M. R., Rands E., and Lowy D. R., 1982, Nature 295, 25-31 CossetF-L., Takeuchi Y., Battini J. L., Weiss R. A., and Collins M. K., 1995, J. Virol. 69, 7430-7436;

Dai H. Y., Etzerodt M., Baekgaard A. J., Lovmand S., Jorgensen P., Kjeldgaard N. O., and Pedersen F. S., 1990, Virology 175, 581-585;

Golan T J and Green-M R 2002. J. Virol 76 (7): 3558-63;

Graham F. L., van der EbA. J., 1973, Virology 52, 456-467;

Hartley, J. W., Wolford N. K., Lloyd J. O., and Rowe W. P., 1977, Proc. Natl. Acad. Sci. USA, 74, 789-792.

Heard J.-M., and Danos O., 1991, J. Virol. 65, 4026-4032.

Jang, S. K., and E. Wimmer. 1990. Genes Dev. 4, 1560-1572.

Jespersen T., Duch M., and Pedersen F. S., 1997, Biotechniques 23, 48-52.

Koo, H. M., A. M. C. Brown, R. J. Kaufman, C. M. Prorock, Y. Ron, and J. P. Dougherty. 1992. Virology 186, 669-675.

Mann R., Mulligan R. C., Baltimore D., 1983, Cell 33, 183-189.

Morgan R. A., Couture L., Elroy-Stein O., Ragheb J., Moss B., and Anderson W. F., 1992, Nucleic Acid Rec. 20, 1293-1299.

Morita S., Kojima T., and Kitamura T., 2000, GeneTher. 7, 1063-1066.

Pear W. S., Nolan G. P., Scott M. L., and Blatimore D., 1993, PNAS 90, 8392-8396.

Pedersen, F. S., Crowther R. L., Tenney D. Y., Reimold A. M., and Hasletine W. A., 1981, Nature 292, 167-170.

Rein A., 1982, Virology 120, 251-257

Rein A., and Schultz A., 1984, Virology 136, 144-152. Towers et al 1999. PNAS vol. 97, no. 22 pp 12295-12299 Van Beveren C., Coffin J., and Hughes 5., 1985, RNA tumour viruses. CSHL Press, New York, 790-805.

Bahrami, S., Duch, M. and Pedersen, F. S.: Change of tropism of SL3-2 murine leukemia virus, using random mutational libraries. J Virol 78 (2004) 9343-51.

Bahrami, S., Jespersen, T., Pedersen, F. S. and Duch, M.: Mutational library analysis of selected amino acids in the receptor binding domain of envelope of Akv murine leukemia virus by conditionally replication competent bicistronic vectors. Gene 315 (2003) 51-61.

Graham, F. L. and van der Eb, A. J.: A new technique for the assay of infectivity of human adenovirus 5 DNA. Virology 52 (1973) 456-67.

Jespersen, T., Duch, M. and Pedersen, F. S.: Efficient non-PCR-mediated overlap extension of PCR fragments by exonuclease "end polishing". Biotechniques 23 (1997) 48, 50, 52.

Morita, S., Kojima, T. and Kitamura, T.: Plat-E: an efficient and stable system for transient packaging of retroviruses. Gene Ther 7 (2000) 1063-6.

Argos, P.: An investigation of oligopeptides linking domains in protein tertiary structures and possible candidates for general gene fusion. J Mol Biol 211 (1990) 943-58.

Wang, H., Kavanaugh, M. P., North, R. A. and Kabat, D.: Cell-surface receptor for ecotropic murine retroviruses is a basic amino-acid transporter. Nature 352 (1991) 729-31.

Wang, H., Klamo, E., Kuhmann, S. E., Kozak, S. L., Kavanaugh, M. P. and Kabat, D.: Modulation of ecotropic murine retroviruses by N-linked glycosylation of the cell surface receptor/amino acid transporter. J Virol 70 (1996) 6884-91.

Argos, P.: An investigation of oligopeptides linking domains in protein tertiary structures and possible candidates for general gene fusion. J Mol Biol 211 (1990) 943-58.

Bahrami, S., Duch, M. and Pedersen, F. S.: Change of tropism of SL3-2 murine leukemia virus, using random mutational libraries. J Virol 78 (2004) 9343-51.

Bahrami, S., Jespersen, T., Pedersen, F. S, and Duch, M.: Mutational library analysis of selected amino acids in the receptor binding domain of envelope of Akv murine leukemia virus by conditionally replication competent bicistronic vectors. Gene 315 (2003) 51-61.

Fan, X., Zhou, N., Zhang, X., Mukhtar, M., Lu, Z., Fang, J., DuBois, G. C. and Pomerantz, R. J.: Structural and functional study of the apelin-13 peptide, an endogenous ligand of the HIV-1 coreceptor, APJ. Biochemistry 42 (2003) 10163-8.

Graham, F. L. and van der Eb, A. J.: A new technique for the assay of infectivity of human adenovirus 5 DNA. Virology 52 (1973) 456-67.

Jespersen, T., Duch, M. and Pedersen, F. S.: Efficient non-PCR-mediated overlap extension of PCR fragments by exonuclease "end polishing". Biotechniques 23 (1997) 48, 50, 52.

Kawamata, Y., Habata, Y., Fukusumi, S., Hosoya, M., Fujii, R., Hinuma, S., Nishizawa, N., Kitada, C., Onda, H., Nishimura, O. and Fujino, M.: Molecular properties of apelin: tissue distribution and receptor binding. Biochim Biophys Acta 1538 (2001) 162-71.

Morita, S., Kojima, T. and Kitamura, T.: Plat-E: an efficient and stable system for transient packaging of retroviruses. Gene Ther 7 (2000) 1063-6.

Pedersen, F. S., Crowther, R. L., Tenney, D. Y., Reimold, A. M. and Haseltine, W. A.: Novel leukaemogenic retroviruses isolated from cell line derived from spontaneous AKR tumour. Nature 292 (1981) 167-70.

Puffer, B. A., Sharron, M., Coughlan, C. M., Baribaud, F., McManus, C. M., Lee, B., David, J., Price, K., Horuk, R., Tsang, M. and Doms, R. W.: Expression and coreceptor function of APJ for primate immunodeficiency viruses. Virology 276 (2000) 435-44.

Quartara, L. and Maggi, C. A.: The tachykinin NK1 receptor. Part I: ligands and mechanisms of cellular activation. Neuropeptides 31 (1997) 537-63.

The invention claimed is:

1. A polynucleotide encoding a chimeric viral envelope polypeptide comprising:

a first polypeptide into which a second polypeptide is inserted at an insertion point; wherein the first polypeptide sequence, prior to the insertion of said second polypeptide, consists of the polypeptide sequence of a murine or feline leukemia virus envelope polypeptide whose amino acid sequence is at least 70% identical to SEQ ID NO:2;

wherein the second polypeptide sequence consists of a receptor-binding domain of a second, different viral envelope polypeptide, wherein said receptor-binding domain is from a virus selected from the group consisting of HIV, HTLV-1, hepatitis virus, vesicular stomatitis virus, cytomegalovirus, and influenza virus;

wherein the insertion point is in a region of the first polypeptide that aligns with amino acids 152 to 181 of SEQ ID NO:2 following a sequence alignment of SEQ ID NO:2 with said polypeptide sequence of a murine or feline leukemia virus envelope polypeptide whose amino acid sequence is at least 70% identical to SEQ ID NO:2; and wherein the chimeric viral envelope polypeptide is capable of binding to the receptor of the second polypeptide sequence.

2. The polynucleotide according to claim 1, wherein said polynucleotide has a sequence according to any of SEQ ID NO: 3-5 or 42-44.

3. A vector comprising the polynucleotide according to claim 1.

4. The vector according to claim 3, wherein said vector is a recombinant virus particle.

5. A cell transfected with the vector according to claim 3.

6. A stable cell line comprising cells according to claim 5.

7. A medicament comprising the vector of claim 3.

8. The polynucleotide according to claim 1, wherein said murine or feline leukemia virus is polytropic.

9. The polynucleotide according to claim 8, where said murine or feline leukemia virus is selected from the group consisting og:SL3-2, MCF-247, MCF C1-3, ERV-1, Friend MCF, Friend SFV, Invitro MCF, MCF 1223, MLV DBA/2, Mo-MCF, Ns-6(168)MCF, Rauscher sfv, “Endogenous from 129 Glx+mice”, Ampho-MCF, MCF (Ter-Grigorov), MCF (Brosclus), Friend MCF#2, R-XC, Feline leukemia virus (FeLV) subtypes A, B, and C, and Xeno R-MCl-1.

10. The polynucleotide according to claim 9, wherein said murine or feline leukemia virus is SL3-2.

11. The polynucleotide according to claim 1, wherein said first polypeptide sequence has a sequence that is at least 80% identical to the amino acid sequence shown in SEQ ID NO:2.

12. The polynucleotide according to claim 1, wherein said receptor binding domain of a second, different viral envelope polypeptide has a sequence selected from the group consisting of SEQ ID NOS: 9-32.

13. The polynucleotide according to claim 1, wherein said second, different viral envelope polypeptide is the V3-loop domain of HIV-1.

14. The polynucleotide according to claim 1, wherein said chimeric viral envelope polypeptide further comprises one or more flexible linker sequences.

15. The polynucleotide according to claim 11, wherein said first polypeptide sequence has a sequence that is at least 90% identical to the amino acid sequence shown in SEQ ID NO:2.

16. The polynucleotide according to claim 15, wherein said first polypeptide sequence has a sequence that is at least 95% identical to the amino acid sequence shown in SEQ ID NO:2.

* * * * *

SEQUENCE LISTING

```
<160> NUMBER OF SEQ ID NOS: 208

<210> SEQ ID NO 1
<211> LENGTH: 1920
<212> TYPE: DNA
<213> ORGANISM: Murine leukaemia virus

<400> SEQUENCE: 1

atggaaggtc cagcgttctc aaaacccctt aaagataaga ttaacccgtg ggccccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcctaa aggccagggc    480

ccctgttatg attcctcggt ggtctccagt agcgcccagg gtgccacacc ggggggtcga    540

tgcaaccccc tagtcctaga attcactgac gcgggtaaaa gggccagctg ggacgcctcc    600

aaagcatggg gactaagact gtaccgatcc acaaggaccg acccggtgac ccggttctct    660

ttgacccgcc aggtcctcaa tatagggccc cgcgtcccca ttgggcctaa tcccgtgatc    720

attgaccagt tacccccctc ccgacccgtg caggtcatgc tccccaggcc tcctcagcct    780

cctccaccag gcgcagcctc tacagtccct gagactgccc caccttccca acaacctggg    840

acgggagaca ggctgctaaa cctggtaaat ggagcctacc aagctctcaa cctcaccagt    900

cctgacaaaa cccaagagtg ctggttgtgt ctggtagcgg gaccccccta ctacgaaggg    960

gttgccgtcc taggtactta ttccaaccat acctctgccc cagctaactg ctccgtggcc   1020

tcccaacaca agctgaccct gtccgaagtg accggacagg gactctgcgt aggagcagtt   1080

cccaaaaccc atcaggccct gtgtaatacc acccagaaga cgagcaacgg gtcctactat   1140

ctggctgctc ccgccgggac catttgggct tgcaacaccg ggctcactcc ctgcctatct   1200

accactgtgc tcgacctcac caccgattac tgtgtcctgg ttgagctctg gccaaaagtg   1260

acctaccact cccctggtta tgtttatggc cagtttgaag aaaaaaccaa atataaaaga   1320

gaacccgtct cactaactct ggccctacta ttaggaggac tcactatggg cggaattgcc   1380

gccggagtgg gaacagggac taccgcccta gtggccactc agcagttcca acaactccag   1440

gctgccatgc aggatgacct taaagaagtt gaaaagtcca tcactaatct agaaaagatct   1500

ttgacctcct tgtccgaagt agtgttacag aatcgtagag gcctagatct actattccta   1560

aaagagggag gtttgtgtgc tgccttaaaa gaagaatgct gtttctatgc cgaccacaca   1620

ggattggtac gggatagcat ggccaaactt agagaaagat tgagtcagag acaaaaactc   1680

tttgaatccc aacaagggtg gtttgaaggg ctgtttaaca agtccccttg gttcaccacc   1740

ctgatatcca ccatcatggg tcccctgata atcctcttgt taattttact ctttgggcct   1800
```

-continued

```
tgtattctca atcacctggt ccagtttatc aaagacaggg tttcggtagt gcaggccctg   1860

gtcctgactc aacaatatca tcaacttaag acaatagaag attgtgaatc acgtgaataa   1920


<210> SEQ ID NO 2
<211> LENGTH: 639
<212> TYPE: PRT
<213> ORGANISM: Murine leukaemia virus

<400> SEQUENCE: 2

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Val Val Ser Ser Ser Ala Gln Gly Ala Thr
                165                 170                 175

Pro Gly Gly Arg Cys Asn Pro Leu Val Leu Glu Phe Thr Asp Ala Gly
            180                 185                 190

Lys Arg Ala Ser Trp Asp Ala Ser Lys Ala Trp Gly Leu Arg Leu Tyr
        195                 200                 205

Arg Ser Thr Arg Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Ile Asp Gln Leu Pro Pro Ser Arg Pro Val Gln Ile Met Leu Pro Arg
                245                 250                 255

Pro Pro Gln Pro Pro Pro Pro Gly Ala Ala Ser Thr Val Pro Glu Thr
            260                 265                 270

Ala Pro Pro Ser Gln Gln Pro Gly Thr Gly Asp Arg Leu Leu Asn Leu
        275                 280                 285

Val Asn Gly Ala Tyr Gln Ala Leu Asn Leu Thr Ser Pro Asp Lys Thr
    290                 295                 300

Gln Glu Cys Trp Leu Cys Leu Val Ala Gly Pro Pro Tyr Tyr Glu Gly
305                 310                 315                 320

Val Ala Val Leu Gly Thr Tyr Ser Asn His Thr Ser Ala Pro Ala Asn
                325                 330                 335

Cys Ser Val Ala Ser Gln His Lys Leu Thr Leu Ser Glu Val Thr Gly
            340                 345                 350

Gln Gly Leu Cys Val Gly Ala Val Pro Lys Thr His Gln Ala Leu Cys
        355                 360                 365
```

```
Asn Thr Thr Gln Lys Thr Ser Asn Gly Ser Tyr Tyr Leu Ala Ala Pro
    370                 375                 380

Ala Gly Thr Ile Trp Ala Cys Asn Thr Gly Leu Thr Pro Cys Leu Ser
385                 390                 395                 400

Thr Thr Val Leu Asp Leu Thr Thr Asp Tyr Cys Val Leu Val Glu Leu
                405                 410                 415

Trp Pro Lys Val Thr Tyr His Ser Pro Gly Tyr Val Tyr Gly Gln Phe
            420                 425                 430

Glu Glu Lys Thr Lys Tyr Lys Arg Glu Pro Val Ser Leu Thr Leu Ala
        435                 440                 445

Leu Leu Leu Gly Gly Leu Thr Met Gly Gly Ile Ala Ala Gly Val Gly
    450                 455                 460

Thr Gly Thr Thr Ala Leu Val Ala Thr Gln Gln Phe Gln Gln Leu Gln
465                 470                 475                 480

Ala Ala Met Gln Asp Asp Leu Lys Glu Val Lys Lys Ser Ile Thr Asn
                485                 490                 495

Leu Glu Arg Ser Leu Thr Ser Leu Ser Glu Val Val Leu Gln Asn Arg
            500                 505                 510

Arg Gly Leu Asp Leu Leu Phe Leu Lys Glu Gly Gly Leu Cys Ala Ala
        515                 520                 525

Leu Lys Glu Glu Cys Cys Phe Tyr Ala Asp His Thr Gly Leu Val Arg
    530                 535                 540

Asp Ser Met Ala Lys Leu Arg Glu Arg Leu Ser Gln Arg Gln Lys Leu
545                 550                 555                 560

Phe Glu Ser Gln Gln Gly Trp Phe Glu Gly Leu Phe Asn Lys Ser Pro
                565                 570                 575

Trp Phe Thr Thr Leu Ile Ser Thr Ile Met Gly Pro Leu Ile Ile Leu
            580                 585                 590

Leu Leu Ile Leu Leu Phe Gly Pro Cys Ile Leu Asn His Leu Val Gln
        595                 600                 605

Phe Ile Lys Asp Arg Val Ser Val Val Gln Ala Leu Val Leu Thr Gln
    610                 615                 620

Gln Tyr His Gln Leu Lys Thr Ile Glu Asp Cys Glu Ser Arg Glu
625                 630                 635
```

<210> SEQ ID NO 3
<211> LENGTH: 2031
<212> TYPE: DNA
<213> ORGANISM: Artificial
<220> FEATURE:
<223> OTHER INFORMATION: SL3-2/V3 loop chimeric envelope polynucleotide

<400> SEQUENCE: 3

```
atggaaggtc cagcgttctc aaaacccctt aaagataaga ttaacccgtg ggcccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcaagg aatctaccag    480

tgtacaagac ccaacaacaa tacaagaaaa agaatccgta tccagagagg accagggaga    540
```

```
gcatttgtta caataggaaa aataggaaat atgagacaag cacattgtgg gccctgttat    600
gattcctcgg tggtctccag tagcgcccag ggtgccacac cggggggtcg atgcaacccc    660
ctagtcctag aattcactga cgcgggtaaa agggccagct gggacgcctc caaagcatgg    720
ggactaagac tgtaccgatc cacaaggacc gacccggtga cccggttctc tttgacccgc    780
caggtcctca atatagggcc ccgcgtcccc attgggccta atcccgtgat cattgaccag    840
ttacccccct cccgacccgt gcaggtcatg ctccccaggc ctcctcagcc tcctccacca    900
ggcgcagcct ctacagtccc tgagactgcc ccaccttccc aacaacctgg gacgggagac    960
aggctgctaa acctggtaaa tggagcctac caagctctca acctcaccag tcctgacaaa   1020
acccaagagt gctggttgtg tctggtagcg ggaccccct actacgaagg ggttgccgtc   1080
ctaggtactt attccaacca tacctctgcc ccagctaact gctccgtggc ctcccaacac   1140
aagctgaccc tgtccgaagt gaccggacag ggactctgcg taggagcagt tcccaaaacc   1200
catcaggccc tgtgtaatac cacccagaag acgagcaacg ggtcctacta tctggctgct   1260
cccgccggga ccatttgggc ttgcaacacc gggctcactc cctgcctatc taccactgtg   1320
ctcgacctca ccaccgatta ctgtgtcctg gttgagctct ggccaaaagt gacctaccac   1380
tcccctggtt atgtttatgg ccagtttgaa gaaaaaacca aatataaaag agaacccgtc   1440
tcactaactc tggccctact attaggagga ctcactatgg gcggaattgc cgccggagtg   1500
ggaacaggga ctaccgccct agtggccact cagcagttcc aacaactcca ggctgccatg   1560
caggatgacc ttaaagaagt tgaaaagtcc atcactaatc tagaaagatc tttgacctcc   1620
ttgtccgaag tagtgttaca gaatcgtaga ggcctagatc tactattcct aaaagaggga   1680
ggtttgtgtg ctgccttaaa agaagaatgc tgtttctatg ccgaccacac aggattggta   1740
cgggatagca tggccaaact tagagaaaga ttgagtcaga gacaaaaact ctttgaatcc   1800
caacaagggt ggtttgaagg gctgtttaac aagtcccctt ggttcaccac cctgatatcc   1860
accatcatgg gtcccctgat aatcctcttg ttaattttac tctttgggcc ttgtattctc   1920
aatcacctgg tccagtttat caaagacagg gtttcggtag tgcaggccct ggtcctgact   1980
caacaatatc atcaacttaa gacaatagaa gattgtgaat cacgtgaata a            2031
```

<210> SEQ ID NO 4
<211> LENGTH: 1968
<212> TYPE: DNA
<213> ORGANISM: Artificial
<220> FEATURE:
<223> OTHER INFORMATION: SL3-2/V3 loop chimeric envelope polynucleotide

<400> SEQUENCE: 4

```
atggaaggtc cagcgttctc aaaacccctt aaagataaga ttaacccgtg ggccccccta     60
atagtcctgg gaatcttaat gagggcaaga gtatcagtac aacatgacag ccctcatcag    120
gtcttcaatg ttacttggag agttaccaac ttaatgacag gacaaacagc taatgctacc    180
tccctcctgg ggacaatgac cgatgccttt cctaaactgt actttgactt gtgcgattta    240
ataggggacg actgggatga gactggactc gggtgtcgca ctcccggggg aagaaaaagg    300
gcaagaatat ttgacttcta tgtttgcccc ggtcacactg tgctagcagg gtgtggaggg    360
ccgagagagg gctactgtgg caaatgggga tgtgagacca ctggacaggc atactggaag    420
ccatcatcat catgggacct aatttccctt aagcgaggaa acactcctaa aggccagggc    480
ccctgtacaa gacccaacaa caatacaaga aaaagaatcc gtatccagag aggaccaggg    540
agagcatttg ttacaatagg aaaaatagga aatatgagac aagcacattg taacccccta    600
```

```
gtcctagaat tcactgacgc gggtaaaagg gccagctggg acgcctccaa agcatgggga    660

ctaagactgt accgatccac aaggaccgac ccggtgaccc ggttctcttt gacccgccag    720

gtcctcaata tagggccccg cgtccccatt gggcctaatc ccgtgatcat tgaccagtta    780

ccccccctccc gacccgtgca ggtcatgctc cccaggcctc ctcagcctcc tccaccaggc    840

gcagcctcta cagtccctga gactgcccca ccttcccaac aacctgggac gggagacagg    900

ctgctaaacc tggtaaatgg agcctaccaa gctctcaacc tcaccagtcc tgacaaaacc    960

caagagtgct ggttgtgtct ggtagcggga cccccctact acgaaggggt tgccgtccta   1020

ggtacttatt ccaaccatac ctctgcccca gctaactgct ccgtggcctc ccaacacaag   1080

ctgaccctgt ccgaagtgac cggacaggga ctctgcgtag gagcagttcc caaaacccat   1140

caggccctgt gtaataccac ccagaagacg agcaacgggt cctactatct ggctgctccc   1200

gccgggacca tttgggcttg caacaccggg ctcactccct gcctatctac cactgtgctc   1260

gacctcacca ccgattactg tgtcctggtt gagctctggc caaaagtgac ctaccactcc   1320

cctggttatg tttatggcca gtttgaagaa aaaaccaaat ataaaagaga acccgtctca   1380

ctaactctgg ccctactatt aggaggactc actatgggcg gaattgccgc cggagtggga   1440

acagggacta ccgccctagt ggccactcag cagttccaac aactccaggc tgccatgcag   1500

gatgacctta aagaagttga aaagtccatc actaatctag aaagatcttt gacctccttg   1560

tccgaagtag tgttacagaa tcgtagaggc ctagatctac tattcctaaa agagggaggt   1620

ttgtgtgctg ccttaaaaga agaatgctgt ttctatgccg accacacagg attggtacgg   1680

gatagcatgg ccaaacttag agaaagattg agtcagagac aaaaactctt tgaatcccaa   1740

caagggtggt ttgaagggct gtttaacaag tccccttggt tcaccaccct gatatccacc   1800

atcatgggtc ccctgataat cctcttgtta attttactct ttgggccttg tattctcaat   1860

cacctggtcc agtttatcaa agacagggtt tcggtagtgc aggccctggt cctgactcaa   1920

caatatcatc aacttaagac aatagaagat tgtgaatcac gtgaataa                1968
```

<210> SEQ ID NO 5
<211> LENGTH: 1983
<212> TYPE: DNA
<213> ORGANISM: Artificial
<220> FEATURE:
<223> OTHER INFORMATION: SL3-2/V3 loop chimeric envelope polynucleotide

<400> SEQUENCE: 5

```
atggaaggtc cagcgttctc aaaacccctt aaagataaga ttaacccgtg ggcccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgtacaaga    240

cccaacaaca atacaagaaa aagaatccgt atccagagag gaccagggag agcatttgtt    300

acaataggaa aaataggaaa tatgagacaa gcacattgtc gcactcccgg gggaagaaaa    360

agggcaagaa tatttgactt ctatgtttgc cccggtcaca ctgtgctagc agggtgtgga    420

gggccgagag agggctactg tggcaaatgg ggatgtgaga ccactggaca ggcatactgg    480

aagccatcat catcatggga cctaatttcc cttaagcgag gaaacactcc taaaggccag    540

ggcccctgtt atgattcctc ggtggtctcc agtagcgccc agggtgccac accgggggt    600

cgatgcaacc ccctagtcct agaattcact gacgcgggta aaagggccag ctgggacgcc    660

tccaaagcat ggggactaag actgtaccga tccacaagga ccgacccggt gacccggttc    720
```

```
tctttgaccc gccaggtcct caatataggg ccccgcgtcc ccattgggcc taatcccgtg    780

atcattgacc agttaccccc ctcccgaccc gtgcaggtca tgctccccag gcctcctcag    840

cctcctccac caggcgcagc ctctacagtc cctgagactg ccccaccttc ccaacaacct    900

gggacgggag acaggctgct aaacctggta aatggagcct accaagctct caacctcacc    960

agtcctgaca aaacccaaga gtgctggttg tgtctggtag cgggaccccc ctactacgaa   1020

ggggttgccg tcctaggtac ttattccaac catacctctg ccccagctaa ctgctccgtg   1080

gcctcccaac acaagctgac cctgtccgaa gtgaccggac agggactctg cgtaggagca   1140

gttcccaaaa cccatcaggc cctgtgtaat accacccaga agacgagcaa cgggtcctac   1200

tatctggctg ctcccgccgg gaccatttgg gcttgcaaca ccgggctcac tccctgccta   1260

tctaccactg tgctcgacct caccaccgat tactgtgtcc tggttgagct ctggccaaaa   1320

gtgacctacc actcccctgg ttatgtttat ggccagtttg aagaaaaaac caaatataaa   1380

agagaacccg tctcactaac tctggcccta ctattaggag gactcactat gggcggaatt   1440

gccgccggag tgggaacagg gactaccgcc ctagtggcca ctcagcagtt ccaacaactc   1500

caggctgcca tgcaggatga ccttaaagaa gttgaaaagt ccatcactaa tctagaaaga   1560

tctttgacct ccttgtccga agtagtgtta cagaatcgta gaggcctaga tctactattc   1620

ctaaaagagg gaggtttgtg tgctgcctta aaagaagaat gctgtttcta tgccgaccac   1680

acaggattgg tacgggatag catggccaaa cttagagaaa gattgagtca gagacaaaaa   1740

ctctttgaat cccaacaagg gtggtttgaa gggctgttta acaagtcccc ttggttcacc   1800

accctgatat ccaccatcat gggtcccctg ataatcctct tgttaatttt actctttggg   1860

ccttgtattc tcaatcacct ggtccagttt atcaaagaca gggtttcggt agtgcaggcc   1920

ctggtcctga ctcaacaata tcatcaactt aagacaatag aagattgtga atcacgtgaa   1980

taa                                                                 1983
```

<210> SEQ ID NO 6
<211> LENGTH: 676
<212> TYPE: PRT
<213> ORGANISM: Artificial
<220> FEATURE:
<223> OTHER INFORMATION: SL3-2/V3 loop chimeric envelope polynucleotide

<400> SEQUENCE: 6

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140
```

```
Trp Asp Leu Ile Ser Leu Lys Arg Gly Asn Thr Gln Gly Ile Tyr Gln
145                 150                 155                 160

Cys Thr Arg Pro Asn Asn Asn Thr Arg Lys Arg Ile Arg Ile Gln Arg
                165                 170                 175

Gly Pro Gly Arg Ala Phe Val Thr Ile Gly Lys Ile Gly Asn Met Arg
            180                 185                 190

Gln Ala His Cys Gly Pro Cys Tyr Asp Ser Ser Val Val Ser Ser Ser
        195                 200                 205

Ala Gln Gly Ala Thr Pro Gly Gly Arg Cys Asn Pro Leu Val Leu Glu
    210                 215                 220

Phe Thr Asp Ala Gly Lys Arg Ala Ser Trp Asp Ala Ser Lys Ala Trp
225                 230                 235                 240

Gly Leu Arg Leu Tyr Arg Ser Thr Arg Thr Asp Pro Val Thr Arg Phe
                245                 250                 255

Ser Leu Thr Arg Gln Val Leu Asn Ile Gly Pro Arg Val Pro Ile Gly
            260                 265                 270

Pro Asn Pro Val Ile Ile Asp Gln Leu Pro Pro Ser Arg Pro Val Gln
        275                 280                 285

Val Met Leu Pro Arg Pro Pro Gln Pro Pro Pro Pro Gly Ala Ala Ser
    290                 295                 300

Thr Val Pro Glu Thr Ala Pro Pro Ser Gln Gln Pro Gly Thr Gly Asp
305                 310                 315                 320

Arg Leu Leu Asn Leu Val Asn Gly Ala Tyr Gln Ala Leu Asn Leu Thr
                325                 330                 335

Ser Pro Asp Lys Thr Gln Glu Cys Trp Leu Cys Leu Val Ala Gly Pro
            340                 345                 350

Pro Tyr Tyr Glu Gly Val Ala Val Leu Gly Thr Tyr Ser Asn His Thr
        355                 360                 365

Ser Ala Pro Ala Asn Cys Ser Val Ala Ser Gln His Lys Leu Thr Leu
    370                 375                 380

Ser Glu Val Thr Gly Gln Gly Leu Cys Val Gly Ala Val Pro Lys Thr
385                 390                 395                 400

His Gln Ala Leu Cys Asn Thr Thr Gln Lys Thr Ser Asn Gly Ser Tyr
                405                 410                 415

Tyr Leu Ala Ala Pro Ala Gly Thr Ile Trp Ala Cys Asn Thr Gly Leu
            420                 425                 430

Thr Pro Cys Leu Ser Thr Thr Val Leu Asp Leu Thr Thr Asp Tyr Cys
        435                 440                 445

Val Leu Val Glu Leu Trp Pro Lys Val Thr Tyr His Ser Pro Gly Tyr
    450                 455                 460

Val Tyr Gly Gln Phe Glu Glu Lys Thr Lys Tyr Lys Arg Glu Pro Val
465                 470                 475                 480

Ser Leu Thr Leu Ala Leu Leu Leu Gly Gly Leu Thr Met Gly Gly Ile
                485                 490                 495

Ala Ala Gly Val Gly Thr Gly Thr Thr Ala Leu Val Ala Thr Gln Gln
            500                 505                 510

Phe Gln Gln Leu Gln Ala Ala Met Gln Asp Asp Leu Lys Glu Val Glu
        515                 520                 525

Lys Ser Ile Thr Asn Leu Glu Arg Ser Leu Thr Ser Leu Ser Glu Val
    530                 535                 540

Val Leu Gln Asn Arg Arg Gly Leu Asp Leu Leu Phe Leu Lys Glu Gly
545                 550                 555                 560

Gly Leu Cys Ala Ala Leu Lys Glu Glu Cys Cys Phe Tyr Ala Asp His
```

```
                565                 570                 575

Thr Gly Leu Val Arg Asp Ser Met Ala Lys Leu Arg Glu Arg Leu Ser
            580                 585                 590

Gln Arg Gln Lys Leu Phe Glu Ser Gln Gln Gly Trp Phe Glu Gly Leu
        595                 600                 605

Phe Asn Lys Ser Pro Trp Phe Thr Thr Leu Ile Ser Thr Ile Met Gly
    610                 615                 620

Pro Leu Ile Ile Leu Leu Leu Ile Leu Leu Phe Gly Pro Cys Ile Leu
625                 630                 635                 640

Asn His Leu Val Gln Phe Ile Lys Asp Arg Val Ser Val Val Gln Ala
                645                 650                 655

Leu Val Leu Thr Gln Gln Tyr His Gln Leu Lys Thr Ile Glu Asp Cys
            660                 665                 670

Glu Ser Arg Glu
        675


<210> SEQ ID NO 7
<211> LENGTH: 655
<212> TYPE: PRT
<213> ORGANISM: Artificial
<220> FEATURE:
<223> OTHER INFORMATION: SL3-2/V3 loop chimeric envelope polynucleotide

<400> SEQUENCE: 7

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Thr Arg Pro Asn Asn Asn Thr Arg Lys Arg Ile Arg Ile Gln
                165                 170                 175

Arg Gly Pro Gly Arg Ala Phe Val Thr Ile Gly Lys Ile Gly Asn Met
            180                 185                 190

Arg Gln Ala His Cys Asn Pro Leu Val Leu Glu Phe Thr Asp Ala Gly
        195                 200                 205

Lys Arg Ala Ser Trp Asp Ala Ser Lys Ala Trp Gly Leu Arg Leu Tyr
    210                 215                 220

Arg Ser Thr Arg Thr Asp Pro Val Thr Arg Phe Ser Leu Thr Arg Gln
225                 230                 235                 240

Val Leu Asn Ile Gly Pro Arg Val Pro Ile Gly Pro Asn Pro Val Ile
                245                 250                 255
```

```
Ile Asp Gln Leu Pro Pro Ser Arg Pro Val Gln Val Met Leu Pro Arg
            260                 265                 270

Pro Pro Gln Pro Pro Pro Pro Gly Ala Ala Ser Thr Val Pro Glu Thr
        275                 280                 285

Ala Pro Pro Ser Gln Gln Pro Gly Thr Gly Asp Arg Leu Leu Asn Leu
    290                 295                 300

Val Asn Gly Ala Tyr Gln Ala Leu Asn Leu Thr Ser Pro Asp Lys Thr
305                 310                 315                 320

Gln Glu Cys Trp Leu Cys Leu Val Ala Gly Pro Pro Tyr Tyr Glu Gly
                325                 330                 335

Val Ala Val Leu Gly Thr Tyr Ser Asn His Thr Ser Ala Pro Ala Asn
            340                 345                 350

Cys Ser Val Ala Ser Gln His Lys Leu Thr Leu Ser Glu Val Thr Gly
        355                 360                 365

Gln Gly Leu Cys Val Gly Ala Val Pro Lys Thr His Gln Ala Leu Cys
    370                 375                 380

Asn Thr Thr Gln Lys Thr Ser Asn Gly Ser Tyr Tyr Leu Ala Ala Pro
385                 390                 395                 400

Ala Gly Thr Ile Trp Ala Cys Asn Thr Gly Leu Thr Pro Cys Leu Ser
                405                 410                 415

Thr Thr Val Leu Asp Leu Thr Thr Asp Tyr Cys Val Leu Val Glu Leu
            420                 425                 430

Trp Pro Lys Val Thr Tyr His Ser Pro Gly Tyr Val Tyr Gly Gln Phe
        435                 440                 445

Glu Glu Lys Thr Lys Tyr Lys Arg Glu Pro Val Ser Leu Thr Leu Ala
    450                 455                 460

Leu Leu Leu Gly Gly Leu Thr Met Gly Gly Ile Ala Ala Gly Val Gly
465                 470                 475                 480

Thr Gly Thr Thr Ala Leu Val Ala Thr Gln Gln Phe Gln Gln Leu Gln
                485                 490                 495

Ala Ala Met Gln Asp Asp Leu Lys Glu Val Glu Lys Ser Ile Thr Asn
            500                 505                 510

Leu Glu Arg Ser Leu Thr Ser Leu Ser Glu Val Val Leu Gln Asn Arg
        515                 520                 525

Arg Gly Leu Asp Leu Leu Phe Leu Lys Glu Gly Gly Leu Cys Ala Ala
    530                 535                 540

Leu Lys Glu Glu Cys Cys Phe Tyr Ala Asp His Thr Gly Leu Val Arg
545                 550                 555                 560

Asp Ser Met Ala Lys Leu Arg Glu Arg Leu Ser Gln Arg Gln Lys Leu
                565                 570                 575

Phe Glu Ser Gln Gln Gly Trp Phe Glu Gly Leu Phe Asn Lys Ser Pro
            580                 585                 590

Trp Phe Thr Thr Leu Ile Ser Thr Ile Met Gly Pro Leu Ile Ile Leu
        595                 600                 605

Leu Leu Ile Leu Leu Phe Gly Pro Cys Ile Leu Asn His Leu Val Gln
    610                 615                 620

Phe Ile Lys Asp Arg Val Ser Val Val Gln Ala Leu Val Leu Thr Gln
625                 630                 635                 640

Gln Tyr His Gln Leu Lys Thr Ile Glu Asp Cys Glu Ser Arg Glu
                645                 650                 655
```

<210> SEQ ID NO 8
<211> LENGTH: 660
<212> TYPE: PRT

<213> ORGANISM: Artificial
<220> FEATURE:
<223> OTHER INFORMATION: SL3-2/V3 loop chimeric envelope polynucleotide

<400> SEQUENCE: 8

Met Glu Gly Pro Ala Phe Ser Lys Pro Leu Lys Asp Lys Ile Asn Pro
1 5 10 15

Trp Gly Pro Leu Ile Val Leu Gly Ile Leu Met Arg Ala Arg Val Ser
20 25 30

Val Gln His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

Thr Met Thr Asp Ala Phe Pro Lys Leu Tyr Phe Asp Leu Cys Thr Arg
65 70 75 80

Pro Asn Asn Asn Thr Arg Lys Arg Ile Arg Ile Gln Arg Gly Pro Gly
85 90 95

Arg Ala Phe Val Thr Ile Gly Lys Ile Gly Asn Met Arg Gln Ala His
100 105 110

Cys Arg Thr Pro Gly Gly Arg Lys Arg Ala Arg Ile Phe Asp Phe Tyr
115 120 125

Val Cys Pro Gly His Thr Val Leu Ala Gly Cys Gly Gly Pro Arg Glu
130 135 140

Gly Tyr Cys Gly Lys Trp Gly Cys Glu Thr Thr Gly Gln Ala Tyr Trp
145 150 155 160

Lys Pro Ser Ser Ser Trp Asp Leu Ile Ser Leu Lys Arg Gly Asn Thr
165 170 175

Pro Lys Gly Gln Gly Pro Cys Tyr Asp Ser Ser Val Val Ser Ser Ser
180 185 190

Ala Gln Gly Ala Thr Pro Gly Gly Arg Cys Asn Pro Leu Val Leu Glu
195 200 205

Phe Thr Asp Ala Gly Lys Arg Ala Ser Trp Asp Ala Ser Lys Ala Trp
210 215 220

Gly Leu Arg Leu Tyr Arg Ser Thr Arg Thr Asp Pro Val Thr Arg Phe
225 230 235 240

Ser Leu Thr Arg Gln Val Leu Asn Ile Gly Pro Arg Val Pro Ile Gly
245 250 255

Pro Asn Pro Val Ile Ile Asp Gln Leu Pro Pro Ser Arg Pro Val Gln
260 265 270

Val Met Leu Pro Arg Pro Pro Gln Pro Pro Pro Pro Gly Ala Ala Ser
275 280 285

Thr Val Pro Glu Thr Ala Pro Pro Ser Gln Gln Pro Gly Thr Gly Asp
290 295 300

Arg Leu Leu Asn Leu Val Asn Gly Ala Tyr Gln Ala Leu Asn Leu Thr
305 310 315 320

Ser Pro Asp Lys Thr Gln Glu Cys Trp Leu Cys Leu Val Ala Gly Pro
325 330 335

Pro Tyr Tyr Glu Gly Val Ala Val Leu Gly Thr Tyr Ser Asn His Thr
340 345 350

Ser Ala Pro Ala Asn Cys Ser Val Ala Ser Gln His Lys Leu Thr Leu
355 360 365

Ser Glu Val Thr Gly Gln Gly Leu Cys Val Gly Ala Val Pro Lys Thr
370 375 380

His Gln Ala Leu Cys Asn Thr Thr Gln Lys Thr Ser Asn Gly Ser Tyr
385 390 395 400

```
Tyr Leu Ala Ala Pro Ala Gly Thr Ile Trp Ala Cys Asn Thr Gly Leu
                405                 410                 415

Thr Pro Cys Leu Ser Thr Thr Val Leu Asp Leu Thr Thr Asp Tyr Cys
            420                 425                 430

Val Leu Val Glu Leu Trp Pro Lys Val Thr Tyr His Ser Pro Gly Tyr
        435                 440                 445

Val Tyr Gly Gln Phe Glu Glu Lys Thr Lys Tyr Lys Arg Glu Pro Val
    450                 455                 460

Ser Leu Thr Leu Ala Leu Leu Leu Gly Gly Leu Thr Met Gly Gly Ile
465                 470                 475                 480

Ala Ala Gly Val Gly Thr Gly Thr Thr Ala Leu Val Ala Thr Gln Gln
                485                 490                 495

Phe Gln Gln Leu Gln Ala Ala Met Gln Asp Asp Leu Lys Glu Val Glu
            500                 505                 510

Lys Ser Ile Thr Asn Leu Glu Arg Ser Leu Thr Ser Leu Ser Glu Val
        515                 520                 525

Val Leu Gln Asn Arg Arg Gly Leu Asp Leu Leu Phe Leu Lys Glu Gly
    530                 535                 540

Gly Leu Cys Ala Ala Leu Lys Glu Glu Cys Cys Phe Tyr Ala Asp His
545                 550                 555                 560

Thr Gly Leu Val Arg Asp Ser Met Ala Lys Leu Arg Glu Arg Leu Ser
                565                 570                 575

Gln Arg Gln Lys Leu Phe Glu Ser Gln Gln Gly Trp Phe Glu Gly Leu
            580                 585                 590

Phe Asn Lys Ser Pro Trp Phe Thr Thr Leu Ile Ser Thr Ile Met Gly
        595                 600                 605

Pro Leu Ile Ile Leu Leu Leu Ile Leu Leu Phe Gly Pro Cys Ile Leu
    610                 615                 620

Asn His Leu Val Gln Phe Ile Lys Asp Arg Val Ser Val Val Gln Ala
625                 630                 635                 640

Leu Val Leu Thr Gln Gln Tyr His Gln Leu Lys Thr Ile Glu Asp Cys
                645                 650                 655

Glu Ser Arg Glu
            660


<210> SEQ ID NO 9
<211> LENGTH: 36
<212> TYPE: PRT
<213> ORGANISM: Artificial
<220> FEATURE:
<223> OTHER INFORMATION: V3 loop variant

<400> SEQUENCE: 9

Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35


<210> SEQ ID NO 10
<211> LENGTH: 36
<212> TYPE: PRT
<213> ORGANISM: Artificial
<220> FEATURE:
<223> OTHER INFORMATION: V3 loop variant

<400> SEQUENCE: 10
```

Cys Thr Arg Pro Asn Asn Asn Ile Arg Ile Arg His Arg Ile Gln Arg
1 5 10 15

Gly Pro Gly Arg Ala Phe Val Thr Ile Gly Lys Ile Gly Asn Met Arg
20 25 30

Gln Ala His Cys
35

<210> SEQ ID NO 11
<211> LENGTH: 37
<212> TYPE: PRT
<213> ORGANISM: Artificial
<220> FEATURE:
<223> OTHER INFORMATION: V3 loop variant

<400> SEQUENCE: 11

Cys Thr Arg Pro Asn Asn Asn Asn Thr Arg Lys Arg Ile Arg Ile Gln
1 5 10 15

Arg Gly Pro Gly Arg Ala Phe Val Thr Ile Gly Lys Ile Gly Asn Met
20 25 30

Arg Gln Ala His Cys
35

<210> SEQ ID NO 12
<211> LENGTH: 35
<212> TYPE: PRT
<213> ORGANISM: Artificial
<220> FEATURE:
<223> OTHER INFORMATION: V3 loop variant

<400> SEQUENCE: 12

Cys Ser Arg Pro Asn Asn Asn Thr Arg Lys Ser Ile His Met Gly Pro
1 5 10 15

Gly Lys Ala Phe Tyr Thr Thr Gly Asp Thr Ile Gly Asp Ile Arg Gln
20 25 30

Ala His Cys
35

<210> SEQ ID NO 13
<211> LENGTH: 35
<212> TYPE: PRT
<213> ORGANISM: Artificial
<220> FEATURE:
<223> OTHER INFORMATION: V3 loop variant

<400> SEQUENCE: 13

Cys Thr Arg Pro Asn Asn Asn Thr Arg Lys Ser Ile His Ile Gly Pro
1 5 10 15

Gly Arg Ala Phe Tyr Thr Thr Gly Asp Ile Ile Gly Asp Ile Arg Gln
20 25 30

Ala His Cys
35

<210> SEQ ID NO 14
<211> LENGTH: 35
<212> TYPE: PRT
<213> ORGANISM: Artificial
<220> FEATURE:
<223> OTHER INFORMATION: V3 loop variant

<400> SEQUENCE: 14

Cys Thr Arg Pro Ser Asn Asn Thr Arg Lys Ser Ile Pro Val Gly Pro
1 5 10 15

```
Gly Lys Ala Leu Tyr Ala Thr Gly Ala Ile Ile Gly Asn Ile Arg Gln
            20                  25                  30

Ala His Cys
        35


<210> SEQ ID NO 15
<211> LENGTH: 35
<212> TYPE: PRT
<213> ORGANISM: Artificial
<220> FEATURE:
<223> OTHER INFORMATION: V3 loop variant

<400> SEQUENCE: 15

Cys Ile Arg Pro Asn Asn Asn Thr Arg Lys Ser Val Arg Ile Gly Pro
1               5                   10                  15

Gly Gln Thr Phe Tyr Ala Thr Gly Glu Ile Ile Gly Asp Ile Arg Ala
            20                  25                  30

Ala Tyr Cys
        35


<210> SEQ ID NO 16
<211> LENGTH: 40
<212> TYPE: PRT
<213> ORGANISM: Artificial
<220> FEATURE:
<223> OTHER INFORMATION: V3 loop variant

<400> SEQUENCE: 16

Pro Val Ser Ile Asn Cys Thr Arg Pro Gly Asn Asn Thr Arg Arg Ser
1               5                   10                  15

Val Arg Ile Gly Pro Gly Gln Thr Phe Tyr Ala Thr Gly Asp Ile Thr
            20                  25                  30

Gly Asp Ile Arg Gln Ala His Cys
        35                  40


<210> SEQ ID NO 17
<211> LENGTH: 35
<212> TYPE: PRT
<213> ORGANISM: Artificial
<220> FEATURE:
<223> OTHER INFORMATION: V3 loop variant

<400> SEQUENCE: 17

Cys Thr Arg Pro Asn Asn Asn Thr Arg Lys Arg Ile Ser Ile Gly Pro
1               5                   10                  15

Gly Arg Ser Phe Tyr Thr Thr Arg Gln Ile Val Gly Asp Ile Arg Gln
            20                  25                  30

Ala His Cys
        35


<210> SEQ ID NO 18
<211> LENGTH: 35
<212> TYPE: PRT
<213> ORGANISM: Artificial
<220> FEATURE:
<223> OTHER INFORMATION: V3 loop variant

<400> SEQUENCE: 18

Cys Thr Arg Pro Asn Asn Asn Thr Arg Lys Ser Ile His Ile Gly Pro
1               5                   10                  15

Gly Lys Ala Phe Tyr Ala Thr Gly Asp Val Ile Gly Asp Ile Arg Lys
            20                  25                  30

Ala His Cys
```

-continued

35

<210> SEQ ID NO 19
<211> LENGTH: 50
<212> TYPE: PRT
<213> ORGANISM: Artificial
<220> FEATURE:
<223> OTHER INFORMATION: V3 loop variant
<220> FEATURE:
<221> NAME/KEY: MISC_FEATURE
<223> OTHER INFORMATION: X can be any naturally occuring aminoacid
<220> FEATURE:
<221> NAME/KEY: MISC_FEATURE
<222> LOCATION: (43)..(43)
<223> OTHER INFORMATION: X can be any naturally occuring aminoacid

<400> SEQUENCE: 19

Asn Glu Ser Val Ala Ile Asn Cys Thr Arg Pro Val Asn Asn Thr Arg
1 5 10 15

Lys Ser Ile Tyr Ile Gly Pro Gly Arg Ala Phe His Thr Thr Gly Arg
20 25 30

Ile Ile Gly Asp Ile Arg Lys Ala His Cys Xaa Ile Ser Arg Ala Gln
35 40 45

Trp Asn
50

<210> SEQ ID NO 20
<211> LENGTH: 37
<212> TYPE: PRT
<213> ORGANISM: Artificial
<220> FEATURE:
<223> OTHER INFORMATION: V3 loop variant

<400> SEQUENCE: 20

Ile Val Cys Thr Arg Pro Gly Asn Asn Thr Arg Lys Gly Ile His Ile
1 5 10 15

Gly Pro Gly Arg Ala Phe Tyr Ala Ser Glu Gly Ile Val Gly Asp Ile
20 25 30

Arg Gln Ala His Cys
35

<210> SEQ ID NO 21
<211> LENGTH: 36
<212> TYPE: PRT
<213> ORGANISM: Artificial
<220> FEATURE:
<223> OTHER INFORMATION: V3 loop variant

<400> SEQUENCE: 21

Cys Thr Arg Pro Asn Asn Asn Ile Arg Ile Arg His Ile His Ile Gly
1 5 10 15

Pro Gly Arg Ala Phe His Ala Thr Glu Ala Ala Thr Gly Asp Ile Arg
20 25 30

Gln Ala His Cys
35

<210> SEQ ID NO 22
<211> LENGTH: 40
<212> TYPE: PRT
<213> ORGANISM: Artificial
<220> FEATURE:
<223> OTHER INFORMATION: V3 loop variant

<400> SEQUENCE: 22

Cys Thr Arg Pro Asn Asn Asn Thr Arg Lys Gly Ile His Ile Gly Pro

```
1               5                   10                  15

Gly Lys Ala Tyr Tyr Thr Thr Gly Asp Ile Ile Gly Asp Ile Arg Gln
            20                  25                  30

Ala His Cys Asn Ile Ser Arg Ala
        35                  40


<210> SEQ ID NO 23
<211> LENGTH: 40
<212> TYPE: PRT
<213> ORGANISM: Artificial
<220> FEATURE:
<223> OTHER INFORMATION: V3 loop variant

<400> SEQUENCE: 23

Ile Asn Cys Thr Arg Pro Asn Asn Asn Ile Arg Lys Arg Ile His Ile
1               5                   10                  15

Gly Pro Gly Arg Ala Phe Tyr Thr Thr Gly Lys Ile Ile Gly Gly Ile
            20                  25                  30

Arg Gln Ala His Cys Asn Leu Ser
        35                  40


<210> SEQ ID NO 24
<211> LENGTH: 41
<212> TYPE: PRT
<213> ORGANISM: Artificial
<220> FEATURE:
<223> OTHER INFORMATION: V3 loop variant

<400> SEQUENCE: 24

Asn Glu Ser Val Thr Ile Thr Cys Ile Arg Pro Tyr Asn Asn Thr Arg
1               5                   10                  15

Gln Ser Val His Met Gly Pro Gly Arg Ala Leu Tyr Thr Gln Glu Ile
            20                  25                  30

Thr Gly Asp Ile Arg Arg Ala His Cys
        35                  40


<210> SEQ ID NO 25
<211> LENGTH: 41
<212> TYPE: PRT
<213> ORGANISM: Artificial
<220> FEATURE:
<223> OTHER INFORMATION: V3 loop variant
<220> FEATURE:
<221> NAME/KEY: MISC_FEATURE
<223> OTHER INFORMATION: X can be any naturally occuring aminoacid
<220> FEATURE:
<221> NAME/KEY: MISC_FEATURE
<222> LOCATION: (1)..(1)
<223> OTHER INFORMATION: X can be any naturally occuring aminoacid

<400> SEQUENCE: 25

Xaa Ser Val Glu Ile Val Cys Thr Arg Pro Asn Asn Asn Thr Arg Glu
1               5                   10                  15

Ser Ile Arg Ile Gly Pro Gly Gln Thr Phe Tyr Ala Thr Gly Asp Ile
            20                  25                  30

Ile Gly Asn Ile Arg Gln Ala His Cys
        35                  40


<210> SEQ ID NO 26
<211> LENGTH: 40
<212> TYPE: PRT
<213> ORGANISM: Artificial
<220> FEATURE:
<223> OTHER INFORMATION: V3 loop variant
```

<400> SEQUENCE: 26

```
Cys Ile Arg Pro Gly Asn Asn Thr Arg Arg Ser Ile His Ile Gln Pro
1               5                   10                  15

Gly Arg Ala Phe Tyr Ala Ser Gly Gly Ile Ile Gly Asp Ile Arg Glu
            20                  25                  30

Ala His Cys Thr Leu Asn Ile Pro
        35                  40
```

<210> SEQ ID NO 27
<211> LENGTH: 40
<212> TYPE: PRT
<213> ORGANISM: Artificial
<220> FEATURE:
<223> OTHER INFORMATION: V3 loop variant

<400> SEQUENCE: 27

```
Val Glu Ile Glu Cys Thr Arg Pro Gly Asn Asn Thr Arg Lys Ser Ile
1               5                   10                  15

Arg Ile Gly Pro Gly Gln Thr Phe Tyr Ala Thr Gly Asp Ile Ile Gly
            20                  25                  30

Asp Ile Arg Gln Ala His Cys Asn
        35                  40
```

<210> SEQ ID NO 28
<211> LENGTH: 35
<212> TYPE: PRT
<213> ORGANISM: Artificial
<220> FEATURE:
<223> OTHER INFORMATION: V3 loop variant

<400> SEQUENCE: 28

```
Cys Thr Arg Pro Asn Asn Asn Thr Arg Lys Ser Ile Pro Met Gly Pro
1               5                   10                  15

Gly Lys Ala Phe Tyr Ala Thr Gly Asp Ile Ile Gly Asp Ile Arg Lys
            20                  25                  30

Ala Phe Cys
        35
```

<210> SEQ ID NO 29
<211> LENGTH: 44
<212> TYPE: PRT
<213> ORGANISM: Artificial
<220> FEATURE:
<223> OTHER INFORMATION: V3 loop variant

<400> SEQUENCE: 29

```
Gln Leu Lys Glu Pro Val Glu Ile Asn Cys Thr Arg Pro Asn Asn Thr
1               5                   10                  15

Thr Arg Arg Gly Ile Tyr Ile Gly Pro Gly Arg Thr Ile Tyr Ala Gly
            20                  25                  30

Glu Lys Ile Ile Gly Asp Ile Arg Arg Ala Tyr Cys
        35                  40
```

<210> SEQ ID NO 30
<211> LENGTH: 40
<212> TYPE: PRT
<213> ORGANISM: Artificial
<220> FEATURE:
<223> OTHER INFORMATION: V3 loop variant

<400> SEQUENCE: 30

```
Ile Asn Cys Thr Arg Pro Asn Asn Asn Thr Arg Lys Ser Ile His Leu
1               5                   10                  15
```

```
Gly Pro Gly Gln Ala Phe Tyr Ala Thr Gly Asp Ile Ile Gly Asp Ile
            20                  25                  30

Arg Lys Ala His Cys Asn Val Ser
        35                  40


<210> SEQ ID NO 31
<211> LENGTH: 40
<212> TYPE: PRT
<213> ORGANISM: Artificial
<220> FEATURE:
<223> OTHER INFORMATION: V3 loop variant

<400> SEQUENCE: 31

Cys Thr Arg Pro Asn Asn Asn Thr Arg Lys Ser Ile His Met Gly Pro
1               5                   10                  15

Gly Arg Ala Phe Tyr Ala Thr Gly Asp Ile Ile Gly Asn Ile Arg Gln
            20                  25                  30

Ala His Cys Asn Ile Ser Arg Glu
        35                  40


<210> SEQ ID NO 32
<211> LENGTH: 35
<212> TYPE: PRT
<213> ORGANISM: Artificial
<220> FEATURE:
<223> OTHER INFORMATION: V3 loop variant

<400> SEQUENCE: 32

Cys Thr Arg Pro Asn Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35


<210> SEQ ID NO 33
<211> LENGTH: 640
<212> TYPE: PRT
<213> ORGANISM: Artificial
<220> FEATURE:
<223> OTHER INFORMATION: SL3-2/V3 chimeric envelope polypeptide

<400> SEQUENCE: 33

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
```

-continued

```
    130                 135                 140

Trp Asp Leu Ile Ser Leu Lys Arg Gly Asn Thr Gln Gly Ile Tyr Gln
145                 150                 155                 160

Gly Pro Cys Tyr Asp Ser Ser Val Val Ser Ser Ser Ala Gln Gly Ala
                165                 170                 175

Thr Pro Gly Gly Arg Cys Asn Pro Leu Val Leu Glu Phe Thr Asp Ala
            180                 185                 190

Gly Lys Arg Ala Ser Trp Asp Ala Ser Lys Ala Trp Gly Leu Arg Leu
        195                 200                 205

Tyr Arg Ser Thr Arg Thr Asp Pro Val Thr Arg Phe Ser Leu Thr Arg
    210                 215                 220

Gln Val Leu Asn Ile Gly Pro Arg Val Pro Ile Gly Pro Asn Pro Val
225                 230                 235                 240

Ile Ile Asp Gln Leu Pro Pro Ser Arg Pro Val Gln Val Met Leu Pro
                245                 250                 255

Arg Pro Pro Gln Pro Pro Pro Pro Gly Ala Ala Ser Thr Val Pro Glu
            260                 265                 270

Thr Ala Pro Pro Ser Gln Gln Pro Gly Thr Gly Asp Arg Leu Leu Asn
        275                 280                 285

Leu Val Asn Gly Ala Tyr Gln Ala Leu Asn Leu Thr Ser Pro Asp Lys
    290                 295                 300

Thr Gln Glu Cys Trp Leu Cys Leu Val Ala Gly Pro Pro Tyr Tyr Glu
305                 310                 315                 320

Gly Val Ala Val Leu Gly Thr Tyr Ser Asn His Thr Ser Ala Pro Ala
                325                 330                 335

Asn Cys Ser Val Ala Ser Gln His Lys Leu Thr Leu Ser Glu Val Thr
            340                 345                 350

Gly Gln Gly Leu Cys Val Gly Ala Val Pro Lys Thr His Gln Ala Leu
        355                 360                 365

Cys Asn Thr Thr Gln Lys Thr Ser Asn Gly Ser Tyr Tyr Leu Ala Ala
    370                 375                 380

Pro Ala Gly Thr Ile Trp Ala Cys Asn Thr Gly Leu Thr Pro Cys Leu
385                 390                 395                 400

Ser Thr Thr Val Leu Asp Leu Thr Thr Asp Tyr Cys Val Leu Val Glu
                405                 410                 415

Leu Trp Pro Lys Val Thr Tyr His Ser Pro Gly Tyr Val Tyr Gly Gln
            420                 425                 430

Phe Glu Glu Lys Thr Lys Tyr Lys Arg Glu Pro Val Ser Leu Thr Leu
        435                 440                 445

Ala Leu Leu Leu Gly Gly Leu Thr Met Gly Gly Ile Ala Ala Gly Val
    450                 455                 460

Gly Thr Gly Thr Thr Ala Leu Val Ala Thr Gln Gln Phe Gln Gln Leu
465                 470                 475                 480

Gln Ala Ala Met Gln Asp Asp Leu Lys Glu Val Glu Lys Ser Ile Thr
                485                 490                 495

Asn Leu Glu Arg Ser Leu Thr Ser Leu Ser Glu Val Val Leu Gln Asn
            500                 505                 510

Arg Arg Gly Leu Asp Leu Leu Phe Leu Lys Glu Gly Gly Leu Cys Ala
        515                 520                 525

Ala Leu Lys Glu Glu Cys Cys Phe Tyr Ala Asp His Thr Gly Leu Val
    530                 535                 540

Arg Asp Ser Met Ala Lys Leu Arg Glu Arg Leu Ser Gln Arg Gln Lys
545                 550                 555                 560
```

-continued

```
Leu Phe Glu Ser Gln Gln Gly Trp Phe Glu Gly Leu Phe Asn Lys Ser
                565                 570                 575

Pro Trp Phe Thr Thr Leu Ile Ser Thr Ile Met Gly Pro Leu Ile Ile
            580                 585                 590

Leu Leu Leu Ile Leu Leu Phe Gly Pro Cys Ile Leu Asn His Leu Val
        595                 600                 605

Gln Phe Ile Lys Asp Arg Val Ser Val Val Gln Ala Leu Val Leu Thr
    610                 615                 620

Gln Gln Tyr His Gln Leu Lys Thr Ile Glu Asp Cys Glu Ser Arg Glu
625                 630                 635                 640


<210> SEQ ID NO 34
<211> LENGTH: 619
<212> TYPE: PRT
<213> ORGANISM: Artificial
<220> FEATURE:
<223> OTHER INFORMATION: SL3-2/V3 chimeric envelope polypeptide

<400> SEQUENCE: 34

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Asn Pro Leu Val Leu Glu Phe Thr Asp Ala Gly Lys Arg Ala Ser
                165                 170                 175

Trp Asp Ala Ser Lys Ala Trp Gly Leu Arg Leu Tyr Arg Ser Thr Arg
            180                 185                 190

Thr Asp Pro Val Thr Arg Phe Ser Leu Thr Arg Gln Val Leu Asn Ile
        195                 200                 205

Gly Pro Arg Val Pro Ile Gly Pro Asn Pro Val Ile Ile Asp Gln Leu
    210                 215                 220

Pro Pro Ser Arg Pro Val Gln Val Met Leu Pro Arg Pro Pro Gln Pro
225                 230                 235                 240

Pro Pro Pro Gly Ala Ala Ser Thr Val Pro Glu Thr Ala Pro Pro Ser
                245                 250                 255

Gln Gln Pro Gly Thr Gly Asp Arg Leu Leu Asn Leu Val Asn Gly Ala
            260                 265                 270

Tyr Gln Ala Leu Asn Leu Thr Ser Pro Asp Lys Thr Gln Glu Cys Trp
        275                 280                 285

Leu Cys Leu Val Ala Gly Pro Pro Tyr Tyr Glu Gly Val Ala Val Leu
```

```
    290                 295                 300

Gly Thr Tyr Ser Asn His Thr Ser Ala Pro Ala Asn Cys Ser Val Ala
305                 310                 315                 320

Ser Gln His Lys Leu Thr Leu Ser Glu Val Thr Gly Gln Gly Leu Cys
                325                 330                 335

Val Gly Ala Val Pro Lys Thr His Gln Ala Leu Cys Asn Thr Thr Gln
            340                 345                 350

Lys Thr Ser Asn Gly Ser Tyr Tyr Leu Ala Ala Pro Ala Gly Thr Ile
        355                 360                 365

Trp Ala Cys Asn Thr Gly Leu Thr Pro Cys Leu Ser Thr Thr Val Leu
    370                 375                 380

Asp Leu Thr Thr Asp Tyr Cys Val Leu Val Glu Leu Trp Pro Lys Val
385                 390                 395                 400

Thr Tyr His Ser Pro Gly Tyr Val Tyr Gly Gln Phe Glu Glu Lys Thr
                405                 410                 415

Lys Tyr Lys Arg Glu Pro Val Ser Leu Thr Leu Ala Leu Leu Leu Gly
            420                 425                 430

Gly Leu Thr Met Gly Gly Ile Ala Ala Gly Val Gly Thr Gly Thr Thr
        435                 440                 445

Ala Leu Val Ala Thr Gln Gln Phe Gln Gln Leu Gln Ala Ala Met Gln
    450                 455                 460

Asp Asp Leu Lys Glu Val Glu Lys Ser Ile Thr Asn Leu Glu Arg Ser
465                 470                 475                 480

Leu Thr Ser Leu Ser Glu Val Val Leu Gln Asn Arg Arg Gly Leu Asp
                485                 490                 495

Leu Leu Phe Leu Lys Glu Gly Gly Leu Cys Ala Ala Leu Lys Glu Glu
            500                 505                 510

Cys Cys Phe Tyr Ala Asp His Thr Gly Leu Val Arg Asp Ser Met Ala
        515                 520                 525

Lys Leu Arg Glu Arg Leu Ser Gln Arg Gln Lys Leu Phe Glu Ser Gln
    530                 535                 540

Gln Gly Trp Phe Glu Gly Leu Phe Asn Lys Ser Pro Trp Phe Thr Thr
545                 550                 555                 560

Leu Ile Ser Thr Ile Met Gly Pro Leu Ile Ile Leu Leu Leu Ile Leu
                565                 570                 575

Leu Phe Gly Pro Cys Ile Leu Asn His Leu Val Gln Phe Ile Lys Asp
            580                 585                 590

Arg Val Ser Val Val Gln Ala Leu Val Leu Thr Gln Gln Tyr His Gln
        595                 600                 605

Leu Lys Thr Ile Glu Asp Cys Glu Ser Arg Glu
    610                 615
```

<210> SEQ ID NO 35
<211> LENGTH: 624
<212> TYPE: PRT
<213> ORGANISM: Artificial
<220> FEATURE:
<223> OTHER INFORMATION: SL3-2/V3 chimeric envelope polypeptide

<400> SEQUENCE: 35

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45
```

-continued

```
Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Arg Thr Pro
65                  70                  75                  80

Gly Gly Arg Lys Arg Ala Arg Ile Phe Asp Phe Tyr Val Cys Pro Gly
                85                  90                  95

His Thr Val Leu Ala Gly Cys Gly Gly Pro Arg Glu Gly Tyr Cys Gly
            100                 105                 110

Lys Trp Gly Cys Glu Thr Thr Gly Gln Ala Tyr Trp Lys Pro Ser Ser
        115                 120                 125

Ser Trp Asp Leu Ile Ser Leu Lys Arg Gly Asn Thr Pro Lys Gly Gln
    130                 135                 140

Gly Pro Cys Tyr Asp Ser Ser Val Val Ser Ser Ser Ala Gln Gly Ala
145                 150                 155                 160

Thr Pro Gly Gly Arg Cys Asn Pro Leu Val Leu Glu Phe Thr Asp Ala
                165                 170                 175

Gly Lys Arg Ala Ser Trp Asp Ala Ser Lys Ala Trp Gly Leu Arg Leu
            180                 185                 190

Tyr Arg Ser Thr Gly Ile Asp Pro Val Thr Arg Phe Ser Leu Thr Arg
        195                 200                 205

Gln Val Leu Asn Ile Gly Pro Arg Val Pro Ile Gly Pro Asn Pro Val
    210                 215                 220

Ile Ile Asp Gln Leu Pro Pro Ser Arg Pro Val Gln Val Met Leu Pro
225                 230                 235                 240

Arg Pro Pro Gln Pro Pro Pro Pro Gly Ala Ala Ser Thr Val Pro Glu
                245                 250                 255

Thr Ala Pro Pro Ser Gln Gln Pro Gly Thr Gly Asp Arg Leu Leu Asn
            260                 265                 270

Leu Val Asn Gly Ala Tyr Gln Ala Leu Asn Leu Thr Ser Pro Asp Lys
        275                 280                 285

Thr Gln Glu Cys Trp Leu Cys Leu Val Ala Gly Pro Pro Tyr Tyr Glu
    290                 295                 300

Gly Val Ala Val Leu Gly Thr Tyr Ser Asn His Thr Ser Ala Pro Ala
305                 310                 315                 320

Asn Cys Ser Val Ala Ser Gln His Lys Leu Thr Leu Ser Glu Val Thr
                325                 330                 335

Gly Gln Gly Leu Cys Val Gly Ala Val Pro Lys Thr His Gln Ala Leu
            340                 345                 350

Cys Asn Thr Thr Gln Lys Thr Ser Asn Gly Ser Tyr Tyr Leu Ala Ala
        355                 360                 365

Pro Ala Gly Thr Ile Trp Ala Cys Asn Thr Gly Leu Thr Pro Cys Leu
    370                 375                 380

Ser Thr Thr Val Leu Asp Leu Thr Thr Asp Tyr Cys Val Leu Val Glu
385                 390                 395                 400

Leu Trp Pro Lys Val Thr Tyr His Ser Pro Gly Tyr Val Tyr Gly Gln
                405                 410                 415

Phe Glu Glu Lys Thr Lys Tyr Lys Arg Glu Pro Val Ser Leu Thr Leu
            420                 425                 430

Ala Leu Leu Leu Gly Gly Leu Thr Met Gly Gly Ile Ala Ala Gly Val
        435                 440                 445

Gly Thr Gly Thr Thr Ala Leu Val Ala Thr Gln Gln Phe Gln Gln Leu
    450                 455                 460

Gln Ala Ala Met Gln Asp Asp Leu Lys Glu Val Glu Lys Ser Ile Thr
```

465 470 475 480

Asn Leu Glu Arg Ser Leu Thr Ser Leu Ser Glu Val Val Leu Gln Asn
485 490 495

Arg Arg Gly Leu Asp Leu Leu Phe Leu Lys Glu Gly Gly Leu Cys Ala
500 505 510

Ala Leu Lys Glu Glu Cys Cys Phe Tyr Ala Asp His Thr Gly Leu Val
515 520 525

Arg Asp Ser Met Ala Lys Leu Arg Glu Arg Leu Ser Gln Arg Gln Lys
530 535 540

Leu Phe Glu Ser Gln Gln Gly Trp Phe Glu Gly Leu Phe Asn Lys Ser
545 550 555 560

Pro Trp Phe Thr Thr Leu Ile Ser Thr Ile Met Gly Pro Leu Ile Ile
565 570 575

Leu Leu Leu Ile Leu Leu Phe Gly Pro Cys Ile Leu Asn His Leu Val
580 585 590

Gln Phe Ile Lys Asp Arg Val Ser Val Val Gln Ala Leu Val Leu Thr
595 600 605

Gln Gln Tyr His Gln Leu Lys Thr Ile Glu Asp Cys Glu Ser Arg Glu
610 615 620

<210> SEQ ID NO 36
<211> LENGTH: 640
<212> TYPE: PRT
<213> ORGANISM: Artificial
<220> FEATURE:
<223> OTHER INFORMATION: SL3-2/V3 chimeric envelope polypeptide

<400> SEQUENCE: 36

Met Glu Gly Pro Ala Phe Ser Lys Pro Leu Lys Asp Lys Ile Asn Pro
1 5 10 15

Trp Gly Pro Leu Ile Val Leu Gly Ile Leu Met Arg Ala Arg Val Ser
20 25 30

Val Gln His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

Thr Met Thr Asp Ala Phe Pro Lys Leu Tyr Phe Asp Leu Cys Asp Leu
65 70 75 80

Ile Gly Asp Asp Trp Asp Glu Thr Gly Leu Gly Cys Arg Thr Pro Gly
85 90 95

Gly Arg Lys Arg Ala Arg Ile Phe Asp Phe Tyr Val Cys Pro Gly His
100 105 110

Thr Val Leu Ala Gly Cys Gly Gly Pro Arg Glu Gly Tyr Cys Gly Lys
115 120 125

Trp Gly Cys Glu Thr Thr Gly Gln Ala Tyr Trp Lys Pro Ser Ser Ser
130 135 140

Trp Asp Leu Ile Ser Leu Lys Arg Gly Asn Thr Gln Gly Ile Tyr Gln
145 150 155 160

Gly Pro Cys Tyr Asp Ser Ser Val Val Ser Ser Ser Ala Gln Gly Ala
165 170 175

Thr Pro Gly Gly Arg Cys Asn Pro Leu Val Leu Glu Phe Thr Asp Ala
180 185 190

Gly Lys Arg Ala Ser Trp Asp Ala Ser Lys Ala Trp Gly Leu Arg Leu
195 200 205

Tyr Arg Ser Thr Gly Ile Asp Pro Val Thr Arg Phe Ser Leu Thr Arg
210 215 220

```
Gln Val Leu Asn Ile Gly Pro Arg Val Pro Ile Gly Pro Asn Pro Val
225                 230                 235                 240

Ile Ile Asp Gln Leu Pro Pro Ser Arg Pro Val Gln Val Met Leu Pro
                245                 250                 255

Arg Pro Pro Gln Pro Pro Pro Pro Gly Ala Ala Ser Thr Val Pro Glu
            260                 265                 270

Thr Ala Pro Pro Ser Gln Gln Pro Gly Thr Gly Asp Arg Leu Leu Asn
        275                 280                 285

Leu Val Asn Gly Ala Tyr Gln Ala Leu Asn Leu Thr Ser Pro Asp Lys
    290                 295                 300

Thr Gln Glu Cys Trp Leu Cys Leu Val Ala Gly Pro Pro Tyr Tyr Glu
305                 310                 315                 320

Gly Val Ala Val Leu Gly Thr Tyr Ser Asn His Thr Ser Ala Pro Ala
                325                 330                 335

Asn Cys Ser Val Ala Ser Gln His Lys Leu Thr Leu Ser Glu Val Thr
            340                 345                 350

Gly Gln Gly Leu Cys Val Gly Ala Val Pro Lys Thr His Gln Ala Leu
        355                 360                 365

Cys Asn Thr Thr Gln Lys Thr Ser Asn Gly Ser Tyr Tyr Leu Ala Ala
    370                 375                 380

Pro Ala Gly Thr Ile Trp Ala Cys Asn Thr Gly Leu Thr Pro Cys Leu
385                 390                 395                 400

Ser Thr Thr Val Leu Asp Leu Thr Thr Asp Tyr Cys Val Leu Val Glu
                405                 410                 415

Leu Trp Pro Lys Val Thr Tyr His Ser Pro Gly Tyr Val Tyr Gly Gln
            420                 425                 430

Phe Glu Glu Lys Thr Lys Tyr Lys Arg Glu Pro Val Ser Leu Thr Leu
        435                 440                 445

Ala Leu Leu Leu Gly Gly Leu Thr Met Gly Gly Ile Ala Ala Gly Val
    450                 455                 460

Gly Thr Gly Thr Thr Ala Leu Val Ala Thr Gln Gln Phe Gln Gln Leu
465                 470                 475                 480

Gln Ala Ala Met Gln Asp Asp Leu Lys Glu Val Glu Lys Ser Ile Thr
                485                 490                 495

Asn Leu Glu Arg Ser Leu Thr Ser Leu Ser Glu Val Val Leu Gln Asn
            500                 505                 510

Arg Arg Gly Leu Asp Leu Leu Phe Leu Lys Glu Gly Gly Leu Cys Ala
        515                 520                 525

Ala Leu Lys Glu Glu Cys Cys Phe Tyr Ala Asp His Thr Gly Leu Val
    530                 535                 540

Arg Asp Ser Met Ala Lys Leu Arg Glu Arg Leu Ser Gln Arg Gln Lys
545                 550                 555                 560

Leu Phe Glu Ser Gln Gln Gly Trp Phe Glu Gly Leu Phe Asn Lys Ser
                565                 570                 575

Pro Trp Phe Thr Thr Leu Ile Ser Thr Ile Met Gly Pro Leu Ile Ile
            580                 585                 590

Leu Leu Leu Ile Leu Leu Phe Gly Pro Cys Ile Leu Asn His Leu Val
        595                 600                 605

Gln Phe Ile Lys Asp Arg Val Ser Val Val Gln Ala Leu Val Leu Thr
    610                 615                 620

Gln Gln Tyr His Gln Leu Lys Thr Ile Glu Asp Cys Glu Ser Arg Glu
625                 630                 635                 640
```

<210> SEQ ID NO 37
<211> LENGTH: 619
<212> TYPE: PRT
<213> ORGANISM: Artificial
<220> FEATURE:
<223> OTHER INFORMATION: SL3-2/V3 chimeric envelope polypeptide

<400> SEQUENCE: 37

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Asn Pro Leu Val Leu Glu Phe Thr Asp Ala Gly Lys Arg Ala Ser
                165                 170                 175

Trp Asp Ala Ser Lys Ala Trp Gly Leu Arg Leu Tyr Arg Ser Thr Gly
            180                 185                 190

Ile Asp Pro Val Thr Arg Phe Ser Leu Thr Arg Gln Val Leu Asn Ile
        195                 200                 205

Gly Pro Arg Val Pro Ile Gly Pro Asn Pro Val Ile Ile Asp Gln Leu
    210                 215                 220

Pro Pro Ser Arg Pro Val Gln Val Met Leu Pro Arg Pro Pro Gln Pro
225                 230                 235                 240

Pro Pro Pro Gly Ala Ala Ser Thr Val Pro Glu Thr Ala Pro Pro Ser
                245                 250                 255

Gln Gln Pro Gly Thr Gly Asp Arg Leu Leu Asn Leu Val Asn Gly Ala
            260                 265                 270

Tyr Gln Ala Leu Asn Leu Thr Ser Pro Asp Lys Thr Gln Glu Cys Trp
        275                 280                 285

Leu Cys Leu Val Ala Gly Pro Pro Tyr Tyr Glu Gly Val Ala Val Leu
    290                 295                 300

Gly Thr Tyr Ser Asn His Thr Ser Ala Pro Ala Asn Cys Ser Val Ala
305                 310                 315                 320

Ser Gln His Lys Leu Thr Leu Ser Glu Val Thr Gly Gln Gly Leu Cys
                325                 330                 335

Val Gly Ala Val Pro Lys Thr His Gln Ala Leu Cys Asn Thr Thr Gln
            340                 345                 350

Lys Thr Ser Asn Gly Ser Tyr Tyr Leu Ala Ala Pro Ala Gly Thr Ile
        355                 360                 365

Trp Ala Cys Asn Thr Gly Leu Thr Pro Cys Leu Ser Thr Thr Val Leu
    370                 375                 380
```

```
Asp Leu Thr Thr Asp Tyr Cys Val Leu Val Glu Leu Trp Pro Lys Val
385                 390                 395                 400

Thr Tyr His Ser Pro Gly Tyr Val Tyr Gly Gln Phe Glu Glu Lys Thr
                405                 410                 415

Lys Tyr Lys Arg Glu Pro Val Ser Leu Thr Leu Ala Leu Leu Leu Gly
            420                 425                 430

Gly Leu Thr Met Gly Gly Ile Ala Ala Gly Val Gly Thr Gly Thr Thr
        435                 440                 445

Ala Leu Val Ala Thr Gln Gln Phe Gln Gln Leu Gln Ala Ala Met Gln
    450                 455                 460

Asp Asp Leu Lys Glu Val Glu Lys Ser Ile Thr Asn Leu Glu Arg Ser
465                 470                 475                 480

Leu Thr Ser Leu Ser Glu Val Val Leu Gln Asn Arg Arg Gly Leu Asp
                485                 490                 495

Leu Leu Phe Leu Lys Glu Gly Gly Leu Cys Ala Ala Leu Lys Glu Glu
            500                 505                 510

Cys Cys Phe Tyr Ala Asp His Thr Gly Leu Val Arg Asp Ser Met Ala
        515                 520                 525

Lys Leu Arg Glu Arg Leu Ser Gln Arg Gln Lys Leu Phe Glu Ser Gln
    530                 535                 540

Gln Gly Trp Phe Glu Gly Leu Phe Asn Lys Ser Pro Trp Phe Thr Thr
545                 550                 555                 560

Leu Ile Ser Thr Ile Met Gly Pro Leu Ile Ile Leu Leu Leu Ile Leu
                565                 570                 575

Leu Phe Gly Pro Cys Ile Leu Asn His Leu Val Gln Phe Ile Lys Asp
            580                 585                 590

Arg Val Ser Val Val Gln Ala Leu Val Leu Thr Gln Gln Tyr His Gln
        595                 600                 605

Leu Lys Thr Ile Glu Asp Cys Glu Ser Arg Glu
    610                 615


<210> SEQ ID NO 38
<211> LENGTH: 624
<212> TYPE: PRT
<213> ORGANISM: Artificial
<220> FEATURE:
<223> OTHER INFORMATION: SL3-2/V3 chimeric envelope polypeptide

<400> SEQUENCE: 38

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Arg Thr Pro
65                  70                  75                  80

Gly Gly Arg Lys Arg Ala Arg Ile Phe Asp Phe Tyr Val Cys Pro Gly
                85                  90                  95

His Thr Val Leu Ala Gly Cys Gly Gly Pro Arg Glu Gly Tyr Cys Gly
            100                 105                 110

Lys Trp Gly Cys Glu Thr Thr Gly Gln Ala Tyr Trp Lys Pro Ser Ser
        115                 120                 125
```

-continued

```
Ser Trp Asp Leu Ile Ser Leu Lys Arg Gly Asn Thr Pro Lys Gly Gln
    130                 135                 140

Gly Pro Cys Tyr Asp Ser Ser Val Val Ser Ser Ser Ala Gln Gly Ala
145                 150                 155                 160

Thr Pro Gly Gly Arg Cys Asn Pro Leu Val Leu Glu Phe Thr Asp Ala
                165                 170                 175

Gly Lys Arg Ala Ser Trp Asp Ala Ser Lys Ala Trp Gly Leu Arg Leu
            180                 185                 190

Tyr Arg Ser Thr Arg Thr Asp Pro Val Thr Arg Phe Ser Leu Thr Arg
        195                 200                 205

Gln Val Leu Asn Ile Gly Pro Arg Val Pro Ile Gly Pro Asn Pro Val
    210                 215                 220

Ile Ile Asp Gln Leu Pro Pro Ser Arg Pro Val Gln Val Met Leu Pro
225                 230                 235                 240

Arg Pro Pro Gln Pro Pro Pro Pro Gly Ala Ala Ser Thr Val Pro Glu
                245                 250                 255

Thr Ala Pro Pro Ser Gln Gln Pro Gly Thr Gly Asp Arg Leu Leu Asn
            260                 265                 270

Leu Val Asn Gly Ala Tyr Gln Ala Leu Asn Leu Thr Ser Pro Asp Lys
        275                 280                 285

Thr Gln Glu Cys Trp Leu Cys Leu Val Ala Gly Pro Pro Tyr Tyr Glu
    290                 295                 300

Gly Val Ala Val Leu Gly Thr Tyr Ser Asn His Thr Ser Ala Pro Ala
305                 310                 315                 320

Asn Cys Ser Val Ala Ser Gln His Lys Leu Thr Leu Ser Glu Val Thr
                325                 330                 335

Gly Gln Gly Leu Cys Val Gly Ala Val Pro Lys Thr His Gln Ala Leu
            340                 345                 350

Cys Asn Thr Thr Gln Lys Thr Ser Asn Gly Ser Tyr Tyr Leu Ala Ala
        355                 360                 365

Pro Ala Gly Thr Ile Trp Ala Cys Asn Thr Gly Leu Thr Pro Cys Leu
    370                 375                 380

Ser Thr Thr Val Leu Asp Leu Thr Thr Asp Tyr Cys Val Leu Val Glu
385                 390                 395                 400

Leu Trp Pro Lys Val Thr Tyr His Ser Pro Gly Tyr Val Tyr Gly Gln
                405                 410                 415

Phe Glu Glu Lys Thr Lys Tyr Lys Arg Glu Pro Val Ser Leu Thr Leu
            420                 425                 430

Ala Leu Leu Leu Gly Gly Leu Thr Met Gly Gly Ile Ala Ala Gly Val
        435                 440                 445

Gly Thr Gly Thr Thr Ala Leu Val Ala Thr Gln Gln Phe Gln Gln Leu
    450                 455                 460

Gln Ala Ala Met Gln Asp Asp Leu Lys Glu Val Glu Lys Ser Ile Thr
465                 470                 475                 480

Asn Leu Glu Arg Ser Leu Thr Ser Leu Ser Glu Val Val Leu Gln Asn
                485                 490                 495

Arg Arg Gly Leu Asp Leu Leu Phe Leu Lys Glu Gly Gly Leu Cys Ala
            500                 505                 510

Ala Leu Lys Glu Glu Cys Cys Phe Tyr Ala Asp His Thr Gly Leu Val
        515                 520                 525

Arg Asp Ser Met Ala Lys Leu Arg Glu Arg Leu Ser Gln Arg Gln Lys
    530                 535                 540

Leu Phe Glu Ser Gln Gln Gly Trp Phe Glu Gly Leu Phe Asn Lys Ser
545                 550                 555                 560
```

-continued

```
Pro Trp Phe Thr Thr Leu Ile Ser Thr Ile Met Gly Pro Leu Ile Ile
                565                 570                 575

Leu Leu Leu Ile Leu Leu Phe Gly Pro Cys Ile Leu Asn His Leu Val
            580                 585                 590

Gln Phe Ile Lys Asp Arg Val Ser Val Val Gln Ala Leu Val Leu Thr
        595                 600                 605

Gln Gln Tyr His Gln Leu Lys Thr Ile Glu Asp Cys Glu Ser Arg Glu
    610                 615                 620


<210> SEQ ID NO 39
<211> LENGTH: 609
<212> TYPE: PRT
<213> ORGANISM: Artificial
<220> FEATURE:
<223> OTHER INFORMATION: Envelope sequence derived from SL3-2

<400> SEQUENCE: 39

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Leu Val Leu Glu Phe Thr Asp
145                 150                 155                 160

Ala Gly Lys Arg Ala Ser Trp Asp Ala Ser Lys Ala Trp Gly Leu Arg
                165                 170                 175

Leu Tyr Arg Ser Thr Arg Thr Asp Pro Val Thr Arg Phe Ser Leu Thr
            180                 185                 190

Arg Gln Val Leu Asn Ile Gly Pro Arg Val Pro Ile Gly Pro Asn Pro
        195                 200                 205

Val Ile Ile Asp Gln Leu Pro Pro Ser Arg Pro Val Gln Ile Met Leu
    210                 215                 220

Pro Arg Pro Pro Gln Pro Pro Pro Pro Gly Ala Ala Ser Thr Val Pro
225                 230                 235                 240

Glu Thr Ala Pro Pro Ser Gln Gln Pro Gly Thr Gly Asp Arg Leu Leu
                245                 250                 255

Asn Leu Val Asn Gly Ala Tyr Gln Ala Leu Asn Leu Thr Ser Pro Asp
            260                 265                 270

Lys Thr Gln Glu Cys Trp Leu Cys Leu Val Ala Gly Pro Pro Tyr Tyr
        275                 280                 285

Glu Gly Val Ala Val Leu Gly Thr Tyr Ser Asn His Thr Ser Ala Pro
    290                 295                 300
```

Ala Asn Cys Ser Val Ala Ser Gln His Lys Leu Thr Leu Ser Glu Val
305 310 315 320

Thr Gly Gln Gly Leu Cys Val Gly Ala Val Pro Lys Thr His Gln Ala
325 330 335

Leu Cys Asn Thr Thr Gln Lys Thr Ser Asn Gly Ser Tyr Tyr Leu Ala
340 345 350

Ala Pro Ala Gly Thr Ile Trp Ala Cys Asn Thr Gly Leu Thr Pro Cys
355 360 365

Leu Ser Thr Thr Val Leu Asp Leu Thr Thr Asp Tyr Cys Val Leu Val
370 375 380

Glu Leu Trp Pro Lys Val Thr Tyr His Ser Pro Gly Tyr Val Tyr Gly
385 390 395 400

Gln Phe Glu Glu Lys Thr Lys Tyr Lys Arg Glu Pro Val Ser Leu Thr
405 410 415

Leu Ala Leu Leu Leu Gly Gly Leu Thr Met Gly Gly Ile Ala Ala Gly
420 425 430

Val Gly Thr Gly Thr Thr Ala Leu Val Ala Thr Gln Gln Phe Gln Gln
435 440 445

Leu Gln Ala Ala Met Gln Asp Asp Leu Lys Glu Val Lys Lys Ser Ile
450 455 460

Thr Asn Leu Glu Arg Ser Leu Thr Ser Leu Ser Glu Val Val Leu Gln
465 470 475 480

Asn Arg Arg Gly Leu Asp Leu Leu Phe Leu Lys Glu Gly Gly Leu Cys
485 490 495

Ala Ala Leu Lys Glu Glu Cys Cys Phe Tyr Ala Asp His Thr Gly Leu
500 505 510

Val Arg Asp Ser Met Ala Lys Leu Arg Glu Arg Leu Ser Gln Arg Gln
515 520 525

Lys Leu Phe Glu Ser Gln Gln Gly Trp Phe Glu Gly Leu Phe Asn Lys
530 535 540

Ser Pro Trp Phe Thr Thr Leu Ile Ser Thr Ile Met Gly Pro Leu Ile
545 550 555 560

Ile Leu Leu Leu Ile Leu Leu Phe Gly Pro Cys Ile Leu Asn His Leu
565 570 575

Val Gln Phe Ile Lys Asp Arg Val Ser Val Val Gln Ala Leu Val Leu
580 585 590

Thr Gln Gln Tyr His Gln Leu Lys Thr Ile Glu Asp Cys Glu Ser Arg
595 600 605

Glu

<210> SEQ ID NO 40
<211> LENGTH: 611
<212> TYPE: PRT
<213> ORGANISM: Artificial
<220> FEATURE:
<223> OTHER INFORMATION: Envelope sequence derived from MCF 247

<400> SEQUENCE: 40

Met Glu Gly Pro Ala Phe Ser Lys Pro Leu Lys Asp Lys Ile Asn Pro
1 5 10 15

Trp Gly Pro Leu Ile Val Leu Gly Ile Leu Ile Arg Ala Gly Val Ser
20 25 30

Val Arg His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

```
Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Leu Val Leu Glu Phe Thr Asp
145                 150                 155                 160

Ala Gly Lys Lys Ala Ser Trp Asp Gly Pro Lys Val Trp Gly Leu Arg
                165                 170                 175

Leu Tyr Arg Ser Thr Gly Ile Asp Pro Val Thr Arg Phe Ser Leu Thr
            180                 185                 190

Arg Gln Val Leu Asn Ile Gly Pro Arg Val Pro Ile Gly Pro Asn Pro
        195                 200                 205

Val Ile Thr Asp Gln Leu Pro Pro Ser Arg Pro Val Gln Ile Met Leu
    210                 215                 220

Pro Arg Pro Pro Gln Pro Pro Pro Pro Gly Ala Ala Ser Thr Val Pro
225                 230                 235                 240

Glu Thr Ala Pro Pro Ser Gln Gln Pro Gly Thr Gly Asp Arg Leu Leu
                245                 250                 255

Asn Leu Val Lys Gly Ala Tyr Gln Ala Leu Asn Leu Thr Ser Pro Asp
            260                 265                 270

Lys Thr Gln Glu Cys Trp Leu Cys Leu Val Ser Gly Pro Pro Tyr Tyr
        275                 280                 285

Glu Gly Val Ala Val Leu Gly Thr Tyr Ser Asn His Thr Ser Ala Pro
    290                 295                 300

Ala Asn Cys Ser Val Ala Ser Gln His Lys Leu Thr Leu Ser Glu Val
305                 310                 315                 320

Thr Gly Gln Gly Leu Cys Ile Gly Ala Val Pro Lys Thr His Gln Ala
                325                 330                 335

Leu Cys Asn Thr Thr Gln Lys Thr Ser Asp Gly Ser Tyr Tyr Leu Ala
            340                 345                 350

Ala Pro Thr Gly Thr Thr Trp Ala Cys Ser Thr Gly Leu Thr Pro Cys
        355                 360                 365

Ile Ser Thr Thr Ile Leu Asp Leu Thr Thr Asp Tyr Cys Val Leu Val
    370                 375                 380

Glu Leu Trp Pro Arg Val Thr Tyr His Ser Pro Ser Tyr Val Tyr His
385                 390                 395                 400

Gln Phe Glu Arg Arg Ala Lys Tyr Lys Arg Glu Pro Val Ser Leu Thr
                405                 410                 415

Leu Ala Leu Leu Leu Gly Gly Leu Thr Met Gly Gly Ile Ala Ala Gly
            420                 425                 430

Val Gly Thr Gly Thr Thr Ala Leu Val Ala Thr Gln Gln Phe Gln Gln
        435                 440                 445

Phe Gln Ala Ala Met Gln Asp Asp Leu Lys Glu Val Glu Lys Ser Ile
    450                 455                 460

Thr Asn Leu Glu Lys Ser Leu Thr Ser Leu Ser Glu Val Val Leu Gln
465                 470                 475                 480

Asn Arg Arg Gly Leu Asp Leu Leu Phe Leu Lys Glu Gly Gly Leu Cys
```

```
            485                 490                 495

Ala Ala Leu Lys Glu Glu Cys Cys Phe Tyr Ala Asp His Thr Gly Leu
        500                 505                 510

Val Arg Asp Ser Met Ala Lys Leu Arg Glu Arg Leu Ser Gln Arg Gln
    515                 520                 525

Lys Leu Phe Glu Ser Gln Gln Gly Trp Phe Glu Gly Leu Phe Asn Lys
    530                 535                 540

Ser Pro Trp Phe Thr Thr Leu Ile Ser Thr Ile Met Gly Pro Leu Ile
545                 550                 555                 560

Ile Leu Leu Leu Ile Leu Leu Phe Gly Pro Cys Ile Leu Asn Arg Leu
                565                 570                 575

Val Gln Phe Val Lys Asp Arg Ile Ser Val Val Gln Ala Leu Val Leu
            580                 585                 590

Thr Gln Gln Tyr His Gln Leu Lys Ser Ile Asp Pro Glu Glu Val Glu
        595                 600                 605

Ser Arg Glu
    610


<210> SEQ ID NO 41
<211> LENGTH: 625
<212> TYPE: PRT
<213> ORGANISM: Artificial
<220> FEATURE:
<223> OTHER INFORMATION: Envelope sequence derived from Feline B

<400> SEQUENCE: 41

Met Glu Gly Pro Thr His Pro Lys Pro Ser Lys Asp Lys Thr Phe Ser
1               5                   10                  15

Trp Asp Leu Met Ile Leu Val Gly Val Leu Leu Arg Leu Asp Val Gly
            20                  25                  30

Met Ala Asn Pro Ser Pro His Gln Ile Tyr Asn Val Thr Trp Thr Ile
        35                  40                  45

Thr Asn Leu Val Thr Gly Thr Lys Ala Asn Ala Thr Ser Met Leu Gly
    50                  55                  60

Thr Leu Thr Asp Ala Phe Pro Thr Met Tyr Phe Asp Leu Cys Asp Ile
65                  70                  75                  80

Ile Gly Asn Thr Trp Asn Pro Ser Asp Gln Glu Pro Phe Pro Gly Tyr
                85                  90                  95

Gly Cys Asp Gln Pro Met Arg Arg Trp Gln Gln Arg Asn Thr Pro Phe
            100                 105                 110

Tyr Val Cys Pro Gly His Ala Asn Arg Lys Gln Cys Gly Gly Pro Gln
        115                 120                 125

Asp Gly Phe Cys Ala Val Trp Gly Cys Glu Thr Thr Gly Glu Thr Tyr
    130                 135                 140

Trp Arg Pro Thr Ser Ser Trp Asp Tyr Ile Thr Val Lys Lys Gly Leu
145                 150                 155                 160

Ile Leu Gln Phe Thr Gln Lys Gly Arg Gln Thr Ser Trp Asp Gly Pro
                165                 170                 175

Lys Ser Trp Gly Leu Arg Leu Tyr Arg Ser Gly Tyr Asp Pro Ile Ala
            180                 185                 190

Leu Phe Ser Val Ser Arg Gln Val Met Thr Ile Thr Leu Pro Gln Ala
        195                 200                 205

Met Gly Pro Asn Leu Val Leu Pro Asp Gln Lys Pro Pro Ser Arg Gln
    210                 215                 220

Ser Gln Ile Glu Ser Arg Val Thr Pro His His Ser Gln Gly Asn Gly
225                 230                 235                 240
```

-continued

```
Gly Thr Pro Gly Ile Thr Leu Val Asn Ala Ser Ile Ala Pro Leu Ser
                245                 250                 255

Thr Pro Val Thr Pro Ala Ser Pro Lys Arg Ile Gly Thr Gly Asn Arg
            260                 265                 270

Leu Ile Asn Leu Val Gln Gly Thr Tyr Leu Ala Leu Asn Val Thr Asn
        275                 280                 285

Pro Asn Lys Thr Lys Asp Cys Trp Leu Cys Leu Val Ser Arg Pro Pro
    290                 295                 300

Tyr Tyr Glu Gly Ile Ala Val Leu Gly Asn Tyr Ser Asn Gln Thr Asn
305                 310                 315                 320

Pro Pro Pro Ser Cys Leu Ser Asp Pro Gln His Lys Leu Thr Ile Ser
                325                 330                 335

Glu Val Ser Gly Gln Gly Ser Cys Ile Gly Thr Val Pro Lys Thr His
            340                 345                 350

Gln Ala Leu Cys Lys Lys Thr Gln Lys Gly His Lys Gly Thr His Tyr
        355                 360                 365

Leu Ala Ala Pro Ser Gly Thr Tyr Trp Ala Cys Asn Thr Gly Leu Thr
    370                 375                 380

Pro Cys Ile Ser Met Ala Val Leu Asn Trp Thr Ser Asp Phe Cys Val
385                 390                 395                 400

Leu Ile Glu Leu Trp Pro Arg Val Thr Tyr His Gln Pro Glu Tyr Val
                405                 410                 415

Tyr Thr His Phe Asp Lys Thr Val Arg Leu Arg Arg Glu Pro Ile Ser
            420                 425                 430

Leu Thr Val Ala Leu Met Leu Gly Gly Leu Thr Val Gly Gly Ile Ala
        435                 440                 445

Ala Gly Val Gly Thr Gly Thr Lys Ala Leu Leu Glu Thr Ala Gln Phe
    450                 455                 460

Gly Gln Leu Gln Met Ala Met His Thr Asp Ile Gln Ala Leu Glu Glu
465                 470                 475                 480

Ser Ile Ser Ala Leu Glu Lys Ser Leu Thr Ser Leu Ser Glu Val Val
                485                 490                 495

Leu Gln Asn Arg Arg Gly Leu Asp Ile Leu Phe Leu Gln Glu Gly Gly
            500                 505                 510

Leu Cys Ala Ala Leu Lys Glu Glu Cys Cys Phe Tyr Ala Asp His Thr
        515                 520                 525

Gly Leu Val Arg Asp Asn Met Ala Lys Leu Arg Glu Arg Leu Lys Gln
    530                 535                 540

Arg Gln Gln Leu Phe Asp Ser Gln Gln Gly Trp Phe Glu Gly Trp Phe
545                 550                 555                 560

Asn Lys Ser Pro Trp Phe Thr Thr Leu Ile Ser Ser Ile Met Gly Pro
                565                 570                 575

Leu Leu Ile Leu Leu Leu Ile Leu Leu Phe Gly Pro Cys Ile Leu Asn
            580                 585                 590

Arg Leu Val Gln Phe Val Lys Asp Arg Ile Ser Val Val Gln Ala Leu
        595                 600                 605

Ile Leu Thr Gln Gln Tyr Gln Gln Ile Lys Gln Tyr Asp Pro Asp Gln
    610                 615                 620

Pro
625
```

<210> SEQ ID NO 42
<211> LENGTH: 2031
<212> TYPE: DNA

<213> ORGANISM: Artificial
<220> FEATURE:
<223> OTHER INFORMATION: SL3-2/V3 loop chimeric envelope

<400> SEQUENCE: 42
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggatga gactggactc gggtgtcgca ctcccggggg aagaaaaagg 300
gcaagaatat ttgacttcta tgtttgcccc ggtcacactg tgctagcagg gtgtggaggg 360
ccgagagagg gctactgtgg caaatgggga tgtgagacca ctggacaggc atactggaag 420
ccatcatcat catgggacct aatttccctt aagcgaggaa acactcaagg aatctaccag 480
tgtacaagac ccaacaacaa tacaagaaaa agaatccgta tccagagagg accagggaga 540
gcatttgtta caataggaaa aataggaaat atgagacaag cacattgtgg gccctgttat 600
gattcctcgg tggtctccag tagcgcccag ggtgccacac cgggggtcg atgcaacccc 660 ctagtcctag aattcactga cgcgggtaaa agggccagct gggacgcctc caaagcatgg 720
ggactaagac tgtaccgatc cacagggatc gacccggtga cccggttctc tttgacccgc 780
caggtcctca atatagggcc ccgcgtcccc attgggccta atcccgtgat cattgaccag 840 ttaccccccct cccgacccgt gcaggtcatg ctccccaggc ctcctcagcc tcctccacca 900
ggcgcagcct ctacagtccc tgagactgcc ccaccttccc aacaacctgg gacgggagac 960
aggctgctaa acctggtaaa tggagcctac caagctctca acctcaccag tcctgacaaa 1020
acccaagagt gctggttgtg tctggtagcg ggacccccct actacgaagg ggttgccgtc 1080
ctaggtactt attccaacca tacctctgcc ccagctaact gctccgtggc ctcccaacac 1140
aagctgaccc tgtccgaagt gaccggacag ggactctgcg taggagcagt tcccaaaacc 1200
catcaggccc tgtgtaatac cacccagaag acgagcaacg ggtcctacta tctggctgct 1260
cccgccggga ccatttgggc ttgcaacacc gggctcactc cctgcctatc taccactgtg 1320
ctcgacctca ccaccgatta ctgtgtcctg gttgagctct ggccaaaagt gacctaccac 1380
tcccctggtt atgtttatgg ccagtttgaa gaaaaaacca aatataaaag agaacccgtc 1440
tcactaactc tggccctact attaggagga ctcactatgg gcggaattgc cgccggagtg 1500
ggaacaggga ctaccgccct agtggccact cagcagttcc aacaactcca ggctgccatg 1560
caggatgacc ttaaagaagt tgaaaagtcc atcactaatc tagaaagatc tttgacctcc 1620
ttgtccgaag tagtgttaca gaatcgtaga ggcctagatc tactattcct aaaagaggga 1680
ggtttgtgtg ctgccttaaa agaagaatgc tgtttctatg ccgaccacac aggattggta 1740
cgggatagca tggccaaact tagagaaaga ttgagtcaga gacaaaaact ctttgaatcc 1800
caacaagggt ggtttgaagg gctgtttaac aagtcccctt ggttcaccac cctgatatcc 1860
accatcatgg gtcccctgat aatcctcttg ttaattttac tctttgggcc ttgtattctc 1920
aatcacctgg tccagtttat caaagacagg gtttcggtag tgcaggccct ggtcctgact 1980
caacaatatc atcaacttaa gacaatagaa gattgtgaat cacgtgaata a 2031

<210> SEQ ID NO 43
<211> LENGTH: 1968
<212> TYPE: DNA
<213> ORGANISM: artificial
<220> FEATURE:

-continued

<223> OTHER INFORMATION: SL3-2/V3 loop chimeric envelope

<400> SEQUENCE: 43

```
atggaaggtc cagcgttctc aaaacccctt aaagataaga ttaacccgtg ggcccccta     60
atagtcctgg gaatcttaat gagggcaaga gtatcagtac aacatgacag ccctcatcag   120
gtcttcaatg ttacttggag agttaccaac ttaatgacag gacaaacagc taatgctacc   180
tccctcctgg ggacaatgac cgatgccttt cctaaactgt actttgactt gtgcgattta   240
ataggggacg actgggatga gactggactc gggtgtcgca ctcccggggg aagaaaaagg   300
gcaagaatat ttgacttcta tgtttgcccc ggtcacactg tgctagcagg gtgtggaggg   360
ccgagagagg gctactgtgg caaatgggga tgtgagacca ctggacaggc atactggaag   420
ccatcatcat catgggacct aatttccctt aagcgaggaa acactcctaa aggccagggc   480
ccctgtacaa gacccaacaa caatacaaga aaaagaatcc gtatccagag aggaccaggg   540
agagcatttg ttacaatagg aaaaatagga aatatgagac aagcacattg taacccccta   600
gtcctagaat tcactgacgc gggtaaaagg gccagctggg acgcctccaa agcatgggga   660
ctaagactgt accgatccac agggatcgac ccggtgaccc ggttctcttt gacccgccag   720
gtcctcaata tagggccccg cgtccccatt gggcctaatc ccgtgatcat tgaccagtta   780
ccccccctccc gacccgtgca ggtcatgctc cccaggcctc ctcagcctcc tccaccaggc   840
gcagcctcta cagtccctga gactgcccca ccttcccaac aacctgggac gggagacagg   900
ctgctaaacc tggtaaatgg agcctaccaa gctctcaacc tcaccagtcc tgacaaaacc   960
caagagtgct ggttgtgtct ggtagcggga cccccctact acgaaggggt tgccgtccta  1020
ggtacttatt ccaaccatac ctctgcccca gctaactgct ccgtggcctc ccaacacaag  1080
ctgaccctgt ccgaagtgac cggacaggga ctctgcgtag gagcagttcc caaaacccat  1140
caggccctgt gtaataccac ccagaagacg agcaacgggt cctactatct ggctgctccc  1200
gccgggacca tttgggcttg caacaccggg ctcactccct gcctatctac cactgtgctc  1260
gacctcacca ccgattactg tgtcctggtt gagctctggc caaaagtgac ctaccactcc  1320
cctggttatg tttatggcca gtttgaagaa aaaaccaaat ataaaagaga acccgtctca  1380
ctaactctgg ccctactatt aggaggactc actatgggcg gaattgccgc cggagtggga  1440
acagggacta ccgccctagt ggccactcag cagttccaac aactccaggc tgccatgcag  1500
gatgacctta aagaagttga aaagtccatc actaatctag aaagatcttt gacctccttg  1560
tccgaagtag tgttacagaa tcgtagaggc ctagatctac tattcctaaa agagggaggt  1620
ttgtgtgctg ccttaaaaga agaatgctgt ttctatgccg accacacagg attggtacgg  1680
gatagcatgg ccaaacttag agaaagattg agtcagagac aaaaactctt tgaatcccaa  1740
caagggtggt ttgaagggct gtttaacaag tccccttggt tcaccaccct gatatccacc  1800
atcatgggtc ccctgataat cctcttgtta attttactct ttgggccttg tattctcaat  1860
cacctggtcc agtttatcaa agacagggtt tcggtagtgc aggccctggt cctgactcaa  1920
caatatcatc aacttaagac aatagaagat tgtgaatcac gtgaataa               1968
```

<210> SEQ ID NO 44
<211> LENGTH: 1983
<212> TYPE: DNA
<213> ORGANISM: artificial
<220> FEATURE:
<223> OTHER INFORMATION: SL3-2/V3 loop chimeric envelope

<400> SEQUENCE: 44

-continued

```
atggaaggtc cagcgttctc aaaacccctt aaagataaga ttaacccgtg gggcccccta     60
atagtcctgg gaatcttaat gagggcaaga gtatcagtac aacatgacag ccctcatcag    120
gtcttcaatg ttacttggag agttaccaac ttaatgacag gacaaacagc taatgctacc    180
tccctcctgg ggacaatgac cgatgccttt cctaaactgt actttgactt gtgtacaaga    240
cccaacaaca atacaagaaa aagaatccgt atccagagag gaccagggag agcatttgtt    300
acaataggaa aaataggaaa tatgagacaa gcacattgtc gcactcccgg gggaagaaaa    360
agggcaagaa tatttgactt ctatgtttgc cccggtcaca ctgtgctagc agggtgtgga    420
gggccgagag agggctactg tggcaaatgg ggatgtgaga ccactggaca ggcatactgg    480
aagccatcat catcatggga cctaatttcc cttaagcgag gaaacactcc taaaggccag    540
ggcccctgtt atgattcctc ggtggtctcc agtagcgccc agggtgccac accggggggt    600
cgatgcaacc ccctagtcct agaattcact gacgcgggta aaagggccag ctgggacgcc    660
tccaaagcat ggggactaag actgtaccga tccacaggga tcgacccggt gacccggttc    720
tctttgaccc gccaggtcct caatataggg ccccgcgtcc ccattgggcc taatcccgtg    780
atcattgacc agttaccccc ctcccgaccc gtgcaggtca tgctccccag gcctcctcag    840
cctcctccac caggcgcagc ctctacagtc cctgagactg ccccaccttc ccaacaacct    900
gggacgggag acaggctgct aaacctggta aatggagcct accaagctct caacctcacc    960
agtcctgaca aaacccaaga gtgctggttg tgtctggtag cgggaccccc ctactacgaa   1020
ggggttgccg tcctaggtac ttattccaac catacctctg ccccagctaa ctgctccgtg   1080
gcctcccaac acaagctgac cctgtccgaa gtgaccggac agggactctg cgtaggagca   1140
gttcccaaaa cccatcaggc cctgtgtaat accacccaga agacgagcaa cgggtcctac   1200
tatctggctg ctcccgccgg gaccatttgg gcttgcaaca ccgggctcac tccctgccta   1260
tctaccactg tgctcgacct caccaccgat tactgtgtcc tggttgagct ctggccaaaa   1320
gtgacctacc actcccctgg ttatgtttat ggccagtttg aagaaaaaac caaatataaa   1380
agagaacccg tctcactaac tctggcccta ctattaggag gactcactat gggcggaatt   1440
gccgccggag tgggaacagg gactaccgcc ctagtggcca ctcagcagtt ccaacaactc   1500
caggctgcca tgcaggatga ccttaaagaa gttgaaaagt ccatcactaa tctagaaaga   1560
tctttgacct ccttgtccga agtagtgtta cagaatcgta gaggcctaga tctactattc   1620
ctaaaagagg gaggtttgtg tgctgcctta aaagaagaat gctgtttcta tgccgaccac   1680
acaggattgg tacgggatag catggccaaa cttagagaaa gattgagtca gagacaaaaa   1740
ctctttgaat cccaacaagg gtggtttgaa gggctgttta acaagtcccc ttggttcacc   1800
accctgatat ccaccatcat gggtcccctg ataatcctct tgttaatttt actctttggg   1860
ccttgtattc tcaatcacct ggtccagttt atcaaagaca gggtttcggt agtgcaggcc   1920
ctggtcctga ctcaacaata tcatcaactt aagacaatag aagattgtga atcacgtgaa   1980
taa                                                                 1983
```

<210> SEQ ID NO 45
<211> LENGTH: 676
<212> TYPE: PRT
<213> ORGANISM: Artificial
<220> FEATURE:
<223> OTHER INFORMATION: SL3-2/V3 loop chimeric envelope

<400> SEQUENCE: 45

```
Met Glu Gly Pro Ala Phe Ser Lys Pro Leu Lys Asp Lys Ile Asn Pro
1               5                   10                  15
```

```
Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Thr Arg Pro Asn Asn Asn Thr Arg Lys Arg Ile Arg Ile Gln Arg
                165                 170                 175

Gly Pro Gly Arg Ala Phe Val Thr Ile Gly Lys Ile Gly Asn Met Arg
            180                 185                 190

Gln Ala His Cys Gly Pro Cys Tyr Asp Ser Ser Val Val Ser Ser Ser
        195                 200                 205

Ala Gln Gly Ala Thr Pro Gly Gly Arg Cys Asn Pro Leu Val Leu Glu
    210                 215                 220

Phe Thr Asp Ala Gly Lys Arg Ala Ser Trp Asp Ala Ser Lys Ala Trp
225                 230                 235                 240

Gly Leu Arg Leu Tyr Arg Ser Thr Gly Ile Asp Pro Val Thr Arg Phe
                245                 250                 255

Ser Leu Thr Arg Gln Val Leu Asn Ile Gly Pro Arg Val Pro Ile Gly
            260                 265                 270

Pro Asn Pro Val Ile Ile Asp Gln Leu Pro Pro Ser Arg Pro Val Gln
        275                 280                 285

Val Met Leu Pro Arg Pro Pro Gln Pro Pro Pro Pro Gly Ala Ala Ser
    290                 295                 300

Thr Val Pro Glu Thr Ala Pro Pro Ser Gln Gln Pro Gly Thr Gly Asp
305                 310                 315                 320

Arg Leu Leu Asn Leu Val Asn Gly Ala Tyr Gln Ala Leu Asn Leu Thr
                325                 330                 335

Ser Pro Asp Lys Thr Gln Glu Cys Trp Leu Cys Leu Val Ala Gly Pro
            340                 345                 350

Pro Tyr Tyr Glu Gly Val Ala Val Leu Gly Thr Tyr Ser Asn His Thr
        355                 360                 365

Ser Ala Pro Ala Asn Cys Ser Val Ala Ser Gln His Lys Leu Thr Leu
    370                 375                 380

Ser Glu Val Thr Gly Gln Gly Leu Cys Val Gly Ala Val Pro Lys Thr
385                 390                 395                 400

His Gln Ala Leu Cys Asn Thr Thr Gln Lys Thr Ser Asn Gly Ser Tyr
                405                 410                 415

Tyr Leu Ala Ala Pro Ala Gly Thr Ile Trp Ala Cys Asn Thr Gly Leu
            420                 425                 430

Thr Pro Cys Leu Ser Thr Thr Val Leu Asp Leu Thr Thr Asp Tyr Cys
```

```
        435                 440                 445

Val Leu Val Glu Leu Trp Pro Lys Val Thr Tyr His Ser Pro Gly Tyr
    450                 455                 460

Val Tyr Gly Gln Phe Glu Glu Lys Thr Lys Tyr Lys Arg Glu Pro Val
465                 470                 475                 480

Ser Leu Thr Leu Ala Leu Leu Leu Gly Gly Leu Thr Met Gly Gly Ile
                485                 490                 495

Ala Ala Gly Val Gly Thr Gly Thr Thr Ala Leu Val Ala Thr Gln Gln
            500                 505                 510

Phe Gln Gln Leu Gln Ala Ala Met Gln Asp Asp Leu Lys Glu Val Glu
        515                 520                 525

Lys Ser Ile Thr Asn Leu Glu Arg Ser Leu Thr Ser Leu Ser Glu Val
    530                 535                 540

Val Leu Gln Asn Arg Arg Gly Leu Asp Leu Leu Phe Leu Lys Glu Gly
545                 550                 555                 560

Gly Leu Cys Ala Ala Leu Lys Glu Glu Cys Cys Phe Tyr Ala Asp His
                565                 570                 575

Thr Gly Leu Val Arg Asp Ser Met Ala Lys Leu Arg Glu Arg Leu Ser
            580                 585                 590

Gln Arg Gln Lys Leu Phe Glu Ser Gln Gln Gly Trp Phe Glu Gly Leu
        595                 600                 605

Phe Asn Lys Ser Pro Trp Phe Thr Thr Leu Ile Ser Thr Ile Met Gly
    610                 615                 620

Pro Leu Ile Ile Leu Leu Leu Ile Leu Leu Phe Gly Pro Cys Ile Leu
625                 630                 635                 640

Asn His Leu Val Gln Phe Ile Lys Asp Arg Val Ser Val Val Gln Ala
                645                 650                 655

Leu Val Leu Thr Gln Gln Tyr His Gln Leu Lys Thr Ile Glu Asp Cys
            660                 665                 670

Glu Ser Arg Glu
        675


<210> SEQ ID NO 46
<211> LENGTH: 655
<212> TYPE: PRT
<213> ORGANISM: Artificial
<220> FEATURE:
<223> OTHER INFORMATION: SL3-2/V3 loop chimeric envelope

<400> SEQUENCE: 46

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125
```

-continued

```
Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Thr Arg Pro Asn Asn Asn Thr Arg Lys Arg Ile Arg Ile Gln
                165                 170                 175

Arg Gly Pro Gly Arg Ala Phe Val Thr Ile Gly Lys Ile Gly Asn Met
            180                 185                 190

Arg Gln Ala His Cys Asn Pro Leu Val Leu Glu Phe Thr Asp Ala Gly
        195                 200                 205

Lys Arg Ala Ser Trp Asp Ala Ser Lys Ala Trp Gly Leu Arg Leu Tyr
    210                 215                 220

Arg Ser Thr Gly Ile Asp Pro Val Thr Arg Phe Ser Leu Thr Arg Gln
225                 230                 235                 240

Val Leu Asn Ile Gly Pro Arg Val Pro Ile Gly Pro Asn Pro Val Ile
                245                 250                 255

Ile Asp Gln Leu Pro Pro Ser Arg Pro Val Gln Val Met Leu Pro Arg
            260                 265                 270

Pro Pro Gln Pro Pro Pro Pro Gly Ala Ala Ser Thr Val Pro Glu Thr
        275                 280                 285

Ala Pro Pro Ser Gln Gln Pro Gly Thr Gly Asp Arg Leu Leu Asn Leu
    290                 295                 300

Val Asn Gly Ala Tyr Gln Ala Leu Asn Leu Thr Ser Pro Asp Lys Thr
305                 310                 315                 320

Gln Glu Cys Trp Leu Cys Leu Val Ala Gly Pro Pro Tyr Tyr Glu Gly
                325                 330                 335

Val Ala Val Leu Gly Thr Tyr Ser Asn His Thr Ser Ala Pro Ala Asn
            340                 345                 350

Cys Ser Val Ala Ser Gln His Lys Leu Thr Leu Ser Glu Val Thr Gly
        355                 360                 365

Gln Gly Leu Cys Val Gly Ala Val Pro Lys Thr His Gln Ala Leu Cys
    370                 375                 380

Asn Thr Thr Gln Lys Thr Ser Asn Gly Ser Tyr Tyr Leu Ala Ala Pro
385                 390                 395                 400

Ala Gly Thr Ile Trp Ala Cys Asn Thr Gly Leu Thr Pro Cys Leu Ser
                405                 410                 415

Thr Thr Val Leu Asp Leu Thr Thr Asp Tyr Cys Val Leu Val Glu Leu
            420                 425                 430

Trp Pro Lys Val Thr Tyr His Ser Pro Gly Tyr Val Tyr Gly Gln Phe
        435                 440                 445

Glu Glu Lys Thr Lys Tyr Lys Arg Glu Pro Val Ser Leu Thr Leu Ala
    450                 455                 460

Leu Leu Leu Gly Gly Leu Thr Met Gly Gly Ile Ala Ala Gly Val Gly
465                 470                 475                 480

Thr Gly Thr Thr Ala Leu Val Ala Thr Gln Gln Phe Gln Gln Leu Gln
                485                 490                 495

Ala Ala Met Gln Asp Asp Leu Lys Glu Val Glu Lys Ser Ile Thr Asn
            500                 505                 510

Leu Glu Arg Ser Leu Thr Ser Leu Ser Glu Val Val Leu Gln Asn Arg
        515                 520                 525

Arg Gly Leu Asp Leu Leu Phe Leu Lys Glu Gly Gly Leu Cys Ala Ala
    530                 535                 540

Leu Lys Glu Glu Cys Cys Phe Tyr Ala Asp His Thr Gly Leu Val Arg
```

```
545                 550                 555                 560

Asp Ser Met Ala Lys Leu Arg Glu Arg Leu Ser Gln Arg Gln Lys Leu
                565                 570                 575

Phe Glu Ser Gln Gln Gly Trp Phe Glu Gly Leu Phe Asn Lys Ser Pro
            580                 585                 590

Trp Phe Thr Thr Leu Ile Ser Thr Ile Met Gly Pro Leu Ile Ile Leu
        595                 600                 605

Leu Leu Ile Leu Leu Phe Gly Pro Cys Ile Leu Asn His Leu Val Gln
    610                 615                 620

Phe Ile Lys Asp Arg Val Ser Val Val Gln Ala Leu Val Leu Thr Gln
625                 630                 635                 640

Gln Tyr His Gln Leu Lys Thr Ile Glu Asp Cys Glu Ser Arg Glu
                645                 650                 655


<210> SEQ ID NO 47
<211> LENGTH: 660
<212> TYPE: PRT
<213> ORGANISM: Artificial
<220> FEATURE:
<223> OTHER INFORMATION: SL3-2/V3 loop chimeric envelope

<400> SEQUENCE: 47

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Thr Arg
65                  70                  75                  80

Pro Asn Asn Asn Thr Arg Lys Arg Ile Arg Ile Gln Arg Gly Pro Gly
                85                  90                  95

Arg Ala Phe Val Thr Ile Gly Lys Ile Gly Asn Met Arg Gln Ala His
            100                 105                 110

Cys Arg Thr Pro Gly Gly Arg Lys Arg Ala Arg Ile Phe Asp Phe Tyr
        115                 120                 125

Val Cys Pro Gly His Thr Val Leu Ala Gly Cys Gly Gly Pro Arg Glu
    130                 135                 140

Gly Tyr Cys Gly Lys Trp Gly Cys Glu Thr Thr Gly Gln Ala Tyr Trp
145                 150                 155                 160

Lys Pro Ser Ser Ser Trp Asp Leu Ile Ser Leu Lys Arg Gly Asn Thr
                165                 170                 175

Pro Lys Gly Gln Gly Pro Cys Tyr Asp Ser Ser Val Val Ser Ser Ser
            180                 185                 190

Ala Gln Gly Ala Thr Pro Gly Gly Arg Cys Asn Pro Leu Val Leu Glu
        195                 200                 205

Phe Thr Asp Ala Gly Lys Arg Ala Ser Trp Asp Ala Ser Lys Ala Trp
    210                 215                 220

Gly Leu Arg Leu Tyr Arg Ser Thr Arg Thr Asp Pro Val Thr Arg Phe
225                 230                 235                 240

Ser Leu Thr Arg Gln Val Leu Asn Ile Gly Pro Arg Val Pro Ile Gly
                245                 250                 255

Pro Asn Pro Val Ile Ile Asp Gln Leu Pro Pro Ser Arg Pro Val Gln
            260                 265                 270
```

```
Val Met Leu Pro Arg Pro Pro Gln Pro Pro Pro Pro Gly Ala Ala Ser
        275                 280                 285

Thr Val Pro Glu Thr Ala Pro Pro Ser Gln Gln Pro Gly Thr Gly Asp
    290                 295                 300

Arg Leu Leu Asn Leu Val Asn Gly Ala Tyr Gln Ala Leu Asn Leu Thr
305                 310                 315                 320

Ser Pro Asp Lys Thr Gln Glu Cys Trp Leu Cys Leu Val Ala Gly Pro
                325                 330                 335

Pro Tyr Tyr Glu Gly Val Ala Val Leu Gly Thr Tyr Ser Asn His Thr
            340                 345                 350

Ser Ala Pro Ala Asn Cys Ser Val Ala Ser Gln His Lys Leu Thr Leu
        355                 360                 365

Ser Glu Val Thr Gly Gln Gly Leu Cys Val Gly Ala Val Pro Lys Thr
    370                 375                 380

His Gln Ala Leu Cys Asn Thr Thr Gln Lys Thr Ser Asn Gly Ser Tyr
385                 390                 395                 400

Tyr Leu Ala Ala Pro Ala Gly Thr Ile Trp Ala Cys Asn Thr Gly Leu
                405                 410                 415

Thr Pro Cys Leu Ser Thr Thr Val Leu Asp Leu Thr Thr Asp Tyr Cys
            420                 425                 430

Val Leu Val Glu Leu Trp Pro Lys Val Thr Tyr His Ser Pro Gly Tyr
        435                 440                 445

Val Tyr Gly Gln Phe Glu Glu Lys Thr Lys Tyr Lys Arg Glu Pro Val
    450                 455                 460

Ser Leu Thr Leu Ala Leu Leu Leu Gly Gly Leu Thr Met Gly Gly Ile
465                 470                 475                 480

Ala Ala Gly Val Gly Thr Gly Thr Thr Ala Leu Val Ala Thr Gln Gln
                485                 490                 495

Phe Gln Gln Leu Gln Ala Ala Met Gln Asp Asp Leu Lys Glu Val Glu
            500                 505                 510

Lys Ser Ile Thr Asn Leu Glu Arg Ser Leu Thr Ser Leu Ser Glu Val
        515                 520                 525

Val Leu Gln Asn Arg Arg Gly Leu Asp Leu Leu Phe Leu Lys Glu Gly
    530                 535                 540

Gly Leu Cys Ala Ala Leu Lys Glu Glu Cys Cys Phe Tyr Ala Asp His
545                 550                 555                 560

Thr Gly Leu Val Arg Asp Ser Met Ala Lys Leu Arg Glu Arg Leu Ser
                565                 570                 575

Gln Arg Gln Lys Leu Phe Glu Ser Gln Gln Gly Trp Phe Glu Gly Leu
            580                 585                 590

Phe Asn Lys Ser Pro Trp Phe Thr Thr Leu Ile Ser Thr Ile Met Gly
        595                 600                 605

Pro Leu Ile Ile Leu Leu Leu Ile Leu Leu Phe Gly Pro Cys Ile Leu
    610                 615                 620

Asn His Leu Val Gln Phe Ile Lys Asp Arg Val Ser Val Val Gln Ala
625                 630                 635                 640

Leu Val Leu Thr Gln Gln Tyr His Gln Leu Lys Thr Ile Glu Asp Cys
                645                 650                 655

Glu Ser Arg Glu
            660
```

<210> SEQ ID NO 48
<211> LENGTH: 1914
<212> TYPE: DNA

<213> ORGANISM: artificial
<220> FEATURE:
<223> OTHER INFORMATION: SL3-2/V3 loop chimeric envelope

<400> SEQUENCE: 48
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggatgg actcgggtgt cgcactcccg gggaagaaa aagggcaaga 300 atatttgact tctatgtttg ccccggtcac actgtgctag cagggtgtgg agggccgaga 360
gagggctact gtggcaaatg ggatgtgag accactggac aggcatactg gaagccatca 420
tcatcatggg acctaatttc ccttaagcga ggaaacactc ctaaaggcca gggcccctgt 480
tatgattcct cggtggtctc cagtagcgcc cagggtgcca caccgggggg tcgatgcaac 540
cccctagtcc tagaattcac tgacgcgggt aaaagggcca gctgggacgc ctccaaagca 600
tggggactaa gactgtaccg atccacaagg accgacccgg tgacccggtt ctctttgacc 660
cgccaggtcc tcaatatagg gccccgcgtc cccattgggc ctaatcccgt gatcattgac 720
cagttacccc cctcccgacc cgtgcaggtc atgctcccca ggcctcctca gcctcctcca 780
ccaggcgcag cctctacagt ccctgagact gccccacctt cccaacaacc tgggacggga 840
gacaggctgc taaacctggt aaatggagcc taccaagctc tcaacctcac cagtcctgac 900
aaaacccaag agtgctggtt gtgtctggta gcgggacccc cctactacga aggggttgcc 960
gtcctaggta cttattccaa ccatacctct gccccagcta actgctccgt ggcctcccaa 1020
cacaagctga ccctgtccga agtgaccgga cagggactct gcgtaggagc agttcccaaa 1080
acccatcagg ccctgtgtaa taccacccag aagacgagca acgggtccta ctatctggct 1140
gctcccgccg ggaccatttg ggcttgcaac accgggctca ctccctgcct atctaccact 1200
gtgctcgacc tcaccaccga ttactgtgtc ctggttgagc tctggccaaa agtgacctac 1260
cactcccctg gttatgttta tggccagttt gaagaaaaaa ccaaatataa aagagaaccc 1320
gtctcactaa ctctggccct actattagga ggactcacta tgggcggaat tgccgccgga 1380
gtgggaacag ggactaccgc cctagtggcc actcagcagt tccaacaact ccaggctgcc 1440
atgcaggatg accttaaaga agttgaaaag tccatcacta atctagaaag atctttgacc 1500
tccttgtccg aagtagtgtt acagaatcgt agaggcctag atctactatt cctaaaagag 1560
ggaggtttgt gtgctgcctt aaaagaagaa tgctgtttct atgccgacca cacaggattg 1620
gtacgggata gcatggccaa acttagagaa agattgagtc agagacaaaa actctttgaa 1680
tcccaacaag ggtggtttga agggctgttt aacaagtccc cttggttcac caccctgata 1740
tccaccatca tgggtcccct gataatcctc ttgttaattt tactctttgg gccttgtatt 1800
ctcaatcacc tggtccagtt tatcaaagac agggtttcgg tagtgcaggc cctggtcctg 1860
actcaacaat atcatcaact taagacaata gaagattgtg aatcacgtga ataa 1914

<210> SEQ ID NO 49
<211> LENGTH: 637
<212> TYPE: PRT
<213> ORGANISM: Artificial
<220> FEATURE:
<223> OTHER INFORMATION: SL3-2/V3 loop chimeric envelope

<400> SEQUENCE: 49

-continued

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Gly Leu Gly Cys Arg Thr Pro Gly Gly Arg
                85                  90                  95

Lys Arg Ala Arg Ile Phe Asp Phe Tyr Val Cys Pro Gly His Thr Val
            100                 105                 110

Leu Ala Gly Cys Gly Gly Pro Arg Glu Gly Tyr Cys Gly Lys Trp Gly
        115                 120                 125

Cys Glu Thr Thr Gly Gln Ala Tyr Trp Lys Pro Ser Ser Ser Trp Asp
    130                 135                 140

Leu Ile Ser Leu Lys Arg Gly Asn Thr Pro Lys Gly Gln Gly Pro Cys
145                 150                 155                 160

Tyr Asp Ser Ser Val Val Ser Ser Ser Ala Gln Gly Ala Thr Pro Gly
                165                 170                 175

Gly Arg Cys Asn Pro Leu Val Leu Glu Phe Thr Asp Ala Gly Lys Arg
            180                 185                 190

Ala Ser Trp Asp Ala Ser Lys Ala Trp Gly Leu Arg Leu Tyr Arg Ser
        195                 200                 205

Thr Arg Thr Asp Pro Val Thr Arg Phe Ser Leu Thr Arg Gln Val Leu
    210                 215                 220

Asn Ile Gly Pro Arg Val Pro Ile Gly Pro Asn Pro Val Ile Ile Asp
225                 230                 235                 240

Gln Leu Pro Pro Ser Arg Pro Val Gln Val Met Leu Pro Arg Pro Pro
                245                 250                 255

Gln Pro Pro Pro Pro Gly Ala Ala Ser Thr Val Pro Glu Thr Ala Pro
            260                 265                 270

Pro Ser Gln Gln Pro Gly Thr Gly Asp Arg Leu Leu Asn Leu Val Asn
        275                 280                 285

Gly Ala Tyr Gln Ala Leu Asn Leu Thr Ser Pro Asp Lys Thr Gln Glu
    290                 295                 300

Cys Trp Leu Cys Leu Val Ala Gly Pro Pro Tyr Tyr Glu Gly Val Ala
305                 310                 315                 320

Val Leu Gly Thr Tyr Ser Asn His Thr Ser Ala Pro Ala Asn Cys Ser
                325                 330                 335

Val Ala Ser Gln His Lys Leu Thr Leu Ser Glu Val Thr Gly Gln Gly
            340                 345                 350

Leu Cys Val Gly Ala Val Pro Lys Thr His Gln Ala Leu Cys Asn Thr
        355                 360                 365

Thr Gln Lys Thr Ser Asn Gly Ser Tyr Tyr Leu Ala Ala Pro Ala Gly
    370                 375                 380

Thr Ile Trp Ala Cys Asn Thr Gly Leu Thr Pro Cys Leu Ser Thr Thr
385                 390                 395                 400

Val Leu Asp Leu Thr Thr Asp Tyr Cys Val Leu Val Glu Leu Trp Pro
                405                 410                 415

Lys Val Thr Tyr His Ser Pro Gly Tyr Val Tyr Gly Gln Phe Glu Glu
            420                 425                 430
```

-continued

```
Lys Thr Lys Tyr Lys Arg Glu Pro Val Ser Leu Thr Leu Ala Leu Leu
        435                 440                 445

Leu Gly Gly Leu Thr Met Gly Gly Ile Ala Ala Gly Val Gly Thr Gly
    450                 455                 460

Thr Thr Ala Leu Val Ala Thr Gln Gln Phe Gln Gln Leu Gln Ala Ala
465                 470                 475                 480

Met Gln Asp Asp Leu Lys Glu Val Glu Lys Ser Ile Thr Asn Leu Glu
                485                 490                 495

Arg Ser Leu Thr Ser Leu Ser Glu Val Val Leu Gln Asn Arg Arg Gly
            500                 505                 510

Leu Asp Leu Leu Phe Leu Lys Glu Gly Gly Leu Cys Ala Ala Leu Lys
        515                 520                 525

Glu Glu Cys Cys Phe Tyr Ala Asp His Thr Gly Leu Val Arg Asp Ser
    530                 535                 540

Met Ala Lys Leu Arg Glu Arg Leu Ser Gln Arg Gln Lys Leu Phe Glu
545                 550                 555                 560

Ser Gln Gln Gly Trp Phe Glu Gly Leu Phe Asn Lys Ser Pro Trp Phe
                565                 570                 575

Thr Thr Leu Ile Ser Thr Ile Met Gly Pro Leu Ile Ile Leu Leu Leu
            580                 585                 590

Ile Leu Leu Phe Gly Pro Cys Ile Leu Asn His Leu Val Gln Phe Ile
        595                 600                 605

Lys Asp Arg Val Ser Val Val Gln Ala Leu Val Leu Thr Gln Gln Tyr
    610                 615                 620

His Gln Leu Lys Thr Ile Glu Asp Cys Glu Ser Arg Glu
625                 630                 635
```

<210> SEQ ID NO 50
<211> LENGTH: 1914
<212> TYPE: DNA
<213> ORGANISM: artificial
<220> FEATURE:
<223> OTHER INFORMATION: SL3-2/V3 loop chimeric envelope

<400> SEQUENCE: 50

```
atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatgg actcgggtgt cgcactcccg ggggaagaaa aagggcaaga    300

atatttgact tctatgtttg ccccggtcac actgtgctag cagggtgtgg agggccgaga    360

gagggctact gtggcaaatg ggatgtgag accactggac aggcatactg gaagccatca    420

tcatcatggg acctaatttc ccttaagcga ggaaacactc ctaaaggcca gggcccctgt    480

tatgattcct cggtggtctc cagtagcgcc cagggtgcca caccgggggg tcgatgcaac    540

cccctagtcc tagaattcac tgacgcgggt aaaagggcca gctgggacgc ctccaaagca    600

tggggactaa gactgtaccg atccacaggg atcgacccgg tgacccggtt ctctttgacc    660

cgccaggtcc tcaatatagg gccccgcgtc cccattgggc ctaatcccgt gatcattgac    720

cagttacccc cctcccgacc cgtgcaggtc atgctcccca ggcctcctca gcctcctcca    780

ccaggcgcag cctctacagt ccctgagact gccccacctt cccaacaacc tgggacggga    840

gacaggctgc taaacctggt aaatggagcc taccaagctc tcaacctcac cagtcctgac    900
```

-continued

```
aaaacccaag agtgctggtt gtgtctggta gcgggacccc cctactacga aggggttgcc    960

gtcctaggta cttattccaa ccatacctct gccccagcta actgctccgt ggcctcccaa   1020

cacaagctga ccctgtccga agtgaccgga cagggactct gcgtaggagc agttcccaaa   1080

acccatcagg ccctgtgtaa taccacccag aagacgagca acgggtccta ctatctggct   1140

gctcccgccg ggaccatttg ggcttgcaac accgggctca ctccctgcct atctaccact   1200

gtgctcgacc tcaccaccga ttactgtgtc ctggttgagc tctggccaaa agtgacctac   1260

cactcccctg gttatgttta tggccagttt gaagaaaaaa ccaaatataa aagagaaccc   1320

gtctcactaa ctctggccct actattagga ggactcacta tgggcggaat tgccgccgga   1380

gtgggaacag ggactaccgc cctagtggcc actcagcagt tccaacaact ccaggctgcc   1440

atgcaggatg accttaaaga agttgaaaag tccatcacta atctagaaag atctttgacc   1500

tccttgtccg aagtagtgtt acagaatcgt agaggcctag atctactatt cctaaaagag   1560

ggaggtttgt gtgctgcctt aaaagaagaa tgctgtttct atgccgacca cacaggattg   1620

gtacgggata gcatggccaa acttagagaa agattgagtc agagacaaaa actctttgaa   1680

tcccaacaag ggtggtttga agggctgttt aacaagtccc cttggttcac caccctgata   1740

tccaccatca tgggtcccct gataatcctc ttgttaattt tactctttgg gccttgtatt   1800

ctcaatcacc tggtccagtt tatcaaagac agggtttcgg tagtgcaggc cctggtcctg   1860

actcaacaat atcatcaact taagacaata gaagattgtg aatcacgtga ataa         1914
```

<210> SEQ ID NO 51
<211> LENGTH: 637
<212> TYPE: PRT
<213> ORGANISM: Artificial
<220> FEATURE:
<223> OTHER INFORMATION: Modified SL3-2 envelope sequence

<400> SEQUENCE: 51

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Gly Leu Gly Cys Arg Thr Pro Gly Gly Arg
                85                  90                  95

Lys Arg Ala Arg Ile Phe Asp Phe Tyr Val Cys Pro Gly His Thr Val
            100                 105                 110

Leu Ala Gly Cys Gly Gly Pro Arg Glu Gly Tyr Cys Gly Lys Trp Gly
        115                 120                 125

Cys Glu Thr Thr Gly Gln Ala Tyr Trp Lys Pro Ser Ser Ser Trp Asp
    130                 135                 140

Leu Ile Ser Leu Lys Arg Gly Asn Thr Pro Lys Gly Gln Gly Pro Cys
145                 150                 155                 160

Tyr Asp Ser Ser Val Val Ser Ser Ser Ala Gln Gly Ala Thr Pro Gly
                165                 170                 175

Gly Arg Cys Asn Pro Leu Val Leu Glu Phe Thr Asp Ala Gly Lys Arg
            180                 185                 190
```

```
Ala Ser Trp Asp Ala Ser Lys Ala Trp Gly Leu Arg Leu Tyr Arg Ser
        195                 200                 205

Thr Gly Ile Asp Pro Val Thr Arg Phe Ser Leu Thr Arg Gln Val Leu
    210                 215                 220

Asn Ile Gly Pro Arg Val Pro Ile Gly Pro Asn Pro Val Ile Ile Asp
225                 230                 235                 240

Gln Leu Pro Pro Ser Arg Pro Val Gln Val Met Leu Pro Arg Pro Pro
                245                 250                 255

Gln Pro Pro Pro Pro Gly Ala Ala Ser Thr Val Pro Glu Thr Ala Pro
            260                 265                 270

Pro Ser Gln Gln Pro Gly Thr Gly Asp Arg Leu Leu Asn Leu Val Asn
        275                 280                 285

Gly Ala Tyr Gln Ala Leu Asn Leu Thr Ser Pro Asp Lys Thr Gln Glu
    290                 295                 300

Cys Trp Leu Cys Leu Val Ala Gly Pro Pro Tyr Tyr Glu Gly Val Ala
305                 310                 315                 320

Val Leu Gly Thr Tyr Ser Asn His Thr Ser Ala Pro Ala Asn Cys Ser
                325                 330                 335

Val Ala Ser Gln His Lys Leu Thr Leu Ser Glu Val Thr Gly Gln Gly
            340                 345                 350

Leu Cys Val Gly Ala Val Pro Lys Thr His Gln Ala Leu Cys Asn Thr
        355                 360                 365

Thr Gln Lys Thr Ser Asn Gly Ser Tyr Tyr Leu Ala Ala Pro Ala Gly
    370                 375                 380

Thr Ile Trp Ala Cys Asn Thr Gly Leu Thr Pro Cys Leu Ser Thr Thr
385                 390                 395                 400

Val Leu Asp Leu Thr Thr Asp Tyr Cys Val Leu Val Glu Leu Trp Pro
                405                 410                 415

Lys Val Thr Tyr His Ser Pro Gly Tyr Val Tyr Gly Gln Phe Glu Glu
            420                 425                 430

Lys Thr Lys Tyr Lys Arg Glu Pro Val Ser Leu Thr Leu Ala Leu Leu
        435                 440                 445

Leu Gly Gly Leu Thr Met Gly Gly Ile Ala Ala Gly Val Gly Thr Gly
    450                 455                 460

Thr Thr Ala Leu Val Ala Thr Gln Gln Phe Gln Gln Leu Gln Ala Ala
465                 470                 475                 480

Met Gln Asp Asp Leu Lys Glu Val Glu Lys Ser Ile Thr Asn Leu Glu
                485                 490                 495

Arg Ser Leu Thr Ser Leu Ser Glu Val Val Leu Gln Asn Arg Arg Gly
            500                 505                 510

Leu Asp Leu Leu Phe Leu Lys Glu Gly Gly Leu Cys Ala Ala Leu Lys
        515                 520                 525

Glu Glu Cys Cys Phe Tyr Ala Asp His Thr Gly Leu Val Arg Asp Ser
    530                 535                 540

Met Ala Lys Leu Arg Glu Arg Leu Ser Gln Arg Gln Lys Leu Phe Glu
545                 550                 555                 560

Ser Gln Gln Gly Trp Phe Glu Gly Leu Phe Asn Lys Ser Pro Trp Phe
                565                 570                 575

Thr Thr Leu Ile Ser Thr Ile Met Gly Pro Leu Ile Ile Leu Leu Leu
            580                 585                 590

Ile Leu Leu Phe Gly Pro Cys Ile Leu Asn His Leu Val Gln Phe Ile
        595                 600                 605

Lys Asp Arg Val Ser Val Val Gln Ala Leu Val Leu Thr Gln Gln Tyr
    610                 615                 620
```

His Gln Leu Lys Thr Ile Glu Asp Cys Glu Ser Arg Glu
625 630 635

<210> SEQ ID NO 52
<211> LENGTH: 1929
<212> TYPE: DNA
<213> ORGANISM: artificial
<220> FEATURE:
<223> OTHER INFORMATION: SL3-2/V3 loop chimeric envelope

<400> SEQUENCE: 52
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggatga gactggactc gggtgtcgca ctcccggggg aagaaaaagg 300
gcaagaatat ttgacttcta tgtttgcccc ggtcacactg tgctagcagg gtgtggaggg 360
ccgagagagg gctactgtgg caaatgggga tgtgagacca ctggacaggc atactggaag 420
ccatcatcat catgggacct aatttccctt aagcgaggaa acactcaagg aatctaccag 480
tgctgtgggc cctgttatga ttcctcggtg gtctccagta gcgcccaggg tgccacaccg 540
gggggtcgat gcaacccccct agtcctagaa ttcactgacg cgggtaaaag ggccagctgg 600
gacgcctcca aagcatgggg actaagactg taccgatcca caaggaccga cccggtgacc 660
cggttctctt tgacccgcca ggtcctcaat atagggcccc gcgtccccat tgggcctaat 720
cccgtgatca ttgaccagtt accccccctcc cgacccgtgc aggtcatgct ccccaggcct 780
cctcagcctc ctccaccagg cgcagcctct acagtccctg agactgcccc accttcccaa 840
caacctggga cgggagacag gctgctaaac ctggtaaatg gagcctacca agctctcaac 900
ctcaccagtc ctgacaaaac ccaagagtgc tggttgtgtc tggtagcggg acccccctac 960
tacgaagggg ttgccgtcct aggtacttat tccaaccata cctctgcccc agctaactgc 1020
tccgtggcct cccaacacaa gctgaccctg tccgaagtga ccggacaggg actctgcgta 1080
ggagcagttc ccaaaaccca tcaggccctg tgtaatacca cccagaagac gagcaacggg 1140
tcctactatc tggctgctcc cgccgggacc atttgggctt gcaacaccgg gctcactccc 1200
tgcctatcta ccactgtgct cgacctcacc accgattact gtgtcctggt tgagctctgg 1260
ccaaaagtga cctaccactc ccctggttat gtttatggcc agtttgaaga aaaaaccaaa 1320
tataaaagag aacccgtctc actaactctg gccctactat taggaggact cactatgggc 1380
ggaattgccg ccggagtggg aacagggact accgccctag tggccactca gcagttccaa 1440
caactccagg ctgccatgca ggatgacctt aaagaagttg aaaagtccat cactaatcta 1500
gaaagatctt tgacctcctt gtccgaagta gtgttacaga atcgtagagg cctagatcta 1560
ctattcctaa aagagggagg tttgtgtgct gccttaaaag aagaatgctg tttctatgcc 1620
gaccacacag gattggtacg ggatagcatg gccaaactta gagaaagatt gagtcagaga 1680
caaaaactct ttgaatccca acaagggtgg tttgaagggc tgtttaacaa gtccccttgg 1740
ttcaccaccc tgatatccac catcatgggt cccctgataa tcctcttgtt aattttactc 1800
tttgggcctt gtattctcaa tcacctggtc cagtttatca aagacagggt ttcggtagtg 1860
caggccctgg tcctgactca acaatatcat caacttaaga caatagaaga ttgtgaatca 1920
cgtgaataa 1929

<210> SEQ ID NO 53
<211> LENGTH: 642
<212> TYPE: PRT
<213> ORGANISM: Artificial
<220> FEATURE:
<223> OTHER INFORMATION: SL3-2/V3 loop chimeric envelope

<400> SEQUENCE: 53

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Cys Gly Pro Cys Tyr Asp Ser Ser Val Val Ser Ser Ser Ala Gln
                165                 170                 175

Gly Ala Thr Pro Gly Gly Arg Cys Asn Pro Leu Val Leu Glu Phe Thr
            180                 185                 190

Asp Ala Gly Lys Arg Ala Ser Trp Asp Ala Ser Lys Ala Trp Gly Leu
        195                 200                 205

Arg Leu Tyr Arg Ser Thr Arg Thr Asp Pro Val Thr Arg Phe Ser Leu
    210                 215                 220

Thr Arg Gln Val Leu Asn Ile Gly Pro Arg Val Pro Ile Gly Pro Asn
225                 230                 235                 240

Pro Val Ile Ile Asp Gln Leu Pro Pro Ser Arg Pro Val Gln Val Met
                245                 250                 255

Leu Pro Arg Pro Pro Gln Pro Pro Pro Pro Gly Ala Ala Ser Thr Val
            260                 265                 270

Pro Glu Thr Ala Pro Pro Ser Gln Gln Pro Gly Thr Gly Asp Arg Leu
        275                 280                 285

Leu Asn Leu Val Asn Gly Ala Tyr Gln Ala Leu Asn Leu Thr Ser Pro
    290                 295                 300

Asp Lys Thr Gln Glu Cys Trp Leu Cys Leu Val Ala Gly Pro Pro Tyr
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
            340                 345                 350

Val Thr Gly Gln Gly Leu Cys Val Gly Ala Val Pro Lys Thr His Gln
        355                 360                 365

Ala Leu Cys Asn Thr Thr Gln Lys Thr Ser Asn Gly Ser Tyr Tyr Leu
```

```
    370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asp Leu Thr Thr Asp Tyr Cys Val Leu
                405                 410                 415

Val Glu Leu Trp Pro Lys Val Thr Tyr His Ser Pro Gly Tyr Val Tyr
            420                 425                 430

Gly Gln Phe Glu Glu Lys Thr Lys Tyr Lys Arg Glu Pro Val Ser Leu
        435                 440                 445

Thr Leu Ala Leu Leu Leu Gly Gly Leu Thr Met Gly Gly Ile Ala Ala
    450                 455                 460

Gly Val Gly Thr Gly Thr Thr Ala Leu Val Ala Thr Gln Gln Phe Gln
465                 470                 475                 480

Gln Leu Gln Ala Ala Met Gln Asp Asp Leu Lys Glu Val Glu Lys Ser
                485                 490                 495

Ile Thr Asn Leu Glu Arg Ser Leu Thr Ser Leu Ser Glu Val Val Leu
            500                 505                 510

Gln Asn Arg Arg Gly Leu Asp Leu Leu Phe Leu Lys Glu Gly Gly Leu
        515                 520                 525

Cys Ala Ala Leu Lys Glu Glu Cys Cys Phe Tyr Ala Asp His Thr Gly
    530                 535                 540

Leu Val Arg Asp Ser Met Ala Lys Leu Arg Glu Arg Leu Ser Gln Arg
545                 550                 555                 560

Gln Lys Leu Phe Glu Ser Gln Gln Gly Trp Phe Glu Gly Leu Phe Asn
                565                 570                 575

Lys Ser Pro Trp Phe Thr Thr Leu Ile Ser Thr Ile Met Gly Pro Leu
            580                 585                 590

Ile Ile Leu Leu Leu Ile Leu Leu Phe Gly Pro Cys Ile Leu Asn His
        595                 600                 605

Leu Val Gln Phe Ile Lys Asp Arg Val Ser Val Val Gln Ala Leu Val
    610                 615                 620

Leu Thr Gln Gln Tyr His Gln Leu Lys Thr Ile Glu Asp Cys Glu Ser
625                 630                 635                 640

Arg Glu
```

<210> SEQ ID NO 54
<211> LENGTH: 1929
<212> TYPE: DNA
<213> ORGANISM: artificial
<220> FEATURE:
<223> OTHER INFORMATION: SL3-2/V3 loop chimeric envelope

<400> SEQUENCE: 54

```
atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcaagg aatctaccag    480

tgctgtgggc cctgttatga ttcctcggtg gtctccagta gcgcccaggg tgccacaccg    540
```

```
gggggtcgat gcaacccct agtcctagaa ttcactgacg cgggtaaaag ggccagctgg    600

gacgcctcca aagcatgggg actaagactg taccgatcca cagggatcga cccggtgacc    660

cggttctctt tgacccgcca ggtcctcaat atagggcccc gcgtccccat tgggcctaat    720

cccgtgatca ttgaccagtt acccccctcc cgacccgtgc aggtcatgct ccccaggcct    780

cctcagcctc ctccaccagg cgcagcctct acagtccctg agactgcccc accttcccaa    840

caacctggga cgggagacag gctgctaaac ctggtaaatg gagcctacca agctctcaac    900

ctcaccagtc ctgacaaaac ccaagagtgc tggttgtgtc tggtagcggg accccctac    960

tacgaagggg ttgccgtcct aggtacttat tccaaccata cctctgcccc agctaactgc   1020

tccgtggcct cccaacacaa gctgaccctg tccgaagtga ccggacaggg actctgcgta   1080

ggagcagttc ccaaaaccca tcaggccctg tgtaatacca cccagaagac gagcaacggg   1140

tcctactatc tggctgctcc cgccgggacc atttgggctt gcaacaccgg gctcactccc   1200

tgcctatcta ccactgtgct cgacctcacc accgattact gtgtcctggt tgagctctgg   1260

ccaaaagtga cctaccactc ccctggttat gtttatggcc agtttgaaga aaaaaccaaa   1320

tataaaagag aacccgtctc actaactctg gccctactat taggaggact cactatgggc   1380

ggaattgccg ccggagtggg aacagggact accgccctag tggccactca gcagttccaa   1440

caactccagg ctgccatgca ggatgacctt aaagaagttg aaaagtccat cactaatcta   1500

gaaagatctt tgacctcctt gtccgaagta gtgttacaga atcgtagagg cctagatcta   1560

ctattcctaa aagagggagg tttgtgtgct gccttaaaag aagaatgctg tttctatgcc   1620

gaccacacag gattggtacg ggatagcatg gccaaactta gagaaagatt gagtcagaga   1680

caaaaactct ttgaatccca acaagggtgg tttgaagggc tgtttaacaa gtccccttgg   1740

ttcaccaccc tgatatccac catcatgggt cccctgataa tcctcttgtt aatttactc    1800

tttgggcctt gtattctcaa tcacctggtc cagtttatca aagacagggt ttcggtagtg   1860

caggccctgg tcctgactca acaatatcat caacttaaga caatagaaga ttgtgaatca   1920

cgtgaataa                                                           1929
```

<210> SEQ ID NO 55
<211> LENGTH: 642
<212> TYPE: PRT
<213> ORGANISM: Artificial
<220> FEATURE:
<223> OTHER INFORMATION: SL3-2/V3 loop chimeric envelope

<400> SEQUENCE: 55

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
```

```
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Cys Gly Pro Cys Tyr Asp Ser Ser Val Val Ser Ser Ser Ala Gln
                165                 170                 175

Gly Ala Thr Pro Gly Gly Arg Cys Asn Pro Leu Val Leu Glu Phe Thr
            180                 185                 190

Asp Ala Gly Lys Arg Ala Ser Trp Asp Ala Ser Lys Ala Trp Gly Leu
        195                 200                 205

Arg Leu Tyr Arg Ser Thr Gly Ile Asp Pro Val Thr Arg Phe Ser Leu
    210                 215                 220

Thr Arg Gln Val Leu Asn Ile Gly Pro Arg Val Pro Ile Gly Pro Asn
225                 230                 235                 240

Pro Val Ile Ile Asp Gln Leu Pro Pro Ser Arg Pro Val Gln Val Met
                245                 250                 255

Leu Pro Arg Pro Pro Gln Pro Pro Pro Pro Gly Ala Ala Ser Thr Val
            260                 265                 270

Pro Glu Thr Ala Pro Pro Ser Gln Gln Pro Gly Thr Gly Asp Arg Leu
        275                 280                 285

Leu Asn Leu Val Asn Gly Ala Tyr Gln Ala Leu Asn Leu Thr Ser Pro
    290                 295                 300

Asp Lys Thr Gln Glu Cys Trp Leu Cys Leu Val Ala Gly Pro Pro Tyr
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
            340                 345                 350

Val Thr Gly Gln Gly Leu Cys Val Gly Ala Val Pro Lys Thr His Gln
        355                 360                 365

Ala Leu Cys Asn Thr Thr Gln Lys Thr Ser Asn Gly Ser Tyr Tyr Leu
    370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asp Leu Thr Thr Asp Tyr Cys Val Leu
                405                 410                 415

Val Glu Leu Trp Pro Lys Val Thr Tyr His Ser Pro Gly Tyr Val Tyr
            420                 425                 430

Gly Gln Phe Glu Glu Lys Thr Lys Tyr Lys Arg Glu Pro Val Ser Leu
        435                 440                 445

Thr Leu Ala Leu Leu Leu Gly Gly Leu Thr Met Gly Gly Ile Ala Ala
    450                 455                 460

Gly Val Gly Thr Gly Thr Thr Ala Leu Val Ala Thr Gln Gln Phe Gln
465                 470                 475                 480

Gln Leu Gln Ala Ala Met Gln Asp Asp Leu Lys Glu Val Glu Lys Ser
                485                 490                 495

Ile Thr Asn Leu Glu Arg Ser Leu Thr Ser Leu Ser Glu Val Val Leu
            500                 505                 510

Gln Asn Arg Arg Gly Leu Asp Leu Leu Phe Leu Lys Glu Gly Gly Leu
        515                 520                 525

Cys Ala Ala Leu Lys Glu Glu Cys Cys Phe Tyr Ala Asp His Thr Gly
    530                 535                 540
```

```
Leu Val Arg Asp Ser Met Ala Lys Leu Arg Glu Arg Leu Ser Gln Arg
545                 550                 555                 560

Gln Lys Leu Phe Glu Ser Gln Gln Gly Trp Phe Glu Gly Leu Phe Asn
                565                 570                 575

Lys Ser Pro Trp Phe Thr Thr Leu Ile Ser Thr Ile Met Gly Pro Leu
            580                 585                 590

Ile Ile Leu Leu Leu Ile Leu Leu Phe Gly Pro Cys Ile Leu Asn His
        595                 600                 605

Leu Val Gln Phe Ile Lys Asp Arg Val Ser Val Val Gln Ala Leu Val
    610                 615                 620

Leu Thr Gln Gln Tyr His Gln Leu Lys Thr Ile Glu Asp Cys Glu Ser
625                 630                 635                 640

Arg Glu


<210> SEQ ID NO 56
<211> LENGTH: 1911
<212> TYPE: DNA
<213> ORGANISM: artificial
<220> FEATURE:
<223> OTHER INFORMATION: SL3-2/V3 loop chimeric envelope

<400> SEQUENCE: 56

atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcctaa aggccagggc    480

ccctgttatg attcctccag tagcgcccag ggtgccacac cgggggtcg atgcaacccc    540

ctagtcctag aattcactga cgcgggtaaa agggccagct gggacgcctc caaagcatgg    600

ggactaagac tgtaccgatc cacaaggacc gacccggtga cccggttctc tttgacccgc    660

caggtcctca atatagggcc ccgcgtcccc attgggccta atcccgtgat cattgaccag    720

ttaccccct cccgacccgt gcaggtcatg ctccccaggc ctcctcagcc tcctccacca    780

ggcgcagcct ctacagtccc tgagactgcc ccaccttccc aacaacctgg gacgggagac    840

aggctgctaa acctggtaaa tggagcctac caagctctca acctcaccag tcctgacaaa    900

acccaagagt gctggttgtg tctggtagcg ggacccccct actacgaagg ggttgccgtc    960

ctaggtactt attccaacca tacctctgcc ccagctaact gctccgtggc ctcccaacac   1020

aagctgaccc tgtccgaagt gaccggacag ggactctgcg taggagcagt tcccaaaacc   1080

catcaggccc tgtgtaatac cacccagaag acgagcaacg ggtcctacta tctggctgct   1140

cccgccggga ccatttgggc ttgcaacacc gggctcactc cctgcctatc taccactgtg   1200

ctcgacctca ccaccgatta ctgtgtcctg gttgagctct ggccaaaagt gacctaccac   1260

tcccctggtt atgtttatgg ccagtttgaa gaaaaaacca aatataaaag agaacccgtc   1320

tcactaactc tggccctact attaggagga ctcactatgg gcggaattgc cgccggagtg   1380

ggaacaggga ctaccgccct agtggccact cagcagttcc aacaactcca ggctgccatg   1440

caggatgacc ttaaagaagt tgaaaagtcc atcactaatc tagaaagatc tttgacctcc   1500
```

-continued

```
ttgtccgaag tagtgttaca gaatcgtaga ggcctagatc tactattcct aaaagaggga   1560

ggtttgtgtg ctgccttaaa agaagaatgc tgtttctatg ccgaccacac aggattggta   1620

cgggatagca tggccaaact tagagaaaga ttgagtcaga gacaaaaact ctttgaatcc   1680

caacaagggt ggtttgaagg gctgtttaac aagtcccctt ggttcaccac cctgatatcc   1740

accatcatgg gtcccctgat aatcctcttg ttaattttac tctttgggcc ttgtattctc   1800

aatcacctgg tccagtttat caaagacagg gtttcggtag tgcaggccct ggtcctgact   1860

caacaatatc atcaacttaa gacaatagaa gattgtgaat cacgtgaata a            1911
```

```
<210> SEQ ID NO 57
<211> LENGTH: 636
<212> TYPE: PRT
<213> ORGANISM: Artificial
<220> FEATURE:
<223> OTHER INFORMATION: SL3-2/V3 loop chimeric envelope

<400> SEQUENCE: 57

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Ser Ser Ala Gln Gly Ala Thr Pro Gly Gly
                165                 170                 175

Arg Cys Asn Pro Leu Val Leu Glu Phe Thr Asp Ala Gly Lys Arg Ala
            180                 185                 190

Ser Trp Asp Ala Ser Lys Ala Trp Gly Leu Arg Leu Tyr Arg Ser Thr
        195                 200                 205

Arg Thr Asp Pro Val Thr Arg Phe Ser Leu Thr Arg Gln Val Leu Asn
    210                 215                 220

Ile Gly Pro Arg Val Pro Ile Gly Pro Asn Pro Val Ile Ile Asp Gln
225                 230                 235                 240

Leu Pro Pro Ser Arg Pro Val Gln Val Met Leu Pro Arg Pro Pro Gln
                245                 250                 255

Pro Pro Pro Pro Gly Ala Ala Ser Thr Val Pro Glu Thr Ala Pro Pro
            260                 265                 270

Ser Gln Gln Pro Gly Thr Gly Asp Arg Leu Leu Asn Leu Val Asn Gly
        275                 280                 285

Ala Tyr Gln Ala Leu Asn Leu Thr Ser Pro Asp Lys Thr Gln Glu Cys
    290                 295                 300
```

```
Trp Leu Cys Leu Val Ala Gly Pro Pro Tyr Tyr Glu Gly Val Ala Val
305                 310                 315                 320

Leu Gly Thr Tyr Ser Asn His Thr Ser Ala Pro Ala Asn Cys Ser Val
                325                 330                 335

Ala Ser Gln His Lys Leu Thr Leu Ser Glu Val Thr Gly Gln Gly Leu
            340                 345                 350

Cys Val Gly Ala Val Pro Lys Thr His Gln Ala Leu Cys Asn Thr Thr
        355                 360                 365

Gln Lys Thr Ser Asn Gly Ser Tyr Tyr Leu Ala Ala Pro Ala Gly Thr
    370                 375                 380

Ile Trp Ala Cys Asn Thr Gly Leu Thr Pro Cys Leu Ser Thr Thr Val
385                 390                 395                 400

Leu Asp Leu Thr Thr Asp Tyr Cys Val Leu Val Glu Leu Trp Pro Lys
                405                 410                 415

Val Thr Tyr His Ser Pro Gly Tyr Val Tyr Gly Gln Phe Glu Glu Lys
            420                 425                 430

Thr Lys Tyr Lys Arg Glu Pro Val Ser Leu Thr Leu Ala Leu Leu Leu
        435                 440                 445

Gly Gly Leu Thr Met Gly Gly Ile Ala Ala Gly Val Gly Thr Gly Thr
    450                 455                 460

Thr Ala Leu Val Ala Thr Gln Gln Phe Gln Gln Leu Gln Ala Ala Met
465                 470                 475                 480

Gln Asp Asp Leu Lys Glu Val Glu Lys Ser Ile Thr Asn Leu Glu Arg
                485                 490                 495

Ser Leu Thr Ser Leu Ser Glu Val Val Leu Gln Asn Arg Arg Gly Leu
            500                 505                 510

Asp Leu Leu Phe Leu Lys Glu Gly Gly Leu Cys Ala Ala Leu Lys Glu
        515                 520                 525

Glu Cys Cys Phe Tyr Ala Asp His Thr Gly Leu Val Arg Asp Ser Met
    530                 535                 540

Ala Lys Leu Arg Glu Arg Leu Ser Gln Arg Gln Lys Leu Phe Glu Ser
545                 550                 555                 560

Gln Gln Gly Trp Phe Glu Gly Leu Phe Asn Lys Ser Pro Trp Phe Thr
                565                 570                 575

Thr Leu Ile Ser Thr Ile Met Gly Pro Leu Ile Ile Leu Leu Leu Ile
            580                 585                 590

Leu Leu Phe Gly Pro Cys Ile Leu Asn His Leu Val Gln Phe Ile Lys
        595                 600                 605

Asp Arg Val Ser Val Val Gln Ala Leu Val Leu Thr Gln Gln Tyr His
    610                 615                 620

Gln Leu Lys Thr Ile Glu Asp Cys Glu Ser Arg Glu
625                 630                 635
```

<210> SEQ ID NO 58
<211> LENGTH: 1911
<212> TYPE: PRT
<213> ORGANISM: Artificial
<220> FEATURE:
<223> OTHER INFORMATION: SL3-2/V3 loop chimeric envelope

<400> SEQUENCE: 58

```
Ala Thr Gly Gly Ala Ala Gly Gly Thr Cys Cys Ala Gly Cys Gly Thr
1               5                   10                  15

Thr Cys Thr Cys Ala Ala Ala Ala Cys Cys Cys Cys Thr Thr Ala Ala
            20                  25                  30
```

```
Ala Gly Ala Thr Ala Ala Gly Ala Thr Thr Ala Ala Cys Cys Cys Gly
        35                  40                  45

Thr Gly Gly Gly Gly Cys Cys Cys Cys Cys Thr Ala Ala Thr Ala Gly
    50                  55                  60

Thr Cys Cys Thr Gly Gly Gly Ala Ala Thr Cys Thr Thr Ala Ala Thr
65                  70                  75                  80

Gly Ala Gly Gly Gly Cys Ala Ala Gly Ala Gly Thr Ala Thr Cys Ala
                85                  90                  95

Gly Thr Ala Cys Ala Ala Cys Ala Thr Gly Ala Cys Ala Gly Cys Cys
            100                 105                 110

Cys Thr Cys Ala Thr Cys Ala Gly Gly Thr Cys Thr Thr Cys Ala Ala
        115                 120                 125

Thr Gly Thr Thr Ala Cys Thr Thr Gly Gly Ala Gly Ala Gly Thr Thr
    130                 135                 140

Ala Cys Cys Ala Ala Cys Thr Thr Ala Ala Thr Gly Ala Cys Ala Gly
145                 150                 155                 160

Gly Ala Cys Ala Ala Ala Cys Ala Gly Cys Thr Ala Ala Thr Gly Cys
                165                 170                 175

Thr Ala Cys Cys Thr Cys Cys Cys Thr Cys Cys Thr Gly Gly Gly Gly
            180                 185                 190

Ala Cys Ala Ala Thr Gly Ala Cys Cys Gly Ala Thr Gly Cys Cys Thr
        195                 200                 205

Thr Thr Cys Cys Thr Ala Ala Ala Cys Thr Gly Thr Ala Cys Thr Thr
    210                 215                 220

Thr Gly Ala Cys Thr Thr Gly Thr Gly Cys Gly Ala Thr Thr Thr Ala
225                 230                 235                 240

Ala Thr Ala Gly Gly Gly Gly Ala Cys Gly Ala Cys Thr Gly Gly Gly
                245                 250                 255

Ala Thr Gly Ala Gly Ala Cys Thr Gly Gly Ala Cys Thr Cys Gly Gly
            260                 265                 270

Gly Thr Gly Thr Cys Gly Cys Ala Cys Thr Cys Cys Cys Gly Gly Gly
        275                 280                 285

Gly Gly Ala Ala Gly Ala Ala Ala Ala Ala Gly Gly Gly Cys Ala Ala
    290                 295                 300

Gly Ala Ala Thr Ala Thr Thr Thr Gly Ala Cys Thr Thr Cys Thr Ala
305                 310                 315                 320

Thr Gly Thr Thr Thr Gly Cys Cys Cys Cys Gly Gly Thr Cys Ala Cys
                325                 330                 335

Ala Cys Thr Gly Thr Gly Cys Thr Ala Gly Cys Ala Gly Gly Gly Thr
            340                 345                 350

Gly Thr Gly Gly Ala Gly Gly Gly Cys Cys Gly Ala Gly Ala Gly Ala
        355                 360                 365

Gly Gly Gly Cys Thr Ala Cys Thr Gly Thr Gly Gly Cys Ala Ala Ala
    370                 375                 380

Thr Gly Gly Gly Gly Ala Thr Gly Thr Gly Ala Gly Ala Cys Cys Ala
385                 390                 395                 400

Cys Thr Gly Gly Ala Cys Ala Gly Gly Cys Ala Thr Ala Cys Thr Gly
                405                 410                 415

Gly Ala Ala Gly Cys Cys Ala Thr Cys Ala Thr Cys Ala Thr Cys Ala
            420                 425                 430

Thr Gly Gly Gly Ala Cys Cys Thr Ala Ala Thr Thr Thr Cys Cys Cys
        435                 440                 445

Thr Thr Ala Ala Gly Cys Gly Ala Gly Gly Ala Ala Ala Cys Ala Cys
    450                 455                 460
```

Thr Cys Cys Thr Ala Ala Ala Gly Gly Cys Cys Ala Gly Gly Gly Cys
465 470 475 480

Cys Cys Cys Thr Gly Thr Thr Ala Thr Gly Ala Thr Thr Cys Cys Thr
485 490 495

Cys Cys Ala Gly Thr Ala Gly Cys Gly Cys Cys Cys Ala Gly Gly Gly
500 505 510

Thr Gly Cys Cys Ala Cys Ala Cys Cys Gly Gly Gly Gly Gly Gly Thr
515 520 525

Cys Gly Ala Thr Gly Cys Ala Ala Cys Cys Cys Cys Cys Thr Ala Gly
530 535 540

Thr Cys Cys Thr Ala Gly Ala Ala Thr Thr Cys Ala Cys Thr Gly Ala
545 550 555 560

Cys Gly Cys Gly Gly Gly Thr Ala Ala Ala Ala Gly Gly Gly Cys Cys
565 570 575

Ala Gly Cys Thr Gly Gly Gly Ala Cys Gly Cys Cys Thr Cys Cys Ala
580 585 590

Ala Ala Gly Cys Ala Thr Gly Gly Gly Gly Ala Cys Thr Ala Ala Gly
595 600 605

Ala Cys Thr Gly Thr Ala Cys Cys Gly Ala Thr Cys Cys Ala Cys Ala
610 615 620

Gly Gly Gly Ala Thr Cys Gly Ala Cys Cys Cys Gly Gly Thr Gly Ala
625 630 635 640

Cys Cys Cys Gly Gly Thr Thr Cys Thr Cys Thr Thr Thr Gly Ala Cys
645 650 655

Cys Cys Gly Cys Cys Ala Gly Gly Thr Cys Cys Thr Cys Ala Ala Thr
660 665 670

Ala Thr Ala Gly Gly Gly Cys Cys Cys Cys Gly Cys Gly Thr Cys Cys
675 680 685

Cys Cys Ala Thr Thr Gly Gly Gly Cys Cys Thr Ala Ala Thr Cys Cys
690 695 700

Cys Gly Thr Gly Ala Thr Cys Ala Thr Thr Gly Ala Cys Cys Ala Gly
705 710 715 720

Thr Thr Ala Cys Cys Cys Cys Cys Cys Thr Cys Cys Cys Gly Ala Cys
725 730 735

Cys Cys Gly Thr Gly Cys Ala Gly Gly Thr Cys Ala Thr Gly Cys Thr
740 745 750

Cys Cys Cys Cys Ala Gly Gly Cys Cys Thr Cys Cys Thr Cys Ala Gly
755 760 765

Cys Cys Thr Cys Cys Thr Cys Cys Ala Cys Cys Ala Gly Gly Cys Gly
770 775 780

Cys Ala Gly Cys Cys Thr Cys Thr Ala Cys Ala Gly Thr Cys Cys Cys
785 790 795 800

Thr Gly Ala Gly Ala Cys Thr Gly Cys Cys Cys Cys Ala Cys Cys Thr
805 810 815

Thr Cys Cys Cys Ala Ala Cys Ala Ala Cys Cys Thr Gly Gly Gly Ala
820 825 830

Cys Gly Gly Gly Ala Gly Ala Cys Ala Gly Gly Cys Thr Gly Cys Thr
835 840 845

Ala Ala Ala Cys Cys Thr Gly Gly Thr Ala Ala Ala Thr Gly Gly Ala
850 855 860

Gly Cys Cys Thr Ala Cys Cys Ala Ala Gly Cys Thr Cys Thr Cys Ala
865 870 875 880

Ala Cys Cys Thr Cys Ala Cys Cys Ala Gly Thr Cys Cys Thr Gly Ala

-continued

```
                885                 890                 895

Cys Ala Ala Ala Ala Cys Cys Cys Ala Ala Gly Ala Gly Thr Gly Cys
            900                 905                 910

Thr Gly Gly Thr Thr Gly Thr Gly Thr Cys Thr Gly Gly Thr Ala Gly
        915                 920                 925

Cys Gly Gly Gly Ala Cys Cys Cys Cys Cys Cys Thr Ala Cys Thr Ala
    930                 935                 940

Cys Gly Ala Ala Gly Gly Gly Gly Thr Thr Gly Cys Cys Gly Thr Cys
945                 950                 955                 960

Cys Thr Ala Gly Gly Thr Ala Cys Thr Thr Ala Thr Thr Cys Cys Ala
                965                 970                 975

Ala Cys Cys Ala Thr Ala Cys Cys Thr Cys Thr Gly Cys Cys Cys Cys
            980                 985                 990

Ala Gly Cys Thr Ala Ala Cys Thr  Gly Cys Thr Cys Cys  Gly Thr Gly
        995                 1000                1005

Gly Cys  Cys Thr Cys Cys Cys  Ala Ala Cys Ala Cys  Ala Ala Gly
    1010                1015                1020

Cys Thr  Gly Ala Cys Cys Cys  Thr Gly Thr Cys Cys  Gly Ala Ala
    1025                1030                1035

Gly Thr  Gly Ala Cys Cys Gly  Gly Ala Cys Ala Gly  Gly Gly Ala
    1040                1045                1050

Cys Thr  Cys Thr Gly Cys Gly  Thr Ala Gly Gly Ala  Gly Cys Ala
    1055                1060                1065

Gly Thr  Thr Cys Cys Cys Ala  Ala Ala Ala Cys Cys  Cys Ala Thr
    1070                1075                1080

Cys Ala  Gly Gly Cys Cys Cys  Thr Gly Thr Gly Thr  Ala Ala Thr
    1085                1090                1095

Ala Cys  Cys Ala Cys Cys Cys  Ala Gly Ala Ala Gly  Ala Cys Gly
    1100                1105                1110

Ala Gly  Cys Ala Ala Cys Gly  Gly Gly Thr Cys Cys  Thr Ala Cys
    1115                1120                1125

Thr Ala  Thr Cys Thr Gly Gly  Cys Thr Gly Cys Thr  Cys Cys Cys
    1130                1135                1140

Gly Cys  Cys Gly Gly Gly Ala  Cys Cys Ala Thr Thr  Thr Gly Gly
    1145                1150                1155

Gly Cys  Thr Thr Gly Cys Ala  Ala Cys Ala Cys Cys  Gly Gly Gly
    1160                1165                1170

Cys Thr  Cys Ala Cys Thr Cys  Cys Cys Thr Gly Cys  Cys Thr Ala
    1175                1180                1185

Thr Cys  Thr Ala Cys Cys Ala  Cys Thr Gly Thr Gly  Cys Thr Cys
    1190                1195                1200

Gly Ala  Cys Cys Thr Cys Ala  Cys Cys Ala Cys Cys  Gly Ala Thr
    1205                1210                1215

Thr Ala  Cys Thr Gly Thr Gly  Thr Cys Cys Thr Gly  Gly Thr Thr
    1220                1225                1230

Gly Ala  Gly Cys Thr Cys Thr  Gly Gly Cys Cys Ala  Ala Ala Ala
    1235                1240                1245

Gly Thr  Gly Ala Cys Cys Thr  Ala Cys Cys Ala Cys  Thr Cys Cys
    1250                1255                1260

Cys Cys  Thr Gly Gly Thr Thr  Ala Thr Gly Thr Thr  Thr Ala Thr
    1265                1270                1275

Gly Gly  Cys Cys Ala Gly Thr  Thr Thr Gly Ala Ala  Gly Ala Ala
    1280                1285                1290
```

```
Ala Ala  Ala Ala Cys Cys Ala  Ala Ala Thr Ala Thr  Ala Ala Ala
    1295                 1300                 1305

Ala Gly  Ala Gly Ala Ala Cys  Cys Cys Gly Thr Cys  Thr Cys Ala
    1310                 1315                 1320

Cys Thr  Ala Ala Cys Thr Cys  Thr Gly Gly Cys Cys  Cys Thr Ala
    1325                 1330                 1335

Cys Thr  Ala Thr Thr Ala Gly  Gly Ala Gly Gly Ala  Cys Thr Cys
    1340                 1345                 1350

Ala Cys  Thr Ala Thr Gly Gly  Gly Cys Gly Gly Ala  Ala Thr Thr
    1355                 1360                 1365

Gly Cys  Cys Gly Cys Cys Gly  Gly Ala Gly Thr Gly  Gly Gly Ala
    1370                 1375                 1380

Ala Cys  Ala Gly Gly Gly Ala  Cys Thr Ala Cys Cys  Gly Cys Cys
    1385                 1390                 1395

Cys Thr  Ala Gly Thr Gly Gly  Cys Cys Ala Cys Thr  Cys Ala Gly
    1400                 1405                 1410

Cys Ala  Gly Thr Thr Cys Cys  Ala Ala Cys Ala Ala  Cys Thr Cys
    1415                 1420                 1425

Cys Ala  Gly Gly Cys Thr Gly  Cys Cys Ala Thr Gly  Cys Ala Gly
    1430                 1435                 1440

Gly Ala  Thr Gly Ala Cys Cys  Thr Thr Ala Ala Ala  Gly Ala Ala
    1445                 1450                 1455

Gly Thr  Thr Gly Ala Ala Ala  Ala Gly Thr Cys Cys  Ala Thr Cys
    1460                 1465                 1470

Ala Cys  Thr Ala Ala Thr Cys  Thr Ala Gly Ala Ala  Ala Gly Ala
    1475                 1480                 1485

Thr Cys  Thr Thr Thr Gly Ala  Cys Cys Thr Cys Cys  Thr Thr Gly
    1490                 1495                 1500

Thr Cys  Cys Gly Ala Ala Gly  Thr Ala Gly Thr Gly  Thr Thr Ala
    1505                 1510                 1515

Cys Ala  Gly Ala Ala Thr Cys  Gly Thr Ala Gly Ala  Gly Gly Cys
    1520                 1525                 1530

Cys Thr  Ala Gly Ala Thr Cys  Thr Ala Cys Thr Ala  Thr Thr Cys
    1535                 1540                 1545

Cys Thr  Ala Ala Ala Ala Gly  Ala Gly Gly Gly Ala  Gly Gly Thr
    1550                 1555                 1560

Thr Thr  Gly Thr Gly Thr Gly  Cys Thr Gly Cys Cys  Thr Thr Ala
    1565                 1570                 1575

Ala Ala  Ala Gly Ala Ala Gly  Ala Ala Thr Gly Cys  Thr Gly Thr
    1580                 1585                 1590

Thr Thr  Cys Thr Ala Thr Gly  Cys Cys Gly Ala Cys  Cys Ala Cys
    1595                 1600                 1605

Ala Cys  Ala Gly Gly Ala Thr  Thr Gly Gly Thr Ala  Cys Gly Gly
    1610                 1615                 1620

Gly Ala  Thr Ala Gly Cys Ala  Thr Gly Gly Cys Cys  Ala Ala Ala
    1625                 1630                 1635

Cys Thr  Thr Ala Gly Ala Gly  Ala Ala Ala Gly Ala  Thr Thr Gly
    1640                 1645                 1650

Ala Gly  Thr Cys Ala Gly Ala  Gly Ala Cys Ala Ala  Ala Ala Ala
    1655                 1660                 1665

Cys Thr  Cys Thr Thr Thr Gly  Ala Ala Thr Cys Cys  Cys Ala Ala
    1670                 1675                 1680

Cys Ala  Ala Gly Gly Gly Thr  Gly Gly Thr Thr Thr  Gly Ala Ala
    1685                 1690                 1695
```

Gly Gly Gly Cys Thr Gly Thr Thr Thr Ala Ala Cys Ala Ala Gly
1700 1705 1710

Thr Cys Cys Cys Cys Thr Thr Gly Gly Thr Thr Cys Ala Cys Cys
1715 1720 1725

Ala Cys Cys Cys Thr Gly Ala Thr Ala Thr Cys Cys Ala Cys Cys
1730 1735 1740

Ala Thr Cys Ala Thr Gly Gly Gly Thr Cys Cys Cys Cys Thr Gly
1745 1750 1755

Ala Thr Ala Ala Thr Cys Cys Thr Cys Thr Thr Gly Thr Thr Ala
1760 1765 1770

Ala Thr Thr Thr Thr Ala Cys Thr Cys Thr Thr Thr Gly Gly Gly
1775 1780 1785

Cys Cys Thr Thr Gly Thr Ala Thr Thr Cys Thr Cys Ala Ala Thr
1790 1795 1800

Cys Ala Cys Cys Thr Gly Gly Thr Cys Cys Ala Gly Thr Thr Thr
1805 1810 1815

Ala Thr Cys Ala Ala Ala Gly Ala Cys Ala Gly Gly Gly Thr Thr
1820 1825 1830

Thr Cys Gly Gly Thr Ala Gly Thr Gly Cys Ala Gly Gly Cys Cys
1835 1840 1845

Cys Thr Gly Gly Thr Cys Cys Thr Gly Ala Cys Thr Cys Ala Ala
1850 1855 1860

Cys Ala Ala Thr Ala Thr Cys Ala Thr Cys Ala Ala Cys Thr Thr
1865 1870 1875

Ala Ala Gly Ala Cys Ala Ala Thr Ala Gly Ala Ala Gly Ala Thr
1880 1885 1890

Thr Gly Thr Gly Ala Ala Thr Cys Ala Cys Gly Thr Gly Ala Ala
1895 1900 1905

Thr Ala Ala
1910

<210> SEQ ID NO 59
<211> LENGTH: 636
<212> TYPE: PRT
<213> ORGANISM: Artificial
<220> FEATURE:
<223> OTHER INFORMATION: SL3-2/V3 loop chimeric envelope

<400> SEQUENCE: 59

Met Glu Gly Pro Ala Phe Ser Lys Pro Leu Lys Asp Lys Ile Asn Pro
1 5 10 15

Trp Gly Pro Leu Ile Val Leu Gly Ile Leu Met Arg Ala Arg Val Ser
20 25 30

Val Gln His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

Thr Met Thr Asp Ala Phe Pro Lys Leu Tyr Phe Asp Leu Cys Asp Leu
65 70 75 80

Ile Gly Asp Asp Trp Asp Glu Thr Gly Leu Gly Cys Arg Thr Pro Gly
85 90 95

Gly Arg Lys Arg Ala Arg Ile Phe Asp Phe Tyr Val Cys Pro Gly His
100 105 110

Thr Val Leu Ala Gly Cys Gly Gly Pro Arg Glu Gly Tyr Cys Gly Lys
115 120 125

```
Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Ser Ser Ala Gln Gly Ala Thr Pro Gly Gly
                165                 170                 175

Arg Cys Asn Pro Leu Val Leu Glu Phe Thr Asp Ala Gly Lys Arg Ala
            180                 185                 190

Ser Trp Asp Ala Ser Lys Ala Trp Gly Leu Arg Leu Tyr Arg Ser Thr
        195                 200                 205

Gly Ile Asp Pro Val Thr Arg Phe Ser Leu Thr Arg Gln Val Leu Asn
    210                 215                 220

Ile Gly Pro Arg Val Pro Ile Gly Pro Asn Pro Val Ile Ile Asp Gln
225                 230                 235                 240

Leu Pro Pro Ser Arg Pro Val Gln Val Met Leu Pro Arg Pro Pro Gln
                245                 250                 255

Pro Pro Pro Pro Gly Ala Ala Ser Thr Val Pro Glu Thr Ala Pro Pro
            260                 265                 270

Ser Gln Gln Pro Gly Thr Gly Asp Arg Leu Leu Asn Leu Val Asn Gly
        275                 280                 285

Ala Tyr Gln Ala Leu Asn Leu Thr Ser Pro Asp Lys Thr Gln Glu Cys
    290                 295                 300

Trp Leu Cys Leu Val Ala Gly Pro Pro Tyr Tyr Glu Gly Val Ala Val
305                 310                 315                 320

Leu Gly Thr Tyr Ser Asn His Thr Ser Ala Pro Ala Asn Cys Ser Val
                325                 330                 335

Ala Ser Gln His Lys Leu Thr Leu Ser Glu Val Thr Gly Gln Gly Leu
            340                 345                 350

Cys Val Gly Ala Val Pro Lys Thr His Gln Ala Leu Cys Asn Thr Thr
        355                 360                 365

Gln Lys Thr Ser Asn Gly Ser Tyr Tyr Leu Ala Ala Pro Ala Gly Thr
    370                 375                 380

Ile Trp Ala Cys Asn Thr Gly Leu Thr Pro Cys Leu Ser Thr Thr Val
385                 390                 395                 400

Leu Asp Leu Thr Thr Asp Tyr Cys Val Leu Val Glu Leu Trp Pro Lys
                405                 410                 415

Val Thr Tyr His Ser Pro Gly Tyr Val Tyr Gly Gln Phe Glu Glu Lys
            420                 425                 430

Thr Lys Tyr Lys Arg Glu Pro Val Ser Leu Thr Leu Ala Leu Leu Leu
        435                 440                 445

Gly Gly Leu Thr Met Gly Gly Ile Ala Ala Gly Val Gly Thr Gly Thr
    450                 455                 460

Thr Ala Leu Val Ala Thr Gln Gln Phe Gln Gln Leu Gln Ala Ala Met
465                 470                 475                 480

Gln Asp Asp Leu Lys Glu Val Glu Lys Ser Ile Thr Asn Leu Glu Arg
                485                 490                 495

Ser Leu Thr Ser Leu Ser Glu Val Val Leu Gln Asn Arg Arg Gly Leu
            500                 505                 510

Asp Leu Leu Phe Leu Lys Glu Gly Gly Leu Cys Ala Ala Leu Lys Glu
        515                 520                 525

Glu Cys Cys Phe Tyr Ala Asp His Thr Gly Leu Val Arg Asp Ser Met
    530                 535                 540

Ala Lys Leu Arg Glu Arg Leu Ser Gln Arg Gln Lys Leu Phe Glu Ser
545                 550                 555                 560
```

```
Gln Gln Gly Trp Phe Glu Gly Leu Phe Asn Lys Ser Pro Trp Phe Thr
                565                 570                 575

Thr Leu Ile Ser Thr Ile Met Gly Pro Leu Ile Ile Leu Leu Leu Ile
            580                 585                 590

Leu Leu Phe Gly Pro Cys Ile Leu Asn His Leu Val Gln Phe Ile Lys
        595                 600                 605

Asp Arg Val Ser Val Val Gln Ala Leu Val Leu Thr Gln Gln Tyr His
    610                 615                 620

Gln Leu Lys Thr Ile Glu Asp Cys Glu Ser Arg Glu
625                 630                 635
```

<210> SEQ ID NO 60
<211> LENGTH: 639
<212> TYPE: PRT
<213> ORGANISM: Murine leukaemia virus;

<400> SEQUENCE: 60

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Val Val Ser Ser Ser Ala Gln Gly Ala Thr
                165                 170                 175

Pro Gly Gly Arg Cys Asn Pro Leu Val Leu Glu Phe Thr Asp Ala Gly
            180                 185                 190

Lys Arg Ala Ser Trp Asp Ala Ser Lys Ala Trp Gly Leu Arg Leu Tyr
        195                 200                 205

Arg Ser Thr Arg Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Ile Asp Gln Leu Pro Pro Ser Arg Pro Val Gln Ile Met Leu Pro Arg
                245                 250                 255

Pro Pro Gln Pro Pro Pro Pro Gly Ala Ala Ser Thr Val Pro Glu Thr
            260                 265                 270

Ala Pro Pro Ser Gln Gln Pro Gly Thr Gly Asp Arg Leu Leu Asn Leu
        275                 280                 285

Val Asn Gly Ala Tyr Gln Ala Leu Asn Leu Thr Ser Pro Asp Lys Thr
    290                 295                 300
```

```
Gln Glu Cys Trp Leu Cys Leu Val Ala Gly Pro Pro Tyr Tyr Glu Gly
305                 310                 315                 320

Val Ala Val Leu Gly Thr Tyr Ser Asn His Thr Ser Ala Pro Ala Asn
                325                 330                 335

Cys Ser Val Ala Ser Gln His Lys Leu Thr Leu Ser Glu Val Thr Gly
            340                 345                 350

Gln Gly Leu Cys Val Gly Ala Val Pro Lys Thr His Gln Ala Leu Cys
        355                 360                 365

Asn Thr Thr Gln Lys Thr Ser Asn Gly Ser Tyr Tyr Leu Ala Ala Pro
    370                 375                 380

Ala Gly Thr Ile Trp Ala Cys Asn Thr Gly Leu Thr Pro Cys Leu Ser
385                 390                 395                 400

Thr Thr Val Leu Asp Leu Thr Thr Asp Tyr Cys Val Leu Val Glu Leu
                405                 410                 415

Trp Pro Lys Val Thr Tyr His Ser Pro Gly Tyr Val Tyr Gly Gln Phe
            420                 425                 430

Glu Glu Lys Thr Lys Tyr Lys Arg Glu Pro Val Ser Leu Thr Leu Ala
        435                 440                 445

Leu Leu Leu Gly Gly Leu Thr Met Gly Gly Ile Ala Ala Gly Val Gly
    450                 455                 460

Thr Gly Thr Thr Ala Leu Val Ala Thr Gln Gln Phe Gln Gln Leu Gln
465                 470                 475                 480

Ala Ala Met Gln Asp Asp Leu Lys Glu Val Lys Lys Ser Ile Thr Asn
                485                 490                 495

Leu Glu Arg Ser Leu Thr Ser Leu Ser Glu Val Val Leu Gln Asn Arg
            500                 505                 510

Arg Gly Leu Asp Leu Leu Phe Leu Lys Glu Gly Gly Leu Cys Ala Ala
        515                 520                 525

Leu Lys Glu Glu Cys Cys Phe Tyr Ala Asp His Thr Gly Leu Val Arg
    530                 535                 540

Asp Ser Met Ala Lys Leu Arg Glu Arg Leu Ser Gln Arg Gln Lys Leu
545                 550                 555                 560

Phe Glu Ser Gln Gln Gly Trp Phe Glu Gly Leu Phe Asn Lys Ser Pro
                565                 570                 575

Trp Phe Thr Thr Leu Ile Ser Thr Ile Met Gly Pro Leu Ile Ile Leu
            580                 585                 590

Leu Leu Ile Leu Leu Phe Gly Pro Cys Ile Leu Asn His Leu Val Gln
        595                 600                 605

Phe Ile Lys Asp Arg Val Ser Val Val Gln Ala Leu Val Leu Thr Gln
    610                 615                 620

Gln Tyr His Gln Leu Lys Thr Ile Glu Asp Cys Glu Ser Arg Glu
625                 630                 635
```

```
<210> SEQ ID NO 61
<211> LENGTH: 659
<212> TYPE: PRT
<213> ORGANISM: Artificial
<220> FEATURE:
<223> OTHER INFORMATION: SL3-2/apelin chimeric envelope

<400> SEQUENCE: 61

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30
```

```
Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Gly Gly Ser Gly Gln Arg Pro Arg Leu Ser
                165                 170                 175

His Lys Gly Pro Met Pro Phe Ser Gly Gly Ser Gly Ser Ser Ser Ala
            180                 185                 190

Gln Gly Ala Thr Pro Gly Gly Arg Cys Asn Pro Leu Val Leu Glu Phe
        195                 200                 205

Thr Asp Ala Gly Lys Arg Ala Ser Trp Asp Ala Ser Lys Ala Trp Gly
    210                 215                 220

Leu Arg Leu Tyr Arg Ser Thr Arg Thr Asp Pro Val Thr Arg Phe Ser
225                 230                 235                 240

Leu Thr Arg Gln Val Leu Asn Ile Gly Pro Arg Val Pro Ile Gly Pro
                245                 250                 255

Asn Pro Val Ile Ile Asp Gln Leu Pro Pro Ser Arg Pro Val Gln Val
            260                 265                 270

Met Leu Pro Arg Pro Pro Gln Pro Pro Pro Pro Gly Ala Ala Ser Thr
        275                 280                 285

Val Pro Glu Thr Ala Pro Pro Ser Gln Gln Pro Gly Thr Gly Asp Arg
    290                 295                 300

Leu Leu Asn Leu Val Asn Gly Ala Tyr Gln Ala Leu Asn Leu Thr Ser
305                 310                 315                 320

Pro Asp Lys Thr Gln Glu Cys Trp Leu Cys Leu Val Ala Gly Pro Pro
                325                 330                 335

Tyr Tyr Glu Gly Val Ala Val Leu Gly Thr Tyr Ser Asn His Thr Ser
            340                 345                 350

Ala Pro Ala Asn Cys Ser Val Ala Ser Gln His Lys Leu Thr Leu Ser
        355                 360                 365

Glu Val Thr Gly Gln Gly Leu Cys Val Gly Ala Val Pro Lys Thr His
    370                 375                 380

Gln Ala Leu Cys Asn Thr Thr Gln Lys Thr Ser Asn Gly Ser Tyr Tyr
385                 390                 395                 400

Leu Ala Ala Pro Ala Gly Thr Ile Trp Ala Cys Asn Thr Gly Leu Thr
                405                 410                 415

Pro Cys Leu Ser Thr Thr Val Leu Asp Leu Thr Thr Asp Tyr Cys Val
            420                 425                 430

Leu Val Glu Leu Trp Pro Lys Val Thr Tyr His Ser Pro Gly Tyr Val
        435                 440                 445

Tyr Gly Gln Phe Glu Glu Lys Thr Lys Tyr Lys Arg Glu Pro Val Ser
    450                 455                 460
```

```
Leu Thr Leu Ala Leu Leu Leu Gly Gly Leu Thr Met Gly Gly Ile Ala
465                 470                 475                 480

Ala Gly Val Gly Thr Gly Thr Thr Ala Leu Val Ala Thr Gln Gln Phe
                485                 490                 495

Gln Gln Leu Gln Ala Ala Met Gln Asp Asp Leu Lys Glu Val Glu Lys
            500                 505                 510

Ser Ile Thr Asn Leu Glu Arg Ser Leu Thr Ser Leu Ser Glu Val Val
        515                 520                 525

Leu Gln Asn Arg Arg Gly Leu Asp Leu Leu Phe Leu Lys Glu Gly Gly
    530                 535                 540

Leu Cys Ala Ala Leu Lys Glu Glu Cys Cys Phe Tyr Ala Asp His Thr
545                 550                 555                 560

Gly Leu Val Arg Asp Ser Met Ala Lys Leu Arg Glu Arg Leu Ser Gln
                565                 570                 575

Arg Gln Lys Leu Phe Glu Ser Gln Gln Gly Trp Phe Glu Gly Leu Phe
            580                 585                 590

Asn Lys Ser Pro Trp Phe Thr Thr Leu Ile Ser Thr Ile Met Gly Pro
        595                 600                 605

Leu Ile Ile Leu Leu Leu Ile Leu Leu Phe Gly Pro Cys Ile Leu Asn
    610                 615                 620

His Leu Val Gln Phe Ile Lys Asp Arg Val Ser Val Val Gln Ala Leu
625                 630                 635                 640

Val Leu Thr Gln Gln Tyr His Gln Leu Lys Thr Ile Glu Asp Cys Glu
                645                 650                 655

Ser Arg Glu
```

<210> SEQ ID NO 62
<211> LENGTH: 676
<212> TYPE: PRT
<213> ORGANISM: Artificial
<220> FEATURE:
<223> OTHER INFORMATION: SL3-2/V3 loop chimeric envelope

<400> SEQUENCE: 62

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Thr Arg Pro Asn Asn Asn Thr Arg Lys Arg Ile Arg Ile Gln Arg
```

```
                165                 170                 175

Gly Pro Gly Arg Ala Phe Val Thr Ile Gly Lys Ile Gly Asn Met Arg
            180                 185                 190

Gln Ala His Cys Gly Pro Cys Tyr Asp Ser Ser Val Val Ser Ser Ser
        195                 200                 205

Ala Gln Gly Ala Thr Pro Gly Gly Arg Cys Asn Pro Leu Val Leu Glu
    210                 215                 220

Phe Thr Asp Ala Gly Lys Arg Ala Ser Trp Asp Ala Ser Lys Ala Trp
225                 230                 235                 240

Gly Leu Arg Leu Tyr Arg Ser Thr Arg Thr Asp Pro Val Thr Arg Phe
                245                 250                 255

Ser Leu Thr Arg Gln Val Leu Asn Ile Gly Pro Arg Val Pro Ile Gly
            260                 265                 270

Pro Asn Pro Val Ile Ile Asp Gln Leu Pro Pro Ser Arg Pro Val Gln
        275                 280                 285

Val Met Leu Pro Arg Pro Pro Gln Pro Pro Pro Pro Gly Ala Ala Ser
    290                 295                 300

Thr Val Pro Glu Thr Ala Pro Pro Ser Gln Gln Pro Gly Thr Gly Asp
305                 310                 315                 320

Arg Leu Leu Asn Leu Val Asn Gly Ala Tyr Gln Ala Leu Asn Leu Thr
                325                 330                 335

Ser Pro Asp Lys Thr Gln Glu Cys Trp Leu Cys Leu Val Ala Gly Pro
            340                 345                 350

Pro Tyr Tyr Glu Gly Val Ala Val Leu Gly Thr Tyr Ser Asn His Thr
        355                 360                 365

Ser Ala Pro Ala Asn Cys Ser Val Ala Ser Gln His Lys Leu Thr Leu
    370                 375                 380

Ser Glu Val Thr Gly Gln Gly Leu Cys Val Gly Ala Val Pro Lys Thr
385                 390                 395                 400

His Gln Ala Leu Cys Asn Thr Thr Gln Lys Thr Ser Asn Gly Ser Tyr
                405                 410                 415

Tyr Leu Ala Ala Pro Ala Gly Thr Ile Trp Ala Cys Asn Thr Gly Leu
            420                 425                 430

Thr Pro Cys Leu Ser Thr Thr Val Leu Asp Leu Thr Thr Asp Tyr Cys
        435                 440                 445

Val Leu Val Glu Leu Trp Pro Lys Val Thr Tyr His Ser Pro Gly Tyr
    450                 455                 460

Val Tyr Gly Gln Phe Glu Glu Lys Thr Lys Tyr Lys Arg Glu Pro Val
465                 470                 475                 480

Ser Leu Thr Leu Ala Leu Leu Leu Gly Gly Leu Thr Met Gly Gly Ile
                485                 490                 495

Ala Ala Gly Val Gly Thr Gly Thr Thr Ala Leu Val Ala Thr Gln Gln
            500                 505                 510

Phe Gln Gln Leu Gln Ala Ala Met Gln Asp Asp Leu Lys Glu Val Glu
        515                 520                 525

Lys Ser Ile Thr Asn Leu Glu Arg Ser Leu Thr Ser Leu Ser Glu Val
    530                 535                 540

Val Leu Gln Asn Arg Arg Gly Leu Asp Leu Leu Phe Leu Lys Glu Gly
545                 550                 555                 560

Gly Leu Cys Ala Ala Leu Lys Glu Glu Cys Cys Phe Tyr Ala Asp His
                565                 570                 575

Thr Gly Leu Val Arg Asp Ser Met Ala Lys Leu Arg Glu Arg Leu Ser
            580                 585                 590
```

```
Gln Arg Gln Lys Leu Phe Glu Ser Gln Gln Gly Trp Phe Glu Gly Leu
        595                 600                 605

Phe Asn Lys Ser Pro Trp Phe Thr Thr Leu Ile Ser Thr Ile Met Gly
    610                 615                 620

Pro Leu Ile Ile Leu Leu Leu Ile Leu Leu Phe Gly Pro Cys Ile Leu
625                 630                 635                 640

Asn His Leu Val Gln Phe Ile Lys Asp Arg Val Ser Val Val Gln Ala
                645                 650                 655

Leu Val Leu Thr Gln Gln Tyr His Gln Leu Lys Thr Ile Glu Asp Cys
            660                 665                 670

Glu Ser Arg Glu
        675


<210> SEQ ID NO 63
<211> LENGTH: 655
<212> TYPE: PRT
<213> ORGANISM: Artificial
<220> FEATURE:
<223> OTHER INFORMATION: SL3-2/V3 loop chimeric envelope

<400> SEQUENCE: 63

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Thr Arg Pro Asn Asn Asn Thr Arg Lys Arg Ile Arg Ile Gln
                165                 170                 175

Arg Gly Pro Gly Arg Ala Phe Val Thr Ile Gly Lys Ile Gly Asn Met
            180                 185                 190

Arg Gln Ala His Cys Asn Pro Leu Val Leu Glu Phe Thr Asp Ala Gly
        195                 200                 205

Lys Arg Ala Ser Trp Asp Ala Ser Lys Ala Trp Gly Leu Arg Leu Tyr
    210                 215                 220

Arg Ser Thr Arg Thr Asp Pro Val Thr Arg Phe Ser Leu Thr Arg Gln
225                 230                 235                 240

Val Leu Asn Ile Gly Pro Arg Val Pro Ile Gly Pro Asn Pro Val Ile
                245                 250                 255

Ile Asp Gln Leu Pro Pro Ser Arg Pro Val Gln Val Met Leu Pro Arg
            260                 265                 270

Pro Pro Gln Pro Pro Pro Pro Gly Ala Ala Ser Thr Val Pro Glu Thr
```

-continued

```
        275                 280                 285

Ala Pro Pro Ser Gln Gln Pro Gly Thr Gly Asp Arg Leu Leu Asn Leu
    290                 295                 300

Val Asn Gly Ala Tyr Gln Ala Leu Asn Leu Thr Ser Pro Asp Lys Thr
305                 310                 315                 320

Gln Glu Cys Trp Leu Cys Leu Val Ala Gly Pro Pro Tyr Tyr Glu Gly
                325                 330                 335

Val Ala Val Leu Gly Thr Tyr Ser Asn His Thr Ser Ala Pro Ala Asn
            340                 345                 350

Cys Ser Val Ala Ser Gln His Lys Leu Thr Leu Ser Glu Val Thr Gly
        355                 360                 365

Gln Gly Leu Cys Val Gly Ala Val Pro Lys Thr His Gln Ala Leu Cys
    370                 375                 380

Asn Thr Thr Gln Lys Thr Ser Asn Gly Ser Tyr Tyr Leu Ala Ala Pro
385                 390                 395                 400

Ala Gly Thr Ile Trp Ala Cys Asn Thr Gly Leu Thr Pro Cys Leu Ser
                405                 410                 415

Thr Thr Val Leu Asp Leu Thr Thr Asp Tyr Cys Val Leu Val Glu Leu
            420                 425                 430

Trp Pro Lys Val Thr Tyr His Ser Pro Gly Tyr Val Tyr Gly Gln Phe
        435                 440                 445

Glu Glu Lys Thr Lys Tyr Lys Arg Glu Pro Val Ser Leu Thr Leu Ala
    450                 455                 460

Leu Leu Leu Gly Gly Leu Thr Met Gly Gly Ile Ala Ala Gly Val Gly
465                 470                 475                 480

Thr Gly Thr Thr Ala Leu Val Ala Thr Gln Gln Phe Gln Gln Leu Gln
                485                 490                 495

Ala Ala Met Gln Asp Asp Leu Lys Glu Val Glu Lys Ser Ile Thr Asn
            500                 505                 510

Leu Glu Arg Ser Leu Thr Ser Leu Ser Glu Val Val Leu Gln Asn Arg
        515                 520                 525

Arg Gly Leu Asp Leu Leu Phe Leu Lys Glu Gly Gly Leu Cys Ala Ala
    530                 535                 540

Leu Lys Glu Glu Cys Cys Phe Tyr Ala Asp His Thr Gly Leu Val Arg
545                 550                 555                 560

Asp Ser Met Ala Lys Leu Arg Glu Arg Leu Ser Gln Arg Gln Lys Leu
                565                 570                 575

Phe Glu Ser Gln Gln Gly Trp Phe Glu Gly Leu Phe Asn Lys Ser Pro
            580                 585                 590

Trp Phe Thr Thr Leu Ile Ser Thr Ile Met Gly Pro Leu Ile Ile Leu
        595                 600                 605

Leu Leu Ile Leu Leu Phe Gly Pro Cys Ile Leu Asn His Leu Val Gln
    610                 615                 620

Phe Ile Lys Asp Arg Val Ser Val Val Gln Ala Leu Val Leu Thr Gln
625                 630                 635                 640

Gln Tyr His Gln Leu Lys Thr Ile Glu Asp Cys Glu Ser Arg Glu
                645                 650                 655
```

<210> SEQ ID NO 64
<211> LENGTH: 660
<212> TYPE: PRT
<213> ORGANISM: Artificial
<220> FEATURE:
<223> OTHER INFORMATION: SL3-2/V3 loop chimeric envelope

<400> SEQUENCE: 64

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Thr Arg
65                  70                  75                  80

Pro Asn Asn Asn Thr Arg Lys Arg Ile Arg Ile Gln Arg Gly Pro Gly
                85                  90                  95

Arg Ala Phe Val Thr Ile Gly Lys Ile Gly Asn Met Arg Gln Ala His
            100                 105                 110

Cys Arg Thr Pro Gly Gly Arg Lys Arg Ala Arg Ile Phe Asp Phe Tyr
        115                 120                 125

Val Cys Pro Gly His Thr Val Leu Ala Gly Cys Gly Gly Pro Arg Glu
    130                 135                 140

Gly Tyr Cys Gly Lys Trp Gly Cys Glu Thr Thr Gly Gln Ala Tyr Trp
145                 150                 155                 160

Lys Pro Ser Ser Ser Trp Asp Leu Ile Ser Leu Lys Arg Gly Asn Thr
                165                 170                 175

Pro Lys Gly Gln Gly Pro Cys Tyr Asp Ser Ser Val Val Ser Ser Ser
            180                 185                 190

Ala Gln Gly Ala Thr Pro Gly Gly Arg Cys Asn Pro Leu Val Leu Glu
        195                 200                 205

Phe Thr Asp Ala Gly Lys Arg Ala Ser Trp Asp Ala Ser Lys Ala Trp
    210                 215                 220

Gly Leu Arg Leu Tyr Arg Ser Thr Arg Thr Asp Pro Val Thr Arg Phe
225                 230                 235                 240

Ser Leu Thr Arg Gln Val Leu Asn Ile Gly Pro Arg Val Pro Ile Gly
                245                 250                 255

Pro Asn Pro Val Ile Ile Asp Gln Leu Pro Pro Ser Arg Pro Val Gln
            260                 265                 270

Val Met Leu Pro Arg Pro Pro Gln Pro Pro Pro Pro Gly Ala Ala Ser
        275                 280                 285

Thr Val Pro Glu Thr Ala Pro Pro Ser Gln Gln Pro Gly Thr Gly Asp
    290                 295                 300

Arg Leu Leu Asn Leu Val Asn Gly Ala Tyr Gln Ala Leu Asn Leu Thr
305                 310                 315                 320

Ser Pro Asp Lys Thr Gln Glu Cys Trp Leu Cys Leu Val Ala Gly Pro
                325                 330                 335

Pro Tyr Tyr Glu Gly Val Ala Val Leu Gly Thr Tyr Ser Asn His Thr
            340                 345                 350

Ser Ala Pro Ala Asn Cys Ser Val Ala Ser Gln His Lys Leu Thr Leu
        355                 360                 365

Ser Glu Val Thr Gly Gln Gly Leu Cys Val Gly Ala Val Pro Lys Thr
    370                 375                 380

His Gln Ala Leu Cys Asn Thr Thr Gln Lys Thr Ser Asn Gly Ser Tyr
385                 390                 395                 400

Tyr Leu Ala Ala Pro Ala Gly Thr Ile Trp Ala Cys Asn Thr Gly Leu
                405                 410                 415

Thr Pro Cys Leu Ser Thr Thr Val Leu Asp Leu Thr Thr Asp Tyr Cys
```

```
            420                 425                 430

Val Leu Val Glu Leu Trp Pro Lys Val Thr Tyr His Ser Pro Gly Tyr
        435                 440                 445

Val Tyr Gly Gln Phe Glu Glu Lys Thr Lys Tyr Lys Arg Glu Pro Val
    450                 455                 460

Ser Leu Thr Leu Ala Leu Leu Leu Gly Gly Leu Thr Met Gly Gly Ile
465                 470                 475                 480

Ala Ala Gly Val Gly Thr Gly Thr Thr Ala Leu Val Ala Thr Gln Gln
                485                 490                 495

Phe Gln Gln Leu Gln Ala Ala Met Gln Asp Asp Leu Lys Glu Val Glu
            500                 505                 510

Lys Ser Ile Thr Asn Leu Glu Arg Ser Leu Thr Ser Leu Ser Glu Val
        515                 520                 525

Val Leu Gln Asn Arg Arg Gly Leu Asp Leu Leu Phe Leu Lys Glu Gly
    530                 535                 540

Gly Leu Cys Ala Ala Leu Lys Glu Glu Cys Cys Phe Tyr Ala Asp His
545                 550                 555                 560

Thr Gly Leu Val Arg Asp Ser Met Ala Lys Leu Arg Glu Arg Leu Ser
                565                 570                 575

Gln Arg Gln Lys Leu Phe Glu Ser Gln Gln Gly Trp Phe Glu Gly Leu
            580                 585                 590

Phe Asn Lys Ser Pro Trp Phe Thr Thr Leu Ile Ser Thr Ile Met Gly
        595                 600                 605

Pro Leu Ile Ile Leu Leu Leu Ile Leu Leu Phe Gly Pro Cys Ile Leu
    610                 615                 620

Asn His Leu Val Gln Phe Ile Lys Asp Arg Val Ser Val Val Gln Ala
625                 630                 635                 640

Leu Val Leu Thr Gln Gln Tyr His Gln Leu Lys Thr Ile Glu Asp Cys
                645                 650                 655

Glu Ser Arg Glu
            660
```

<210> SEQ ID NO 65
<211> LENGTH: 1920
<212> TYPE: DNA
<213> ORGANISM: Murine leukemia virus

<400> SEQUENCE: 65

```
atggaaggtc cagcgttctc aaaacccctt aaagataaga ttaacccgtg gggcccccta      60

atagtcctgg gaatcttaat gagggcaaga gtatcagtac aacatgacag ccctcatcag     120

gtcttcaatg ttacttggag agttaccaac ttaatgacag gacaaacagc taatgctacc     180

tccctcctgg ggacaatgac cgatgccttt cctaaactgt actttgactt gtgcgattta     240

ataggggacg actgggatga gactggactc gggtgtcgca ctcccggggg aagaaaaagg     300

gcaagaatat ttgacttcta tgtttgcccc ggtcacactg tgctagcagg gtgtggaggg     360

ccgagagagg gctactgtgg caaatgggga tgtgagacca ctggacaggc atactggaag     420

ccatcatcat catgggacct aatttccctt aagcgaggaa acactcctaa aggccagggc     480

ccctgttatg attcctcggt ggtctccagt agcgcccagg gtgccacacc ggggggtcga     540

tgcaaccccc tagtcctaga attcactgac gcgggtaaaa gggccagctg ggacgcctcc     600

aaagcatggg gactaagact gtaccgatcc acaaggaccg acccggtgac ccggttctct     660

ttgacccgcc aggtcctcaa tatagggccc cgcgtcccca ttgggcctaa tcccgtgatc     720

attgaccagt tacccccctc ccgacccgtg caggtcatgc tccccaggcc tcctcagcct     780
```

```
cctccaccag gcgcagcctc tacagtccct gagactgccc caccttccca acaacctggg    840

acgggagaca ggctgctaaa cctggtaaat ggagcctacc aagctctcaa cctcaccagt    900

cctgacaaaa cccaagagtg ctggttgtgt ctggtagcgg gacccccta ctacgaaggg    960

gttgccgtcc taggtactta ttccaaccat acctctgccc cagctaactg ctccgtggcc   1020

tcccaacaca agctgaccct gtccgaagtg accggacagg gactctgcgt aggagcagtt   1080

cccaaaaccc atcaggccct gtgtaatacc acccagaaga cgagcaacgg gtcctactat   1140

ctggctgctc ccgccgggac catttgggct tgcaacaccg ggctcactcc ctgcctatct   1200

accactgtgc tcgacctcac caccgattac tgtgtcctgg ttgagctctg gccaaaagtg   1260

acctaccact cccctggtta tgtttatggc cagtttgaag aaaaaaccaa atataaaaga   1320

gaacccgtct cactaactct ggccctacta ttaggaggac tcactatggg cggaattgcc   1380

gccggagtgg gaacagggac taccgcccta gtggccactc agcagttcca acaactccag   1440

gctgccatgc aggatgacct taaagaagtt gaaaagtcca tcactaatct agaaaagatct   1500

ttgacctcct tgtccgaagt agtgttacag aatcgtagag gcctagatct actattccta   1560

aaagagggag gtttgtgtgc tgccttaaaa gaagaatgct gtttctatgc cgaccacaca   1620

ggattggtac gggatagcat ggccaaactt agagaaagat tgagtcagag acaaaaactc   1680

tttgaatccc aacaagggtg gtttgaaggg ctgtttaaca agtccccttg gttcaccacc   1740

ctgatatcca ccatcatggg tcccctgata atcctcttgt taattttact ctttgggcct   1800

tgtattctca atcacctggt ccagtttatc aaagacaggg tttcggtagt gcaggccctg   1860

gtcctgactc aacaatatca tcaacttaag acaatagaag attgtgaatc acgtgaataa   1920
```

<210> SEQ ID NO 66
<211> LENGTH: 2031
<212> TYPE: DNA
<213> ORGANISM: artificial
<220> FEATURE:
<223> OTHER INFORMATION: SL3-2/V3 loop chimeric envelope

<400> SEQUENCE: 66

```
atggaaggtc cagcgttctc aaaacccctt aaagataaga ttaacccgtg ggccccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcaagg aatctaccag    480

tgtacaagac ccaacaacaa tacaagaaaa agaatccgta tccagagagg accagggaga    540

gcatttgtta caataggaaa aataggaaat atgagacaag cacattgtgg gccctgttat    600

gattcctcgg tggtctccag tagcgcccag ggtgccacac cgggggggtcg atgcaacccc    660

ctagtcctag aattcactga cgcgggtaaa agggccagct gggacgcctc caaagcatgg    720

ggactaagac tgtaccgatc cacaaggacc gacccggtga cccggttctc tttgacccgc    780

caggtcctca atatagggcc ccgcgtcccc attgggccta atcccgtgat cattgaccag    840

ttaccccccct cccgacccgt gcaggtcatg ctccccaggc ctcctcagcc tcctccacca    900

ggcgcagcct ctacagtccc tgagactgcc ccaccttccc aacaacctgg gacgggagac    960
```

```
aggctgctaa acctggtaaa tggagcctac caagctctca acctcaccag tcctgacaaa   1020
acccaagagt gctggttgtg tctggtagcg ggaccccct actacgaagg ggttgccgtc    1080
ctaggtactt attccaacca tacctctgcc ccagctaact gctccgtggc ctcccaacac   1140
aagctgaccc tgtccgaagt gaccggacag ggactctgcg taggagcagt tcccaaaacc   1200
catcaggccc tgtgtaatac cacccagaag acgagcaacg ggtcctacta tctggctgct   1260
cccgccggga ccatttgggc ttgcaacacc gggctcactc cctgcctatc taccactgtg   1320
ctcgacctca ccaccgatta ctgtgtcctg gttgagctct ggccaaaagt gacctaccac   1380
tcccctggtt atgtttatgg ccagtttgaa gaaaaaacca aatataaaag agaacccgtc   1440
tcactaactc tggccctact attaggagga ctcactatgg gcggaattgc cgccggagtg   1500
ggaacaggga ctaccgccct agtggccact cagcagttcc aacaactcca ggctgccatg   1560
caggatgacc ttaaagaagt tgaaaagtcc atcactaatc tagaaagatc tttgacctcc   1620
ttgtccgaag tagtgttaca gaatcgtaga ggcctagatc tactattcct aaaagaggga   1680
ggtttgtgtg ctgccttaaa agaagaatgc tgtttctatg ccgaccacac aggattggta   1740
cgggatagca tggccaaact tagagaaaga ttgagtcaga gacaaaaact ctttgaatcc   1800
caacaagggt ggtttgaagg gctgtttaac aagtcccctt ggttcaccac cctgatatcc   1860
accatcatgg gtcccctgat aatcctcttg ttaattttac tctttgggcc ttgtattctc   1920
aatcacctgg tccagtttat caaagacagg gtttcggtag tgcaggccct ggtcctgact   1980
caacaatatc atcaacttaa gacaatagaa gattgtgaat cacgtgaata a            2031
```

<210> SEQ ID NO 67
<211> LENGTH: 1968
<212> TYPE: DNA
<213> ORGANISM: artificial
<220> FEATURE:
<223> OTHER INFORMATION: SL3-2/V3 loop chimeric envelope

<400> SEQUENCE: 67

```
atggaaggtc cagcgttctc aaaacccctt aaagataaga ttaacccgtg ggcccccta      60
atagtcctgg gaatcttaat gagggcaaga gtatcagtac aacatgacag ccctcatcag   120
gtcttcaatg ttacttggag agttaccaac ttaatgacag gacaaacagc taatgctacc   180
tccctcctgg ggacaatgac cgatgccttt cctaaactgt actttgactt gtgcgattta   240
atagggggacg actgggatga gactggactc gggtgtcgca ctcccggggg aagaaaaagg  300
gcaagaatat ttgacttcta tgtttgcccc ggtcacactg tgctagcagg gtgtggaggg   360
ccgagagagg gctactgtgg caaatgggga tgtgagacca ctggacaggc atactggaag   420
ccatcatcat catgggacct aatttccctt aagcgaggaa acactcctaa aggccagggc   480
ccctgtacaa gacccaacaa caatacaaga aaaagaatcc gtatccagag aggaccaggg   540
agagcatttg ttacaatagg aaaaatagga aatatgagac aagcacattg taacccccta   600
gtcctagaat tcactgacgc gggtaaaagg gccagctggg acgcctccaa agcatgggga   660
ctaagactgt accgatccac aaggaccgac ccggtgaccc ggttctcttt gacccgccag   720
gtcctcaata tagggccccg cgtccccatt gggcctaatc ccgtgatcat tgaccagtta   780
ccccccctccc gacccgtgca ggtcatgctc cccaggcctc ctcagcctcc tccaccaggc  840
gcagcctcta cagtccctga gactgcccca ccttcccaac aacctgggac gggagacagg   900
ctgctaaacc tggtaaatgg agcctaccaa gctctcaacc tcaccagtcc tgacaaaacc   960
caagagtgct ggttgtgtct ggtagcggga ccccccctact acgaaggggt tgccgtccta  1020
```

```
ggtacttatt ccaaccatac ctctgcccca gctaactgct ccgtggcctc ccaacacaag   1080

ctgaccctgt ccgaagtgac cggacaggga ctctgcgtag gagcagttcc caaaacccat   1140

caggccctgt gtaataccac ccagaagacg agcaacgggt cctactatct ggctgctccc   1200

gccgggacca tttgggcttg caacaccggg ctcactccct gcctatctac cactgtgctc   1260

gacctcacca ccgattactg tgtcctggtt gagctctggc caaaagtgac ctaccactcc   1320

cctggttatg tttatggcca gtttgaagaa aaaaccaaat ataaaagaga acccgtctca   1380

ctaactctgg ccctactatt aggaggactc actatgggcg gaattgccgc cggagtggga   1440

acagggacta ccgccctagt ggccactcag cagttccaac aactccaggc tgccatgcag   1500

gatgacctta aagaagttga aaagtccatc actaatctag aaagatcttt gacctccttg   1560

tccgaagtag tgttacagaa tcgtagaggc ctagatctac tattcctaaa agagggaggt   1620

ttgtgtgctg ccttaaaaga agaatgctgt ttctatgccg accacacagg attggtacgg   1680

gatagcatgg ccaaacttag agaaagattg agtcagagac aaaaactctt tgaatcccaa   1740

caagggtggt ttgaagggct gtttaacaag tccccttggt tcaccaccct gatatccacc   1800

atcatgggtc ccctgataat cctcttgtta attttactct ttgggccttg tattctcaat   1860

cacctggtcc agtttatcaa agacagggtt tcggtagtgc aggccctggt cctgactcaa   1920

caatatcatc aacttaagac aatagaagat tgtgaatcac gtgaataa                 1968
```

<210> SEQ ID NO 68
<211> LENGTH: 1983
<212> TYPE: DNA
<213> ORGANISM: artificial
<220> FEATURE:
<223> OTHER INFORMATION: SL3-2/V3 loop chimeric envelope

<400> SEQUENCE: 68

```
atggaaggtc cagcgttctc aaaacccctt aaagataaga ttaacccgtg ggggccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgtacaaga    240

cccaacaaca atacaagaaa aagaatccgt atccagagag gaccagggag agcatttgtt    300

acaataggaa aaataggaaa tatgagacaa gcacattgtc gcactcccgg gggaagaaaa    360

agggcaagaa tatttgactt ctatgtttgc cccggtcaca ctgtgctagc agggtgtgga    420

gggccgagag agggctactg tggcaaatgg ggatgtgaga ccactggaca ggcatactgg    480

aagccatcat catcatggga cctaatttcc cttaagcgag gaaacactcc taaaggccag    540

ggcccctgtt atgattcctc ggtggtctcc agtagcgccc agggtgccac accgggggt     600

cgatgcaacc ccctagtcct agaattcact gacgcgggta aaagggccag ctgggacgcc    660

tccaaagcat ggggactaag actgtaccga tccacaagga ccgacccggt gacccggttc    720

tctttgaccc gccaggtcct caatataggg ccccgcgtcc ccattgggcc taatcccgtg    780

atcattgacc agttaccccc ctcccgaccc gtgcaggtca tgctccccag gcctcctcag    840

cctcctccac caggcgcagc ctctacagtc cctgagactg ccccaccttc ccaacaacct    900

gggacgggag acaggctgct aaacctggta aatggagcct accaagctct caacctcacc    960

agtcctgaca aaacccaaga gtgctggttg tgtctggtag cgggaccccc ctactacgaa   1020

ggggttgccg tcctaggtac ttattccaac catacctctg ccccagctaa ctgctccgtg   1080

gcctcccaac acaagctgac cctgtccgaa gtgaccggac agggactctg cgtaggagca   1140
```

gttcccaaaa cccatcaggc cctgtgtaat accacccaga agacgagcaa cgggtcctac 1200
tatctggctg ctcccgccgg gaccatttgg gcttgcaaca ccgggctcac tccctgccta 1260
tctaccactg tgctcgacct caccaccgat tactgtgtcc tggttgagct ctggccaaaa 1320
gtgacctacc actcccctgg ttatgtttat ggccagtttg aagaaaaaac caaatataaa 1380
agagaacccg tctcactaac tctggcccta ctattaggag gactcactat gggcggaatt 1440
gccgccggag tgggaacagg gactaccgcc ctagtggcca ctcagcagtt ccaacaactc 1500
caggctgcca tgcaggatga ccttaaagaa gttgaaaagt ccatcactaa tctagaaaga 1560
tctttgacct ccttgtccga agtagtgtta cagaatcgta gaggcctaga tctactattc 1620
ctaaaagagg gaggtttgtg tgctgcctta aaagaagaat gctgtttcta tgccgaccac 1680
acaggattgg tacgggatag catggccaaa cttagagaaa gattgagtca gagacaaaaa 1740
ctctttgaat cccaacaagg gtggtttgaa gggctgttta acaagtcccc ttggttcacc 1800
accctgatat ccaccatcat gggtcccctg ataatcctct tgttaatttt actctttggg 1860
ccttgtattc tcaatcacct ggtccagttt atcaaagaca gggtttcggt agtgcaggcc 1920
ctggtcctga ctcaacaata tcatcaactt aagacaatag aagattgtga atcacgtgaa 1980
taa 1983

<210> SEQ ID NO 69
<211> LENGTH: 36
<212> TYPE: PRT
<213> ORGANISM: Artificial
<220> FEATURE:
<223> OTHER INFORMATION: V3 loop sequence

<400> SEQUENCE: 69

Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35

<210> SEQ ID NO 70
<211> LENGTH: 36
<212> TYPE: PRT
<213> ORGANISM: Artificial
<220> FEATURE:
<223> OTHER INFORMATION: V3 loop sequence

<400> SEQUENCE: 70

Cys Thr Arg Pro Asn Asn Asn Ile Arg Ile Arg His Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35

<210> SEQ ID NO 71
<211> LENGTH: 37
<212> TYPE: PRT
<213> ORGANISM: Artificial
<220> FEATURE:
<223> OTHER INFORMATION: V3 loop sequence

<400> SEQUENCE: 71

Cys Thr Arg Pro Asn Asn Asn Asn Thr Arg Lys Arg Ile Arg Ile Gln

```
1               5                   10                  15

Arg Gly Pro Gly Arg Ala Phe Val Thr Ile Gly Lys Ile Gly Asn Met
            20                  25                  30

Arg Gln Ala His Cys
        35


<210> SEQ ID NO 72
<211> LENGTH: 640
<212> TYPE: PRT
<213> ORGANISM: Artificial
<220> FEATURE:
<223> OTHER INFORMATION: Modified SL3-2 envelope

<400> SEQUENCE: 72

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Gly Pro Cys Tyr Asp Ser Ser Val Val Ser Ser Ser Ala Gln Gly Ala
                165                 170                 175

Thr Pro Gly Gly Arg Cys Asn Pro Leu Val Leu Glu Phe Thr Asp Ala
            180                 185                 190

Gly Lys Arg Ala Ser Trp Asp Ala Ser Lys Ala Trp Gly Leu Arg Leu
        195                 200                 205

Tyr Arg Ser Thr Arg Thr Asp Pro Val Thr Arg Phe Ser Leu Thr Arg
    210                 215                 220

Gln Val Leu Asn Ile Gly Pro Arg Val Pro Ile Gly Pro Asn Pro Val
225                 230                 235                 240

Ile Ile Asp Gln Leu Pro Pro Ser Arg Pro Val Gln Val Met Leu Pro
                245                 250                 255

Arg Pro Pro Gln Pro Pro Pro Pro Gly Ala Ala Ser Thr Val Pro Glu
            260                 265                 270

Thr Ala Pro Pro Ser Gln Gln Pro Gly Thr Gly Asp Arg Leu Leu Asn
        275                 280                 285

Leu Val Asn Gly Ala Tyr Gln Ala Leu Asn Leu Thr Ser Pro Asp Lys
    290                 295                 300

Thr Gln Glu Cys Trp Leu Cys Leu Val Ala Gly Pro Pro Tyr Tyr Glu
305                 310                 315                 320

Gly Val Ala Val Leu Gly Thr Tyr Ser Asn His Thr Ser Ala Pro Ala
                325                 330                 335
```

```
Asn Cys Ser Val Ala Ser Gln His Lys Leu Thr Leu Ser Glu Val Thr
            340                 345                 350

Gly Gln Gly Leu Cys Val Gly Ala Val Pro Lys Thr His Gln Ala Leu
        355                 360                 365

Cys Asn Thr Thr Gln Lys Thr Ser Asn Gly Ser Tyr Tyr Leu Ala Ala
    370                 375                 380

Pro Ala Gly Thr Ile Trp Ala Cys Asn Thr Gly Leu Thr Pro Cys Leu
385                 390                 395                 400

Ser Thr Thr Val Leu Asp Leu Thr Thr Asp Tyr Cys Val Leu Val Glu
                405                 410                 415

Leu Trp Pro Lys Val Thr Tyr His Ser Pro Gly Tyr Val Tyr Gly Gln
            420                 425                 430

Phe Glu Glu Lys Thr Lys Tyr Lys Arg Glu Pro Val Ser Leu Thr Leu
        435                 440                 445

Ala Leu Leu Leu Gly Gly Leu Thr Met Gly Gly Ile Ala Ala Gly Val
    450                 455                 460

Gly Thr Gly Thr Thr Ala Leu Val Ala Thr Gln Gln Phe Gln Gln Leu
465                 470                 475                 480

Gln Ala Ala Met Gln Asp Asp Leu Lys Glu Val Glu Lys Ser Ile Thr
                485                 490                 495

Asn Leu Glu Arg Ser Leu Thr Ser Leu Ser Glu Val Val Leu Gln Asn
            500                 505                 510

Arg Arg Gly Leu Asp Leu Leu Phe Leu Lys Glu Gly Gly Leu Cys Ala
        515                 520                 525

Ala Leu Lys Glu Glu Cys Cys Phe Tyr Ala Asp His Thr Gly Leu Val
    530                 535                 540

Arg Asp Ser Met Ala Lys Leu Arg Glu Arg Leu Ser Gln Arg Gln Lys
545                 550                 555                 560

Leu Phe Glu Ser Gln Gln Gly Trp Phe Glu Gly Leu Phe Asn Lys Ser
                565                 570                 575

Pro Trp Phe Thr Thr Leu Ile Ser Thr Ile Met Gly Pro Leu Ile Ile
            580                 585                 590

Leu Leu Leu Ile Leu Leu Phe Gly Pro Cys Ile Leu Asn His Leu Val
        595                 600                 605

Gln Phe Ile Lys Asp Arg Val Ser Val Val Gln Ala Leu Val Leu Thr
    610                 615                 620

Gln Gln Tyr His Gln Leu Lys Thr Ile Glu Asp Cys Glu Ser Arg Glu
625                 630                 635                 640
```

<210> SEQ ID NO 73
<211> LENGTH: 619
<212> TYPE: PRT
<213> ORGANISM: Artificial
<220> FEATURE:
<223> OTHER INFORMATION: Modified SL3-2 envelope

<400> SEQUENCE: 73

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60
```

```
Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Asn Pro Leu Val Leu Glu Phe Thr Asp Ala Gly Lys Arg Ala Ser
                165                 170                 175

Trp Asp Ala Ser Lys Ala Trp Gly Leu Arg Leu Tyr Arg Ser Thr Arg
            180                 185                 190

Thr Asp Pro Val Thr Arg Phe Ser Leu Thr Arg Gln Val Leu Asn Ile
        195                 200                 205

Gly Pro Arg Val Pro Ile Gly Pro Asn Pro Val Ile Ile Asp Gln Leu
    210                 215                 220

Pro Pro Ser Arg Pro Val Gln Val Met Leu Pro Arg Pro Pro Gln Pro
225                 230                 235                 240

Pro Pro Pro Gly Ala Ala Ser Thr Val Pro Glu Thr Ala Pro Pro Ser
                245                 250                 255

Gln Gln Pro Gly Thr Gly Asp Arg Leu Leu Asn Leu Val Asn Gly Ala
            260                 265                 270

Tyr Gln Ala Leu Asn Leu Thr Ser Pro Asp Lys Thr Gln Glu Cys Trp
        275                 280                 285

Leu Cys Leu Val Ala Gly Pro Pro Tyr Tyr Glu Gly Val Ala Val Leu
    290                 295                 300

Gly Thr Tyr Ser Asn His Thr Ser Ala Pro Ala Asn Cys Ser Val Ala
305                 310                 315                 320

Ser Gln His Lys Leu Thr Leu Ser Glu Val Thr Gly Gln Gly Leu Cys
                325                 330                 335

Val Gly Ala Val Pro Lys Thr His Gln Ala Leu Cys Asn Thr Thr Gln
            340                 345                 350

Lys Thr Ser Asn Gly Ser Tyr Tyr Leu Ala Ala Pro Ala Gly Thr Ile
        355                 360                 365

Trp Ala Cys Asn Thr Gly Leu Thr Pro Cys Leu Ser Thr Thr Val Leu
    370                 375                 380

Asp Leu Thr Thr Asp Tyr Cys Val Leu Val Glu Leu Trp Pro Lys Val
385                 390                 395                 400

Thr Tyr His Ser Pro Gly Tyr Val Tyr Gly Gln Phe Glu Glu Lys Thr
                405                 410                 415

Lys Tyr Lys Arg Glu Pro Val Ser Leu Thr Leu Ala Leu Leu Leu Gly
            420                 425                 430

Gly Leu Thr Met Gly Gly Ile Ala Ala Gly Val Gly Thr Gly Thr Thr
        435                 440                 445

Ala Leu Val Ala Thr Gln Gln Phe Gln Gln Leu Gln Ala Ala Met Gln
    450                 455                 460

Asp Asp Leu Lys Glu Val Glu Lys Ser Ile Thr Asn Leu Glu Arg Ser
465                 470                 475                 480

Leu Thr Ser Leu Ser Glu Val Val Leu Gln Asn Arg Arg Gly Leu Asp
                485                 490                 495
```

```
Leu Leu Phe Leu Lys Glu Gly Gly Leu Cys Ala Ala Leu Lys Glu Glu
            500                 505                 510

Cys Cys Phe Tyr Ala Asp His Thr Gly Leu Val Arg Asp Ser Met Ala
        515                 520                 525

Lys Leu Arg Glu Arg Leu Ser Gln Arg Gln Lys Leu Phe Glu Ser Gln
    530                 535                 540

Gln Gly Trp Phe Glu Gly Leu Phe Asn Lys Ser Pro Trp Phe Thr Thr
545                 550                 555                 560

Leu Ile Ser Thr Ile Met Gly Pro Leu Ile Ile Leu Leu Leu Ile Leu
                565                 570                 575

Leu Phe Gly Pro Cys Ile Leu Asn His Leu Val Gln Phe Ile Lys Asp
            580                 585                 590

Arg Val Ser Val Val Gln Ala Leu Val Leu Thr Gln Gln Tyr His Gln
        595                 600                 605

Leu Lys Thr Ile Glu Asp Cys Glu Ser Arg Glu
    610                 615
```

```
<210> SEQ ID NO 74
<211> LENGTH: 624
<212> TYPE: PRT
<213> ORGANISM: Artificial
<220> FEATURE:
<223> OTHER INFORMATION: Modified SL3-2 envelope

<400> SEQUENCE: 74

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Arg Thr Pro
65                  70                  75                  80

Gly Gly Arg Lys Arg Ala Arg Ile Phe Asp Phe Tyr Val Cys Pro Gly
                85                  90                  95

His Thr Val Leu Ala Gly Cys Gly Gly Pro Arg Glu Gly Tyr Cys Gly
            100                 105                 110

Lys Trp Gly Cys Glu Thr Thr Gly Gln Ala Tyr Trp Lys Pro Ser Ser
        115                 120                 125

Ser Trp Asp Leu Ile Ser Leu Lys Arg Gly Asn Thr Pro Lys Gly Gln
    130                 135                 140

Gly Pro Cys Tyr Asp Ser Ser Val Val Ser Ser Ser Ala Gln Gly Ala
145                 150                 155                 160

Thr Pro Gly Gly Arg Cys Asn Pro Leu Val Leu Glu Phe Thr Asp Ala
                165                 170                 175

Gly Lys Arg Ala Ser Trp Asp Ala Ser Lys Ala Trp Gly Leu Arg Leu
            180                 185                 190

Tyr Arg Ser Thr Gly Ile Asp Pro Val Thr Arg Phe Ser Leu Thr Arg
        195                 200                 205

Gln Val Leu Asn Ile Gly Pro Arg Val Pro Ile Gly Pro Asn Pro Val
    210                 215                 220

Ile Ile Asp Gln Leu Pro Pro Ser Arg Pro Val Gln Val Met Leu Pro
225                 230                 235                 240
```

```
Arg Pro Pro Gln Pro Pro Pro Pro Gly Ala Ala Ser Thr Val Pro Glu
                245                 250                 255

Thr Ala Pro Pro Ser Gln Gln Pro Gly Thr Gly Asp Arg Leu Leu Asn
            260                 265                 270

Leu Val Asn Gly Ala Tyr Gln Ala Leu Asn Leu Thr Ser Pro Asp Lys
        275                 280                 285

Thr Gln Glu Cys Trp Leu Cys Leu Val Ala Gly Pro Pro Tyr Tyr Glu
    290                 295                 300

Gly Val Ala Val Leu Gly Thr Tyr Ser Asn His Thr Ser Ala Pro Ala
305                 310                 315                 320

Asn Cys Ser Val Ala Ser Gln His Lys Leu Thr Leu Ser Glu Val Thr
                325                 330                 335

Gly Gln Gly Leu Cys Val Gly Ala Val Pro Lys Thr His Gln Ala Leu
            340                 345                 350

Cys Asn Thr Thr Gln Lys Thr Ser Asn Gly Ser Tyr Tyr Leu Ala Ala
        355                 360                 365

Pro Ala Gly Thr Ile Trp Ala Cys Asn Thr Gly Leu Thr Pro Cys Leu
    370                 375                 380

Ser Thr Thr Val Leu Asp Leu Thr Thr Asp Tyr Cys Val Leu Val Glu
385                 390                 395                 400

Leu Trp Pro Lys Val Thr Tyr His Ser Pro Gly Tyr Val Tyr Gly Gln
                405                 410                 415

Phe Glu Glu Lys Thr Lys Tyr Lys Arg Glu Pro Val Ser Leu Thr Leu
            420                 425                 430

Ala Leu Leu Leu Gly Gly Leu Thr Met Gly Gly Ile Ala Ala Gly Val
        435                 440                 445

Gly Thr Gly Thr Thr Ala Leu Val Ala Thr Gln Gln Phe Gln Gln Leu
    450                 455                 460

Gln Ala Ala Met Gln Asp Asp Leu Lys Glu Val Glu Lys Ser Ile Thr
465                 470                 475                 480

Asn Leu Glu Arg Ser Leu Thr Ser Leu Ser Glu Val Val Leu Gln Asn
                485                 490                 495

Arg Arg Gly Leu Asp Leu Leu Phe Leu Lys Glu Gly Gly Leu Cys Ala
            500                 505                 510

Ala Leu Lys Glu Glu Cys Cys Phe Tyr Ala Asp His Thr Gly Leu Val
        515                 520                 525

Arg Asp Ser Met Ala Lys Leu Arg Glu Arg Leu Ser Gln Arg Gln Lys
    530                 535                 540

Leu Phe Glu Ser Gln Gln Gly Trp Phe Glu Gly Leu Phe Asn Lys Ser
545                 550                 555                 560

Pro Trp Phe Thr Thr Leu Ile Ser Thr Ile Met Gly Pro Leu Ile Ile
                565                 570                 575

Leu Leu Leu Ile Leu Leu Phe Gly Pro Cys Ile Leu Asn His Leu Val
            580                 585                 590

Gln Phe Ile Lys Asp Arg Val Ser Val Val Gln Ala Leu Val Leu Thr
        595                 600                 605

Gln Gln Tyr His Gln Leu Lys Thr Ile Glu Asp Cys Glu Ser Arg Glu
    610                 615                 620
```

<210> SEQ ID NO 75
<211> LENGTH: 640
<212> TYPE: PRT
<213> ORGANISM: Artificial
<220> FEATURE:
<223> OTHER INFORMATION: Modified SL3-2 envelope

<400> SEQUENCE: 75

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Gly Pro Cys Tyr Asp Ser Ser Val Val Ser Ser Ser Ala Gln Gly Ala
                165                 170                 175

Thr Pro Gly Gly Arg Cys Asn Pro Leu Val Leu Glu Phe Thr Asp Ala
            180                 185                 190

Gly Lys Arg Ala Ser Trp Asp Ala Ser Lys Ala Trp Gly Leu Arg Leu
        195                 200                 205

Tyr Arg Ser Thr Gly Ile Asp Pro Val Thr Arg Phe Ser Leu Thr Arg
    210                 215                 220

Gln Val Leu Asn Ile Gly Pro Arg Val Pro Ile Gly Pro Asn Pro Val
225                 230                 235                 240

Ile Ile Asp Gln Leu Pro Pro Ser Arg Pro Val Gln Val Met Leu Pro
                245                 250                 255

Arg Pro Pro Gln Pro Pro Pro Pro Gly Ala Ala Ser Thr Val Pro Glu
            260                 265                 270

Thr Ala Pro Pro Ser Gln Gln Pro Gly Thr Gly Asp Arg Leu Leu Asn
        275                 280                 285

Leu Val Asn Gly Ala Tyr Gln Ala Leu Asn Leu Thr Ser Pro Asp Lys
    290                 295                 300

Thr Gln Glu Cys Trp Leu Cys Leu Val Ala Gly Pro Pro Tyr Tyr Glu
305                 310                 315                 320

Gly Val Ala Val Leu Gly Thr Tyr Ser Asn His Thr Ser Ala Pro Ala
                325                 330                 335

Asn Cys Ser Val Ala Ser Gln His Lys Leu Thr Leu Ser Glu Val Thr
            340                 345                 350

Gly Gln Gly Leu Cys Val Gly Ala Val Pro Lys Thr His Gln Ala Leu
        355                 360                 365

Cys Asn Thr Thr Gln Lys Thr Ser Asn Gly Ser Tyr Tyr Leu Ala Ala
    370                 375                 380

Pro Ala Gly Thr Ile Trp Ala Cys Asn Thr Gly Leu Thr Pro Cys Leu
385                 390                 395                 400

Ser Thr Thr Val Leu Asp Leu Thr Thr Asp Tyr Cys Val Leu Val Glu
                405                 410                 415

```
Leu Trp Pro Lys Val Thr Tyr His Ser Pro Gly Tyr Val Tyr Gly Gln
            420                 425                 430

Phe Glu Glu Lys Thr Lys Tyr Lys Arg Glu Pro Val Ser Leu Thr Leu
        435                 440                 445

Ala Leu Leu Leu Gly Gly Leu Thr Met Gly Gly Ile Ala Ala Gly Val
    450                 455                 460

Gly Thr Gly Thr Thr Ala Leu Val Ala Thr Gln Gln Phe Gln Gln Leu
465                 470                 475                 480

Gln Ala Ala Met Gln Asp Asp Leu Lys Glu Val Glu Lys Ser Ile Thr
                485                 490                 495

Asn Leu Glu Arg Ser Leu Thr Ser Leu Ser Glu Val Val Leu Gln Asn
            500                 505                 510

Arg Arg Gly Leu Asp Leu Leu Phe Leu Lys Glu Gly Gly Leu Cys Ala
        515                 520                 525

Ala Leu Lys Glu Glu Cys Cys Phe Tyr Ala Asp His Thr Gly Leu Val
    530                 535                 540

Arg Asp Ser Met Ala Lys Leu Arg Glu Arg Leu Ser Gln Arg Gln Lys
545                 550                 555                 560

Leu Phe Glu Ser Gln Gln Gly Trp Phe Glu Gly Leu Phe Asn Lys Ser
                565                 570                 575

Pro Trp Phe Thr Thr Leu Ile Ser Thr Ile Met Gly Pro Leu Ile Ile
            580                 585                 590

Leu Leu Leu Ile Leu Leu Phe Gly Pro Cys Ile Leu Asn His Leu Val
        595                 600                 605

Gln Phe Ile Lys Asp Arg Val Ser Val Val Gln Ala Leu Val Leu Thr
    610                 615                 620

Gln Gln Tyr His Gln Leu Lys Thr Ile Glu Asp Cys Glu Ser Arg Glu
625                 630                 635                 640


<210> SEQ ID NO 76
<211> LENGTH: 619
<212> TYPE: PRT
<213> ORGANISM: Artificial
<220> FEATURE:
<223> OTHER INFORMATION: Modified SL3-2 envelope

<400> SEQUENCE: 76

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
```

-continued

```
145                 150                 155                 160

Pro Asn Pro Leu Val Leu Glu Phe Thr Asp Ala Gly Lys Arg Ala Ser
                165                 170                 175

Trp Asp Ala Ser Lys Ala Trp Gly Leu Arg Leu Tyr Arg Ser Thr Gly
            180                 185                 190

Ile Asp Pro Val Thr Arg Phe Ser Leu Thr Arg Gln Val Leu Asn Ile
        195                 200                 205

Gly Pro Arg Val Pro Ile Gly Pro Asn Pro Val Ile Ile Asp Gln Leu
    210                 215                 220

Pro Pro Ser Arg Pro Val Gln Val Met Leu Pro Arg Pro Pro Gln Pro
225                 230                 235                 240

Pro Pro Pro Gly Ala Ala Ser Thr Val Pro Glu Thr Ala Pro Pro Ser
                245                 250                 255

Gln Gln Pro Gly Thr Gly Asp Arg Leu Leu Asn Leu Val Asn Gly Ala
            260                 265                 270

Tyr Gln Ala Leu Asn Leu Thr Ser Pro Asp Lys Thr Gln Glu Cys Trp
        275                 280                 285

Leu Cys Leu Val Ala Gly Pro Pro Tyr Tyr Glu Gly Val Ala Val Leu
    290                 295                 300

Gly Thr Tyr Ser Asn His Thr Ser Ala Pro Ala Asn Cys Ser Val Ala
305                 310                 315                 320

Ser Gln His Lys Leu Thr Leu Ser Glu Val Thr Gly Gln Gly Leu Cys
                325                 330                 335

Val Gly Ala Val Pro Lys Thr His Gln Ala Leu Cys Asn Thr Thr Gln
            340                 345                 350

Lys Thr Ser Asn Gly Ser Tyr Tyr Leu Ala Ala Pro Ala Gly Thr Ile
        355                 360                 365

Trp Ala Cys Asn Thr Gly Leu Thr Pro Cys Leu Ser Thr Thr Val Leu
    370                 375                 380

Asp Leu Thr Thr Asp Tyr Cys Val Leu Val Glu Leu Trp Pro Lys Val
385                 390                 395                 400

Thr Tyr His Ser Pro Gly Tyr Val Tyr Gly Gln Phe Glu Glu Lys Thr
                405                 410                 415

Lys Tyr Lys Arg Glu Pro Val Ser Leu Thr Leu Ala Leu Leu Leu Gly
            420                 425                 430

Gly Leu Thr Met Gly Gly Ile Ala Ala Gly Val Gly Thr Gly Thr Thr
        435                 440                 445

Ala Leu Val Ala Thr Gln Gln Phe Gln Gln Leu Gln Ala Ala Met Gln
    450                 455                 460

Asp Asp Leu Lys Glu Val Glu Lys Ser Ile Thr Asn Leu Glu Arg Ser
465                 470                 475                 480

Leu Thr Ser Leu Ser Glu Val Val Leu Gln Asn Arg Arg Gly Leu Asp
                485                 490                 495

Leu Leu Phe Leu Lys Glu Gly Gly Leu Cys Ala Ala Leu Lys Glu Glu
            500                 505                 510

Cys Cys Phe Tyr Ala Asp His Thr Gly Leu Val Arg Asp Ser Met Ala
        515                 520                 525

Lys Leu Arg Glu Arg Leu Ser Gln Arg Gln Lys Leu Phe Glu Ser Gln
    530                 535                 540

Gln Gly Trp Phe Glu Gly Leu Phe Asn Lys Ser Pro Trp Phe Thr Thr
545                 550                 555                 560

Leu Ile Ser Thr Ile Met Gly Pro Leu Ile Ile Leu Leu Leu Ile Leu
                565                 570                 575
```

```
Leu Phe Gly Pro Cys Ile Leu Asn His Leu Val Gln Phe Ile Lys Asp
            580                 585                 590

Arg Val Ser Val Val Gln Ala Leu Val Leu Thr Gln Gln Tyr His Gln
        595                 600                 605

Leu Lys Thr Ile Glu Asp Cys Glu Ser Arg Glu
    610                 615


<210> SEQ ID NO 77
<211> LENGTH: 624
<212> TYPE: PRT
<213> ORGANISM: Artificial
<220> FEATURE:
<223> OTHER INFORMATION: Modified SL3-2 envelope sequence

<400> SEQUENCE: 77

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Arg Thr Pro
65                  70                  75                  80

Gly Gly Arg Lys Arg Ala Arg Ile Phe Asp Phe Tyr Val Cys Pro Gly
                85                  90                  95

His Thr Val Leu Ala Gly Cys Gly Gly Pro Arg Glu Gly Tyr Cys Gly
            100                 105                 110

Lys Trp Gly Cys Glu Thr Thr Gly Gln Ala Tyr Trp Lys Pro Ser Ser
        115                 120                 125

Ser Trp Asp Leu Ile Ser Leu Lys Arg Gly Asn Thr Pro Lys Gly Gln
    130                 135                 140

Gly Pro Cys Tyr Asp Ser Ser Val Val Ser Ser Ser Ala Gln Gly Ala
145                 150                 155                 160

Thr Pro Gly Gly Arg Cys Asn Pro Leu Val Leu Glu Phe Thr Asp Ala
                165                 170                 175

Gly Lys Arg Ala Ser Trp Asp Ala Ser Lys Ala Trp Gly Leu Arg Leu
            180                 185                 190

Tyr Arg Ser Thr Arg Thr Asp Pro Val Thr Arg Phe Ser Leu Thr Arg
        195                 200                 205

Gln Val Leu Asn Ile Gly Pro Arg Val Pro Ile Gly Pro Asn Pro Val
    210                 215                 220

Ile Ile Asp Gln Leu Pro Pro Ser Arg Pro Val Gln Val Met Leu Pro
225                 230                 235                 240

Arg Pro Pro Gln Pro Pro Pro Pro Gly Ala Ala Ser Thr Val Pro Glu
                245                 250                 255

Thr Ala Pro Pro Ser Gln Gln Pro Gly Thr Gly Asp Arg Leu Leu Asn
            260                 265                 270

Leu Val Asn Gly Ala Tyr Gln Ala Leu Asn Leu Thr Ser Pro Asp Lys
        275                 280                 285

Thr Gln Glu Cys Trp Leu Cys Leu Val Ala Gly Pro Pro Tyr Tyr Glu
    290                 295                 300

Gly Val Ala Val Leu Gly Thr Tyr Ser Asn His Thr Ser Ala Pro Ala
305                 310                 315                 320

Asn Cys Ser Val Ala Ser Gln His Lys Leu Thr Leu Ser Glu Val Thr
```

```
                325                 330                 335

Gly Gln Gly Leu Cys Val Gly Ala Val Pro Lys Thr His Gln Ala Leu
            340                 345                 350

Cys Asn Thr Thr Gln Lys Thr Ser Asn Gly Ser Tyr Tyr Leu Ala Ala
        355                 360                 365

Pro Ala Gly Thr Ile Trp Ala Cys Asn Thr Gly Leu Thr Pro Cys Leu
    370                 375                 380

Ser Thr Thr Val Leu Asp Leu Thr Thr Asp Tyr Cys Val Leu Val Glu
385                 390                 395                 400

Leu Trp Pro Lys Val Thr Tyr His Ser Pro Gly Tyr Val Tyr Gly Gln
                405                 410                 415

Phe Glu Glu Lys Thr Lys Tyr Lys Arg Glu Pro Val Ser Leu Thr Leu
            420                 425                 430

Ala Leu Leu Leu Gly Gly Leu Thr Met Gly Gly Ile Ala Ala Gly Val
        435                 440                 445

Gly Thr Gly Thr Thr Ala Leu Val Ala Thr Gln Gln Phe Gln Gln Leu
    450                 455                 460

Gln Ala Ala Met Gln Asp Asp Leu Lys Glu Val Glu Lys Ser Ile Thr
465                 470                 475                 480

Asn Leu Glu Arg Ser Leu Thr Ser Leu Ser Glu Val Val Leu Gln Asn
                485                 490                 495

Arg Arg Gly Leu Asp Leu Leu Phe Leu Lys Glu Gly Gly Leu Cys Ala
            500                 505                 510

Ala Leu Lys Glu Glu Cys Cys Phe Tyr Ala Asp His Thr Gly Leu Val
        515                 520                 525

Arg Asp Ser Met Ala Lys Leu Arg Glu Arg Leu Ser Gln Arg Gln Lys
    530                 535                 540

Leu Phe Glu Ser Gln Gln Gly Trp Phe Glu Gly Leu Phe Asn Lys Ser
545                 550                 555                 560

Pro Trp Phe Thr Thr Leu Ile Ser Thr Ile Met Gly Pro Leu Ile Ile
                565                 570                 575

Leu Leu Leu Ile Leu Leu Phe Gly Pro Cys Ile Leu Asn His Leu Val
            580                 585                 590

Gln Phe Ile Lys Asp Arg Val Ser Val Val Gln Ala Leu Val Leu Thr
        595                 600                 605

Gln Gln Tyr His Gln Leu Lys Thr Ile Glu Asp Cys Glu Ser Arg Glu
    610                 615                 620


<210> SEQ ID NO 78
<211> LENGTH: 609
<212> TYPE: PRT
<213> ORGANISM: Artificial
<220> FEATURE:
<223> OTHER INFORMATION: Modified SL3-2 envelope

<400> SEQUENCE: 78

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80
```

```
Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Leu Val Leu Glu Phe Thr Asp
145                 150                 155                 160

Ala Gly Lys Arg Ala Ser Trp Asp Ala Ser Lys Ala Trp Gly Leu Arg
                165                 170                 175

Leu Tyr Arg Ser Thr Arg Thr Asp Pro Val Thr Arg Phe Ser Leu Thr
            180                 185                 190

Arg Gln Val Leu Asn Ile Gly Pro Arg Val Pro Ile Gly Pro Asn Pro
        195                 200                 205

Val Ile Ile Asp Gln Leu Pro Pro Ser Arg Pro Val Gln Ile Met Leu
    210                 215                 220

Pro Arg Pro Pro Gln Pro Pro Pro Pro Gly Ala Ala Ser Thr Val Pro
225                 230                 235                 240

Glu Thr Ala Pro Pro Ser Gln Gln Pro Gly Thr Gly Asp Arg Leu Leu
                245                 250                 255

Asn Leu Val Asn Gly Ala Tyr Gln Ala Leu Asn Leu Thr Ser Pro Asp
            260                 265                 270

Lys Thr Gln Glu Cys Trp Leu Cys Leu Val Ala Gly Pro Pro Tyr Tyr
        275                 280                 285

Glu Gly Val Ala Val Leu Gly Thr Tyr Ser Asn His Thr Ser Ala Pro
    290                 295                 300

Ala Asn Cys Ser Val Ala Ser Gln His Lys Leu Thr Leu Ser Glu Val
305                 310                 315                 320

Thr Gly Gln Gly Leu Cys Val Gly Ala Val Pro Lys Thr His Gln Ala
                325                 330                 335

Leu Cys Asn Thr Thr Gln Lys Thr Ser Asn Gly Ser Tyr Tyr Leu Ala
            340                 345                 350

Ala Pro Ala Gly Thr Ile Trp Ala Cys Asn Thr Gly Leu Thr Pro Cys
        355                 360                 365

Leu Ser Thr Thr Val Leu Asp Leu Thr Thr Asp Tyr Cys Val Leu Val
    370                 375                 380

Glu Leu Trp Pro Lys Val Thr Tyr His Ser Pro Gly Tyr Val Tyr Gly
385                 390                 395                 400

Gln Phe Glu Glu Lys Thr Lys Tyr Lys Arg Glu Pro Val Ser Leu Thr
                405                 410                 415

Leu Ala Leu Leu Leu Gly Gly Leu Thr Met Gly Gly Ile Ala Ala Gly
            420                 425                 430

Val Gly Thr Gly Thr Thr Ala Leu Val Ala Thr Gln Gln Phe Gln Gln
        435                 440                 445

Leu Gln Ala Ala Met Gln Asp Asp Leu Lys Glu Val Lys Lys Ser Ile
    450                 455                 460

Thr Asn Leu Glu Arg Ser Leu Thr Ser Leu Ser Glu Val Val Leu Gln
465                 470                 475                 480

Asn Arg Arg Gly Leu Asp Leu Leu Phe Leu Lys Glu Gly Gly Leu Cys
                485                 490                 495

Ala Ala Leu Lys Glu Glu Cys Cys Phe Tyr Ala Asp His Thr Gly Leu
```

```
            500                 505                 510

Val Arg Asp Ser Met Ala Lys Leu Arg Glu Arg Leu Ser Gln Arg Gln
        515                 520                 525

Lys Leu Phe Glu Ser Gln Gln Gly Trp Phe Glu Gly Leu Phe Asn Lys
    530                 535                 540

Ser Pro Trp Phe Thr Thr Leu Ile Ser Thr Ile Met Gly Pro Leu Ile
545                 550                 555                 560

Ile Leu Leu Leu Ile Leu Leu Phe Gly Pro Cys Ile Leu Asn His Leu
                565                 570                 575

Val Gln Phe Ile Lys Asp Arg Val Ser Val Val Gln Ala Leu Val Leu
            580                 585                 590

Thr Gln Gln Tyr His Gln Leu Lys Thr Ile Glu Asp Cys Glu Ser Arg
        595                 600                 605

Glu


<210> SEQ ID NO 79
<211> LENGTH: 611
<212> TYPE: PRT
<213> ORGANISM: Artificial
<220> FEATURE:
<223> OTHER INFORMATION: Modified envelope sequence derived from MCF247

<400> SEQUENCE: 79

Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Arg His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Leu Val Leu Glu Phe Thr Asp
145                 150                 155                 160

Ala Gly Lys Lys Ala Ser Trp Asp Gly Pro Lys Val Trp Gly Leu Arg
                165                 170                 175

Leu Tyr Arg Ser Thr Gly Ile Asp Pro Val Thr Arg Phe Ser Leu Thr
            180                 185                 190

Arg Gln Val Leu Asn Ile Gly Pro Arg Val Pro Ile Gly Pro Asn Pro
        195                 200                 205

Val Ile Thr Asp Gln Leu Pro Pro Ser Arg Pro Val Gln Ile Met Leu
    210                 215                 220

Pro Arg Pro Pro Gln Pro Pro Pro Pro Gly Ala Ala Ser Thr Val Pro
225                 230                 235                 240

Glu Thr Ala Pro Pro Ser Gln Gln Pro Gly Thr Gly Asp Arg Leu Leu
                245                 250                 255
```

```
Asn Leu Val Lys Gly Ala Tyr Gln Ala Leu Asn Leu Thr Ser Pro Asp
            260                 265                 270

Lys Thr Gln Glu Cys Trp Leu Cys Leu Val Ser Gly Pro Pro Tyr Tyr
        275                 280                 285

Glu Gly Val Ala Val Leu Gly Thr Tyr Ser Asn His Thr Ser Ala Pro
    290                 295                 300

Ala Asn Cys Ser Val Ala Ser Gln His Lys Leu Thr Leu Ser Glu Val
305                 310                 315                 320

Thr Gly Gln Gly Leu Cys Ile Gly Ala Val Pro Lys Thr His Gln Ala
                325                 330                 335

Leu Cys Asn Thr Thr Gln Lys Thr Ser Asp Gly Ser Tyr Tyr Leu Ala
            340                 345                 350

Ala Pro Thr Gly Thr Thr Trp Ala Cys Ser Thr Gly Leu Thr Pro Cys
        355                 360                 365

Ile Ser Thr Thr Ile Leu Asp Leu Thr Thr Asp Tyr Cys Val Leu Val
    370                 375                 380

Glu Leu Trp Pro Arg Val Thr Tyr His Ser Pro Ser Tyr Val Tyr His
385                 390                 395                 400

Gln Phe Glu Arg Arg Ala Lys Tyr Lys Arg Glu Pro Val Ser Leu Thr
                405                 410                 415

Leu Ala Leu Leu Leu Gly Gly Leu Thr Met Gly Gly Ile Ala Ala Gly
            420                 425                 430

Val Gly Thr Gly Thr Thr Ala Leu Val Ala Thr Gln Gln Phe Gln Gln
        435                 440                 445

Phe Gln Ala Ala Met Gln Asp Asp Leu Lys Glu Val Glu Lys Ser Ile
    450                 455                 460

Thr Asn Leu Glu Lys Ser Leu Thr Ser Leu Ser Glu Val Val Leu Gln
465                 470                 475                 480

Asn Arg Arg Gly Leu Asp Leu Leu Phe Leu Lys Glu Gly Gly Leu Cys
                485                 490                 495

Ala Ala Leu Lys Glu Glu Cys Cys Phe Tyr Ala Asp His Thr Gly Leu
            500                 505                 510

Val Arg Asp Ser Met Ala Lys Leu Arg Glu Arg Leu Ser Gln Arg Gln
        515                 520                 525

Lys Leu Phe Glu Ser Gln Gln Gly Trp Phe Glu Gly Leu Phe Asn Lys
    530                 535                 540

Ser Pro Trp Phe Thr Thr Leu Ile Ser Thr Ile Met Gly Pro Leu Ile
545                 550                 555                 560

Ile Leu Leu Leu Ile Leu Leu Phe Gly Pro Cys Ile Leu Asn Arg Leu
                565                 570                 575

Val Gln Phe Val Lys Asp Arg Ile Ser Val Val Gln Ala Leu Val Leu
            580                 585                 590

Thr Gln Gln Tyr His Gln Leu Lys Ser Ile Asp Pro Glu Glu Val Glu
        595                 600                 605

Ser Arg Glu
    610
```

```
<210> SEQ ID NO 80
<211> LENGTH: 625
<212> TYPE: PRT
<213> ORGANISM: Artificial
<220> FEATURE:
<223> OTHER INFORMATION: Modified envelope sequence derived from
      Feline B

<400> SEQUENCE: 80
```

-continued

```
Met Glu Gly Pro Thr His Pro Lys Pro Ser Lys Asp Lys Thr Phe Ser
1               5                   10                  15

Trp Asp Leu Met Ile Leu Val Gly Val Leu Leu Arg Leu Asp Val Gly
            20                  25                  30

Met Ala Asn Pro Ser Pro His Gln Ile Tyr Asn Val Thr Trp Thr Ile
        35                  40                  45

Thr Asn Leu Val Thr Gly Thr Lys Ala Asn Ala Thr Ser Met Leu Gly
    50                  55                  60

Thr Leu Thr Asp Ala Phe Pro Thr Met Tyr Phe Asp Leu Cys Asp Ile
65                  70                  75                  80

Ile Gly Asn Thr Trp Asn Pro Ser Asp Gln Glu Pro Phe Pro Gly Tyr
                85                  90                  95

Gly Cys Asp Gln Pro Met Arg Arg Trp Gln Gln Arg Asn Thr Pro Phe
            100                 105                 110

Tyr Val Cys Pro Gly His Ala Asn Arg Lys Gln Cys Gly Gly Pro Gln
        115                 120                 125

Asp Gly Phe Cys Ala Val Trp Gly Cys Glu Thr Thr Gly Glu Thr Tyr
    130                 135                 140

Trp Arg Pro Thr Ser Ser Trp Asp Tyr Ile Thr Val Lys Lys Gly Leu
145                 150                 155                 160

Ile Leu Gln Phe Thr Gln Lys Gly Arg Gln Thr Ser Trp Asp Gly Pro
                165                 170                 175

Lys Ser Trp Gly Leu Arg Leu Tyr Arg Ser Gly Tyr Asp Pro Ile Ala
            180                 185                 190

Leu Phe Ser Val Ser Arg Gln Val Met Thr Ile Thr Leu Pro Gln Ala
        195                 200                 205

Met Gly Pro Asn Leu Val Leu Pro Asp Gln Lys Pro Pro Ser Arg Gln
    210                 215                 220

Ser Gln Ile Glu Ser Arg Val Thr Pro His His Ser Gln Gly Asn Gly
225                 230                 235                 240

Gly Thr Pro Gly Ile Thr Leu Val Asn Ala Ser Ile Ala Pro Leu Ser
                245                 250                 255

Thr Pro Val Thr Pro Ala Ser Pro Lys Arg Ile Gly Thr Gly Asn Arg
            260                 265                 270

Leu Ile Asn Leu Val Gln Gly Thr Tyr Leu Ala Leu Asn Val Thr Asn
        275                 280                 285

Pro Asn Lys Thr Lys Asp Cys Trp Leu Cys Leu Val Ser Arg Pro Pro
    290                 295                 300

Tyr Tyr Glu Gly Ile Ala Val Leu Gly Asn Tyr Ser Asn Gln Thr Asn
305                 310                 315                 320

Pro Pro Pro Ser Cys Leu Ser Asp Pro Gln His Lys Leu Thr Ile Ser
                325                 330                 335

Glu Val Ser Gly Gln Gly Ser Cys Ile Gly Thr Val Pro Lys Thr His
            340                 345                 350

Gln Ala Leu Cys Lys Lys Thr Gln Lys Gly His Lys Gly Thr His Tyr
        355                 360                 365

Leu Ala Ala Pro Ser Gly Thr Tyr Trp Ala Cys Asn Thr Gly Leu Thr
    370                 375                 380

Pro Cys Ile Ser Met Ala Val Leu Asn Trp Thr Ser Asp Phe Cys Val
385                 390                 395                 400

Leu Ile Glu Leu Trp Pro Arg Val Thr Tyr His Gln Pro Glu Tyr Val
                405                 410                 415

Tyr Thr His Phe Asp Lys Thr Val Arg Leu Arg Arg Glu Pro Ile Ser
            420                 425                 430
```

```
Leu Thr Val Ala Leu Met Leu Gly Gly Leu Thr Val Gly Gly Ile Ala
        435                 440                 445

Ala Gly Val Gly Thr Gly Thr Lys Ala Leu Leu Glu Thr Ala Gln Phe
    450                 455                 460

Gly Gln Leu Gln Met Ala Met His Thr Asp Ile Gln Ala Leu Glu Glu
465                 470                 475                 480

Ser Ile Ser Ala Leu Glu Lys Ser Leu Thr Ser Leu Ser Glu Val Val
                485                 490                 495

Leu Gln Asn Arg Arg Gly Leu Asp Ile Leu Phe Leu Gln Glu Gly Gly
            500                 505                 510

Leu Cys Ala Ala Leu Lys Glu Glu Cys Cys Phe Tyr Ala Asp His Thr
        515                 520                 525

Gly Leu Val Arg Asp Asn Met Ala Lys Leu Arg Glu Arg Leu Lys Gln
    530                 535                 540

Arg Gln Gln Leu Phe Asp Ser Gln Gln Gly Trp Phe Glu Gly Trp Phe
545                 550                 555                 560

Asn Lys Ser Pro Trp Phe Thr Thr Leu Ile Ser Ser Ile Met Gly Pro
                565                 570                 575

Leu Leu Ile Leu Leu Leu Ile Leu Leu Phe Gly Pro Cys Ile Leu Asn
            580                 585                 590

Arg Leu Val Gln Phe Val Lys Asp Arg Ile Ser Val Val Gln Ala Leu
        595                 600                 605

Ile Leu Thr Gln Gln Tyr Gln Gln Ile Lys Gln Tyr Asp Pro Asp Gln
    610                 615                 620

Pro
625


<210> SEQ ID NO 81
<211> LENGTH: 2031
<212> TYPE: DNA
<213> ORGANISM: artificial
<220> FEATURE:
<223> OTHER INFORMATION: SL3-2/V3 loop chimeric envelope

<400> SEQUENCE: 81

atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcaagg aatctaccag    480

tgtacaagac ccaacaacaa tacaagaaaa agaatccgta tccagagagg accagggaga    540

gcatttgtta caataggaaa aataggaaat atgagacaag cacattgtgg gccctgttat    600

gattcctcgg tggtctccag tagcgcccag ggtgccacac cgggggggtcg atgcaacccc    660

ctagtcctag aattcactga cgcgggtaaa agggccagct gggacgcctc caaagcatgg    720

ggactaagac tgtaccgatc cacagggatc gacccggtga cccggttctc tttgacccgc    780

caggtcctca atatagggcc ccgcgtcccc attgggccta atcccgtgat cattgaccag    840

ttaccccccct cccgacccgt gcaggtcatg ctccccaggc ctcctcagcc tcctccacca    900
```

```
ggcgcagcct ctacagtccc tgagactgcc ccaccttccc aacaacctgg gacgggagac    960

aggctgctaa acctggtaaa tggagcctac caagctctca acctcaccag tcctgacaaa   1020

acccaagagt gctggttgtg tctggtagcg ggaccccccct actacgaagg ggttgccgtc   1080

ctaggtactt attccaacca tacctctgcc ccagctaact gctccgtggc ctcccaacac   1140

aagctgaccc tgtccgaagt gaccggacag ggactctgcg taggagcagt tcccaaaacc   1200

catcaggccc tgtgtaatac cacccagaag acgagcaacg ggtcctacta tctggctgct   1260

cccgccggga ccatttgggc ttgcaacacc gggctcactc cctgcctatc taccactgtg   1320

ctcgacctca ccaccgatta ctgtgtcctg gttgagctct ggccaaaagt gacctaccac   1380

tcccctggtt atgtttatgg ccagtttgaa gaaaaaacca aatataaaag agaacccgtc   1440

tcactaactc tggccctact attaggagga ctcactatgg gcggaattgc cgcccggagtg   1500

ggaacaggga ctaccgccct agtggccact cagcagttcc aacaactcca ggctgccatg   1560

caggatgacc ttaaagaagt tgaaaagtcc atcactaatc tagaaaagatc tttgacctcc   1620

ttgtccgaag tagtgttaca gaatcgtaga ggcctagatc tactattcct aaaagaggga   1680

ggtttgtgtg ctgccttaaa agaagaatgc tgtttctatg ccgaccacac aggattggta   1740

cgggatagca tggccaaact tagagaaaga ttgagtcaga gacaaaaact ctttgaatcc   1800

caacaagggt ggtttgaagg gctgtttaac aagtcccctt ggttcaccac cctgatatcc   1860

accatcatgg gtcccctgat aatcctcttg ttaattttac tctttgggcc ttgtattctc   1920

aatcacctgg tccagtttat caaagacagg gtttcggtag tgcaggccct ggtcctgact   1980

caacaatatc atcaacttaa gacaatagaa gattgtgaat cacgtgaata a             2031
```

<210> SEQ ID NO 82
<211> LENGTH: 1968
<212> TYPE: DNA
<213> ORGANISM: artificial
<220> FEATURE:
<223> OTHER INFORMATION: SL3-2/V3 loop chimeric envelope

<400> SEQUENCE: 82

```
atggaaggtc cagcgttctc aaaacccctt aaagataaga ttaacccgtg ggggccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcctaa aggccagggc    480

ccctgtacaa gacccaacaa caatacaaga aaaagaatcc gtatccagag aggaccaggg    540

agagcatttg ttacaatagg aaaaatagga aatatgagac aagcacattg taacccccta    600

gtcctagaat tcactgacgc gggtaaaagg gccagctggg acgcctccaa agcatgggga    660

ctaagactgt accgatccac agggatcgac ccggtgaccc ggttctcttt gacccgccag    720

gtcctcaata tagggccccg cgtccccatt gggcctaatc ccgtgatcat tgaccagtta    780

ccccccctccc gacccgtgca ggtcatgctc cccaggcctc ctcagcctcc tccaccaggc    840

gcagcctcta cagtccctga gactgcccca ccttcccaac aacctgggac gggagacagg    900

ctgctaaacc tggtaaatgg agcctaccaa gctctcaacc tcaccagtcc tgacaaaacc    960
```

```
caagagtgct ggttgtgtct ggtagcggga ccccccctact acgaaggggt tgccgtccta   1020

ggtacttatt ccaaccatac ctctgcccca gctaactgct ccgtggcctc ccaacacaag   1080

ctgaccctgt ccgaagtgac cggacaggga ctctgcgtag gagcagttcc caaaacccat   1140

caggccctgt gtaataccac ccagaagacg agcaacgggt cctactatct ggctgctccc   1200

gccgggacca tttgggcttg caacaccggg ctcactccct gcctatctac cactgtgctc   1260

gacctcacca ccgattactg tgtcctggtt gagctctggc caaaagtgac ctaccactcc   1320

cctggttatg tttatggcca gtttgaagaa aaaaccaaat ataaaagaga acccgtctca   1380

ctaactctgg ccctactatt aggaggactc actatgggcg gaattgccgc cggagtggga   1440

acagggacta ccgccctagt ggccactcag cagttccaac aactccaggc tgccatgcag   1500

gatgacctta aagaagttga aaagtccatc actaatctag aaagatcttt gacctccttg   1560

tccgaagtag tgttacagaa tcgtagaggc ctagatctac tattcctaaa agagggaggt   1620

ttgtgtgctg ccttaaaaga agaatgctgt ttctatgccg accacacagg attggtacgg   1680

gatagcatgg ccaaacttag agaaagattg agtcagagac aaaaactctt tgaatcccaa   1740

caagggtggt ttgaagggct gtttaacaag tccccttggt tcaccaccct gatatccacc   1800

atcatgggtc ccctgataat cctcttgtta attttactct ttgggccttg tattctcaat   1860

cacctggtcc agtttatcaa agacagggtt tcggtagtgc aggccctggt cctgactcaa   1920

caatatcatc aacttaagac aatagaagat tgtgaatcac gtgaataa                1968
```

<210> SEQ ID NO 83
<211> LENGTH: 1983
<212> TYPE: DNA
<213> ORGANISM: artificial
<220> FEATURE:
<223> OTHER INFORMATION: SL3-2/V3 loop chimeric envelope

<400> SEQUENCE: 83

```
atggaaggtc cagcgttctc aaaacccctt aaagataaga ttaacccgtg ggggccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgtacaaga    240

cccaacaaca atacaagaaa aagaatccgt atccagagag gaccagggag agcatttgtt    300

acaataggaa aaataggaaa tatgagacaa gcacattgtc gcactcccgg gggaagaaaa    360

agggcaagaa tatttgactt ctatgtttgc cccggtcaca ctgtgctagc agggtgtgga    420

gggccgagag agggctactg tggcaaatgg ggatgtgaga ccactggaca ggcatactgg    480

aagccatcat catcatggga cctaatttcc cttaagcgag gaaacactcc taaaggccag    540

ggcccctgtt atgattcctc ggtggtctcc agtagcgccc agggtgccac accgggggt    600

cgatgcaacc ccctagtcct agaattcact gacgcgggta aaagggccag ctgggacgcc    660

tccaaagcat ggggactaag actgtaccga tccacaggga tcgacccggt gacccggttc    720

tctttgaccc gccaggtcct caatataggg ccccgcgtcc ccattgggcc taatcccgtg    780

atcattgacc agttaccccc ctcccgaccc gtgcaggtca tgctccccag gcctcctcag    840

cctcctccac caggcgcagc ctctacagtc cctgagactg ccccaccttc ccaacaacct    900

gggacgggag acaggctgct aaacctggta aatggagcct accaagctct caacctcacc    960

agtcctgaca aaacccaaga gtgctggttg tgtctggtag cgggaccccc ctactacgaa   1020

ggggttgccg tcctaggtac ttattccaac catacctctg ccccagctaa ctgctccgtg   1080
```

```
gcctcccaac acaagctgac cctgtccgaa gtgaccggac agggactctg cgtaggagca   1140

gttcccaaaa cccatcaggc cctgtgtaat accacccaga agacgagcaa cgggtcctac   1200

tatctggctg ctcccgccgg gaccatttgg gcttgcaaca ccgggctcac tccctgccta   1260

tctaccactg tgctcgacct caccaccgat tactgtgtcc tggttgagct ctggccaaaa   1320

gtgacctacc actcccctgg ttatgtttat ggccagtttg aagaaaaaac caaatataaa   1380

agagaacccg tctcactaac tctggcccta ctattaggag gactcactat gggcggaatt   1440

gccgccggag tgggaacagg gactaccgcc ctagtggcca ctcagcagtt ccaacaactc   1500

caggctgcca tgcaggatga ccttaaagaa gttgaaaagt ccatcactaa tctagaaaga   1560

tctttgacct ccttgtccga agtagtgtta cagaatcgta gaggcctaga tctactattc   1620

ctaaaagagg gaggtttgtg tgctgcctta aaagaagaat gctgtttcta tgccgaccac   1680

acaggattgg tacgggatag catggccaaa cttagagaaa gattgagtca gagacaaaaa   1740

ctctttgaat cccaacaagg gtggtttgaa gggctgttta acaagtcccc ttggttcacc   1800

accctgatat ccaccatcat gggtcccctg ataatcctct tgttaatttt actctttggg   1860

ccttgtattc tcaatcacct ggtccagttt atcaaagaca gggtttcggt agtgcaggcc   1920

ctggtcctga ctcaacaata tcatcaactt aagacaatag aagattgtga atcacgtgaa   1980

taa                                                                 1983
```

<210> SEQ ID NO 84
<211> LENGTH: 676
<212> TYPE: PRT
<213> ORGANISM: Artificial
<220> FEATURE:
<223> OTHER INFORMATION: SL3-2/V3 loop chimeric envelope

<400> SEQUENCE: 84

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Thr Arg Pro Asn Asn Asn Thr Arg Lys Arg Ile Arg Ile Gln Arg
                165                 170                 175

Gly Pro Gly Arg Ala Phe Val Thr Ile Gly Lys Ile Gly Asn Met Arg
            180                 185                 190

Gln Ala His Cys Gly Pro Cys Tyr Asp Ser Ser Val Val Ser Ser Ser
        195                 200                 205
```

-continued

```
Ala Gln Gly Ala Thr Pro Gly Gly Arg Cys Asn Pro Leu Val Leu Glu
    210                 215                 220

Phe Thr Asp Ala Gly Lys Arg Ala Ser Trp Asp Ala Ser Lys Ala Trp
225                 230                 235                 240

Gly Leu Arg Leu Tyr Arg Ser Thr Gly Ile Asp Pro Val Thr Arg Phe
                245                 250                 255

Ser Leu Thr Arg Gln Val Leu Asn Ile Gly Pro Arg Val Pro Ile Gly
            260                 265                 270

Pro Asn Pro Val Ile Ile Asp Gln Leu Pro Pro Ser Arg Pro Val Gln
        275                 280                 285

Val Met Leu Pro Arg Pro Pro Gln Pro Pro Pro Pro Gly Ala Ala Ser
    290                 295                 300

Thr Val Pro Glu Thr Ala Pro Pro Ser Gln Gln Pro Gly Thr Gly Asp
305                 310                 315                 320

Arg Leu Leu Asn Leu Val Asn Gly Ala Tyr Gln Ala Leu Asn Leu Thr
                325                 330                 335

Ser Pro Asp Lys Thr Gln Glu Cys Trp Leu Cys Leu Val Ala Gly Pro
            340                 345                 350

Pro Tyr Tyr Glu Gly Val Ala Val Leu Gly Thr Tyr Ser Asn His Thr
        355                 360                 365

Ser Ala Pro Ala Asn Cys Ser Val Ala Ser Gln His Lys Leu Thr Leu
    370                 375                 380

Ser Glu Val Thr Gly Gln Gly Leu Cys Val Gly Ala Val Pro Lys Thr
385                 390                 395                 400

His Gln Ala Leu Cys Asn Thr Thr Gln Lys Thr Ser Asn Gly Ser Tyr
                405                 410                 415

Tyr Leu Ala Ala Pro Ala Gly Thr Ile Trp Ala Cys Asn Thr Gly Leu
            420                 425                 430

Thr Pro Cys Leu Ser Thr Thr Val Leu Asp Leu Thr Thr Asp Tyr Cys
        435                 440                 445

Val Leu Val Glu Leu Trp Pro Lys Val Thr Tyr His Ser Pro Gly Tyr
    450                 455                 460

Val Tyr Gly Gln Phe Glu Glu Lys Thr Lys Tyr Lys Arg Glu Pro Val
465                 470                 475                 480

Ser Leu Thr Leu Ala Leu Leu Leu Gly Gly Leu Thr Met Gly Gly Ile
                485                 490                 495

Ala Ala Gly Val Gly Thr Gly Thr Thr Ala Leu Val Ala Thr Gln Gln
            500                 505                 510

Phe Gln Gln Leu Gln Ala Ala Met Gln Asp Asp Leu Lys Glu Val Glu
        515                 520                 525

Lys Ser Ile Thr Asn Leu Glu Arg Ser Leu Thr Ser Leu Ser Glu Val
    530                 535                 540

Val Leu Gln Asn Arg Arg Gly Leu Asp Leu Leu Phe Leu Lys Glu Gly
545                 550                 555                 560

Gly Leu Cys Ala Ala Leu Lys Glu Glu Cys Cys Phe Tyr Ala Asp His
                565                 570                 575

Thr Gly Leu Val Arg Asp Ser Met Ala Lys Leu Arg Glu Arg Leu Ser
            580                 585                 590

Gln Arg Gln Lys Leu Phe Glu Ser Gln Gln Gly Trp Phe Glu Gly Leu
        595                 600                 605

Phe Asn Lys Ser Pro Trp Phe Thr Thr Leu Ile Ser Thr Ile Met Gly
    610                 615                 620

Pro Leu Ile Ile Leu Leu Leu Ile Leu Leu Phe Gly Pro Cys Ile Leu
```

```
625                 630                 635                 640

Asn His Leu Val Gln Phe Ile Lys Asp Arg Val Ser Val Val Gln Ala
                645                 650                 655

Leu Val Leu Thr Gln Gln Tyr His Gln Leu Lys Thr Ile Glu Asp Cys
            660                 665                 670

Glu Ser Arg Glu
        675


<210> SEQ ID NO 85
<211> LENGTH: 655
<212> TYPE: PRT
<213> ORGANISM: Artificial
<220> FEATURE:
<223> OTHER INFORMATION: SL3-2/V3 loop chimeric envelope

<400> SEQUENCE: 85

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Thr Arg Pro Asn Asn Asn Thr Arg Lys Arg Ile Arg Ile Gln
                165                 170                 175

Arg Gly Pro Gly Arg Ala Phe Val Thr Ile Gly Lys Ile Gly Asn Met
            180                 185                 190

Arg Gln Ala His Cys Asn Pro Leu Val Leu Glu Phe Thr Asp Ala Gly
        195                 200                 205

Lys Arg Ala Ser Trp Asp Ala Ser Lys Ala Trp Gly Leu Arg Leu Tyr
    210                 215                 220

Arg Ser Thr Gly Ile Asp Pro Val Thr Arg Phe Ser Leu Thr Arg Gln
225                 230                 235                 240

Val Leu Asn Ile Gly Pro Arg Val Pro Ile Gly Pro Asn Pro Val Ile
                245                 250                 255

Ile Asp Gln Leu Pro Pro Ser Arg Pro Val Gln Val Met Leu Pro Arg
            260                 265                 270

Pro Pro Gln Pro Pro Pro Pro Gly Ala Ala Ser Thr Val Pro Glu Thr
        275                 280                 285

Ala Pro Pro Ser Gln Gln Pro Gly Thr Gly Asp Arg Leu Leu Asn Leu
    290                 295                 300

Val Asn Gly Ala Tyr Gln Ala Leu Asn Leu Thr Ser Pro Asp Lys Thr
305                 310                 315                 320
```

```
Gln Glu Cys Trp Leu Cys Leu Val Ala Gly Pro Pro Tyr Tyr Glu Gly
                325                 330                 335

Val Ala Val Leu Gly Thr Tyr Ser Asn His Thr Ser Ala Pro Ala Asn
            340                 345                 350

Cys Ser Val Ala Ser Gln His Lys Leu Thr Leu Ser Glu Val Thr Gly
        355                 360                 365

Gln Gly Leu Cys Val Gly Ala Val Pro Lys Thr His Gln Ala Leu Cys
    370                 375                 380

Asn Thr Thr Gln Lys Thr Ser Asn Gly Ser Tyr Tyr Leu Ala Ala Pro
385                 390                 395                 400

Ala Gly Thr Ile Trp Ala Cys Asn Thr Gly Leu Thr Pro Cys Leu Ser
                405                 410                 415

Thr Thr Val Leu Asp Leu Thr Thr Asp Tyr Cys Val Leu Val Glu Leu
            420                 425                 430

Trp Pro Lys Val Thr Tyr His Ser Pro Gly Tyr Val Tyr Gly Gln Phe
        435                 440                 445

Glu Glu Lys Thr Lys Tyr Lys Arg Glu Pro Val Ser Leu Thr Leu Ala
    450                 455                 460

Leu Leu Leu Gly Gly Leu Thr Met Gly Gly Ile Ala Ala Gly Val Gly
465                 470                 475                 480

Thr Gly Thr Thr Ala Leu Val Ala Thr Gln Gln Phe Gln Gln Leu Gln
                485                 490                 495

Ala Ala Met Gln Asp Asp Leu Lys Glu Val Glu Lys Ser Ile Thr Asn
            500                 505                 510

Leu Glu Arg Ser Leu Thr Ser Leu Ser Glu Val Val Leu Gln Asn Arg
        515                 520                 525

Arg Gly Leu Asp Leu Leu Phe Leu Lys Glu Gly Gly Leu Cys Ala Ala
    530                 535                 540

Leu Lys Glu Glu Cys Cys Phe Tyr Ala Asp His Thr Gly Leu Val Arg
545                 550                 555                 560

Asp Ser Met Ala Lys Leu Arg Glu Arg Leu Ser Gln Arg Gln Lys Leu
                565                 570                 575

Phe Glu Ser Gln Gln Gly Trp Phe Glu Gly Leu Phe Asn Lys Ser Pro
            580                 585                 590

Trp Phe Thr Thr Leu Ile Ser Thr Ile Met Gly Pro Leu Ile Ile Leu
        595                 600                 605

Leu Leu Ile Leu Leu Phe Gly Pro Cys Ile Leu Asn His Leu Val Gln
    610                 615                 620

Phe Ile Lys Asp Arg Val Ser Val Val Gln Ala Leu Val Leu Thr Gln
625                 630                 635                 640

Gln Tyr His Gln Leu Lys Thr Ile Glu Asp Cys Glu Ser Arg Glu
                645                 650                 655


<210> SEQ ID NO 86
<211> LENGTH: 660
<212> TYPE: PRT
<213> ORGANISM: Artificial
<220> FEATURE:
<223> OTHER INFORMATION: SL3-2/V3 loop chimeric envelope

<400> SEQUENCE: 86

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30
```

-continued

```
Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Thr Arg
65                  70                  75                  80

Pro Asn Asn Asn Thr Arg Lys Arg Ile Arg Ile Gln Arg Gly Pro Gly
                85                  90                  95

Arg Ala Phe Val Thr Ile Gly Lys Ile Gly Asn Met Arg Gln Ala His
            100                 105                 110

Cys Arg Thr Pro Gly Gly Arg Lys Arg Ala Arg Ile Phe Asp Phe Tyr
        115                 120                 125

Val Cys Pro Gly His Thr Val Leu Ala Gly Cys Gly Gly Pro Arg Glu
    130                 135                 140

Gly Tyr Cys Gly Lys Trp Gly Cys Glu Thr Thr Gly Gln Ala Tyr Trp
145                 150                 155                 160

Lys Pro Ser Ser Ser Trp Asp Leu Ile Ser Leu Lys Arg Gly Asn Thr
                165                 170                 175

Pro Lys Gly Gln Gly Pro Cys Tyr Asp Ser Ser Val Val Ser Ser Ser
            180                 185                 190

Ala Gln Gly Ala Thr Pro Gly Gly Arg Cys Asn Pro Leu Val Leu Glu
        195                 200                 205

Phe Thr Asp Ala Gly Lys Arg Ala Ser Trp Asp Ala Ser Lys Ala Trp
    210                 215                 220

Gly Leu Arg Leu Tyr Arg Ser Thr Arg Thr Asp Pro Val Thr Arg Phe
225                 230                 235                 240

Ser Leu Thr Arg Gln Val Leu Asn Ile Gly Pro Arg Val Pro Ile Gly
                245                 250                 255

Pro Asn Pro Val Ile Ile Asp Gln Leu Pro Pro Ser Arg Pro Val Gln
            260                 265                 270

Val Met Leu Pro Arg Pro Pro Gln Pro Pro Pro Pro Gly Ala Ala Ser
        275                 280                 285

Thr Val Pro Glu Thr Ala Pro Pro Ser Gln Gln Pro Gly Thr Gly Asp
    290                 295                 300

Arg Leu Leu Asn Leu Val Asn Gly Ala Tyr Gln Ala Leu Asn Leu Thr
305                 310                 315                 320

Ser Pro Asp Lys Thr Gln Glu Cys Trp Leu Cys Leu Val Ala Gly Pro
                325                 330                 335

Pro Tyr Tyr Glu Gly Val Ala Val Leu Gly Thr Tyr Ser Asn His Thr
            340                 345                 350

Ser Ala Pro Ala Asn Cys Ser Val Ala Ser Gln His Lys Leu Thr Leu
        355                 360                 365

Ser Glu Val Thr Gly Gln Gly Leu Cys Val Gly Ala Val Pro Lys Thr
    370                 375                 380

His Gln Ala Leu Cys Asn Thr Thr Gln Lys Thr Ser Asn Gly Ser Tyr
385                 390                 395                 400

Tyr Leu Ala Ala Pro Ala Gly Thr Ile Trp Ala Cys Asn Thr Gly Leu
                405                 410                 415

Thr Pro Cys Leu Ser Thr Thr Val Leu Asp Leu Thr Thr Asp Tyr Cys
            420                 425                 430

Val Leu Val Glu Leu Trp Pro Lys Val Thr Tyr His Ser Pro Gly Tyr
        435                 440                 445

Val Tyr Gly Gln Phe Glu Glu Lys Thr Lys Tyr Lys Arg Glu Pro Val
    450                 455                 460
```

Ser Leu Thr Leu Ala Leu Leu Leu Gly Gly Leu Thr Met Gly Gly Ile
465 470 475 480

Ala Ala Gly Val Gly Thr Gly Thr Thr Ala Leu Val Ala Thr Gln Gln
485 490 495

Phe Gln Gln Leu Gln Ala Ala Met Gln Asp Asp Leu Lys Glu Val Glu
500 505 510

Lys Ser Ile Thr Asn Leu Glu Arg Ser Leu Thr Ser Leu Ser Glu Val
515 520 525

Val Leu Gln Asn Arg Arg Gly Leu Asp Leu Leu Phe Leu Lys Glu Gly
530 535 540

Gly Leu Cys Ala Ala Leu Lys Glu Glu Cys Cys Phe Tyr Ala Asp His
545 550 555 560

Thr Gly Leu Val Arg Asp Ser Met Ala Lys Leu Arg Glu Arg Leu Ser
565 570 575

Gln Arg Gln Lys Leu Phe Glu Ser Gln Gln Gly Trp Phe Glu Gly Leu
580 585 590

Phe Asn Lys Ser Pro Trp Phe Thr Thr Leu Ile Ser Thr Ile Met Gly
595 600 605

Pro Leu Ile Ile Leu Leu Leu Ile Leu Leu Phe Gly Pro Cys Ile Leu
610 615 620

Asn His Leu Val Gln Phe Ile Lys Asp Arg Val Ser Val Val Gln Ala
625 630 635 640

Leu Val Leu Thr Gln Gln Tyr His Gln Leu Lys Thr Ile Glu Asp Cys
645 650 655

Glu Ser Arg Glu
660

<210> SEQ ID NO 87
<211> LENGTH: 1914
<212> TYPE: DNA
<213> ORGANISM: artificial
<220> FEATURE:
<223> OTHER INFORMATION: Modified SL3-2 envelope sequence

<400> SEQUENCE: 87
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggatgg actcgggtgt cgcactcccg ggggaagaaa aagggcaaga 300
atatttgact tctatgtttg ccccggtcac actgtgctag cagggtgtgg agggccgaga 360
gagggctact gtggcaaatg ggatgtgag accactggac aggcatactg gaagccatca 420
tcatcatggg acctaatttc ccttaagcga ggaaacactc ctaaaggcca gggcccctgt 480
tatgattcct cggtggtctc cagtagcgcc cagggtgcca caccgggggg tcgatgcaac 540
cccctagtcc tagaattcac tgacgcgggt aaaagggcca gctgggacgc ctccaaagca 600
tggggactaa gactgtaccg atccacaagg accgacccgg tgacccggtt ctctttgacc 660
cgccaggtcc tcaatatagg gccccgcgtc cccattgggc ctaatcccgt gatcattgac 720
cagttacccc cctcccgacc cgtgcaggtc atgctcccca ggcctcctca gcctcctcca 780
ccaggcgcag cctctacagt ccctgagact gccccacctt cccaacaacc tgggacggga 840
gacaggctgc taaacctggt aaatggagcc taccaagctc tcaacctcac cagtcctgac 900

```
aaaacccaag agtgctggtt gtgtctggta gcgggacccc cctactacga aggggttgcc    960

gtcctaggta cttattccaa ccatacctct gccccagcta actgctccgt ggcctcccaa   1020

cacaagctga ccctgtccga agtgaccgga cagggactct gcgtaggagc agttcccaaa   1080

acccatcagg ccctgtgtaa taccacccag aagacgagca acgggtccta ctatctggct   1140

gctcccgccg ggaccatttg ggcttgcaac accgggctca ctccctgcct atctaccact   1200

gtgctcgacc tcaccaccga ttactgtgtc ctggttgagc tctggccaaa agtgacctac   1260

cactcccctg gttatgttta tggccagttt gaagaaaaaa ccaaatataa aagagaaccc   1320

gtctcactaa ctctggccct actattagga ggactcacta tgggcggaat tgccgccgga   1380

gtgggaacag ggactaccgc cctagtggcc actcagcagt tccaacaact ccaggctgcc   1440

atgcaggatg accttaaaga agttgaaaag tccatcacta atctagaaag atctttgacc   1500

tccttgtccg aagtagtgtt acagaatcgt agaggcctag atctactatt cctaaaagag   1560

ggaggtttgt gtgctgcctt aaaagaagaa tgctgtttct atgccgacca cacaggattg   1620

gtacgggata gcatggccaa acttagagaa agattgagtc agagacaaaa actctttgaa   1680

tcccaacaag ggtggtttga agggctgttt aacaagtccc cttggttcac caccctgata   1740

tccaccatca tgggtcccct gataatcctc ttgttaattt tactctttgg gccttgtatt   1800

ctcaatcacc tggtccagtt tatcaaagac agggtttcgg tagtgcaggc cctggtcctg   1860

actcaacaat atcatcaact taagacaata gaagattgtg aatcacgtga ataa         1914
```

<210> SEQ ID NO 88
<211> LENGTH: 637
<212> TYPE: PRT
<213> ORGANISM: Artificial
<220> FEATURE:
<223> OTHER INFORMATION: Modified SL3-2 envelope sequence

<400> SEQUENCE: 88

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Gly Leu Gly Cys Arg Thr Pro Gly Gly Arg
                85                  90                  95

Lys Arg Ala Arg Ile Phe Asp Phe Tyr Val Cys Pro Gly His Thr Val
            100                 105                 110

Leu Ala Gly Cys Gly Gly Pro Arg Glu Gly Tyr Cys Gly Lys Trp Gly
        115                 120                 125

Cys Glu Thr Thr Gly Gln Ala Tyr Trp Lys Pro Ser Ser Ser Trp Asp
    130                 135                 140

Leu Ile Ser Leu Lys Arg Gly Asn Thr Pro Lys Gly Gln Gly Pro Cys
145                 150                 155                 160

Tyr Asp Ser Ser Val Val Ser Ser Ser Ala Gln Gly Ala Thr Pro Gly
                165                 170                 175

Gly Arg Cys Asn Pro Leu Val Leu Glu Phe Thr Asp Ala Gly Lys Arg
            180                 185                 190
```

```
Ala Ser Trp Asp Ala Ser Lys Ala Trp Gly Leu Arg Leu Tyr Arg Ser
        195                 200                 205

Thr Arg Thr Asp Pro Val Thr Arg Phe Ser Leu Thr Arg Gln Val Leu
    210                 215                 220

Asn Ile Gly Pro Arg Val Pro Ile Gly Pro Asn Pro Val Ile Ile Asp
225                 230                 235                 240

Gln Leu Pro Pro Ser Arg Pro Val Gln Val Met Leu Pro Arg Pro Pro
                245                 250                 255

Gln Pro Pro Pro Pro Gly Ala Ala Ser Thr Val Pro Glu Thr Ala Pro
            260                 265                 270

Pro Ser Gln Gln Pro Gly Thr Gly Asp Arg Leu Leu Asn Leu Val Asn
        275                 280                 285

Gly Ala Tyr Gln Ala Leu Asn Leu Thr Ser Pro Asp Lys Thr Gln Glu
    290                 295                 300

Cys Trp Leu Cys Leu Val Ala Gly Pro Pro Tyr Tyr Glu Gly Val Ala
305                 310                 315                 320

Val Leu Gly Thr Tyr Ser Asn His Thr Ser Ala Pro Ala Asn Cys Ser
                325                 330                 335

Val Ala Ser Gln His Lys Leu Thr Leu Ser Glu Val Thr Gly Gln Gly
            340                 345                 350

Leu Cys Val Gly Ala Val Pro Lys Thr His Gln Ala Leu Cys Asn Thr
        355                 360                 365

Thr Gln Lys Thr Ser Asn Gly Ser Tyr Tyr Leu Ala Ala Pro Ala Gly
    370                 375                 380

Thr Ile Trp Ala Cys Asn Thr Gly Leu Thr Pro Cys Leu Ser Thr Thr
385                 390                 395                 400

Val Leu Asp Leu Thr Thr Asp Tyr Cys Val Leu Val Glu Leu Trp Pro
                405                 410                 415

Lys Val Thr Tyr His Ser Pro Gly Tyr Val Tyr Gly Gln Phe Glu Glu
            420                 425                 430

Lys Thr Lys Tyr Lys Arg Glu Pro Val Ser Leu Thr Leu Ala Leu Leu
        435                 440                 445

Leu Gly Gly Leu Thr Met Gly Gly Ile Ala Ala Gly Val Gly Thr Gly
    450                 455                 460

Thr Thr Ala Leu Val Ala Thr Gln Gln Phe Gln Gln Leu Gln Ala Ala
465                 470                 475                 480

Met Gln Asp Asp Leu Lys Glu Val Glu Lys Ser Ile Thr Asn Leu Glu
                485                 490                 495

Arg Ser Leu Thr Ser Leu Ser Glu Val Val Leu Gln Asn Arg Arg Gly
            500                 505                 510

Leu Asp Leu Leu Phe Leu Lys Glu Gly Gly Leu Cys Ala Ala Leu Lys
        515                 520                 525

Glu Glu Cys Cys Phe Tyr Ala Asp His Thr Gly Leu Val Arg Asp Ser
    530                 535                 540

Met Ala Lys Leu Arg Glu Arg Leu Ser Gln Arg Gln Lys Leu Phe Glu
545                 550                 555                 560

Ser Gln Gln Gly Trp Phe Glu Gly Leu Phe Asn Lys Ser Pro Trp Phe
                565                 570                 575

Thr Thr Leu Ile Ser Thr Ile Met Gly Pro Leu Ile Ile Leu Leu Leu
            580                 585                 590

Ile Leu Leu Phe Gly Pro Cys Ile Leu Asn His Leu Val Gln Phe Ile
        595                 600                 605

Lys Asp Arg Val Ser Val Val Gln Ala Leu Val Leu Thr Gln Gln Tyr
    610                 615                 620
```

His Gln Leu Lys Thr Ile Glu Asp Cys Glu Ser Arg Glu
625 630 635

<210> SEQ ID NO 89
<211> LENGTH: 1914
<212> TYPE: DNA
<213> ORGANISM: artificial
<220> FEATURE:
<223> OTHER INFORMATION: Modified SL3-2 envelope sequence

<400> SEQUENCE: 89

```
atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatgg actcgggtgt cgcactcccg gggaagaaa aagggcaaga    300

atatttgact tctatgtttg ccccggtcac actgtgctag cagggtgtgg agggccgaga    360

gagggctact gtggcaaatg ggatgtgag accactggac aggcatactg gaagccatca    420

tcatcatggg acctaatttc ccttaagcga ggaaacactc ctaaaggcca gggcccctgt    480

tatgattcct cggtggtctc cagtagcgcc cagggtgcca caccgggggg tcgatgcaac    540

cccctagtcc tagaattcac tgacgcgggt aaaagggcca gctgggacgc ctccaaagca    600

tggggactaa gactgtaccg atccacaggg atcgacccgg tgacccggtt ctctttgacc    660

cgccaggtcc tcaatatagg gccccgcgtc cccattgggc ctaatcccgt gatcattgac    720

cagttacccc cctcccgacc cgtgcaggtc atgctcccca ggcctcctca gcctcctcca    780

ccaggcgcag cctctacagt ccctgagact gccccacctt cccaacaacc tgggacggga    840

gacaggctgc taaacctggt aaatggagcc taccaagctc tcaacctcac cagtcctgac    900

aaaacccaag agtgctggtt gtgtctggta gcgggacccc cctactacga aggggttgcc    960

gtcctaggta cttattccaa ccatacctct gccccagcta actgctccgt ggcctcccaa   1020

cacaagctga ccctgtccga agtgaccgga cagggactct gcgtaggagc agttcccaaa   1080

acccatcagg ccctgtgtaa taccacccag aagacgagca acgggtccta ctatctggct   1140

gctcccgccg ggaccatttg ggcttgcaac accgggctca ctccctgcct atctaccact   1200

gtgctcgacc tcaccaccga ttactgtgtc ctggttgagc tctggccaaa agtgacctac   1260

cactcccctg gttatgttta tggccagttt gaagaaaaaa ccaaatataa aagagaaccc   1320

gtctcactaa ctctggccct actattagga ggactcacta tgggcggaat tgccgccgga   1380

gtgggaacag ggactaccgc cctagtggcc actcagcagt tccaacaact ccaggctgcc   1440

atgcaggatg accttaaaga agttgaaaag tccatcacta atctagaaag atctttgacc   1500

tccttgtccg aagtagtgtt acagaatcgt agaggcctag atctactatt cctaaaagag   1560

ggaggtttgt gtgctgcctt aaaagaagaa tgctgtttct atgccgacca cacaggattg   1620

gtacgggata gcatggccaa acttagagaa agattgagtc agagacaaaa actctttgaa   1680

tcccaacaag ggtggtttga agggctgttt aacaagtccc cttggttcac caccctgata   1740

tccaccatca tgggtcccct gataatcctc ttgttaattt tactctttgg gccttgtatt   1800

ctcaatcacc tggtccagtt tatcaaagac agggtttcgg tagtgcaggc cctggtcctg   1860

actcaacaat atcatcaact taagacaata gaagattgtg aatcacgtga ataa         1914
```

<210> SEQ ID NO 90

<211> LENGTH: 637
<212> TYPE: PRT
<213> ORGANISM: Artificial
<220> FEATURE:
<223> OTHER INFORMATION: Modified SL3-2 envelope sequence

<400> SEQUENCE: 90

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Gly Leu Gly Cys Arg Thr Pro Gly Gly Arg
                85                  90                  95

Lys Arg Ala Arg Ile Phe Asp Phe Tyr Val Cys Pro Gly His Thr Val
            100                 105                 110

Leu Ala Gly Cys Gly Gly Pro Arg Glu Gly Tyr Cys Gly Lys Trp Gly
        115                 120                 125

Cys Glu Thr Thr Gly Gln Ala Tyr Trp Lys Pro Ser Ser Ser Trp Asp
    130                 135                 140

Leu Ile Ser Leu Lys Arg Gly Asn Thr Pro Lys Gly Gln Gly Pro Cys
145                 150                 155                 160

Tyr Asp Ser Ser Val Val Ser Ser Ser Ala Gln Gly Ala Thr Pro Gly
                165                 170                 175

Gly Arg Cys Asn Pro Leu Val Leu Glu Phe Thr Asp Ala Gly Lys Arg
            180                 185                 190

Ala Ser Trp Asp Ala Ser Lys Ala Trp Gly Leu Arg Leu Tyr Arg Ser
        195                 200                 205

Thr Gly Ile Asp Pro Val Thr Arg Phe Ser Leu Thr Arg Gln Val Leu
    210                 215                 220

Asn Ile Gly Pro Arg Val Pro Ile Gly Pro Asn Pro Val Ile Ile Asp
225                 230                 235                 240

Gln Leu Pro Pro Ser Arg Pro Val Gln Val Met Leu Pro Arg Pro Pro
                245                 250                 255

Gln Pro Pro Pro Pro Gly Ala Ala Ser Thr Val Pro Glu Thr Ala Pro
            260                 265                 270

Pro Ser Gln Gln Pro Gly Thr Gly Asp Arg Leu Leu Asn Leu Val Asn
        275                 280                 285

Gly Ala Tyr Gln Ala Leu Asn Leu Thr Ser Pro Asp Lys Thr Gln Glu
    290                 295                 300

Cys Trp Leu Cys Leu Val Ala Gly Pro Pro Tyr Tyr Glu Gly Val Ala
305                 310                 315                 320

Val Leu Gly Thr Tyr Ser Asn His Thr Ser Ala Pro Ala Asn Cys Ser
                325                 330                 335

Val Ala Ser Gln His Lys Leu Thr Leu Ser Glu Val Thr Gly Gln Gly
            340                 345                 350

Leu Cys Val Gly Ala Val Pro Lys Thr His Gln Ala Leu Cys Asn Thr
        355                 360                 365

Thr Gln Lys Thr Ser Asn Gly Ser Tyr Tyr Leu Ala Ala Pro Ala Gly
    370                 375                 380
```

```
Thr Ile Trp Ala Cys Asn Thr Gly Leu Thr Pro Cys Leu Ser Thr Thr
385                 390                 395                 400

Val Leu Asp Leu Thr Thr Asp Tyr Cys Val Leu Val Glu Leu Trp Pro
                405                 410                 415

Lys Val Thr Tyr His Ser Pro Gly Tyr Val Tyr Gly Gln Phe Glu Glu
            420                 425                 430

Lys Thr Lys Tyr Lys Arg Glu Pro Val Ser Leu Thr Leu Ala Leu Leu
        435                 440                 445

Leu Gly Gly Leu Thr Met Gly Gly Ile Ala Ala Gly Val Gly Thr Gly
    450                 455                 460

Thr Thr Ala Leu Val Ala Thr Gln Gln Phe Gln Gln Leu Gln Ala Ala
465                 470                 475                 480

Met Gln Asp Asp Leu Lys Glu Val Glu Lys Ser Ile Thr Asn Leu Glu
                485                 490                 495

Arg Ser Leu Thr Ser Leu Ser Glu Val Val Leu Gln Asn Arg Arg Gly
            500                 505                 510

Leu Asp Leu Leu Phe Leu Lys Glu Gly Gly Leu Cys Ala Ala Leu Lys
        515                 520                 525

Glu Glu Cys Cys Phe Tyr Ala Asp His Thr Gly Leu Val Arg Asp Ser
    530                 535                 540

Met Ala Lys Leu Arg Glu Arg Leu Ser Gln Arg Gln Lys Leu Phe Glu
545                 550                 555                 560

Ser Gln Gln Gly Trp Phe Glu Gly Leu Phe Asn Lys Ser Pro Trp Phe
                565                 570                 575

Thr Thr Leu Ile Ser Thr Ile Met Gly Pro Leu Ile Ile Leu Leu Leu
            580                 585                 590

Ile Leu Leu Phe Gly Pro Cys Ile Leu Asn His Leu Val Gln Phe Ile
        595                 600                 605

Lys Asp Arg Val Ser Val Val Gln Ala Leu Val Leu Thr Gln Gln Tyr
    610                 615                 620

His Gln Leu Lys Thr Ile Glu Asp Cys Glu Ser Arg Glu
625                 630                 635
```

<210> SEQ ID NO 91
<211> LENGTH: 1929
<212> TYPE: DNA
<213> ORGANISM: artificial
<220> FEATURE:
<223> OTHER INFORMATION: Modified SL3-2 envelope sequence

<400> SEQUENCE: 91

```
atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcaagg aatctaccag    480

tgctgtgggc cctgttatga ttcctcggtg gtctccagta gcgcccaggg tgccacaccg    540

gggggtcgat gcaacccccct agtcctagaa ttcactgacg cgggtaaaag ggccagctgg    600

gacgcctcca aagcatgggg actaagactg taccgatcca caaggaccga cccggtgacc    660
```

```
cggttctctt tgacccgcca ggtcctcaat atagggcccc gcgtccccat tgggcctaat    720
cccgtgatca ttgaccagtt accccccctcc cgacccgtgc aggtcatgct ccccaggcct    780
cctcagcctc ctccaccagg cgcagcctct acagtccctg agactgcccc acctttcccaa    840
caacctggga cgggagacag gctgctaaac ctggtaaatg gagcctacca agctctcaac    900
ctcaccagtc ctgacaaaac ccaagagtgc tggttgtgtc tggtagcggg acccccctac    960
tacgaagggg ttgccgtcct aggtacttat tccaaccata cctctgcccc agctaactgc   1020
tccgtggcct cccaacacaa gctgaccctg tccgaagtga ccggacaggg actctgcgta   1080
ggagcagttc ccaaaaccca tcaggccctg tgtaatacca cccagaagac gagcaacggg   1140
tcctactatc tggctgctcc cgccgggacc atttgggctt gcaacaccgg gctcactccc   1200
tgcctatcta ccactgtgct cgacctcacc accgattact gtgtcctggt tgagctctgg   1260
ccaaaagtga cctaccactc ccctggttat gtttatggcc agtttgaaga aaaaaccaaa   1320
tataaaagag aacccgtctc actaactctg gccctactat taggaggact cactatgggc   1380
ggaattgccg ccggagtggg aacagggact accgccctag tggccactca gcagttccaa   1440
caactccagg ctgccatgca ggatgacctt aaagaagttg aaaagtccat cactaatcta   1500
gaaagatctt tgacctcctt gtccgaagta gtgttacaga atcgtagagg cctagatcta   1560
ctattcctaa aagagggagg tttgtgtgct gccttaaaag aagaatgctg tttctatgcc   1620
gaccacacag gattggtacg ggatagcatg gccaaactta gagaaagatt gagtcagaga   1680
caaaaactct ttgaatccca acaagggtgg tttgaagggc tgtttaacaa gtccccttgg   1740
ttcaccaccc tgatatccac catcatgggt cccctgataa tcctcttgtt aattttactc   1800
tttgggcctt gtattctcaa tcacctggtc cagtttatca aagacagggt ttcggtagtg   1860
caggccctgg tcctgactca acaatatcat caacttaaga caatagaaga ttgtgaatca   1920
cgtgaataa                                                           1929

<210> SEQ ID NO 92
<211> LENGTH: 642
<212> TYPE: PRT
<213> ORGANISM: Artificial
<220> FEATURE:
<223> OTHER INFORMATION: Modified SL3-2 envelope sequence

<400> SEQUENCE: 92

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140
```

-continued

```
Trp Asp Leu Ile Ser Leu Lys Arg Gly Asn Thr Gln Gly Ile Tyr Gln
145                 150                 155                 160

Cys Cys Gly Pro Cys Tyr Asp Ser Ser Val Val Ser Ser Ser Ala Gln
                165                 170                 175

Gly Ala Thr Pro Gly Gly Arg Cys Asn Pro Leu Val Leu Glu Phe Thr
            180                 185                 190

Asp Ala Gly Lys Arg Ala Ser Trp Asp Ala Ser Lys Ala Trp Gly Leu
        195                 200                 205

Arg Leu Tyr Arg Ser Thr Arg Thr Asp Pro Val Thr Arg Phe Ser Leu
    210                 215                 220

Thr Arg Gln Val Leu Asn Ile Gly Pro Arg Val Pro Ile Gly Pro Asn
225                 230                 235                 240

Pro Val Ile Ile Asp Gln Leu Pro Pro Ser Arg Pro Val Gln Val Met
                245                 250                 255

Leu Pro Arg Pro Pro Gln Pro Pro Pro Pro Gly Ala Ala Ser Thr Val
            260                 265                 270

Pro Glu Thr Ala Pro Pro Ser Gln Gln Pro Gly Thr Gly Asp Arg Leu
        275                 280                 285

Leu Asn Leu Val Asn Gly Ala Tyr Gln Ala Leu Asn Leu Thr Ser Pro
    290                 295                 300

Asp Lys Thr Gln Glu Cys Trp Leu Cys Leu Val Ala Gly Pro Pro Tyr
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
            340                 345                 350

Val Thr Gly Gln Gly Leu Cys Val Gly Ala Val Pro Lys Thr His Gln
        355                 360                 365

Ala Leu Cys Asn Thr Thr Gln Lys Thr Ser Asn Gly Ser Tyr Tyr Leu
    370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asp Leu Thr Thr Asp Tyr Cys Val Leu
                405                 410                 415

Val Glu Leu Trp Pro Lys Val Thr Tyr His Ser Pro Gly Tyr Val Tyr
            420                 425                 430

Gly Gln Phe Glu Glu Lys Thr Lys Tyr Lys Arg Glu Pro Val Ser Leu
        435                 440                 445

Thr Leu Ala Leu Leu Leu Gly Gly Leu Thr Met Gly Gly Ile Ala Ala
    450                 455                 460

Gly Val Gly Thr Gly Thr Thr Ala Leu Val Ala Thr Gln Gln Phe Gln
465                 470                 475                 480

Gln Leu Gln Ala Ala Met Gln Asp Asp Leu Lys Glu Val Glu Lys Ser
                485                 490                 495

Ile Thr Asn Leu Glu Arg Ser Leu Thr Ser Leu Ser Glu Val Val Leu
            500                 505                 510

Gln Asn Arg Arg Gly Leu Asp Leu Leu Phe Leu Lys Glu Gly Gly Leu
        515                 520                 525

Cys Ala Ala Leu Lys Glu Glu Cys Cys Phe Tyr Ala Asp His Thr Gly
    530                 535                 540

Leu Val Arg Asp Ser Met Ala Lys Leu Arg Glu Arg Leu Ser Gln Arg
545                 550                 555                 560

Gln Lys Leu Phe Glu Ser Gln Gln Gly Trp Phe Glu Gly Leu Phe Asn
```

-continued

```
565 570 575

Lys Ser Pro Trp Phe Thr Thr Leu Ile Ser Thr Ile Met Gly Pro Leu
            580                 585                 590

Ile Ile Leu Leu Leu Ile Leu Leu Phe Gly Pro Cys Ile Leu Asn His
        595                 600                 605

Leu Val Gln Phe Ile Lys Asp Arg Val Ser Val Val Gln Ala Leu Val
    610                 615                 620

Leu Thr Gln Gln Tyr His Gln Leu Lys Thr Ile Glu Asp Cys Glu Ser
625                 630                 635                 640

Arg Glu
```

<210> SEQ ID NO 93
<211> LENGTH: 1929
<212> TYPE: DNA
<213> ORGANISM: artificial
<220> FEATURE:
<223> OTHER INFORMATION: Modified SL3-2 envelope sequence

<400> SEQUENCE: 93

```
atggaaggtc cagcgttctc aaaacccctt aaagataaga ttaacccgtg ggcccccta      60
atagtcctgg gaatcttaat gagggcaaga gtatcagtac aacatgacag ccctcatcag    120
gtcttcaatg ttacttggag agttaccaac ttaatgacag gacaaacagc taatgctacc    180
tccctcctgg ggacaatgac cgatgccttt cctaaactgt actttgactt gtgcgattta    240
ataggggacg actgggatga gactggactc gggtgtcgca ctcccggggg aagaaaaagg    300
gcaagaatat ttgacttcta tgtttgcccc ggtcacactg tgctagcagg gtgtggaggg    360
ccgagagagg gctactgtgg caaatgggga tgtgagacca ctggacaggc atactggaag    420
ccatcatcat catgggacct aatttccctt aagcgaggaa acactcaagg aatctaccag    480
tgctgtgggc cctgttatga ttcctcggtg gtctccagta gcgcccaggg tgccacaccg    540
gggggtcgat gcaacccccct agtcctagaa ttcactgacg cgggtaaaag ggccagctgg    600
gacgcctcca aagcatgggg actaagactg taccgatcca cagggatcga cccggtgacc    660
cggttctctt tgacccgcca ggtcctcaat atagggcccc gcgtccccat tgggcctaat    720
cccgtgatca ttgaccagtt acccccctcc cgacccgtgc aggtcatgct ccccaggcct    780
cctcagcctc ctccaccagg cgcagcctct acagtccctg agactgcccc accttcccaa    840
caacctggga cgggagacag gctgctaaac ctggtaaatg gagcctacca agctctcaac    900
ctcaccagtc ctgacaaaac ccaagagtgc tggttgtgtc tggtagcggg acccccctac    960
tacgaagggg ttgccgtcct aggtacttat tccaaccata cctctgcccc agctaactgc   1020
tccgtggcct cccaacacaa gctgaccctg tccgaagtga ccggacaggg actctgcgta   1080
ggagcagttc ccaaaaccca tcaggccctg tgtaatacca cccagaagac gagcaacggg   1140
tcctactatc tggctgctcc cgccgggacc atttgggctt gcaacaccgg gctcactccc   1200
tgcctatcta ccactgtgct cgacctcacc accgattact gtgtcctggt tgagctctgg   1260
ccaaaagtga cctaccactc ccctggttat gtttatggcc agtttgaaga aaaaaccaaa   1320
tataaaagag aacccgtctc actaactctg gccctactat taggaggact cactatgggc   1380
ggaattgccg ccggagtggg aacagggact accgccctag tggccactca gcagttccaa   1440
caactccagg ctgccatgca ggatgacctt aaagaagttg aaaagtccat cactaatcta   1500
gaaagatctt tgacctcctt gtccgaagta gtgttacaga atcgtagagg cctagatcta   1560
ctattcctaa aagagggagg tttgtgtgct gccttaaaag aagaatgctg tttctatgcc   1620
```

```
gaccacacag gattggtacg ggatagcatg gccaaactta gagaaagatt gagtcagaga   1680

caaaaactct ttgaatccca acaagggtgg tttgaagggc tgtttaacaa gtccccttgg   1740

ttcaccaccc tgatatccac catcatgggt cccctgataa tcctcttgtt aattttactc   1800

tttgggcctt gtattctcaa tcacctggtc cagtttatca aagacagggt ttcggtagtg   1860

caggccctgg tcctgactca acaatatcat caacttaaga caatagaaga ttgtgaatca   1920

cgtgaataa                                                           1929
```

<210> SEQ ID NO 94
<211> LENGTH: 642
<212> TYPE: PRT
<213> ORGANISM: Artificial
<220> FEATURE:
<223> OTHER INFORMATION: Modified SL3-2 envelope sequence

<400> SEQUENCE: 94

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Cys Gly Pro Cys Tyr Asp Ser Ser Val Val Ser Ser Ser Ala Gln
                165                 170                 175

Gly Ala Thr Pro Gly Gly Arg Cys Asn Pro Leu Val Leu Glu Phe Thr
            180                 185                 190

Asp Ala Gly Lys Arg Ala Ser Trp Asp Ala Ser Lys Ala Trp Gly Leu
        195                 200                 205

Arg Leu Tyr Arg Ser Thr Gly Ile Asp Pro Val Thr Arg Phe Ser Leu
    210                 215                 220

Thr Arg Gln Val Leu Asn Ile Gly Pro Arg Val Pro Ile Gly Pro Asn
225                 230                 235                 240

Pro Val Ile Ile Asp Gln Leu Pro Pro Ser Arg Pro Val Gln Val Met
                245                 250                 255

Leu Pro Arg Pro Pro Gln Pro Pro Pro Pro Gly Ala Ala Ser Thr Val
            260                 265                 270

Pro Glu Thr Ala Pro Pro Ser Gln Gln Pro Gly Thr Gly Asp Arg Leu
        275                 280                 285

Leu Asn Leu Val Asn Gly Ala Tyr Gln Ala Leu Asn Leu Thr Ser Pro
    290                 295                 300

Asp Lys Thr Gln Glu Cys Trp Leu Cys Leu Val Ala Gly Pro Pro Tyr
```

```
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
            340                 345                 350

Val Thr Gly Gln Gly Leu Cys Val Gly Ala Val Pro Lys Thr His Gln
        355                 360                 365

Ala Leu Cys Asn Thr Thr Gln Lys Thr Ser Asn Gly Ser Tyr Tyr Leu
    370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asp Leu Thr Thr Asp Tyr Cys Val Leu
                405                 410                 415

Val Glu Leu Trp Pro Lys Val Thr Tyr His Ser Pro Gly Tyr Val Tyr
            420                 425                 430

Gly Gln Phe Glu Glu Lys Thr Lys Tyr Lys Arg Glu Pro Val Ser Leu
        435                 440                 445

Thr Leu Ala Leu Leu Leu Gly Gly Leu Thr Met Gly Gly Ile Ala Ala
    450                 455                 460

Gly Val Gly Thr Gly Thr Thr Ala Leu Val Ala Thr Gln Gln Phe Gln
465                 470                 475                 480

Gln Leu Gln Ala Ala Met Gln Asp Asp Leu Lys Glu Val Glu Lys Ser
                485                 490                 495

Ile Thr Asn Leu Glu Arg Ser Leu Thr Ser Leu Ser Glu Val Val Leu
            500                 505                 510

Gln Asn Arg Arg Gly Leu Asp Leu Leu Phe Leu Lys Glu Gly Gly Leu
        515                 520                 525

Cys Ala Ala Leu Lys Glu Glu Cys Cys Phe Tyr Ala Asp His Thr Gly
    530                 535                 540

Leu Val Arg Asp Ser Met Ala Lys Leu Arg Glu Arg Leu Ser Gln Arg
545                 550                 555                 560

Gln Lys Leu Phe Glu Ser Gln Gln Gly Trp Phe Glu Gly Leu Phe Asn
                565                 570                 575

Lys Ser Pro Trp Phe Thr Thr Leu Ile Ser Thr Ile Met Gly Pro Leu
            580                 585                 590

Ile Ile Leu Leu Leu Ile Leu Leu Phe Gly Pro Cys Ile Leu Asn His
        595                 600                 605

Leu Val Gln Phe Ile Lys Asp Arg Val Ser Val Val Gln Ala Leu Val
    610                 615                 620

Leu Thr Gln Gln Tyr His Gln Leu Lys Thr Ile Glu Asp Cys Glu Ser
625                 630                 635                 640

Arg Glu
```

<210> SEQ ID NO 95
<211> LENGTH: 1911
<212> TYPE: DNA
<213> ORGANISM: artificial
<220> FEATURE:
<223> OTHER INFORMATION: Modified SL3-2 envelope sequence

<400> SEQUENCE: 95

```
atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180
```

```
tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcctaa aggccagggc    480

ccctgttatg attcctccag tagcgcccag ggtgccacac cggggggtcg atgcaacccc    540

ctagtcctag aattcactga cgcgggtaaa agggccagct gggacgcctc caaagcatgg    600

ggactaagac tgtaccgatc cacaaggacc gacccggtga cccggttctc tttgacccgc    660

caggtcctca atatagggcc ccgcgtcccc attgggccta atcccgtgat cattgaccag    720

ttacccccct cccgacccgt gcaggtcatg ctccccaggc ctcctcagcc tcctccacca    780

ggcgcagcct ctacagtccc tgagactgcc ccaccttccc aacaacctgg gacgggagac    840

aggctgctaa acctggtaaa tggagcctac caagctctca acctcaccag tcctgacaaa    900

acccaagagt gctggttgtg tctggtagcg ggacccccct actacgaagg ggttgccgtc    960

ctaggtactt attccaacca tacctctgcc ccagctaact gctccgtggc ctcccaacac   1020

aagctgaccc tgtccgaagt gaccggacag ggactctgcg taggagcagt tcccaaaacc   1080

catcaggccc tgtgtaatac cacccagaag acgagcaacg ggtcctacta tctggctgct   1140

cccgccggga ccatttgggc ttgcaacacc gggctcactc cctgcctatc taccactgtg   1200

ctcgacctca ccaccgatta ctgtgtcctg gttgagctct ggccaaaagt gacctaccac   1260

tcccctggtt atgtttatgg ccagtttgaa gaaaaaacca aatataaaag agaacccgtc   1320

tcactaactc tggccctact attaggagga ctcactatgg gcggaattgc cgccggagtg   1380

ggaacaggga ctaccgccct agtggccact cagcagttcc aacaactcca ggctgccatg   1440

caggatgacc ttaaagaagt tgaaaagtcc atcactaatc tagaaaagatc tttgacctcc  1500

ttgtccgaag tagtgttaca gaatcgtaga ggcctagatc tactattcct aaaagaggga   1560

ggtttgtgtg ctgccttaaa agaagaatgc tgtttctatg ccgaccacac aggattggta   1620

cgggatagca tggccaaact tagagaaaga ttgagtcaga gacaaaaact ctttgaatcc   1680

caacaagggt ggtttgaagg gctgtttaac aagtcccctt ggttcaccac cctgatatcc   1740

accatcatgg gtcccctgat aatcctcttg ttaattttac tctttgggcc ttgtattctc   1800

aatcacctgg tccagtttat caaagacagg gtttcggtag tgcaggccct ggtcctgact   1860

caacaatatc atcaacttaa gacaatagaa gattgtgaat cacgtgaata a            1911
```

<210> SEQ ID NO 96
<211> LENGTH: 636
<212> TYPE: PRT
<213> ORGANISM: Artificial
<220> FEATURE:
<223> OTHER INFORMATION: Modified SL3-2 envelope sequence

<400> SEQUENCE: 96

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60
```

-continued

```
Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Ser Ser Ala Gln Gly Ala Thr Pro Gly Gly
                165                 170                 175

Arg Cys Asn Pro Leu Val Leu Glu Phe Thr Asp Ala Gly Lys Arg Ala
            180                 185                 190

Ser Trp Asp Ala Ser Lys Ala Trp Gly Leu Arg Leu Tyr Arg Ser Thr
        195                 200                 205

Arg Thr Asp Pro Val Thr Arg Phe Ser Leu Thr Arg Gln Val Leu Asn
    210                 215                 220

Ile Gly Pro Arg Val Pro Ile Gly Pro Asn Pro Val Ile Ile Asp Gln
225                 230                 235                 240

Leu Pro Pro Ser Arg Pro Val Gln Val Met Leu Pro Arg Pro Pro Gln
                245                 250                 255

Pro Pro Pro Pro Gly Ala Ala Ser Thr Val Pro Glu Thr Ala Pro Pro
            260                 265                 270

Ser Gln Gln Pro Gly Thr Gly Asp Arg Leu Leu Asn Leu Val Asn Gly
        275                 280                 285

Ala Tyr Gln Ala Leu Asn Leu Thr Ser Pro Asp Lys Thr Gln Glu Cys
    290                 295                 300

Trp Leu Cys Leu Val Ala Gly Pro Pro Tyr Tyr Glu Gly Val Ala Val
305                 310                 315                 320

Leu Gly Thr Tyr Ser Asn His Thr Ser Ala Pro Ala Asn Cys Ser Val
                325                 330                 335

Ala Ser Gln His Lys Leu Thr Leu Ser Glu Val Thr Gly Gln Gly Leu
            340                 345                 350

Cys Val Gly Ala Val Pro Lys Thr His Gln Ala Leu Cys Asn Thr Thr
        355                 360                 365

Gln Lys Thr Ser Asn Gly Ser Tyr Tyr Leu Ala Ala Pro Ala Gly Thr
    370                 375                 380

Ile Trp Ala Cys Asn Thr Gly Leu Thr Pro Cys Leu Ser Thr Thr Val
385                 390                 395                 400

Leu Asp Leu Thr Thr Asp Tyr Cys Val Leu Val Glu Leu Trp Pro Lys
                405                 410                 415

Val Thr Tyr His Ser Pro Gly Tyr Val Tyr Gly Gln Phe Glu Glu Lys
            420                 425                 430

Thr Lys Tyr Lys Arg Glu Pro Val Ser Leu Thr Leu Ala Leu Leu Leu
        435                 440                 445

Gly Gly Leu Thr Met Gly Gly Ile Ala Ala Gly Val Gly Thr Gly Thr
    450                 455                 460

Thr Ala Leu Val Ala Thr Gln Gln Phe Gln Gln Leu Gln Ala Ala Met
465                 470                 475                 480

Gln Asp Asp Leu Lys Glu Val Glu Lys Ser Ile Thr Asn Leu Glu Arg
                485                 490                 495
```

```
Ser Leu Thr Ser Leu Ser Glu Val Val Leu Gln Asn Arg Arg Gly Leu
            500                 505                 510

Asp Leu Leu Phe Leu Lys Glu Gly Gly Leu Cys Ala Ala Leu Lys Glu
        515                 520                 525

Glu Cys Cys Phe Tyr Ala Asp His Thr Gly Leu Val Arg Asp Ser Met
    530                 535                 540

Ala Lys Leu Arg Glu Arg Leu Ser Gln Arg Gln Lys Leu Phe Glu Ser
545                 550                 555                 560

Gln Gln Gly Trp Phe Glu Gly Leu Phe Asn Lys Ser Pro Trp Phe Thr
                565                 570                 575

Thr Leu Ile Ser Thr Ile Met Gly Pro Leu Ile Ile Leu Leu Leu Ile
            580                 585                 590

Leu Leu Phe Gly Pro Cys Ile Leu Asn His Leu Val Gln Phe Ile Lys
        595                 600                 605

Asp Arg Val Ser Val Val Gln Ala Leu Val Leu Thr Gln Gln Tyr His
    610                 615                 620

Gln Leu Lys Thr Ile Glu Asp Cys Glu Ser Arg Glu
625                 630                 635


<210> SEQ ID NO 97
<211> LENGTH: 1911
<212> TYPE: DNA
<213> ORGANISM: artificial
<220> FEATURE:
<223> OTHER INFORMATION: Modified SL3-2 envelope sequence

<400> SEQUENCE: 97

atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcctaa aggccagggc    480

ccctgttatg attcctccag tagcgcccag ggtgccacac cgggggggtcg atgcaacccc    540

ctagtcctag aattcactga cgcgggtaaa agggccagct gggacgcctc caaagcatgg    600

ggactaagac tgtaccgatc cacagggatc gacccggtga cccggttctc tttgacccgc    660

caggtcctca atatagggcc ccgcgtcccc attgggccta atcccgtgat cattgaccag    720

ttaccccct cccgacccgt gcaggtcatg ctccccaggc ctcctcagcc tcctccacca    780

ggcgcagcct ctacagtccc tgagactgcc ccaccttccc aacaacctgg gacgggagac    840

aggctgctaa acctggtaaa tggagcctac caagctctca acctcaccag tcctgacaaa    900

acccaagagt gctggttgtg tctggtagcg ggaccccct actacgaagg ggttgccgtc    960

ctaggtactt attccaacca tacctctgcc ccagctaact gctccgtggc ctcccaacac   1020

aagctgaccc tgtccgaagt gaccggacag ggactctgcg taggagcagt tcccaaaacc   1080

catcaggccc tgtgtaatac cacccagaag acgagcaacg ggtcctacta tctggctgct   1140

cccgccggga ccatttgggc ttgcaacacc gggctcactc cctgcctatc taccactgtg   1200

ctcgacctca ccaccgatta ctgtgtcctg gttgagctct ggccaaaagt gacctaccac   1260
```

```
tcccctggtt atgtttatgg ccagtttgaa gaaaaaacca aatataaaag agaacccgtc   1320

tcactaactc tggccctact attaggagga ctcactatgg gcggaattgc cgccggagtg   1380

ggaacaggga ctaccgccct agtggccact cagcagttcc aacaactcca ggctgccatg   1440

caggatgacc ttaaagaagt tgaaaagtcc atcactaatc tagaaagatc tttgacctcc   1500

ttgtccgaag tagtgttaca gaatcgtaga ggcctagatc tactattcct aaaagaggga   1560

ggtttgtgtg ctgccttaaa agaagaatgc tgtttctatg ccgaccacac aggattggta   1620

cgggatagca tggccaaact tagagaaaga ttgagtcaga gacaaaaact ctttgaatcc   1680

caacaagggt ggtttgaagg gctgtttaac aagtcccctt ggttcaccac cctgatatcc   1740

accatcatgg gtcccctgat aatcctcttg ttaattttac tctttgggcc ttgtattctc   1800

aatcacctgg tccagtttat caaagacagg gtttcggtag tgcaggccct ggtcctgact   1860

caacaatatc atcaacttaa gacaatagaa gattgtgaat cacgtgaata a            1911
```

<210> SEQ ID NO 98
<211> LENGTH: 636
<212> TYPE: PRT
<213> ORGANISM: Artificial
<220> FEATURE:
<223> OTHER INFORMATION: Modified SL3-2 envelope sequence

<400> SEQUENCE: 98

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Ser Ser Ala Gln Gly Ala Thr Pro Gly Gly
                165                 170                 175

Arg Cys Asn Pro Leu Val Leu Glu Phe Thr Asp Ala Gly Lys Arg Ala
            180                 185                 190

Ser Trp Asp Ala Ser Lys Ala Trp Gly Leu Arg Leu Tyr Arg Ser Thr
        195                 200                 205

Gly Ile Asp Pro Val Thr Arg Phe Ser Leu Thr Arg Gln Val Leu Asn
    210                 215                 220

Ile Gly Pro Arg Val Pro Ile Gly Pro Asn Pro Val Ile Ile Asp Gln
225                 230                 235                 240

Leu Pro Pro Ser Arg Pro Val Gln Val Met Leu Pro Arg Pro Pro Gln
                245                 250                 255
```

-continued

```
Pro Pro Pro Pro Gly Ala Ala Ser Thr Val Pro Glu Thr Ala Pro Pro
            260                 265                 270

Ser Gln Gln Pro Gly Thr Gly Asp Arg Leu Leu Asn Leu Val Asn Gly
        275                 280                 285

Ala Tyr Gln Ala Leu Asn Leu Thr Ser Pro Asp Lys Thr Gln Glu Cys
    290                 295                 300

Trp Leu Cys Leu Val Ala Gly Pro Pro Tyr Tyr Glu Gly Val Ala Val
305                 310                 315                 320

Leu Gly Thr Tyr Ser Asn His Thr Ser Ala Pro Ala Asn Cys Ser Val
                325                 330                 335

Ala Ser Gln His Lys Leu Thr Leu Ser Glu Val Thr Gly Gln Gly Leu
            340                 345                 350

Cys Val Gly Ala Val Pro Lys Thr His Gln Ala Leu Cys Asn Thr Thr
        355                 360                 365

Gln Lys Thr Ser Asn Gly Ser Tyr Tyr Leu Ala Ala Pro Ala Gly Thr
    370                 375                 380

Ile Trp Ala Cys Asn Thr Gly Leu Thr Pro Cys Leu Ser Thr Thr Val
385                 390                 395                 400

Leu Asp Leu Thr Thr Asp Tyr Cys Val Leu Val Glu Leu Trp Pro Lys
                405                 410                 415

Val Thr Tyr His Ser Pro Gly Tyr Val Tyr Gly Gln Phe Glu Glu Lys
            420                 425                 430

Thr Lys Tyr Lys Arg Glu Pro Val Ser Leu Thr Leu Ala Leu Leu Leu
        435                 440                 445

Gly Gly Leu Thr Met Gly Gly Ile Ala Ala Gly Val Gly Thr Gly Thr
    450                 455                 460

Thr Ala Leu Val Ala Thr Gln Gln Phe Gln Gln Leu Gln Ala Ala Met
465                 470                 475                 480

Gln Asp Asp Leu Lys Glu Val Glu Lys Ser Ile Thr Asn Leu Glu Arg
                485                 490                 495

Ser Leu Thr Ser Leu Ser Glu Val Val Leu Gln Asn Arg Arg Gly Leu
            500                 505                 510

Asp Leu Leu Phe Leu Lys Glu Gly Gly Leu Cys Ala Ala Leu Lys Glu
        515                 520                 525

Glu Cys Cys Phe Tyr Ala Asp His Thr Gly Leu Val Arg Asp Ser Met
    530                 535                 540

Ala Lys Leu Arg Glu Arg Leu Ser Gln Arg Gln Lys Leu Phe Glu Ser
545                 550                 555                 560

Gln Gln Gly Trp Phe Glu Gly Leu Phe Asn Lys Ser Pro Trp Phe Thr
                565                 570                 575

Thr Leu Ile Ser Thr Ile Met Gly Pro Leu Ile Ile Leu Leu Leu Ile
            580                 585                 590

Leu Leu Phe Gly Pro Cys Ile Leu Asn His Leu Val Gln Phe Ile Lys
        595                 600                 605

Asp Arg Val Ser Val Val Gln Ala Leu Val Leu Thr Gln Gln Tyr His
    610                 615                 620

Gln Leu Lys Thr Ile Glu Asp Cys Glu Ser Arg Glu
625                 630                 635
```

<210> SEQ ID NO 99
<211> LENGTH: 1983
<212> TYPE: DNA
<213> ORGANISM: artificial
<220> FEATURE:
<223> OTHER INFORMATION: SL3-2/apelin chimeric envelope sequence

<400> SEQUENCE: 99
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggattc cggtggcagt ggacagcggc cccgcctctc ccataaggga 300
cccatgcctt tcagcggtgg atctggcgga ctcgggtgtc gcactcccgg gggaagaaaa 360
agggcaagaa tatttgactt ctatgtttgc cccggtcaca ctgtgctagc agggtgtgga 420
gggccgagag agggctactg tggcaaatgg ggatgtgaga ccactggaca ggcatactgg 480
aagccatcat catcatggga cctaatttcc cttaagcgag gaaacactcc taaaggccag 540
ggcccctgtt atgattcctc ggtggtctcc agtagcgccc agggtgccac accggggggt 600
cgatgcaacc ccctagtcct agaattcact gacgcgggta aaagggccag ctgggacgcc 660
tccaaagcat ggggactaag actgtaccga tccacaagga ccgacccggt gacccggttc 720
tctttgaccc gccaggtcct caatataggg ccccgcgtcc ccattgggcc taatcccgtg 780
atcattgacc agttaccccc ctcccgaccc gtgcaggtca tgctccccag gcctcctcag 840
cctcctccac caggcgcagc ctctacagtc cctgagactg ccccaccttc ccaacaacct 900
gggacgggag acaggctgct aaacctggta aatggagcct accaagctct caacctcacc 960
agtcctgaca aaacccaaga gtgctggttg tgtctggtag cgggaccccc ctactacgaa 1020
ggggttgccg tcctaggtac ttattccaac catacctctg ccccagctaa ctgctccgtg 1080
gcctcccaac acaagctgac cctgtccgaa gtgaccggac agggactctg cgtaggagca 1140
gttcccaaaa cccatcaggc cctgtgtaat accacccaga agacgagcaa cgggtcctac 1200
tatctggctg ctcccgccgg gaccatttgg gcttgcaaca ccgggctcac tccctgccta 1260
tctaccactg tgctcgacct caccaccgat tactgtgtcc tggttgagct ctggccaaaa 1320
gtgacctacc actcccctgg ttatgtttat ggccagtttg aagaaaaaac caaatataaa 1380
agagaacccg tctcactaac tctggcccta ctattaggag gactcactat gggcggaatt 1440
gccgccggag tgggaacagg gactaccgcc ctagtggcca ctcagcagtt ccaacaactc 1500
caggctgcca tgcaggatga ccttaaagaa gttgaaaagt ccatcactaa tctagaaaga 1560
tctttgacct ccttgtccga agtagtgtta cagaatcgta gaggcctaga tctactattc 1620
ctaaaagagg gaggtttgtg tgctgcctta aaagaagaat gctgtttcta tgccgaccac 1680
acaggattgg tacgggatag catggccaaa cttagagaaa gattgagtca gagacaaaaa 1740
ctctttgaat cccaacaagg gtggtttgaa gggctgttta acaagtcccc ttggttcacc 1800
accctgatat ccaccatcat gggtcccctg ataatcctct tgttaatttt actctttggg 1860
ccttgtattc tcaatcacct ggtccagttt atcaaagaca gggtttcggt agtgcaggcc 1920
ctggtcctga ctcaacaata tcatcaactt aagacaatag aagattgtga atcacgtgaa 1980
taa 1983

<210> SEQ ID NO 100
<211> LENGTH: 660
<212> TYPE: PRT
<213> ORGANISM: Artificial
<220> FEATURE:
<223> OTHER INFORMATION: SL3-2/apeline chimeric envelope sequence

<400> SEQUENCE: 100

-continued

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Ser Gly Gly Ser Gly Gln Arg Pro Arg Leu
                85                  90                  95

Ser His Lys Gly Pro Met Pro Phe Ser Gly Gly Ser Gly Gly Leu Gly
            100                 105                 110

Cys Arg Thr Pro Gly Gly Arg Lys Arg Ala Arg Ile Phe Asp Phe Tyr
        115                 120                 125

Val Cys Pro Gly His Thr Val Leu Ala Gly Cys Gly Gly Pro Arg Glu
    130                 135                 140

Gly Tyr Cys Gly Lys Trp Gly Cys Glu Thr Thr Gly Gln Ala Tyr Trp
145                 150                 155                 160

Lys Pro Ser Ser Ser Trp Asp Leu Ile Ser Leu Lys Arg Gly Asn Thr
                165                 170                 175

Pro Lys Gly Gln Gly Pro Cys Tyr Asp Ser Ser Val Val Ser Ser Ser
            180                 185                 190

Ala Gln Gly Ala Thr Pro Gly Gly Arg Cys Asn Pro Leu Val Leu Glu
        195                 200                 205

Phe Thr Asp Ala Gly Lys Arg Ala Ser Trp Asp Ala Ser Lys Ala Trp
    210                 215                 220

Gly Leu Arg Leu Tyr Arg Ser Thr Arg Thr Asp Pro Val Thr Arg Phe
225                 230                 235                 240

Ser Leu Thr Arg Gln Val Leu Asn Ile Gly Pro Arg Val Pro Ile Gly
                245                 250                 255

Pro Asn Pro Val Ile Ile Asp Gln Leu Pro Pro Ser Arg Pro Val Gln
            260                 265                 270

Val Met Leu Pro Arg Pro Pro Gln Pro Pro Pro Pro Gly Ala Ala Ser
        275                 280                 285

Thr Val Pro Glu Thr Ala Pro Pro Ser Gln Gln Pro Gly Thr Gly Asp
    290                 295                 300

Arg Leu Leu Asn Leu Val Asn Gly Ala Tyr Gln Ala Leu Asn Leu Thr
305                 310                 315                 320

Ser Pro Asp Lys Thr Gln Glu Cys Trp Leu Cys Leu Val Ala Gly Pro
                325                 330                 335

Pro Tyr Tyr Glu Gly Val Ala Val Leu Gly Thr Tyr Ser Asn His Thr
            340                 345                 350

Ser Ala Pro Ala Asn Cys Ser Val Ala Ser Gln His Lys Leu Thr Leu
        355                 360                 365

Ser Glu Val Thr Gly Gln Gly Leu Cys Val Gly Ala Val Pro Lys Thr
    370                 375                 380

His Gln Ala Leu Cys Asn Thr Thr Gln Lys Thr Ser Asn Gly Ser Tyr
385                 390                 395                 400

Tyr Leu Ala Ala Pro Ala Gly Thr Ile Trp Ala Cys Asn Thr Gly Leu
                405                 410                 415

Thr Pro Cys Leu Ser Thr Thr Val Leu Asp Leu Thr Thr Asp Tyr Cys
            420                 425                 430
```

```
Val Leu Val Glu Leu Trp Pro Lys Val Thr Tyr His Ser Pro Gly Tyr
        435                 440                 445

Val Tyr Gly Gln Phe Glu Glu Lys Thr Lys Tyr Lys Arg Glu Pro Val
    450                 455                 460

Ser Leu Thr Leu Ala Leu Leu Leu Gly Gly Leu Thr Met Gly Gly Ile
465                 470                 475                 480

Ala Ala Gly Val Gly Thr Gly Thr Thr Ala Leu Val Ala Thr Gln Gln
                485                 490                 495

Phe Gln Gln Leu Gln Ala Ala Met Gln Asp Asp Leu Lys Glu Val Glu
            500                 505                 510

Lys Ser Ile Thr Asn Leu Glu Arg Ser Leu Thr Ser Leu Ser Glu Val
        515                 520                 525

Val Leu Gln Asn Arg Arg Gly Leu Asp Leu Leu Phe Leu Lys Glu Gly
    530                 535                 540

Gly Leu Cys Ala Ala Leu Lys Glu Glu Cys Cys Phe Tyr Ala Asp His
545                 550                 555                 560

Thr Gly Leu Val Arg Asp Ser Met Ala Lys Leu Arg Glu Arg Leu Ser
                565                 570                 575

Gln Arg Gln Lys Leu Phe Glu Ser Gln Gln Gly Trp Phe Glu Gly Leu
            580                 585                 590

Phe Asn Lys Ser Pro Trp Phe Thr Thr Leu Ile Ser Thr Ile Met Gly
        595                 600                 605

Pro Leu Ile Ile Leu Leu Leu Ile Leu Leu Phe Gly Pro Cys Ile Leu
    610                 615                 620

Asn His Leu Val Gln Phe Ile Lys Asp Arg Val Ser Val Val Gln Ala
625                 630                 635                 640

Leu Val Leu Thr Gln Gln Tyr His Gln Leu Lys Thr Ile Glu Asp Cys
                645                 650                 655

Glu Ser Arg Glu
            660
```

<210> SEQ ID NO 101
<211> LENGTH: 1983
<212> TYPE: DNA
<213> ORGANISM: artificial
<220> FEATURE:
<223> OTHER INFORMATION: SL3-2/apelin chimeric envelope sequence

<400> SEQUENCE: 101

```
atggaaggtc cagcgttctc aaaacccctt aaagataaga ttaacccgtg ggcccccta     60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

atagggggacg actgggattc cggtggcagt ggacagcggc cccgcctctc ccataaggga    300

cccatgcctt tcagcggtgg atctggcgga ctcgggtgtc gcactcccgg gggaagaaaa    360

agggcaagaa tatttgactt ctatgtttgc cccggtcaca ctgtgctagc agggtgtgga    420

gggccgagag agggctactg tggcaaatgg ggatgtgaga ccactggaca ggcatactgg    480

aagccatcat catcatggga cctaatttcc cttaagcgag gaaacactcc taaaggccag    540

ggcccctgtt atgattcctc ggtggtctcc agtagcgccc agggtgccac accggggggt    600

cgatgcaacc ccctagtcct agaattcact gacgcgggta aaagggccag ctgggacgcc    660

tccaaagcat ggggactaag actgtaccga tccacaggga tcgacccggt gacccggttc    720
```

```
tctttgaccc gccaggtcct caatataggg ccccgcgtcc ccattgggcc taatcccgtg    780

atcattgacc agttaccccc ctcccgaccc gtgcaggtca tgctccccag gcctcctcag    840

cctcctccac caggcgcagc ctctacagtc cctgagactg ccccaccttc ccaacaacct    900

gggacgggag acaggctgct aaacctggta aatggagcct accaagctct caacctcacc    960

agtcctgaca aaacccaaga gtgctggttg tgtctggtag cgggaccccc ctactacgaa   1020

ggggttgccg tcctaggtac ttattccaac catacctctg ccccagctaa ctgctccgtg   1080

gcctcccaac acaagctgac cctgtccgaa gtgaccggac agggactctg cgtaggagca   1140

gttcccaaaa cccatcaggc cctgtgtaat accacccaga agacgagcaa cgggtcctac   1200

tatctggctg ctcccgccgg gaccatttgg gcttgcaaca ccgggctcac tccctgccta   1260

tctaccactg tgctcgacct caccaccgat tactgtgtcc tggttgagct ctggccaaaa   1320

gtgacctacc actcccctgg ttatgtttat ggccagtttg aagaaaaaac caaatataaa   1380

agagaacccg tctcactaac tctggcccta ctattaggag gactcactat gggcggaatt   1440

gccgccggag tgggaacagg gactaccgcc ctagtggcca ctcagcagtt ccaacaactc   1500

caggctgcca tgcaggatga ccttaaagaa gttgaaaagt ccatcactaa tctagaaaga   1560

tctttgacct ccttgtccga agtagtgtta cagaatcgta gaggcctaga tctactattc   1620

ctaaaagagg gaggtttgtg tgctgcctta aaagaagaat gctgtttcta tgccgaccac   1680

acaggattgg tacgggatag catggccaaa cttagagaaa gattgagtca gagacaaaaa   1740

ctctttgaat cccaacaagg gtggtttgaa gggctgttta acaagtcccc ttggttcacc   1800

accctgatat ccaccatcat gggtcccctg ataatcctct tgttaatttt actctttggg   1860

ccttgtattc tcaatcacct ggtccagttt atcaaagaca gggtttcggt agtgcaggcc   1920

ctggtcctga ctcaacaata tcatcaactt aagacaatag aagattgtga atcacgtgaa   1980

taa                                                                 1983
```

```
<210> SEQ ID NO 102
<211> LENGTH: 660
<212> TYPE: PRT
<213> ORGANISM: Artificial
<220> FEATURE:
<223> OTHER INFORMATION: SL3-2/apelin chimeric envelope sequence

<400> SEQUENCE: 102

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Ser Gly Gly Ser Gly Gln Arg Pro Arg Leu
                85                  90                  95

Ser His Lys Gly Pro Met Pro Phe Ser Gly Gly Ser Gly Gly Leu Gly
            100                 105                 110

Cys Arg Thr Pro Gly Gly Arg Lys Arg Ala Arg Ile Phe Asp Phe Tyr
        115                 120                 125

Val Cys Pro Gly His Thr Val Leu Ala Gly Cys Gly Gly Pro Arg Glu
    130                 135                 140
```

```
Gly Tyr Cys Gly Lys Trp Gly Cys Glu Thr Thr Gly Gln Ala Tyr Trp
145                 150                 155                 160

Lys Pro Ser Ser Ser Trp Asp Leu Ile Ser Leu Lys Arg Gly Asn Thr
                165                 170                 175

Pro Lys Gly Gln Gly Pro Cys Tyr Asp Ser Ser Val Val Ser Ser Ser
            180                 185                 190

Ala Gln Gly Ala Thr Pro Gly Gly Arg Cys Asn Pro Leu Val Leu Glu
        195                 200                 205

Phe Thr Asp Ala Gly Lys Arg Ala Ser Trp Asp Ala Ser Lys Ala Trp
    210                 215                 220

Gly Leu Arg Leu Tyr Arg Ser Thr Gly Ile Asp Pro Val Thr Arg Phe
225                 230                 235                 240

Ser Leu Thr Arg Gln Val Leu Asn Ile Gly Pro Arg Val Pro Ile Gly
                245                 250                 255

Pro Asn Pro Val Ile Ile Asp Gln Leu Pro Pro Ser Arg Pro Val Gln
            260                 265                 270

Val Met Leu Pro Arg Pro Pro Gln Pro Pro Pro Pro Gly Ala Ala Ser
        275                 280                 285

Thr Val Pro Glu Thr Ala Pro Pro Ser Gln Gln Pro Gly Thr Gly Asp
    290                 295                 300

Arg Leu Leu Asn Leu Val Asn Gly Ala Tyr Gln Ala Leu Asn Leu Thr
305                 310                 315                 320

Ser Pro Asp Lys Thr Gln Glu Cys Trp Leu Cys Leu Val Ala Gly Pro
                325                 330                 335

Pro Tyr Tyr Glu Gly Val Ala Val Leu Gly Thr Tyr Ser Asn His Thr
            340                 345                 350

Ser Ala Pro Ala Asn Cys Ser Val Ala Ser Gln His Lys Leu Thr Leu
        355                 360                 365

Ser Glu Val Thr Gly Gln Gly Leu Cys Val Gly Ala Val Pro Lys Thr
    370                 375                 380

His Gln Ala Leu Cys Asn Thr Thr Gln Lys Thr Ser Asn Gly Ser Tyr
385                 390                 395                 400

Tyr Leu Ala Ala Pro Ala Gly Thr Ile Trp Ala Cys Asn Thr Gly Leu
                405                 410                 415

Thr Pro Cys Leu Ser Thr Thr Val Leu Asp Leu Thr Thr Asp Tyr Cys
            420                 425                 430

Val Leu Val Glu Leu Trp Pro Lys Val Thr Tyr His Ser Pro Gly Tyr
        435                 440                 445

Val Tyr Gly Gln Phe Glu Glu Lys Thr Lys Tyr Lys Arg Glu Pro Val
    450                 455                 460

Ser Leu Thr Leu Ala Leu Leu Leu Gly Gly Leu Thr Met Gly Gly Ile
465                 470                 475                 480

Ala Ala Gly Val Gly Thr Gly Thr Thr Ala Leu Val Ala Thr Gln Gln
                485                 490                 495

Phe Gln Gln Leu Gln Ala Ala Met Gln Asp Asp Leu Lys Glu Val Glu
            500                 505                 510

Lys Ser Ile Thr Asn Leu Glu Arg Ser Leu Thr Ser Leu Ser Glu Val
        515                 520                 525

Val Leu Gln Asn Arg Arg Gly Leu Asp Leu Leu Phe Leu Lys Glu Gly
    530                 535                 540

Gly Leu Cys Ala Ala Leu Lys Glu Glu Cys Cys Phe Tyr Ala Asp His
545                 550                 555                 560

Thr Gly Leu Val Arg Asp Ser Met Ala Lys Leu Arg Glu Arg Leu Ser
```

-continued

```
                565                 570                 575

Gln Arg Gln Lys Leu Phe Glu Ser Gln Gln Gly Trp Phe Glu Gly Leu
            580                 585                 590

Phe Asn Lys Ser Pro Trp Phe Thr Thr Leu Ile Ser Thr Ile Met Gly
        595                 600                 605

Pro Leu Ile Ile Leu Leu Leu Ile Leu Leu Phe Gly Pro Cys Ile Leu
    610                 615                 620

Asn His Leu Val Gln Phe Ile Lys Asp Arg Val Ser Val Val Gln Ala
625                 630                 635                 640

Leu Val Leu Thr Gln Gln Tyr His Gln Leu Lys Thr Ile Glu Asp Cys
                645                 650                 655

Glu Ser Arg Glu
            660
```

<210> SEQ ID NO 103
<211> LENGTH: 1998
<212> TYPE: DNA
<213> ORGANISM: artificial
<220> FEATURE:
<223> OTHER INFORMATION: SL3-2/apelin chimeric envelope sequence

<400> SEQUENCE: 103

```
atggaaggtc cagcgttctc aaaacccctt aaagataaga ttaacccgtg ggcccccta      60

atagtcctgg gaatcttaat gagggcaaga gtatcagtac aacatgacag ccctcatcag    120

gtcttcaatg ttacttggag agttaccaac ttaatgacag gacaaacagc taatgctacc    180

tccctcctgg ggacaatgac cgatgccttt cctaaactgt actttgactt gtgcgattta    240

ataggggacg actgggatga gactggactc gggtgtcgca ctcccggggg aagaaaaagg    300

gcaagaatat ttgacttcta tgtttgcccc ggtcacactg tgctagcagg gtgtggaggg    360

ccgagagagg gctactgtgg caaatgggga tgtgagacca ctggacaggc atactggaag    420

ccatcatcat catgggacct aatttccctt aagcgaggaa acactcaagg aatctaccag    480

tgctccggtg gcagtggaca gcggccccgc ctctcccata agggacccat gcctttcagc    540

ggtggatctg gctgtgggcc ctgttatgat tcctcggtgg tctccagtag cgcccagggt    600

gccacaccgg ggggtcgatg caacccccta gtcctagaat tcactgacgc gggtaaaagg    660

gccagctggg acgcctccaa agcatgggga ctaagactgt accgatccac aaggaccgac    720

ccggtgaccc ggttctcttt gacccgccag gtcctcaata tagggccccg cgtccccatt    780

gggcctaatc ccgtgatcat tgaccagtta cccccctccc gacccgtgca ggtcatgctc    840

cccaggcctc ctcagcctcc tccaccaggc gcagcctcta cagtccctga gactgcccca    900

ccttcccaac aacctgggac gggagacagg ctgctaaacc tggtaaatgg agcctaccaa    960

gctctcaacc tcaccagtcc tgacaaaacc caagagtgct ggttgtgtct ggtagcggga   1020

ccccccctact acgaaggggt tgccgtccta ggtacttatt ccaaccatac ctctgcccca   1080

gctaactgct ccgtggcctc ccaacacaag ctgaccctgt ccgaagtgac cggacaggga   1140

ctctgcgtag gagcagttcc caaaacccat caggccctgt gtaataccac ccagaagacg   1200

agcaacgggt cctactatct ggctgctccc gccgggacca tttgggcttg caacaccggg   1260

ctcactccct gcctatctac cactgtgctc gacctcacca ccgattactg tgtcctggtt   1320

gagctctggc caaaagtgac ctaccactcc cctggttatg tttatggcca gtttgaagaa   1380

aaaaccaaat ataaaagaga acccgtctca ctaactctgg ccctactatt aggaggactc   1440

actatgggcg gaattgccgc cggagtggga acagggacta ccgccctagt ggccactcag   1500
```

```
cagttccaac aactccaggc tgccatgcag gatgacctta aagaagttga aaagtccatc   1560

actaatctag aaagatcttt gacctccttg tccgaagtag tgttacagaa tcgtagaggc   1620

ctagatctac tattcctaaa agagggaggt ttgtgtgctg ccttaaaaga agaatgctgt   1680

ttctatgccg accacacagg attggtacgg gatagcatgg ccaaacttag agaaagattg   1740

agtcagagac aaaaactctt tgaatcccaa caagggtggt ttgaagggct gtttaacaag   1800

tccccttggt tcaccaccct gatatccacc atcatgggtc ccctgataat cctcttgtta   1860

attttactct ttgggccttg tattctcaat cacctggtcc agtttatcaa agacagggtt   1920

tcggtagtgc aggccctggt cctgactcaa caatatcatc aacttaagac aatagaagat   1980

tgtgaatcac gtgaataa                                                 1998
```

<210> SEQ ID NO 104
<211> LENGTH: 665
<212> TYPE: PRT
<213> ORGANISM: Artificial
<220> FEATURE:
<223> OTHER INFORMATION: SL3-2/apelin chimeric envelope sequence

<400> SEQUENCE: 104

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Ser Gly Gly Ser Gly Gln Arg Pro Arg Leu Ser His Lys Gly Pro
                165                 170                 175

Met Pro Phe Ser Gly Gly Ser Gly Cys Gly Pro Cys Tyr Asp Ser Ser
            180                 185                 190

Val Val Ser Ser Ser Ala Gln Gly Ala Thr Pro Gly Gly Arg Cys Asn
        195                 200                 205

Pro Leu Val Leu Glu Phe Thr Asp Ala Gly Lys Arg Ala Ser Trp Asp
    210                 215                 220

Ala Ser Lys Ala Trp Gly Leu Arg Leu Tyr Arg Ser Thr Arg Thr Asp
225                 230                 235                 240

Pro Val Thr Arg Phe Ser Leu Thr Arg Gln Val Leu Asn Ile Gly Pro
                245                 250                 255

Arg Val Pro Ile Gly Pro Asn Pro Val Ile Ile Asp Gln Leu Pro Pro
            260                 265                 270

Ser Arg Pro Val Gln Val Met Leu Pro Arg Pro Pro Gln Pro Pro Pro
```

-continued

```
        275                 280                 285

Pro Gly Ala Ala Ser Thr Val Pro Glu Thr Ala Pro Pro Ser Gln Gln
    290                 295                 300

Pro Gly Thr Gly Asp Arg Leu Leu Asn Leu Val Asn Gly Ala Tyr Gln
305                 310                 315                 320

Ala Leu Asn Leu Thr Ser Pro Asp Lys Thr Gln Glu Cys Trp Leu Cys
                325                 330                 335

Leu Val Ala Gly Pro Pro Tyr Tyr Glu Gly Val Ala Val Leu Gly Thr
            340                 345                 350

Tyr Ser Asn His Thr Ser Ala Pro Ala Asn Cys Ser Val Ala Ser Gln
        355                 360                 365

His Lys Leu Thr Leu Ser Glu Val Thr Gly Gln Gly Leu Cys Val Gly
    370                 375                 380

Ala Val Pro Lys Thr His Gln Ala Leu Cys Asn Thr Thr Gln Lys Thr
385                 390                 395                 400

Ser Asn Gly Ser Tyr Tyr Leu Ala Ala Pro Ala Gly Thr Ile Trp Ala
                405                 410                 415

Cys Asn Thr Gly Leu Thr Pro Cys Leu Ser Thr Thr Val Leu Asp Leu
            420                 425                 430

Thr Thr Asp Tyr Cys Val Leu Val Glu Leu Trp Pro Lys Val Thr Tyr
        435                 440                 445

His Ser Pro Gly Tyr Val Tyr Gly Gln Phe Glu Glu Lys Thr Lys Tyr
    450                 455                 460

Lys Arg Glu Pro Val Ser Leu Thr Leu Ala Leu Leu Leu Gly Gly Leu
465                 470                 475                 480

Thr Met Gly Gly Ile Ala Ala Gly Val Gly Thr Gly Thr Thr Ala Leu
                485                 490                 495

Val Ala Thr Gln Gln Phe Gln Gln Leu Gln Ala Ala Met Gln Asp Asp
            500                 505                 510

Leu Lys Glu Val Glu Lys Ser Ile Thr Asn Leu Glu Arg Ser Leu Thr
        515                 520                 525

Ser Leu Ser Glu Val Val Leu Gln Asn Arg Arg Gly Leu Asp Leu Leu
    530                 535                 540

Phe Leu Lys Glu Gly Gly Leu Cys Ala Ala Leu Lys Glu Glu Cys Cys
545                 550                 555                 560

Phe Tyr Ala Asp His Thr Gly Leu Val Arg Asp Ser Met Ala Lys Leu
                565                 570                 575

Arg Glu Arg Leu Ser Gln Arg Gln Lys Leu Phe Glu Ser Gln Gln Gly
            580                 585                 590

Trp Phe Glu Gly Leu Phe Asn Lys Ser Pro Trp Phe Thr Thr Leu Ile
        595                 600                 605

Ser Thr Ile Met Gly Pro Leu Ile Ile Leu Leu Leu Ile Leu Leu Phe
    610                 615                 620

Gly Pro Cys Ile Leu Asn His Leu Val Gln Phe Ile Lys Asp Arg Val
625                 630                 635                 640

Ser Val Val Gln Ala Leu Val Leu Thr Gln Gln Tyr His Gln Leu Lys
                645                 650                 655

Thr Ile Glu Asp Cys Glu Ser Arg Glu
            660                 665
```

<210> SEQ ID NO 105
<211> LENGTH: 1998
<212> TYPE: DNA
<213> ORGANISM: artificial
<220> FEATURE:

-continued

<223> OTHER INFORMATION: SL3-2/apelin chimeric envelope sequence

<400> SEQUENCE: 105

```
atggaaggtc cagcgttctc aaaacccctt aaagataaga ttaacccgtg ggcccccta     60
atagtcctgg gaatcttaat gagggcaaga gtatcagtac aacatgacag ccctcatcag    120
gtcttcaatg ttacttggag agttaccaac ttaatgacag gacaaacagc taatgctacc    180
tccctcctgg ggacaatgac cgatgccttt cctaaactgt actttgactt gtgcgattta    240
ataggggacg actgggatga gactggactc gggtgtcgca ctcccggggg aagaaaaagg    300
gcaagaatat ttgacttcta tgtttgcccc ggtcacactg tgctagcagg gtgtggaggg    360
ccgagagagg gctactgtgg caaatgggga tgtgagacca ctggacaggc atactggaag    420
ccatcatcat catgggacct aatttccctt aagcgaggaa acactcaagg aatctaccag    480
tgctccggtg gcagtggaca gcggccccgc ctctcccata agggacccat gcctttcagc    540
ggtggatctg gctgtgggcc ctgttatgat tcctcggtgg tctccagtag cgcccagggt    600
gccacaccgg ggggtcgatg caacccccta gtcctagaat tcactgacgc gggtaaaagg    660
gccagctggg acgcctccaa agcatgggga ctaagactgt accgatccac agggatcgac    720
ccggtgaccc ggttctcttt gacccgccag gtcctcaata tagggccccg cgtccccatt    780
gggcctaatc ccgtgatcat tgaccagtta cccccctccc gacccgtgca ggtcatgctc    840
cccaggcctc ctcagcctcc tccaccaggc gcagcctcta cagtccctga gactgcccca    900
ccttcccaac aacctgggac gggagacagg ctgctaaacc tggtaaatgg agcctaccaa    960
gctctcaacc tcaccagtcc tgacaaaacc caagagtgct ggttgtgtct ggtagcggga   1020
ccccctact acgaaggggt tgccgtccta ggtacttatt ccaaccatac ctctgcccca   1080
gctaactgct ccgtggcctc ccaacacaag ctgaccctgt ccgaagtgac cggacaggga   1140
ctctgcgtag gagcagttcc caaaacccat caggccctgt gtaataccac ccagaagacg   1200
agcaacgggt cctactatct ggctgctccc gccgggacca tttgggcttg caacaccggg   1260
ctcactccct gcctatctac cactgtgctc gacctcacca ccgattactg tgtcctggtt   1320
gagctctggc caaaagtgac ctaccactcc cctggttatg tttatggcca gtttgaagaa   1380
aaaaccaaat ataaaagaga acccgtctca ctaactctgg ccctactatt aggaggactc   1440
actatgggcg gaattgccgc cggagtggga acagggacta ccgccctagt ggccactcag   1500
cagttccaac aactccaggc tgccatgcag gatgacctta aagaagttga aaagtccatc   1560
actaatctag aaagatcttt gacctccttg tccgaagtag tgttacagaa tcgtagaggc   1620
ctagatctac tattcctaaa agagggaggt ttgtgtgctg ccttaaaaga agaatgctgt   1680
ttctatgccg accacacagg attggtacgg gatagcatgg ccaaacttag agaaagattg   1740
agtcagagac aaaaactctt tgaatcccaa caagggtggt ttgaagggct gtttaacaag   1800
tccccttggt tcaccaccct gatatccacc atcatgggtc ccctgataat cctcttgtta   1860
attttactct ttgggccttg tattctcaat cacctggtcc agtttatcaa agacagggtt   1920
tcggtagtgc aggccctggt cctgactcaa caatatcatc aacttaagac aatagaagat   1980
tgtgaatcac gtgaataa                                                 1998
```

<210> SEQ ID NO 106
<211> LENGTH: 665
<212> TYPE: PRT
<213> ORGANISM: Artificial
<220> FEATURE:
<223> OTHER INFORMATION: SL3-2/apelin chimeric envelope sequence

<400> SEQUENCE: 106

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Gln Gly Ile Tyr Gln
145                 150                 155                 160

Cys Ser Gly Gly Ser Gly Gln Arg Pro Arg Leu Ser His Lys Gly Pro
                165                 170                 175

Met Pro Phe Ser Gly Gly Ser Gly Cys Gly Pro Cys Tyr Asp Ser Ser
            180                 185                 190

Val Val Ser Ser Ser Ala Gln Gly Ala Thr Pro Gly Gly Arg Cys Asn
        195                 200                 205

Pro Leu Val Leu Glu Phe Thr Asp Ala Gly Lys Arg Ala Ser Trp Asp
    210                 215                 220

Ala Ser Lys Ala Trp Gly Leu Arg Leu Tyr Arg Ser Thr Gly Ile Asp
225                 230                 235                 240

Pro Val Thr Arg Phe Ser Leu Thr Arg Gln Val Leu Asn Ile Gly Pro
                245                 250                 255

Arg Val Pro Ile Gly Pro Asn Pro Val Ile Ile Asp Gln Leu Pro Pro
            260                 265                 270

Ser Arg Pro Val Gln Val Met Leu Pro Arg Pro Pro Gln Pro Pro Pro
        275                 280                 285

Pro Gly Ala Ala Ser Thr Val Pro Glu Thr Ala Pro Pro Ser Gln Gln
    290                 295                 300

Pro Gly Thr Gly Asp Arg Leu Leu Asn Leu Val Asn Gly Ala Tyr Gln
305                 310                 315                 320

Ala Leu Asn Leu Thr Ser Pro Asp Lys Thr Gln Glu Cys Trp Leu Cys
                325                 330                 335

Leu Val Ala Gly Pro Pro Tyr Tyr Glu Gly Val Ala Val Leu Gly Thr
            340                 345                 350

Tyr Ser Asn His Thr Ser Ala Pro Ala Asn Cys Ser Val Ala Ser Gln
        355                 360                 365

His Lys Leu Thr Leu Ser Glu Val Thr Gly Gln Gly Leu Cys Val Gly
    370                 375                 380

Ala Val Pro Lys Thr His Gln Ala Leu Cys Asn Thr Thr Gln Lys Thr
385                 390                 395                 400

Ser Asn Gly Ser Tyr Tyr Leu Ala Ala Pro Ala Gly Thr Ile Trp Ala
                405                 410                 415
```

-continued

```
Cys Asn Thr Gly Leu Thr Pro Cys Leu Ser Thr Thr Val Leu Asp Leu
            420                 425                 430

Thr Thr Asp Tyr Cys Val Leu Val Glu Leu Trp Pro Lys Val Thr Tyr
        435                 440                 445

His Ser Pro Gly Tyr Val Tyr Gly Gln Phe Glu Glu Lys Thr Lys Tyr
    450                 455                 460

Lys Arg Glu Pro Val Ser Leu Thr Leu Ala Leu Leu Leu Gly Gly Leu
465                 470                 475                 480

Thr Met Gly Gly Ile Ala Ala Gly Val Gly Thr Gly Thr Thr Ala Leu
                485                 490                 495

Val Ala Thr Gln Gln Phe Gln Gln Leu Gln Ala Ala Met Gln Asp Asp
            500                 505                 510

Leu Lys Glu Val Glu Lys Ser Ile Thr Asn Leu Glu Arg Ser Leu Thr
        515                 520                 525

Ser Leu Ser Glu Val Val Leu Gln Asn Arg Arg Gly Leu Asp Leu Leu
    530                 535                 540

Phe Leu Lys Glu Gly Gly Leu Cys Ala Ala Leu Lys Glu Glu Cys Cys
545                 550                 555                 560

Phe Tyr Ala Asp His Thr Gly Leu Val Arg Asp Ser Met Ala Lys Leu
                565                 570                 575

Arg Glu Arg Leu Ser Gln Arg Gln Lys Leu Phe Glu Ser Gln Gln Gly
            580                 585                 590

Trp Phe Glu Gly Leu Phe Asn Lys Ser Pro Trp Phe Thr Thr Leu Ile
        595                 600                 605

Ser Thr Ile Met Gly Pro Leu Ile Ile Leu Leu Leu Ile Leu Leu Phe
    610                 615                 620

Gly Pro Cys Ile Leu Asn His Leu Val Gln Phe Ile Lys Asp Arg Val
625                 630                 635                 640

Ser Val Val Gln Ala Leu Val Leu Thr Gln Gln Tyr His Gln Leu Lys
                645                 650                 655

Thr Ile Glu Asp Cys Glu Ser Arg Glu
            660                 665
```

<210> SEQ ID NO 107
<211> LENGTH: 1980
<212> TYPE: DNA
<213> ORGANISM: artificial
<220> FEATURE:
<223> OTHER INFORMATION: SL3-2/apelin chimeric envelope sequence

<400> SEQUENCE: 107

```
atggaaggtc cagcgttctc aaaacccctt aaagataaga ttaacccgtg ggccccccta      60

atagtcctgg gaatcttaat gagggcaaga gtatcagtac aacatgacag ccctcatcag     120

gtcttcaatg ttacttggag agttaccaac ttaatgacag gacaaacagc taatgctacc     180

tccctcctgg ggacaatgac cgatgccttt cctaaactgt actttgactt gtgcgattta     240

ataggggacg actgggatga gactggactc gggtgtcgca ctcccggggg aagaaaaagg     300

gcaagaatat ttgacttcta tgtttgcccc ggtcacactg tgctagcagg gtgtggaggg     360

ccgagagagg gctactgtgg caaatgggga tgtgagacca ctggacaggc atactggaag     420

ccatcatcat catgggacct aatttccctt aagcgaggaa acactcctaa aggccagggc     480

ccctgttatg attcctccgg tggcagtgga cagcggcccc gcctctccca taagggaccc     540

atgcctttca gcggtggatc tggctccagt agcgcccagg gtgccacacc ggggggtcga     600

tgcaaccccc tagtcctaga attcactgac gcgggtaaaa gggccagctg ggacgcctcc     660
```

-continued

```
aaagcatggg gactaagact gtaccgatcc acaaggaccg acccggtgac ccggttctct    720
ttgacccgcc aggtcctcaa tatagggccc cgcgtcccca ttgggcctaa tcccgtgatc    780
attgaccagt tacccccctc ccgacccgtg caggtcatgc tccccaggcc tcctcagcct    840
cctccaccag gcgcagcctc tacagtccct gagactgccc caccttccca acaacctggg    900
acgggagaca ggctgctaaa cctggtaaat ggagcctacc aagctctcaa cctcaccagt    960
cctgacaaaa cccaagagtg ctggttgtgt ctggtagcgg gaccccccta ctacgaaggg   1020
gttgccgtcc taggtactta ttccaaccat acctctgccc cagctaactg ctccgtggcc   1080
tcccaacaca agctgaccct gtccgaagtg accggacagg gactctgcgt aggagcagtt   1140
cccaaaaccc atcaggccct gtgtaatacc acccagaaga cgagcaacgg gtcctactat   1200
ctggctgctc ccgccgggac catttgggct tgcaacaccg ggctcactcc ctgcctatct   1260
accactgtgc tcgacctcac caccgattac tgtgtcctgg ttgagctctg gccaaaagtg   1320
acctaccact cccctggtta tgtttatggc cagtttgaag aaaaaaccaa atataaaaga   1380
gaacccgtct cactaactct ggccctacta ttaggaggac tcactatggg cggaattgcc   1440
gccggagtgg gaacagggac taccgcccta gtggccactc agcagttcca acaactccag   1500
gctgccatgc aggatgacct taaagaagtt gaaaagtcca tcactaatct agaaagatct   1560
ttgacctcct tgtccgaagt agtgttacag aatcgtagag gcctagatct actattccta   1620
aaagagggag gtttgtgtgc tgccttaaaa gaagaatgct gtttctatgc cgaccacaca   1680
ggattggtac gggatagcat ggccaaactt agagaaagat tgagtcagag acaaaaactc   1740
tttgaatccc aacaagggtg gtttgaaggg ctgtttaaca agtccccttg gttcaccacc   1800
ctgatatcca ccatcatggg tcccctgata atcctcttgt taattttact ctttgggcct   1860
tgtattctca atcacctggt ccagtttatc aaagacaggg tttcggtagt gcaggccctg   1920
gtcctgactc aacaatatca tcaacttaag acaatagaag attgtgaatc acgtgaataa   1980
```

<210> SEQ ID NO 108
<211> LENGTH: 1980
<212> TYPE: DNA
<213> ORGANISM: artificial
<220> FEATURE:
<223> OTHER INFORMATION: SL3-2/apelin chimeric envelope sequence

<400> SEQUENCE: 108

```
atggaaggtc cagcgttctc aaaacccctt aaagataaga ttaacccgtg gggcccccta     60
atagtcctgg gaatcttaat gagggcaaga gtatcagtac aacatgacag ccctcatcag    120
gtcttcaatg ttacttggag agttaccaac ttaatgacag gacaaacagc taatgctacc    180
tccctcctgg ggacaatgac cgatgccttt cctaaactgt actttgactt gtgcgattta    240
ataggggacg actgggatga gactggactc gggtgtcgca ctcccggggg aagaaaaagg    300
gcaagaatat ttgacttcta tgtttgcccc ggtcacactg tgctagcagg gtgtggaggg    360
ccgagagagg gctactgtgg caaatgggga tgtgagacca ctggacaggc atactggaag    420
ccatcatcat catgggacct aatttccctt aagcgaggaa acactcctaa aggccagggc    480
ccctgttatg attcctccgg tggcagtgga cagcggcccc gcctctccca taagggaccc    540
atgcctttca gcggtggatc tggctccagt agcgcccagg gtgccacacc ggggggtcga    600
tgcaaccccc tagtcctaga attcactgac gcgggtaaaa gggccagctg ggacgcctcc    660
aaagcatggg gactaagact gtaccgatcc acagggatcg acccggtgac ccggttctct    720
ttgacccgcc aggtcctcaa tatagggccc cgcgtcccca ttgggcctaa tcccgtgatc    780
```

```
attgaccagt taccccccctc ccgacccgtg caggtcatgc tccccaggcc tcctcagcct    840

cctccaccag gcgcagcctc tacagtccct gagactgccc caccttccca acaacctggg    900

acgggagaca ggctgctaaa cctggtaaat ggagcctacc aagctctcaa cctcaccagt    960

cctgacaaaa cccaagagtg ctggttgtgt ctggtagcgg gacccccccta ctacgaaggg   1020

gttgccgtcc taggtactta ttccaaccat acctctgccc cagctaactg ctccgtggcc   1080

tcccaacaca agctgaccct gtccgaagtg accggacagg gactctgcgt aggagcagtt   1140

cccaaaaccc atcaggccct gtgtaatacc acccagaaga cgagcaacgg gtcctactat   1200

ctggctgctc ccgccgggac catttgggct tgcaacaccg ggctcactcc ctgcctatct   1260

accactgtgc tcgacctcac caccgattac tgtgtcctgg ttgagctctg gccaaaagtg   1320

acctaccact cccctggtta tgtttatggc cagtttgaag aaaaaaccaa atataaaaga   1380

gaacccgtct cactaactct ggccctacta ttaggaggac tcactatggg cggaattgcc   1440

gccggagtgg gaacagggac taccgcccta gtggccactc agcagttcca acaactccag   1500

gctgccatgc aggatgacct taaagaagtt gaaaagtcca tcactaatct agaaaagatct   1560

ttgacctcct tgtccgaagt agtgttacag aatcgtagag gcctagatct actattccta   1620

aaagagggag gtttgtgtgc tgccttaaaa gaagaatgct gtttctatgc cgaccacaca   1680

ggattggtac gggatagcat ggccaaactt agagaaagat tgagtcagag acaaaaactc   1740

tttgaatccc aacaagggtg gtttgaaggg ctgtttaaca agtccccttg gttcaccacc   1800

ctgatatcca ccatcatggg tcccctgata atcctcttgt taattttact ctttgggcct   1860

tgtattctca atcacctggt ccagtttatc aaagacaggg tttcggtagt gcaggccctg   1920

gtcctgactc aacaatatca tcaacttaag acaatagaag attgtgaatc acgtgaataa   1980
```

<210> SEQ ID NO 109
<211> LENGTH: 659
<212> TYPE: PRT
<213> ORGANISM: Artificial
<220> FEATURE:
<223> OTHER INFORMATION: SL3-2/apelin chimeric envelope sequence

<400> SEQUENCE: 109

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160
```

```
Pro Cys Tyr Asp Ser Ser Gly Gly Ser Gly Gln Arg Pro Arg Leu Ser
                165                 170                 175

His Lys Gly Pro Met Pro Phe Ser Gly Gly Ser Gly Ser Ser Ser Ala
            180                 185                 190

Gln Gly Ala Thr Pro Gly Gly Arg Cys Asn Pro Leu Val Leu Glu Phe
        195                 200                 205

Thr Asp Ala Gly Lys Arg Ala Ser Trp Asp Ala Ser Lys Ala Trp Gly
    210                 215                 220

Leu Arg Leu Tyr Arg Ser Thr Gly Ile Asp Pro Val Thr Arg Phe Ser
225                 230                 235                 240

Leu Thr Arg Gln Val Leu Asn Ile Gly Pro Arg Val Pro Ile Gly Pro
                245                 250                 255

Asn Pro Val Ile Ile Asp Gln Leu Pro Pro Ser Arg Pro Val Gln Val
            260                 265                 270

Met Leu Pro Arg Pro Pro Gln Pro Pro Pro Pro Gly Ala Ala Ser Thr
        275                 280                 285

Val Pro Glu Thr Ala Pro Pro Ser Gln Gln Pro Gly Thr Gly Asp Arg
    290                 295                 300

Leu Leu Asn Leu Val Asn Gly Ala Tyr Gln Ala Leu Asn Leu Thr Ser
305                 310                 315                 320

Pro Asp Lys Thr Gln Glu Cys Trp Leu Cys Leu Val Ala Gly Pro Pro
                325                 330                 335

Tyr Tyr Glu Gly Val Ala Val Leu Gly Thr Tyr Ser Asn His Thr Ser
            340                 345                 350

Ala Pro Ala Asn Cys Ser Val Ala Ser Gln His Lys Leu Thr Leu Ser
        355                 360                 365

Glu Val Thr Gly Gln Gly Leu Cys Val Gly Ala Val Pro Lys Thr His
    370                 375                 380

Gln Ala Leu Cys Asn Thr Thr Gln Lys Thr Ser Asn Gly Ser Tyr Tyr
385                 390                 395                 400

Leu Ala Ala Pro Ala Gly Thr Ile Trp Ala Cys Asn Thr Gly Leu Thr
                405                 410                 415

Pro Cys Leu Ser Thr Thr Val Leu Asp Leu Thr Thr Asp Tyr Cys Val
            420                 425                 430

Leu Val Glu Leu Trp Pro Lys Val Thr Tyr His Ser Pro Gly Tyr Val
        435                 440                 445

Tyr Gly Gln Phe Glu Glu Lys Thr Lys Tyr Lys Arg Glu Pro Val Ser
    450                 455                 460

Leu Thr Leu Ala Leu Leu Leu Gly Gly Leu Thr Met Gly Gly Ile Ala
465                 470                 475                 480

Ala Gly Val Gly Thr Gly Thr Thr Ala Leu Val Ala Thr Gln Gln Phe
                485                 490                 495

Gln Gln Leu Gln Ala Ala Met Gln Asp Asp Leu Lys Glu Val Glu Lys
            500                 505                 510

Ser Ile Thr Asn Leu Glu Arg Ser Leu Thr Ser Leu Ser Glu Val Val
        515                 520                 525

Leu Gln Asn Arg Arg Gly Leu Asp Leu Leu Phe Leu Lys Glu Gly Gly
    530                 535                 540

Leu Cys Ala Ala Leu Lys Glu Glu Cys Cys Phe Tyr Ala Asp His Thr
545                 550                 555                 560

Gly Leu Val Arg Asp Ser Met Ala Lys Leu Arg Glu Arg Leu Ser Gln
                565                 570                 575

Arg Gln Lys Leu Phe Glu Ser Gln Gln Gly Trp Phe Glu Gly Leu Phe
            580                 585                 590
```

Asn Lys Ser Pro Trp Phe Thr Thr Leu Ile Ser Thr Ile Met Gly Pro
595 600 605

Leu Ile Ile Leu Leu Leu Ile Leu Leu Phe Gly Pro Cys Ile Leu Asn
610 615 620

His Leu Val Gln Phe Ile Lys Asp Arg Val Ser Val Val Gln Ala Leu
625 630 635 640

Val Leu Thr Gln Gln Tyr His Gln Leu Lys Thr Ile Glu Asp Cys Glu
645 650 655

Ser Arg Glu

<210> SEQ ID NO 110
<211> LENGTH: 657
<212> TYPE: PRT
<213> ORGANISM: Artificial
<220> FEATURE:
<223> OTHER INFORMATION: SL3-2/apelin chimeric envelope sequence

<400> SEQUENCE: 110

Met Glu Gly Pro Ala Phe Ser Lys Pro Leu Lys Asp Lys Ile Asn Pro
1 5 10 15

Trp Gly Pro Leu Ile Val Leu Gly Ile Leu Met Arg Ala Arg Val Ser
20 25 30

Val Gln His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

Thr Met Thr Asp Ala Phe Pro Lys Leu Tyr Phe Asp Leu Cys Asp Leu
65 70 75 80

Ile Gly Asp Asp Trp Asp Glu Thr Gly Leu Gly Cys Arg Thr Pro Gly
85 90 95

Gly Arg Lys Arg Ala Arg Ile Phe Asp Phe Tyr Val Cys Pro Gly His
100 105 110

Thr Val Leu Ala Gly Cys Gly Gly Pro Arg Glu Gly Tyr Cys Gly Lys
115 120 125

Trp Gly Cys Glu Thr Thr Gly Gln Ala Tyr Trp Lys Pro Ser Ser Ser
130 135 140

Trp Asp Leu Ile Ser Leu Lys Arg Gly Asn Thr Pro Lys Gly Gln Gly
145 150 155 160

Pro Cys Tyr Asp Ser Ser Gly Gly Ser Gly Arg Pro Lys Pro Glu Glu
165 170 175

Phe Phe Gly Leu Met Ser Gly Gly Ser Gly Ser Ser Ser Ala Gln Gly
180 185 190

Ala Thr Pro Gly Gly Arg Cys Asn Pro Leu Val Leu Glu Phe Thr Asp
195 200 205

Ala Gly Lys Arg Ala Ser Trp Asp Ala Ser Lys Ala Trp Gly Leu Arg
210 215 220

Leu Tyr Arg Ser Thr Gly Ile Asp Pro Val Thr Arg Phe Ser Leu Thr
225 230 235 240

Arg Gln Val Leu Asn Ile Gly Pro Arg Val Pro Ile Gly Pro Asn Pro
245 250 255

Val Ile Ile Asp Gln Leu Pro Pro Ser Arg Pro Val Gln Val Met Leu
260 265 270

Pro Arg Pro Pro Gln Pro Pro Pro Pro Gly Ala Ala Ser Thr Val Pro
275 280 285

Glu Thr Ala Pro Pro Ser Gln Gln Pro Gly Thr Gly Asp Arg Leu Leu

```
    290                 295                 300

Asn Leu Val Asn Gly Ala Tyr Gln Ala Leu Asn Leu Thr Ser Pro Asp
305                 310                 315                 320

Lys Thr Gln Glu Cys Trp Leu Cys Leu Val Ala Gly Pro Pro Tyr Tyr
                325                 330                 335

Glu Gly Val Ala Val Leu Gly Thr Tyr Ser Asn His Thr Ser Ala Pro
            340                 345                 350

Ala Asn Cys Ser Val Ala Ser Gln His Lys Leu Thr Leu Ser Glu Val
        355                 360                 365

Thr Gly Gln Gly Leu Cys Val Gly Ala Val Pro Lys Thr His Gln Ala
    370                 375                 380

Leu Cys Asn Thr Thr Gln Lys Thr Ser Asn Gly Ser Tyr Tyr Leu Ala
385                 390                 395                 400

Ala Pro Ala Gly Thr Ile Trp Ala Cys Asn Thr Gly Leu Thr Pro Cys
                405                 410                 415

Leu Ser Thr Thr Val Leu Asp Leu Thr Thr Asp Tyr Cys Val Leu Val
            420                 425                 430

Glu Leu Trp Pro Lys Val Thr Tyr His Ser Pro Gly Tyr Val Tyr Gly
        435                 440                 445

Gln Phe Glu Glu Lys Thr Lys Tyr Lys Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Val Gly Thr Gly Thr Thr Ala Leu Val Ala Thr Gln Gln Phe Gln Gln
                485                 490                 495

Leu Gln Ala Ala Met Gln Asp Asp Leu Lys Glu Val Glu Lys Ser Ile
            500                 505                 510

Thr Asn Leu Glu Arg Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Ser Gln Arg Gln
                565                 570                 575

Lys Leu Phe Glu Ser Gln Gln Gly Trp Phe Glu Gly Leu Phe Asn Lys
            580                 585                 590

Ser Pro Trp Phe Thr Thr Leu Ile Ser Thr Ile Met Gly Pro Leu Ile
        595                 600                 605

Ile Leu Leu Leu Ile Leu Leu Phe Gly Pro Cys Ile Leu Asn His Leu
    610                 615                 620

Val Gln Phe Ile Lys Asp Arg Val Ser Val Val Gln Ala Leu Val Leu
625                 630                 635                 640

Thr Gln Gln Tyr His Gln Leu Lys Thr Ile Glu Asp Cys Glu Ser Arg
                645                 650                 655

Glu
```

<210> SEQ ID NO 111
<211> LENGTH: 11
<212> TYPE: PRT
<213> ORGANISM: Artificial
<220> FEATURE:
<223> OTHER INFORMATION: Substance P

<400> SEQUENCE: 111

Arg Pro Lys Pro Glu Glu Phe Phe Gly Leu Met
1 5 10

<210> SEQ ID NO 112
<211> LENGTH: 650
<212> TYPE: PRT
<213> ORGANISM: Artificial
<220> FEATURE:
<223> OTHER INFORMATION: Modified SL3-2 envelope sequence

<400> SEQUENCE: 112

Met Glu Gly Pro Ala Phe Ser Lys Pro Leu Lys Asp Lys Ile Asn Pro
1 5 10 15

Trp Gly Pro Leu Ile Val Leu Gly Ile Leu Met Arg Ala Arg Val Ser
20 25 30

Val Gln His Asp Ser Pro His Gln Val Phe Asn Val Thr Trp Arg Val
35 40 45

Thr Asn Leu Met Thr Gly Gln Thr Ala Asn Ala Thr Ser Leu Leu Gly
50 55 60

Thr Met Thr Asp Ala Phe Pro Lys Leu Tyr Phe Asp Leu Cys Asp Leu
65 70 75 80

Ile Gly Asp Asp Trp Asp Glu Thr Gly Leu Gly Cys Arg Thr Pro Gly
85 90 95

Gly Arg Lys Arg Ala Arg Ile Phe Asp Phe Tyr Val Cys Pro Gly His
100 105 110

Thr Val Leu Ala Gly Cys Gly Gly Pro Arg Glu Gly Tyr Cys Gly Lys
115 120 125

Trp Gly Cys Glu Thr Thr Gly Gln Ala Tyr Trp Lys Pro Ser Ser Ser
130 135 140

Trp Asp Leu Ile Ser Leu Lys Arg Gly Asn Thr Pro Lys Gly Gln Gly
145 150 155 160

Pro Cys Tyr Asp Ser Ser Gly Gly Ser Gly Gly Lys Tyr Leu Ser Gly
165 170 175

Gly Ser Gly Ser Ser Ser Ala Gln Gly Ala Thr Pro Gly Gly Arg Cys
180 185 190

Asn Pro Leu Val Leu Glu Phe Thr Asp Ala Gly Lys Arg Ala Ser Trp
195 200 205

Asp Ala Ser Lys Ala Trp Gly Leu Arg Leu Tyr Arg Ser Thr Arg Thr
210 215 220

Asp Pro Val Thr Arg Phe Ser Leu Thr Arg Gln Val Leu Asn Ile Gly
225 230 235 240

Pro Arg Val Pro Ile Gly Pro Asn Pro Val Ile Ile Asp Gln Leu Pro
245 250 255

Pro Ser Arg Pro Val Gln Ile Met Leu Pro Arg Pro Pro Gln Pro Pro
260 265 270

Pro Pro Gly Ala Ala Ser Thr Val Pro Glu Thr Ala Pro Pro Ser Gln
275 280 285

Gln Pro Gly Thr Gly Asp Arg Leu Leu Asn Leu Val Asn Gly Ala Tyr
290 295 300

Gln Ala Leu Asn Leu Thr Ser Pro Asp Lys Thr Gln Glu Cys Trp Leu
305 310 315 320

Cys Leu Val Ala Gly Pro Pro Tyr Tyr Glu Gly Val Ala Val Leu Gly
325 330 335

Thr Tyr Ser Asn His Thr Ser Ala Pro Ala Asn Cys Ser Val Ala Ser
340 345 350

Gln His Lys Leu Thr Leu Ser Glu Val Thr Gly Gln Gly Leu Cys Val

```
        355                 360                 365

Gly Ala Val Pro Lys Thr His Gln Ala Leu Cys Asn Thr Thr Gln Lys
    370                 375                 380

Thr Ser Asn Gly Ser Tyr Tyr Leu Ala Ala Pro Ala Gly Thr Ile Trp
385                 390                 395                 400

Ala Cys Asn Thr Gly Leu Thr Pro Cys Leu Ser Thr Thr Val Leu Asp
                405                 410                 415

Leu Thr Thr Asp Tyr Cys Val Leu Val Glu Leu Trp Pro Lys Val Thr
            420                 425                 430

Tyr His Ser Pro Gly Tyr Val Tyr Gly Gln Phe Glu Glu Lys Thr Lys
        435                 440                 445

Tyr Lys Arg Glu Pro Val Ser Leu Thr Leu Ala Leu Leu Leu Gly Gly
    450                 455                 460

Leu Thr Met Gly Gly Ile Ala Ala Gly Val Gly Thr Gly Thr Thr Ala
465                 470                 475                 480

Leu Val Ala Thr Gln Gln Phe Gln Gln Leu Gln Ala Ala Met Gln Asp
                485                 490                 495

Asp Leu Lys Glu Val Lys Lys Ser Ile Thr Asn Leu Glu Arg Ser Leu
            500                 505                 510

Thr Ser Leu Ser Glu Val Val Leu Gln Asn Arg Arg Gly Leu Asp Leu
        515                 520                 525

Leu Phe Leu Lys Glu Gly Gly Leu Cys Ala Ala Leu Lys Glu Glu Cys
    530                 535                 540

Cys Phe Tyr Ala Asp His Thr Gly Leu Val Arg Asp Ser Met Ala Lys
545                 550                 555                 560

Leu Arg Glu Arg Leu Ser Gln Arg Gln Lys Leu Phe Glu Ser Gln Gln
                565                 570                 575

Gly Trp Phe Glu Gly Leu Phe Asn Lys Ser Pro Trp Phe Thr Thr Leu
            580                 585                 590

Ile Ser Thr Ile Met Gly Pro Leu Ile Ile Leu Leu Leu Ile Leu Leu
        595                 600                 605

Phe Gly Pro Cys Ile Leu Asn His Leu Val Gln Phe Ile Lys Asp Arg
    610                 615                 620

Val Ser Val Val Gln Ala Leu Val Leu Thr Gln Gln Tyr His Gln Leu
625                 630                 635                 640

Lys Thr Ile Glu Asp Cys Glu Ser Arg Glu
                645                 650
```

<210> SEQ ID NO 113
<211> LENGTH: 650
<212> TYPE: PRT
<213> ORGANISM: Artificial
<220> FEATURE:
<223> OTHER INFORMATION: Modified SL3-2 envelope sequence

<400> SEQUENCE: 113

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80
```

```
Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Gly Gly Ser Gly Phe Trp Val Pro Ser Gly
                165                 170                 175

Gly Ser Gly Ser Ser Ser Ala Gln Gly Ala Thr Pro Gly Gly Arg Cys
            180                 185                 190

Asn Pro Leu Val Leu Glu Phe Thr Asp Ala Gly Lys Arg Ala Ser Trp
        195                 200                 205

Asp Ala Ser Lys Ala Trp Gly Leu Arg Leu Tyr Arg Ser Thr Arg Thr
    210                 215                 220

Asp Pro Val Thr Arg Phe Ser Leu Thr Arg Gln Val Leu Asn Ile Gly
225                 230                 235                 240

Pro Arg Val Pro Ile Gly Pro Asn Pro Val Ile Ile Asp Gln Leu Pro
                245                 250                 255

Pro Ser Arg Pro Val Gln Ile Met Leu Pro Arg Pro Pro Gln Pro Pro
            260                 265                 270

Pro Pro Gly Ala Ala Ser Thr Val Pro Glu Thr Ala Pro Pro Ser Gln
        275                 280                 285

Gln Pro Gly Thr Gly Asp Arg Leu Leu Asn Leu Val Asn Gly Ala Tyr
    290                 295                 300

Gln Ala Leu Asn Leu Thr Ser Pro Asp Lys Thr Gln Glu Cys Trp Leu
305                 310                 315                 320

Cys Leu Val Ala Gly Pro Pro Tyr Tyr Glu Gly Val Ala Val Leu Gly
                325                 330                 335

Thr Tyr Ser Asn His Thr Ser Ala Pro Ala Asn Cys Ser Val Ala Ser
            340                 345                 350

Gln His Lys Leu Thr Leu Ser Glu Val Thr Gly Gln Gly Leu Cys Val
        355                 360                 365

Gly Ala Val Pro Lys Thr His Gln Ala Leu Cys Asn Thr Thr Gln Lys
    370                 375                 380

Thr Ser Asn Gly Ser Tyr Tyr Leu Ala Ala Pro Ala Gly Thr Ile Trp
385                 390                 395                 400

Ala Cys Asn Thr Gly Leu Thr Pro Cys Leu Ser Thr Thr Val Leu Asp
                405                 410                 415

Leu Thr Thr Asp Tyr Cys Val Leu Val Glu Leu Trp Pro Lys Val Thr
            420                 425                 430

Tyr His Ser Pro Gly Tyr Val Tyr Gly Gln Phe Glu Glu Lys Thr Lys
        435                 440                 445

Tyr Lys Arg Glu Pro Val Ser Leu Thr Leu Ala Leu Leu Leu Gly Gly
    450                 455                 460

Leu Thr Met Gly Gly Ile Ala Ala Gly Val Gly Thr Gly Thr Thr Ala
465                 470                 475                 480

Leu Val Ala Thr Gln Gln Phe Gln Gln Leu Gln Ala Ala Met Gln Asp
                485                 490                 495

Asp Leu Lys Glu Val Lys Lys Ser Ile Thr Asn Leu Glu Arg Ser Leu
```

```
            500                 505                 510

Thr Ser Leu Ser Glu Val Val Leu Gln Asn Arg Arg Gly Leu Asp Leu
        515                 520                 525

Leu Phe Leu Lys Glu Gly Gly Leu Cys Ala Ala Leu Lys Glu Glu Cys
    530                 535                 540

Cys Phe Tyr Ala Asp His Thr Gly Leu Val Arg Asp Ser Met Ala Lys
545                 550                 555                 560

Leu Arg Glu Arg Leu Ser Gln Arg Gln Lys Leu Phe Glu Ser Gln Gln
                565                 570                 575

Gly Trp Phe Glu Gly Leu Phe Asn Lys Ser Pro Trp Phe Thr Thr Leu
            580                 585                 590

Ile Ser Thr Ile Met Gly Pro Leu Ile Ile Leu Leu Leu Ile Leu Leu
        595                 600                 605

Phe Gly Pro Cys Ile Leu Asn His Leu Val Gln Phe Ile Lys Asp Arg
    610                 615                 620

Val Ser Val Val Gln Ala Leu Val Leu Thr Gln Gln Tyr His Gln Leu
625                 630                 635                 640

Lys Thr Ile Glu Asp Cys Glu Ser Arg Glu
                645                 650


<210> SEQ ID NO 114
<211> LENGTH: 652
<212> TYPE: PRT
<213> ORGANISM: Artificial
<220> FEATURE:
<223> OTHER INFORMATION: Modified SL3-2 envelope sequence

<400> SEQUENCE: 114

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Gly Gly Ser Gly Arg Arg Arg Trp Arg Phe
                165                 170                 175

Ser Gly Gly Ser Gly Ser Ser Ser Ala Gln Gly Ala Thr Pro Gly Gly
            180                 185                 190

Arg Cys Asn Pro Leu Val Leu Glu Phe Thr Asp Ala Gly Lys Arg Ala
        195                 200                 205

Ser Trp Asp Ala Ser Lys Ala Trp Gly Leu Arg Leu Tyr Arg Ser Thr
    210                 215                 220
```

-continued

```
Arg Thr Asp Pro Val Thr Arg Phe Ser Leu Thr Arg Gln Val Leu Asn
225                 230                 235                 240

Ile Gly Pro Arg Val Pro Ile Gly Pro Asn Pro Val Ile Ile Asp Gln
                245                 250                 255

Leu Pro Pro Ser Arg Pro Val Gln Ile Met Leu Pro Arg Pro Pro Gln
            260                 265                 270

Pro Pro Pro Pro Gly Ala Ala Ser Thr Val Pro Glu Thr Ala Pro Pro
        275                 280                 285

Ser Gln Gln Pro Gly Thr Gly Asp Arg Leu Leu Asn Leu Val Asn Gly
    290                 295                 300

Ala Tyr Gln Ala Leu Asn Leu Thr Ser Pro Asp Lys Thr Gln Glu Cys
305                 310                 315                 320

Trp Leu Cys Leu Val Ala Gly Pro Pro Tyr Tyr Glu Gly Val Ala Val
                325                 330                 335

Leu Gly Thr Tyr Ser Asn His Thr Ser Ala Pro Ala Asn Cys Ser Val
            340                 345                 350

Ala Ser Gln His Lys Leu Thr Leu Ser Glu Val Thr Gly Gln Gly Leu
        355                 360                 365

Cys Val Gly Ala Val Pro Lys Thr His Gln Ala Leu Cys Asn Thr Thr
    370                 375                 380

Gln Lys Thr Ser Asn Gly Ser Tyr Tyr Leu Ala Ala Pro Ala Gly Thr
385                 390                 395                 400

Ile Trp Ala Cys Asn Thr Gly Leu Thr Pro Cys Leu Ser Thr Thr Val
                405                 410                 415

Leu Asp Leu Thr Thr Asp Tyr Cys Val Leu Val Glu Leu Trp Pro Lys
            420                 425                 430

Val Thr Tyr His Ser Pro Gly Tyr Val Tyr Gly Gln Phe Glu Glu Lys
        435                 440                 445

Thr Lys Tyr Lys Arg Glu Pro Val Ser Leu Thr Leu Ala Leu Leu Leu
    450                 455                 460

Gly Gly Leu Thr Met Gly Gly Ile Ala Ala Gly Val Gly Thr Gly Thr
465                 470                 475                 480

Thr Ala Leu Val Ala Thr Gln Gln Phe Gln Gln Leu Gln Ala Ala Met
                485                 490                 495

Gln Asp Asp Leu Lys Glu Val Lys Lys Ser Ile Thr Asn Leu Glu Arg
            500                 505                 510

Ser Leu Thr Ser Leu Ser Glu Val Val Leu Gln Asn Arg Arg Gly Leu
        515                 520                 525

Asp Leu Leu Phe Leu Lys Glu Gly Gly Leu Cys Ala Ala Leu Lys Glu
    530                 535                 540

Glu Cys Cys Phe Tyr Ala Asp His Thr Gly Leu Val Arg Asp Ser Met
545                 550                 555                 560

Ala Lys Leu Arg Glu Arg Leu Ser Gln Arg Gln Lys Leu Phe Glu Ser
                565                 570                 575

Gln Gln Gly Trp Phe Glu Gly Leu Phe Asn Lys Ser Pro Trp Phe Thr
            580                 585                 590

Thr Leu Ile Ser Thr Ile Met Gly Pro Leu Ile Ile Leu Leu Leu Ile
        595                 600                 605

Leu Leu Phe Gly Pro Cys Ile Leu Asn His Leu Val Gln Phe Ile Lys
    610                 615                 620

Asp Arg Val Ser Val Val Gln Ala Leu Val Leu Thr Gln Gln Tyr His
625                 630                 635                 640

Gln Leu Lys Thr Ile Glu Asp Cys Glu Ser Arg Glu
```

645 650

<210> SEQ ID NO 115
<211> LENGTH: 17
<212> TYPE: PRT
<213> ORGANISM: Murine leukemia virus

<400> SEQUENCE: 115

Ala Ser Lys Ala Trp Gly Leu Arg Leu Tyr Arg Ser Thr Arg Thr Asp
1 5 10 15

Pro

<210> SEQ ID NO 116
<211> LENGTH: 17
<212> TYPE: PRT
<213> ORGANISM: Murine leukemia virus

<400> SEQUENCE: 116

Gly Pro Lys Val Trp Gly Leu Arg Leu Tyr Arg Ser Thr Gly Ile Asp
1 5 10 15

Pro

<210> SEQ ID NO 117
<211> LENGTH: 17
<212> TYPE: PRT
<213> ORGANISM: Murine leukemia virus

<400> SEQUENCE: 117

Gly Pro Lys Val Trp Gly Leu Arg Leu Tyr Arg Ser Thr Gly Thr Asp
1 5 10 15

Pro

<210> SEQ ID NO 118
<211> LENGTH: 17
<212> TYPE: PRT
<213> ORGANISM: Murine leukemia virus

<400> SEQUENCE: 118

Gly Pro Lys Val Trp Gly Leu Arg Leu Tyr Gln Ser Thr Gly Ile Asp
1 5 10 15

Pro

<210> SEQ ID NO 119
<211> LENGTH: 17
<212> TYPE: PRT
<213> ORGANISM: Murine leukemia virus

<400> SEQUENCE: 119

Gly Pro Lys Val Trp Gly Leu Arg Leu Tyr Arg Ser Thr Gly Thr Asp
1 5 10 15

Pro

<210> SEQ ID NO 120
<211> LENGTH: 17
<212> TYPE: PRT
<213> ORGANISM: Murine leukemia virus

<400> SEQUENCE: 120

Gly Pro Lys Val Trp Gly Leu Arg Leu Tyr Arg Ser Thr Gly Thr Asp
1 5 10 15

Pro

<210> SEQ ID NO 121
<211> LENGTH: 17
<212> TYPE: PRT
<213> ORGANISM: Murine leukemia virus

<400> SEQUENCE: 121

Gly Pro Lys Val Trp Gly Leu Arg Leu Tyr Arg Ser Thr Gly Thr Asp
1 5 10 15

Pro

<210> SEQ ID NO 122
<211> LENGTH: 17
<212> TYPE: PRT
<213> ORGANISM: Murine leukemia virus

<400> SEQUENCE: 122

Gly Pro Lys Val Trp Gly Leu Arg Leu Tyr Arg Ser Thr Gly Ile Asp
1 5 10 15

Pro

<210> SEQ ID NO 123
<211> LENGTH: 17
<212> TYPE: PRT
<213> ORGANISM: Murine leukemia virus

<400> SEQUENCE: 123

Gly Pro Lys Val Trp Gly Leu Arg Leu Tyr Arg Ser Thr Gly Thr Asp
1 5 10 15

Pro

<210> SEQ ID NO 124
<211> LENGTH: 17
<212> TYPE: PRT
<213> ORGANISM: Murine leukemia virus

<400> SEQUENCE: 124

Gly Pro Lys Val Trp Gly Leu Arg Leu Tyr Arg Ser Thr Gly Thr Asp
1 5 10 15

Pro

<210> SEQ ID NO 125
<211> LENGTH: 17
<212> TYPE: PRT
<213> ORGANISM: Murine leukemia virus

<400> SEQUENCE: 125

Gly Pro Lys Val Trp Gly Leu Arg Leu Tyr Arg Pro Thr Gly Thr Asp
1 5 10 15

Pro

<210> SEQ ID NO 126
<211> LENGTH: 17
<212> TYPE: PRT
<213> ORGANISM: Murine leukemia virus

<400> SEQUENCE: 126

Gly Pro Lys Val Trp Gly Leu Arg Leu Tyr Arg Ser Thr Gly Thr Asp
1 5 10 15

Pro

<210> SEQ ID NO 127

<211> LENGTH: 17
<212> TYPE: PRT
<213> ORGANISM: Murine leukemia virus

<400> SEQUENCE: 127

Gly Pro Lys Val Trp Gly Leu Arg Leu Tyr Gln Ser Thr Gly Ile Asp
1 5 10 15

Pro

<210> SEQ ID NO 128
<211> LENGTH: 17
<212> TYPE: PRT
<213> ORGANISM: Murine leukemia virus

<400> SEQUENCE: 128

Gly Pro Lys Val Trp Gly Leu Arg Leu Tyr Arg Ser Thr Gly Ile Asp
1 5 10 15

Pro

<210> SEQ ID NO 129
<211> LENGTH: 17
<212> TYPE: PRT
<213> ORGANISM: Murine leukemia virus

<400> SEQUENCE: 129

Gly Pro Lys Val Trp Gly Leu Arg Leu Tyr Arg Ser Thr Gly Ile Asp
1 5 10 15

Pro

<210> SEQ ID NO 130
<211> LENGTH: 17
<212> TYPE: PRT
<213> ORGANISM: Murine leukemia virus

<400> SEQUENCE: 130

Gly Pro Lys Val Trp Gly Leu Arg Leu Tyr Arg Ser Thr Gly Thr Asp
1 5 10 15

Pro

<210> SEQ ID NO 131
<211> LENGTH: 17
<212> TYPE: PRT
<213> ORGANISM: Murine leukemia virus

<400> SEQUENCE: 131

Gly Pro Lys Val Trp Gly Leu Arg Leu Tyr Arg Ser Thr Gly Thr Asp
1 5 10 15

Pro

<210> SEQ ID NO 132
<211> LENGTH: 17
<212> TYPE: PRT
<213> ORGANISM: Murine leukemia virus

<400> SEQUENCE: 132

Gly Pro Lys Val Trp Gly Leu Arg Leu Tyr Arg Ser Thr Gly Thr Asp
1 5 10 15

Pro

<210> SEQ ID NO 133
<211> LENGTH: 16
<212> TYPE: PRT

<213> ORGANISM: Murine leukemia virus

<400> SEQUENCE: 133

Thr Gly His Trp Trp Gly Leu Arg Leu Tyr Val Ser Gly His Asp Pro
1 5 10 15

<210> SEQ ID NO 134
<211> LENGTH: 16
<212> TYPE: PRT
<213> ORGANISM: Murine leukemia virus

<400> SEQUENCE: 134

Ile Gly His Tyr Trp Gly Leu Arg Leu Tyr Val Ser Gly Gln Asp Pro
1 5 10 15

<210> SEQ ID NO 135
<211> LENGTH: 16
<212> TYPE: PRT
<213> ORGANISM: Murine leukemia virus

<400> SEQUENCE: 135

Thr Gly His Tyr Trp Gly Leu Arg Leu Tyr Val Ser Gly Gln Asp Pro
1 5 10 15

<210> SEQ ID NO 136
<211> LENGTH: 16
<212> TYPE: PRT
<213> ORGANISM: Murine leukemia virus

<400> SEQUENCE: 136

Thr Gly His Trp Trp Gly Leu Arg Leu Tyr Val Ser Gly His Asp Pro
1 5 10 15

<210> SEQ ID NO 137
<211> LENGTH: 16
<212> TYPE: PRT
<213> ORGANISM: Murine leukemia virus

<400> SEQUENCE: 137

Thr Gly His Tyr Trp Gly Leu Arg Leu Tyr Val Ser Gly Arg Asp Pro
1 5 10 15

<210> SEQ ID NO 138
<211> LENGTH: 16
<212> TYPE: PRT
<213> ORGANISM: Murine leukemia virus

<400> SEQUENCE: 138

Gly Pro Lys Ser Trp Gly Leu Arg Leu Tyr Arg Thr Gly Thr Asp Pro
1 5 10 15

<210> SEQ ID NO 139
<211> LENGTH: 16
<212> TYPE: PRT
<213> ORGANISM: Murine leukemia virus

<400> SEQUENCE: 139

Gly Pro Lys Ser Trp Gly Leu Arg Leu Tyr Arg Thr Gly Thr Asp Pro
1 5 10 15

<210> SEQ ID NO 140
<211> LENGTH: 17
<212> TYPE: PRT
<213> ORGANISM: Murine leukemia virus

<400> SEQUENCE: 140

Ala Pro Lys Val Trp Gly Leu Arg Leu Tyr Arg Ser Thr Gly Ala Asp
1               5                   10                  15

Pro

<210> SEQ ID NO 141
<211> LENGTH: 17
<212> TYPE: PRT
<213> ORGANISM: Murine leukemia virus

<400> SEQUENCE: 141

Ala Pro Lys Val Trp Gly Leu Arg Leu Tyr Arg Ser Thr Gly Ala Asp
1               5                   10                  15

Pro

<210> SEQ ID NO 142
<211> LENGTH: 17
<212> TYPE: PRT
<213> ORGANISM: Murine leukemia virus

<400> SEQUENCE: 142

Ala Pro Lys Val Trp Gly Leu Arg Leu Tyr Arg Ser Thr Gly Ala Asp
1               5                   10                  15

Pro

<210> SEQ ID NO 143
<211> LENGTH: 17
<212> TYPE: PRT
<213> ORGANISM: Murine leukemia virus

<400> SEQUENCE: 143

Ala Pro Lys Val Trp Gly Leu Arg Leu Tyr Arg Ser Thr Gly Ala Asp
1               5                   10                  15

Pro

<210> SEQ ID NO 144
<211> LENGTH: 17
<212> TYPE: PRT
<213> ORGANISM: Murine leukemia virus

<400> SEQUENCE: 144

Gly Pro Lys Val Trp Gly Leu Arg Leu Tyr Arg Ser Thr Gly Thr Asp
1               5                   10                  15

Pro

<210> SEQ ID NO 145
<211> LENGTH: 17
<212> TYPE: PRT
<213> ORGANISM: Murine leukemia virus

<400> SEQUENCE: 145

Gly Pro Lys Val Trp Gly Leu Arg Leu Tyr Arg Ser Thr Gly Thr Asp
1               5                   10                  15

Pro

<210> SEQ ID NO 146
<211> LENGTH: 639
<212> TYPE: PRT
<213> ORGANISM: Murine leukemia virus

<400> SEQUENCE: 146

Met Glu Gly Pro Ala Phe Ser Lys Pro Leu Lys Asp Lys Ile Asn Pro

-continued

```
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Val Val Ser Ser Ser Ala Gln Gly Ala Thr
                165                 170                 175

Pro Gly Gly Arg Cys Asn Pro Leu Val Leu Glu Phe Thr Asp Ala Gly
            180                 185                 190

Lys Arg Ala Ser Trp Asp Ala Ser Lys Ala Trp Gly Leu Arg Leu Tyr
        195                 200                 205

Arg Ser Thr Arg Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Ile Asp Gln Leu Pro Pro Ser Arg Pro Val Gln Ile Met Leu Pro Arg
                245                 250                 255

Pro Pro Gln Pro Pro Pro Pro Gly Ala Ala Ser Thr Val Pro Glu Thr
            260                 265                 270

Ala Pro Pro Ser Gln Gln Pro Gly Thr Gly Asp Arg Leu Leu Asn Leu
        275                 280                 285

Val Asn Gly Ala Tyr Gln Ala Leu Asn Leu Thr Ser Pro Asp Lys Thr
    290                 295                 300

Gln Glu Cys Trp Leu Cys Leu Val Ala Gly Pro Pro Tyr Tyr Glu Gly
305                 310                 315                 320

Val Ala Val Leu Gly Thr Tyr Ser Asn His Thr Ser Ala Pro Ala Asn
                325                 330                 335

Cys Ser Val Ala Ser Gln His Lys Leu Thr Leu Ser Glu Val Thr Gly
            340                 345                 350

Gln Gly Leu Cys Val Gly Ala Val Pro Lys Thr His Gln Ala Leu Cys
        355                 360                 365

Asn Thr Thr Gln Lys Thr Ser Asn Gly Ser Tyr Tyr Leu Ala Ala Pro
    370                 375                 380

Ala Gly Thr Ile Trp Ala Cys Asn Thr Gly Leu Thr Pro Cys Leu Ser
385                 390                 395                 400

Thr Thr Val Leu Asp Leu Thr Thr Asp Tyr Cys Val Leu Val Glu Leu
                405                 410                 415

Trp Pro Lys Val Thr Tyr His Ser Pro Gly Tyr Val Tyr Gly Gln Phe
            420                 425                 430
```

```
Glu Glu Lys Thr Lys Tyr Lys Arg Glu Pro Val Ser Leu Thr Leu Ala
        435                 440                 445

Leu Leu Leu Gly Gly Leu Thr Met Gly Gly Ile Ala Ala Gly Val Gly
    450                 455                 460

Thr Gly Thr Thr Ala Leu Val Ala Thr Gln Gln Phe Gln Gln Leu Gln
465                 470                 475                 480

Ala Ala Met Gln Asp Asp Leu Lys Glu Val Lys Lys Ser Ile Thr Asn
                485                 490                 495

Leu Glu Arg Ser Leu Thr Ser Leu Ser Glu Val Val Leu Gln Asn Arg
            500                 505                 510

Arg Gly Leu Asp Leu Leu Phe Leu Lys Glu Gly Gly Leu Cys Ala Ala
        515                 520                 525

Leu Lys Glu Glu Cys Cys Phe Tyr Ala Asp His Thr Gly Leu Val Arg
    530                 535                 540

Asp Ser Met Ala Lys Leu Arg Glu Arg Leu Ser Gln Arg Gln Lys Leu
545                 550                 555                 560

Phe Glu Ser Gln Gln Gly Trp Phe Glu Gly Leu Phe Asn Lys Ser Pro
                565                 570                 575

Trp Phe Thr Thr Leu Ile Ser Thr Ile Met Gly Pro Leu Ile Ile Leu
            580                 585                 590

Leu Leu Ile Leu Leu Phe Gly Pro Cys Ile Leu Asn His Leu Val Gln
        595                 600                 605

Phe Ile Lys Asp Arg Val Ser Val Val Gln Ala Leu Val Leu Thr Gln
    610                 615                 620

Gln Tyr His Gln Leu Lys Thr Ile Glu Asp Cys Glu Ser Arg Glu
625                 630                 635
```

```
<210> SEQ ID NO 147
<211> LENGTH: 644
<212> TYPE: PRT
<213> ORGANISM: Murine leukemia virus

<400> SEQUENCE: 147

Met Glu Gly Ser Ala Phe Ser Lys Pro Leu Lys Asp Lys Ile Asn Pro
1               5                   10                  15

Trp Gly Pro Leu Ile Val Met Gly Ile Leu Val Arg Ala Gly Ala Ser
            20                  25                  30

Val Gln Arg Asp Ser Pro His Gln Ile Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Tyr Trp Asp Asp Pro Glu Pro Asp Ile Gly Asp Gly Cys
                85                  90                  95

Arg Thr Pro Gly Gly Arg Arg Arg Thr Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175
```

-continued

```
Gly Ala Thr Pro Gly Gly Arg Cys Asn Pro Leu Val Leu Glu Phe Thr
            180                 185                 190

Asp Ala Gly Arg Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Pro Arg Val Pro Ile Gly Pro Asn
225                 230                 235                 240

Pro Val Ile Thr Asp Gln Leu Pro Pro Ser Gln Pro Val Gln Ile Met
                245                 250                 255

Leu Pro Arg Pro Pro His Pro Pro Pro Ser Gly Thr Val Ser Met Val
            260                 265                 270

Pro Gly Ala Pro Pro Pro Ser Gln Gln Pro Gly Thr Gly Asp Arg Leu
        275                 280                 285

Leu Asn Leu Val Glu Gly Ala Tyr Gln Ala Leu Asn Leu Thr Ser Pro
    290                 295                 300

Asp Lys Thr Gln Glu Cys Trp Leu Cys Leu Val Ser Gly Pro Pro Tyr
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
            340                 345                 350

Val Thr Gly Gln Gly Leu Cys Val Gly Ala Val Pro Lys Thr His Gln
        355                 360                 365

Ala Leu Cys Asn Thr Thr Gln Lys Thr Ser Asp Gly Ser Tyr Tyr Leu
    370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asn Leu Thr Thr Asp Tyr Cys Val Leu
                405                 410                 415

Val Glu Leu Trp Pro Lys Val Thr Tyr His Ser Pro Asp Tyr Val Tyr
            420                 425                 430

Gly Gln Phe Glu Lys Lys Thr Lys Tyr Lys Arg Glu Pro Val Ser Leu
        435                 440                 445

Thr Leu Ala Leu Leu Leu Gly Gly Leu Thr Met Gly Gly Ile Ala Ala
    450                 455                 460

Gly Val Gly Thr Gly Thr Thr Ala Leu Val Ala Thr Lys Gln Phe Glu
465                 470                 475                 480

Gln Leu Gln Ala Ala Ile His Thr Asp Leu Gly Ala Leu Glu Lys Ser
                485                 490                 495

Val Ser Ala Leu Glu Lys Ser Leu Thr Ser Leu Ser Glu Val Val Leu
            500                 505                 510

Gln Asn Arg Arg Gly Leu Asp Leu Leu Phe Leu Lys Glu Gly Gly Leu
        515                 520                 525

Cys Ala Ala Leu Lys Glu Glu Cys Cys Phe Tyr Ala Asp His Thr Gly
    530                 535                 540

Val Val Arg Asp Ser Met Ala Lys Leu Arg Glu Arg Leu Asn Gln Arg
545                 550                 555                 560

Gln Lys Leu Phe Glu Ser Gly Gln Gly Trp Phe Glu Gly Leu Phe Asn
                565                 570                 575

Arg Ser Pro Trp Phe Thr Thr Leu Ile Ser Thr Ile Met Gly Pro Leu
            580                 585                 590

Ile Val Leu Leu Leu Ile Leu Leu Leu Gly Pro Cys Ile Leu Asn Arg
        595                 600                 605
```

Leu Val Gln Phe Val Lys Asp Arg Ile Ser Val Val Gln Ala Leu Ile
    610                 615                 620

Leu Thr Gln Gln Tyr His Gln Leu Lys Ser Ile Glu Pro Glu Glu Val
625                 630                 635                 640

Glu Ser Arg Glu

<210> SEQ ID NO 148
<211> LENGTH: 665
<212> TYPE: PRT
<213> ORGANISM: Murine leukemia virus

<400> SEQUENCE: 148

Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
            20                  25                  30

Thr Ala Ser Pro Gly Ser Ser Pro His Gln Val Tyr Asn Ile Thr Trp
        35                  40                  45

Glu Val Thr Asn Gly Asp Arg Glu Thr Val Trp Ala Thr Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
    130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
        195                 200                 205

Cys Lys Asp Asn Lys Trp Cys Asn Pro Leu Val Ile Arg Phe Thr Asp
    210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Leu Gly Pro Arg Val Pro Ile Gly Pro Asn Pro
            260                 265                 270

Val Leu Ala Asp Gln Gln Pro Leu Ser Lys Pro Lys Pro Val Lys Ser
        275                 280                 285

Pro Ser Val Thr Lys Pro Pro Ser Gly Thr Pro Leu Ser Pro Thr Gln
    290                 295                 300

Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
                325                 330                 335

```
Trp Leu Cys Leu Val Ala Gly Pro Pro Tyr Tyr Glu Gly Val Ala Val
            340                 345                 350

Leu Gly Thr Tyr Ser Asn His Thr Ser Ala Pro Ala Asn Cys Ser Val
        355                 360                 365

Ala Ser Gln His Lys Leu Thr Leu Ser Glu Val Thr Gly Gln Gly Leu
    370                 375                 380

Cys Ile Gly Ala Val Pro Lys Thr His Gln Ala Leu Cys Asn Thr Thr
385                 390                 395                 400

Gln Thr Ser Ser Arg Gly Ser Tyr Tyr Leu Val Ala Pro Thr Gly Thr
                405                 410                 415

Met Trp Ala Cys Ser Thr Gly Leu Thr Pro Cys Ile Ser Thr Thr Ile
            420                 425                 430

Leu Asn Leu Thr Thr Asp Tyr Cys Val Leu Val Glu Leu Trp Pro Arg
        435                 440                 445

Val Thr Tyr His Ser Pro Ser Tyr Val Tyr Gly Leu Phe Glu Arg Ser
    450                 455                 460

Asn Arg His Lys Arg Glu Pro Val Ser Leu Thr Leu Ala Leu Leu Leu
465                 470                 475                 480

Gly Gly Leu Thr Met Gly Gly Ile Ala Ala Gly Ile Gly Thr Gly Thr
                485                 490                 495

Thr Ala Leu Met Ala Thr Gln Gln Phe Gln Gln Leu Gln Ala Ala Val
            500                 505                 510

Gln Asp Asp Leu Arg Glu Val Glu Lys Ser Ile Ser Asn Leu Glu Lys
        515                 520                 525

Ser Leu Thr Ser Leu Ser Glu Val Val Leu Gln Asn Arg Arg Gly Leu
    530                 535                 540

Asp Leu Leu Phe Leu Lys Glu Gly Gly Leu Cys Ala Ala Leu Lys Glu
545                 550                 555                 560

Glu Cys Cys Phe Tyr Ala Asp His Thr Gly Leu Val Arg Asp Ser Met
                565                 570                 575

Ala Lys Leu Arg Glu Arg Leu Asn Gln Arg Gln Lys Leu Phe Glu Ser
            580                 585                 590

Thr Gln Gly Trp Phe Glu Gly Leu Phe Asn Arg Ser Pro Trp Phe Thr
        595                 600                 605

Thr Leu Ile Ser Thr Ile Met Gly Pro Leu Ile Val Leu Leu Met Ile
    610                 615                 620

Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
                645                 650                 655

Gln Leu Lys Pro Ile Glu Tyr Glu Pro
            660                 665
```

<210> SEQ ID NO 149
<211> LENGTH: 654
<212> TYPE: PRT
<213> ORGANISM: Murine leukemia virus

<400> SEQUENCE: 149

```
Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
            20                  25                  30

Glu Ser Pro His Gln Val Phe Asn Val Thr Trp Arg Val Thr Asn Leu
        35                  40                  45
```

-continued

```
Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Pro Ser Pro Leu Asn
            260                 265                 270

Thr Ser Tyr Pro Pro Ser Thr Thr Ser Thr Pro Ser Thr Ser Pro Thr
        275                 280                 285

Ser Pro Ser Val Pro Gln Pro Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
        355                 360                 365

Thr Gly Gln Gly Leu Cys Met Gly Ala Val Pro Lys Thr His Gln Ala
    370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
        435                 440                 445

Gln Leu Glu Gln Arg Thr Lys Tyr Lys Arg Glu Pro Val Ser Leu Thr
    450                 455                 460

Leu Ala Leu Leu Leu Gly Gly Leu Thr Met Gly Gly Ile Ala Ala Gly
465                 470                 475                 480
```

```
Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650
```

<210> SEQ ID NO 150
<211> LENGTH: 641
<212> TYPE: PRT
<213> ORGANISM: Murine leukemia virus

<400> SEQUENCE: 150

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Arg His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205
```

-continued

```
Arg Ser Thr Gly Ile Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro Pro Gly Ala Ala Ser Thr Val Pro Glu Thr
            260                 265                 270

Ala Pro Pro Ser Gln Gln Pro Gly Thr Gly Asp Arg Leu Leu Asn Leu
        275                 280                 285

Val Lys Gly Ala Tyr Gln Ala Leu Asn Leu Thr Ser Pro Asp Lys Thr
    290                 295                 300

Gln Glu Cys Trp Leu Cys Leu Val Ser Gly Pro Pro Tyr Tyr Glu Gly
305                 310                 315                 320

Val Ala Val Leu Gly Thr Tyr Ser Asn His Thr Ser Ala Pro Ala Asn
                325                 330                 335

Cys Ser Val Ala Ser Gln His Lys Leu Thr Leu Ser Glu Val Thr Gly
            340                 345                 350

Gln Gly Leu Cys Ile Gly Ala Val Pro Lys Thr His Gln Ala Leu Cys
        355                 360                 365

Asn Thr Thr Gln Lys Thr Ser Asp Gly Ser Tyr Tyr Leu Ala Ala Pro
    370                 375                 380

Thr Gly Thr Thr Trp Ala Cys Ser Thr Gly Leu Thr Pro Cys Ile Ser
385                 390                 395                 400

Thr Thr Ile Leu Asp Leu Thr Thr Asp Tyr Cys Val Leu Val Glu Leu
                405                 410                 415

Trp Pro Arg Val Thr Tyr His Ser Pro Ser Tyr Val Tyr His Gln Phe
            420                 425                 430

Glu Arg Arg Ala Lys Tyr Lys Arg Glu Pro Val Ser Leu Thr Leu Ala
        435                 440                 445

Leu Leu Leu Gly Gly Leu Thr Met Gly Gly Ile Ala Ala Gly Val Gly
    450                 455                 460

Thr Gly Thr Thr Ala Leu Val Ala Thr Gln Gln Phe Gln Gln Phe Gln
465                 470                 475                 480

Ala Ala Met Gln Asp Asp Leu Lys Glu Val Glu Lys Ser Ile Thr Asn
                485                 490                 495

Leu Glu Lys Ser Leu Thr Ser Leu Ser Glu Val Val Leu Gln Asn Arg
            500                 505                 510

Arg Gly Leu Asp Leu Leu Phe Leu Lys Glu Gly Gly Leu Cys Ala Ala
        515                 520                 525

Leu Lys Glu Glu Cys Cys Phe Tyr Ala Asp His Thr Gly Leu Val Arg
    530                 535                 540

Asp Ser Met Ala Lys Leu Arg Glu Arg Leu Ser Gln Arg Gln Lys Leu
545                 550                 555                 560

Phe Glu Ser Gln Gln Gly Trp Phe Glu Gly Leu Phe Asn Lys Ser Pro
                565                 570                 575

Trp Phe Thr Thr Leu Ile Ser Thr Ile Met Gly Pro Leu Ile Ile Leu
            580                 585                 590

Leu Leu Ile Leu Leu Phe Gly Pro Cys Ile Leu Asn Arg Leu Val Gln
        595                 600                 605

Phe Val Lys Asp Arg Ile Ser Val Val Gln Ala Leu Val Leu Thr Gln
    610                 615                 620

Gln Tyr His Gln Leu Lys Ser Ile Asp Pro Glu Glu Val Glu Ser Arg
```

```
625                 630                 635                 640

Glu


<210> SEQ ID NO 151
<211> LENGTH: 662
<212> TYPE: PRT
<213> ORGANISM: Murine leukemia virus

<400> SEQUENCE: 151

Met Glu Gly Pro Thr His Pro Lys Pro Ser Lys Asp Lys Thr Phe Ser
1               5                   10                  15

Trp Asp Leu Met Ile Leu Val Gly Val Leu Leu Arg Leu Asp Val Gly
            20                  25                  30

Met Ala Asn Pro Ser Pro His Gln Ile Tyr Asn Val Thr Trp Thr Ile
        35                  40                  45

Thr Asn Leu Val Thr Gly Thr Lys Ala Asn Ala Thr Ser Met Leu Gly
    50                  55                  60

Thr Leu Thr Asp Ala Phe Pro Thr Met Tyr Phe Asp Leu Cys Asp Ile
65                  70                  75                  80

Ile Gly Asn Thr Trp Asn Pro Ser Asp Gln Glu Pro Phe Pro Gly Tyr
                85                  90                  95

Gly Cys Asp Gln Pro Met Arg Arg Trp Gln Gln Arg Asn Thr Pro Phe
            100                 105                 110

Tyr Val Cys Pro Gly His Ala Asn Arg Lys Gln Cys Gly Gly Pro Gln
        115                 120                 125

Asp Gly Phe Cys Ala Val Trp Gly Cys Glu Thr Thr Gly Glu Thr Tyr
    130                 135                 140

Trp Arg Pro Thr Ser Ser Trp Asp Tyr Ile Thr Val Lys Lys Gly Val
145                 150                 155                 160

Thr Gln Gly Ile Tyr Gln Cys Ser Gly Gly Gly Trp Cys Gly Pro Cys
                165                 170                 175

Tyr Asp Lys Ala Val His Ser Ser Ile Thr Gly Ala Ser Glu Gly Gly
            180                 185                 190

Arg Cys Asn Pro Leu Ile Leu Gln Phe Thr Gln Lys Gly Arg Gln Thr
        195                 200                 205

Ser Trp Asp Gly Pro Lys Ser Trp Gly Leu Arg Leu Tyr Arg Ser Gly
    210                 215                 220

Tyr Asp Pro Ile Ala Leu Phe Ser Val Ser Arg Gln Val Met Thr Ile
225                 230                 235                 240

Thr Leu Pro Gln Ala Met Gly Pro Asn Leu Val Leu Pro Asp Gln Lys
                245                 250                 255

Pro Pro Ser Arg Gln Ser Gln Ile Glu Ser Arg Val Thr Pro His His
            260                 265                 270

Ser Gln Gly Asn Gly Gly Thr Pro Gly Ile Thr Leu Val Asn Ala Ser
        275                 280                 285

Ile Ala Pro Leu Ser Thr Pro Val Thr Pro Ala Ser Pro Lys Arg Ile
    290                 295                 300

Gly Thr Gly Asn Arg Leu Ile Asn Leu Val Gln Gly Thr Tyr Leu Ala
305                 310                 315                 320

Leu Asn Val Thr Asn Pro Asn Lys Thr Lys Asp Cys Trp Leu Cys Leu
                325                 330                 335

Val Ser Arg Pro Pro Tyr Tyr Glu Gly Ile Ala Val Leu Gly Asn Tyr
            340                 345                 350

Ser Asn Gln Thr Asn Pro Pro Pro Ser Cys Leu Ser Asp Pro Gln His
        355                 360                 365
```

Lys Leu Thr Ile Ser Glu Val Ser Gly Gln Gly Ser Cys Ile Gly Thr
370 375 380

Val Pro Lys Thr His Gln Ala Leu Cys Lys Lys Thr Gln Lys Gly His
385 390 395 400

Lys Gly Thr His Tyr Leu Ala Ala Pro Ser Gly Thr Tyr Trp Ala Cys
405 410 415

Asn Thr Gly Leu Thr Pro Cys Ile Ser Met Ala Val Leu Asn Trp Thr
420 425 430

Ser Asp Phe Cys Val Leu Ile Glu Leu Trp Pro Arg Val Thr Tyr His
435 440 445

Gln Pro Glu Tyr Val Tyr Thr His Phe Asp Lys Thr Val Arg Leu Arg
450 455 460

Arg Glu Pro Ile Ser Leu Thr Val Ala Leu Met Leu Gly Gly Leu Thr
465 470 475 480

Val Gly Gly Ile Ala Ala Gly Val Gly Thr Gly Thr Lys Ala Leu Leu
485 490 495

Glu Thr Ala Gln Phe Gly Gln Leu Gln Met Ala Met His Thr Asp Ile
500 505 510

Gln Ala Leu Glu Glu Ser Ile Ser Ala Leu Glu Lys Ser Leu Thr Ser
515 520 525

Leu Ser Glu Val Val Leu Gln Asn Arg Arg Gly Leu Asp Ile Leu Phe
530 535 540

Leu Gln Glu Gly Gly Leu Cys Ala Ala Leu Lys Glu Glu Cys Cys Phe
545 550 555 560

Tyr Ala Asp His Thr Gly Leu Val Arg Asp Asn Met Ala Lys Leu Arg
565 570 575

Glu Arg Leu Lys Gln Arg Gln Gln Leu Phe Asp Ser Gln Gln Gly Trp
580 585 590

Phe Glu Gly Trp Phe Asn Lys Ser Pro Trp Phe Thr Thr Leu Ile Ser
595 600 605

Ser Ile Met Gly Pro Leu Leu Ile Leu Leu Leu Ile Leu Leu Phe Gly
610 615 620

Pro Cys Ile Leu Asn Arg Leu Val Gln Phe Val Lys Asp Arg Ile Ser
625 630 635 640

Val Val Gln Ala Leu Ile Leu Thr Gln Gln Tyr Gln Gln Ile Lys Gln
645 650 655

Tyr Asp Pro Asp Gln Pro
660

<210> SEQ ID NO 152
<211> LENGTH: 623
<212> TYPE: PRT
<213> ORGANISM: Murine leukemia virus

<400> SEQUENCE: 152

Met Glu Gly Ser Thr Phe Ser Lys Pro Leu Lys Asp Lys Ile Asn Pro
1 5 10 15

Trp Gly Pro Leu Ile Val Leu Gly Ile Leu Leu Arg Ala Gly Val Ser
20 25 30

Val Asp Ser Pro His Gln Val Phe Asn Val Thr Trp Arg Val Thr Asn
35 40 45

Leu Met Thr Gly Gln Thr Ala Asn Ala Thr Ser Leu Leu Gly Thr Met
50 55 60

Thr Asp Ala Phe Pro Lys Leu Tyr Phe Asp Leu Cys Asp Leu Ile Gly
65 70 75 80

-continued

```
Asp Asp Trp Asp Glu Pro Glu Gly Gly Cys Arg Thr Pro Gly Gly Arg
                85                  90                  95

Lys Arg Arg Phe Asp Phe Tyr Val Cys Pro Gly His Thr Val Gly Cys
            100                 105                 110

Gly Gly Pro Glu Gly Tyr Cys Gly Lys Trp Gly Cys Glu Thr Thr Gly
        115                 120                 125

Gln Ala Tyr Trp Lys Pro Ser Ser Ser Trp Asp Leu Ile Ser Leu Lys
    130                 135                 140

Arg Gly Asn Thr Pro Gln Gly Pro Cys Tyr Asp Ser Ser Val Ser Ser
145                 150                 155                 160

Ser Ile Gln Gly Ala Thr Pro Gly Gly Arg Cys Asn Pro Leu Val Leu
                165                 170                 175

Glu Phe Thr Asp Ala Gly Lys Lys Ala Ser Trp Asp Gly Pro Lys Ser
            180                 185                 190

Trp Gly Leu Arg Leu Tyr Arg Ser Thr Gly Asp Pro Val Thr Arg Phe
        195                 200                 205

Ser Leu Thr Arg Gln Val Leu Asn Ile Gly Pro Arg Val Pro Ile Gly
    210                 215                 220

Pro Asn Pro Val Ile Asp Gln Leu Pro Pro Ser Arg Pro Val Gln Ile
225                 230                 235                 240

Met Leu Pro Arg Pro Pro Pro Pro Pro Ser Gly Ala Ala Ser Ser Val
                245                 250                 255

Pro Thr Pro Pro Pro Ser Gln Gln Pro Gly Thr Gly Asp Arg Leu Leu
            260                 265                 270

Asn Leu Val Gly Ala Tyr Gln Ala Leu Asn Leu Thr Ser Pro Asp Lys
        275                 280                 285

Thr Gln Glu Cys Trp Leu Cys Leu Val Ser Gly Pro Pro Tyr Tyr Glu
    290                 295                 300

Gly Val Ala Val Leu Gly Thr Tyr Ser Asn His Thr Ser Ala Pro Ala
305                 310                 315                 320

Asn Cys Ser Val Ala Ser Gln His Lys Leu Thr Leu Ser Glu Val Thr
                325                 330                 335

Gly Gln Gly Leu Cys Ile Gly Ala Val Pro Lys Thr His Gln Ala Leu
            340                 345                 350

Cys Asn Thr Thr Gln Lys Thr Ser Gly Ser Tyr Tyr Leu Ala Ala Pro
        355                 360                 365

Ala Gly Thr Ile Trp Ala Cys Ser Thr Gly Leu Thr Pro Cys Ile Ser
    370                 375                 380

Thr Thr Val Leu Asn Leu Thr Thr Asp Tyr Cys Val Leu Val Glu Leu
385                 390                 395                 400

Trp Pro Arg Val Thr Tyr His Ser Pro Asp Tyr Val Tyr Gly Gln Phe
                405                 410                 415

Glu Lys Lys Thr Lys Tyr Lys Arg Glu Pro Val Ser Leu Thr Leu Ala
            420                 425                 430

Leu Leu Leu Gly Gly Leu Thr Met Gly Gly Ile Ala Ala Gly Val Gly
        435                 440                 445

Thr Gly Thr Thr Ala Leu Val Ala Thr Gln Gln Phe Gln Gln Leu Gln
    450                 455                 460

Ala Ala Met Gln Thr Asp Leu Lys Glu Val Glu Lys Ser Ile Ser Asn
465                 470                 475                 480

Leu Glu Lys Ser Leu Thr Ser Leu Ser Glu Val Val Leu Gln Asn Arg
                485                 490                 495

Arg Gly Leu Asp Leu Leu Phe Leu Lys Glu Gly Gly Leu Cys Ala Ala
```

```
            500                 505                 510

Leu Lys Glu Glu Cys Cys Phe Tyr Ala Asp His Thr Gly Leu Val Arg
        515                 520                 525

Asp Ser Met Ala Lys Leu Arg Glu Arg Leu Asn Gln Arg Gln Lys Leu
    530                 535                 540

Phe Glu Ser Gln Gln Gly Trp Phe Glu Gly Leu Phe Asn Lys Ser Pro
545                 550                 555                 560

Trp Phe Thr Thr Leu Ile Ser Thr Ile Met Gly Pro Leu Ile Ile Leu
                565                 570                 575

Leu Leu Ile Leu Leu Phe Gly Pro Cys Ile Leu Asn Arg Leu Val Gln
            580                 585                 590

Phe Val Lys Asp Arg Ile Ser Val Val Gln Ala Leu Val Leu Thr Gln
        595                 600                 605

Gln Tyr His Gln Leu Lys Ser Ile Glu Pro Glu Glu Ser Arg Glu
    610                 615                 620


<210> SEQ ID NO 153
<211> LENGTH: 262
<212> TYPE: PRT
<213> ORGANISM: Murine leukemia virus

<400> SEQUENCE: 153

Met Glu Gly Pro Ala Phe Ser Lys Pro Leu Lys Asp Lys Ile Asn Pro
1               5                   10                  15

Trp Gly Pro Leu Ile Val Leu Gly Ile Leu Met Arg Ala Arg Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Leu Ala Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Lys Gly Gln Gly
145                 150                 155                 160

Pro Cys Tyr Asp Ser Ser Val Val Ser Ser Ser Ala Gln Gly Ala Thr
                165                 170                 175

Pro Gly Gly Arg Cys Asn Pro Leu Val Leu Glu Phe Thr Asp Ala Gly
            180                 185                 190

Lys Arg Ala Ser Trp Asp Ala Ser Lys Ala Trp Gly Leu Arg Leu Tyr
        195                 200                 205

Arg Ser Thr Arg Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Ile Asp Gln Leu Pro Pro Ser Arg Pro Val Gln Ile Met Leu Pro Arg
                245                 250                 255

Pro Pro Gln Pro Pro Pro
```

260

<210> SEQ ID NO 154
<211> LENGTH: 262
<212> TYPE: PRT
<213> ORGANISM: Murine leukemia virus

<400> SEQUENCE: 154

Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Arg His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Ile Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260

<210> SEQ ID NO 155
<211> LENGTH: 262
<212> TYPE: PRT
<213> ORGANISM: Murine leukemia virus

<400> SEQUENCE: 155

Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

```
Thr Met Thr Asp Ala Phe Pro Lys Leu Tyr Phe Asp Leu Cys Asp Leu
65                  70                  75                  80

Val Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Phe Arg Val Pro Ile Gly Phe Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260
```

<210> SEQ ID NO 156
<211> LENGTH: 262
<212> TYPE: PRT
<213> ORGANISM: Murine leukemia virus

<400> SEQUENCE: 156

```
Met Glu Gly Pro Ala Leu Ser Lys Pro Leu Lys Asp Lys Ile Asn Pro
1               5                   10                  15

Trp Gly Pro Leu Ile Val Leu Gly Ile Leu Ile Arg Ala Gly Asp Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175
```

```
Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Ser Ile Gly Pro Arg Val Pro Ile Gly Phe Asn Pro Val Ile
225                 230                 235                 240

Ser Asp Gln Leu Pro Pro Ser Arg Pro Val Gln Ile Leu Leu Pro Arg
                245                 250                 255

Pro Pro Gln Pro Pro Pro
            260


<210> SEQ ID NO 157
<211> LENGTH: 262
<212> TYPE: PRT
<213> ORGANISM: Murine leukemia virus

<400> SEQUENCE: 157

Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Gln His Asp Ser Pro His Gln Val Pro Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Met Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Val Val Ser Ser Gly Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Ile Asp Pro Val Thr Arg Phe Ser Leu Thr Arg Gln
    210                 215                 220

Val Leu Asn Ile Gly Phe Arg Ile Pro Ile Gly Phe Asn Pro Val Ile
225                 230                 235                 240

Thr Gly Gln Leu Pro Pro Ser Arg Pro Val Gln Ile Arg Leu Pro Arg
                245                 250                 255

Pro Pro Gln Pro Pro Pro
            260


<210> SEQ ID NO 158
```

<211> LENGTH: 262
<212> TYPE: PRT
<213> ORGANISM: Murine leukemia virus

<400> SEQUENCE: 158

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Lys Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Ile Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260
```

<210> SEQ ID NO 159
<211> LENGTH: 262
<212> TYPE: PRT
<213> ORGANISM: Murine leukemia virus

<400> SEQUENCE: 159

```
Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80
```

-continued

```
Val Gly Asp Asp Trp Asp Glu Thr Gly Leu Gly Gly Arg Thr Phe Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260


<210> SEQ ID NO 160
<211> LENGTH: 262
<212> TYPE: PRT
<213> ORGANISM: Murine leukemia virus

<400> SEQUENCE: 160

Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190
```

```
Lys Lys Ala Ser Trp Asp Gly Pro Lys Val Trp Gly Leu Arg Leu Tyr
        195                 200                 205

Arg Pro Thr Gly Thr Asp Pro Val Thr Arg Phe Ser Leu Thr Arg Arg
    210                 215                 220

Val Leu Asn Ile Gly Pro Arg Val Pro Ile Gly Pro Asn Pro Val Ile
225                 230                 235                 240

Ala Asp Gln Leu Pro Pro Ser Arg Pro Val Gln Ile Met Leu Pro Arg
                245                 250                 255

Pro Pro Gln Pro Pro Pro
            260


<210> SEQ ID NO 161
<211> LENGTH: 262
<212> TYPE: PRT
<213> ORGANISM: Murine leukemia virus

<400> SEQUENCE: 161

Met Glu Gly Pro Ala Phe Ser Lys Pro Leu Lys Asp Lys Ile Asn Pro
1               5                   10                  15

Trp Ala Pro Leu Ile Val Leu Gly Ile Leu Ile Arg Ala Gly Val Ser
            20                  25                  30

Val Pro His Gly Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Gly Thr Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Ile Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Ser Pro
            260


<210> SEQ ID NO 162
<211> LENGTH: 262
<212> TYPE: PRT
<213> ORGANISM: Murine leukemia virus
```

<400> SEQUENCE: 162

Met Glu Gly Pro Ala Phe Ser Lys Pro Leu Lys Asp Lys Ile Asn Pro
1               5                   10                  15

Trp Cys Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Val Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Leu Ser Ser Ala Val Ser Ser Asn Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Ile Asp Pro Val Thr Arg Phe Ser Leu Thr Arg Gln
    210                 215                 220

Val Leu Asn Ile Gly Pro Arg Val Ser Ile Gly Pro Asn Pro Val Ile
225                 230                 235                 240

Thr Asn Gln Leu Pro Pro Ser Arg Pro Val Gln Ile Met Leu Pro Arg
                245                 250                 255

Pro Pro Gln Pro Pro Pro
            260

<210> SEQ ID NO 163
<211> LENGTH: 262
<212> TYPE: PRT
<213> ORGANISM: Murine leukemia virus

<400> SEQUENCE: 163

Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His

```
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Val Val Ser Ser Gly Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Ile Asp Pro Val Thr Arg Phe Ser Leu Thr Arg Gln
    210                 215                 220

Val Leu Asn Ile Gly Pro Arg Leu Pro Ile Gly Pro Asn Pro Val Ile
225                 230                 235                 240

Thr Gly Gln Leu Pro Pro Ser Arg Pro Val Gln Ile Arg Leu Pro Arg
                245                 250                 255

Pro Pro Gln Pro Pro Pro
            260


<210> SEQ ID NO 164
<211> LENGTH: 262
<212> TYPE: PRT
<213> ORGANISM: Murine leukemia virus

<400> SEQUENCE: 164

Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
```

-continued

```
    210                 215                 220

Val Leu Asn Ile Gly Pro Arg Val Pro Ile Gly Phe Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260


<210> SEQ ID NO 165
<211> LENGTH: 262
<212> TYPE: PRT
<213> ORGANISM: Murine leukemia virus

<400> SEQUENCE: 165

Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Arg Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Phe Arg Val Pro Ile Gly Phe Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260


<210> SEQ ID NO 166
<211> LENGTH: 262
<212> TYPE: PRT
<213> ORGANISM: Murine leukemia virus

<400> SEQUENCE: 166

Met Glu Gly Pro Ala Phe Ser Lys Pro Leu Lys Asp Lys Ile Asn Pro
1               5                   10                  15
```

```
Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Met Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Val Val Ser Ser Gly Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Gln Ser Thr Gly Ile Asp Pro Val Thr Arg Phe Ser Leu Thr Arg Gln
    210                 215                 220

Val Leu Asn Ile Gly Pro Arg Ile Pro Ile Gly Phe Asn Pro Val Ile
225                 230                 235                 240

Thr Gly Gln Leu Pro Pro Ser Arg Pro Val Gln Ile Arg Leu Pro Arg
                245                 250                 255

Pro Pro Gln Thr Pro Pro
            260


<210> SEQ ID NO 167
<211> LENGTH: 262
<212> TYPE: PRT
<213> ORGANISM: Murine leukemia virus

<400> SEQUENCE: 167

Met Glu Gly Pro Ala Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Val Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125
```

```
Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Gln
    210                 215                 220

Val Leu Asn Ile Gly Pro Arg Val Pro Ile Gly Phe Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro
            260
```

<210> SEQ ID NO 168
<211> LENGTH: 262
<212> TYPE: PRT
<213> ORGANISM: Murine leukemia virus

<400> SEQUENCE: 168

```
Met Glu Gly Pro Ala Phe Ser Lys Pro Leu Lys Asp Lys Ile Asn Pro
1               5                   10                  15

Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Met Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Arg Asn Gln Gly
145                 150                 155                 160

Pro Cys Tyr Asp Ser Ser Val Val Ser Ser Gly Ile Gln Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Gln Ser Thr Gly Ile Asp Pro Val Thr Arg Phe Ser Leu Thr Arg Gln
    210                 215                 220

Val Leu Asn Ile Gly Pro Arg Ile Pro Ile Gly Phe Asn Pro Val Ile
225                 230                 235                 240
```

```
Thr Gly Gln Leu Pro Pro Ser Arg Pro Val Gln Ile Arg Leu Pro Arg
                245                 250                 255

Pro Pro Gln Thr Pro Pro
            260


<210> SEQ ID NO 169
<211> LENGTH: 262
<212> TYPE: PRT
<213> ORGANISM: Murine leukemia virus

<400> SEQUENCE: 169

Met Ala Cys Ser Thr Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Ala Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Gln Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Arg
    210                 215                 220

Val Leu Asn Ile Gly Pro Arg Val Pro Ile Gly Pro Asn Pro Val Ile
225                 230                 235                 240

Ile Asp Gln Leu Pro Pro Ser Arg Pro Val Gln Ile Met Leu Pro Arg
                245                 250                 255

Pro Pro Gln Pro Pro Pro
            260


<210> SEQ ID NO 170
<211> LENGTH: 262
<212> TYPE: PRT
<213> ORGANISM: Murine leukemia virus

<400> SEQUENCE: 170

Met Ala Cys Ser Thr Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30
```

```
Val Gln His Asp Glu Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Gly Glu Gly Tyr Cys Gly Lys
        115                 120                 125

Trp Gly Cys Glu Thr Thr Gly Gln Ala Tyr Trp Lys Pro Ser Ser Glu
    130                 135                 140

Trp Asp Leu Ile Ser Leu Lys Arg Gly Asn Thr Pro Arg Asp Gln Gly
145                 150                 155                 160

Pro Cys Tyr Asp Ser Ser Ala Val Ser Asn Asp Ile Lys Gly Ala Thr
                165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
        195                 200                 205

Arg Ser Thr Gly Thr Asp Pro Val Thr Arg Phe Ser Leu Thr Arg Arg
    210                 215                 220

Val Leu Asn Ile Gly Pro Arg Val Pro Ile Gly Pro Asn Ser Val Ile
225                 230                 235                 240

Ile Asp Gln Leu Pro Pro Ser Arg Pro Val Gln Ile Met Leu Pro Arg
                245                 250                 255

Pro Pro Gln Pro Pro Pro
            260
```

<210> SEQ ID NO 171
<211> LENGTH: 265
<212> TYPE: PRT
<213> ORGANISM: Murine leukemia virus

<400> SEQUENCE: 171

```
Met Ala Cys Ser Thr Phe Ser Lys Pro Leu Lys Asp Lys Ile Asn Pro
1               5                   10                  15

Trp Gly Pro Leu Ile Ile Leu Gly Ile Leu Ile Arg Ala Gly Val Ser
            20                  25                  30

Val Gln His Asp Glu Pro His Lys Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Val Gly Asp Tyr Trp Asp Asp Pro Glu Pro Asp Ile Gly Asp Gly Cys
                85                  90                  95

Arg Thr Pro Gly Gly Arg Arg Arg Thr Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140
```

```
Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Asp Thr Lys
                165                 170                 175

Gly Ala Thr Pro Gly Gly Arg Cys Asn Pro Leu Val Leu Glu Phe Thr
            180                 185                 190

Asp Ala Gly Lys Lys Ala Ser Trp Asp Gly Pro Lys Val Trp Gly Leu
        195                 200                 205

Arg Leu Tyr Arg Ser Thr Gly Thr Asp Pro Val Thr Arg Phe Ser Leu
    210                 215                 220

Thr Arg Arg Val Leu Asn Thr Gly Pro Arg Val Pro Ile Gly Pro Asn
225                 230                 235                 240

Pro Val Ile Ile Asp Gln Leu Pro Pro Ser Arg Pro Val Gln Thr Met
                245                 250                 255

Leu Pro Arg Pro Pro Gln Pro Pro Pro
            260                 265


<210> SEQ ID NO 172
<211> LENGTH: 265
<212> TYPE: PRT
<213> ORGANISM: Murine leukemia virus

<400> SEQUENCE: 172

Met Glu Gly Pro Ala Phe Ser Lys Pro Leu Lys Asp Lys Ile Asn Pro
1               5                   10                  15

Trp Gly Pro Leu Ile Val Met Gly Ile Leu Val Arg Ala Gly Ala Ser
            20                  25                  30

Val Gln Arg Asp Ser Pro His Gln Ile Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Tyr Trp Asp Asp Pro Glu Pro Asp Ile Gly Asp Gly Cys
                85                  90                  95

Arg Thr Pro Gly Gly Arg Arg Arg Thr Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175

Gly Ala Thr Pro Gly Gly Arg Cys Asn Pro Leu Val Leu Glu Phe Thr
            180                 185                 190

Asp Ala Gly Arg Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Pro Arg Ile Pro Ile Gly Pro Asn
225                 230                 235                 240

Pro Val Ile Thr Asp Gln Leu Pro Pro Ser Gln Pro Val Gln Ile Met
                245                 250                 255
```

```
Leu Pro Arg Pro Pro His Pro Pro Pro
            260                 265


<210> SEQ ID NO 173
<211> LENGTH: 265
<212> TYPE: PRT
<213> ORGANISM: Murine leukemia virus

<400> SEQUENCE: 173

Met Glu Gly Ser Ala Phe Ser Lys Pro Leu Lys Asp Lys Ile Asn Pro
1               5                   10                  15

Trp Gly Pro Leu Ile Val Met Gly Ile Leu Val Arg Ala Gly Ala Ser
            20                  25                  30

Val Gln Arg Asp Ser Pro His Gln Ile Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp Tyr Trp Asp Asp Pro Glu Pro Asp Ile Gly Asp Gly Cys
                85                  90                  95

Arg Thr Pro Gly Gly Arg Arg Arg Thr Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175

Gly Ala Thr Pro Gly Gly Arg Cys Asn Pro Leu Val Leu Glu Phe Thr
            180                 185                 190

Asp Ala Gly Arg Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Phe Arg Val Pro Ile Gly Pro Asn
225                 230                 235                 240

Pro Val Ile Thr Asp Gln Leu Pro Pro Ser Gln Pro Val Gln Ile Met
                245                 250                 255

Leu Pro Arg Pro Pro His Pro Pro Pro
            260                 265


<210> SEQ ID NO 174
<211> LENGTH: 265
<212> TYPE: PRT
<213> ORGANISM: Murine leukemia virus

<400> SEQUENCE: 174

Met Glu Gly Pro Ala Phe Ser Lys Pro Leu Lys Asp Lys Ile Asn Pro
1               5                   10                  15

Trp Gly Pro Leu Ile Val Ile Gly Ile Leu Val Arg Ala Gly Ala Ser
            20                  25                  30

Val Gln Arg Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
```

-continued

```
    50                  55                  60

Thr Met Thr Asp Thr Phe Pro Lys Leu Tyr Phe Asp Leu Cys Asp Leu
65                  70                  75                  80

Val Gly Asp His Trp Asp Asp Pro Glu Pro Asp Ile Gly Asp Gly Cys
                85                  90                  95

Arg Ser Pro Gly Gly Arg Lys Arg Ser Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175

Gly Ala Thr Pro Gly Gly Arg Cys Asn Pro Leu Val Leu Glu Phe Thr
            180                 185                 190

Asp Ala Gly Lys Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Phe Arg Val Pro Ile Gly Phe Asn
225                 230                 235                 240

Pro Val Ile Thr Glu Gln Leu Pro Pro Ser Gln Pro Val Gln Ile Met
                245                 250                 255

Leu Pro Arg Pro Pro His Pro Pro Pro
            260                 265


<210> SEQ ID NO 175
<211> LENGTH: 265
<212> TYPE: PRT
<213> ORGANISM: Murine leukemia virus

<400> SEQUENCE: 175

Met Glu Gly Pro Ala Phe Ser Lys Pro Leu Lys Asp Lys Ile Asn Pro
1               5                   10                  15

Trp Gly Pro Leu Ile Val Ile Gly Ile Leu Val Arg Ala Gly Ala Ser
            20                  25                  30

Val Gln Arg Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Thr Phe Pro Lys Leu Tyr Phe Asp Leu Cys Asp Leu
65                  70                  75                  80

Val Gly Asp His Trp Asp Asp Pro Glu Pro Asp Ile Gly Asp Gly Cys
                85                  90                  95

Arg Ser Pro Gly Gly Arg Lys Arg Ser Arg Leu Tyr Asp Phe Tyr Val
            100                 105                 110

Cys Pro Gly His Thr Val Pro Ile Gly Cys Gly Gly Pro Gly Glu Gly
        115                 120                 125

Tyr Cys Gly Lys Trp Gly Cys Glu Thr Thr Gly Gln Ala Tyr Trp Lys
    130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
```

```
                165                 170                 175

Gly Ala Thr Pro Gly Gly Arg Cys Asn Pro Leu Val Leu Glu Phe Thr
            180                 185                 190

Asp Ala Gly Lys Lys Ala Ser Trp Asp Ala Pro Lys Val Trp Gly Leu
        195                 200                 205

Arg Leu Tyr Arg Ser Thr Gly Ala Asp Pro Val Thr Arg Phe Ser Leu
    210                 215                 220

Thr Arg Gln Val Leu Asn Val Gly Phe Arg Val Pro Ile Gly Phe Asn
225                 230                 235                 240

Pro Val Ile Thr Glu Gln Leu Pro Pro Ser Gln Pro Val Gln Ile Met
                245                 250                 255

Leu Pro Arg Pro Pro His Pro Pro Pro
            260                 265


<210> SEQ ID NO 176
<211> LENGTH: 271
<212> TYPE: PRT
<213> ORGANISM: Murine leukemia virus

<400> SEQUENCE: 176

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Phe Arg
225                 230                 235                 240

Val Pro Ile Gly Phe Asn Pro Val Leu Pro Asp Gln Arg Leu Pro Ser
                245                 250                 255

Ser Pro Ile Glu Ile Val Pro Ala Pro Gln Pro Pro Ser Pro Leu
            260                 265                 270
```

<210> SEQ ID NO 177
<211> LENGTH: 271
<212> TYPE: PRT
<213> ORGANISM: Murine leukemia virus

<400> SEQUENCE: 177

```
Met Ala Arg Ser Thr Leu Ser Lys Pro Leu Lys Asp Lys Ile Asn Pro
1               5                   10                  15

Trp Lys Ser Leu Met Val Met Gly Val Leu Leu Arg Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Arg Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Gly Gly Arg Lys Arg Thr Arg Thr Phe Asp Phe Tyr Val Cys
            100                 105                 110

Pro Gly His Thr Val Lys Ser Gly Cys Gly Gly Pro Arg Glu Gly Tyr
        115                 120                 125

Cys Gly Glu Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Met Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Ile Gly Phe Arg
225                 230                 235                 240

Ile Pro Ile Gly Phe Asn Pro Val Ile Thr Gly Gln Leu Pro Pro Ser
                245                 250                 255

Arg Pro Val Gln Ile Arg Leu Pro Arg Pro Pro Gln Pro Pro Pro
            260                 265                 270
```

<210> SEQ ID NO 178
<211> LENGTH: 314
<212> TYPE: PRT
<213> ORGANISM: Murine leukemia virus

<400> SEQUENCE: 178

```
Met Asp Thr Arg Arg Pro Arg Gln Gly Ser Asp His Ala Pro Asp Lys
1               5                   10                  15

Thr Ile Met Glu Ser Thr Thr Leu Ser Lys Pro Phe Lys Asn Gln Val
            20                  25                  30

Asn Pro Trp Gly Pro Leu Ile Val Leu Leu Ile Leu Gly Gly Val Asn
        35                  40                  45

Pro Val Thr Leu Gly Asn Ser Pro His Gln Val Phe Asn Leu Thr Trp
    50                  55                  60

Glu Val Thr Asn Gly Asp Arg Glu Thr Val Trp Ala Ile Thr Gly Asn
65                  70                  75                  80
```

His Pro Leu Trp Thr Trp Trp Pro Asp Leu Thr Pro Asp Leu Cys Met
85 90 95

Leu Ala Leu His Gly Pro Ser Tyr Trp Gly Leu Glu Tyr Arg Ala Pro
100 105 110

Phe Ser Pro Pro Pro Gly Pro Pro Cys Cys Ser Gly Ser Ser Asp Ser
115 120 125

Thr Phe Gly Cys Ser Arg Asp Cys Glu Glu Pro Leu Thr Ser Tyr Thr
130 135 140

Pro Arg Cys Asn Thr Ala Trp Asn Arg Leu Lys Leu Ser Lys Val Thr
145 150 155 160

His Ala His Asn Gly Gly Phe Tyr Val Cys Pro Gly Pro His Arg Pro
165 170 175

Arg Trp Ala Arg Ser Cys Gly Gly Pro Glu Ser Phe Tyr Cys Ala Ser
180 185 190

Trp Gly Cys Glu Thr Thr Gly Arg Ala Ser Trp Lys Pro Ser Ser Ser
195 200 205

Trp Asp Tyr Ile Thr Val Ser Asn Asn Leu Thr Ser Asp Gln Ala Thr
210 215 220

Pro Val Cys Lys Gly Asn Glu Trp Cys Asn Ser Leu Thr Ile Arg Phe
225 230 235 240

Thr Ser Phe Gly Lys Gln Ala Thr Ser Trp Val Thr Gly His Trp Trp
245 250 255

Gly Leu Arg Leu Tyr Val Ser Gly His Asp Pro Gly Leu Ile Phe Gly
260 265 270

Ile Arg Leu Lys Ile Thr Asp Ser Gly Phe Arg Val Pro Ile Gly Phe
275 280 285

Asn Pro Val Leu Ser Asp Arg Arg Pro Pro Ser Arg Pro Arg Pro Thr
290 295 300

Arg Ser Pro Pro Pro Ser Asn Ser Thr Pro
305 310

<210> SEQ ID NO 179
<211> LENGTH: 314
<212> TYPE: PRT
<213> ORGANISM: Murine leukemia virus

<400> SEQUENCE: 179

Met Asp Thr Arg Arg Pro Arg Gln Gly Ser Asp His Ala Pro Asp Lys
1 5 10 15

Thr Ile Met Glu Ser Thr Thr Leu Ser Lys Pro Phe Lys Asn Gln Val
20 25 30

Asn Pro Trp Gly Pro Leu Ile Val Leu Leu Ile Leu Gly Gly Val Asn
35 40 45

Pro Val Thr Leu Gly Asn Ser Pro His Gln Val Phe Asn Leu Thr Trp
50 55 60

Glu Val Thr Asn Gly Asp Arg Glu Thr Val Trp Ala Ile Thr Gly Asn
65 70 75 80

His Pro Leu Trp Thr Trp Trp Pro Asp Leu Thr Pro Asp Leu Cys Met
85 90 95

Leu Ala Leu His Gly Pro Ser Tyr Trp Gly Leu Glu Tyr Arg Ala Pro
100 105 110

Phe Ser Pro Pro Pro Gly Pro Pro Cys Cys Ser Gly Ser Ser Asp Ser
115 120 125

Thr Phe Gly Cys Ser Arg Asp Cys Glu Glu Pro Leu Thr Ser Tyr Thr
130 135 140

```
Pro Arg Cys Asn Thr Ala Trp Asn Arg Leu Lys Leu Ser Lys Val Thr
145                 150                 155                 160

His Ala His Asn Gly Gly Phe Tyr Val Cys Pro Gly Pro His Arg Pro
                165                 170                 175

Arg Trp Ala Arg Ser Cys Gly Gly Pro Glu Ser Pro Tyr Cys Ala Ser
            180                 185                 190

Trp Gly Cys Glu Thr Thr Gly Arg Ala Ser Trp Lys Pro Ser Ser Ser
        195                 200                 205

Trp Asp Tyr Ile Thr Val Ser Asn Asn Leu Thr Ser Asp Gln Ala Thr
    210                 215                 220

Pro Val Cys Lys Gly Asn Glu Trp Cys Asn Ser Leu Thr Ile Arg Phe
225                 230                 235                 240

Thr Ser Phe Gly Lys Gln Ala Thr Ser Trp Val Thr Gly His Trp Trp
                245                 250                 255

Gly Leu Arg Leu Tyr Val Ser Gly His Asp Pro Gly Leu Ile Phe Gly
            260                 265                 270

Ile Arg Leu Lys Ile Thr Asp Ser Gly Pro Arg Val Pro Ile Gly Pro
        275                 280                 285

Asn Pro Val Leu Ser Asp Arg Arg Pro Pro Ser Arg Pro Arg Pro Thr
    290                 295                 300

Arg Ser Pro Pro Pro Ser Asn Ser Thr Pro
305                 310


<210> SEQ ID NO 180
<211> LENGTH: 299
<212> TYPE: PRT
<213> ORGANISM: Murine leukemia virus

<400> SEQUENCE: 180

Met Ala Cys Ser Thr Leu Ser Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Phe Gly Ser Ser Phe His Gln Val Tyr Asn Ile Thr
        35                  40                  45

Trp Glu Val Thr Asn Gly Asp Arg Glu Thr Val Trp Ala Ile Ser Gly
    50                  55                  60

Asn His Pro Leu Trp Thr Trp Trp Pro Asp Leu Thr Pro Asp Leu Cys
65                  70                  75                  80

Met Leu Ala Leu Ser Gly Pro Pro His Trp Gly Leu Glu Tyr Arg Ala
                85                  90                  95

Pro Tyr Ser Ser Pro Pro Gly Pro Pro Cys Cys Ser Gly Ser Ser Gly
            100                 105                 110

Asn Arg Ala Gly Cys Ala Arg Asp Cys Asp Glu Pro Leu Thr Ser Leu
        115                 120                 125

Thr Pro Arg Cys Asn Thr Ala Trp Asn Arg Leu Lys Leu Asp Gln Val
    130                 135                 140

Thr His Lys Ser Ser Gly Gly Phe Tyr Val Cys Pro Gly Ser His Arg
145                 150                 155                 160

Pro Arg Lys Ala Lys Ser Cys Gly Gly Pro Asp Ser Phe Tyr Cys Ala
                165                 170                 175

Ser Trp Gly Cys Glu Thr Thr Gly Arg Ala Tyr Trp Lys Pro Ser Ser
            180                 185                 190

Ser Trp Asp Tyr Ile Thr Val Asp Asn Asn Leu Thr Thr Asn Gln Ala
        195                 200                 205
```

```
Ala Gln Val Cys Lys Asp Asn Lys Trp Cys Asn Pro Leu Ala Ile Gln
    210                 215                 220

Phe Thr Asn Ala Gly Lys Gln Val Thr Ser Trp Thr Ile Gly His Tyr
225                 230                 235                 240

Trp Gly Leu Arg Leu Tyr Val Ser Gly Gln Asp Pro Gly Leu Thr Phe
                245                 250                 255

Gly Ile Arg Leu Lys Tyr Gln Asn Leu Gly Pro Arg Val Pro Ile Gly
            260                 265                 270

Pro Asn Pro Val Leu Ala Asp Gln Leu Ser Phe Pro Leu Pro Asn Pro
        275                 280                 285

Leu Pro Lys Pro Ala Lys Ser Pro Ser Ala Ser
    290                 295


<210> SEQ ID NO 181
<211> LENGTH: 296
<212> TYPE: PRT
<213> ORGANISM: Murine leukemia virus

<400> SEQUENCE: 181

Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
            20                  25                  30

Thr Ala Ser Pro Gly Ser Ser Pro His Gln Val Tyr Asn Ile Thr Trp
        35                  40                  45

Glu Val Thr Asn Gly Asp Arg Glu Thr Val Trp Ala Thr Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
    130                 135                 140

Ser Asn Glu Gly Phe Tyr Val Gly Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
        195                 200                 205

Cys Lys Asp Asn Lys Trp Cys Asn Pro Leu Val Ile Arg Phe Thr Asp
    210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Ile Gly Pro Arg Val Pro Ile Gly Pro Asn Pro
            260                 265                 270

Val Leu Ala Asp Gln Gln Pro Leu Ser Lys Pro Lys Pro Val Lys Ser
        275                 280                 285
```

```
Pro Ser Val Thr Lys Pro Pro Ser
    290                 295


<210> SEQ ID NO 182
<211> LENGTH: 299
<212> TYPE: PRT
<213> ORGANISM: Murine leukemia virus

<400> SEQUENCE: 182

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Phe Gly Ser Ser Pro His Gln Val Tyr Asn Ile Thr
        35                  40                  45

Trp Glu Val Thr Asn Gly Asp Arg Glu Thr Val Trp Ala Ile Ser Gly
    50                  55                  60

Asn His Pro Leu Trp Thr Trp Trp Pro Val Leu Thr Pro Asp Leu Cys
65                  70                  75                  80

Met Leu Ala Leu Ser Gly Pro Pro His Trp Gly Leu Glu Tyr Gln Ala
                85                  90                  95

Pro Tyr Ser Ser Pro Pro Gly Pro Pro Cys Cys Ser Gly Ser Ser Gly
            100                 105                 110

Ser Ser Ala Gly Cys Ser Arg Asp Cys Asp Glu Pro Leu Thr Ser Leu
        115                 120                 125

Thr Pro Arg Cys Asn Thr Ala Trp Asn Arg Leu Lys Leu Asp Gln Val
    130                 135                 140

Thr His Lys Ser Ser Glu Gly Phe Tyr Val Cys Pro Gly Ser His Arg
145                 150                 155                 160

Pro Arg Glu Ala Lys Ser Cys Gly Gly Pro Asp Ser Phe Tyr Cys Ala
                165                 170                 175

Ser Trp Gly Cys Glu Thr Thr Gly Arg Val Tyr Trp Lys Pro Ser Ser
            180                 185                 190

Ser Trp Asp Tyr Ile Thr Val Gly Asn Asn Leu Thr Thr Ser Gln Ala
        195                 200                 205

Val Gln Val Cys Lys Asp Asn Lys Trp Cys Asn Pro Leu Ala Ile Gln
    210                 215                 220

Phe Thr Asn Ala Gly Lys Gln Val Thr Ser Trp Thr Thr Gly His Tyr
225                 230                 235                 240

Trp Gly Leu Arg Leu Tyr Val Ser Gly Arg Asp Pro Gly Leu Thr Phe
                245                 250                 255

Gly Ile Arg Leu Arg Tyr Gln Asn Leu Gly Pro Arg Val Pro Ile Gly
            260                 265                 270

Pro Asn Pro Val Leu Ala Asp Gln Leu Ser Leu Pro Arg Pro Asn Pro
        275                 280                 285

Leu Pro Lys Pro Ala Lys Ser Pro Pro Ala Ser
    290                 295


<210> SEQ ID NO 183
<211> LENGTH: 259
<212> TYPE: PRT
<213> ORGANISM: Murine leukemia virus

<400> SEQUENCE: 183

Met Glu Gly Pro Ala Phe Ser Lys Pro Leu Lys Asp Lys Ile Asn Pro
1               5                   10                  15
```

-continued

```
Trp Gly Pro Leu Ile Val Leu Gly Ile Leu Ile Arg Ala Gly Val Ser
            20                  25                  30

Val Gln His Asp Ser Pro His Gln Val Phe Asn Val Thr Trp Arg Val
        35                  40                  45

Thr Asn Leu Met Thr Gly Gln Thr Ala Asn Ala Thr Ser Leu Leu Gly
    50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                85                  90                  95

Gly Arg Lys Arg Ala Arg Thr Phe Asp Phe Tyr Val Cys Pro Gly His
            100                 105                 110

Thr Val Pro Thr Gly Cys Gly Gly Pro Arg Glu Gly Tyr Cys Gly Lys
        115                 120                 125

Trp Gly Cys Glu Thr Thr Gly Gln Ala Tyr Trp Lys Pro Ser Ser Ser
    130                 135                 140

Trp Asp Leu Ile Ser Leu Lys Arg Gly Asn Thr Pro Asn Gln Gly Pro
145                 150                 155                 160

Cys Tyr Asp Ser Ser Val Ser Ser Ile Gln Gly Ala Thr Pro Gly Gly
                165                 170                 175

Arg Cys Asn Pro Leu Val Leu Glu Phe Thr Asp Ala Gly Lys Lys Ala
            180                 185                 190

Ser Trp Asp Gly Pro Lys Val Trp Gly Leu Arg Leu Tyr Arg Ser Thr
        195                 200                 205

Gly Thr Asp Pro Val Thr Arg Phe Ser Leu Thr Arg Gln Val Leu Asn
    210                 215                 220

Ile Gly Pro Arg Val Pro Ile Gly Phe Asn Pro Val Ile Thr Asp Gln
225                 230                 235                 240

Leu Pro Pro Ser Arg Pro Val Gln Ile Met Leu Pro Arg Pro Pro Gln
                245                 250                 255

Pro Pro Pro


<210> SEQ ID NO 184
<211> LENGTH: 7697
<212> TYPE: DNA
<213> ORGANISM: Artificial sequence
<220> FEATURE:
<223> OTHER INFORMATION: EgfpHIVMo vector

<400> SEQUENCE: 184

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ctaccttacg tttccccgac    420

cagagctgat gttctcagaa aaacaagaac aaggaagtac agagaggctg gaaagtaccg    480

ggactagggc caaacaggat atctgtggtc aagcactagg gccccggccc agggccaaga    540

acagatggtc cccagaaaca gagaggctgg aaagtaccgg gactagggcc aaacaggata    600

tctgtggtca agcactaggg ccccggccca gggccaagaa cagatggtcc ccagaaatag    660

ctaaaacaac aacagtttca agagacccag aaactgtctc aaggttcccc agatgaccgg    720
```

-continued

```
ggatcaaccc caagcctcat ttaaactaac caatcagctc gcttctcgct tctgtacccg    780
cgcttattgc tgcccagctc tataaaaagg gtaagaaccc cacactcggc gcgccagtcc    840
tccgatagac tgagtcgccc gggtacccgt gtatccaata aagccttttg ctgttgcatc    900
cgaatcgtgg tctcgctgat ccttgggagg gtctcctcag agtgattgac tgcccagcct    960
gggggtcttt catttggggg ctcgtccggg atttggagac ccccgcccag ggaccaccga   1020
cccaccgtcg ggaggtaagc tggccagcga tcgttttgtc tccgtctctg tctttgtgcg   1080
tgtgtgtgtg tgtgccggca tctacttttt gcgcctgcgt ctgattctgt actagttagc   1140
taactagatc tgtatctggc ggctccgtgg aagaactgac gagttcgtat tcccgaccgc   1200
agccctggga gacgtctcag aggcatcggg ggggggatcc agagctcgag atggtgagca   1260
agggcgagga gctgttcacc ggggtggtgc ccatcctggt cgagctggac ggcgacgtaa   1320
acggccacaa gttcagcgtg tccggcgagg gcgagggcga tgccacctac ggcaagctga   1380
ccctgaagtt catctgcacc accggcaagc tgcccgtgcc ctggcccacc ctcgtgacca   1440
ccctgaccta cggcgtgcag tgcttcagcc gctaccccga ccacatgaag cagcacgact   1500
tcttcaagtc cgccatgccc gaaggctacg tccaggagcg caccatcttc ttcaaggacg   1560
acggcaacta caagacccgc gccgaggtga agttcgaggg cgacaccctg gtgaaccgca   1620
tcgagctgaa gggcatcgac ttcaaggagg acggcaacat cctggggcac aagctggagt   1680
acaactacaa cagccacaac gtctatatca tggccgacaa gcagaagaac ggcatcaagg   1740
tgaacttcaa gatccgccac aacatcgagg acggcagcgt gcagctcgcc gaccactacc   1800
agcagaacac ccccatcggc gacggccccg tgctgctgcc cgacaaccac tacctgagca   1860
cccagtccgc cctgagcaaa gaccccaacg agaagcgcga tcacatggtc ctgctggagt   1920
tcgtgaccgc cgccgggatc actctcggca tggacgagct gtacaagtaa agcggccgta   1980
cgcgttgatc agttaacgaa ttcgaagggt cccaggcctc ggagatctgg gcccatgcgg   2040
ccgcccccta acgttactgg ccgaagccgc ttggaataag gccggtgtgc gtttgtctat   2100
atgttatttt ccaccatatt gccgtctttt ggcaatgtga gggcccggaa acctggccct   2160
gtcttcttga cgagcattcc taggggtctt tcccctctcg ccaaaggaat gcaaggtctg   2220
ttgaatgtcg tgaaggaagc agttcctctg gaagcttctt gaagacaaac aacgtctgta   2280
gcgacccttt gcaggcagcg gaacccccca cctggcgaca ggtgcctctg cggccaaaag   2340
ccacgtgtat aagatacacc tgcaaaggcg gcacaacccc agtgccacgt tgtgagttgg   2400
atagttgtgg aaagagtcaa atggctctcc tcaagcgtat tcaacaaggg gctgaaggat   2460
gcccagaagg taccccattg tatgggatct gatctggggc ctcggtgcac atgctttaca   2520
tgtgtttagt cgaggttaaa aaacgtctag gccccccgaa ccacggggac gtggttttcc   2580
tttgaaaaac acgataatac catgagagca gaagacagtg gcaatgagag tgaaggagaa   2640
atatcagcac ttgtggagat gggggtggag atggggcacc atgctccttg ggatgttgat   2700
gatctgtagt gctacagaaa aattgtgggt cacagtctat tatggggtac ctgtgtggaa   2760
ggaagcaacc accactctat tttgtgcatc agatgctaaa gcatatgata cagaggtaca   2820
taatgtttgg gccacacatg cctgtgtacc cacagacccc aacccacaag aagtagtatt   2880
ggtaaatgtg acagaaaatt ttaacatgtg gaaaaatgac atggtagaac agatgcatga   2940
ggatataatc agtttatggg atcaaagcct aaagccatgt gtaaaattaa ccccactctg   3000
tgttagttta aagtgcactg atttgaagaa tgatactaat accaatagta gtagcgggag   3060
aatgataatg gagaaaggag agataaaaaa ctgctctttc aatatcagca caagcataag   3120
```

aggtaaggtg cagaaagaat atgcattttt ttataaactt gatataatac caatagataa 3180
tgatactacc agctataagt tgacaagttg taacacctca gtcattacac aggcctgtcc 3240
aaaggtatcc tttgagccaa ttcccataca ttattgtgcc ccggctggtt ttgcgattct 3300
aaaatgtaat aataagacgt tcaatggaac aggaccatgt acaaatgtca gcacagtaca 3360
atgtacacat ggaattaggc cagtagtatc aactcaactg ctgttaaatg gcagtctagc 3420
agaagaagag gtagtaatta gatctgtcaa tttcacggac aatgctaaaa ccataatagt 3480
acagctgaac acatctgtag aaattaattg tacaagaccc aacaacaata caagaaaaag 3540
aatccgtatc cagagaggac cagggagagc atttgttaca ataggaaaaa taggaaatat 3600
gagacaagca cattgtaaca ttagtagagc aaaatggaat aacactttaa aacagatagc 3660
tagcaaatta agagaacaat ttggaaataa taaaacaata atctttaagc aatcctcagg 3720
aggggaccca gaaattgtaa cgcacagttt taattgtgga ggggaatttt tctactgtaa 3780
ttcaacacaa ctgtttaata gtacttggtt taatagtact tggagtactg aagggtcaaa 3840
taacactgaa ggaagtgaca caatcaccct cccatgcaga ataaaacaaa ttataaacat 3900
gtggcagaaa gtaggaaaag caatgtatgc ccctcccatc agtggacaaa ttagatgttc 3960
atcaaatatt acagggctgc tattaacaag agatggtggt aatagcaaca atgagtccga 4020
gatcttcaga cctggaggag gagatatgag ggacaattgg agaagtgaat tatataaata 4080
taaagtagta aaaattgaac cattaggagt agcacccacc aaggcaaaga gaagagtggt 4140
gcagagagaa aaaagagcag tgggaatagg agctttgttc cttgggttct tgggagcagc 4200
aggaagcact atgggcgcag cctcaatgac gctgacggta caggccagac aattattgtc 4260
tggtatagtg cagcagcaga acaatttgct gagggctatt gaggcgcaac agcatctgtt 4320
gcaactcaca gtctggggca tcaagcagct ccaggcaaga atcctggctg tggaaagata 4380
cctaaaggat caacagctcc tggggatttg gggttgctct ggaaaactca tttgcaccac 4440
tgctgtgcct tggaatgcta gttggagtaa taaatctctg gaacagattt ggaatcacac 4500
gacctggatg gagtgggaca gagaaattaa caattacaca agcttaatac actccttaat 4560
tgaagaatcg caaaaccagc aagaaaagaa tgaacaagaa ttattggaat tagataaatg 4620
ggcaagtttg tggaattggt ttaacataac aaattggctg tggtatataa aattattcat 4680
aatgatagta ggaggcttgg taggtttaag aatagttttt gctgtacttt ctatagtgaa 4740
tagagttagg cagggatatt aaccattatc gttcttaaga caatagaaga ttgtaaatca 4800
cgtgaataaa agattttatt cagtttacag aaagaggggg gaatgaaaga ccccttcata 4860
aggcttagcc agctaactgc agtaacgcca ttttgcaagg catgggaaaa taccagagct 4920
gatgttctca gaaaaacaag aacaaggaag tacagagagg ctggaaagta ccgggactag 4980
ggccaaacag gatatctgtg gtcaagcact agggccccgg cccagggcca agaacagatg 5040
gtccccagaa acagagaggc tggaaagtac cgggactagg gccaaacagg atatctgtgg 5100
tcaagcacta gggccccggc ccagggccaa gaacagatgg tccccagaaa tagctaaaac 5160
aacaacagtt tcaagagacc cagaaactgt ctcaaggttc cccagatgac cggggatcaa 5220
ccccaagcct catttaaact aaccaatcag ctcgcttctc gcttctgtac ccgcgcttat 5280
tgctgcccag ctctataaaa agggtaagaa ccccacactc ggcgcgccag tcctccgata 5340
gactgagtcg cccgggtacc cgtgtatcca ataaagcctt ttgctgttgc atccgaatcg 5400
tggtctcgct gatccttggg agggtctcct cctctgtcgg tcgacctgca ggcatgcaag 5460
cttggcgtaa tcatggtcat agctgtttcc tgtgtgaaat tgttatccgc tcacaattcc 5520

```
acacaacata cgagccggaa gcataaagtg taaagcctgg ggtgcctaat gagtgagcta   5580
actcacatta attgcgttgc gctcactgcc cgctttccag tcgggaaacc tgtcgtgcca   5640
gctgcattaa tgaatcggcc aacgcgcggg gagaggcggt ttgcgtattg ggcgctcttc   5700
cgcttcctcg ctcactgact cgctgcgctc ggtcgttcgg ctgcggcgag cggtatcagc   5760
tcactcaaag gcggtaatac ggttatccac agaatcaggg gataacgcag gaaagaacat   5820
gtgagcaaaa ggccagcaaa aggccaggaa ccgtaaaaag gccgcgttgc tggcgttttt   5880
ccataggctc cgcccccctg acgagcatca caaaaatcga cgctcaagtc agaggtggcg   5940
aaacccgaca ggactataaa gataccaggc gtttccccct ggaagctccc tcgtgcgctc   6000
tcctgttccg accctgccgc ttaccggata cctgtccgcc tttctccctt cgggaagcgt   6060
ggcgctttct caatgctcac gctgtaggta tctcagttcg gtgtaggtcg ttcgctccaa   6120
gctgggctgt gtgcacgaac cccccgttca gcccgaccgc tgcgccttat ccggtaacta   6180
tcgtcttgag tccaacccgg taagacacga cttatcgcca ctggcagcag ccactggtaa   6240
caggattagc agagcgaggt atgtaggcgg tgctacagag ttcttgaagt ggtggcctaa   6300
ctacggctac actagaagga cagtatttgg tatctgcgct ctgctgaagc cagttacctt   6360
cggaaaaaga gttggtagct cttgatccgg caaacaaacc accgctggta gcggtggttt   6420
ttttgtttgc aagcagcaga ttacgcgcag aaaaaaagga tctcaagaag atcctttgat   6480
cttttctacg gggtctgacg ctcagtggaa cgaaaactca cgttaaggga ttttggtcat   6540
gagattatca aaaaggatct tcacctagat ccttttaaat taaaaatgaa gttttaaatc   6600
aatctaaagt atatatgagt aaacttggtc tgacagttac caatgcttaa tcagtgaggc   6660
acctatctca gcgatctgtc tatttcgttc atccatagtt gcctgactcc ccgtcgtgta   6720
gataactacg atacgggagg gcttaccatc tggccccagt gctgcaatga taccgcgaga   6780
cccacgctca ccggctccag atttatcagc aataaaccag ccagccggaa gggccgagcg   6840
cagaagtggt cctgcaactt tatccgcctc catccagtct attaattgtt gccgggaagc   6900
tagagtaagt agttcgccag ttaatagttt gcgcaacgtt gttgccattg ctacaggcat   6960
cgtggtgtca cgctcgtcgt ttggtatggc ttcattcagc tccggttccc aacgatcaag   7020
gcgagttaca tgatccccca tgttgtgcaa aaaagcggtt agctccttcg gtcctccgat   7080
cgttgtcaga agtaagttgg ccgcagtgtt atcactcatg gttatggcag cactgcataa   7140
ttctcttact gtcatgccat ccgtaagatg cttttctgtg actggtgagt actcaaccaa   7200
gtcattctga gaatagtgta tgcggcgacc gagttgctct tgcccggcgt caatacggga   7260
taataccgcg ccacatagca gaactttaaa agtgctcatc attggaaaac gttcttcggg   7320
gcgaaaactc tcaaggatct taccgctgtt gagatccagt tcgatgtaac ccactcgtgc   7380
acccaactga tcttcagcat cttttacttt caccagcgtt tctgggtgag caaaaacagg   7440
aaggcaaaat gccgcaaaaa agggaataag ggcgacacgg aaatgttgaa tactcatact   7500
cttccttttt caatattatt gaagcattta tcagggttat tgtctcatga gcggatacat   7560
atttgaatgt atttagaaaa ataaacaaat aggggttccg cgcacatttc cccgaaaagt   7620
gccacctgac gtctaagaaa ccattattat catgacatta acctataaaa ataggcgtat   7680
cacgaggccc tttcgtc                                                  7697
```

<210> SEQ ID NO 185
<211> LENGTH: 26
<212> TYPE: DNA
<213> ORGANISM: Artificial sequence
<220> FEATURE:
<223> OTHER INFORMATION: Primer

<400> SEQUENCE: 185
ctctccaagc tcacttacag gccctc 26

<210> SEQ ID NO 186
<211> LENGTH: 32
<212> TYPE: DNA
<213> ORGANISM: Artificial sequence
<220> FEATURE:
<223> OTHER INFORMATION: Primer

<400> SEQUENCE: 186
tgcggccgcg tcgactggct aagccttatg aa 32

<210> SEQ ID NO 187
<211> LENGTH: 35
<212> TYPE: PRT
<213> ORGANISM: Artificial sequence
<220> FEATURE:
<223> OTHER INFORMATION: Linker

<400> SEQUENCE: 187

```
Gln Gly Ile Tyr Gln Cys Ser Gly Gly Ser Gly Gln Arg Pro Arg Leu
1               5                   10                  15

Ser His Lys Gly Pro Met Pro Phe Ser Gly Gly Ser Gly Cys Gly Pro
            20                  25                  30

Cys Tyr Asp
        35
```

<210> SEQ ID NO 188
<211> LENGTH: 99
<212> TYPE: DNA
<213> ORGANISM: Artificial sequence
<220> FEATURE:
<223> OTHER INFORMATION: Primer

<400> SEQUENCE: 188
tccggtggca gtggacagcg gccccgcctc tcccataagg gacccatgcc tttcagcggt 60
ggatctggct gtgggccctg ttatgattcc tcggtggtc 99

<210> SEQ ID NO 189
<211> LENGTH: 63
<212> TYPE: DNA
<213> ORGANISM: Artificial sequence
<220> FEATURE:
<223> OTHER INFORMATION: Primer

<400> SEQUENCE: 189
gggccgctgt ccactgccac cggagcactg gtagattcct tgagtgtttc ctcgcttaag 60
gga 63

<210> SEQ ID NO 190
<211> LENGTH: 35
<212> TYPE: PRT
<213> ORGANISM: Artificial sequence
<220> FEATURE:
<223> OTHER INFORMATION: Linker

<400> SEQUENCE: 190

```
Pro Cys Tyr Asp Ser Ser Gly Gly Ser Gly Gln Arg Pro Arg Leu Ser
1               5                   10                  15

His Lys Gly Pro Met Pro Phe Ser Gly Gly Ser Gly Ser Ser Ser Ala
```

20 25 30

Gln Gly Ala
35

<210> SEQ ID NO 191
<211> LENGTH: 93
<212> TYPE: DNA
<213> ORGANISM: Artificial sequence
<220> FEATURE:
<223> OTHER INFORMATION: Primer

<400> SEQUENCE: 191
tccggtggca gtggacagcg gccccgcctc tcccataagg gacccatgcc tttcagcggt 60
ggatctggct ccagtagcgc ccagggtgcc aca 93

<210> SEQ ID NO 192
<211> LENGTH: 48
<212> TYPE: DNA
<213> ORGANISM: Artificial sequence
<220> FEATURE:
<223> OTHER INFORMATION: Linker

<400> SEQUENCE: 192
gggccgctgt ccactgccac cggaggaatc ataacagggg ccctggcc 48

<210> SEQ ID NO 193
<211> LENGTH: 27
<212> TYPE: DNA
<213> ORGANISM: Artificial sequence
<220> FEATURE:
<223> OTHER INFORMATION: Linker

<400> SEQUENCE: 193
tcaggtggct ccggagggtc tggctcg 27

<210> SEQ ID NO 194
<211> LENGTH: 21
<212> TYPE: DNA
<213> ORGANISM: Murine leukemia virus

<400> SEQUENCE: 194
ccctgttatg attccagtag c 21

<210> SEQ ID NO 195
<211> LENGTH: 48
<212> TYPE: DNA
<213> ORGANISM: Artificial sequence
<220> FEATURE:
<223> OTHER INFORMATION: Linker

<400> SEQUENCE: 195
ccctgttatg attcctcagg tggctccgga gggtctggct cgagtagc 48

<210> SEQ ID NO 196
<211> LENGTH: 51
<212> TYPE: DNA
<213> ORGANISM: Artificial sequence
<220> FEATURE:
<223> OTHER INFORMATION: Primer

<400> SEQUENCE: 196
tcaggtggct ccggagggtc tggctcgagt agcgcccagg gtgccacacc g 51

<210> SEQ ID NO 197
<211> LENGTH: 21

<212> TYPE: DNA
<213> ORGANISM: Artificial sequence
<220> FEATURE:
<223> OTHER INFORMATION: Primer

<400> SEQUENCE: 197
cgggtcggga ggggggtaac t 21

<210> SEQ ID NO 198
<211> LENGTH: 48
<212> TYPE: DNA
<213> ORGANISM: Artificial sequence
<220> FEATURE:
<223> OTHER INFORMATION: Primer

<400> SEQUENCE: 198
gccagaccct ccggagccac ctgaggaatc ataacagggg ccctggcc 48

<210> SEQ ID NO 199
<211> LENGTH: 21
<212> TYPE: DNA
<213> ORGANISM: Artificial sequence
<220> FEATURE:
<223> OTHER INFORMATION: Primer

<400> SEQUENCE: 199
tgaaaaacac gataatacca t 21

<210> SEQ ID NO 200
<211> LENGTH: 1935
<212> TYPE: DNA
<213> ORGANISM: Artificial sequence
<220> FEATURE:
<223> OTHER INFORMATION: Chimeric gene

<400> SEQUENCE: 200
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240 atagggggacg actgggatga gactggactc gggtgtcgca ctcccggggg aagaaaaagg 300
gcaagaatat ttgacttcta tgtttgcccc ggtcacactg tgctagcagg gtgtggaggg 360
ccgagagagg gctactgtgg caaatgggga tgtgagacca ctggacaggc atactggaag 420
ccatcatcat catgggacct aatttccctt aagcgaggaa acactcctaa aggccagggc 480
ccctgttatg attcctcagg tggctccgga gggtctggct cgagtagcgc ccagggtgcc 540
acaccggggg gtcgatgcaa ccccctagtc ctagaattca ctgacgcggg taaaagggcc 600
agctgggacg cctccaaagc atggggacta agactgtacc gatccacaag gaccgacccg 660
gtgacccggt tctctttgac ccgccaggtc ctcaatatag ggccccgcgt ccccattggg 720
cctaatcccg tgatcattga ccagttaccc ccctcccgac ccgtgcagat catgctcccc 780
aggcctcctc agcctcctcc accaggcgca gcctctacag tccctgagac tgccccacct 840
tcccaacaac ctgggacggg agacaggctg ctaaacctgg taaatggagc ctaccaagct 900
ctcaacctca ccagtcctga caaaacccaa gagtgctggt tgtgtctggt agcgggaccc 960
ccctactacg aaggggttgc cgtcctaggt acttattcca accatacctc tgccccagct 1020
aactgctccg tggcctccca acacaagctg accctgtccg aagtgaccgg acagggactc 1080
tgcgtaggag cagttcccaa aacccatcag gccctgtgta ataccaccca gaagacgagc 1140

```
aacgggtcct actatctggc tgctcccgcc gggaccattt gggcttgcaa caccgggctc   1200

actccctgcc tatctaccac tgtgctcgac ctcaccaccg attactgtgt cctggttgag   1260

ctctggccaa aagtgaccta ccactcccct ggttatgttt atggccagtt tgaagaaaaa   1320

accaaatata aaagagaacc cgtctcacta actctggccc tactattagg aggactcact   1380

atgggcggaa ttgccgccgg agtgggaaca gggactaccg ccctagtggc cactcagcag   1440

ttccaacaac tccaggctgc catgcaggat gaccttaaag aagttgaaaa gtccatcact   1500

aatctagaaa gatctttgac ctccttgtcc gaagtagtgt tacagaatcg tagaggccta   1560

gatctactat tcctaaaaga gggaggtttg tgtgctgcct taaaagaaga atgctgtttc   1620

tatgccgacc acacaggatt ggtacgggat agcatggcca aacttagaga aagattgagt   1680

cagagacaaa aactctttga atcccaacaa gggtggtttg aagggctgtt taacaagtcc   1740

ccttggttca ccaccctgat atccaccatc atgggtcccc tgataatcct cttgttaatt   1800

ttactctttg ggccttgtat tctcaatcac ctggtccagt ttatcaaaga cagggtttcg   1860

gtagtgcagg ccctggtcct gactcaacaa tatcatcaac ttaagacaat agaagattgt   1920

gaatcacgtg aataa                                                     1935
```

<210> SEQ ID NO 201
<211> LENGTH: 16
<212> TYPE: PRT
<213> ORGANISM: Artificial sequence
<220> FEATURE:
<223> OTHER INFORMATION: Tetracysteine motif

<400> SEQUENCE: 201

```
Ser Gly Gly Ser Gly Cys Cys Pro Gly Cys Cys Ser Gly Gly Ser Gly
1               5                   10                  15
```

<210> SEQ ID NO 202
<211> LENGTH: 22
<212> TYPE: PRT
<213> ORGANISM: Artificial sequence
<220> FEATURE:
<223> OTHER INFORMATION: Tetracysteine motif

<400> SEQUENCE: 202

```
Ser Gly Gly Ser Gly His Arg Trp Cys Cys Pro Gly Cys Cys Lys Thr
1               5                   10                  15

Phe Ser Gly Gly Ser Gly
            20
```

<210> SEQ ID NO 203
<211> LENGTH: 48
<212> TYPE: DNA
<213> ORGANISM: Artificial sequence
<220> FEATURE:
<223> OTHER INFORMATION: Primer

<400> SEQUENCE: 203

```
tcaggtggct ccggttgttg tccaggctgc tgcagtgggg gcagcggc                  48
```

<210> SEQ ID NO 204
<211> LENGTH: 49
<212> TYPE: DNA
<213> ORGANISM: Artificial sequence
<220> FEATURE:
<223> OTHER INFORMATION: Primer

<400> SEQUENCE: 204
tcgagccgct gcccccactg cagcagcctg gacaacaacc ggagccacc 49

<210> SEQ ID NO 205
<211> LENGTH: 66
<212> TYPE: DNA
<213> ORGANISM: Artificial sequence
<220> FEATURE:
<223> OTHER INFORMATION: Primer

<400> SEQUENCE: 205
tcaggtggct ccggtcatag atggtgttgt ccaggctgct gcaagacgtt cagtgggggc 60
agcggc 66

<210> SEQ ID NO 206
<211> LENGTH: 67
<212> TYPE: DNA
<213> ORGANISM: Artificial sequence
<220> FEATURE:
<223> OTHER INFORMATION: Primer

<400> SEQUENCE: 206
tcgagccgct gcccccactg aacgtcttgc agcagcctgg acaacaccat ctatgaccgg 60
agccacc 67

<210> SEQ ID NO 207
<211> LENGTH: 1959
<212> TYPE: DNA
<213> ORGANISM: Artificial sequence
<220> FEATURE:
<223> OTHER INFORMATION: Chimeric gene

<400> SEQUENCE: 207
atggaaggtc cagcgttctc aaaacccctt aaagataaga ttaacccgtg gggcccccta 60
atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggatga gactggactc gggtgtcgca ctcccggggg aagaaaaagg 300
gcaagaatat ttgacttcta tgtttgcccc ggtcacactg tgctagcagg gtgtggaggg 360
ccgagagagg gctactgtgg caaatgggga tgtgagacca ctggacaggc atactggaag 420
ccatcatcat catgggacct aatttccctt aagcgaggaa acactcctaa aggccagggc 480
ccctgttatg attcctcagg tggctccggt tgttgtccag gctgctgcag tgggggcagc 540
ggctcgagta gcgcccaggg tgccacaccg gggggtcgat gcaacccccct agtcctagaa 600 ttcactgacg cgggtaaaag ggccagctgg gacgcctcca aagcatgggg actaagactg 660
taccgatcca caaggaccga cccggtgacc cggttctctt tgacccgcca ggtcctcaat 720
atagggcccc gcgtccccat tggcctaat cccgtgatca ttgaccagtt acccccctcc 780
cgacccgtgc agatcatgct ccccaggcct cctcagcctc ctccaccagg cgcagcctct 840
acagtccctg agactgcccc accttcccaa caacctggga cgggagacag gctgctaaac 900
ctggtaaatg gagcctacca agctctcaac ctcaccagtc ctgacaaaac ccaagagtgc 960
tggttgtgtc tggtagcggg accccccctac tacgaagggg ttgccgtcct aggtacttat 1020
tccaaccata cctctgcccc agctaactgc tccgtggcct cccaacacaa gctgaccctg 1080
tccgaagtga ccggacaggg actctgcgta ggagcagttc ccaaaaccca tcaggccctg 1140
tgtaatacca cccagaagac gagcaacggg tcctactatc tggctgctcc cgccgggacc 1200
atttgggctt gcaacaccgg gctcactccc tgcctatcta ccactgtgct cgacctcacc 1260
accgattact gtgtcctggt tgagctctgg ccaaaagtga cctaccactc ccctggttat 1320
gtttatggcc agtttgaaga aaaaaccaaa tataaaagag aacccgtctc actaactctg 1380
gccctactat taggaggact cactatgggc ggaattgccg ccggagtggg aacagggact 1440
accgccctag tggccactca gcagttccaa caactccagg ctgccatgca ggatgacctt 1500
aaagaagttg aaaagtccat cactaatcta gaaagatctt tgacctcctt gtccgaagta 1560
gtgttacaga atcgtagagg cctagatcta ctattcctaa aagagggagg tttgtgtgct 1620
gccttaaaag aagaatgctg tttctatgcc gaccacacag gattggtacg ggatagcatg 1680
gccaaactta gagaaagatt gagtcagaga caaaaactct ttgaatccca acaagggtgg 1740
tttgaagggc tgtttaacaa gtccccttgg ttcaccaccc tgatatccac catcatgggt 1800
cccctgataa tcctcttgtt aattttactc tttgggcctt gtattctcaa tcacctggtc 1860
cagtttatca aagacagggt ttcggtagtg caggccctgg tcctgactca acaatatcat 1920
caacttaaga caatagaaga ttgtgaatca cgtgaataa 1959

<210> SEQ ID NO 208
<211> LENGTH: 1977
<212> TYPE: DNA
<213> ORGANISM: Artificial sequence
<220> FEATURE:
<223> OTHER INFORMATION: Chimeric gene

<400> SEQUENCE: 208
atggaaggtc cagcgttctc aaaacccctt aaagataaga ttaacccgtg ggcccccta 60 atagtcctgg gaatcttaat gagggcaaga gtatcagtac aacatgacag ccctcatcag 120
gtcttcaatg ttacttggag agttaccaac ttaatgacag gacaaacagc taatgctacc 180
tccctcctgg ggacaatgac cgatgccttt cctaaactgt actttgactt gtgcgattta 240
ataggggacg actgggatga gactggactc gggtgtcgca ctcccggggg aagaaaaagg 300
gcaagaatat ttgacttcta tgtttgcccc ggtcacactg tgctagcagg gtgtggaggg 360
ccgagagagg gctactgtgg caaatgggga tgtgagacca ctggacaggc atactggaag 420
ccatcatcat catgggacct aatttccctt aagcgaggaa acactcctaa aggccagggc 480
ccctgttatg attcctcagg tggctccggt catagatggt gttgtccagg ctgctgcaag 540
acgttcagtg gggcagcgg ctcgagtagc gcccagggtg ccacaccggg gggtcgatgc 600
aaccccctag tcctagaatt cactgacgcg ggtaaaaggg ccagctggga cgcctccaaa 660
gcatggggac taagactgta ccgatccaca aggaccgacc cggtgacccg gttctctttg 720
acccgccagg tcctcaatat agggccccgc gtccccattg ggcctaatcc cgtgatcatt 780
gaccagttac ccccctcccg acccgtgcag atcatgctcc ccaggcctcc tcagcctcct 840
ccaccaggcg cagcctctac agtccctgag actgccccac cttcccaaca acctgggacg 900
ggagacaggc tgctaaacct ggtaaatgga gcctaccaag ctctcaacct caccagtcct 960
gacaaaaccc aagagtgctg gttgtgtctg gtagcgggac ccccctacta cgaaggggtt 1020
gccgtcctag gtacttattc caaccatacc tctgccccag ctaactgctc cgtggcctcc 1080
caacacaagc tgaccctgtc cgaagtgacc ggacagggac tctgcgtagg agcagttccc 1140
aaaacccatc aggccctgtg taataccacc cagaagacga gcaacgggtc ctactatctg 1200
gctgctcccg ccgggaccat ttgggcttgc aacaccgggc tcactccctg cctatctacc 1260
actgtgctcg acctcaccac cgattactgt gtcctggttg agctctggcc aaaagtgacc 1320

-continued

```
taccactccc ctggttatgt ttatggccag tttgaagaaa aaaccaaata taaaagagaa   1380

cccgtctcac taactctggc cctactatta ggaggactca ctatgggcgg aattgccgcc   1440

ggagtgggaa cagggactac cgccctagtg gccactcagc agttccaaca actccaggct   1500

gccatgcagg atgaccttaa agaagttgaa aagtccatca ctaatctaga aagatctttg   1560

acctccttgt ccgaagtagt gttacagaat cgtagaggcc tagatctact attcctaaaa   1620

gagggaggtt tgtgtgctgc cttaaaagaa gaatgctgtt tctatgccga ccacacagga   1680

ttggtacggg atagcatggc caaacttaga gaaagattga gtcagagaca aaaactcttt   1740

gaatcccaac aagggtggtt tgaagggctg tttaacaagt ccccttggtt caccaccctg   1800

atatccacca tcatgggtcc cctgataatc ctcttgttaa ttttactctt tgggccttgt   1860

attctcaatc acctggtcca gtttatcaaa gacagggttt cggtagtgca ggccctggtc   1920

ctgactcaac aatatcatca acttaagaca atagaagatt gtgaatcacg tgaataa      1977
```